United States Patent
McComas et al.

(10) Patent No.: US 10,562,909 B2
(45) Date of Patent: Feb. 18, 2020

(54) FUSED QUADRACYCLIC COMPOUNDS, COMPOSITIONS AND USES THEREOF

(71) Applicant: Tabomedex Biosciences, LLC, Boxford, MA (US)

(72) Inventors: Casey C. McComas, Phoenixville, PA (US); Michael H. Serrano-Wu, Cambridge, MA (US); Joseph P. Vacca, Telford, PA (US)

(73) Assignee: Tabomedex Biosciences, LLC, Boxford, MA (US)

( * ) Notice: Subject to any disclaimer, the term of this patent is extended or adjusted under 35 U.S.C. 154(b) by 0 days.

(21) Appl. No.: 16/039,877

(22) Filed: Jul. 19, 2018

(65) Prior Publication Data

US 2018/0319809 A1 Nov. 8, 2018

Related U.S. Application Data

(63) Continuation of application No. 15/397,212, filed on Jan. 3, 2017, now Pat. No. 10,059,718.

(60) Provisional application No. 62/274,640, filed on Jan. 4, 2016.

(51) Int. Cl.

| | | |
|---|---|---|
| *A61K 31/551* | (2006.01) | |
| *A61K 31/5517* | (2006.01) | |
| *C07D 471/22* | (2006.01) | |
| *C07D 487/14* | (2006.01) | |
| *C07D 487/22* | (2006.01) | |
| *C07D 519/00* | (2006.01) | |
| *A61K 45/06* | (2006.01) | |

(52) U.S. Cl.
CPC ........ *C07D 487/14* (2013.01); *A61K 31/5517* (2013.01); *A61K 45/06* (2013.01); *C07D 519/00* (2013.01)

(58) Field of Classification Search
CPC .............. A61K 31/551; A61K 31/5517; C07D 471/22; C07D 487/14; C07D 487/22; C07D 519/00
See application file for complete search history.

(56) References Cited

U.S. PATENT DOCUMENTS

| 4,521,534 A | 6/1985 | Gauthier et al. |
|---|---|---|
| 4,596,799 A | 6/1986 | Wasley |
| 10,059,718 B2 | 8/2018 | McComas et al. |

FOREIGN PATENT DOCUMENTS

| WO | WO-02/40487 A2 | 5/2002 |
|---|---|---|
| WO | WO-2004/058176 A2 | 7/2004 |
| WO | WO-2004/058762 A1 | 7/2004 |
| WO | WO-2014/149164 A1 | 9/2014 |

OTHER PUBLICATIONS

International Search Report and Written Opinion for International Application No. PCT/US2017/012092, dated Mar. 26, 2017.
Rao et al., "Facile synthesis of tetracyclic azepine and oxazocine derivatives and their potential as MAPKAP-K2 (MK2) inhibitors," Bioorg Med Chem Lett, 22(2):1068-1072 (2012).
Wang et al., "Applications of 3D-QSAR and structure-based pharmacophore modeling, virtual screening, ADMET, and molecular docking of putative MAPKAP-K2 (MK2) inhibitors," Med Chem Res, 22(10): 4818-4829 (2013).
Xiong, et al., "Synthesis and SAR studies of indole-based MK2 inhibitors," Bioorg Med Chem Lett, 18(6): 1994-1999 (2008).
Extended European Search Report issued by the European Patent Office in corresponding Application No. EP 17736213 dated Jul. 11, 2019.

*Primary Examiner* — Brenda L Coleman
(74) *Attorney, Agent, or Firm* — Foley Hoag LLP

(57) ABSTRACT

Provided herein are substituted fused quadracyclic compounds useful as inhibitors of MK2. The invention further provides pharmaceutical compositions of the compounds of the invention. The invention also provides medical uses of substituted fused quadracyclic compounds.

34 Claims, No Drawings

FUSED QUADRACYCLIC COMPOUNDS, COMPOSITIONS AND USES THEREOF

CROSS-REFERENCE TO RELATED APPLICATIONS

This application is a continuation of U.S. patent application Ser. No. 15/397,212, filed Jan. 3, 2017, which claims the benefit of priority to U.S. Provisional Patent Application Ser. No. 62/274,640, filed Jan. 4, 2016, the entire contents of each of which are hereby incorporated by reference in their entireties.

BACKGROUND p38 mitogen activated protein kinase (p38 MAPK) transduces a range of extracellular signals that result in inflammatory response, cell division and differentiation, apoptosis, and cell motility. p38 MAPK was initially believed to be an ideal target for anti-inflammatory therapeutics. However, the failure of more than a dozen chemically different compounds in the clinical phase suggests that p38 MAPK might be a poor therapeutic target. Many of these compounds were found to be hepatotoxic to various degree and tolerance to the anti-inflammatory effect developed within weeks. In hindsight, the failures in clinical trials due to unwanted side effects is perhaps not unexpected as p38 MAPK regulates the activity for more than 60 substrates.

One of the downstream substrates of p38 MAPK is mitogen-activated protein kinase activated protein kinase-2 (MAPKAPK or MK2). Among other roles, MK2 regulates the biosynthesis of tumor necrosis factor α and other cytokines. In addition, MK2 is activated after DNA damage resulting in cell cycle arrest, such that cells have the capacity to repair their DNA and continue to proliferate. MK2 also phosphorylates heat shock 27 (Hsp27), a prominent biomarker of cancer progression. Thus, MK2 could serve as a potential anti-inflammatory target and an anticancer target to improve the efficacy of chemotherapy without the unwanted side effects that affect targets further upstream (i.e., p38 MAPK).

Therefore, there is a continuing need to discover and develop new compounds that inhibit MK2 and that may be useful therapeutics.

SUMMARY OF INVENTION

In certain embodiments, the invention relates to compounds having the structure of Formula (I):

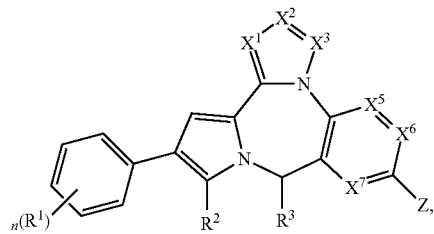

and pharmaceutically acceptable salts thereof, wherein $R^1$—$R^3$, $X^1$—$X^3$, $X^5$—$X^7$, Z and n are as defined in the specification.

In certain embodiments, the invention relates to compounds having the structure of Formula (II):

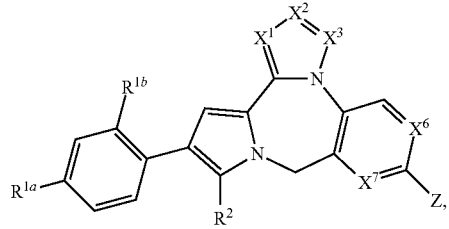

and pharmaceutically acceptable salts thereof, wherein $R^{1a}$, $R^{1b}$, $R^2$, $R^3$, $X^1$—$X^3$, $X^6$, $X^7$ and Z are as defined in the specification.

In some embodiments, the invention relates to pharmaceutical compositions of a compound of Formula (I) or Formula (II), and a pharmaceutically acceptable carrier.

The invention also relates to methods of treating a MK2-related disorder, comprising administering to a subject a compound of the invention.

The invention further relates to methods of inhibiting proliferation of a cancer cell comprising contacting a cancer cell with a compound of the invention.

The invention also provides methods of inhibiting MK2 activity in a cell, comprising contacting a cell with a compound of the invention.

The invention also provides methods of treating or preventing a metabolic disorder, comprising administering to a subject a compound of the invention.

DETAILED DESCRIPTION OF THE INVENTION

In certain aspects, the invention provides substituted fused quadracyclic compounds, and pharmaceutical compositions thereof. In particular, such substituted fused quadracyclic compounds are useful as MK2 inhibitors, and thus can be used as anti-cancer agents, anti-inflammatory agents, or anti-diabetic agents.

I. Compounds

In certain embodiments, the invention relates to compounds having the structure of Formula (I), or a pharmaceutically acceptable salt thereof:

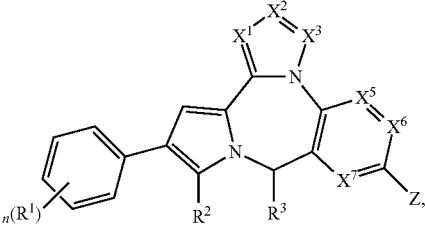

wherein
$X^1$, $X^2$, and $X^3$ are, independently for each occurrence, $CR^5$ or N;
$X^5$, $X^6$, and $X^7$ are, independently for each occurrence, $CR^7$ or N;
$R^1$ is, independently for each occurrence, H, halo, —OH, —CN, or optionally substituted alkyl, alkoxy, ether, carbamate, or ester;
$R^2$ is H, halo, —CN, alkyl, or ester;
$R^3$ is H, alkyl, or cycloalkyl;

$R^5$ is H, halo, —CN or optionally substituted alkyl, alkoxy, aryl, heteroaryl, carbamate, or ester;
$R^7$ is H, halo, —OH, —CN, or optionally substituted alkyl, alkoxy, carbamate, or ester;
Z is halo or optionally substituted amino, alkylamino, heteroalkylamino, cycloalkylamino, or heterocycloalkylamino; and
n is an integer from 0-5.

In certain embodiments, the invention relates to compounds having the structure of Formula (II), or a pharmaceutically acceptable salt thereof:

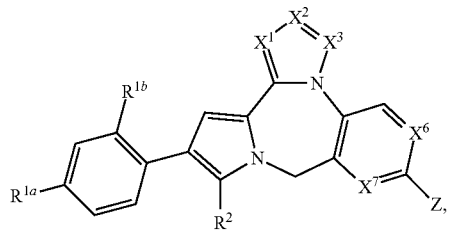

II wherein
$X^1$ is N or CH;
$X^2$ and $X^3$ are, independently for each occurrence, $CR^5$ or N;
$R^{1a}$ is H, halo, —CN, —OH, or optionally substituted alkyl;
$R^{1b}$ is H, halo, —CN, —OH, or optionally substituted alkyl;
$R^2$ is H or halo;
$R^5$ is H, halo, or optionally substituted alkyl; and
Z is halo or optionally substituted amino, alkylamino, heteroalkylamino, cycloalkylamino, or heterocycloalkylamino.

In certain embodiments of Formulas I and II, $X^1$ is N; and $X^2$ and $X^3$ are CH. In certain embodiments of Formulas I and II, $X^1$ and $X^2$ are N; and $X^3$ is CH. In certain embodiments of Formulas I and II, $X^1$ and $X^3$ are N; and $X^2$ is CH. In certain embodiments of Formulas I and II, $X^1$, $X^2$, and $X^3$ are N.

In certain embodiments of Formulas I and II, Z is halo, preferably bromo. In alternative embodiments, Z is optionally substituted amino, alkylamino, heteroalkylamino, cycloalkylamino, or heterocycloalkylamino.

In certain embodiments of Formulas I and II, Z is optionally substituted alkylamino, heterocycloalkylamino, cycloalkylamino, or —$NR^8R^9$; and $R^8$ and $R^9$ are each, independently, H or optionally substituted, alkyl, cycloalkyl, or heterocycloalkyl; or $R^8$ and $R^9$ together with the N to which they are bound combine to form an optionally substituted 4-, 5-, or 6-membered heterocyclic ring.

In certain embodiments of Formulas I and II, Z is

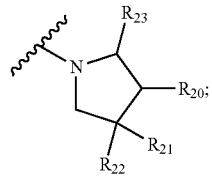

and
$R^{20}$, $R^{21}$, $R^{22}$, and $R^{23}$, are each independently H, halo, hydroxyl, amino, or optionally substituted alkyl, alkoxy, aminoalkyl, alkylaminoalkyl, alkylamino, cycloalkyl, or heterocycloalkyl; or $R^{23}$ and $R^{20}$ combine to form an optionally substituted 3-, 4-, 5-, or 6-membered ring;
$R^{21}$ and $R^{20}$ combine to form an optionally substituted 3-, 4-, 5-, or 6-membered ring; or
$R^{21}$ and $R^{22}$ combine to form an optionally substituted 4-, 5-, or 6-membered ring. In some embodiments, the optionally substituted 4-, 5-, or 6-membered ring comprises a heteroatom. In some embodiments, the heteroatom is N.

In certain embodiments of Formulas I and II, Z is

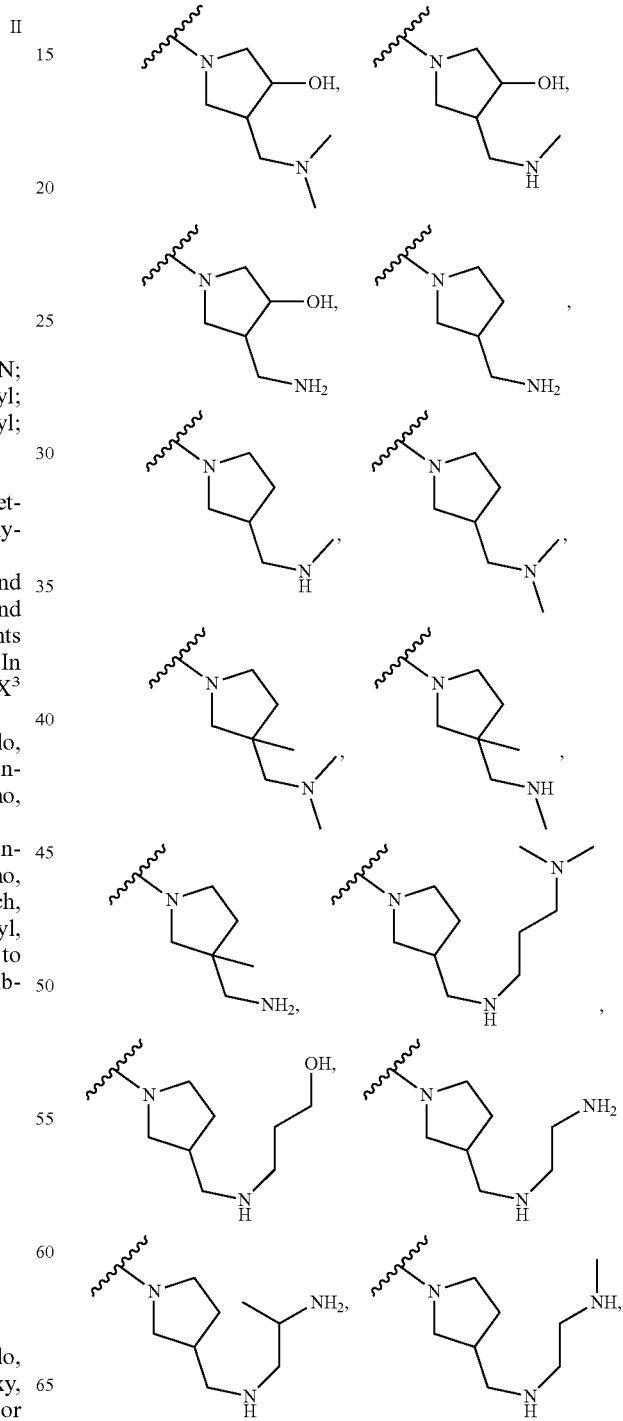

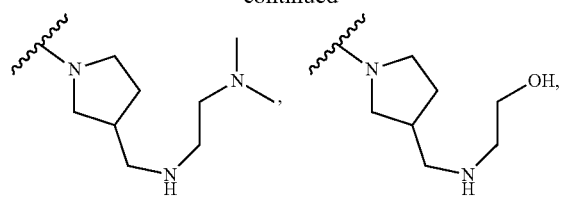
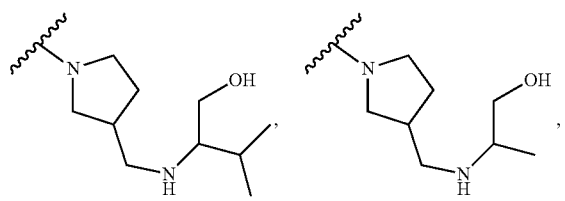
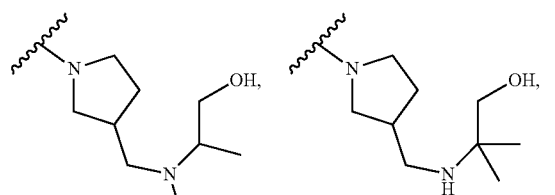
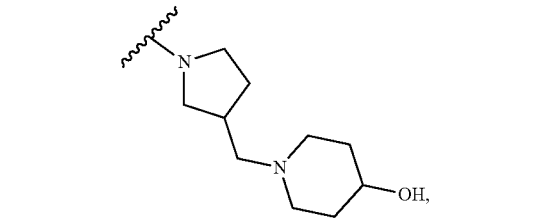
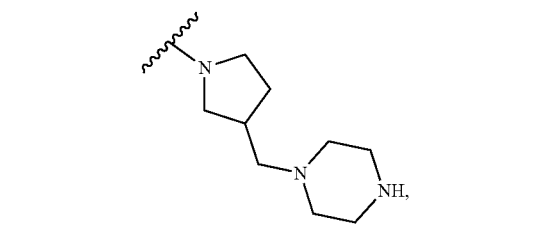
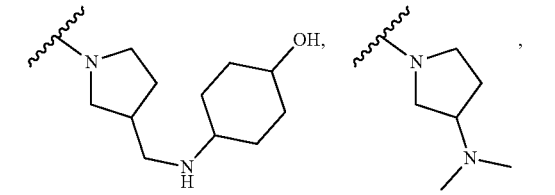
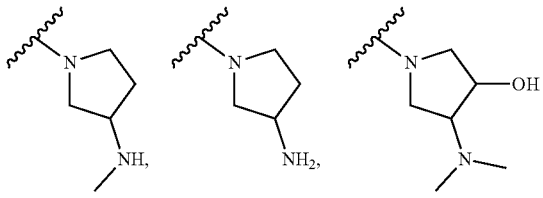
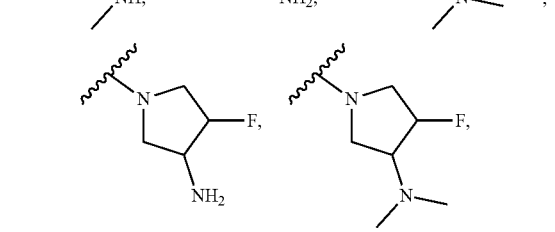
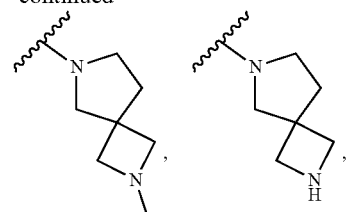
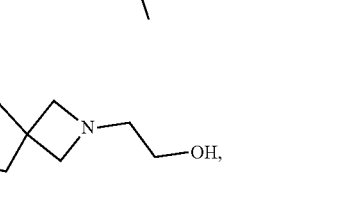
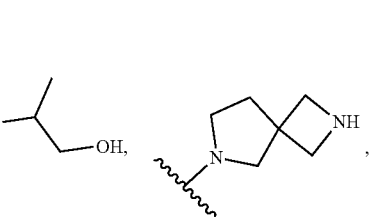
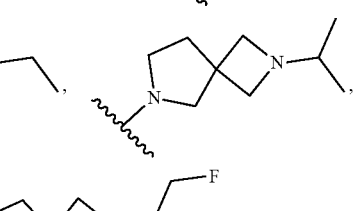
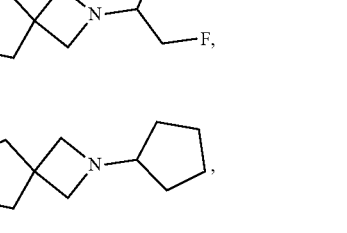
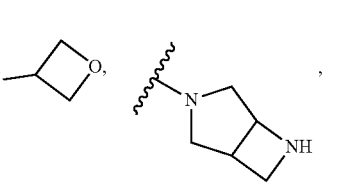
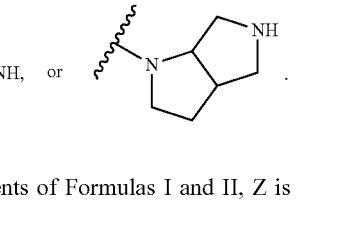
In certain embodiments of Formulas I and II, Z is
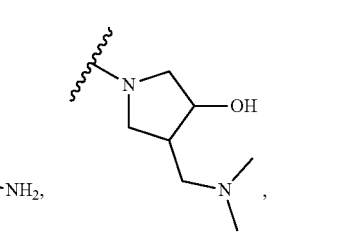

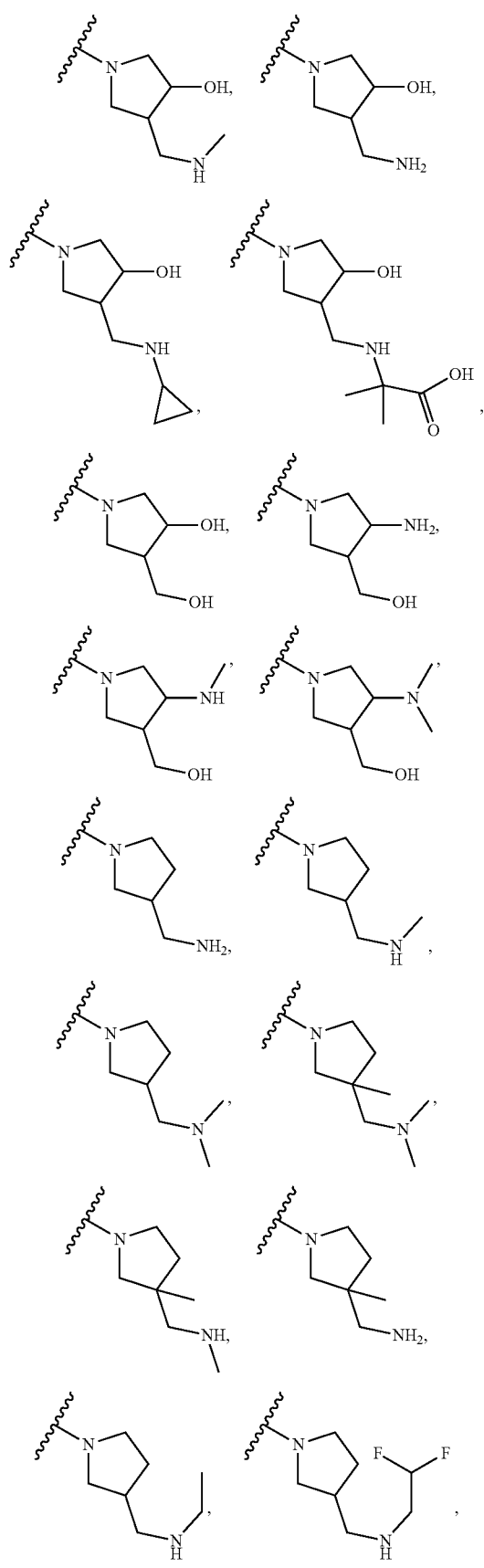
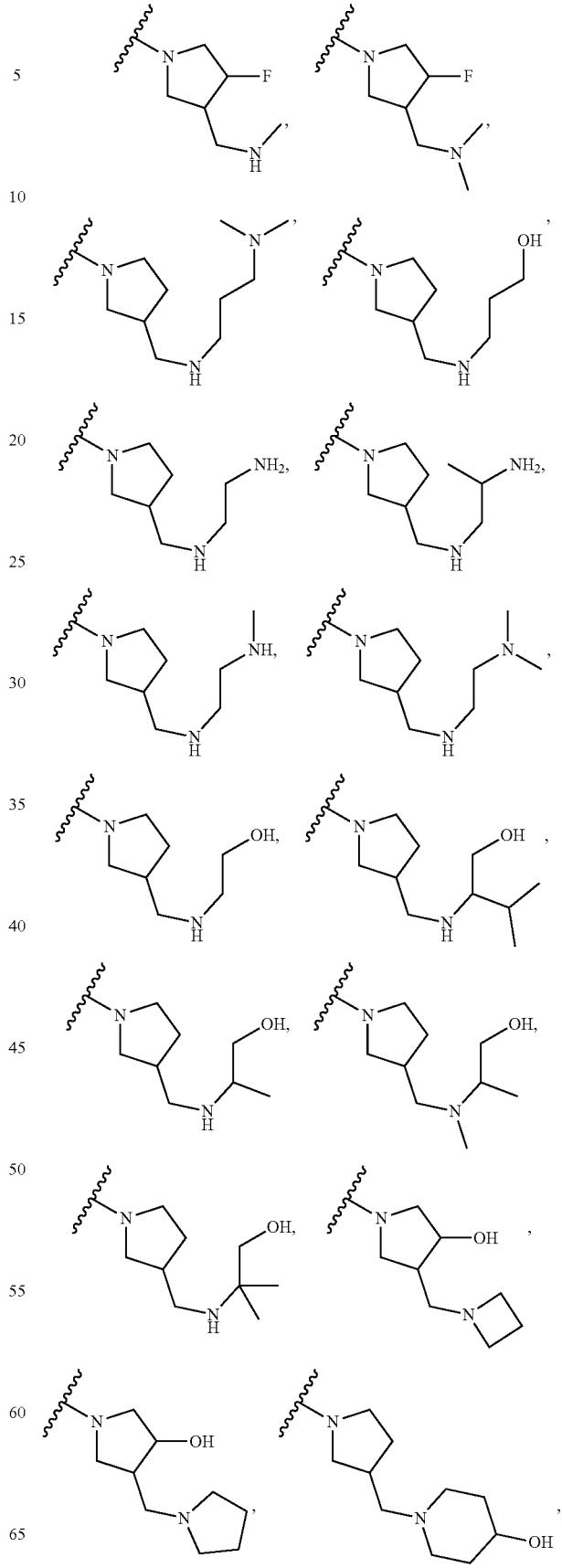

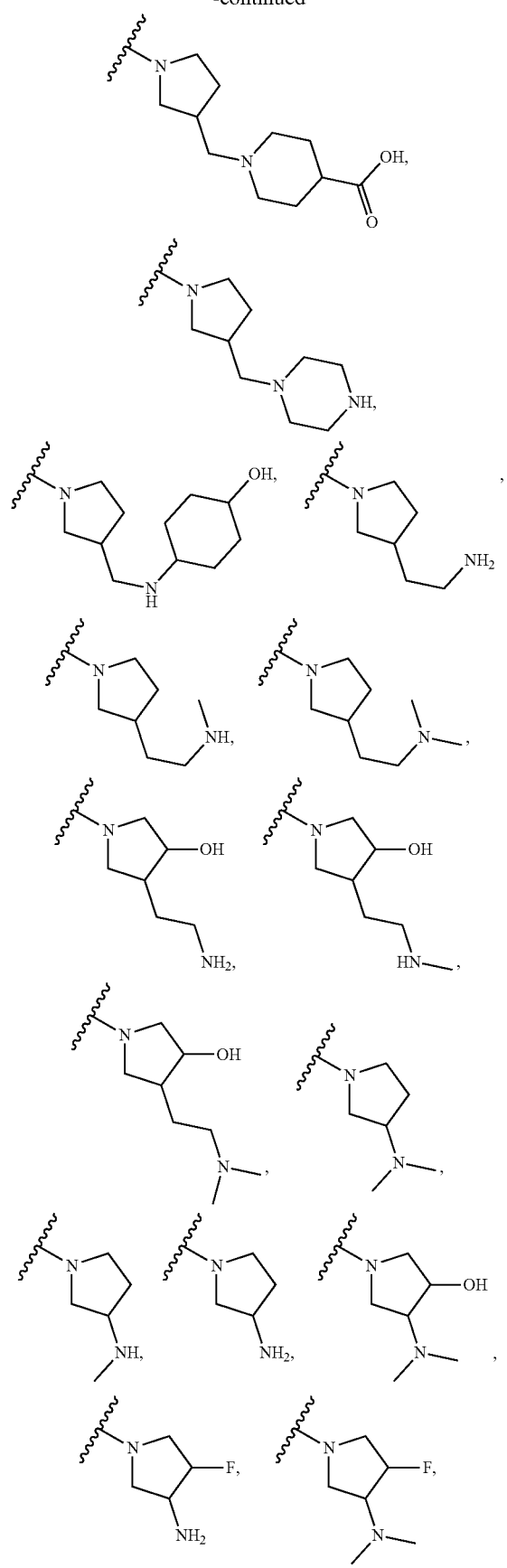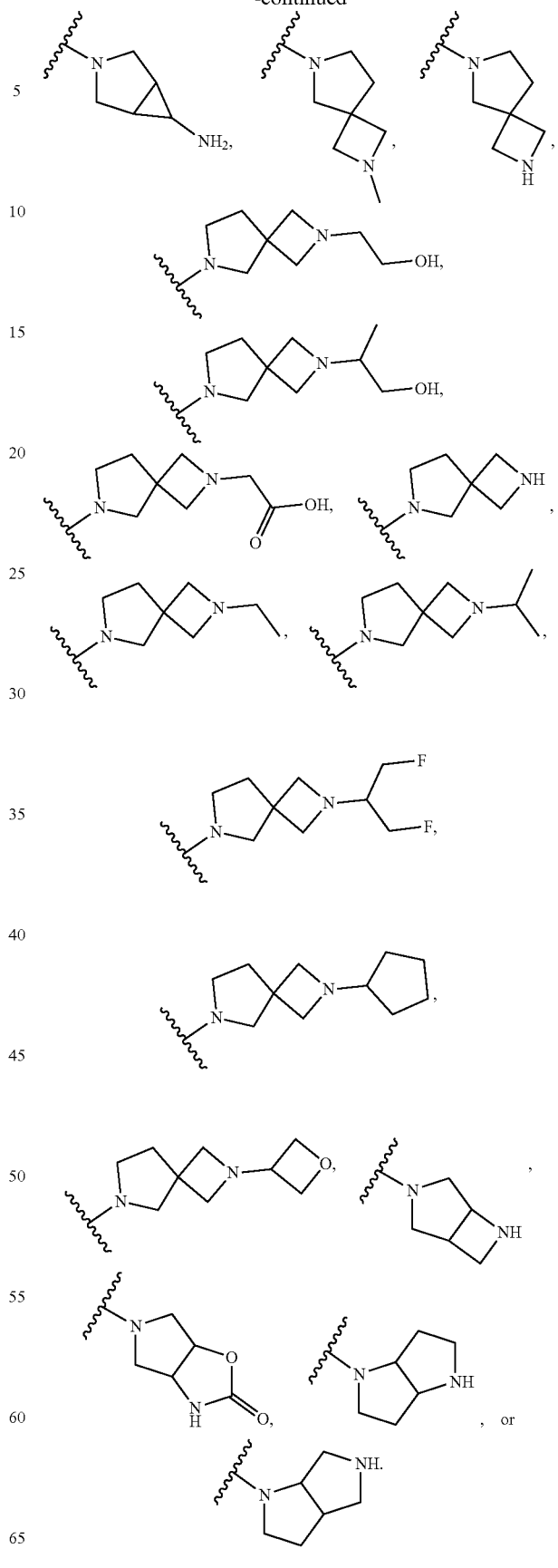

In certain embodiments of Formulas I and II, Z is

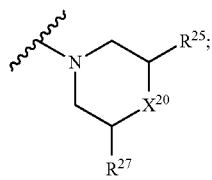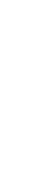

$X^{20}$ is $CR^{24}R^{26}$, NH, or O; and $R^{24}$, $R^{25}$, $R^{26}$, and $R^{27}$ are each independently H, amino, or optionally substituted alkyl, aminoalkyl, alkylaminoalkyl, alkylamino, cycloalkyl, or heterocycloalkyl; or $R^{24}$ and $R^{26}$ combine to form an optionally substituted 4-, 5-, or 6-membered ring. In some embodiments, the optionally substituted 4-, 5-, or 6-membered ring comprises a heteroatom. In some embodiments, the heteroatom is N.

In certain embodiments of Formulas I and II, Z is

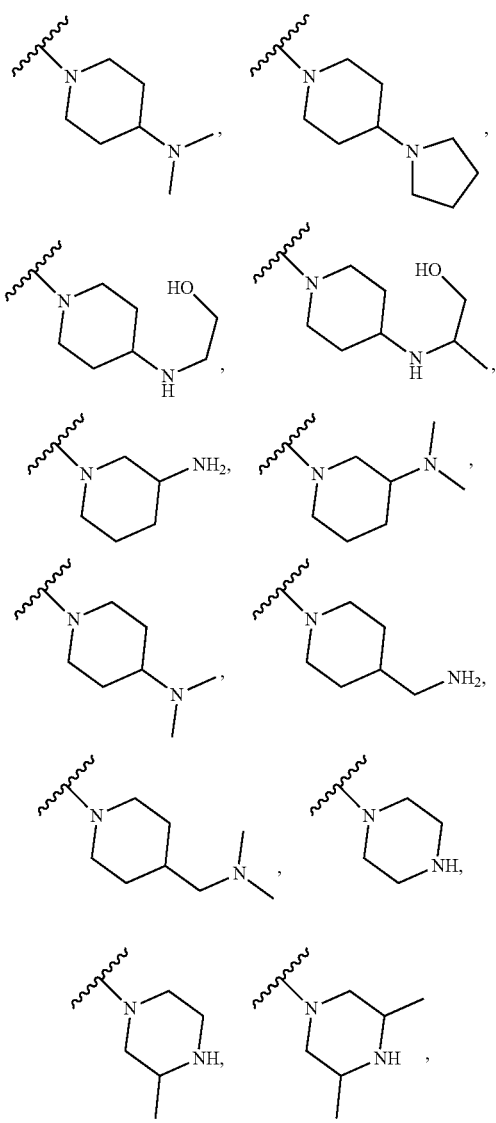

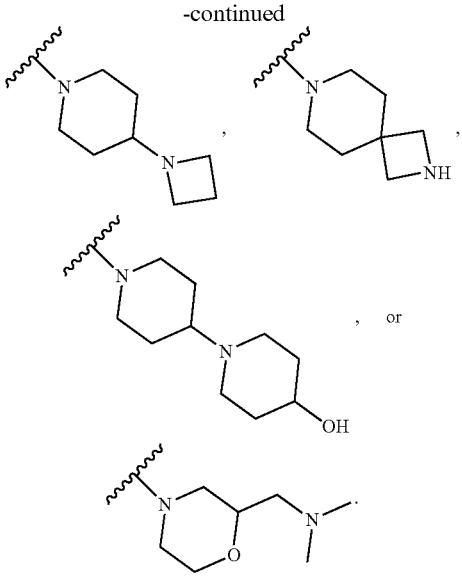

In certain embodiments of Formulas I and II, Z is and $R^{28}$ and $R^{29}$ are each independently H, amino, or optionally substituted alkyl, alkoxy, aminoalkyl, alkylaminoalkyl, alkylamino, cycloalkyl, or heterocycloalkyl; or $R^{28}$ and $R^{29}$ combine to form an optionally substituted 4-, 5-, or 6-membered ring. In some embodiments, the optionally substituted 4-, 5-, or 6-membered ring comprises a heteroatom. In some embodiments, the heteroatom is N.

In certain embodiments of Formulas I and II, Z is

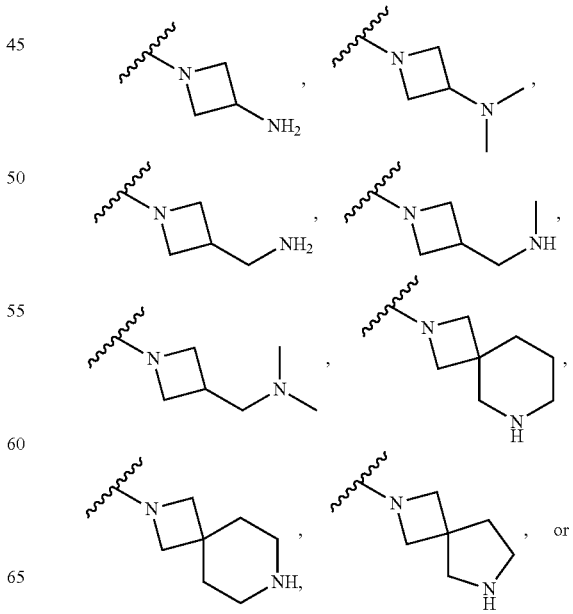

-continued

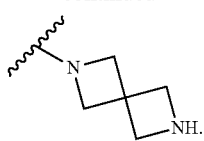

In certain embodiments of Formulas I and II, Z is

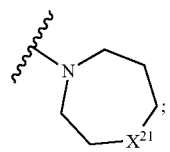

and $X^{21}$ is NH or O. In some embodiments, Z is

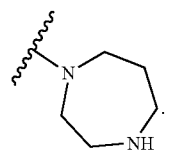 [SMILES: *N1CCCNCC1]

In certain embodiments of Formulas I and II, Z is optionally substituted alkylamino, cycloalkylamino, or heterocycloalkylamino.

In certain embodiments of Formulas I and II, Z is

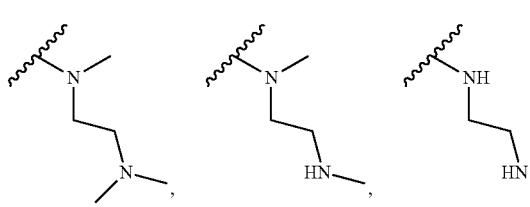

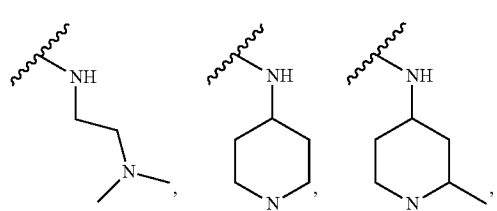

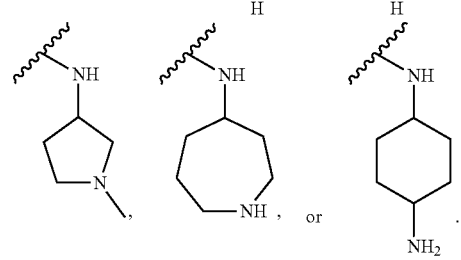

In certain embodiments of Formulas I and II, Z is

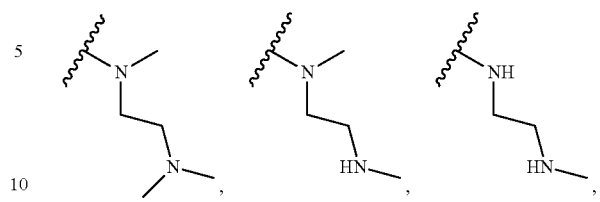

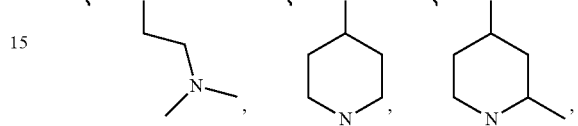

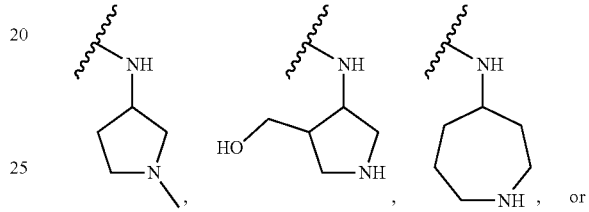

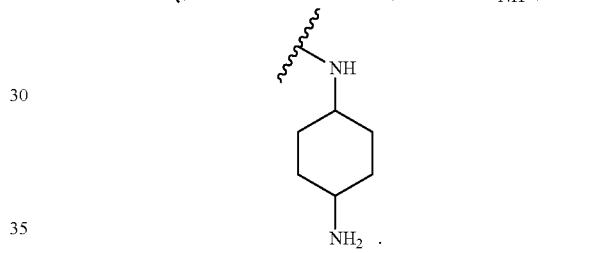

In certain embodiments of Formula I, $R^1$ is, independently for each occurrence, fluoro, chloro, —CN, —O—$R^{31}$, —OCF$_3$, —O—C(O)—NR$^{31}$R$^{32}$, or —C(O)—OR$^{31}$; and $R^{31}$ and $R^{32}$ are, independently for each occurrence, optionally substituted alkyl, alkenyl, alkynyl, cycloalkyl, (cycloalkyl)alkyl, aryl, or aralkyl. In certain preferred embodiments of Formula I, $R^1$ is fluoro or —CN.

In certain embodiments of Formula II, $R^{1a}$ and $R^{1b}$ are, independently for each occurrence, fluoro, chloro, —CN, —O—$R^{31}$, —OCF$_3$, —O—C(O)—NR$^{31}$R$^{32}$, or —C(O)—OR$^{31}$; and $R^{31}$ and $R^{32}$ are, independently for each occurrence, optionally substituted alkyl, alkenyl, alkynyl, cycloalkyl, (cycloalkyl)alkyl, aryl, or aralkyl. In certain preferred embodiments of Formula II, $R^{1a}$ and $R^{1b}$ are, independently for each occurrence, fluoro or —CN.

In certain embodiments of Formulas I and II, $R^2$ is —C(O)—OR$^{41}$; and $R^{41}$ is optionally substituted alkyl, alkenyl, alkynyl, cycloalkyl, (cycloalkyl)alkyl, aryl, or aralkyl. In some embodiments, $R^2$ is H or chloro.

In certain embodiments of Formula I, $R^3$ is optionally substituted $C_{1-6}$alkyl or $C_{3-6}$cycloalkyl, preferably cyclopropyl In some embodiments of Formula I, $R^3$ is H.

In certain embodiments of Formulas I and II, $R^5$ is optionally substituted alkyl, —O—C(O)—NR$^{61}$R$^{62}$ or —C(O)—OR$^{61}$; $R^{61}$ and $R^{62}$ are, independently for each occurrence, optionally substituted alkyl, alkenyl, alkynyl, cycloalkyl, (cycloalkyl)alkyl, aryl, or aralkyl.

In certain embodiments of Formulas I and II, $R^7$ is —O—C(O)—NR$^{71}_2$ or —C(O)—OR$^{71}$; and $R^{71}$ is optionally substituted alkyl, alkenyl, alkynyl, cycloalkyl, (cycloalkyl)alkyl, aryl, or aralkyl.

In certain embodiments of Formula I, n is 0, 1 or 2.

In certain embodiments, compounds of the invention may be prodrugs of the compounds of Formula I or Formula II, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, as will be described in detail below, the present invention relates to methods of treating or preventing cancer or an inflammatory disorder with a compound of Formula I or Formula II, or a pharmaceutically acceptable salt thereof. In certain embodiments, the therapeutic preparation may be enriched to provide predominantly one enantiomer of a compound (e.g., of Formula I or II). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of Formula I or II). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient in the treatment of cancer an inflammatory disorder, comprising an effective amount of any compound of Formula I or Formula II, and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Exemplary compounds of Formula I and Formula II are depicted in the examples. The compounds disclosed in the examples are understood to encompass both the free base and the conjugate acid. For example, the compounds in the examples may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

II. Uses of MK2 Inhibitors

In certain aspects, the invention provides methods of treating cancer, comprising administering to a subject a compound of Formula I or Formula II, e.g., in a therapeutically effective amount.

In certain embodiments, the cancer may be one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioblastoma, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Chronic Myeloid Leukemia (CML), Acute Myelogenous Leukemia (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Retinoblastoma, Rhabdomyosarcoma, Salivary Gland Cancer, Sarcoma (such as Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor.

In certain embodiments, the cancer is a KRAS- or BRAF-dependent cancer.

In certain embodiments, the cancer is a solid tumor. The subject is generally one who has been diagnosed as having a cancerous tumor or one who has been previously treated for a cancerous tumor (e.g., where the tumor has been previously removed by surgery). The cancerous tumor may be a primary tumor and/or a secondary (e.g., metastatic) tumor.

In certain embodiments, the subject is a mammal, e.g., a human.

In certain embodiments, the cancer is associated with tissue of the bladder, bone marrow, breast, colon, kidney, liver, lung, ovary, pancreas, prostate, skin or thyroid.

In certain embodiments, the method of treating cancer further comprises conjointly administering radiation therapy.

In some embodiments, the method of treating cancer further comprises conjointly administering one or more additional chemotherapeutic agents.

Chemotherapeutic agents that may be conjointly administered with compounds of the invention include: ABT-263, aminoglutethimide, amsacrine, anastrozole, asparaginase, AZD5363, *Bacillus* Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil and 5-fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, LY2603618, mechlorethamine, medroxyprogesterone, megestrol, melphalan, mercaptopurine, mesna, metformin, methotrexate, miltefosine, mitomycin, mitotane, mitoxantrone, MK2206, nilutamide, nocodazole, octreotide, oxaliplatin, paclitaxel, pamidronate, pentostatin, pazopanib, perifosine, PF-04691502, PF477736, plicamycin, pomalidomide, porfimer, procarbazine, raltitrexed, rituximab, romidepsin, selumetinib, sorafenib, streptozocin, sunitinib, suramin, tamoxifen, temozolomide, temsirolimus, teniposide, testosterone, thalidomide, thioguanine, thiotepa, titanocene dichloride, topotecan, trametinib, trastuzumab, tretinoin, vinblastine, vincristine, vindesine, vinorelbine, and vorinostat (SAHA). For example, chemotherapeutic agents that may be conjointly administered with compounds of the invention include: aminoglutethimide, amsacrine, anastrozole, asparaginase, bcg, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, pomalidomide, porfimer, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, and vinorelbine. In certain embodiments, the chemotherapeutic agent is cisplatin. In certain embodiments, the additional chemotherapeutic agent is an CHK1 inhibitor.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP (B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |

TABLE 1-continued

Exemplary combinatorial therapies for the treatment of cancer.

| Name | Therapeutic agents |
|---|---|
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |

TABLE 1-continued

Exemplary combinatorial therapies for the treatment of cancer.

| Name | Therapeutic agents |
|---|---|
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In some embodiments, the conjointly administered chemotherapeutic agent is an immune-oncology therapeutic, such as an inhibitor of CTLA-4, indoleamine 2,3-dioxygenase, and/or PD-1/PD-L1.

In certain embodiments, conjoint administration of the MK2 inhibitor(s) of Formula I or Formula II with one or more additional therapeutic agent(s) (e.g., one or more additional chemotherapeutic agent(s)) provides improved efficacy relative to each individual administration of the MK2 inhibitor (e.g., a compound of Formula I or II) or the one or more additional therapeutic agent(s). In certain such embodiments, the conjoint administration provides an additive effect, wherein an additive effect refers to the sum of each of the effects of individual administration of the MK2 inhibitor and the one or more additional therapeutic agent(s). In certain embodiments, coadministration produces a synergistic effect.

In certain embodiments, the MK2 inhibitor and the one or more additional chemotherapeutic agents are administered simultaneously. In alternative embodiments, the one or more additional chemotherapeutic agents are administered within about 5 minutes to within about 168 hours prior to or after administration of the MK2 inhibitor.

In certain embodiments, the invention provides methods of inhibiting proliferation of a cancerous cell comprising contacting a cancerous cell with an effective amount of a compound of Formula I or Formula II.

The invention also provides methods of inhibiting MK2 activity in a cell, comprising contacting a cell with a compound of Formula I or Formula II. In certain embodiments, the cell is a cancer cell. Such methods may be performed in vivo or in vitro.

The invention also provides a method of treating or preventing a metabolic disorder, comprising administering to a subject a compound of Formula I or II. In certain embodiments, the metabolic disorder is diabetes, insulin resistance, obesity, or metabolic syndrome. In some embodiments, the diabetes is Type I, Type II, or gestational diabetes. In some embodiments, the treating or preventing affects glycogenolysis or gluceoneogensis in the subject. In some embodiments, the treating or preventing reduces hepatic glucose production, hyperglycemis, fatty liver, insulin resistance, insulin-resistance-associated inflammation, insuling resistance-associated dyslipidemia, or any combination thereof, in the subject.

In certain embodiments, e.g., of methods of treating diabetes, the method further comprises conjointly administering one or more additional antidiabetic agents. Antidiabetic agents that may be conjointly administered with compounds of the invention include, but not limited to, sulfonylurea, biguanides, alpha-glucosidase inhibitors, thiazolidinediones (TZDs), dipeptidyl peptidase-inhibitors (DPP-4 inhibitors), nonsulfonylurea insulin secretagogues, glucagon-like peptide-1 analogs (GLP-1 analogs) and insulin. More specifically, the antidiabetic drugs include, but are not limited to metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, dutogliptin, repaglinide, nateglinide, mitiglindine, exenatide, liraglutide, albiglutide and insulin.

III. Pharmaceutical Compositions

In certain embodiments, the present invention provides pharmaceutical compositions comprising a compound of Formula I or II and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I or Formula II. As another example, the salt may comprise less than one inorganic or organic acid molecule per molecule of base, such as two molecules of compound of Formula I or Formula II per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

IV. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. C0 alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

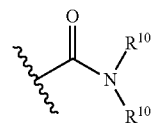

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

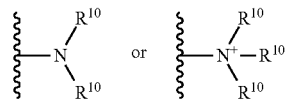

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

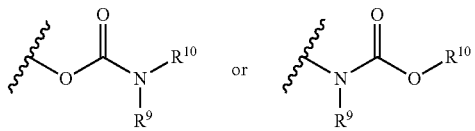

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a ═O or ═S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a ═O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

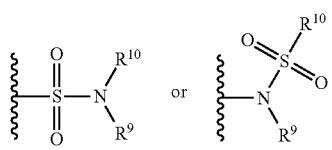

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

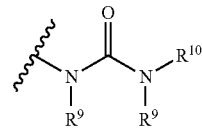

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The term "MK2-related disorder" is a disorder or condition that MK2 plays a role in the morbidity or symptoms of the disease or disorder. For example, an MK2-related disorder includes, but is not limited to, inflammatory diseases, autoimmune diseases, destructive bone disorders, proliferative disorders, angiogenic disorders, infectious diseases, neurodegenerative diseases, and viral diseases.

As used herein, the term "inflammatory disorder" or "inflammatory disease" includes diseases and disorders that are caused or primarily caused by inflammation, as well as diseases and disorders in which inflammation plays a role in the morbidity or symptoms of the disease or disorder, the propagation of the disease or disorder, the worsening of symptoms of a disease or disorder and/or the worsening of a patient's prognosis or survival time due to a disease or disorder.

EXAMPLES

Examples of compounds of Formula (I) or Formula (II) or pharmaceutically acceptable salts thereof having useful biological activity are are described below. The preparation of these compounds can be realized by one of skilled in the art of organic synthesis using known techniques and methodology.

A. Chemical Syntheses

The general procedures used in the methods to prepare the compounds of the present invention are described below.

Scheme 1

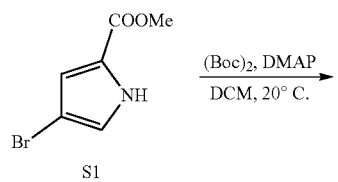

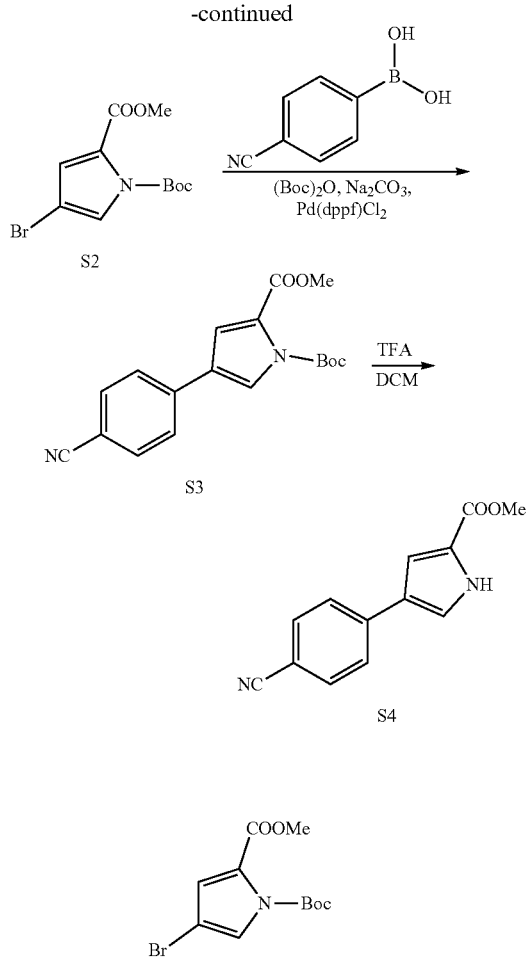

1-tert-butyl 2-methyl 4-bromo-1H-pyrrole-1, 2-dicarboxylate, S2. To a solution of methyl 4-bromo-1H-pyrrole-2-carboxylate (120 g, 588 mmol, 1.0 eq.) in MeCN (1200 mL) was added DMAP (7.2 g, 58 mmol, 0.1 eq.) followed by (Boc)$_2$O (141 g, 647 mmol, 1.1 eq.) at 0° C. The mixture was stirred at 25° C. for 2 hr. The mixture was concentrated and the residue was dissolved in ethyl acetate (2.0 L). The solution was washed with ice 1M HCl (200 mL*2), sat.aq.NaHCO$_3$ (200 mL) and brine (100 mL). The organic phase was dried over anhydrous Na$_2$SO$_4$, filtered and concentrated in vacuum to give crude 1-tert-butyl 2-methyl 4-bromo-1H-pyrrole-1,2-dicarboxylate (174 g) as a yellow oil, which was used into the next step without further purification. TLC: R$_f$=0.77 (Petroleum ether: Ethyl acetate=5:1). 1H NMR (400 MHz, CHLOROFORM-d) δ=7.29 (d, J=1.8 Hz, 1H), 6.77 (d, J=1.3 Hz, 1H), 3.82 (s, 3H), 1.56 (s, 9H).

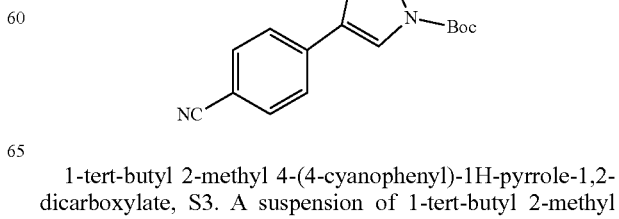

1-tert-butyl 2-methyl 4-(4-cyanophenyl)-1H-pyrrole-1,2-dicarboxylate, S3. A suspension of 1-tert-butyl 2-methyl 4-bromo-1H-pyrrole-1,2-dicarboxylate (131 g, 432 mmol, 1.0 eq.), (4-cyanophenyl)boronic acid (95.3 g, 648.5 mmol, 1.5 eq.), $Na_2CO_3$ (91 g, 864 mmol, 2.0 eq) and $(Boc)_2O$ (141 g, 648 mmol, 1.5 eq.), $Pd(dppf)Cl_2$ (15.8 g, 21.6 mmol, 0.05 eq.) in dioxane/$H_2O$ (4.9 L, 10:1) was de-gassed and then heated to 80~100° C. for 12 hr under $N_2$. The mixture was concentrated under reduced pressure and the residue was portioned between Ethyl acetate (3.0 L) and brine (500 mL). The organic layer was dried over anhydrous $Na_2SO_4$, filtered and concentrated to give crude 1-tert-butyl 2-methyl 4-(4-cyanophenyl)-1H-pyrrole-1,2-dicarboxylate (150 g) as a yellow oil which was used into the next step without further purification. ESI [M+H]=327.2

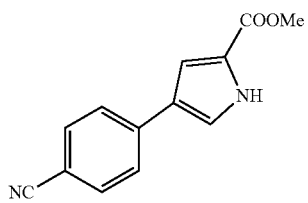 [SMILES: COC(=O)c1cc(-c2ccc(C#N)cc2)c[nH]1]

Methyl 4-(4-cyanophenyl)-1H-pyrrole-2-carboxylate, S4. A solution of 1-tert-butyl 2-methyl 4-(4-cyanophenyl)-1H-pyrrole-1,2-dicarboxylate (150 g, crude) in TFA (500 mL) was stirred for 2 hr at 50° C. The solution was concentrated under reduced pressure. The residue was added MeOH (300 mL) and stirred for 1 hr. The precipitate was collected by filtration to give methyl 4-(4-cyanophenyl)-1H-pyrrole-2-carboxylate (80 g, 353 mmol) as a white solid. 1H NMR (400 MHz, DMSO-d6) δ=12.30 (br. s., 1H), 7.84 (d, J=8.4 Hz, 2H), 7.79-7.69 (m, 3H), 7.33 (br. s., 1H), 3.80 (s, 3H). ESI [M+H]=227.1

Scheme 2

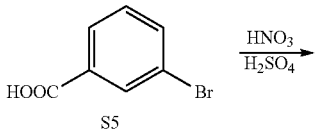

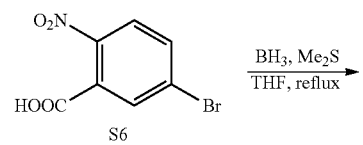

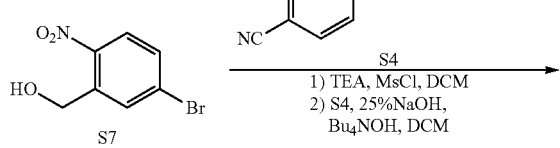

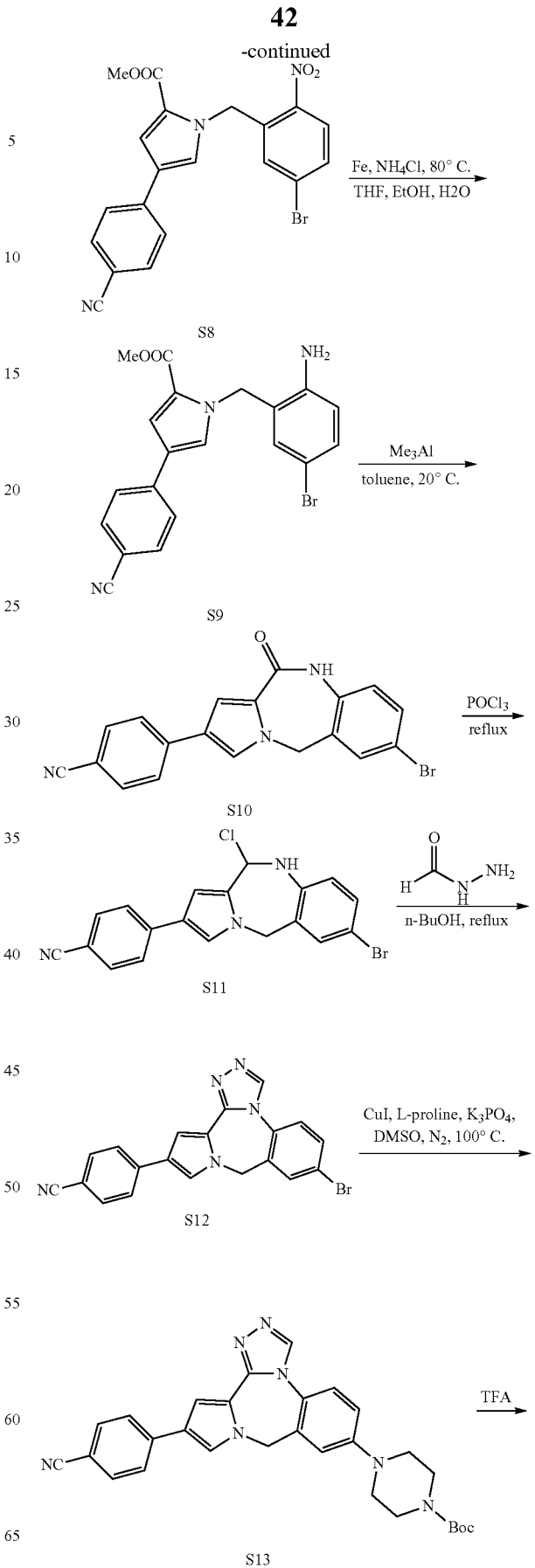

-continued

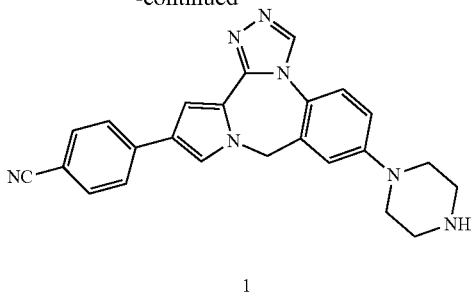

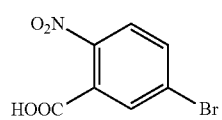

5-bromo-2-nitrobenzoic acid, S6. A suspension of 3-bromobenzoic acid (249 g, 1.24 mol, 1.0 eq.) in conc.sulfuric acid (800 mL) was cooled at 0° C. Conc. nitric acid (57.1 mL, 1.2 mol) was added dropwise and the mixture was warmed to 20° C. and stirred 1 hr. The mixture was poured into poured into ice-water (2 L). The precipitate was collected by filtration, washed with water (1000 mL*2) and dried to give 5-bromo-2-nitrobenzoic acid (280 g, 1.14 mol, 91.94% yield) as a white solid. 1H NMR (400 MHz, DMSO-d6) δ=14.12 (br. s., 1H), 8.00 (d, J=1.8 Hz, 1H), 7.98-7.90 (m, 2H).

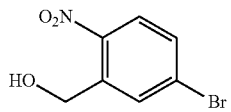 [SMILES: O=[N+]([O-])c1ccc(Br)cc1CO]

(5-bromo-2-nitrophenyl)methanol, S7. To a solution of 5-bromo-2-nitrobenzoic acid (280 g, 1.14 mol, 1.0 eq.) in THF (1.5 L) was added 10 M solution of $BH_3\text{-}Me_2S$ in THF (119.7 mL, 1.05 eq.) dropwise over 30 minutes. After addition, the mixture was heated to 70° C. for 3 hr. The mixture was cooled to 0° C., quenched by MeOH (100 mL) slowly and then concentrated in vacuum. The residue was added Petroleum ether/ethyl acetate (1000 mL, 10:1) and stirred for 1 hr. The precipitate was collected by filtration to give (5-bromo-2-nitrophenyl)methanol (160 g, 689 mmol, 60.49% yield) as a white solid. 1H NMR (400 MHz, CHLOROFORM-d) δ=7.98-7.91 (m, 2H), 7.55 (dd, J=1.8, 8.8 Hz, 1H), 4.97 (br. s., 2H), 2.77 (br. s., 1H). ESI [M+H]=232.2/234.2

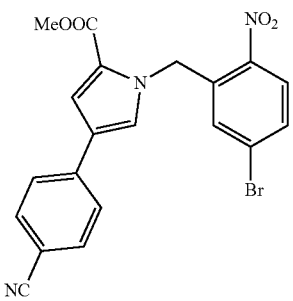 [SMILES: COC(=O)c1cc(-c2ccc(C#N)cc2)cn1Cc1cc(Br)ccc1[N+](=O)[O-]]

Methyl 1-(5-bromo-2-nitrobenzyl)-4-(4-cyanophenyl)-1H-pyrrole-2-carboxylate, S8. To a solution of (5-bromo-2-nitrophenyl)methanol (80 g, 344 mmol, 1.0 eq.) and TEA (48.8 g, 482 mmol, 1.40 eq.) in DCM (1.5 L) was added MsCl (41.4 g, 362 mmol, 1.05 eq.) at 0° C. and the mixture was stirred for 0.5 hr at 20° C. Then methyl 4-(4-cyanophenyl)-1H-pyrrole-2-carboxylate (74.1 g, 327 mmol, 0.95 eq.) was added to the solution followed by tetrabutylammoniumhydroxide (35.8 g, 34.5 mmol, 0.1 eq.) and a solution of NaOH (69 g, 1724 mmol, 5.0 eq) in $H_2O$ (210 mL) at 0° C. The mixture was stirred for 10 hr at 20° C. and then diluted with ice-water (500 mL) and DCM (2000 mL). The organic layer was separated, dried over anhydrous $Na_2SO_4$, filtered and concentrated. The residue was added EtOH (200 mL) and stirred for 1 hr. The precipitate was collected by filtration to give methyl 1-(5-bromo-2-nitrobenzyl)-4-(4-cyanophenyl)-1H-pyrrole-2-carboxylate (127 g, 239 mmol, 69.3% yield) as a off-white solid. TLC: $R_f$=0.32 (Petroleum ether: Ethyl acetate=4:1). 1H NMR (400 MHz, DMSO-d6) δ=8.08 (d, J=8.8 Hz, 1H), 8.00 (d, J=1.8 Hz, 1H), 7.84-7.76 (m, 5H), 7.55 (d, J=1.8 Hz, 1H), 6.71 (d, J=1.3 Hz, 1H), 5.86 (s, 2H), 3.29 (s, 3H). ESI [M+H]=440.1/442.1

Methyl 1-(2-amino-5-bromobenzyl)-4-(4-cyanophenyl)-1H-pyrrole-2-carboxylate, S9. A suspension of methyl 1-(5-bromo-2-nitrobenzyl)-4-(4-cyanophenyl)-1H-pyrrole-2-carboxylate (125 g, 284 mmol, 1.00 eq.), Fe (79 g, 1420 mmol, 5.0 eq.) and $NH_4Cl$ (76 g, 1420 mmol, 5.0 eq.) in EtOH (800 mL), $H_2O$ (400 mL) and THF (800 mL) was heated to 80° C. for 2 hr. The mixture was concentrated to dryness and the residue was added hot THF (5.0 L). The mixture was filtered and the filtrate was concentrated. The residue was added EtOH (300 mL) and stirred for 1 hr. The precipitated was collected by filtration to give methyl 1-(2-amino-5-bromobenzyl)-4-(4-cyanophenyl)-1H-pyrrole-2-carboxylate (106 g, 242 mmol, 85.54% yield) as a yellow solid. 1H NMR (400 MHz, DMSO-d6) δ=7.88 (br. s., 1H), 7.85-7.68 (m, 4H), 7.50 (br. s., 1H), 7.09 (d, J=7.9 Hz, 1H), 6.62 (d, J=8.4 Hz, 1H), 6.33 (br. s., 1H), 5.37 (br. s., 4H), 3.73 (br. s., 3H). ESI [M+H]=410.2/412.2

4-(7-bromo-11-oxo-10,11-dihydro-5H-benzo[e]pyrrolo[1,2-a][1,4]diazepin-2-yl)benzonitrile, S10. To a suspension of methyl 1-(2-amino-5-bromobenzyl)-4-(4-cyanophenyl)-

1H-pyrrole-2-carboxylate (105 g, 256 mmol, 1.0 eq.) in toluene (1.5 L) was added Me₃Al (2 M in toluene, 500 mL, 3.9 eq.) at 0° C. and the mixture was stirred for 10 hr at 20° C. The mixture was poured into 1M ice-HCl (300 mL) and extracted with hot EtOAc/THF(1:1, 500 mL*4). The organic layer was dried over anhydrous Na₂SO₄, filtered and concentrated. The residue was added EtOH (100 mL) and stirred for 1 hr. The precipitate was collected by filtration to give 4-(7-bromo-11-oxo-10,11-dihydro-5H-benzo[e]pyrrolo[1,2-a][1,4]diazepin-2-yl)benzonitrile (86 g, 166 mmol, 65% yield) as a white solid. 1H NMR (400 MHz, DMSO-d6) δ=10.30 (s, 1H), 7.73 (s, 4H), 7.66 (dd, J=2.0, 4.2 Hz, 2H), 7.50 (dd, J=2.2, 8.4 Hz, 1H), 7.27 (d, J=1.8 Hz, 1H), 7.13 (d, J=8.8 Hz, 1H), 5.21 (s, 2H). ESI [M+H]=378.2/380.2

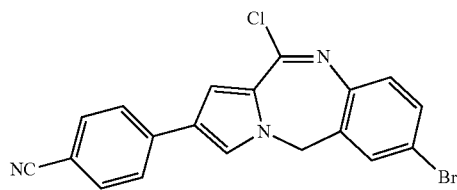 [SMILES: N#Cc1ccc(-c2cc3n(c2)Cc2cc(Br)ccc2N=C3Cl)cc1]

4-(7-bromo-11-chloro-5H-benzo[e]pyrrolo[1,2-a][1,4]diazepin-2-yl)benzonitrile, S11. A solution of 4-(7-bromo-11-oxo-10, 11-dihydro-5H-benzo[e]pyrrolo[1,2-a][1,4]diazepin-2-yl) benzonitrile (6.2 g, 16 mol, 1.0 eq.) in POCl₃ (100 mL) was stirred for 2 hr at 100° C. The solution was concentrated under reduced pressure to give crude 4-(7-bromo-11-chloro-5H-benzo[e]pyrrolo[1,2-a][1,4]diazepin-2-yl)benzonitrile (16 g, crude) as a black brown oil, which was used into the next step without further purification.

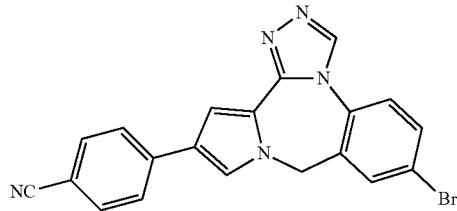 [SMILES: N#Cc1ccc(-c2cc3n(c2)Cc2cc(Br)ccc2-n2cnnc2-3)cc1]

4-(7-bromo-9H-benzo[e]pyrrolo[1,2-a][1,2,4]triazolo[3,4-c][1,4]diazepin-12-yl)benzonitrile, S12. To a solution of 4-(7-bromo-11-chloro-5H-benzo[e]pyrrolo[1,2-a][1,4]diazepin-2-yl) benzonitrile (2 g, 4.4 mmol, 1 eq.) in THF/dioxane (1:1, 40 mL) was added TEA to adjust pH=7. Then formohydrazide (8 g, 133 mmol, 30.0 eq.) was added and the mixture was heated to 120° C. for 10 hr in sealing tube. The mixture was concentrated to dryness and the residue was dissolved in hot EtOAc/THF(1:1, 2.0 L). The solution was washed with ice 1M HCl (100 mL*2), sat.aq. NaHCO₃ (100 mL) and brine (100 mL). The organic phase was dried over anhydrous Na₂SO₄, filtered and concentrated in vacuum. The residue was added MeOH (10 mL) and stirred for 1 hr. The precipitate was collected by filtration to give 4-(7-bromo-9H-benzo[e]pyrrolo[1,2-a][1,2,4] triazolo[3,4-c][1,4]diazepin-12-yl)benzonitrile (900 mg, 2.2 mmol, 50.4% yield) as a yellow solid. 1H NMR (400 MHz, DMSO-d6) δ=9.25 (s, 1H), 7.97 (br. s., 1H), 7.82-7.76 (m, 6H), 7.70 (d, J=8.5 Hz, 1H), 7.28 (s, 1H), 5.33 (s, 2H). ESI [M+H]=402.1/404.1

General Procedure A—Ullmann Reaction.

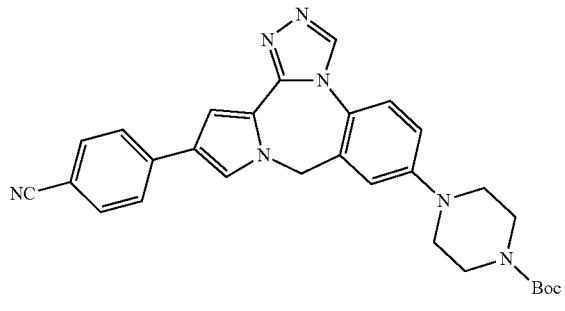 [SMILES: CC(C)(C)OC(=O)N1CCN(c2ccc3c(c2)Cn2cc(-c4ccc(C#N)cc4)cc2-c2nncn2-3)CC1]

Tert-butyl-4-(12-(4-cyanophenyl)-9H-benzo[e]pyrrolo[1,2-a][1,2,4]triazolo[3,4-c][1,4]diazepin-7-yl)piperazine-1-carboxylate, S13. A mixture of 4-(7-bromo-9H-benzo[e]pyrrolo[1,2-a][1,2,4]triazolo[3,4-c][1,4]diazepin-12-yl)benzonitrile (30.0 mg, 74 umol, 1.0 eq.), tert-butyl piperazine-1-carboxylate (41 mg, 223 umol, 3.0 eq.), K₃PO₄ (47 mg, 223 umol, 3.0 eq.), L-proline (4.2 mg, 37.2 umol, 0.5 eq.) and CuI (14 mg, 74 umol, 1.0 eq.) in DMSO (2 mL) was de-gassed and stirred at 100° C. for 12 hr under N₂. The mixture was diluted with ethyl acetate/THF (2:1, 20 mL) and filtered. The filtrate was washed with brine (5 mL), dried with anhydrous Na₂SO₄, filtered and concentrated to afford tert-butyl 4-(12-(4-cyanophenyl)-9H-benzo[e] pyrrolo[1,2-a][1,2,4]triazolo[3,4-c][1,4]diazepin-7-yl)piperazine-1-carboxylate (30 mg, crude) as a yellow solid, which was used into the next step without further purification. ESI [M+H]=508.2

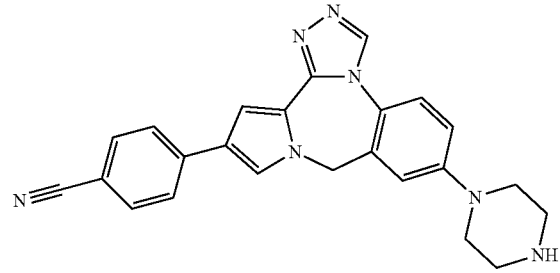 [SMILES: N#Cc1ccc(-c2cc3n(c2)Cc2cc(N4CCNCC4)ccc2-n2cnnc2-3)cc1]

4-(7-(piperazin-1-yl)-9H-benzo[e]pyrrolo[1,2-a][1,2,4]triazolo[3,4-c][1,4]diazepin-12-yl)benzonitrile, 1. To a solution of tert-butyl 4-(12-(4-cyanophenyl)-9H-benzo[e]pyrrolo[1,2-a][1,2,4]triazolo[3,4-c][1,4]diazepin-7-yl)piperazine-1-carboxylate (30 mg, 59.1 umol, 1.0 eq.) in CH₂Cl₂ (2 mL) was added CF₃COOH (2 mL) and the mixture was stirred at 40° C. for 30 min. The mixture was concentrated to dryness and the residue was purified by prep-HPLC to give 4-(7-(piperazin-1-yl)-9H-benzo[e]pyrrolo[1,2-a][1,2,4]triazolo[3,4-c][1,4]diazepin-12-yl)benzonitrile (15 mg, 27.9 umol, 47.2% yield) as yellow solid. 1H NMR (400 MHz, DMSO-d6) δ=9.13 (s, 1H), 8.85 (br. s., 2H), 7.80-7.68 (m, 5H), 7.57 (d, J=8.8 Hz, 1H), 7.24 (dd, J=2.0, 17.2 Hz, 2H), 7.14 (dd, J=2.4, 8.8 Hz, 1H), 5.21 (s, 2H), 3.23 (br. s., 4H), 2.52 (br. s., 4H). ESI [M+H]=408.1

Scheme 3

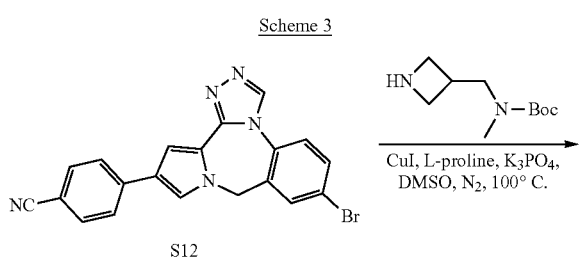

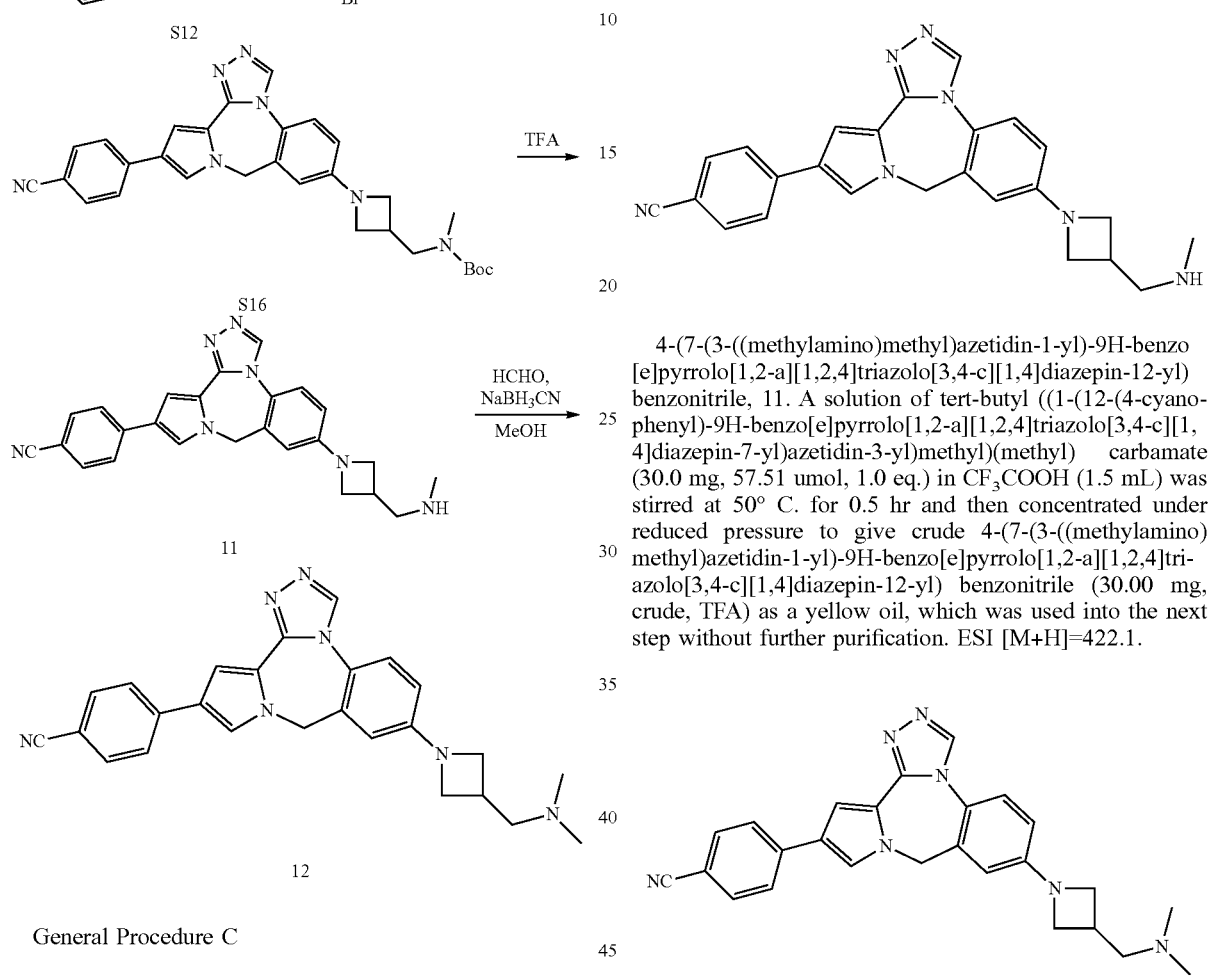

General Procedure C

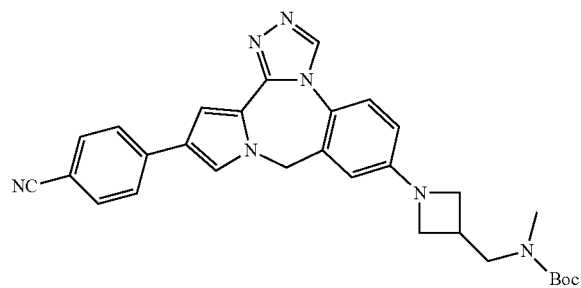 [SMILES: CN(CC1CN(c2ccc3c(c2)Cn2cc(-c4ccc(C#N)cc4)cc2-c2nncn2-3)C1)C(=O)OC(C)(C)C]

Tert-butyl ((1-(12-(4-cyanophenyl)-9H-benzo[e]pyrrolo[1,2-a][1,2,4]triazolo[3,4-c][1,4]diazepin-7-yl)azetidin-3-yl)methyl)(methyl)carbamate, S16. To a solution of 4-(7-bromo-9H-benzo[e]pyrrolo[1,2-a][1,2,4]triazolo[3,4-c][1,4]diazepin-12-yl)benzonitrile (25 mg, 62.1 umol, 1.0 eq.) in DMSO (2.0 mL) was added tert-butyl (azetidin-3-ylmethyl)(methyl)carbamate (17.6 mg, 74 umol, 1.2 eq., HCl), pyrrolidine-2-carboxylic acid (3.6 mg, 31 umol, 0.5 eq.), CuI (5.9 mg, 31 umol, 0.5 eq.) and $K_3PO_4$ (40 mg, 186 umol, 3.0 eq.). The mixture was stirred at 100° C. for 12 hr under $N_2$ and then filtered. The filtrate was concentrated and purified by prep-TLC ($SiO_2$, DCM: MeOH=20:1) to give tert-butyl ((1-(12-(4-cyanophenyl)-9H-benzo[e]pyrrolo[1,2-a][1,2,4]triazolo[3,4-c][1,4]diazepin-7-yl)azetidin-3-yl)methyl)(methyl) carbamate (30 mg, 34.5 umol, 55.5% yield, 60% purity) as a yellow oil, which was used into the next step without further purification. ESI [M+H]=522.3

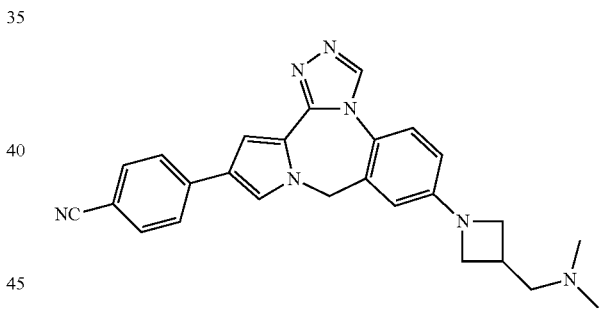

4-(7-(3-((methylamino)methyl)azetidin-1-yl)-9H-benzo[e]pyrrolo[1,2-a][1,2,4]triazolo[3,4-c][1,4]diazepin-12-yl)benzonitrile, 11. A solution of tert-butyl ((1-(12-(4-cyanophenyl)-9H-benzo[e]pyrrolo[1,2-a][1,2,4]triazolo[3,4-c][1,4]diazepin-7-yl)azetidin-3-yl)methyl)(methyl) carbamate (30.0 mg, 57.51 umol, 1.0 eq.) in $CF_3COOH$ (1.5 mL) was stirred at 50° C. for 0.5 hr and then concentrated under reduced pressure to give crude 4-(7-(3-((methylamino)methyl)azetidin-1-yl)-9H-benzo[e]pyrrolo[1,2-a][1,2,4]triazolo[3,4-c][1,4]diazepin-12-yl) benzonitrile (30.00 mg, crude, TFA) as a yellow oil, which was used into the next step without further purification. ESI [M+H]=422.1.

4-(7-(3-((dimethylamino)methyl)azetidin-1-yl)-9H-benzo[e]pyrrolo[1,2-a][1,2,4]triazolo[3,4-c][1,4]diazepin-12-yl)benzonitrile, 12. To a solution of 4-(7-(3-((methylamino) methyl)azetidin-1-yl)-9H-benzo[e]pyrrolo[1,2-a][1,2,4]triazolo[3,4-c][1,4]diazepin-12-yl)benzonitrile (30.0 mg, 71.17 umol, 1.0 eq.) in MeOH (2.0 mL) was added HCHO (57.7 mg, 711.7 umol, 10.0 eq.) and the mixture was stirred at 15° C. for 2 hr. Then $NaBH_3CN$ (6.71 mg, 106.7 umol, 1.5 eq.) was added and the mixture stirred at 15° C. for 14 hr. The mixture was concentrated under reduced pressure and purified by prep-HPLC to give 4-(7-(3-((dimethyl amino)methyl) azetidin-1-yl)-9H-benzo[e]pyrrolo[1,2-a][1,2,4]triazolo[3,4-c][1,4]diazepin-12-yl)benzonitrile (6.0 mg, 13.6 umol, 19.1% yield, 99% purity) as a white solid. 1HNMR (400 MHz, METHANOL-d4) δ=9.12 (br. s., 1H), 7.78-7.62 (m, 5H), 7.51 (d, J=8.7 Hz, 1H), 7.25 (br. s., 1H), 6.71 (d, J=2.4 Hz, 1H), 6.61 (dd, J=2.4, 8.7 Hz, 1H), 5.17 (s, 2H), 4.21 (t, J=7.8 Hz, 2H), 3.82-3.74 (m, 2H), 3.54 (d, J=7.3 Hz, 2H), 3.29-3.23 (m, 1H), 2.95 (s, 6H). ESI [M+H]=436.2

Scheme 5

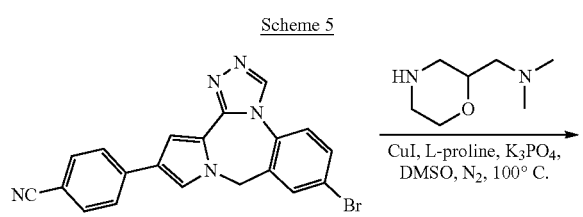

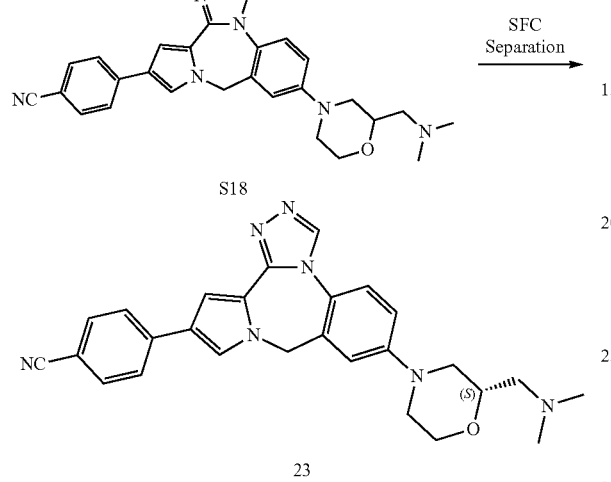

General Procedure E

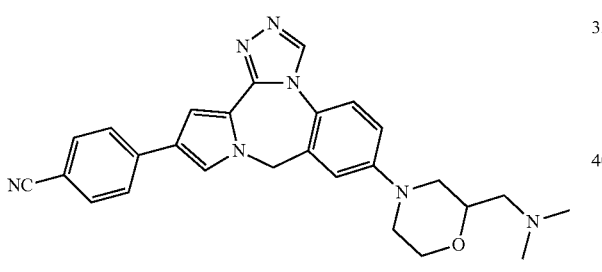

4-(7-(2-((dimethylamino)methyl)morpholino)-9H-benzo[e]pyrrolo[1,2-a][1,2,4]triazolo[3,4-c][1,4]diazepin-12-yl)benzonitrile, S18. Synthesized using General Procedure A, replacing tert-butyl piperazine-1-carboxylate with N,N-dimethyl-1-(morpholin-2-yl)methanamine. ESI [M+H]=466.2

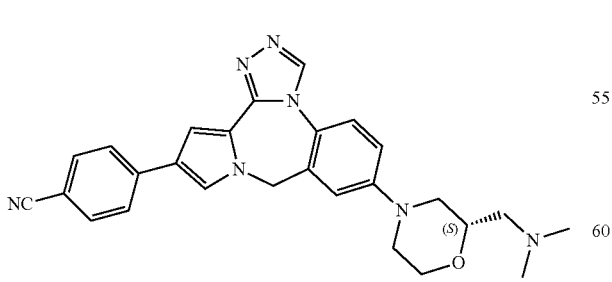

(S)-4-(7-(2-((dimethylamino)methyl)morpholino)-9H-benzo[e]pyrrolo[1,2-a][1,2,4]triazolo[3,4-c][1,4]diazepin-12-yl)benzonitrile, 23. 4-(7-(2-((dimethylamino) methyl) morpholino)-9H-benzo[e]pyrrolo[1,2-a][1,2,4]triazolo[3,4-c][1,4]diazepin-12-yl)benzonitrile was separated by SFC to give (S)-4-(7-(2-((dimethylamino)methyl)morpholino)-9H-benzo[e]pyrrolo[1,2-a][1,2,4]triazolo[3,4-c][1,4]diazepin-12-yl)benzonitrile as a white solid. $^1$H NMR (400 MHz, METHANOL-d4) δ=9.01 (s, 1H), 7.74-7.68 (m, 2H), 7.68-7.63 (m, 2H), 7.61 (s, 1H), 7.54 (d, J=8.8 Hz, 1H), 7.21 (d, J=4.4 Hz, 2H), 7.10 (dd, J=2.2, 8.8 Hz, 1H), 5.18 (s, 2H), 4.10 (d, J=9.7 Hz, 1H), 4.00 (t, J=9.3 Hz, 1H), 3.87-3.78 (m, 1H), 3.72 (d, J=11.5 Hz, 1H), 3.64 (d, J=11.9 Hz, 1H), 3.17-3.01 (m, 2H), 2.90 (dt, J=3.1, 11.9 Hz, 1H), 2.76 (s, 6H), 2.59 (t, J=11.0 Hz, 1H). ESI [M+H]=466.2

Scheme 7

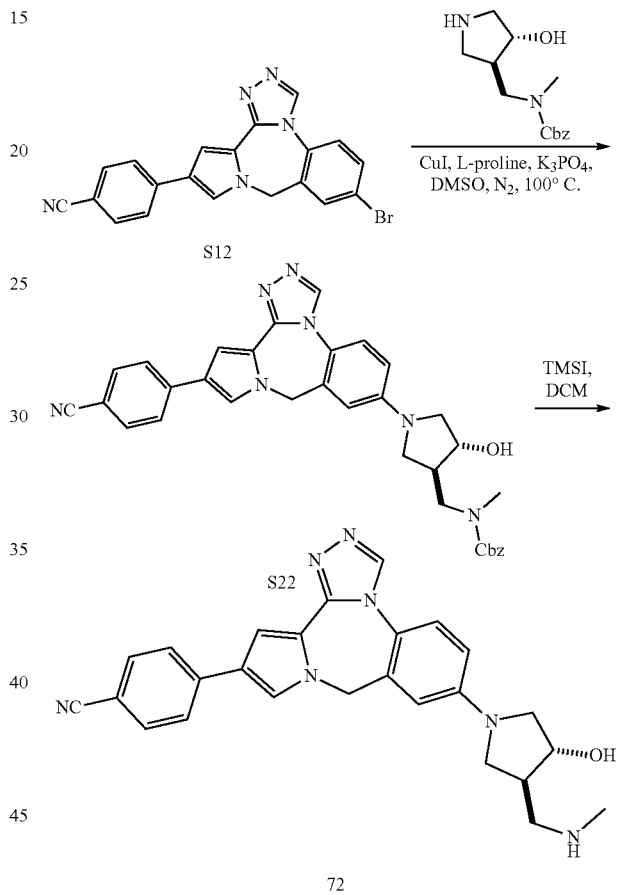

General Procedure G

Benzyl ((trans-1-(12-(4-cyanophenyl)-9H-benzo[e]pyrrolo[1,2-a][1,2,4]triazolo[3,4-c][1,4]diazepin-7-yl)-4-hydroxypyrrolidin-3-yl)methyl)(methyl)carbamate, S22. Synthesized using General Procedure A, replacing tert-butyl piperazine-1-carboxylate with benzyl ((trans-4-hydroxypyrrolidin-3-yl) methyl)(methyl) carbamate. ESI [M+H]=586.2

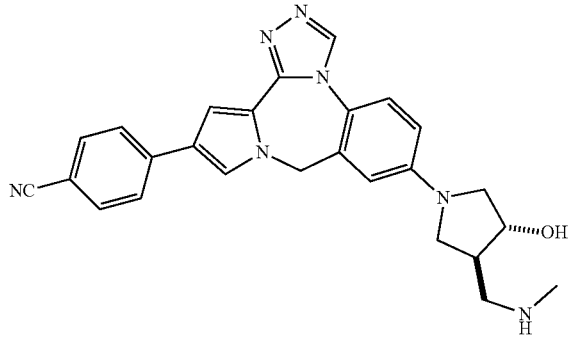 [SMILES: CNC[C@H]1CN(c2ccc3c(c2)Cn2cc(-c4ccc(C#N)cc4)cc2-c2nncn2-3)C[C@@H]1O]

4-(7-(trans-3-hydroxy-4-((methylamino)methyl)pyrrolidin-1-yl)-9H-benzo[e]pyrrolo[1,2-a][1,2,4]triazolo[3,4-c][1,4]diazepin-12-yl)benzonitrile, 72. To a solution of benzyl ((trans-1-(12-(4-cyanophenyl)-9H-benzo[e]pyrrolo[1,2-a][1,2,4]triazolo[3,4-c][1,4]diazepin-7-yl)-4-hydroxypyrrolidin-3-yl)methyl)(methyl)carbamate (30 mg, 20 umol, 1.0 eq.) in DCM (2.0 mL) was added TMSI (20.5 mg, 102.4 umol, 14 uL, 5.0 eq.). The mixture was stirred at 26° C. for 0.5 hr and then concentrated. The residue was purified by acidic prep-HPLC to give 4-(7-(trans-3-hydroxy-4-((methylamino)methyl)pyrrolidin-1-yl)-9H-benzo[e]pyrrolo[1,2-a][1,2,4]triazolo[3,4-c][1,4]diazepin-12-yl)benzonitrile (1.93 mg, 3.28 umol, 16.% yield) as a yellow solid. $^1$H NMR (400 MHz, METHANOL-d4) δ=9.00 (s, 1H), 7.77-7.70 (m, 2H), 7.70-7.64 (m, 2H), 7.62 (s, 1H), 7.50 (d, J=8.8 Hz, 1H), 7.23 (s, 1H), 6.80 (d, J=2.2 Hz, 1H), 6.70 (dd, J=2.6, 8.8 Hz, 1H), 5.18 (s, 2H), 4.30 (q, J=6.6 Hz, 1H), 3.78-3.64 (m, 2H), 3.27-3.10 (m, 4H), 2.77 (s, 3H), 2.62-2.52 (m, 1H). ESI [M+H]=452.1

Scheme 8

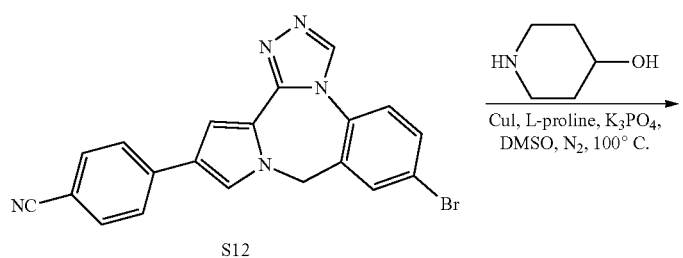

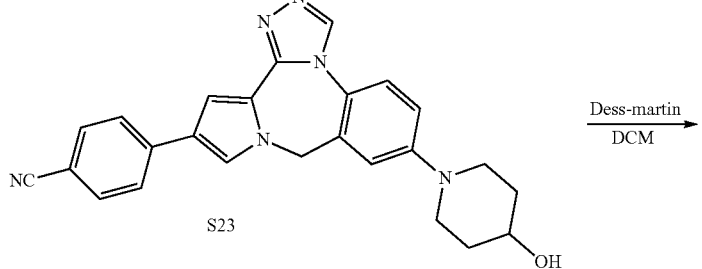

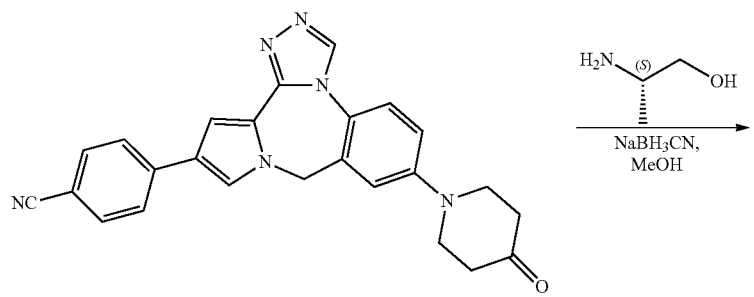

-continued

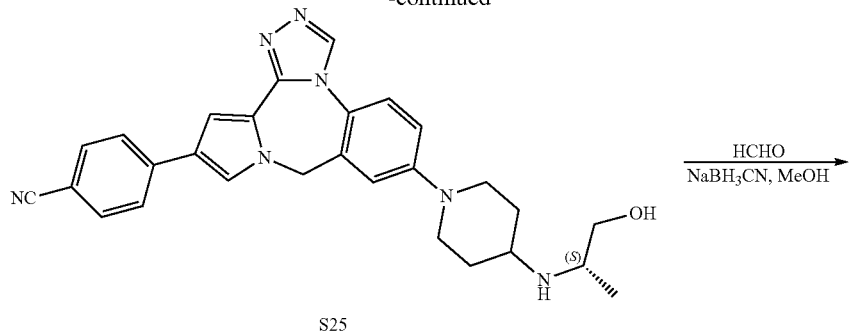

S25

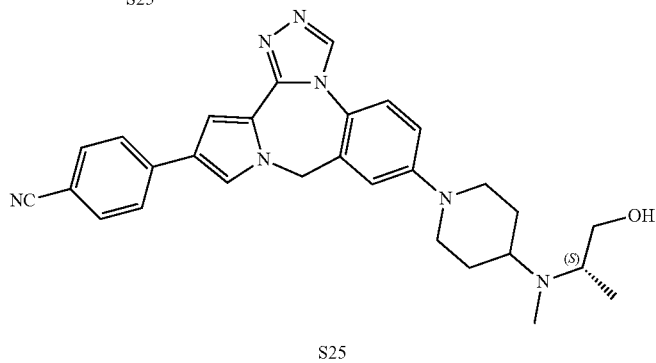

S25

General Procedure H

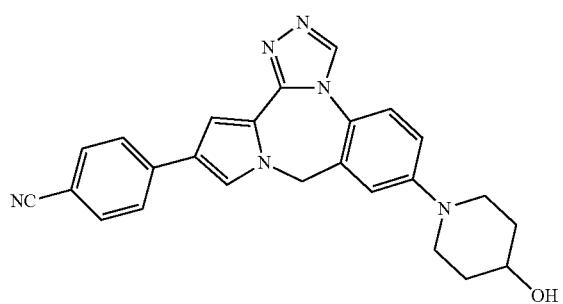 [SMILES: N#Cc1ccc(-c2cc3n(c2)Cc2cc(N4CCC(O)CC4)ccc2-n2cnnc2-3)cc1]

4-(7-(4-hydroxypiperidin-1-yl)-9H-benzo[e]pyrrolo[1,2-a][1,2,4]triazolo[3,4-c][1,4]diazepin-12-yl)benzonitrile, S23. Synthesized using General Procedure A, replacing tert-butyl piperazine-1-carboxylate with piperidin-4-ol. ESI [M+H]=423.2

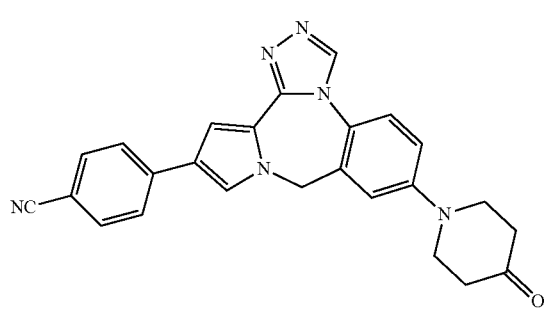 [SMILES: N#Cc1ccc(-c2cc3n(c2)Cc2cc(N4CCC(=O)CC4)ccc2-n2cnnc2-3)cc1]

4-(7-(4-oxopiperidin-1-yl)-9H-benzo[e] pyrrolo[1,2-a][1,2,4]triazolo[3,4-c][1,4]diazepin-12-yl)benzonitrile, S24. To a solution of 4-(7-(4-hydroxypiperidin-1-yl)-9H-benzo[e] pyrrolo[1,2-a][1,2,4]triazolo[3,4-c][1,4]diazepin-12-yl)benzonitrile (690 mg, 1.6 mmol, 1.0 eq.) in DCM (20 mL) was added Dess-Martin (898 mg, 2.1 mmol, 1.3 eq.) in one portion and the mixture was stirred at 20° C. for 16 hr. After the reaction was complete, the mixture was filtered. The filtrate was concentrated and the residue was purified by silica gel chromatography (DCM:MeOH=20:1, Rf=0.50) to give 4-(7-(4-oxopiperidin-1-yl)-9H-benzo[e]pyrrolo[1,2-a][1,2,4]triazolo[3,4-c][1,4]diazepin-12-yl)benzonitrile (600 mg, 78.8% yield, 90% purity) as a yellow solid. 1H NMR (400 MHz, DMSO-d6) δ=9.14-9.07 (m, 1H), 7.80-7.68 (m, 5H), 7.57-7.49 (m, 1H), 7.27 (d, J=2.6 Hz, 1H), 7.20 (d, J=1.8 Hz, 1H), 7.13 (dd, J=2.6, 8.8 Hz, 1H), 5.25-5.14 (m, 2H), 3.68 (t, J=5.8 Hz, 4H), 2.44-2.34 (m, 4H). ESI [M+H]= 421.0

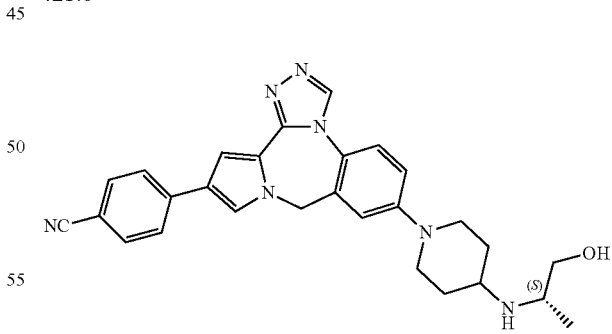

(S)-4-(7-(4-((1-hydroxypropan-2-yl)amino)piperidin-1-yl)-9H-benzo[e]pyrrolo[1,2-a][1,2,4]triazolo[3,4-c][1,4]diazepin-12-yl)benzonitrile, S25. A mixture of 4-(7-(4-oxopiperidin-1-yl)-9H-benzo[e]pyrrolo[1,2-a][1,2,4]triazolo[3,4-c][1,4]diazepin-12-yl)benzonitrile (40 mg, 95 umol, 1.0 eq.) and (2S)-2-aminopropan-1-ol (7.1 mg, 95.1 umol, 1.0 eq.) in MeOH (3.0 mL) was stirred for 2 hr at 25° C., then Ti(i-PrO)4 (5.4 mg, 19.0 umol, 5.6 uL, 0.2 eq.) and NaBH3CN (11.9 mg, 190.2 umol, 2.0 eq.) was added. The mixture was stirred at 25° C. for 10 hr and concentrated. The residue was purified by prep-HPLC (TFA condition) to give (S)-4-(7-(4-((1-hydroxypropan-2-yl)amino)piperidin-1-yl)-9H-benzo[e]pyrrolo[1,2-a][1,2,4]triazolo[3,4-c][1,4]diazepin-12-yl) benzonitrile (15.8 mg, 26.7 umol, 28% yield, 100% purity, TFA salt) as a white solid. 1H NMR (400 MHz, METHANOL-d4) δ=9.04 (s, 1H), 7.74-7.57 (m, 5H), 7.51 (d, J=8.8 Hz, 1H), 7.25-7.18 (m, 2H), 7.11 (dd, J=2.2, 8.8 Hz, 1H), 5.16 (s, 2H), 4.00 (d, J=12.8 Hz, 2H), 3.82 (dd, J=3.5, 11.9 Hz, 1H), 3.64-3.41 (m, 3H), 2.94 (t, J=12.1 Hz, 2H), 2.18 (d, J=11.5 Hz, 2H), 1.90-1.65 (m, 2H), 1.33 (d, J=6.6 Hz, 3H). ESI [M+H]=480.2

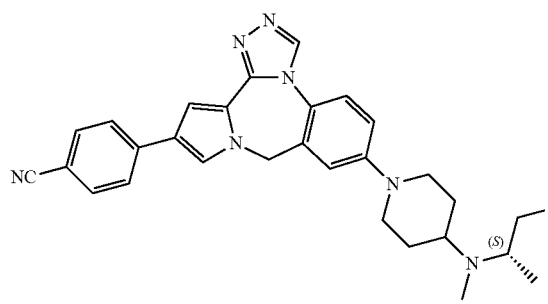

(S)-4-(7-(4-((1-hydroxypropan-2-yl)(methyl)amino)piperidin-1-yl)-9H-benzo[e]pyrrolo[1,2-a][1,2,4]triazolo[3,4-c][1,4]diazepin-12-yl)benzonitrile, 104. A mixture of (S)-4-(7-(4-((1-hydroxypropan-2-yl)amino)piperidin-1-yl)-9H-benzo[e]pyrrolo[1,2-a][1,2,4]triazolo[3,4-c][1,4] diazepin-12-yl)benzonitrile (20 mg, 41.7 umol, 1.0 eq.) and formaldehyde (16.9 mg, 208.5 umol, 15.5 uL, 5.0 eq.) in MeOH (2.0 mL) was stirred at 30° C. for 1 hr, then NaBH$_3$CN (5.2 mg, 83.4 umol, 2.0 eq.) was added and the mixture was stirred for 1 hr. The mixture was concentrated and the residue was purified by prep-HPLC (TFA condition) to give (S)-4-(7-(4-((1-hydroxypropan-2-yl)(methyl)amino) piperidin-1-yl)-9H-benzo[e]pyrrolo[1,2-a][1,2,4]triazolo[3,4-c][1,4] diazepin-12-yl)benzonitrile (4.5 mg, 7.2 umol, 17.4% yield, 98% purity, TFA) as a white solid. 1H NMR (400 MHz, METHANOL-d4) δ=9.04 (d, J=3.5 Hz, 1H), 7.76-7.59 (m, 5H), 7.53 (d, J=8.8 Hz, 1H), 7.26-7.20 (m, 2H), 7.12 (d, J=9.3 Hz, 1H), 5.19 (s, 2H), 4.04 (d, J=12.3 Hz, 2H), 3.83-3.74 (m, 2H), 3.63 (d, J=4.0 Hz, 2H), 2.92 (t, J=12.6 Hz, 2H), 2.84 (s, 1H), 2.76 (s, 2H), 2.34-2.13 (m, 2H), 1.99-1.75 (m, 2H), 1.37 (d, J=6.2 Hz, 1H), 1.27 (d, J=6.6 Hz, 2H). ESI [M+H]=494.2

Scheme 9

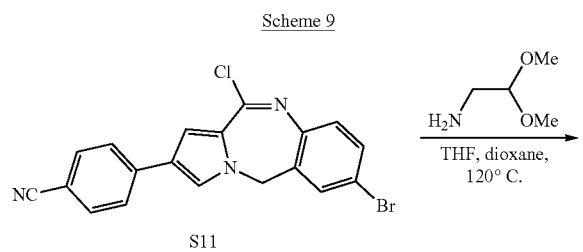

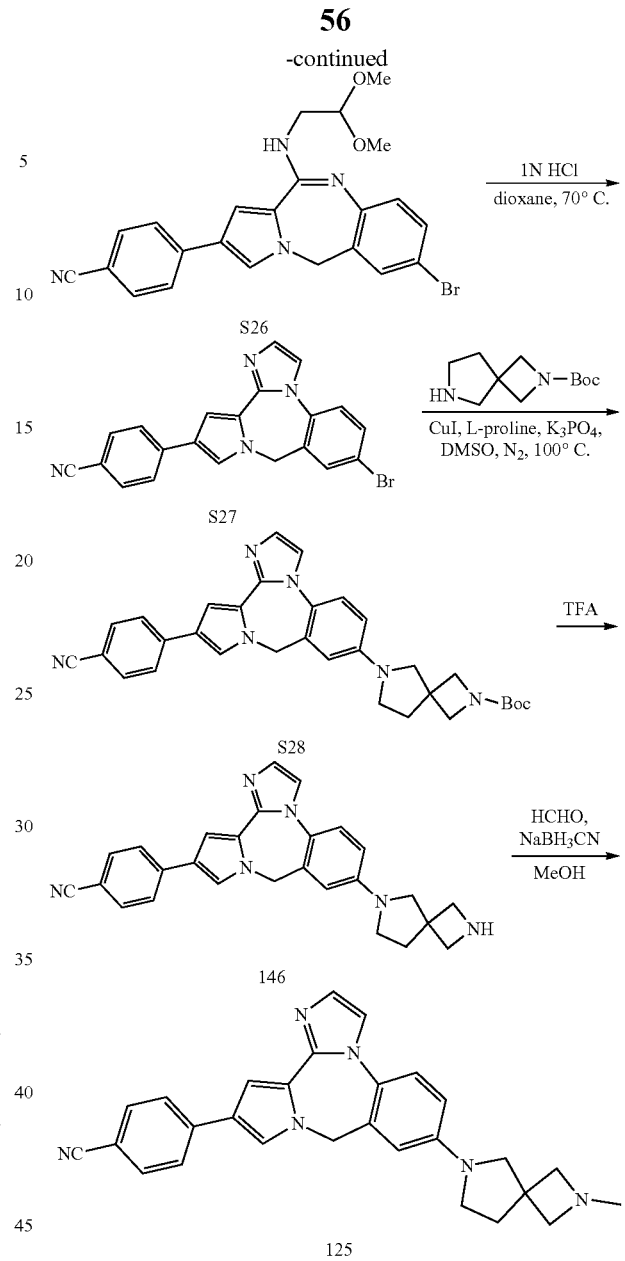

Chemistry Experimental Methods:

4-(7-bromo-11-((2,2-dimethoxyethyl)amino)-5H-benzo[e]pyrrolo[1,2-a][1,4]diazepin-2-yl) benzonitrile, S26. To a solution of 4-(7-bromo-11-chloro-5H-benzo[e]pyrrolo[1,2-a][1,4] diazepin-2-yl)benzonitrile (2.1 g, 5.2 mmol, 1.0 eq.) in THF (20 mL) and dioxane (40 mL) was added 2,2- dimethoxyethanamine (8.8 g, 83.8 mmol, 15 eq.) and the mixture was heated at 100° C. for 16 hr in sealing tube. The resulting mixture was concentrated and then partitioned between EtOAc (1000 mL) and 0.5 M HCl (150 mL). The organic layer was dried and concentrated to afford 4-(7-bromo-11-((2,2-dimethoxyethyl)amino)-5H-benzo[e]pyrrolo[1,2-a] [1,4]diazepin-2-yl)benzonitrile (1.6 g) as a brown solid. 1H NMR (400 MHz, DMSO-d6) δ=11.51(s, 1H), 10.15(s, 1H), 8.01-7.27(m, 9H), 5.38(s, 2H), 4.77(s, 1H), 3.98-3.90(s, 2H), 3.57-3.39(s, 6H). ESI [M+H]=464.9/466.9

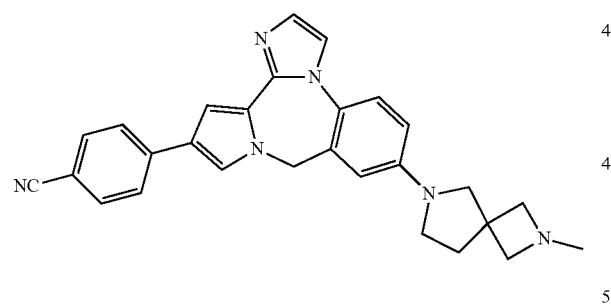

4-(7-bromo-9H-benzo[e]imidazo[2,1-c]pyrrolo[1,2-a][1,4]diazepin-12-yl)benzonitrile, S27. A mixture of 4-(7-bromo-11-((2,2-dimethoxyethyl)amino)-5H-benzo[e]pyrrolo[1,2-a][1,4]diazepin-2-yl)benzonitrile (1.6 g, 3.4 mmol, 1.0 eq.) in 1 M HCl (60 mL) and dioxane (60 mL) was stirred at 60° C. for 20 hr. The reaction mixture was concentrated to afford 4-(7-bromo-9H-benzo[e]imidazo[2,1-c]pyrrolo[1,2-a][1,4]diazepin-12-yl)benzonitrile (1.4 g, crude) as a gray solid, which was used into the next step without further purification. 1H NMR (400 MHz, DMSO-d6) δ=8.30(s, 1H), 8.01(s, 1H), 7.93(s, 2H), 7.86-7.83(m, 4H), 7.76-7.70(m, 2H), 7.46(s, 1H), 5.47(s, 2H). ESI [M+H]= 401.0/402.9

4-(7-(2-methyl-2,6-diazaspiro[3.4]octan-6-yl)-9H-benzo[e]imidazo[2,1-c]pyrrolo[1,2-a][1,4] diazepin-12-yl)benzonitrile, 125. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl) benzonitrile, replacing tert-butyl (azetidin-3-ylmethyl) (methyl)carbamate with tert-butyl 2,6-diazaspiro[3.4] octane-2-carboxylate. 1H NMR (400 MHz, METHANOL-d4) δ=7.99 (d, J=1.8 Hz, 1H), 7.78-7.67 (m, 6H), 7.54 (d, J=8.8 Hz, 1H), 7.28 (s, 1H), 6.84-6.72 (m, 2H), 5.29 (s, 2H), 4.40-4.24 (m, 2H), 4.20-4.06 (m, 2H), 3.71-3.59 (m, 2H), 3.46 (br. s., 2H), 2.98 (br. s., 3H), 2.40 (br. s., 2H). ESI [M+H]=447.1

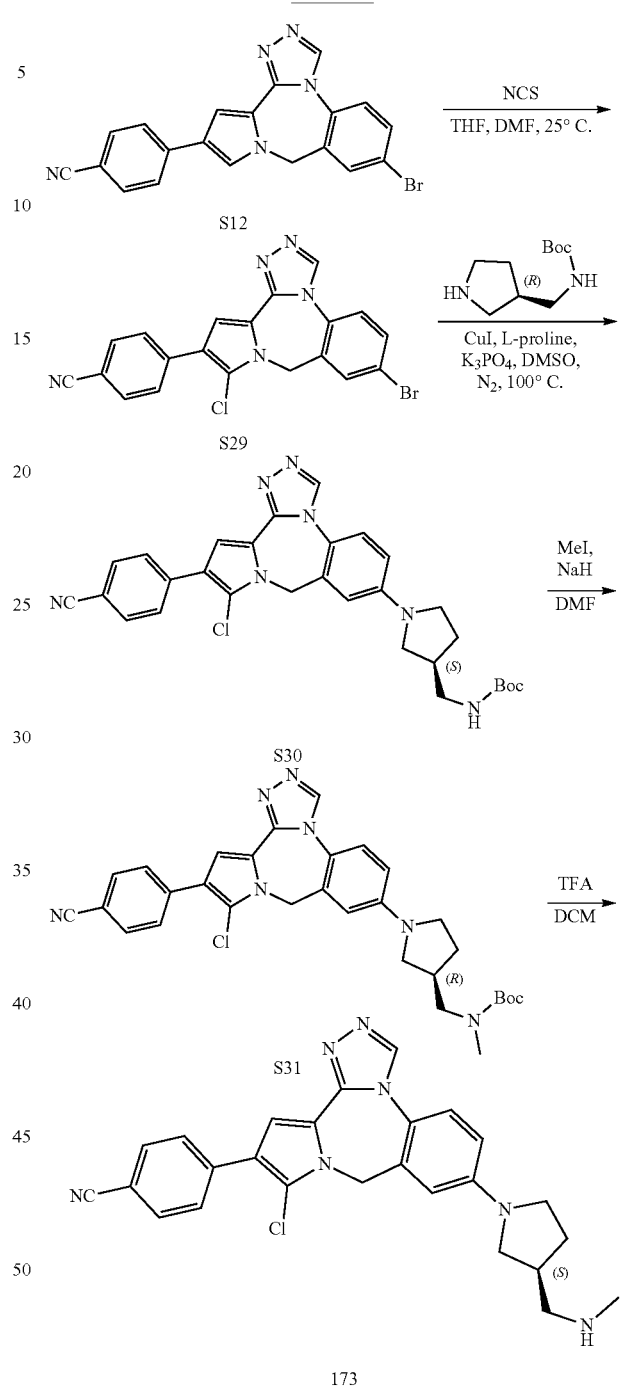

173

General Procedure I

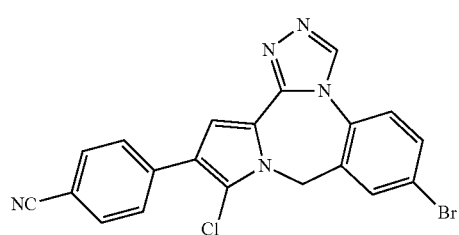 [SMILES: N#Cc1ccc(-c2cc3n(c2Cl)Cc2cc(Br)ccc2-n2cnnc2-3)cc1]

4-(7-bromo-11-chloro-9H-benzo[e]pyrrolo[1,2-a][1,2,4]triazolo[3,4-c][1,4]diazepin-12-yl) benzonitrile, S29. To a solution of 4-(7-bromo-9H-benzo[e]pyrrolo[1,2-a][1,2,4]triazolo[3,4-c][1,4]diazepin-12-yl)benzonitrile (1.0 g, 2.5 mmol, 1.0 eq.) in THF (20 mL) and DMF (30 mL) was added NCS (399 mg, 3 mmol, 1.2 eq.) and the mixture was stirred at 25° C. for 16 hr. The reaction mixture was concentrated and purified by column chromatography (SiO₂, Petroleum ether/Ethyl acetate/THF=5/1/1 to 1/1/1) to afford 4-(7-bromo-11-chloro-9H-benzo[e]pyrrolo[1,2-a][1,2,4]triazolo[3,4-c][1,4]diazepin-12-yl)benzonitrile (760 mg, 1.7 mmol, 69.8% yield) as a grey solid. ESI [M+H]=435.9/437.9

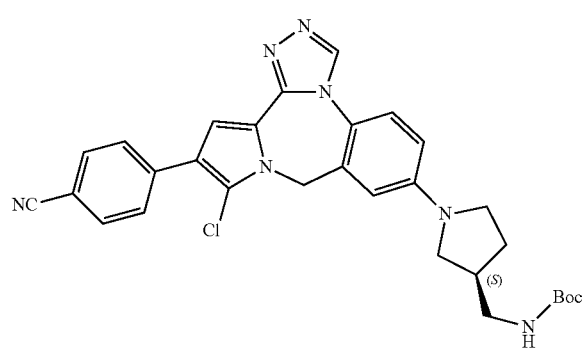

(S)-tert-butyl((1-(11-chloro-12-(4-cyanophenyl)-9H-benzo[e]pyrrolo[1,2-a][1,2,4]triazolo[3,4-c][1,4]diazepin-7-yl)pyrrolidin-3-yl)methyl)carbamate, S30. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-11-chloro-9H-benzo[e]pyrrolo[1,2-a][1,2,4]triazolo[3,4-c][1,4]diazepin-12-yl)benzonitrile and replacing tert-butyl piperazine-1-carboxylate with (R)-tert-butyl (pyrrolidin-3-ylmethyl)carbamate. ESI [M+H]=556.4

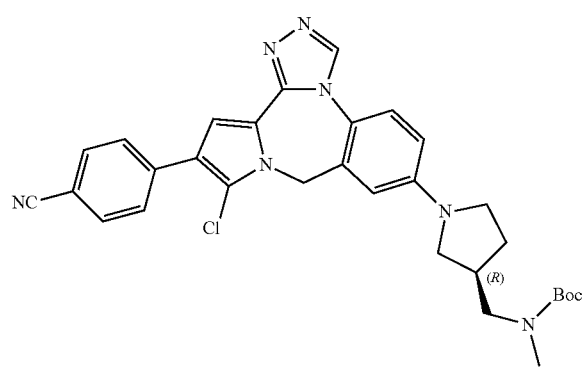

(R)-tert-butyl((1-(11-chloro-12-(4-cyanophenyl)-9H-benzo[e]pyrrolo[1,2-a][1,2,4]triazolo[3,4-c][1,4]diazepin-7-yl)pyrrolidin-3-yl)methyl)(methyl)carbamate, S31. To a solution of (S)-tert-butyl((1-(11-chloro-12-(4-cyanophenyl)-9H-benzo[e]pyrrolo[1,2-a][1,2,4]triazolo[3,4-c][1,4]diazepin-7-yl)pyrrolidin-3-yl)methyl)carbamate (15 mg, 26.9 umol, 1.0 eq.) and MeI (11.4 mg, 80.9 umol, 5.04 uL, 3.0 eq.) in DMF (2.0 mL) was added NaH (2.1 mg, 53.9 umol, 60% purity, 2.0 eq.) and the mixture was stirred at 25° C. for 20 min. Then the mixture was poured into water (10 mL) and extracted with EtOAc (30 mL*3). The organic layer was washed with brine (10 mL), dried over MgSO₄, filtered and concentrated to give crude (R)-tert-butyl ((1-(11-chloro-12-(4-cyanophenyl)-9H-benzo[e]pyrrolo[1,2-a][1,2,4]triazolo[3,4-c][1,4]diazepin-7-yl) pyrrolidin-3-yl)methyl) (methyl)carbamate (20 mg) as a brown oil, which was used into the next step without further purification. ESI [M+H]=570.1

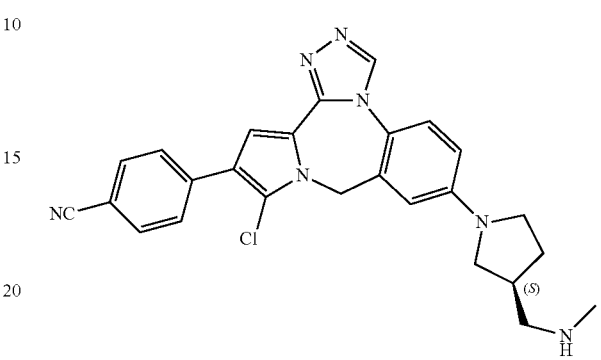

(S)-4-(11-chloro-7-(3-((methylamino)methyl)pyrrolidin-1-yl)-9H-benzo[e]pyrrolo[1,2-a][1,2,4]triazolo[3,4-c][1,4]diazepin-12-yl)benzonitrile, 173. A solution of (R)-tert-butyl ((1-(11-chloro-12-(4-cyanophenyl)-9H-benzo[e]pyrrolo[1,2-a][1,2,4]triazolo[3,4-c][1,4]diazepin-7-yl)pyrrolidin-3-yl)methyl)(methyl)carbamate (20 mg, 35 umol, 1.0 eq.) in TFA (2.0 mL) was stirred at 50° C. for 5 min. The reaction was concentrated and purified by prep-HPLC (TFA condition) to afford (S)-4-(11-chloro-7-(3-((methylamino)methyl)pyrrolidin-1-yl)-9H-benzo[e] pyrrolo[1,2-a][1,2,4]triazolo[3,4-c][1,4]diazepin-12-yl)benzonitrile (2.31 mg, 3.83 umol, 10.91% yield, 96.8% purity, TFA salt) as a yellow solid. 1H NMR (400 MHz, METHANOL-d4) δ=9.03 (br. s., 1H), 7.87-7.79 (m, 2H), 7.78-7.70 (m, 2H), 7.51 (d, J=8.8 Hz, 1H), 7.13 (s, 1H), 6.80 (d, J=2.2 Hz, 1H), 6.73 (dd, J=2.4, 8.8 Hz, 1H), 5.25 (br. s., 2H), 3.68-3.58 (m, 1H), 3.53 (dt, J=3.9, 8.9 Hz, 1H), 3.48-3.38 (m, 1H), 3.24-3.10 (m, 3H), 2.82-2.66 (m, 4H), 2.33 (dd, J=4.5, 11.4 Hz, 1H), 1.89 (qd, J=8.4, 12.4 Hz, 1H). ESI [M+H]=470.1

Scheme 11

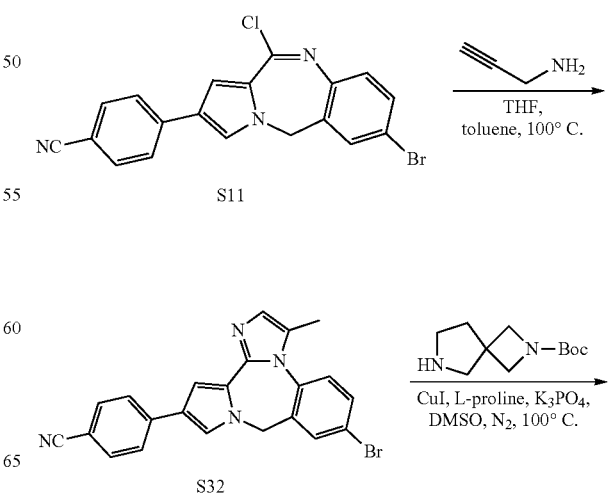

-continued

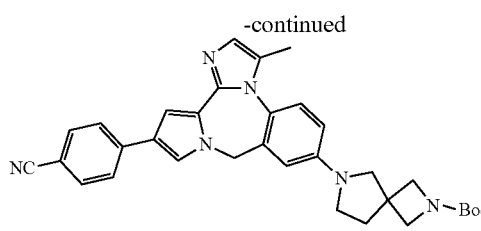
S33

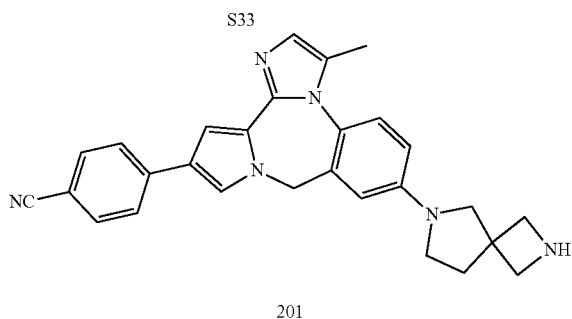
201

Chemistry Experimental Methods:

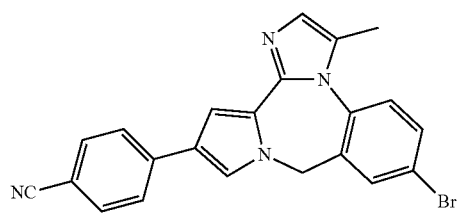 [SMILES: Cc1cnc2n1-c1ccc(Br)cc1Cn1cc(-c3ccc(C#N)cc3)cc1-2]

4-(7-bromo-3-methyl-9H-benzo[e]imidazo[2,1-c]pyrrolo[1,2-a][1,4]diazepin-12-yl)benzo nitrile, S32. To a solution of 4-(7-bromo-11-chloro-5H-benzo[e]pyrrolo[1,2-a][1,4]diazepin-2-yl)benzonitrile (2.1 g, 5.3 mmol, 1.0 eq.) in toluene/THF (5:2, 70 mL) was added prop-2-yn-1-amine (5 g, 91.1 mmol, 17.2 eq.) and the mixture was heated at 120° C. for 56 hr in sealing tube. The resulting mixture was concentrated and partitioned between THF/EtOAc (1:1, 200 mL) and 0.25 M ice-HCl (100 mL). The separated aqueous layer was extracted with THF/EtOAc (1:1, 100 mL*3). The combined organic layers were washed with brine (100 mL), dried over anhydrous MgSO₄, filtered and concentrated in vacuum. The residue was purified by column chromatography to afford 4-(7-bromo-3-methyl-9H-benzo[e]imidazo[2,1-c]pyrrolo[1,2-a][1,4] diazepin-12-yl)benzonitrile (1.8 g, 3.0 mmol, 57% yield) as a grey solid. 1H NMR (400 MHz, CHLOROFORM-d) δ=7.63 (s, 1H), 7.63-7.51 (m, 5H), 7.20 (d, J=8.4 Hz, 1H), 7.13 (d, J=1.6 Hz, 1H), 7.07 (s, 1H), 7.01 (s, 1H), 5.07 (d, 14.0 Hz, 1H), 4.81 (d, 14.2 Hz, 1H), 2.38 (s, 3H). ESI [M+H]=415.2/417.2

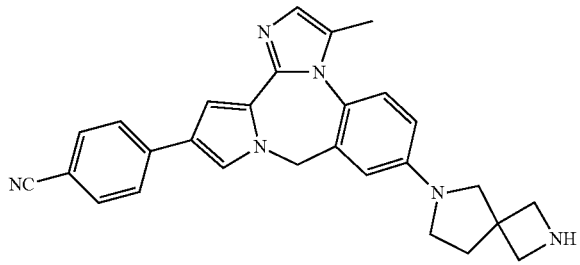 [SMILES: Cc1cnc2n1-c1ccc(N3CCC4(CNC4)C3)cc1Cn1cc(-c3ccc(C#N)cc3)cc1-2]

4-(3-methyl-7-(2,6-diazaspiro[3.4]octan-6-yl)-9H-benzo[e]imidazo[2,1-c]pyrrolo[1,2-a][1,4]diazepin-12-yl)benzonitrile, 201. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-methyl-9H-benzo[e]imidazo[2,1-c]pyrrolo[1,2-a][1,4]diazepin-12-yl)benzonitrile, replacing tert-butyl piperazine-1-carboxylate with tert-butyl 2,6-diazaspiro[3.4]octane-2-carboxylate. 1H NMR (400 MHz, METHANOL-d4) δ=7.81 (s, 1H), 7.78-7.72 (m, 4H), 7.59 (s, 1H), 7.50 (d, J=8.8 Hz, 1H), 7.28 (s, 1H), 6.88 (br. s., 1H), 6.77 (d, J=8.8 Hz, 1H), 5.26 (s, 2H), 4.23-4.17 (m, 2H), 4.15-4.08 (m, 2H), 3.67 (s, 2H), 3.50 (t, J=6.8 Hz, 2H), 2.53 (s, 3H), 2.43 (t, J=6.8 Hz, 2H). ESI [M+H]=447.1

Scheme 12

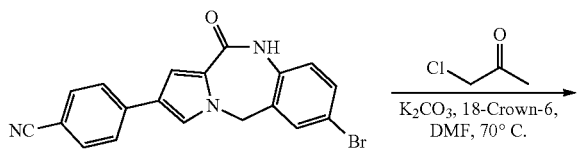
S10

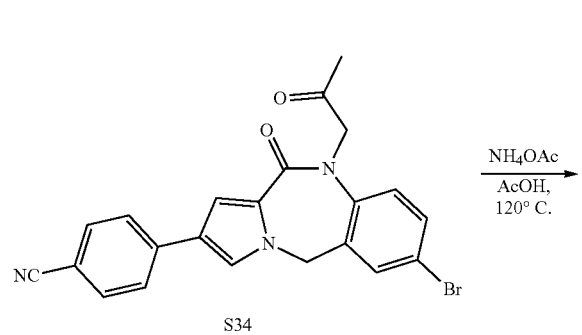
S34

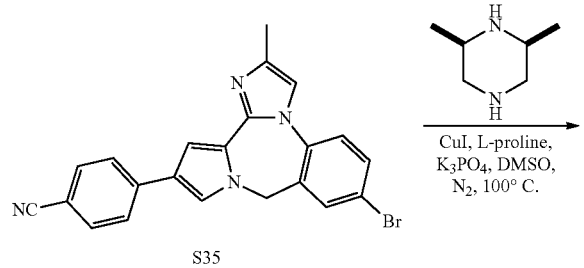
S35

215

Chemistry Experimental Methods:

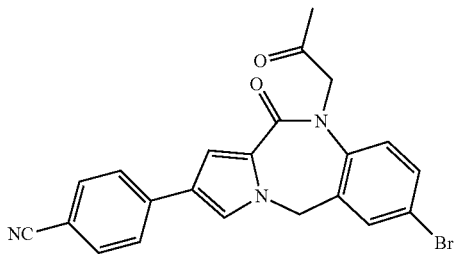 [SMILES: CC(=O)CN1C(=O)c2cc(-c3ccc(C#N)cc3)cn2Cc2cc(Br)ccc21]

4-(7-bromo-11-oxo-10-(2-oxopropyl)-10,11-dihydro-5H-benzo[e]pyrrolo[1,2-a][1,4]diazepin-2-yl)benzonitrile, S34. To a mixture of 4-(7-bromo-11-oxo-10,11-dihydro-5H-benzo[e]pyrrolo[1,2-a][1,4]diazepin-2-yl)benzonitrile (2.5 g, 6.6 mmol, 1.0 eq.), 18-crown-6 (192 mg, 727 umol, 0.11 eq.) and $K_2CO_3$ (5.0 g, 36.1 mmol, 5.4 eq.) in DMF (40 mL) was added 1-chloropropan-2-one (12 g, 129.7 mmol, 19.6 eq.) at 15° C. The reaction mixture was heated to 70° C. (oil bath) and stirred for 4 days. The reaction mixture was concentrated in vacuum, diluted with EtOAc (100 mL), washed with water (10 mL×2) and brine (50 mL), dried over $Na_2SO_4$, then concentrated to give 4-(7-bromo-11-oxo-10-(2-oxopropyl)-10,11-dihydro-5H-benzo[e] pyrrolo[1,2-a][1,4]diazepin-2-yl)benzonitrile (3.0 g, crude) as a black-brown oil, which was used directly without purification. ESI [M+H]=434.0/436.0

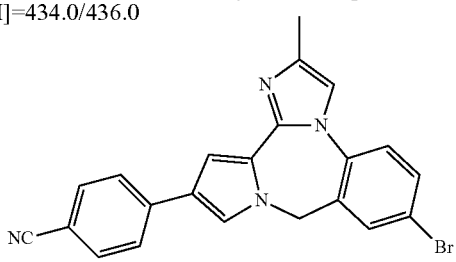

4-(7-bromo-2-methyl-9H-benzo[e]imidazo[2,1-c]pyrrolo[1,2-a][1,4]diazepin-12-yl) benzonitrile, S35. A mixture of 4-(7-bromo-11-oxo-10-(2-oxopropyl)-10,11-dihydro-5H-benzo[e]pyrrolo[1,2-a][1,4]diazepin-2-yl)benzonitrile (2.5 g, 5.7 mmol, 1.0 eq.) and $NH_4OAc$ (25 g, 324 mmol, 56.3 eq.) in AcOH (200 mL) was stirred at 120° C. for 48 hr. The mixture was concentrated and the residue was purified by prep-HPLC (TFA) to give 4-(7-bromo-2-methyl-9H-benzo[e]imidazo[2,1-c]pyrrolo[1,2-a][1,4]diazepin-12-yl)benzonitrile (450 mg, 845 umol, 14.68% yield, 78% purity) as a brown solid, which was used directly. ESI [M+H]=414.8/416.8

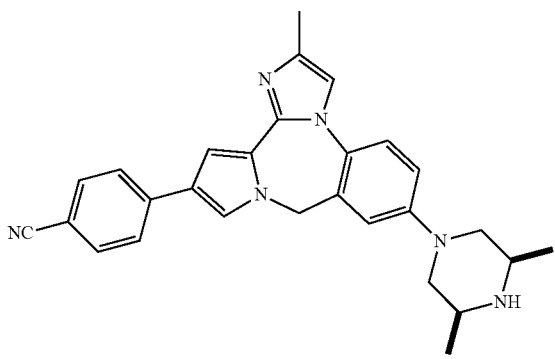 [SMILES: Cc1cn2c(n1)-c1cc(-c3ccc(C#N)cc3)cn1Cc1cc(N3C[C@@H](C)N[C@@H](C)C3)ccc1-2]

4-(7-(cis-3,5-dimethylpiperazin-1-yl)-2-methyl-9H-benzo[e]imidazo[2,1-c]pyrrolo[1,2-a][1,4]diazepin-12-yl)benzonitrile, 215. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-2-methyl-9H-benzo[e]imidazo[2,1-c]pyrrolo[1,2-a][1,4]diazepin-12-yl)benzonitrile and replacing tert-butyl piperazine-1-carboxylate with cis-2,6-dimethylpiperazine. $^1$H NMR (400 MHz, METHANOL-$d_4$) δ=7.83-7.69 (m, 6H), 7.62 (d, J=8.8 Hz, 1H), 7.32 (dd, J=2.2, 11.9 Hz, 2H), 7.26 (dd, J=2.6, 8.8 Hz, 1H), 5.35 (s, 2H), 4.08 (d, J=11.5 Hz, 2H), 3.51 (d, J=6.8 Hz, 2H), 2.82 (dd, J=11.6, 13.3 Hz, 2H), 2.49 (s, 3H), 1.42 (d, J=6.4 Hz, 6H). ESI [M+H]=449.2

Scheme 13

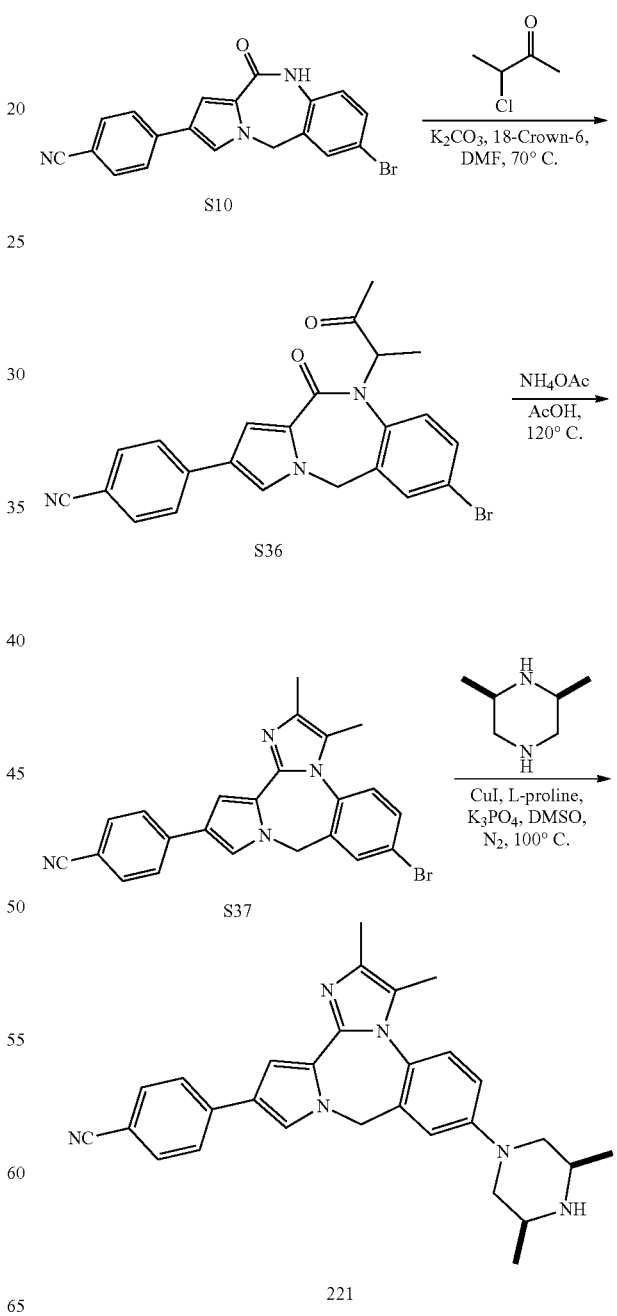

Chemistry Experimental Methods:

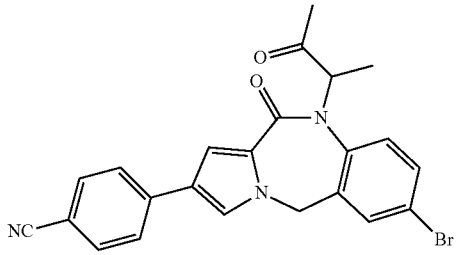 [SMILES: CC(=O)C(C)N1C(=O)c2cc(-c3ccc(C#N)cc3)cn2Cc2cc(Br)ccc21]

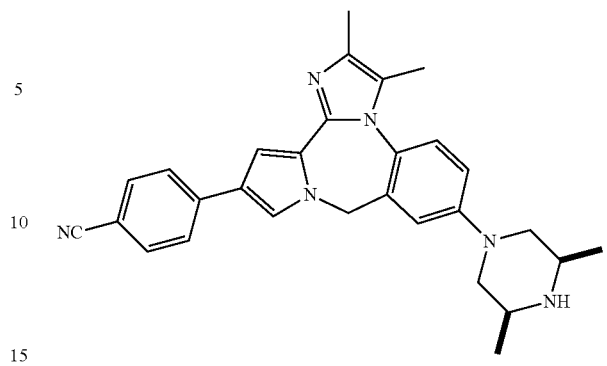

4-(7-bromo-11-oxo-10-(3-oxobutan-2-yl)-10,11-dihydro-5H-benzo[e]pyrrolo[1,2-a][1,4] diazepin-2-yl)benzonitrile, S36. To a solution of 4-(7-bromo-11-oxo-10,11-dihydro-5H-benzo[e]pyrrolo[1,2-a][1,4]diazepin-2-yl)benzonitrile (1.0 g, 2.6 mmol, 1.0 eq.) and 3-chlorobutan-2-one (560 mg, 2.0 eq.) in DMF (20 mL) was added $K_2CO_3$ (1.8 g, 13.2 mmol, 5.0 eq.) and 18-C-6 (348 mg, 1.3 mmol, 0.5 eq.). The mixture was stirred at 70° C. for 12 hr and poured into ice-water (100 mL). The mixture was extracted with ethyl acetate (200 mL*3), washed with brine (30 mL*2), dried with anhydrous $Na_2SO_4$, filtered and concentrated to give 4-(7-bromo-11-oxo-10-(3-oxobutan-2-yl)-10,11-dihydro-5H-benzo[e]pyrrolo[1,2-a][1,4]diazepin-2-yl)benzonitrile (1.5 g, crude) as a black brown oil. ESI [M+H]=447.9/449.9

4-(7-(cis-3,5-dimethylpiperazin-1-yl)-2,3-dimethyl-9H-benzo[e]imidazo[2,1-c]pyrrolo[1,2-a][1,4]diazepin-12-yl) benzonitrile, 221. Synthesized using General Procedure A, replacing 4-(7-bromo-9H-benzo[e]pyrrolo[1,2-a][1,2,4]triazolo[3,4-c]-[1,4]diazepin-12-yl)benzonitrile with 4-(7-bromo-2,3-dimethyl-9H-benzo[e]imidazo-[2,1-c]pyrrolo[1,2-a][1,4]diazepin-12-yl)benzonitrile, tert-butyl piperazine-1-car-boxylate with cis-2,6-dimethylpiperazine. 1H NMR (400 MHz, METHANOL-d4) δ=7.77-7.66 (m, 5H), 7.52 (d, J=8.8 Hz, 1H), 7.35 (br. s., 1H), 7.28-7.17 (m, 2H), 5.26 (s, 2H), 4.07 (d, J=13.2 Hz, 2H), 3.50 (br. s., 2H), 2.87-2.76 (m, 2H), 2.42 (d, J=4.4 Hz, 6H), 1.41 (d, J=6.2 Hz, 6H). ESI [M+H]=463.2

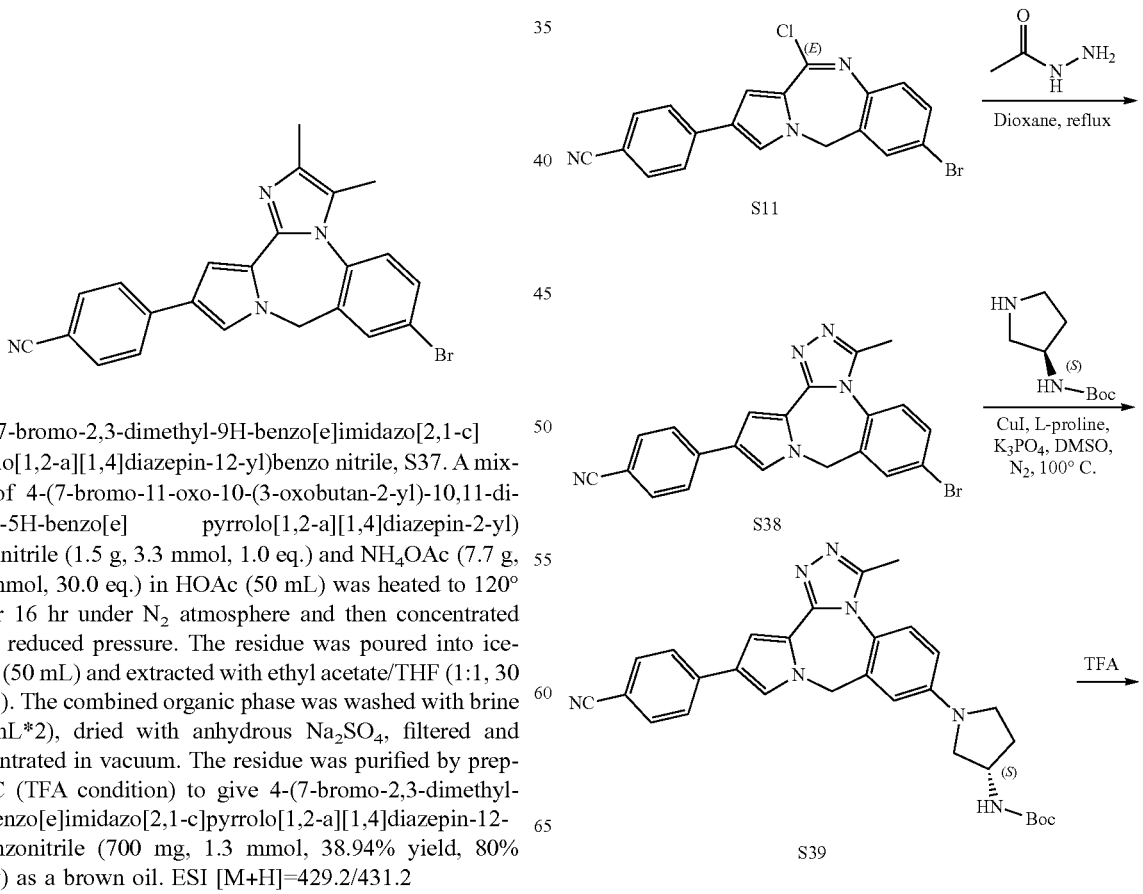

4-(7-bromo-2,3-dimethyl-9H-benzo[e]imidazo[2,1-c] pyrrolo[1,2-a][1,4]diazepin-12-yl)benzo nitrile, S37. A mixture of 4-(7-bromo-11-oxo-10-(3-oxobutan-2-yl)-10,11-dihydro-5H-benzo[e] pyrrolo[1,2-a][1,4]diazepin-2-yl) benzonitrile (1.5 g, 3.3 mmol, 1.0 eq.) and $NH_4OAc$ (7.7 g, 100 mmol, 30.0 eq.) in HOAc (50 mL) was heated to 120° C. for 16 hr under $N_2$ atmosphere and then concentrated under reduced pressure. The residue was poured into ice-water (50 mL) and extracted with ethyl acetate/THF (1:1, 30 mL*5). The combined organic phase was washed with brine (30 mL*2), dried with anhydrous $Na_2SO_4$, filtered and concentrated in vacuum. The residue was purified by prep-HPLC (TFA condition) to give 4-(7-bromo-2,3-dimethyl-9H-benzo[e]imidazo[2,1-c]pyrrolo[1,2-a][1,4]diazepin-12-yl)benzonitrile (700 mg, 1.3 mmol, 38.94% yield, 80% purity) as a brown oil. ESI [M+H]=429.2/431.2

-continued

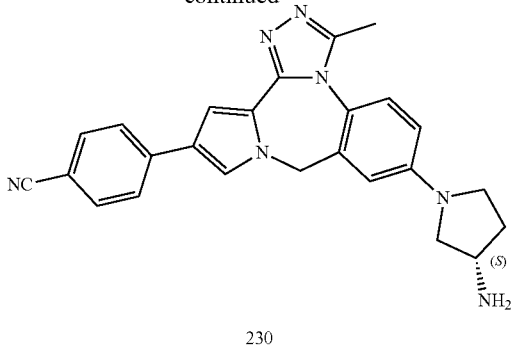

230

Chemistry Experimental Methods:

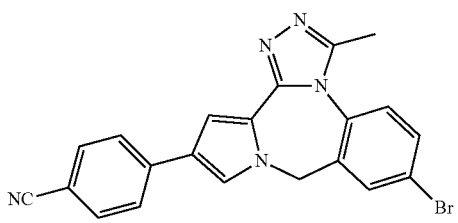

4-(7-bromo-3-methyl-9H-benzo[e]pyrrolo[1,2-a][1,2,4]triazolo[3,4-c][1,4]-diazepin-12-yl)benzonitrile, S38. A solution of 4-(7-bromo-11-chloro-5H-benzo[e]-pyrrolo-[1,2-a][1,4] diazepin-2-yl)benzonitrile (2.0 g, 5 mmol, 1.0 eq.) and acetohydrazide (746 mg, 10 mmol, 2.0 eq.) in dioxane (25 mL) was stirred at 110° C. for 16 hr. The reaction mixture was concentrated under reduced pressure to remove solvent. The residue was diluted with ice-water (20 mL) and extracted with hot ethyl acetate/THF (2:1, 25 mL*3). The combined organic phase was washed with brine (30 mL), dried with anhydrous $Na_2SO_4$, filtered and concentrated in vacuum to afford black brown solid. The solid was washed with MeOH (10 mL) to give 4-(7-bromo-3-methyl-9H-benzo[e]pyrrolo[1,2-a]-[1,2,4]triazolo-[3,4-c][1,4]-diazepin-12-yl)benzonitrile (1.30 g, crude) as a light yellow solid. 1H NMR (400 MHz, DMSO-d6) δ=7.97 (s, 1H), 7.80-7.50 (m, 6H), 7.70-7.64 (m, 1H), 7.19 (s, 1H), 5.34-5.13 (m, 2H), 2.58 (s, 3H).

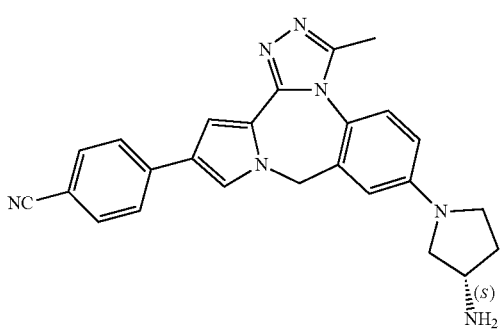

4-(7-((S)-3-aminopyrrolidin-1-yl)-3-methyl-9H-benzo[e]pyrrolo[1,2-a][1,2,4]triazolo[3,4-c][1,4]diazepin-12-yl)benzonitrile, 230. Synthesized using General Procedure A, replacing 4-(7-bromo-9H-benzo[e]pyrrolo[1,2-a][1,2,4]triazolo[3,4-c]-[1,4]diazepin-12-yl)benzonitrile with 4-(7-bromo-3-methyl-9H-benzo[e]pyrrolo-[1,2-a][1,2,4]-triazolo-[3,4-c][1,4]-diazepin-12-yl) benzonitrile, replacing tert-butyl piperazine-1-carboxylate with (S)-tert-butyl pyrrolidin-3-ylcarbamate. 1H NMR (400 MHz, METHANOL-d4) δ=7.71-7.62 (m, 5H), 7.46 (d, J=8.8 Hz, 1H), 7.23 (br. s., 1H), 6.89 (br. s., 1H), 6.75 (d, J=8.8 Hz, 1H), 5.17 (br. s., 2H), 4.07 (br. s., 1H), 3.75-3.60 (m, 2H), 3.54-3.43 (m, 2H), 2.70 (br. s., 3H), 2.55-2.44 (m, 1H), 2.25-2.16 (m, 1H). ESI [M+H]=422.1

Scheme 15

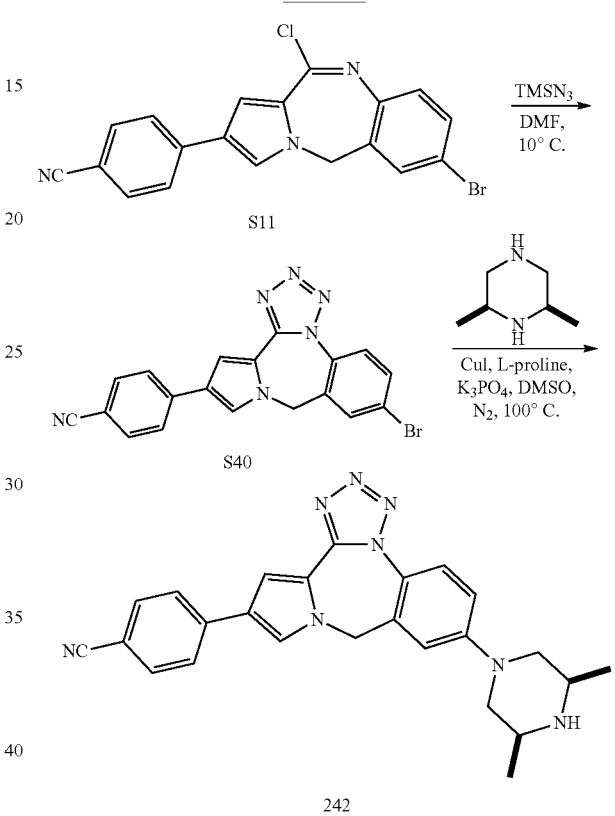

Chemistry Experimental Methods:

4-(7-bromo-9H-benzo[e]pyrrolo[1,2-a]tetrazolo[5,1-c][1,4]diazepin-12-yl)benzonitrile, S40. A mixture of 4-(7-bromo-11-chloro-5H-benzo[e]pyrrolo[1,2-a][1,4]diazepin-2-yl)benzonitrile (850 mg, 2.1 mmol, 1.0 eq.) and $TMSN_3$ (271.5 mg, 2.3 mmol, 1.1 eq.) in DMF (10 mL) was stirred at 10° C. for 16 hr and then concentrated. The residue was added MeOH (20 mL) and stirred for 1 hr. The precipitate was collected by filtration to give 4-(7-bromo-9H-benzo[e]pyrrolo[1,2-a]tetrazolo[5,1-c][1,4]diazepin-12-yl)benzonitrile (600 mg, 62.5% yield, 90% purity) as a red solid. ESI [M+H]=403.0/405.0

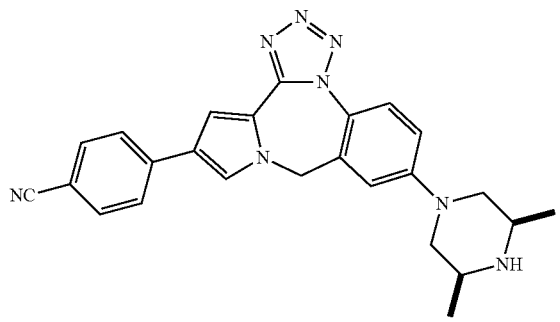 [SMILES: C[C@@H]1CN(c2ccc3c(c2)Cn2cc(-c4ccc(C#N)cc4)cc2-c2nnnn2-3)C[C@H](C)N1]

4-(7-(cis-3,5-dimethylpiperazin-1-yl)-9H-benzo[e]pyrrolo[1,2-a]tetrazolo[5,1-c][1,4]diazepin-12-yl)benzonitrile, 242. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c][1,4]diazepin-12-yl)benzonitrile and replacing tert-butyl piperazine-1-carboxylate with cis-2,6-dimethylpiperazine. 1H NMR (400 MHz, METHANOL-d4) δ=7.89 (d, J=8.8 Hz, 1H), 7.78-7.74 (m, 2H), 7.71-7.68 (m, 3H), 7.40 (d, J=1.8 Hz, 1H), 7.34-7.24 (m, 2H), 5.30 (s, 2H), 4.09 (d, J=11.5 Hz, 2H), 3.52 (d, J=7.1 Hz, 2H), 2.86-2.79 (m, 2H), 1.42 (d, J=6.6 Hz, 6H). ESI [M+H]=437.2

Scheme 16

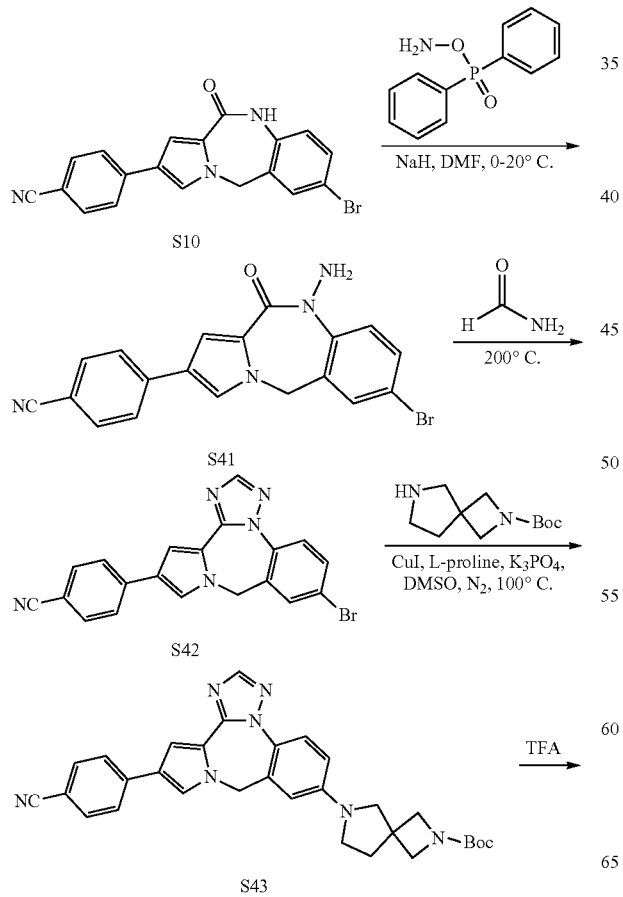

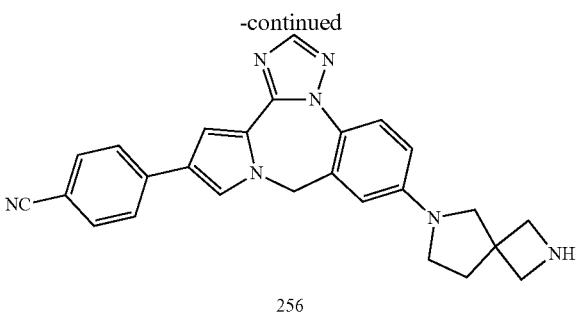

256

Chemistry Experimental Methods:

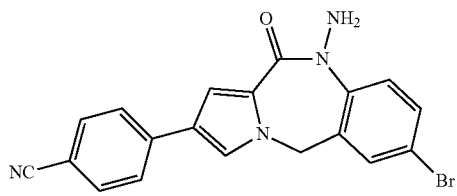 [SMILES: N#Cc1ccc(-c2cc3n(c2)Cc2cc(Br)ccc2N(N)C3=O)cc1]

4-(10-amino-7-bromo-11-oxo-10,11-dihydro-5H-benzo[e]pyrrolo[1,2-a][1,4]diazepin-2-yl)benzonitrile, S41. To a solution of 4-(7-bromo-11-oxo-10,11-dihydro-5H-benzo[e]pyrrolo[1,2-a][1,4]diazepin-2-yl)benzonitrile (1 g, 2.64 mmol, 1.0 eq.) in DMF (20 mL) was added NaH (169 mg, 4.2 mmol, 60% purity, 1.6 eq.) at 0° C. After stirred for 1 hr at 0° C., (aminooxy) diphenylphosphine oxide (738 mg, 3.2 mmol, 1.2 eq.) was added and the mixture was stirred at 20° C. for 1 hr. The mixture was poured into ice-water (100 mL) and extracted with EtOAc (300 mL*3). The organic layer was washed with brine (100 mL), dried over MgSO4 and concentrated in vacuo. The residue was added MTBE (20 mL) and stirred for 1 hr. The precipitate was collected by filtration to give 4-(10-amino-7-bromo-11-oxo-10,11-dihydro-5H-benzo[e]pyrrolo[1,2-a][1,4]diazepin-2-yl)benzonitrile (1.0 g, crude) as a yellow solid, which was used into the next step without further purification. ESI [M+H]= 393.1/395.1

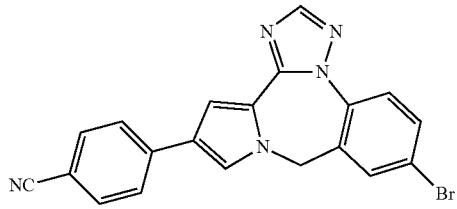 [SMILES: N#Cc1ccc(-c2cc3n(c2)Cc2cc(Br)ccc2-n2ncnc2-3)cc1]

4-(7-bromo-9H-benzo[e]pyrrolo[1,2-a][1,2,4]triazolo[5,1-c][1,4]diazepin-12-yl)benzonitrile, S42. To a solution of 4-(10-amino-7-bromo-11-oxo-10,11-dihydro-5H-benzo[e]pyrrolo[1,2-a] [1,4]diazepin-2-yl)benzonitrile (900 mg, 2.29 mmol, 1.0 eq.) in formamide (10 mL) was stirred at 200° C. for 1.5 hr, then the mixture was poured into ice-water (20 mL) and filtered. The filter cake was added EtOH (10 mL) and stirred for 1 hr. The precipitate was collected by filtration to give 4-(7-bromo-9H-benzo[e]pyrrolo[1,2-a][1,2,4]triazolo[5,1-c][1,4]diazepin-12-yl)benzonitrile (600 mg) as a yellow solid. 1H NMR (400 MHz, DMSO-d6) δ=8.34 (br. s., 1H), 7.93 (br. s., 1H), 7.78 (br. s., 6H), 7.40-7.11 (m, 2H), 5.38 (br. s., 2H). ESI [M+H]=402.1/404.1

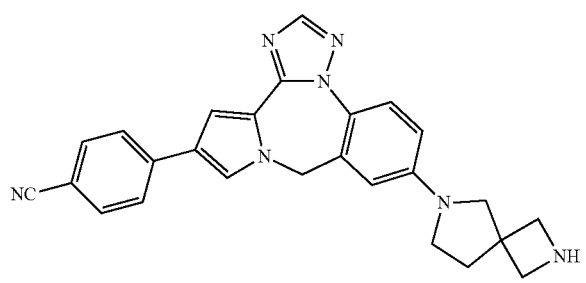 [SMILES: N#Cc1ccc(-c2cc3n(c2)Cc2cc(N4CCC5(CNC5)C4)ccc2-n2ncnc2-3)cc1]

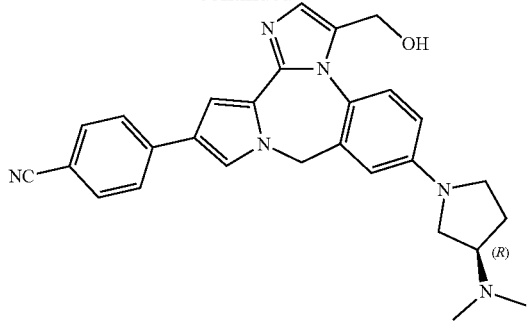

274

4-(7-(2,6-diazaspiro[3.4]octan-6-yl)-9H-benzo[e]pyrrolo[1,2-a][1,2,4]triazolo[5,1-c][1,4] diazepin-12-yl)benzonitrile, 256. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile, replacing tert-butyl piperazine-1-carboxylate with tert-butyl 2,6-diazaspiro[3.4]octane-2-carboxylate. 1H NMR (400 MHz, METHANOL-d4) δ=8.16 (s, 1H), 7.79-7.64 (m, 5H), 7.62 (s, 1H), 7.21 (s, 1H), 6.80-6.70 (m, 2H), 5.19 (s, 2H), 4.21-4.13 (m, 2H), 4.12-4.04 (m, 2H), 3.63 (s, 2H), 3.47 (t, J=6.8 Hz, 2H), 2.39 (t, J=6.9 Hz, 2H). ESI [M+H]=434.1

Chemistry Experimental Methods:

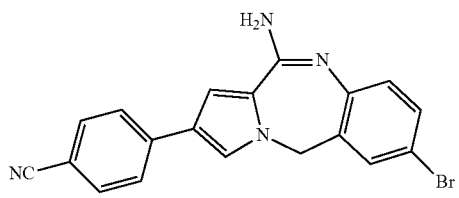 [SMILES: N#Cc1ccc(-c2cc3n(c2)Cc2cc(Br)ccc2N=C3N)cc1]

4-(11-amino-7-bromo-5H-benzo[e]pyrrolo[1,2-a][1,4]diazepin-2-yl)benzonitrile, S49. To a solution of 4-(7-bromo-11-chloro-5H-benzo[e]pyrrolo[1,2-a][1,4]diazepin-2-yl)benzonitrile (1.6 g, 4 mmol, 1.0 eq.) in MeCN (20 mL) and THF (20 mL) was added NH₃·H₂O (1.4 g, 40 mmol, 10.0 eq.) and the mixture was heated at 120° C. in sealing tube for 16 hr. The reaction mixture was concentrated to give 4-(11-amino-7-bromo-5H-benzo[e]pyrrolo[1,2-a][1,4]diazepin-2-yl) benzonitrile (1.4 g, crude) as a yellow solid, which was used directly for next step without further purification. ESI [M+H]=377.1/379.1

Scheme 19

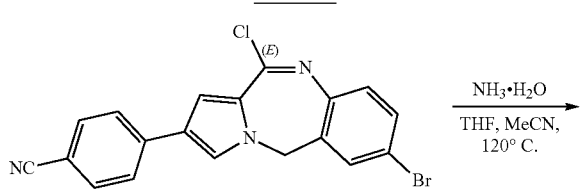

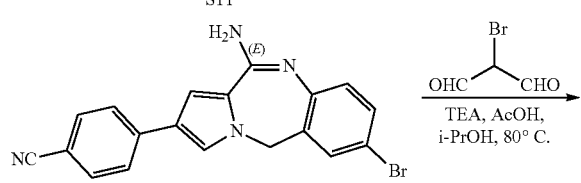

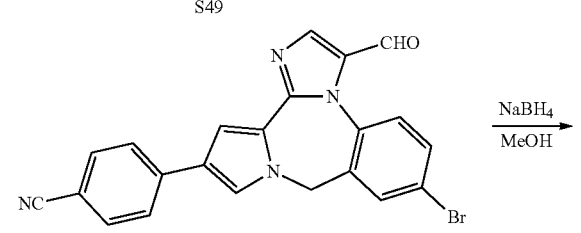

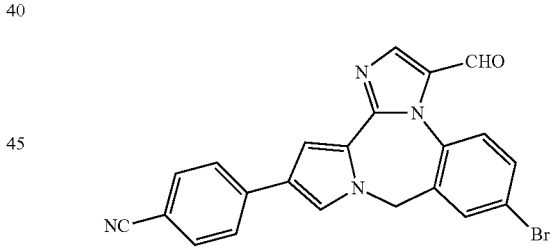

4-(7-bromo-3-formyl-9H-benzo[e]imidazo[2,1-c]pyrrolo[1,2-a][1,4]diazepin-12-yl)benzo nitrile, S50. To a solution of 4-(11-amino-7-bromo-5H-benzo[e]pyrrolo[1,2-a][1,4]diazepin-2-yl)benzonitrile (1.4 g, 3.7 mmol, 1.0 eq.) in i-PrOH (10 mL) was added Et₃N (413 mg, 4 mmol, 1.1 eq.) and 2-bromomalonaldehyde (616 mg, 4 mmol, 1.0 eq.). The mixture was stirred at 10° C. for 0.1 hr and then AcOH (267 mg, 4.4 mmol, 1.2 eq.) was added. The mixture was heated to 90° C. for 2 hr and concentrated. The residue was purified by prep-HPLC (TFA condition) to afford 4-(7-bromo-3-formyl-9H-benzo[e]imidazo[2,1-c]pyrrolo[1,2-a][1,4]diazepin-12-yl)benzonitrile (300 mg, 545 umol, 14.68% yield) as a yellow solid. 1H NMR (400 MHz, DMSO-d6) δ=9.71 (s., 1H), 8.24 (s, 1H), 7.88 (s, 1H), 7.78 (s, 1H), 7.75 (s, 4H), 7.62(d, J=12 Hz, 1H), 7.34 (d, J=12 Hz, 1H), 7.29(s, 1H), 5.35 (d, J=12 Hz, 1H), 5.22 (d, J=12 Hz, 1H). ESI [M+H]= 429.0/431.0

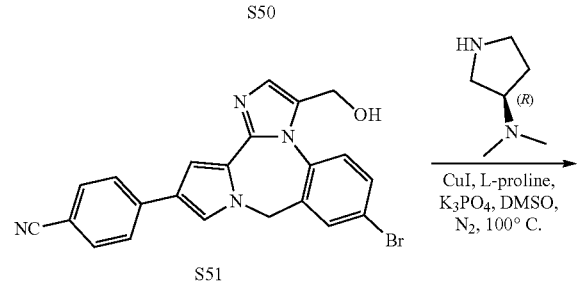

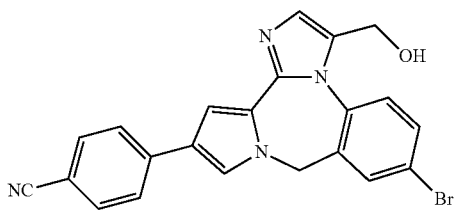 [SMILES: N#Cc1ccc(-c2cc3n(c2)Cc2cc(Br)ccc2-n2c(CO)cnc2-3)cc1]

4-(7-bromo-3-(hydroxymethyl)-9H-benzo[e]imidazo[2,1-c]pyrrolo[1,2-a][1,4]diazepin-12-yl)benzonitrile, S51. To a solution of 4-(7-bromo-3-formyl-9H-benzo[e]imidazo[2,1-c]pyrrolo[1,2-a][1,4]diazepin-12-yl)benzonitrile (300 mg, 699 umol, 1.0 eq.) in MeOH (30 mL) was added NaBH$_4$ (105 mg, 2.8 mmol, 4.0 eq.) and the mixture was stirred at 10° C. for 16 hr. The reaction mixture was concentrated, diluted with water (30 mL) and extracted with EtOAc (30 mL*3). The organic phase was concentrated to afford 4-(7-bromo-3-(hydroxymethyl)-9H-benzo[e]imidazo[2,1-c]pyrrolo[1,2-a][1,4]diazepin-12-yl)benzonitrile (300 mg, 695.6 umol, 99.53% yield) as a light yellow solid, which was used directly for next step without further purification. ESI [M+H]=431.1/433.1

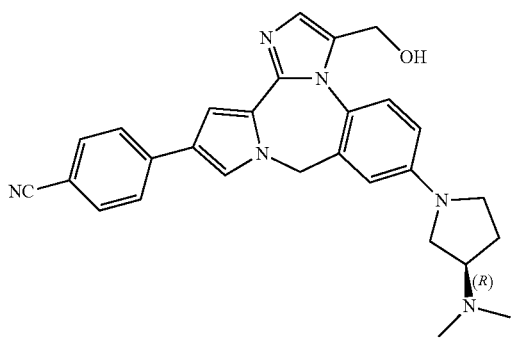

4-(7-((R)-3-(dimethylamino)pyrrolidin-1-yl)-3-(hydroxymethyl)-9H-benzo[e]imidazo[2,1-c]pyrrolo[1,2-a][1,4]diazepin-12-yl)benzonitrile, 274. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-(hydroxymethyl)-9H-benzo[e]imidazo[2,1-c]pyrrolo[1,2-a][1,4]diazepin-12-yl)benzonitrile, replacing tert-butyl piperazine-1-carboxylate with (R)—N,N-dimethyl pyrrolidin-3-amine. 1H NMR (400 MHz, METHANOL-d4) δ=7.82 (d, J=8.8 Hz, 1H), 7.79-7.75 (m, 2H), 7.74-7.70 (m, 2H), 7.70-7.65 (m, 2H), 7.28 (d, J=1.8 Hz, 1H), 6.92 (d, J=2.2 Hz, 1H), 6.80 (dd, J=2.4, 9.0 Hz, 1H), 5.24 (d, J=7.1 Hz, 2H), 4.81 (d, J=14.1 Hz, 1H), 4.62 (d, J=14.1 Hz, 1H), 4.07 (quin, J=7.2 Hz, 1H), 3.82 (ddd, J=3.7, 7.2, 10.7 Hz, 1H), 3.73-3.57 (m, 2H), 3.45 (q, J=7.5 Hz, 1H), 3.00-2.94 (m, 6H), 2.65-2.54 (m, 1H), 2.39-2.27 (m, 1H). ESI [M+H]=465.1

Scheme 20

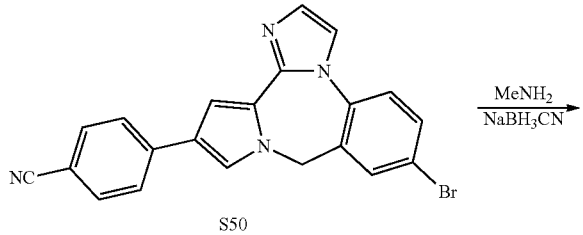

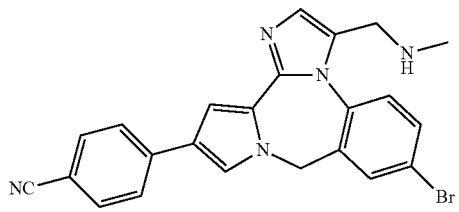 [SMILES: CNCc1cnc2n1-c1ccc(Br)cc1Cn1cc(-c3ccc(C#N)cc3)cc1-2]

4-(7-bromo-3-((methylamino)methyl)-9H-benzo[e]imidazo[2,1-c]pyrrolo[1,2-a][1,4]diazepin-12-yl)benzonitrile, S52. To a solution of 4-(7-bromo-3-formyl-9H-benzo[e]imidazo[2,1-c]pyrrolo[1,2-a][1,4]diazepin-12-yl)benzonitrile (100 mg, 232 umol, 1.0 eq.) in MeOH (5.0 mL) was Chemistry Experimental Methods:

added MeNH$_2$ (144 mg, 4.6 mmol, 20 eq.) and the mixture was stirred at 10° C. for 1 hr. Then NaBH$_3$CN (58.5 mg, 931.8 umol, 4.0 eq.) was added, the mixture was stirred at 10° C. for 16 hr and concentrated to give 4-(7-bromo-3-((methylamino)methyl)-9H-benzo[e]imidazo[2,1-c]pyrrolo[1,2-a][1,4]diazepin-12-yl)benzonitrile (110 mg, crude) as a black brown solid, which was used directly for next step without further purification. ESI [M+H]=444.0/446.0

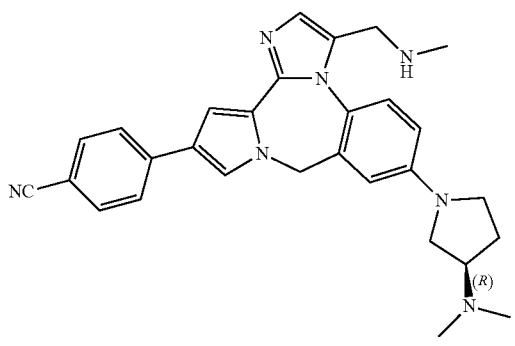

Tert-butyl((7-bromo-12-(4-cyanophenyl)-9H-benzo[e]imidazo[2,1-c]pyrrolo[1,2-a][1,4] diazepin-3-yl)methyl)(methyl)carbamate, S53. To a solution of 4-(7-bromo-3-((methylamino) methyl)-9H-benzo[e]imidazo[2,1-c]pyrrolo[1,2-a][1,4]diazepin-12-yl)benzonitrile (110 mg, 247 umol, 1.0 eq.) in THF (5 mL) was added (Boc)$_2$O (59 mg, 272 umol, 1.1 eq.) and Et$_3$N (50.1 mg, 495 umol, 2.0 eq.). The mixture was stirred at 10° C. for 1 hr and concentrated to dryness, purified by prep-TLC (SiO$_2$, Ethyl acetate:Methanol=20:1) to give tert-butyl((7-bromo-12-(4-cyanophenyl)-9H-benzo[e]imidazo[2,1-c]pyrrolo[1,2-a][1,4]diazepin-3-yl)methyl)(methyl) carbamate (150 mg, crude) as a yellow solid. ESI [M+H]=544.1/546.1

4-(7-((R)-3-(dimethylamino)pyrrolidin-1-yl)-3-((methylamino)methyl)-9H-benzo[e]imidazo[2,1-c]pyrrolo[1,2-a][1,4]diazepin-12-yl)benzonitrile, 276. Synthesized using General Procedure A, replacing 4-(7-bromo-9H-benzo[e]pyrrolo[1,2-a][1,2,4]triazolo[3,4-c][1,4]diazepin-12-yl)benzonitrile with tert-butyl((7-bromo-12-(4-cyanophenyl)-9H-benzo[e]imidazo[2,1-c] pyrrolo[1,2-a][1,4]diazepin-3-yl)methyl)(methyl)carbamate, replacing tert-butyl piperazine-1-carboxylate with (R)—N,N-dimethylpyrrolidin-3-amine. 1H NMR (400 MHz, METHANOL-d4) δ=7.74-7.70 (m, 2H), 7.69-7.64 (m, 4H), 7.30 (d, J=8.8 Hz, 1H), 7.17 (s, 1H), 6.95 (d, J=2.2 Hz, 1H), 6.83-6.77 (m, 1H), 5.25-5.16 (m, 2H), 4.67-4.60 (m, 1H), 4.54-4.45 (m, 1H), 4.14-4.04 (m, 1H), 3.87-3.76 (m, 1H), 3.75-3.60 (m, 1H), 3.51-3.40 (m, 1H), 2.99 (s, 6H), 2.68 (s, 3H), 2.66-2.56 (m, 1H), 2.38-2.27 (m, 1H). ESI [M+H]=478.2

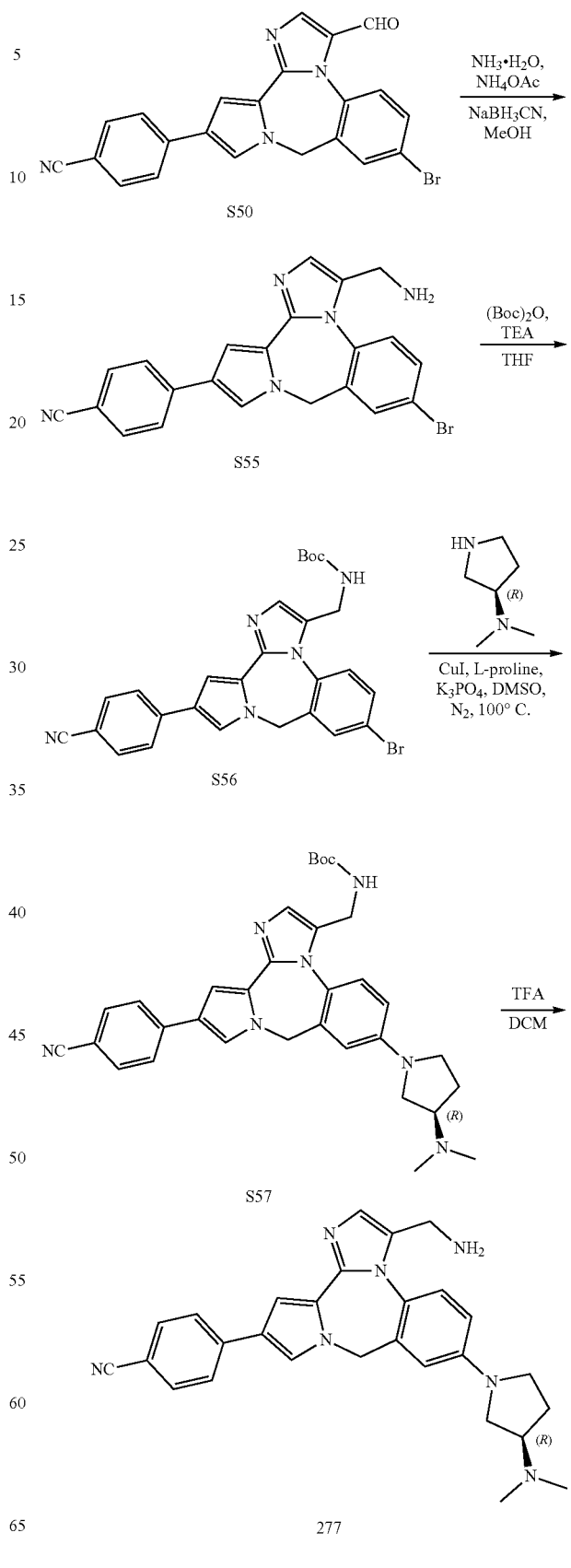

Scheme 21

Chemistry Experimental Methods:

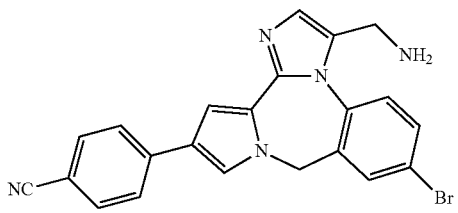

4-(3-(aminomethyl)-7-bromo-9H-benzo[e]imidazo[2,1-c]pyrrolo[1,2-a][1,4]diazepin-12-yl)benzonitrile, S55. To a solution of 4-(7-bromo-3-formyl-9H-benzo[e]imidazo[2,1-c]pyrrolo[1,2-a][1,4]diazepin-12-yl)benzonitrile (100 mg, 233 umol, 1.0 eq.) in MeOH (5.0 mL) was added NH$_3$.H$_2$O (81 mg, 2.3 mmol, 10 eq.) and NH$_4$OAc (35.9 mg, 465.9 umol, 2.0 eq.). The mixture was stirred at 80° C. for 2 hr and then added NaBH$_3$CN (29 mg, 465.9 umol, 2.0 eq.). The reaction mixture was heated at 80° C. for 16 hr and concentrated to give the crude 4-(3-(aminomethyl)-7-bromo-9H-benzo[e]imidazo[2,1-c]pyrrolo[1,2-a][1,4]diazepin-12-yl)benzonitrile (110 mg) as a black brown solid, which was used directly for next step without further purification. ESI [M+H]=430.2/432.0

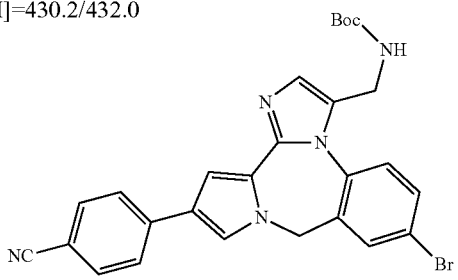

Tert-butyl ((7-bromo-12-(4-cyanophenyl)-9H-benzo[e]imidazo[2,1-c]pyrrolo[1,2-a][1,4]diazepin-3-yl)methyl)carbamate, S56. To a solution of 4-(3-(aminomethyl)-7-bromo-9H-benzo[e] imidazo[2,1-c]pyrrolo[1,2-a][1,4]diazepin-12-yl)benzonitrile (110 mg, 255 umol, 1.0 eq.) in THF (5 mL) was added (Boc)$_2$O (61.3 mg, 281.2 umol, 1.1 eq.) and Et$_3$N (51.7 mg, 511.2 umol, 2.0 eq.). The reaction mixture was stirred at 10° C. for 1 hr, concentrated and purified by prep-TLC (SiO$_2$, Dichloromethane:Methanol=10:1, R$_f$=0.75) to afford tert-butyl ((7-bromo-12-(4-cyanophenyl)-9H-benzo[e]imidazo[2,1-c]pyrrolo[1,2-a][1,4]diazepin-3-yl)methyl)carbamate (120 mg) as a yellow solid. ESI [M+H]= 530.1/532.1

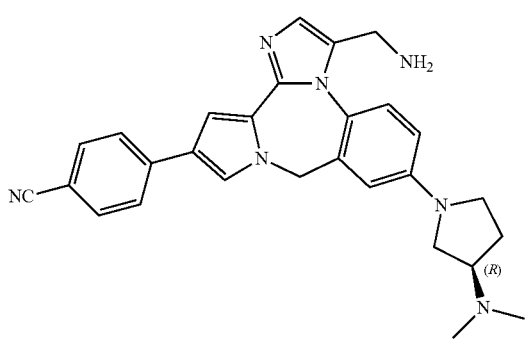

4-(3-(aminomethyl)-7-((R)-3-(dimethylamino)pyrrolidin-1-yl)-9H-benzo[e]imidazo[2,1-c]pyrrolo[1,2-a][1,4]diazepin-12-yl)benzonitrile, 277. Synthesized using General Procedure A, replacing 4-(7-bromo-9H-benzo[e]pyrrolo[1,2-a][1,2,4]triazolo[3,4-c][1,4]diazepin-12-yl)benzonitrile with tert-butyl ((7-bromo-12-(4-cyanophenyl)-9H-benzo[e]imidazo[2,1-c]pyrrolo[1,2-a] [1,4]diazepin-3-yl)methyl)carbamate, replacing tert-butyl piperazine-1-carboxylate with (R)—N,N-dimethylpyrrolidin-3-amine. 1H NMR (400 MHz, METHANOL-d4) δ=7.74-7.68 (m, 2H), 7.68-7.63 (m, 2H), 7.58 (s, 1H), 7.50 (s, 1H), 7.28 (d, J=8.4 Hz, 1H), 7.10 (s, 1H), 6.95 (s, 1H), 6.79 (d, J=8.8 Hz, 1H), 5.25-5.06 (m, 2H), 4.53 (d, J=15.0 Hz, 1H), 4.32 (d, J=15.4 Hz, 1H), 4.13-4.04 (m, 1H), 3.81 (br. s., 1H), 3.72-3.69 (m, 1H), 3.61 (br. s., 1H), 3.50-3.39 (m, 1H), 2.99 (s, 6H), 2.66-2.57 (m, 1H), 2.32 (d, J=12.8 Hz, 1H). ESI [M+H]=464.2

Scheme 22

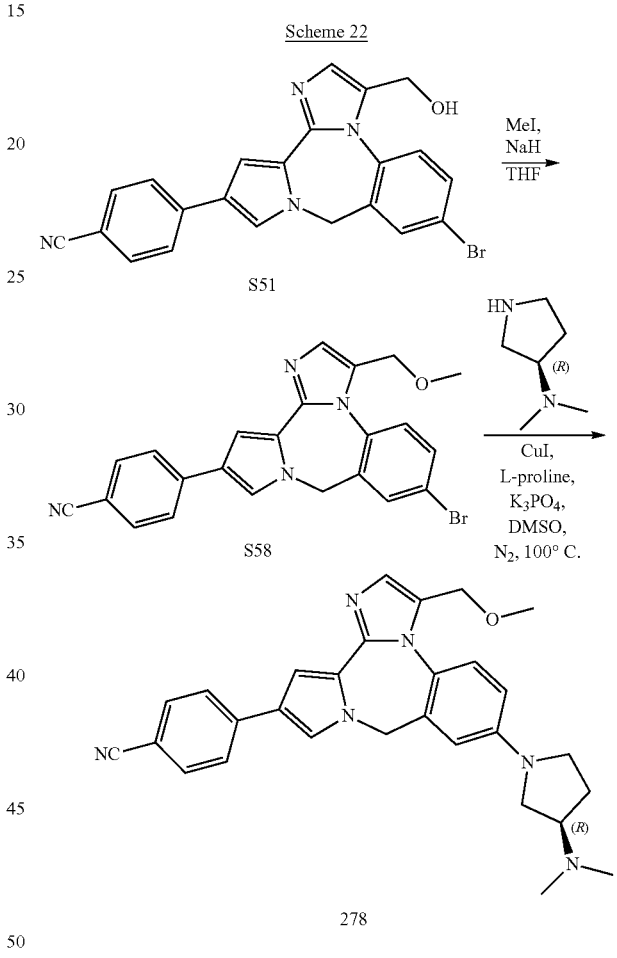

278

Chemistry Experimental Methods:

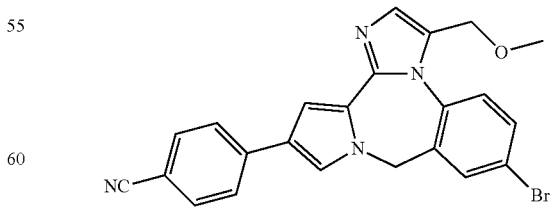

4-(7-bromo-3-(methoxymethyl)-9H-benzo[e]imidazo[2,1-c]pyrrolo[1,2-a][1,4]diazepin-12-yl)benzonitrile, S58. To a solution of 4-(7-bromo-3-(hydroxymethyl)-9H-benzo[e]imidazo[2,1-c]pyrrolo[1,2-a][1,4]diazepin-12-yl)benzonitrile (60 mg, 139 umol, 1.0 eq.) in THF (10 mL) was added NaH (11 mg, 278 umol, 2.0 eq.) at 0° C. After stirred for 0.1 hr, MeI (23.7 mg, 167 umol, 1.2 eq.) was added into the reaction mixture and the mixture was stirred at 10° C. for 16 hr. The mixture was quenched with sat.NH$_4$Cl solution (50 mL), extracted with EtOAc (30 mL*2) and concentrated. The residue was purified by prep-TLC (Sift, Petroleum ether:Ethyl acetate=1:1, R$_f$=0.30) to afford 4-(7-bromo-3-(methoxymethyl)-9H-benzo[e]imidazo[2,1-c]pyrrolo[1,2-a][1,4]diazepin-12-yl)benzonitrile (40 mg) as a yellow solid. ESI [M+H]=445.0/447.0

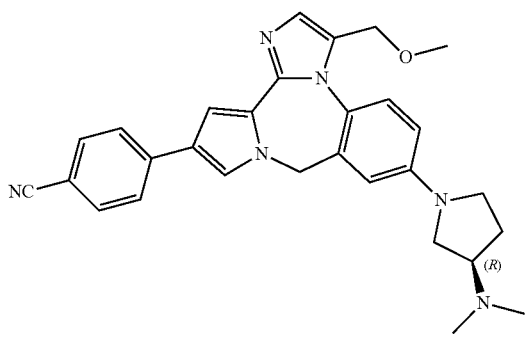

4-(7-((R)-3-(dimethylamino)pyrrolidin-1-yl)-3-(methoxymethyl)-9H-benzo[e]imidazo[2,1-c]pyrrolo[1,2-a][1,4]diazepin-12-yl)benzonitrile, 278. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-(methoxymethyl)-9H-benzo[e]imidazo[2,1-c]pyrrolo[1,2-a][1,4]diazepin-12-yl)benzonitrile, replacing tert-butyl piperazine-1-carboxylate with (R)—N,N-dimethyl pyrrolidin-3-amine. 1H NMR (400 MHz, METHANOL-d4) δ=7.80 (s, 1H), 7.77-7.72 (m, 3H), 7.72-7.66 (m, 3H), 7.25 (d, J=1.3 Hz, 1H), 6.92 (d, J=2.2 Hz, 1H), 6.80 (dd, J=2.6, 8.8 Hz, 1H), 5.27-5.17 (m, 2H), 4.63 (d, J=12.8 Hz, 1H), 4.45 (d, J=12.8 Hz, 1H), 4.08 (quin, J=7.1 Hz, 1H), 3.87-3.78 (m, 1H), 3.74-3.58 (m, 2H), 3.46 (br. s., 1H), 3.42 (s, 3H), 3.03-2.95 (m, 6H), 2.67-2.55 (m, 1H), 2.39-2.24 (m, 1H). ESI [M+H]=479.2

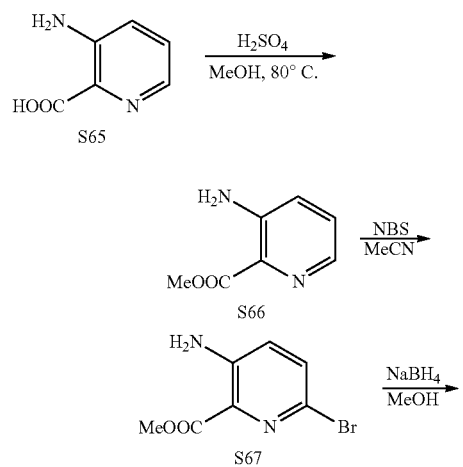

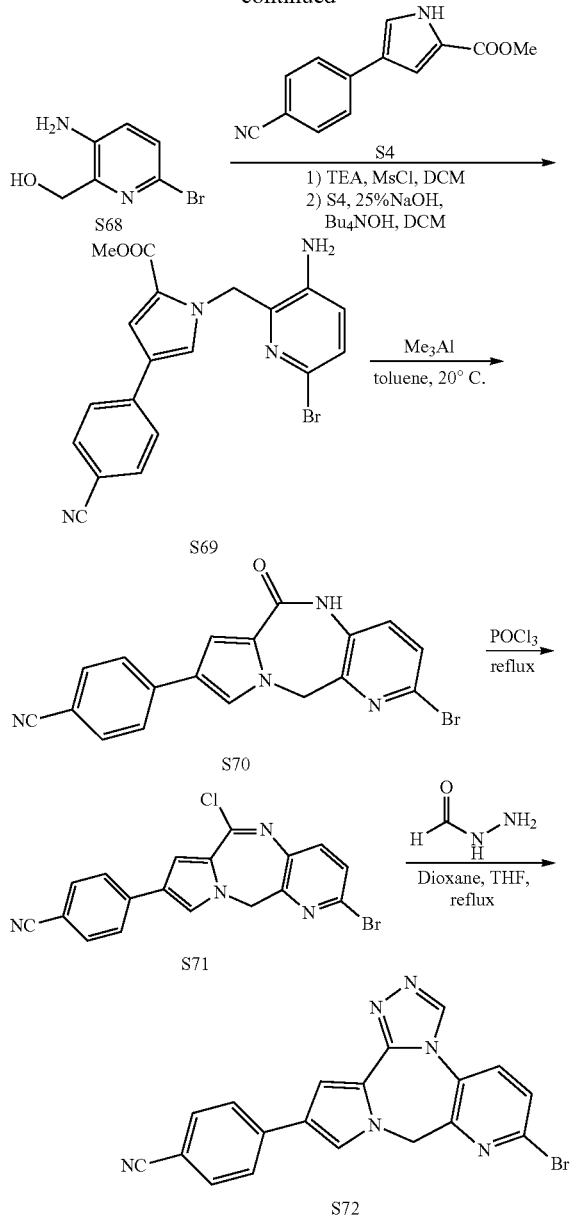

Chemistry Experimental Methods:

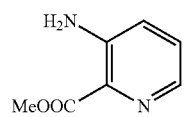

Methyl 3-aminopicolinate, S66. To a suspension of 3-aminopicolinic acid (100 g, 724 mmol, 1.0 eq.) in dry MeOH (1.5 L) was added conc.H$_2$SO$_4$ (460 g, 4.69 mol, 6.48 eq.) dropwise at 15° C. and the mixture was heated to 80° C. and stirred for 5 days. The reaction mixture was concentrated to about 500 mL and diluted with cold water (2 L). The resulting mixture was adjusted to about 9 with solid Na$_2$CO$_3$ at 0° C. and extracted with DCM/MeOH (10:1, 1.0 L×5). The combined orange layers were dried over Na$_2$SO$_4$, filtered and concentrated to give methyl 3-aminopicolinate (60 g, 394.35 mmol, 54.47% yield, 100% purity) as a brown solid. ¹H NMR (400 MHz, CDCl₃) δ=8.08-8.06 (m, 1H), 7.24-7.20 (m, 1H), 7.06-7.01 (m, 1H), 5.75 (br. s, 1H), 3.97 (s, 3H). ESI [M+H]=153.1

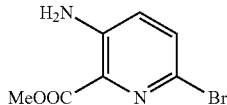

Methyl 3-amino-6-bromopicolinate, S67. To a solution of methyl 3-aminopicolinate (50 g, 328 mmol, 1.0 eq.) in MeCN (600 mL) was added NBS (60 g, 337 mmol, 1.0 eq.) portionwise at 0° C. and the reaction mixture was stirred at 15° C. for 16 hr. The precipitate was collected by filtration to give methyl 3-amino-6-bromo-pyridine-2-carboxylate (48 g, 187 mmol, 56.9% yield, 90% purity) as a light yellow solid, which was used directly without further purification. ¹H NMR (400 MHz, CDCl₃) δ=7.35 (d, J=8.4 Hz, 1H), 6.96 (d, J=8.4 Hz, 1H), 5.83 (br. s, 1H), 3.96 (s, 3H). ESI [M+H]=231.0/233.0

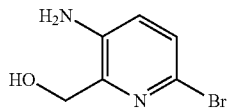

(3-amino-6-bromopyridin-2-yl)methanol, S68. To a solution of methyl 3-amino-6-bromo picolinate (16 g, 69 mmol, 1.0 eq.) in THF (500 mL) and MeOH (50 mL) was added NaBH₄ (10.5 g, 277 mmol, 4.0 eq.) portionwise at 0° C. and the mixture was stirred at 15° C. for 16 hr. The mixture was diluted with EtOAc (2 L) and washed with 10% aq.NH₄Cl (300 mL). The aqueous layer was separated and extracted with EtOAc (200 mL×2). The combined organic layers were dried over Na₂SO₄ and concentrated to give (3-amino-6-bromo-2-pyridyl)methanol (13 g, 57.6 mmol, 83.2% yield, 90% purity) as a light yellow solid. ¹H NMR (400 MHz, DMSO-d6) δ 7.18 (d, J=8.4 Hz, 1H), 6.96 (d, J=8.4 Hz, 1H), 5.36 (br. s, 1H), 5.19 (t, J=5.6 Hz, 1H), 4.43 (d, J=5.6 Hz, 2H). ESI [M+H]=203.0/205.0

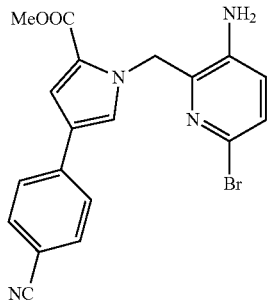 [SMILES: COC(=O)c1cc(-c2ccc(C#N)cc2)cn1Cc1nc(Br)ccc1N]

Methyl 1-((3-amino-6-bromopyridin-2-yl)methyl)-4-(4-cyanophenyl)-1H-pyrrole-2-carboxylate, S69. To a solution of (3-amino-6-bromopyridin-2-yl)methanol (10 g, 49 mmol, 1.0 eq.) and Et₃N (15 g, 148.2 mmol, 3 eq.) in dry DCM (1 L) was added MsCl (6.50 g, 56.7 mmol, 1.15 eq.) dropwise at −70° C. under N₂ atmosphere. The mixture was warmed to 15° C. and stirred for 30 min. Then the mixture was cooled to 0° C. and methyl 4-(4-cyanophenyl)-1H-pyrrole-2-carboxylate (8.5 g, 37 mmol, 0.76 eq.), Bu₄NOH (25% in H₂O, 5.0 g, 4.8 mmol, 0.1 eq.) and NaOH aq. (25% in H2O, 30 g, 187 mmol, 3.8 eq.) was added in turn. The reaction mixture was warmed to 15° C. and stirred for another 16 hr. The mixture was washed with brine (1 L), dried over Na₂SO₄, then concentrated to give methyl 1-((3-amino-6-bromo pyridin-2-yl)methyl)-4-(4-cyanophenyl)-1H-pyrrole-2-carboxylate (13 g, crude) as a brown solid, which was used directly. ESI [M+H]=411.0/413.0

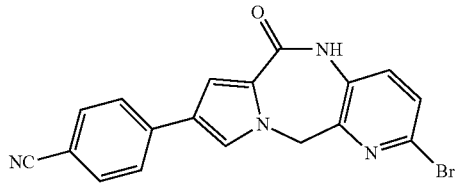 [SMILES: N#Cc1ccc(-c2cc3n(c2)Cc2nc(Br)ccc2NC3=O)cc1]

4-(2-bromo-6-oxo-6,11-dihydro-5H-pyrido[3,2-e]pyrrolo[1,2-a][1,4]diazepin-8-yl)benzonitrile, S70. To a suspension of methyl 1-[(3-amino-6-bromo-2-pyridyl)methyl]-4-(4-cyano phenyl)pyrrole-2-carboxylate (22 g, 24 mmol, 1.0 eq.) in dry toluene (2.0 L) was added AlMe₃ (2 M in toluene, 65 mL, 5.4 eq.) dropwise at 0° C. under N₂ atmosphere. The reaction mixture was warmed to 15° C. and stirred for 16 hr. Cold sat. NH₄Cl aq. (500 mL) and water (500 mL) was added. The resulting precipitate was collected by filtration (Little product dissolved in toluene layer). The crude product was washed with THF (1 L) and the solid was collected by filtration to give 4-(2-bromo-6-oxo-6,11-dihydro-5H-pyrido[3,2-e]pyrrolo[1,2-a][1,4]diazepin-8-yl)benzonitrile (12 g, 27.5 mmol, 57% yield, 86.8% purity) as a light yellow solid, which was used directly. ¹H NMR (400 MHz, DMSO-d₆) δ=10.43 (br. s, 1H), 7.91 (br. s, 1H), 7.77 (br. s, 4H), 7.67-7.65 (m, 1H), 7.56-7.54 (m, 1H), 7.36 (br. s, 1H), 5.37 (s, 2H). ESI [M+H]=379.0.

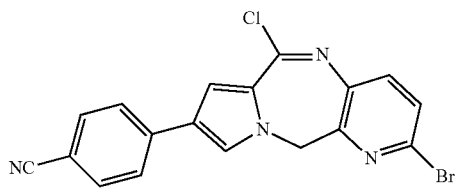 [SMILES: N#Cc1ccc(-c2cc3n(c2)Cc2nc(Br)ccc2N=C3Cl)cc1]

4-(2-bromo-6-chloro-11H-pyrido[3,2-e]pyrrolo[1,2-a][1,4]diazepin-8-yl)benzonitrile, S71. A suspension of 4-(2-bromo-6-oxo-6,11-dihydro-5H-pyrido[3,2-e]pyrrolo[1,2-a][1,4]diazepin-8-yl)benzonitrile (2.0 g, 4.54 mmol, 1.0 eq.) in POCl₃ (100 mL) was heated to 100° C. and stirred for 3.5 hr. The reaction mixture was concentrated to give 4-(2-bromo-6-chloro-11H-pyrido[3,2-e]pyrrolo[1,2-a][1,4]diazepin-8-yl)benzonitrile (2.0 g, crude) as a dark-yellow solid, which was used directly.

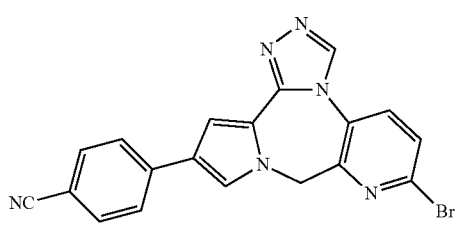

4-(7-bromo-9H-pyrido[3,2-e]pyrrolo[1,2-a][1,2,4]triazolo[3,4-c][1,4]diazepin-12-yl) benzonitrile, S72. A mixture of 4-(2-bromo-6-chloro-11H-pyrido[3,2-e]pyrrolo[1,2-a][1,4] diazepin-8-yl)benzonitrile (1.8 g, 4.5 mmol, 1.0 eq.) and formohydrazide (1.8 g, 30 mmol, 6.6 eq.) in dry dioxane (40 mL) and dry THF (10 mL) was stirred at 120° C. in sealing tube for 16 hr. The mixture was concentrated and the residue solid was washed with 1M HCl (20 mL) and EtOAc (20 mL), filtered and dried in vacuum to give 4-(7-bromo-9H-pyrido[3,2-e]pyrrolo[1,2-a][1,2,4]triazolo[3,4-c][1,4]diazepin-12-yl)benzonitrile (1.33 g, crude) as a yellow solid, which was used directly. ESI [M+H]=403.0/405.0

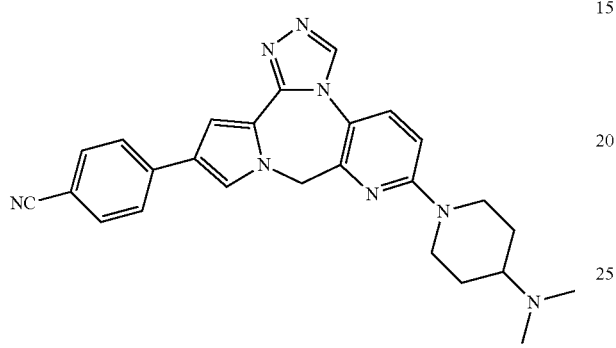

4-(7-(4-(dimethylamino)piperidin-1-yl)-9H-pyrido[3,2-e]pyrrolo[1,2-a][1,2,4]triazolo[3,4-c][1,4]diazepin-12-yl)benzonitrile, 293. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-pyrido[3,2-e]pyrrolo[1,2-a][1,2,4]triazolo[3,4-c][1,4]diazepin-12-yl)benzonitrile and replacing tert-butyl piperazine-1-carboxylate with N,N-dimethylpiperidin-4-amine. $^1$H NMR (400 MHz, METHANOL-d$_4$) δ=9.07 (br. s., 1H), 7.87 (d, J=9.0 Hz, 1H), 7.77-7.71 (m, 2H), 7.70-7.64 (m, 3H), 7.27 (br. s., 1H), 7.02 (d, J=9.0 Hz, 1H), 5.24 (s, 2H), 4.72 (d, J=13.7 Hz, 2H), 3.51 (ddd, J=3.9, 8.3, 11.9 Hz, 1H), 3.00 (t, J=12.2 Hz, 2H), 2.89 (s, 6H), 2.18 (d, J=11.2 Hz, 2H), 1.70 (dq, J=4.0, 12.1 Hz, 2H). ESI [M+H]=451.2

Scheme 26

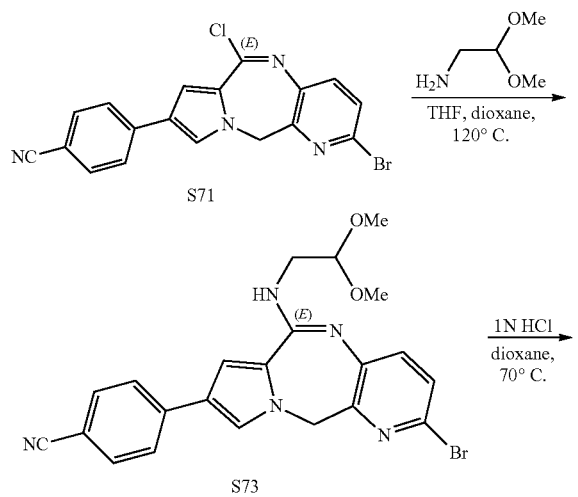

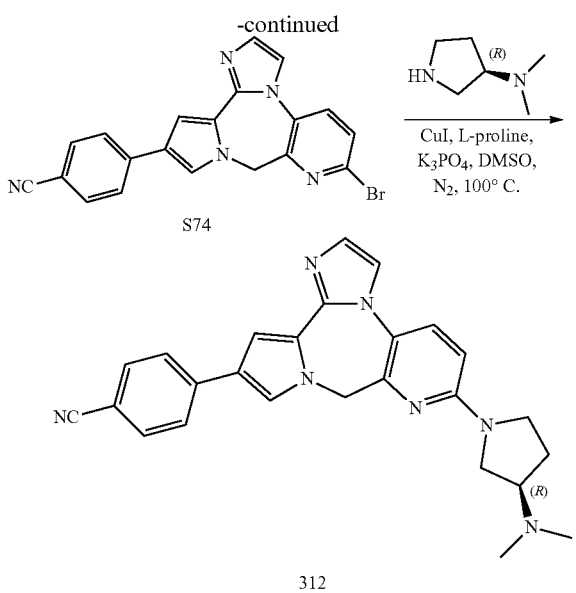

Chemistry Experimental Methods:

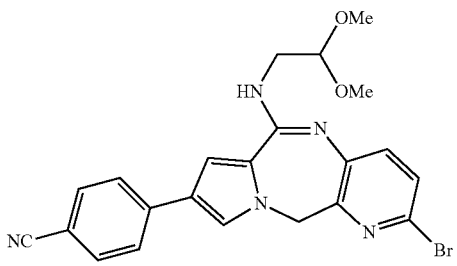 [SMILES: COC(CNC1=Nc2ccc(Br)nc2Cn2cc(-c3ccc(C#N)cc3)cc21)OC]

4-(2-bromo-6-((2,2-dimethoxyethyl)amino)-11H-pyrido[3,2-e]pyrrolo[1,2-a][1,4]diazepin-8-yl)benzonitrile, S73. A mixture of 4-(2-bromo-6-chloro-11H-pyrido[3,2-e]pyrrolo[1,2-a][1,4]diazepin-8-yl)benzonitrile (2.1 g, crude) and 2,2-dimethoxyethanamine (12 g, 100 mmol, 19.07 eq.) in dry dioxane (100 mL) was heated to 100° C. for 16 hr and then concentrated. The residue was dissolved in EtOAc (200 mL), washed with sat.Na$_2$CO$_3$ (50 mL), 1M HCl (50 mL) and brine (50 mL). The organic layer was dried and concentrated to give 4-(2-bromo-6-((2,2-dimethoxyethyl)amino)-11H-pyrido[3,2-e]pyrrolo[1,2-a][1,4]diazepin-8-yl)benzonitrile (2.5 g, crude) as a brown solid, which was used directly. ESI [M+H]=466.0/468.0

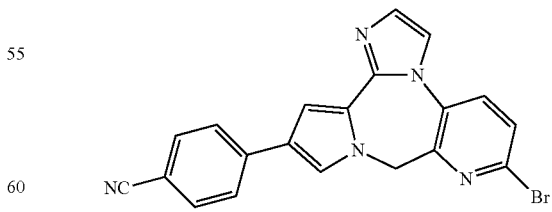

4-(7-bromo-9H-imidazo[2,1-c]pyrido[3,2-e]pyrrolo[1,2-a][1,4]diazepin-12-yl)benzonitrile, S74. A suspension of 4-(2-bromo-6-((2,2-dimethoxyethyl)amino)-11H-pyrido[3,2-e]pyrrolo[1,2-a][1,4]diazepin-8-yl)benzonitrile (700 mg, 1.50 mmol, 1.0 eq.) in dioxane (25 mL) and 1 M HCl (25 mL) was heated to 60° C. for 10 hr and then concentrated. The residue solid was washed with THF (30 mL) to give 4-(7-bromo-9H-imidazo[2,1-c]pyrido[3,2-e]pyrrolo[1,2-a][1,4]diazepin-12-yl)benzonitrile (450 mg, 1.04 mmol, 69.36% yield, 93% purity) as a white solid, which was used directly without further purification.

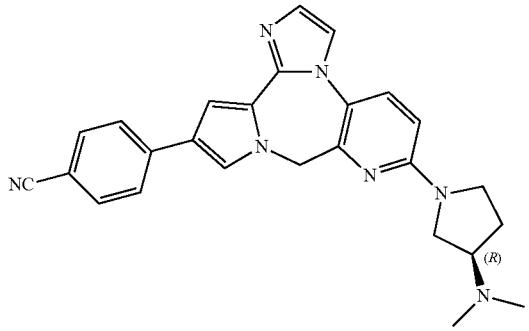

(R)-4-(7-(3-(dimethylamino)pyrrolidin-1-yl)-9H-imidazo[2,1-c]pyrido[3,2-e]pyrrolo[1,2-a][1,4]diazepin-12-yl)benzonitrile, 312. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile and replacing tert-butyl piperazine-1-carboxylate with (R)—N,N-dimethylpyrrolidin-3-amine. $^1$H NMR (400 MHz, METHANOL-$d_4$) δ=8.06-7.99 (m, 1H), 7.93 (d, J=9.0 Hz, 1H), 7.84 (s, 1H), 7.78-7.76 (m, 3H), 7.73-7.68 (m, 2H), 7.36 (s, 1H), 6.77 (d, J=9.0 Hz, 1H), 5.37 (s, 2H), 4.16-4.04 (m, 2H), 3.91-3.83 (m, 1H), 3.82-3.73 (m, 1H), 3.65-3.55 (m, 1H), 3.00 (s, 6H), 2.68-2.56 (m, 1H), 2.41-2.29 (m, 1H). ESI [M+H]=436.1

Scheme 27

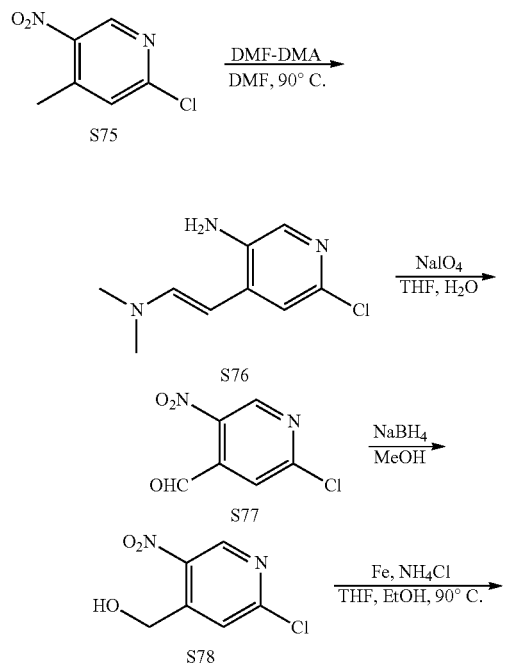

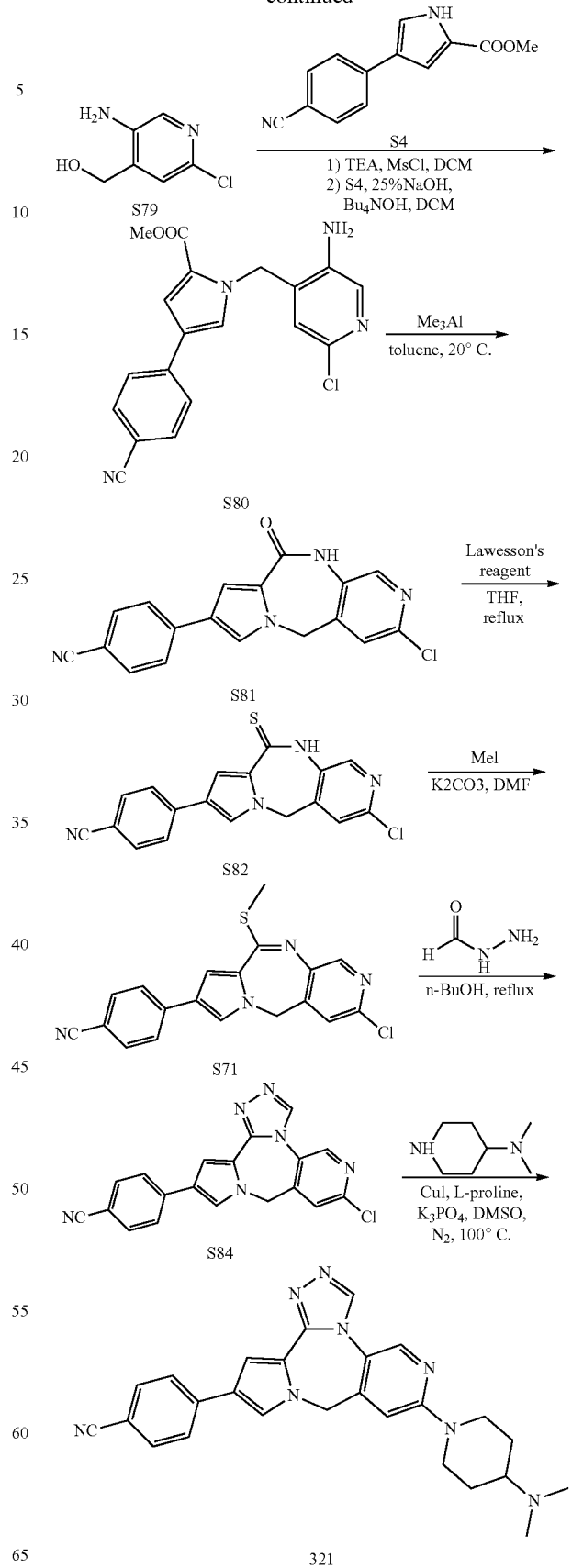

Chemistry Experimental Methods:

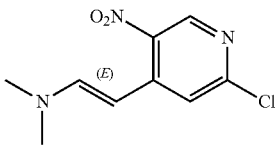

(E)-2-(2-chloro-5-nitropyridin-4-yl)-N,N-dimethylethenamine, S76. To a solution of 2-chloro-4-methyl-5-nitropyridine (40 g, 231 mmol, 1.0 eq.) in DMF (200 mL) was added DMF-DMA (55 g, 463 mmol, 2.0 eq.) at 20° C. and the mixture was stirred at 90° C. for 5 hr. Then the mixture was poured into cold water (300 mL) and the precipitate was collected by filtration to give crude (E)-2-(2-chloro-5-nitro-4-pyridyl)-N,N-dimethyl-ethenamine (44.3 g, crude) as a red solid, without further purification.

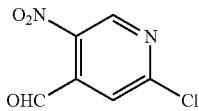

2-chloro-5-nitroisonicotinaldehyde, S77. To a solution of (E)-2-(2-chloro-5-nitro-4-pyridyl)-N,N-dimethyl-ethenamine (44.3 g, 194.6 mmol, 1.0 eq.) in THF (250 mL) and H$_2$O (250 mL) was added NaIO$_4$ (145 g, 681 mmol, 3.5 eq.) portionwise at 20° C. and the reaction mixture was stirred at 20° C. for 16 hr. Then the mixture was filtered and filter cake was washed with EtOAc (100 mL×2). The filtrate was extracted with EtOAc (500 mL×2). The combined organic layers were washed with brine (300 mL), dried over Na$_2$SO$_4$ and concentrated to give 2-chloro-5-nitroisonicotinaldehyde (37.2 g, 92% yield, 90% purity) as a black brown oil. 1H NMR (400 MHz, CHLOROFORM-d) δ=10.49 (br. s., 1H), 9.23 (br. s., 1H), 7.74(br. s., 1H).

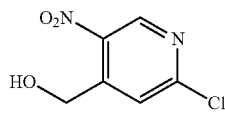

(2-chloro-5-nitropyridin-4-yl)methanol, S78. To a solution of 2-chloro-5-nitroisonicotinaldehyde (40 g, 214 mmol, 1.0 eq.) in MeOH (300 mL) was added NaBH$_4$ (12.1 g, 321.6 mmol, 1.5 eq.) portionwise at 0° C. The mixture was stirred at 0° C. for 3 hr and quenched by sat.NH$_4$Cl (200 mL). After MeOH was removed, the aqueous layer was extracted with EtOAc (200 mL*2). The organic layer was washed with brine (200 mL), dried over MgSO$_4$ and concentrated. The residue was purified by column chromatography (SiO$_2$, Petroleum ether:Ethyl acetate from 20:1 to 10:1) to give (2-chloro-5-nitropyridin-4-yl)methanol (19.5 g, 103.4 mmol, 48.2% yield) as a yellow solid. 1H NMR (400 MHz, CHLOROFORM-d) δ=9.12 (br. s., 1H), 7.92 (br. s., 1H), 5.16-5.14 (m, J=2.2 Hz, 2H).

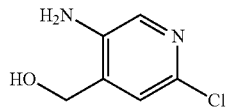

(5-amino-2-chloropyridin-4-yl)methanol, S79. To a solution of (2-chloro-5-nitropyridin-4-yl) methanol (16 g, 84.8 mmol, 1.0 eq.) in EtOH (160 mL) and THF (160 mL) was added Fe (23.6 g, 424 mmol, 5.0 eq.) and sat.NH$_4$Cl (80 mL). The mixture was stirred at 90° C. for 1 hr and filtered. The filtrate was concentrated and the residue was purified by column chromatography (Petroleum ether:Ethyl acetate=2:1, Rf=0.12) to give (5-amino-2-chloropyridin-4-yl)methanol (12.9 g, 74.83 mmol, 88.19% yield, 92% purity) as yellow solid. ESI [M+H]=158.8

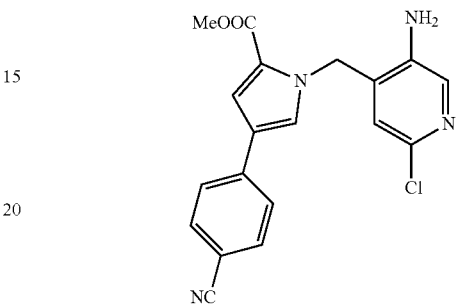

Methyl 1-((5-amino-2-chloropyridin-4-yl)methyl)-4-(4-cyanophenyl)-1H-pyrrole-2-carboxylate, S80. To a solution of (5-amino-2-chloropyridin-4-yl)methanol (4.0 g, 25.2 mmol, 1.0 eq.) and TEA (7.6 g, 75.6 mmol, 3.0 eq.) in DCM (320 mL) was added MsCl (4.3 g, 37.8 mmol, 1.5 eq.) at −70° C. The mixture was allowed to warm to 20° C. slowly and stirred for 3 hr. Then methyl 4-(4-cyanophenyl)-1H-pyrrole-2-carboxylate (4.5 g, 20.1 mmol, 0.8 eq.) was added followed by aq.NaOH (25%, 6.00 eq.) and tetrabutylammonium hydroxide (2.62 g, 2.52 mmol, 0.1 eq.) at 0° C. After addition, the mixture was stirred at 15° C. for 16 hr. Then the resulting mixture was diluted with water (500 mL) and extracted with DCM (100 mL*2). The combined organic layers were dried over anhydrous MgSO$_4$, filtered and concentrated to afford methyl 1-((5-amino-2-chloropyridin-4-yl)methyl)-4-(4-cyanophenyl)-1H-pyrrole-2-carboxylate (2.2 g, 4.4 mmol, 17.6% yield, 74% purity) as a yellow solid. 1H NMR (400 MHz, CHLOROFORM-d) δ=7.86 (s, 1H), 7.64-7.62 (m, 2H), 7.58-7.56 (m, 2H), 7.34-7.33 (m, 1H), 7.21 (br. s., 1H), 6.71 (br. s., 1H), 5.45 (br. s., 2H), 3.86-3.85 (m, 3H). ESI [M+H]=367.0

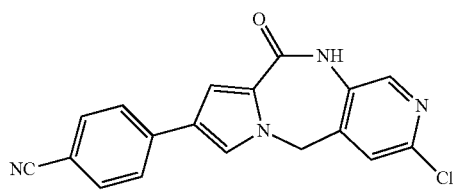 [SMILES: N#Cc1ccc(-c2cc3n(c2)Cc2cc(Cl)ncc2NC3=O)cc1]

4-(3-chloro-10-oxo-10,11-dihydro-5H-pyrido[3,4-e]pyrrolo[1,2-a][1,4]diazepin-8-yl)benzonitrile, S81. To a solution of methyl 1-((5-amino-2-chloropyridin-4-yl)methyl)-4-(4-cyano phenyl)-1H-pyrrole-2-carboxylate (2.3 g, 6.2 mmol, 1.0 eq.) in toluene (25 mL) was added AlMe$_3$ (2 M, 15.6 mL, 5.0 eq.) and the mixture was stirred at 20° C. for 16 hr. The mixture was poured into cold water (100 mL) and extracted with EtOAc (200 mL*2). The organic layer was washed with brine (100 mL), dried over MgSO$_4$ and concentrated. The residue solid was washed with EtOH (20 mL). After filtration, the filter cake was collected to give 4-(3-chloro-10-oxo-10,11-dihydro-5H-pyrido[3,4-e]pyrrolo[1,2-a][1,4]diazepin-8-yl)benzonitrile (1.82 g, 4.73 mmol, 75.44% yield, 87% purity) as a yellow solid. ESI [M+H]= 334.9

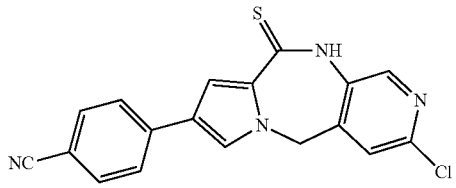 [SMILES: N#Cc1ccc(-c2cc3n(c2)Cc2cc(Cl)ncc2NC3=S)cc1]

4-(3-chloro-10-thioxo-10,11-dihydro-5H-pyrido[3,4-e]pyrrolo[1,2-a][1,4]diazepin-8-yl)benzonitrile, S82. To a solution of 4-(3-chloro-10-oxo-10,11-dihydro-5H-pyrido[3,4-e] pyrrolo[1,2-a][1,4]diazepin-8-yl)benzonitrile (1.8 g, 5.4 mmol, 1.0 eq.) in THF (20 mL) was added Lawesson's reagent (2.6 g, 6.5 mmol, 1.2 eq.) and the mixture was stirred at 70° C. for 1 hr. The mixture was concentrated and the residue was washed with MeOH (20 mL). After filtration, the filter cake was collected and concentrated to give crude 4-(3-chloro-10-thioxo-10,11-dihydro-5H-pyrido[3,4-e]pyrrolo[1,2-a][1,4]diazepin-8-yl)benzonitrile (1.39 g, crude) as a yellow solid.

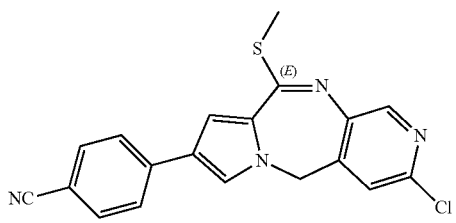 [SMILES: CSC1=Nc2cnc(Cl)cc2Cn2cc(-c3ccc(C#N)cc3)cc21]

4-(3-chloro-10-(methylthio)-5H-pyrido[3,4-e]pyrrolo[1,2-a][1,4]diazepin-8-yl)benzonitrile, S83. To a suspension of 4-(3-chloro-10-thioxo-10,11-dihydro-5H-pyrido[3,4-e]pyrrolo[1,2-a] [1,4]diazepin-8-yl)benzonitrile (1.4 g, 3.9 mmol, 1.0 eq.) and $K_2CO_3$ (3.8 g, 27.7 mmol, 7.0 eq.) in DMF (20 mL) was added MeI (1.1 g, 7.9 mmol, 2.0 eq.) at 0° C. The mixture was stirred at 20° C. for 1 hr and filtered. The filtrate was concentrated to give 4-(3-chloro-10-(methylthio)-5H-pyrido[3,4-e]pyrrolo[1,2-a][1,4]diazepin-8-yl)benzonitrile (1.3 g, crude) as a yellow solid.

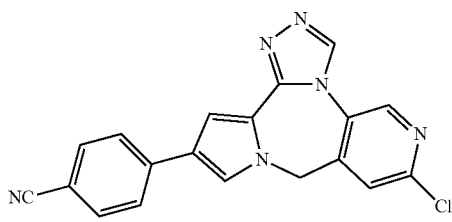 [SMILES: N#Cc1ccc(-c2cc3n(c2)Cc2cc(Cl)ncc2-n2cnnc2-3)cc1]

4-(7-chloro-9H-pyrido[3,4-e]pyrrolo[1,2-a][1,2,4]triazolo[3,4-c][1,4]diazepin-12-yl)benzonitrile, S84. A mixture of 4-(3-chloro-10-(methylthio)-5H-pyrido[3,4-e]pyrrolo[1,2-a][1,4] diazepin-8-yl)benzonitrile (535 mg, 8.9 mmol, 2.5 eq.) and formohydrazide (3.0 g) in n-BuOH (20 mL) was stirred at 130° C. for 16 hr and concentrated. The residue was washed with 1N HCl (20 mL) and EtOH (10 mL). After filtration, the filter cake was colleted to give 4-(7-chloro-9H-pyrido[3,4-e]pyrrolo[1,2-a][1,2,4]triazolo[3,4-c][1,4]diazepin-12-yl)benzonitrile (600 mg, 33.3% yield, 71% purity) as a yellow solid. ESI [M+H]=358.9

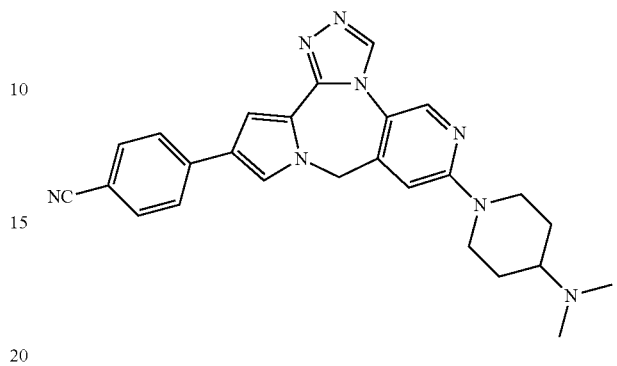

4-(7-(4-(dimethylamino)piperidin-1-yl)-9H-pyrido[3,4-e]pyrrolo[1,2-a][1,2,4]triazolo[3,4-c][1,4]diazepin-12-yl)benzonitrile, 321. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-chloro-9H-pyrido[3,4-e]pyrrolo[1,2-a][1,2,4]triazolo[3,4-c][1,4]diazepin-12-yl)benzonitrile and replacing tert-butyl piperazine-1-carboxylate with N,N-dimethylpiperidin-4-amine. 1H NMR (400 MHz, METHANOL-d4) δ=9.15 (br. s., 1H), 8.42 (s, 1H), 7.76-7.58 (m, 5H), 7.26 (br. s., 1H), 7.13 (s, 1H), 5.22 (s, 2H), 4.66 (d, J=13.7 Hz, 2H), 3.51 (ddd, J=3.9, 8.3, 11.9 Hz, 1H), 3.01 (t, J=12.5 Hz, 2H), 2.92-2.80 (m, 6H), 2.16 (d, J=11.5 Hz, 2H), 1.70 (dq, J=4.0, 12.1 Hz, 2H). ESI [M+H]=451.2

Scheme 28

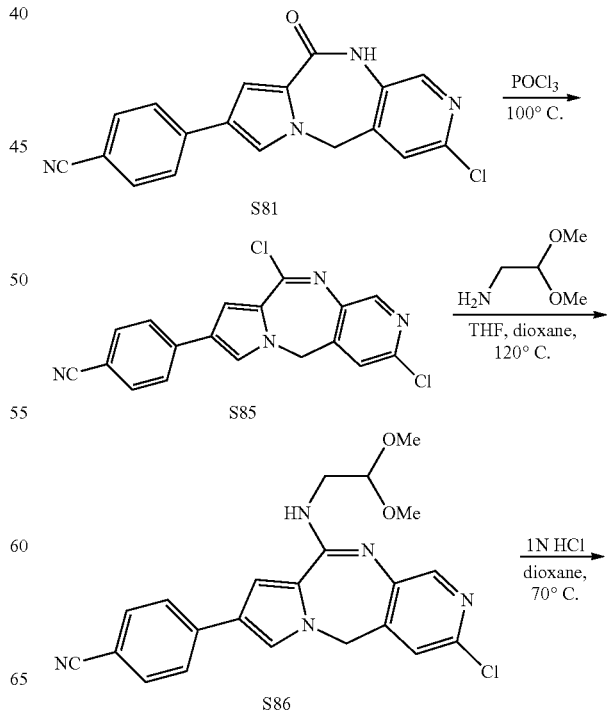

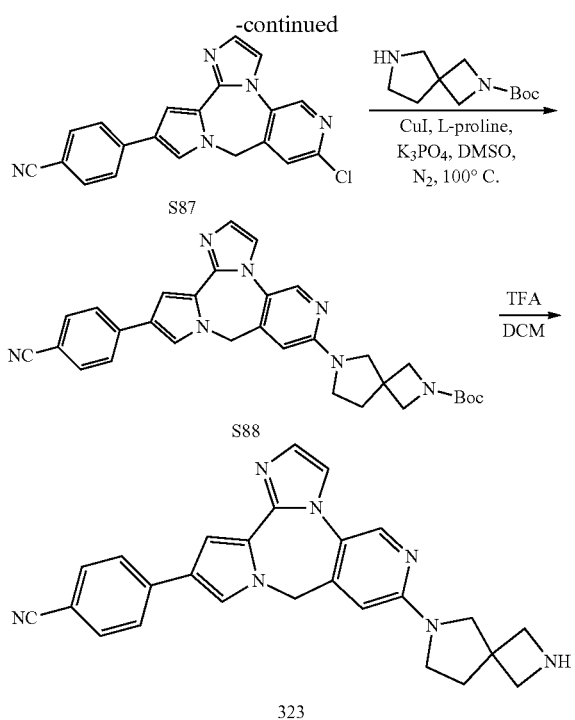

Chemistry Experimental Methods:

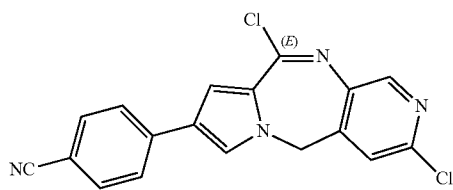 [SMILES: N#Cc1ccc(-c2cc3n(c2)Cc2cc(Cl)ncc2N=C3Cl)cc1]

4-(3,10-dichloro-5H-pyrido[3,4-e]pyrrolo[1,2-a][1,4]diazepin-8-yl)benzonitrile, S85. A solution of 4-(3-chloro-10-oxo-10,11-dihydro-5H-pyrido[3,4-e]pyrrolo[1,2-a][1,4]diazepin-8-yl) benzonitrile (500 mg, 1.49 mmol, 1.0 eq.) in POCl₃ (30 mL) was stirred at 90° C. for 1 hr and concentrated to give 4-(3,10-dichloro-5H-pyrido[3,4-e]pyrrolo[1,2-a][1,4]diazepin-8-yl)benzonitrile (550 mg, crude, HCl) as a black brown oil.

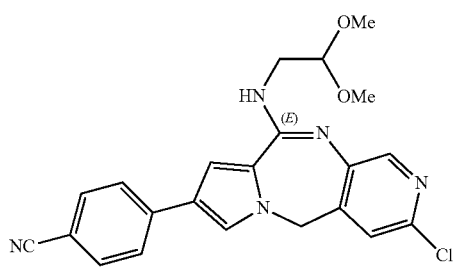 [SMILES: COC(CNC1=Nc2cnc(Cl)cc2Cn2cc(-c3ccc(C#N)cc3)cc21)OC]

4-(3-chloro-10-((2,2-dimethoxyethyl)amino)-5H-pyrido[3,4-e]pyrrolo[1,2-a][1,4]diazepin-8-yl)benzonitrile, S86. A solution of 4-(3,10-dichloro-5H-pyrido[3,4-e]pyrrolo[1,2-a][1,4] diazepin-8-yl)benzonitrile (550 mg, 1.41 mmol, 1.0 eq., HCl) in THF (10 mL) and dioxane (10 mL) was adjusted to pH=9 with TEA, then 2,2-dimethoxyethanamine (1.48 g, 14.1 mmol, 1.53 mL, 10.0 eq.) was added and the mixture was stirred at 120° C. for 16 hr under sealing tube. After the reaction was complete, the mixture was poured into 0.5 M HCl (50 mL) and extracted with hot EtOAc/THF=1/1 (50 mL*3). The organic layer was washed with brine (50 mL), dried over MgSO₄ and concentrated. The residue was purified by column chromatography (Petroleum ether:Ethyl acetate=1:1, Rf=0.53) to give 4-(3-chloro-10-((2,2-dimethoxyethyl)amino)-5H-pyrido[3,4-e]pyrrolo[1,2-a][1,4]diazepin-8-yl)benzonitrile (130 mg, 150 umol, 10.6% yield, 48.8% purity) as a yellow solid. ESI [M+H]=422.1

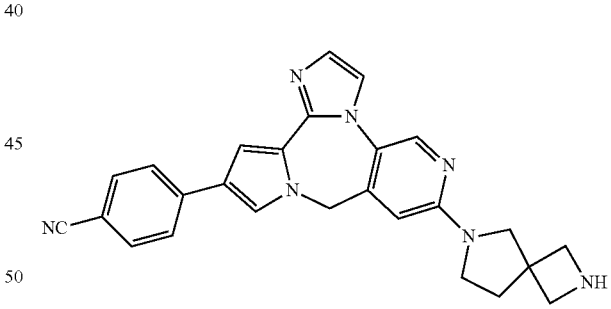

4-(7-chloro-9H-imidazo[2,1-c]pyrido[3,4-e]pyrrolo[1,2-a][1,4]diazepin-12-yl)benzonitrile, S87. A solution of 4-(3-chloro-10-((2,2-dimethoxyethyl)amino)-5H-pyrido[3,4-e]pyrrolo[1,2-a][1,4]diazepin-8-yl)benzonitrile (130 mg, 150 umol, 1.0 eq.) in dioxane (6.0 mL) and 1M HCl (6.0 mL) was stirred at 80° C. for 16 hr. After the reaction was complete, the mixture was concentrated. The residue solid was washed with THF (5 mL) and filtered. The filter cake was collected to give crude product 4-(7-chloro-9H-imidazo[2,1-c]pyrido[3,4-e]pyrrolo[1,2-a][1,4] diazepin-12-yl)benzonitrile (70 mg, crude, HCl) as a black solid without further purification. ESI [M+H]=358.1

4-(7-(2,6-diazaspiro[3.4]octan-6-yl)-9H-imidazo[2,1-c]pyrido[3,4-e]pyrrolo[1,2-a][1,4] diazepin-12-yl)benzonitrile, 323. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-chloro-9H-imidazo[2,1-c]pyrido[3,4-e]pyrrolo[1,2-a][1,4]diazepin-12-yl)benzonitrile and replacing tert-butyl piperazine-1-carboxylate with tert-butyl 2,6-diazaspiro[3.4]octane-2-carboxylate. 1H NMR (400 MHz, METHANOL-d4) δ=8.40 (s, 1H), 8.08 (m, 1H), 7.80-7.68 (d, J=9.9 Hz, 6H), 7.34 (d, J=1.8 Hz, 1H), 7.33 (d, J=1.1 Hz, 1H), 5.11 (s, 2H), 4.00-3.92 (m, 2H), 3.91-3.83 (m, 2H), 3.73 (s, 2H), 3.54 (t, J=6.9 Hz, 2H), 2.33 (t, J=6.9 Hz, 2H). ESI [M+H]=434.1

Scheme 29
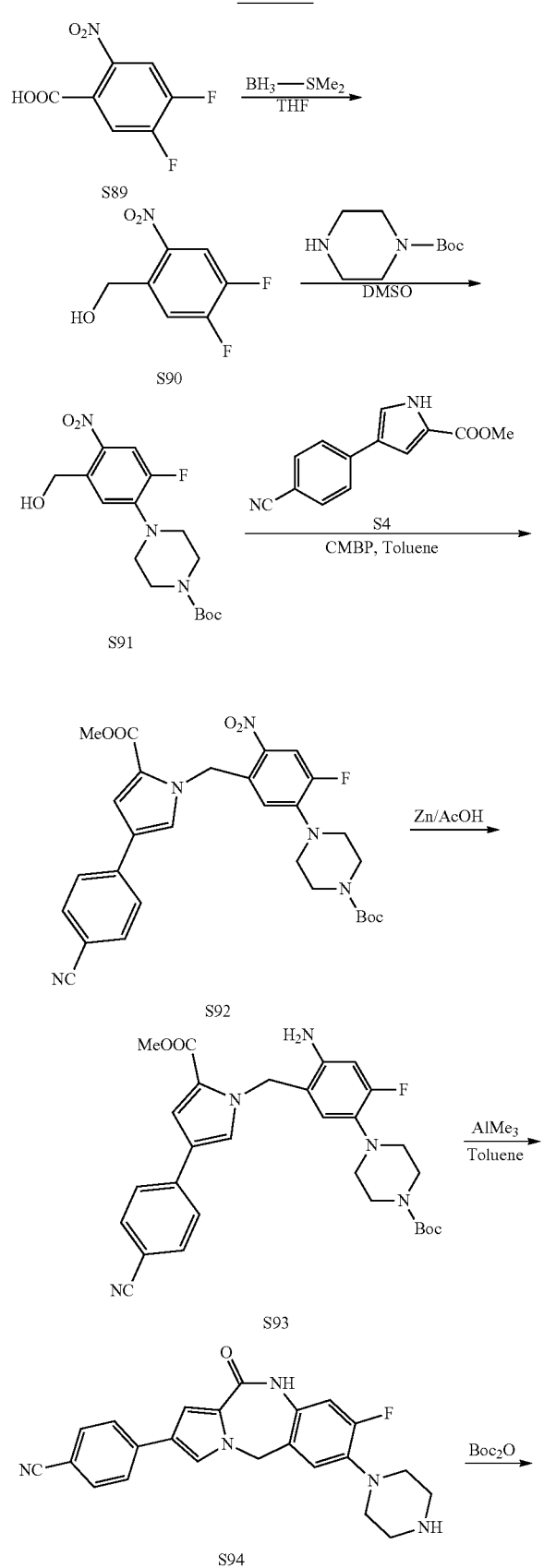
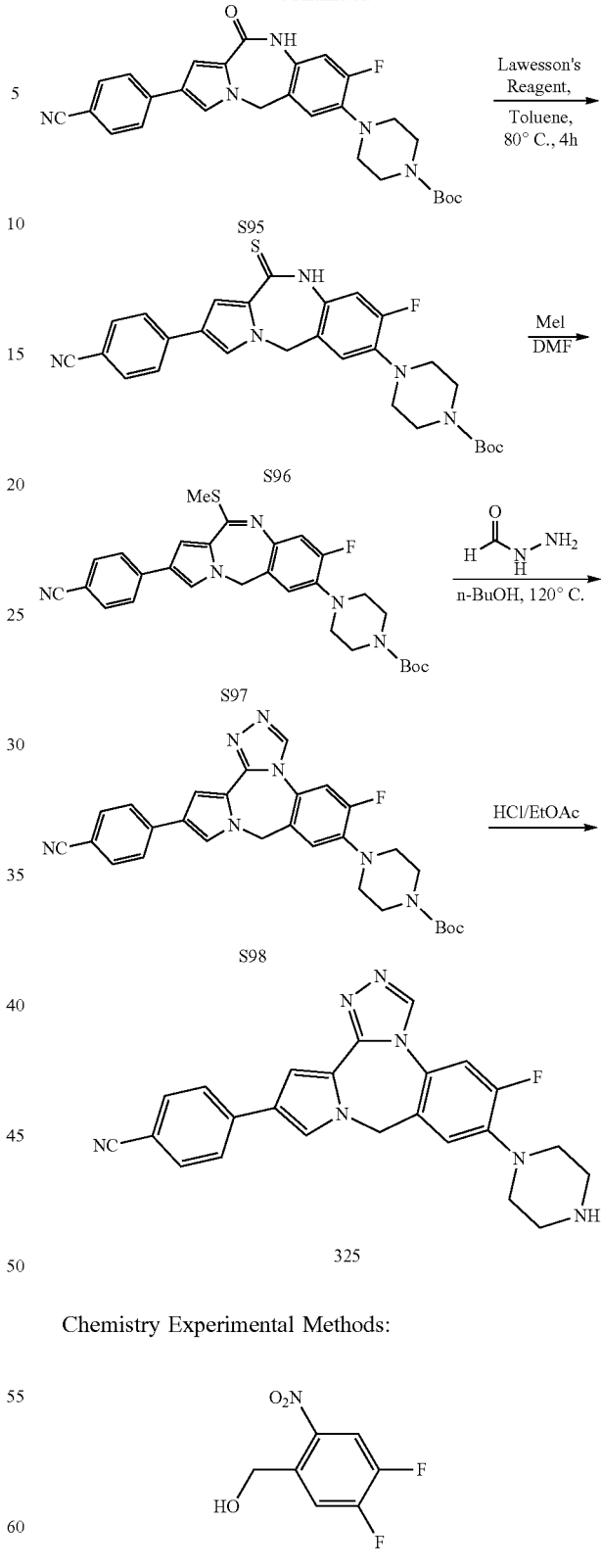
Chemistry Experimental Methods:
(4,5-difluoro-2-nitrophenyl)methanol, S90. To a solution of 4,5-difluoro-2-nitrobenzoic acid (8.0 g, 39.39 mmol, 1.0 eq.) in THF (80 mL) was added a solution of $BH_3\text{-}Me_2S$ (10 M, 11.82 mL, 3.0 eq.) drop-wise at 0° C. over a period of 30 min under $N_2$. The reaction mixture was heated to 70° C.

over a period of 30 min and stirred at 70° C. for 3 hr. The reaction was quenched by ice water slowly and then extracted with ethyl acetate (50 mL*3). The combined organic phase was washed with brine (10 mL*2), dried over Na$_2$SO$_4$, filtered and concentrated to give (4,5-difluoro-2-nitrophenyl)methanol (7.2 g, crude) as a yellow solid. TLC: R$_f$=0.6 (Petroleum ether/Ethyl acetate=3/1).

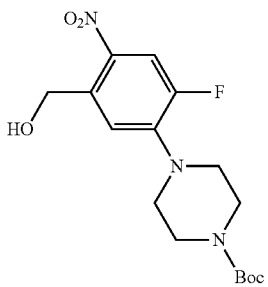

Tert-butyl 4-(2-fluoro-5-(hydroxymethyl)-4-nitrophenyl)piperazine-1-carboxylate, S91. A mixture of (4,5-difluoro-2-nitrophenyl)methanol (7.6 g, 40.3 mmol, 1.00 eq.) and tert-butyl piperazine-1-carboxylate (9.0 g, 48.4 mmol, 1.2 eq.) in DMSO (80 mL) was heated to 90° C. for 3 hr and poured into ice-water (100 mL). The aqueous phase was extracted with ethyl acetate (200 mL*3). The combined organic phase was washed with brine (20 mL*2), dried with anhydrous Na$_2$SO$_4$, filtered and concentrated in vacuum to afford tert-butyl 4-(2-fluoro-5-(hydroxylmethyl)-4-nitrophenyl)piperazine-1-carboxylate (11.26 g, crude) as a yellow solid. TLC: R$_f$=0.35 (Petroleum ether/Ethyl acetate=3/1). 1H NMR (400 MHz, CHLOROFORM-d) δ=7.85 (d, J=13.2 Hz, 1H), 7.09 (d, J=8.4 Hz, 1H), 4.89 (br. s., 2H), 3.61-3.49 (m, 4H), 3.31-3.14 (m, 4H), 1.42 (s, 9H).

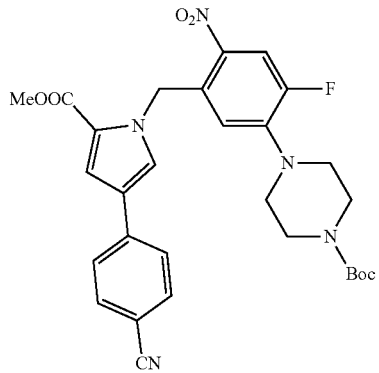 [SMILES: COC(=O)c1cc(-c2ccc(C#N)cc2)cn1Cc1cc(N2CCN(C(=O)OC(C)(C)C)CC2)c(F)cc1[N+](=O)[O-]]

Tert-butyl 4-(5-((4-(4-cyanophenyl)-2-(methoxycarbonyl)-1H-pyrrol-1-yl)methyl)-2-fluoro-4-nitrophenyl)piperazine-1-carboxylate, S92. To a mixture of tert-butyl 4-(2-fluoro-5-(hydroxymethyl)-4-nitrophenyl)piperazine-1-carboxylate (863 mg, 2.43 mmol, 1.1 eq.) and methyl 4-(4-cyanophenyl)-1H-pyrrole-2-carboxylate (500 mg, 2.21 mmol, 1.0 eq.) in Tol. (10 mL) was added 2-(tributylphosphanylidene)acetonitrile (1.07 g, 4.42 mmol, 2.0 eq.) in one portion at 30° C. under N$_2$. The mixture was stirred at 30° C. for 30 min, then heated to 100° C. and stirred for 11.5 hr. The mixture was concentrated and diluted with ice-water (50 mL). The aqueous phase was extracted with ethyl acetate (50 mL*3). The combined organic phase was washed with brine (10 mL*2), dried with anhydrous Na$_2$SO$_4$, filtered and concentrated in vacuum. The residue was purified by Pre-HPLC to afford tert-butyl 4-(5-((4-(4-cyanophenyl)-2-(methoxycarbonyl)-1H-pyrrol-1-yl)methyl)-2-fluoro-4-nitrophenyl)piperazine-1-carboxylate (600 mg, 1.0 mmol, 45.76% yield, 95% purity) as a yellow solid. TLC: R$_f$=0.3 (Petroleum ether/Ethyl acetate=3/1). 1H NMR (400 MHz, CHLOROFORM-d) δ=7.96 (d, J=13.2 Hz, 1H), 7.69-7.57 (m, 4H), 7.39 (s, 1H), 7.29 (s, 2H), 5.99 (s, 2H), 3.79 (s, 3H), 3.53-3.42 (m, 4H), 3.02 (br. s., 4H), 1.44 (s, 9H). ESI [M+H]=564.5

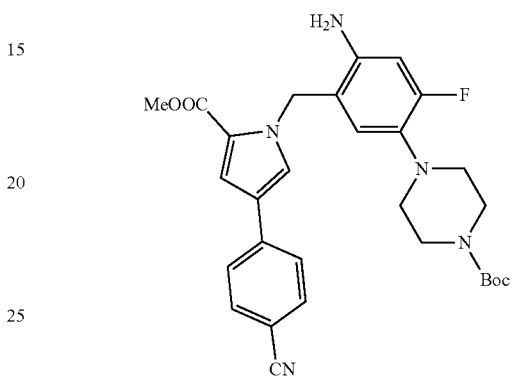

Tert-butyl 4-(4-amino-5-((4-(4-cyanophenyl)-2-(methoxycarbonyl)-1H-pyrrol-1-yl)methyl)-2-fluorophenyl)piperazine-1-carboxylate, S93. To a mixture of tert-butyl 4-(5-((4-(4-cyanophenyl)-2-(methoxycarbonyl)-1H-pyrrol-1-yl)methyl)-2-fluoro-4-nitrophenyl)piperazine-1-carboxylate (620 mg, 1.1 mmol, 1.0 eq.) in AcOH (10 mL) was added Zn (719 mg, 11.0 mmol, 10.0 eq.) in one portion at 30° C. under N$_2$. The mixture was stirred at 30° C. for 1 hr, filtered and concentrated. The residue was diluted with ice-water (20 mL) extracted with ethyl acetate (15 mL*3). The combined organic phase was washed with brine (5 mL*2), dried over anhydrous Na$_2$SO$_4$, filtered and concentrated in vacuum to afford tert-butyl 4-(4-amino-5-((4-(4-cyano phenyl)-2-(methoxycarbonyl)-1H-pyrrol-1-yl)methyl)-2-fluorophenyl)piperazine-1-carboxylate (580 mg, crude) as a yellow solid. TLC: R$_f$=0.26 (Petroleum ether/Ethyl acetate=3/1). ESI [M+H]=533.9

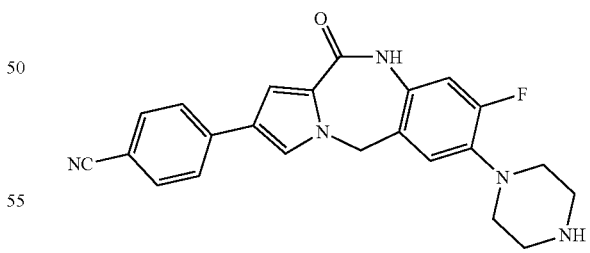

4-(8-fluoro-11-oxo-7-(piperazin-1-yl)-10,11-dihydro-5H-benzo[e]pyrrolo[1,2-a][1,4]diazepin-2-yl)benzonitrile, S94. To a solution of tert-butyl 4-(4-amino-5-((4-(4-cyanophenyl)-2-(methoxycarbonyl)-1H-pyrrol-1-yl)methyl)-2-fluorophenyl)piperazine-1-carboxylate (300 mg, 562 umol, 1.0 eq.) in toluene (20 mL) was added a solution of AlMe$_3$ (2 M, 1.41 mL, 5.0 eq.) dropwise at 0° C. over a period of 30 min under N$_2$. The reaction mixture was warmed to 30° C. and stirred for 3 hr. The reaction was quenched by ice water (30 mL) slowly and extracted with DCM (30 mL*3). The combined organic phase was washed with saturated brine (5 mL*2), dried over anhydrous Na₂SO₄, filtered and concentrated to give crude 4-(8-fluoro-11-oxo-7-(piperazin-1-yl)-10,11-dihydro-5H-benzo[e]pyrrolo[1,2-a][1,4]diazepin-2-yl)benzonitrile (140 mg, crude) as a yellow solid. TLC: $R_f$=0.46 (Petroleum ether/Ethyl acetate=3/1). ESI [M+H]= 402.1

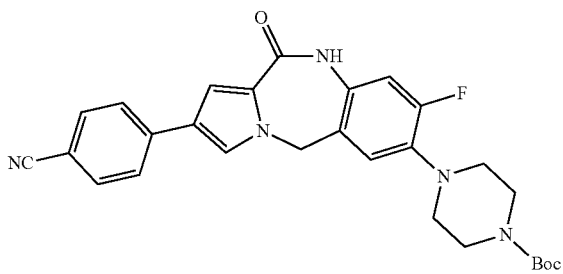 [SMILES: CC(C)(C)OC(=O)N1CCN(c2cc3c(cc2F)NC(=O)c2cc(-c4ccc(C#N)cc4)cn2C3)CC1]

Tert-butyl 4-(2-(4-cyanophenyl)-8-fluoro-11-oxo-10,11-dihydro-5H-benzo[e]pyrrolo[1,2-a] [1,4]diazepin-7-yl)piperazine-1-carboxylate, S95. To a solution of 4-(8-fluoro-11-oxo-7-(piperazin-1-yl)-10,11-dihydro-5H-benzo[e]pyrrolo[1,2-a][1,4]diazepin-2-yl)benzonitrile (150 mg, 373 umol, 1.0 eq.) in MeOH (5.0 mL) was added Boc₂O (97 mg, 448 umol, 1.2 eq.) in one portion. The mixture was stirred at 30° C. for 2 hr and concentrated in reduced pressure to afford tert-butyl 4-(2-(4-cyanophenyl)-8-fluoro-11-oxo-10,11-dihydro-5H-benzo[e]pyrrolo[1,2-a][1,4] diazepin-7-yl)piperazine-1-carboxylate (200 mg, crude) as a yellow solid. TLC: $R_f$=0.53 (Petroleum ether/Ethyl acetate=3/1). ESI [M+H]= 502.2

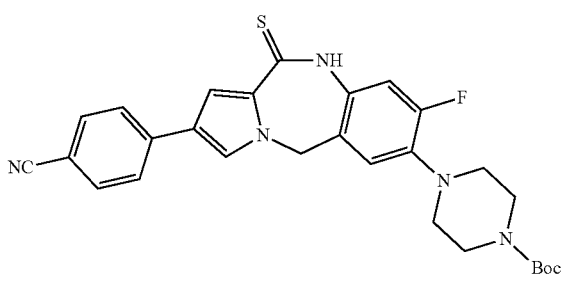 [SMILES: CC(C)(C)OC(=O)N1CCN(c2cc3c(cc2F)NC(=S)c2cc(-c4ccc(C#N)cc4)cn2C3)CC1]

Tert-butyl 4-(2-(4-cyanophenyl)-8-fluoro-11-thioxo-10,11-dihydro-5H-benzo[e]pyrrolo[1,2-a][1,4]diazepin-7-yl) piperazine-1-carboxylate, S96. A solution of tert-butyl 4-(2-(4-cyanophenyl)-8-fluoro-11-oxo-10,11-dihydro-5H-benzo [e]pyrrolo[1,2-a][1,4]diazepin-7-yl) piperazine-1-carboxylate (200 mg, 398 umol, 1.0 eq.) and lawesson's reagent (193 mg, 478 umol, 1.2 eq.) in THF (10.0 mL) was stirred at 80° C. for 16 hr and concentrated. The residue was purified by Pre-TLC (DCM/Methanol=15/1) to give tert-butyl 4-(2-(4-cyanophenyl)-8-fluoro-11-thioxo-10,11-dihydro-5H-benzo[e]pyrrolo[1,2-a][1,4]diazepin-7-yl)piperazine-1-carboxylate (80 mg, 123 umol, 31%yield, 80% purity) as a white solid. TLC: $R_f$=0.33 (Dichloromethane/Methanol=20/1).

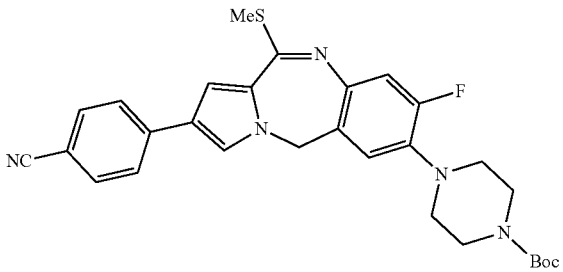 [SMILES: CSC1=Nc2cc(F)c(N3CCN(C(=O)OC(C)(C)C)CC3)cc2Cn2cc(-c3ccc(C#N)cc3)cc21]

Tert-butyl 4-(2-(4-cyanophenyl)-8-fluoro-11-(methylthio)-5H-benzo[e]pyrrolo[1,2-a][1,4]diazepin-7-yl)piperazine-1-carboxylate, S97. To a mixture of tert-butyl 4-(2-(4-cyanophenyl)-8-fluoro-11-thioxo-10,11-dihydro-5H-benzo [e]pyrrolo[1,2-a][1,4]diazepin-7-yl)piperazine-1-carboxylate (80 mg, 154 umol, 1.0 eq.) and K₂CO₃ (42.7 mg, 309 umol, 2.0 eq.) in MeCN (3.0 mL) was added MeI (109 mg, 772 umol, 5.0 eq.). The mixture was stirred at 28° C. for 16 hr and concentrated in vacuum. The residue was purified by Pre-TLC (Petroleum ether/Ethyl acetate=2/1) to afford tert-butyl 4-(2-(4-cyanophenyl)-8-fluoro-11-(methylthio)-5H-benzo[e]pyrrolo[1,2-a][1,4]diazepin-7-yl)piperazine-1-carboxylate (75 mg, 112 umol, 73% yield, 80% purity) as a orange oil. TLC: $R_f$=0.23 (Petroleum ether/Ethyl acetate=3/1).

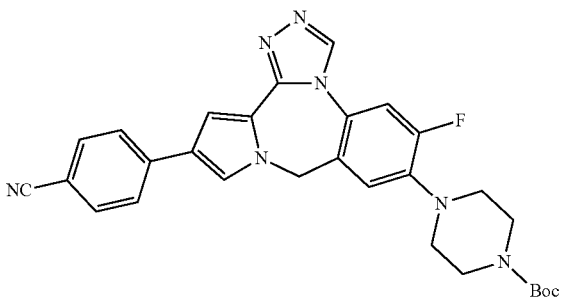 [SMILES: CC(C)(C)OC(=O)N1CCN(c2cc3c(cc2F)-n2cnnc2-c2cc(-c4ccc(C#N)cc4)cn2C3)CC1]

Tert-butyl 4-(12-(4-cyanophenyl)-6-fluoro-9H-benzo[e] pyrrolo[1,2-a][1,2,4]triazolo[3,4-c] [1,4]diazepin-7-yl)piperazine-1-carboxylate, S98. A mixture of formohydrazide (18 mg, 300 umol, 2.0 eq.) and tert-butyl 4-(2-(4-cyanophenyl)-8-fluoro-11-(methylthio)-5H-benzo[e]pyrrolo[1,2-a][1,4]diazepin-7-yl)piperazine-1-carboxylate (80 mg, 150 umol, 1.0 eq.) in n-BuOH (2.0 mL) was stirred at 130° C. for 16 hr and concentrated in reduced pressure to give tert-butyl 4-(12-(4-cyanophenyl)-6-fluoro-9H-benzo[e]pyrrolo[1,2-a] [1,2,4]triazolo[3,4-c][1,4]diazepin-7-yl) piperazine-1-carboxylate (50 mg, crude) without further purification. TLC: $R_f$=0.05 (Petroleum ether/Ethyl acetate=3/1).

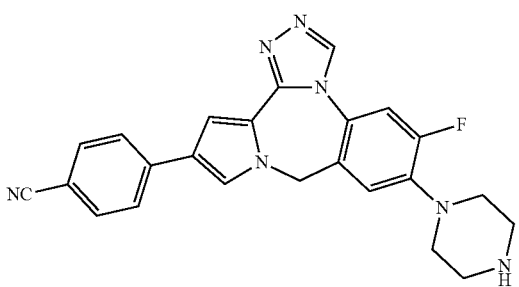 [SMILES: N#Cc1ccc(-c2cc3n(c2)Cc2cc(N4CCNCC4)c(F)cc2-n2cnnc2-3)cc1]

4-(6-fluoro-7-(piperazin-1-yl)-9H-benzo[e]pyrrolo[1,2-a][1,2,4]triazolo[3,4-c][1,4]diazepin-12-yl)benzonitrile, 325. Tert-butyl 4-(12-(4-cyanophenyl)-6-fluoro-9H-benzo[e]pyrrolo[1,2-a][1,2,4]triazolo[3,4-c][1,4]diazepin-7-yl)piperazine-1-carboxylate (80 mg, 152 umol, 1.0 eq.) was dissolved in HCl/EtOAc (4 M, 3.0 mL) and the mixture was stirred at 28° C. for 0.5 hr. The mixture was concentrated and the residue was purified by pre-HPLC to give 4-(6-fluoro-7-(piperazin-1-yl)-9H-benzo[e]pyrrolo[1,2-a][1,2,4]triazolo[3,4-c][1,4]diazepin-12-yl)benzonitrile (30 mg, 70 umol, 46.3% yield, 100% purity). 1H NMR (400 MHz, METHANOL-d4) δ=9.07 (s, 1H), 7.77-7.65 (m, 4H), 7.65-7.58 (m, 2H), 7.41 (d, J=8.8 Hz, 1H), 7.26 (s, 1H), 5.25 (s, 2H), 3.50-3.39 (m, 8H). ESI [M+H]=426.1

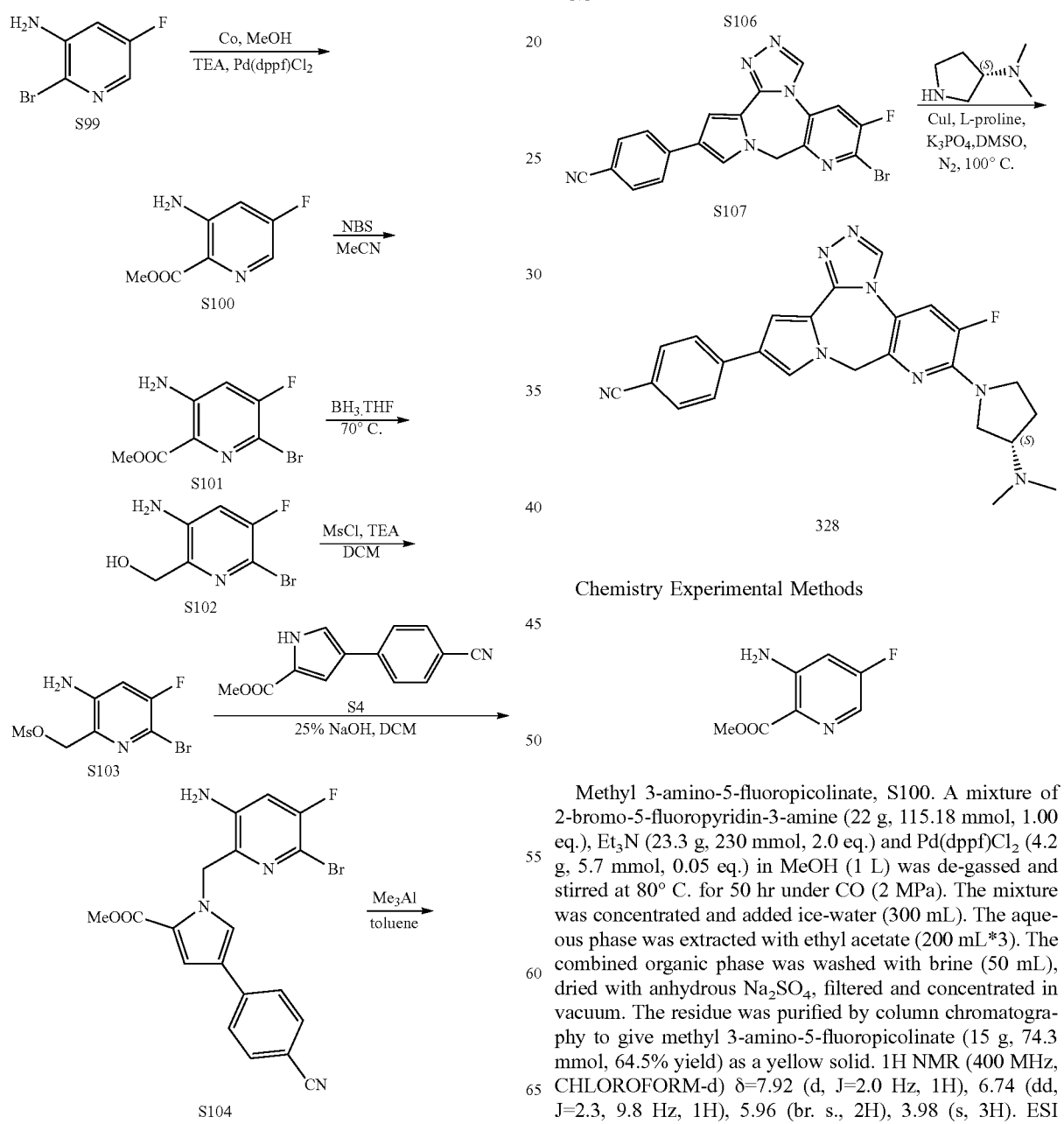

Chemistry Experimental Methods

Methyl 3-amino-5-fluoropicolinate, S100. A mixture of 2-bromo-5-fluoropyridin-3-amine (22 g, 115.18 mmol, 1.00 eq.), Et$_3$N (23.3 g, 230 mmol, 2.0 eq.) and Pd(dppf)Cl$_2$ (4.2 g, 5.7 mmol, 0.05 eq.) in MeOH (1 L) was de-gassed and stirred at 80° C. for 50 hr under CO (2 MPa). The mixture was concentrated and added ice-water (300 mL). The aqueous phase was extracted with ethyl acetate (200 mL*3). The combined organic phase was washed with brine (50 mL), dried with anhydrous Na$_2$SO$_4$, filtered and concentrated in vacuum. The residue was purified by column chromatography to give methyl 3-amino-5-fluoropicolinate (15 g, 74.3 mmol, 64.5% yield) as a yellow solid. 1H NMR (400 MHz, CHLOROFORM-d) δ=7.92 (d, J=2.0 Hz, 1H), 6.74 (dd, J=2.3, 9.8 Hz, 1H), 5.96 (br. s., 2H), 3.98 (s, 3H). ESI [M+H]=171.1

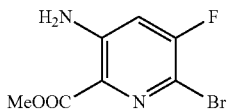

Methyl 3-amino-6-bromo-5-fluoropicolinate, S101. To a solution of methyl 3-amino-5-fluoropicolinate (15 g, 88 mmol, 1.0 eq.) in MeCN (500 mL) was added NBS (15.7 g, 88.4 mmol, 1.0 eq.) and the mixture was stirred at 15° C. for 14 hr. The mixture was concentrated and the residue was partitioned between EtOAc (500 mL) and ice-water (100 mL). The organic phase was washed with brine (50 mL), dried with anhydrous $Na_2SO_4$, filtered and concentrated in vacuum. The residue was purified by silica gel chromatography to give methyl 3-amino-6-bromo-5-fluoropicolinate (18 g, 62 mmol, 70.27% yield) as a white solid. 1H NMR (400 MHz, CHLOROFORM-d) δ=6.79 (d, J=8.4 Hz, 1H), 5.98 (br. s., 2H), 3.95 (s, 3H). ESI [M+H]=249.2/251.2

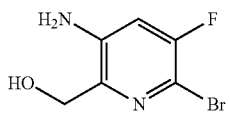

(3-amino-6-bromo-5-fluoropyridin-2-yl)methanol, S102. To a solution of methyl 3-amino-6-bromo-5-fluoropicolinate (13.8 g, 55.5 mmol, 1.0 eq.) in THF (200 mL) was added aq.LiOH (11.6 g, 277 mmol, 5.00 eq., 1 M in $H_2O$) and the mixture was stirred at 15° C. for 2 hr. The solution was adjusted to pH=2 with 4 M HCl and then concentrated. The residue was partitioned between EtOAc (300 mL) and ice-water (100 mL). The organic phase was washed with brine (20 mL), dried with anhydrous $Na_2SO_4$, filtered and concentrated to give 3-amino-6-bromo-5-fluoropicolinic acid (13 g, crude) as a yellow solid, which was used into the next step without further purification.

To a solution of 3-amino-6-bromo-5-fluoropicolinic acid (11.0 g, 46.8 mmol, 1.0 eq.) in THF (20 mL) was added $BH_3$.THF (1 M, 300 mL, 6.4 eq.) and the mixture was heated to 70° C. for 16 hr. The mixture was cooled to 0° C., quenched by MeOH (400 mL) slowly and then concentrated in vacuo. The residue was added MeOH (30 mL) and stirred for 1 hr. The precipitate was collected by filtration to give (3-amino-6-bromo-5-fluoropyridin-2-yl)methanol (8.0 g, 36.19 mmol, 77.31% yield) as a white solid. ESI [M+H]= 221.2/223.2

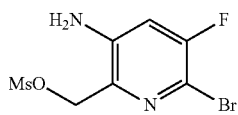

(3-amino-6-bromo-5-fluoropyridin-2-yl)methyl methanesulfonate, S103. To a solution of (3-amino-6-bromo-5-fluoropyridin-2-yl)methanol (6 g, 27.12 mmol, 1.0 eq.) and TEA (5.49 g, 54.24 mmol, 2.0 eq.) in DCM (200 mL) was added methanesulfonyl chloride (3.26 g, 28.5 mmol, 1.05 eq.) dropwise at −70° C. under $N_2$. After addition, the mixture was warmed to 15° C. and stirred over 30 min. The solution was used for next step directly.

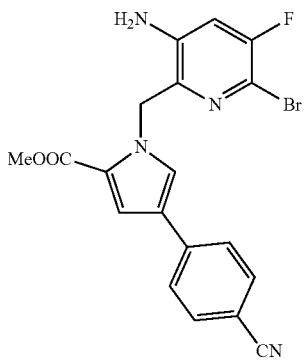 [SMILES: COC(=O)c1cc(-c2ccc(C#N)cc2)cn1Cc1nc(Br)c(F)cc1N]

Methyl-1-((3-amino-6-bromo-5-fluoropyridin-2-yl) methyl)-4-(4-cyanophenyl)-1H-pyrrole-2-carboxylate, S104. To the above solution was added methyl 4-(4-cyanophenyl)-1H-pyrrole-2-carboxylate (4.9 g, 21.8 mmol, 0.80 eq.), $Bu_4NOH$ (2.6 g, 2.7 mmol, 0.1 eq.) and NaOH (10.4 g, 163.7 mmol, 6.0 eq. 25%, w %) at 0° C. The mixture was stirred for 3.5 hr at 15° C. and then diluted with ice-water (100 mL). The organic layer was washed with brine (100 mL*2), dried over anhydrous $MgSO_4$, filtered and concentrated in vacuum. The residue was purified by prep-HPLC to afford methyl-1-((3-amino-6-bromo-5-fluoropyridin-2-yl) methyl)-4-(4-cyano phenyl)-1H-pyrrole-2-carboxylate (3 g, 4.9 mmol) as a yellow solid. 1H NMR (400 MHz, CHLORO FORM-d) δ=7.56-7.52 (m, 2H), 7.49 (s, 1H), 7.47-7.45 (m, 1H), 7.19 (s, 2H), 6.67 (d, J=8.8 Hz, 1H), 5.52 (s, 2H), 3.83 (s, 3H). ESI [M+H]=429.1/431.1

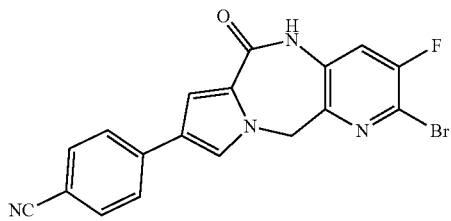 [SMILES: N#Cc1ccc(-c2cc3n(c2)Cc2nc(Br)c(F)cc2NC3=O)cc1]

4-(2-bromo-3-fluoro-6-oxo-6,11-dihydro-5H-pyrido[3,2-e]pyrrolo[1,2-a][1,4]diazepin-8-yl)benzonitrile, S105. To a suspension of methyl-1-((3-amino-6-bromo-5-fluoropyridin-2-yl)methyl)-4-(4-cyanophenyl)-1H-pyrrole-2-carboxylate (2.80 g, 6.52 mmol, 1.0 eq.) in toluene (50 mL) was added $Me_3Al$ (2 M in toluene, 16.30 mL, 5.0 eq.) at 0° C. and the mixture was stirred for 12 hr at 15° C. The mixture was poured into ice-water (100 mL) and extracted with hot EtOAc/THF(1:1, 100 mL*4). The organic layer was dried over anhydrous $Na_2SO_4$, filtered and concentrated. The residue was added THF (20 mL) and stirred for 1 hr at 0° C. The precipitate was collected by filtration to give 4-(2-bromo-3-fluoro-6-oxo-6,11-dihydro-5H-pyrido[3,2-e]pyrrolo[1,2-a][1,4]diazepin-8-yl)benzonitrile (1.0 g, 2.11 mmol, 32.44% yield) as a white solid. ESI [M+H]=397.1/399.1

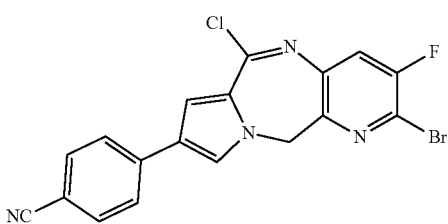 [SMILES: N#Cc1ccc(-c2cc3n(c2)Cc2nc(Br)c(F)cc2N=C3Cl)cc1]

4-(2-bromo-6-chloro-3-fluoro-11H-pyrido[3,2-e]pyrrolo[1,2-a][1,4]diazepin-8-yl)benzonitrile, S106. A solution of 4-(2-bromo-3-fluoro-6-oxo-6,11-dihydro-5H-pyrido[3,2-e]pyrrolo[1,2-a][1,4]diazepin-8-yl)benzonitrile (550 mg, 1.38 mmol, 1.0 eq.) in POCl₃ (30 mL) was stirred for 2 hr at 90° C. The solution was concentrated under reduced pressure to give crude 4-(2-bromo-6-chloro-3-fluoro-11H-pyrido[3,2-e]pyrrolo[1,2-a][1,4]diazepin-8-yl)benzonitrile (575.00 mg, crude) as a black brown oil, which was used into the next step without further purification.

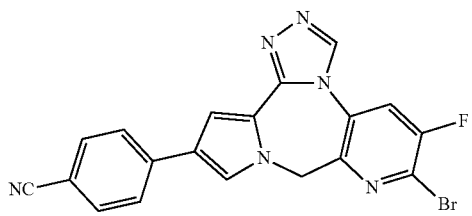 [SMILES: N#Cc1ccc(-c2cc3n(c2)Cc2nc(Br)c(F)cc2-n2cnnc2-3)cc1]

4-(7-bromo-6-fluoro-9H-pyrido[3,2-e]pyrrolo[1,2-a][1,2,4]triazolo[3,4-c][1,4]diazepin-12-yl)benzonitrile, S107. To a solution of 4-(2-bromo-6-chloro-3-fluoro-11H-pyrido[3,2-e]pyrrolo[1,2-a][1,4]diazepin-8-yl)benzonitrile (575 mg, 1.38 mmol, 1.0 eq.) in dioxane (50 mL) was added TEA to adjust pH=7. Then formohydrazide (1.7 g, 28.9 mmol, 21.0 eq.) was added and the mixture was heated to 120° C. for 10 hr in sealing tube. The mixture was concentrated to dryness and the residue was dissolved in hot EtOAc/THF(1:1, 200 mL). The solution was washed with 1M ice HCl (10 mL), sat.aq. NaHCO₃ (10 mL) and brine (10 mL). The organic phase was dried over anhydrous Na₂SO₄, filtered and concentrated in vacuum. The residue was added EtOH (5 mL) and stirred for 1 hr. The precipitate was collected by filtration to give 4-(7-bromo-6-fluoro-9H-pyrido[3,2-e]pyrrolo[1,2-a][1,2,4]triazolo[3,4-c][1,4]diazepin-12-yl)benzonitrile (450 mg, crude) as a white solid. 1H NMR (400 MHz, DMSO-d6) δ=9.21 (s, 1H), 8.45 (d, J=8.4 Hz, 1H), 7.94 (br. s., 1H), 7.76 (s, 4H), 7.31 (s, 1H), 5.43 (br. s., 2H). ESI [M+H]=421.2/423.2

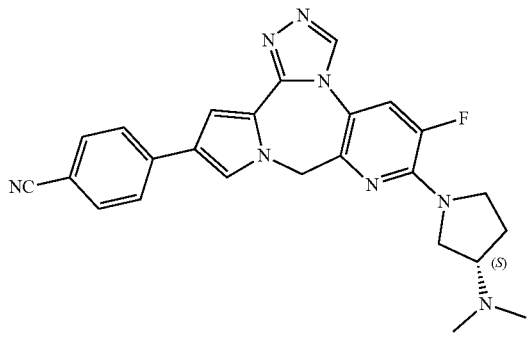

(S)-4-(7-(3-(dimethylamino)pyrrolidin-1-yl)-6-fluoro-9H-pyrido[3,2-e]pyrrolo[1,2-a][1,2,4] triazolo[3,4-c][1,4]diazepin-12-yl)benzonitrile, 328. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-6-fluoro-9H-pyrido[3,2-e]pyrrolo[1,2-a][1,2,4]triazolo[3,4-c][1,4]diazepin-12-yl)benzonitrile, replacing tert-butyl piperazine-1-carboxylate with (S)—N,N-dimethyl pyrrolidin-3-amine. 1H NMR (400 MHz, METHANOL-d4) δ=9.04 (br. s., 1H), 7.87 (d, J=12.3 Hz, 1H), 7.76-7.60 (m, 5H), 7.26 (br. s., 1H), 5.23 (s, 2H), 4.24-4.12 (m, 1H), 4.09-3.97 (m, 2H), 3.96-3.87 (m, 1H), 3.78 (d, J=9.3 Hz, 1H), 3.01 (s, 6H), 2.56 (d, J=6.2 Hz, 1H), 2.29 (dd, J=8.6, 12.6 Hz, 1H). ESI [M+H]=455.2

Scheme 31

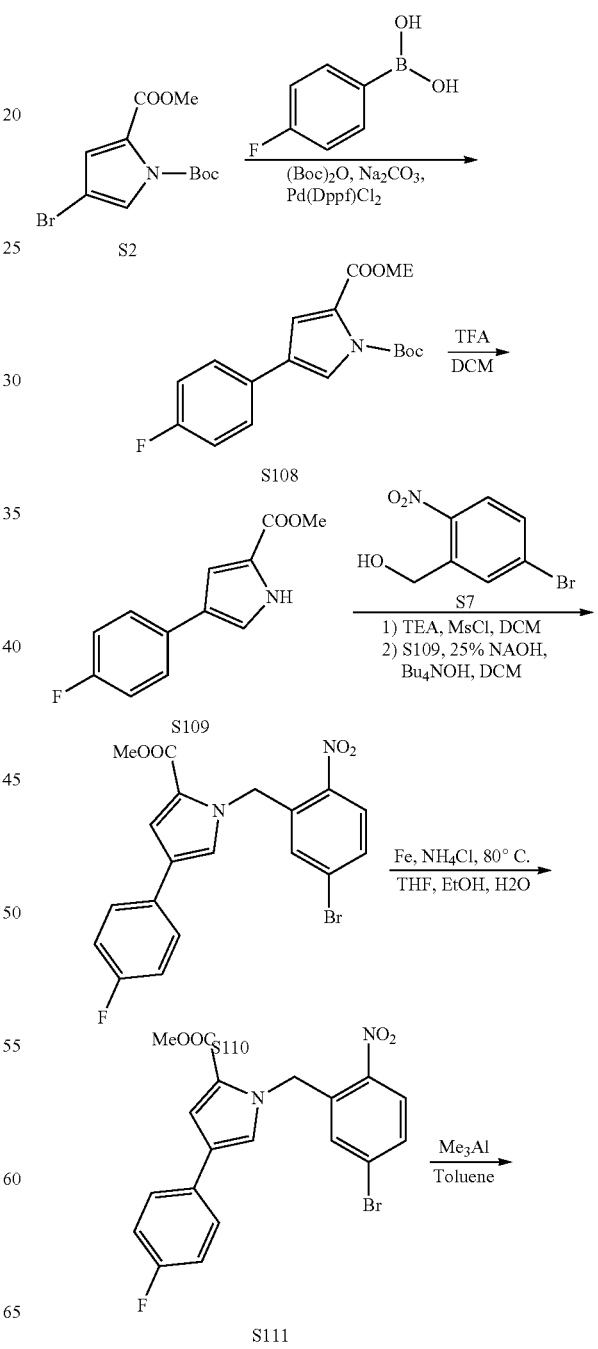

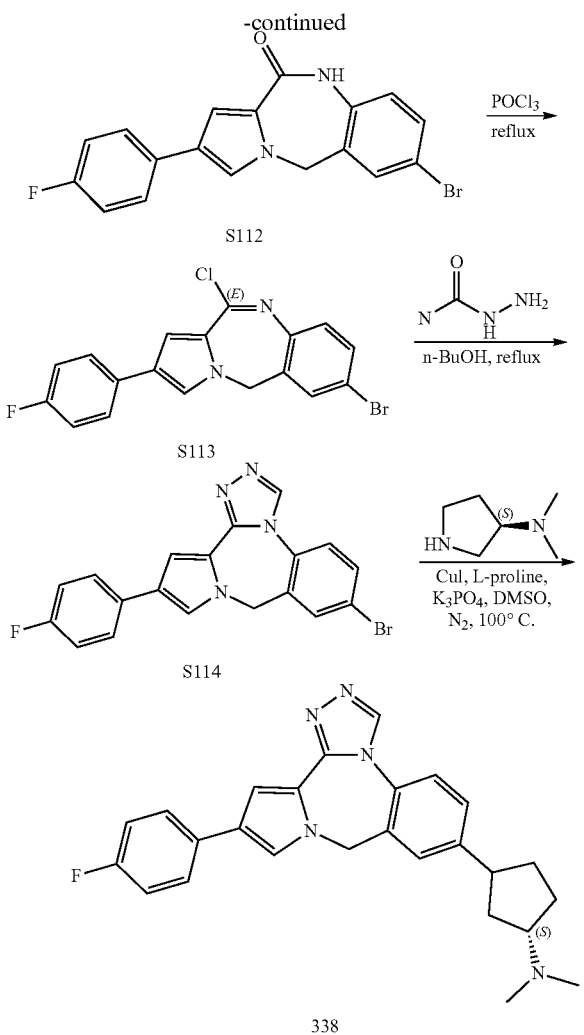

S112

S113

S114

338

Chemistry Experimental Methods:

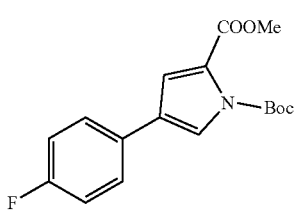 [SMILES: COC(=O)c1cc(-c2ccc(F)cc2)cn1C(=O)OC(C)(C)C]

1-tert-butyl 2-methyl 4-(4-fluorophenyl)-1H-pyrrole-1,2-dicarboxylate, S108. To a mixture of 1-tert-butyl 2-methyl 4-bromo-1H-pyrrole-1,2-dicarboxylate (59.8 g, 196.6 mmol, 1.0 eq.) and (4-fluorophenyl)boronic acid (41 g, 294 mmol, 1.5 eq.) in dioxane (1.8 L) and H$_2$O (180 mL) was added Boc$_2$O (64.3 g, 294.9 mmol, 1.50 eq.), Na$_2$CO$_3$ (41.68 g, 393.24 mmol, 2.00 eq.) and Pd(dppf)Cl$_2$ (7.1 g, 9.8 mmol, 0.05 eq.). The mixture was stirred at 100° C. for 12 hr and then concentrated. The residue was partitioned between ethyl acetate/THF (700 mL/100 mL) and water (500 mL). The organic layer was washed with brine (400 mL), dried over anhydrous MgSO$_4$, filtered and concentrated to provide 1-tert-butyl 2-methyl 4-(4-fluorophenyl)-1H-pyrrole-1,2-dicarboxylate (75 g, crude, black solid). ESI [M+H]=320.1

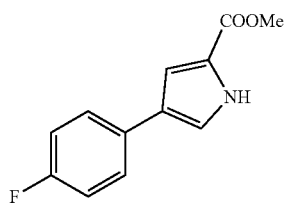 [SMILES: COC(=O)c1cc(-c2ccc(F)cc2)c[nH]1]

Methyl 4-(4-fluorophenyl)-1H-pyrrole-2-carboxylate, S109. A solution of 1-tert-butyl 2-methyl 4-(4-fluorophenyl)-1H-pyrrole-1,2-dicarboxylate (75 g, 234 mmol, 1.0 eq.) in TFA (500 mL) was stirred at 50° C. for 1 hr and then concentrated in vacuum. The residue was added MeOH (250 mL) and stirred for 1 hr. The precipitate was collected by filtration to give methyl 4-(4-fluorophenyl)-1H-pyrrole-2-carboxylate (25 g, 112 mmol, 47.8% yield, 98.6% purity) as a gray solid. 1H NMR (400 MHz, methanol-d4) δ=7.55 (dd, J=8.8, 5.6 Hz, 2H), 7.30 (d, J=1.2 Hz, 1H), 7.15 (d, J=1.6 Hz, 1H), 7.06 (t, J=8.8 Hz, 2H), 3.86 (s, 3H). ESI [M+H]=220.1

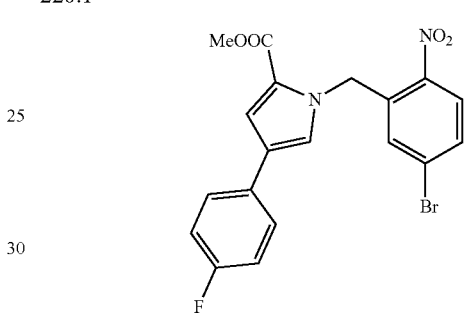

Methyl 1-(5-bromo-2-nitrobenzyl)-4-(4-fluorophenyl)-1H-pyrrole-2-carboxylate, S110. To a solution of (5-bromo-2-nitrophenyl)methanol (30 g, 129 mmol, 1.0 eq.) and TEA (19 g, 193 mmol, 1.50 eq.) in DCM (600 mL) was added MsCl (16 g, 142 mmol, 1.1 eq.) at 0° C. and the mixture was stirred at 20° C. for 30 min. Then methyl 4-(4-fluorophenyl)-1H-pyrrole-2-carboxylate (24 g, 110 mmol, 0.95 eq.) was added, followed by NaOH (aq.25%, 5.00 eq.) and tetrabutylammonium;hydroxide (12.0 g, 11.6 mmol, 0.10 eq.) at 0° C. The mixture was stirred at 20° C. of 16 hr and then poured into cold water (800 mL), extracted with DCM (300 mL*3). The organic layer was dried over with MgSO$_4$ and concentrated in vacuum. The residue was added EtOH/MeOH (220 mL, 10/1) and stirred for 1 hr. The precipitate was collected by filtration to provide methyl 1-(5-bromo-2-nitrobenzyl)-4-(4-fluorophenyl)-1H-pyrrole-2-carboxylate (48.6 g, 107.45 mmol, 92.57% yield, 95.78% purity) as a yellow solid. 1H NMR (400 MHz, chloroform-d) δ=8.05 (d, J=8.8 Hz, 1H), 7.53 (d, J=5.6 Hz, 1H), 7.52-7.50 (m, 2H), 7.33 (d, J=2.0 Hz, 1H), 7.19 (d, J=2.0 Hz, 1H), 7.10 (t, J=8.4 Hz, 2H), 6.77 (s, 1H), 5.95 (s, 2H), 3.78 (s, 3H). ESI [M+H]=435.0

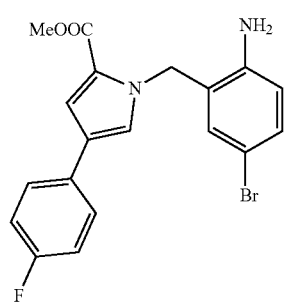 [SMILES: COC(=O)c1cc(-c2ccc(F)cc2)cn1Cc1cc(Br)ccc1N]

Methyl 1-(2-amino-5-bromobenzyl)-4-(4-fluorophenyl)-1H-pyrrole-2-carboxylate, S111. To a solution of methyl 1-(5-bromo-2-nitrobenzyl)-4-(4-fluorophenyl)-1H-pyrrole-2-carboxylate (47.60 g, 109.87 mmol, 1.0 eq.) in THF (480 mL) and EtOH (480 mL) was added Fe (30.68 g, 549.35 mmol, 5.0 eq.) and sat.aq.NH₄Cl (240 mL). The mixture was stirred at 90° C. for 30 min and concentrated in vacuum. The residue was dissolved in hot THF (2 L). After filtration, the filtrate was concentrated to provide methyl 1-(2-amino-5-bromobenzyl)-4-(4-fluorophenyl)-1H-pyrrole-2-carboxylate (66 g, crude) as a yellow solid. TLC: $R_f$=0.25 (Petroleum ether:Ethyl acetate=5:1).

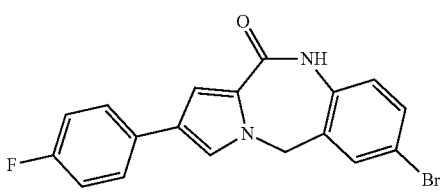 [SMILES: O=C1Nc2ccc(Br)cc2Cn2cc(-c3ccc(F)cc3)cc21]

7-bromo-2-(4-fluorophenyl)-5H-benzo[e]pyrrolo[1,2-a][1,4]diazepin-11(10H)-one, S112. To a suspension of methyl 1-(2-amino-5-bromobenzyl)-4-(4-fluorophenyl)-1H-pyrrole-2-carboxylate (65 g, 101.55 mmol, 1.0 eq.) in toluene (650 mL) was added AlMe₃ (2 M, 253.88 mL, 5.0 eq.) and the mixture was stirred at 20° C. for 16 hr. The mixture was quenched by 1M ice-HCl (2 L) and extracted with Ethyl acetate/THF (2/1, 1000 mL*3). The organic layer was washed with brine (1 L), dried over MgSO₄ and concentrated in vacuum. The residue was added EtOH/MeOH (220 mL) and filtered. The filter cake was collected and dried to provide 7-bromo-2-(4-fluorophenyl)-5H-benzo[e]pyrrolo[1,2-a][1,4]diazepin-11(10H)-one (28 g, 67.89 mmol, 66.85% yield, 90% purity) as a yellow solid. ESI [M+H]=370.9/372.9

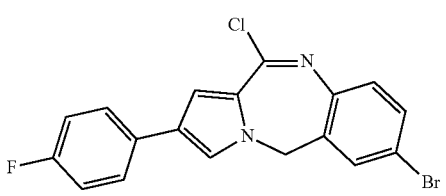 [SMILES: Fc1ccc(-c2cc3n(c2)Cc2cc(Br)ccc2N=C3Cl)cc1]

7-bromo-11-chloro-2-(4-fluorophenyl)-5H-benzo[e]pyrrolo[1,2-a][1,4]diazepine, S113. A solution of 7-bromo-2-(4-fluorophenyl)-5H-benzo[e]pyrrolo[1,2-a][1,4]-diazepin-11(10H)-one (2.00 g, 5.39 mmol, 1.0 eq.) in POCl₃ (50 mL) was stirred at 90° C. for 1 hr and then concentrated to give 7-bromo-11-chloro-2-(4-fluorophenyl)-5H-benzo[e]pyrrolo[1,2-a][1,4]diazepine (2.3 g, crude) as a black brown oil.

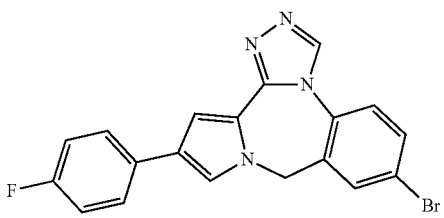 [SMILES: Fc1ccc(-c2cc3n(c2)Cc2cc(Br)ccc2-n2cnnc2-3)cc1]

7-bromo-12-(4-fluorophenyl)-9H-benzo[e]pyrrolo[1,2-a][1,2,4]triazolo[3,4-c][1,4]diazepine, S114. A solution of 7-bromo-11-chloro-2-(4-fluorophenyl)-5H-benzo[e]pyrrolo[1,2-a][1,4] diazepine (2.30 g, 5.90 mmol, 1.0 eq.) in THF (20 mL) and dioxane (20.00 mL) was adjusted to pH=9 with TEA. Then formohydrazide (5.45 g, 90 mmol, 20.0 eq.) was added into the solution and the mixture was stirred at 120° C. for 16 hr in sealing tube. The reaction was concentrated in vacuum and the residue was purified by column chromatography (SiO₂, Petroleum ether/Ethyl acetate=10:1 to 3:1) to give 7-bromo-12-(4-fluorophenyl)-9H-benzo[e]pyrrolo[1,2-a][1,2,4] triazolo[3,4-c][1,4]diazepine (2.3 g, 3.4 mmol) as a yellow solid. 1H NMR (400 MHz, DMSO-d6) δ=9.22 (s, 1H), 7.95 (s, 1H), 7.80 (d, J=8.4 Hz, 1H), 7.69 (d, J=8.8 Hz, 1H), 7.61 (t, J=6.0 Hz, 2H), 7.53 (s, 1H), 7.17 (t, J=8.4 Hz, 2H), 7.11 (s, 1H), 5.29 (s, 2H).

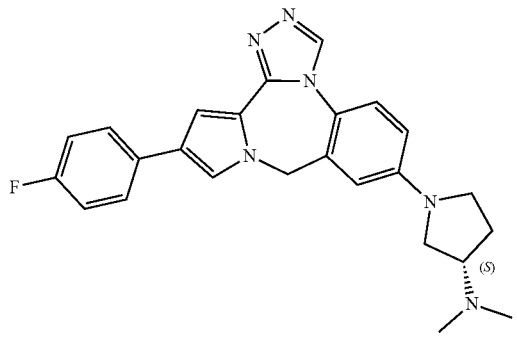

(S)-1-(12-(4-fluorophenyl)-9H-benzo[e]pyrrolo[1,2-a][1,2,4]triazolo[3,4-c][1,4]diazepin-7-yl)-N,N-dimethylpyrrolidin-3-amine, 338. Synthesized using General Procedure A, replacing 4-(7-bromo-9H-benzo[e]pyrrolo[1,2-a][1,2,4]triazolo[3,4-c]-[1,4]diazepin-12-yl)benzonitrile with 7-bromo-12-(4-fluorophenyl)-9H-benzo[e]-pyrrolo[1,2-a]-[1,2,4]triazolo[3,4-c][1,4] diazepine, replacing tert-butyl piperazine-1-carboxylate with (S)—N,N-dimethylpyrrolidin-3-amine. 1H NMR (400 MHz, METHANOL-d4) δ=9.06 (s, 1H), 7.61-7.49 (m, 3H), 7.43 (s, 1H), 7.13 (s, 1H), 7.06 (t, J=8.6 Hz, 2H), 6.89 (br. s., 1H), 6.79 (d, J=8.4 Hz, 1H), 5.17 (s, 2H), 4.17-4.01 (m, 1H), 3.87-3.75 (m, 1H), 3.72-3.56 (m, 2H), 3.44 (q, J=8.3 Hz, 1H), 2.99 (s, 6H), 2.60 (br. s., 1H), 2.40-2.22 (m, 1H). ESI [M+H]=429.2

Scheme 32

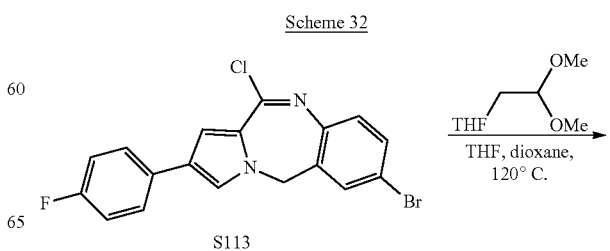

S113

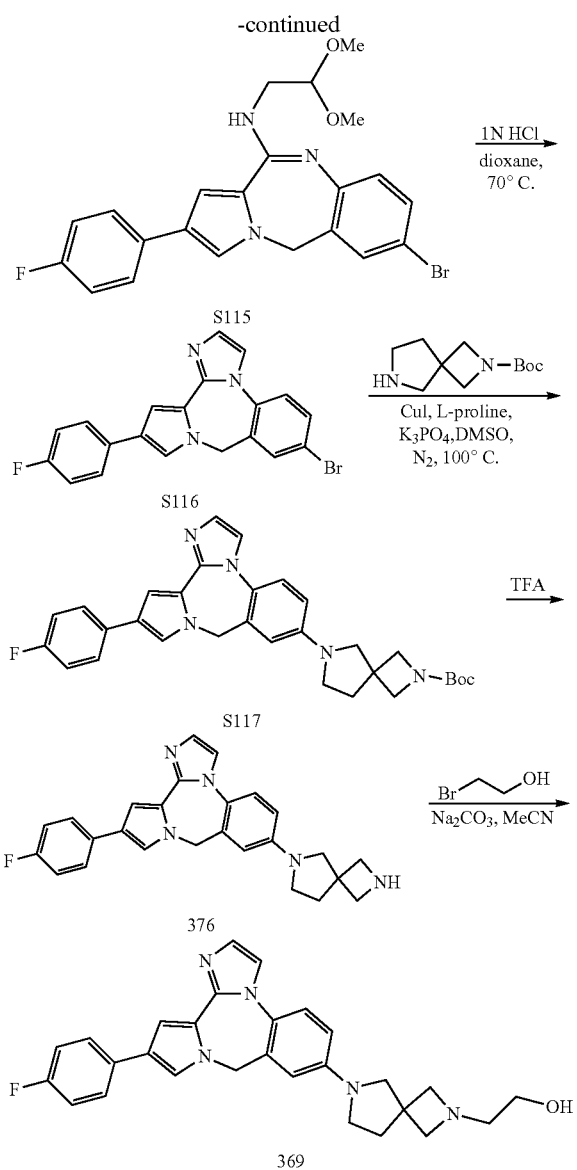

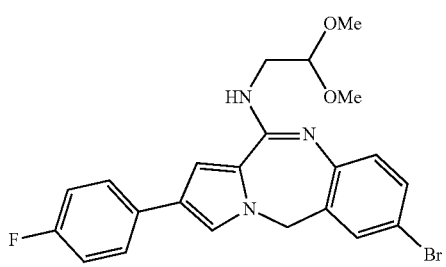 [SMILES: COC(CNC1=Nc2ccc(Br)cc2Cn2cc(-c3ccc(F)cc3)cc21)OC]

7-bromo-N-(2,2-dimethoxyethyl)-2-(4-fluorophenyl)-5H-benzo[e]pyrrolo[1,2-a][1,4] diazepin-11-amine, S115. To a solution of 7-bromo-11-chloro-2-(4-fluorophenyl)-5H-benzo[e]pyrrolo[1,2-a][1,4]diazepine (3.0 g, 8.0 mmol, 1.0 eq.) in THF (30 mL) and dioxane (30 mL) was added 2,2-dimethoxyethanamine (8.5 g, 80.8 mmol, 10.0 eq.) and the mixture was stirred at 130° C. for 16 hr in sealing tube. The mixture was poured into 1N ice-HCl solution (300 mL) and extracted with ethyl acetate (300 mL*3). The combined organic phase was washed with brine (400 mL), dried over anhydrous Na$_2$SO$_4$, filtered and concentrated to give 7-bromo-N-(2,2-dimethoxyethyl)-2-(4-fluorophenyl)-5H-benzo[e]pyrrolo[1,2-a][1,4]diazepin-11-amine (3.70 g, crude) as a black brown solid, which was used without any purification. ESI [M+H]=458.1/460.1

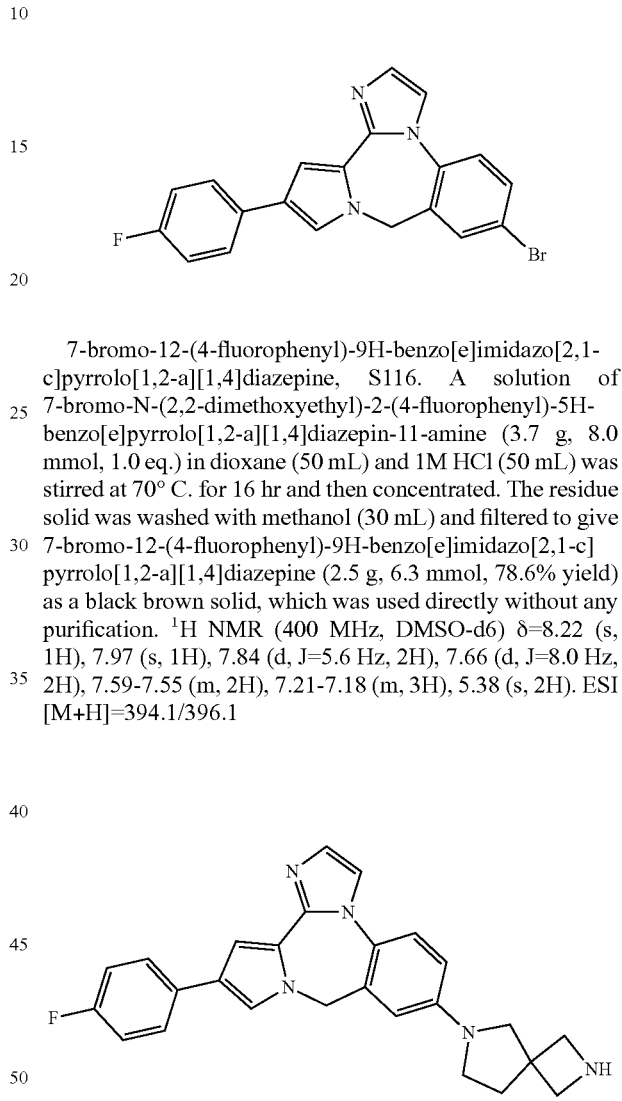

7-bromo-12-(4-fluorophenyl)-9H-benzo[e]imidazo[2,1-c]pyrrolo[1,2-a][1,4]diazepine, S116. A solution of 7-bromo-N-(2,2-dimethoxyethyl)-2-(4-fluorophenyl)-5H-benzo[e]pyrrolo[1,2-a][1,4]diazepin-11-amine (3.7 g, 8.0 mmol, 1.0 eq.) in dioxane (50 mL) and 1M HCl (50 mL) was stirred at 70° C. for 16 hr and then concentrated. The residue solid was washed with methanol (30 mL) and filtered to give 7-bromo-12-(4-fluorophenyl)-9H-benzo[e]imidazo[2,1-c]pyrrolo[1,2-a][1,4]diazepine (2.5 g, 6.3 mmol, 78.6% yield) as a black brown solid, which was used directly without any purification. $^1$H NMR (400 MHz, DMSO-d6) δ=8.22 (s, 1H), 7.97 (s, 1H), 7.84 (d, J=5.6 Hz, 2H), 7.66 (d, J=8.0 Hz, 2H), 7.59-7.55 (m, 2H), 7.21-7.18 (m, 3H), 5.38 (s, 2H). ESI [M+H]=394.1/396.1

12-(4-fluorophenyl)-7-(2,6-diazaspiro[3.4]octan-6-yl)-9H-benzo[e]imidazo[2,1-c]pyrrolo[1,2-a][1,4]diazepine, S376. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with tert-butyl 2,6-diazaspiro[3.4]octane-2-carboxylate. $^1$H NMR (400 MHz, CHLOROFORM-d) δ=7.42 (dd, J=5.5, 8.6 Hz, 2H), 7.30 (s, 1H), 7.24-7.18 (m, 2H), 7.05-6.92 (m, 4H), 6.57-6.46 (m, 2H), 4.93 (br. s., 2H), 3.70-3.54 (m, 4H), 3.50 (s, 2H), 3.34 (t, J=6.6 Hz, 2H), 2.24 (t, J=6.6 Hz, 2H). ESI [M+H]=426.1

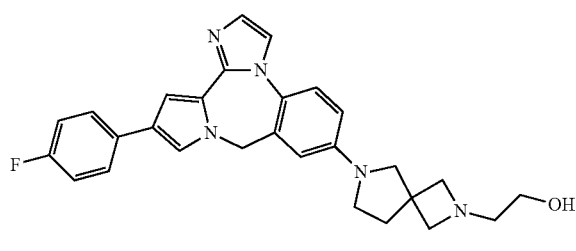 [SMILES: OCCN1CC2(CCN(c3ccc4c(c3)Cn3cc(-c5ccc(F)cc5)cc3-c3nccn3-4)C2)C1]

General Procedure J as below:

2-(6-(12-(4-fluorophenyl)-9H-benzo[e]imidazo[2,1-c]pyrrolo[1,2-a][1,4]diazepin-7-yl)-2,6-diazaspiro[3.4]octan-2-yl)ethanol, S369. To a solution of 12-(4-fluorophenyl)-7-(2,6-diazaspiro[3.4]octan-6-yl)-9H-benzo[e]imidazo[2,1-c]pyrrolo[1,2-a][1,4]diazepine (16 mg, 37 umol, 1.0 eq.) and 2-bromoethanol (14.1 mg, 112.8 umol, 8.0 uL, 3.0 eq.) in CH$_3$CN (3.0 mL) was added Na$_2$CO$_3$ (7.9 mg, 75.2 umol, 2.0 eq.) and the mixture was stirred at 60° C. for 16 hr. The mixture was concentrated and the residue was purified by neutral prep-HPLC to give 2-(6-(12-(4-fluorophenyl)-9H-benzo[e]imidazo[2,1-c]pyrrolo[1,2-a][1,4]diazepin-7-yl)-2,6-diazaspiro[3.4]octan-2-yl)ethanol (2.4 mg, 4.7 umol, 12.6% yield) as a white solid. $^1$H NMR (400 MHz, METHANOL-d$_4$) δ=7.56-7.48 (m, 3H), 7.32 (d, J=8.4 Hz, 1H), 7.26 (s, 1H), 7.17 (s, 1H), 7.02 (t, J=8.8 Hz, 2H), 6.89 (d, J=0.9 Hz, 1H), 6.70 (s, 1H), 6.62 (d, J=8.8 Hz, 1H), 5.01 (s, 2H), 3.58 (t, J=5.7 Hz, 2H), 3.47 (s, 2H), 3.42-3.32 (m, 6H), 2.69 (t, J=5.7 Hz, 2H), 2.22 (t, J=6.6 Hz, 2H). ESI [M+H]=470.3

Chemistry Experimental Methods:

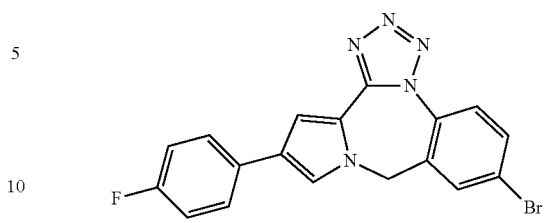

7-bromo-12-(4-fluorophenyl)-9H-benzo[e]pyrrolo[1,2-a]tetrazolo[5,1-c][1,4]diazepine, S118. To a solution of 7-bromo-11-chloro-2-(4-fluorophenyl)-5H-benzo[e]pyrrolo[1,2-a][1,4]diazepine (2.1 g, crude) in dry DMF (10 mL) was added TMSN$_3$ (1.86 g, 16.17 mmol, 3.0 eq.) dropwise at 20° C. The reaction mixture was stirred at 20° C. for 16 hr and poured into ice-water (50 mL). The resulting mixture was extracted with EtOAc (50 mL×3). The combined organic layers were washed with brine (30 mL), dried over MgSO$_4$ and concentrated. The residue solid was washed with MeOH (20 mL) and dried to give give 7-bromo-12-(4-fluorophenyl)-9H-benzo[e]pyrrolo[1,2-a]tetrazolo[5,1-c][1,4]diazepine (1.6 g, crude) as a gray solid, which was used directly without further purification. ESI [M+H]=396.0/398.0

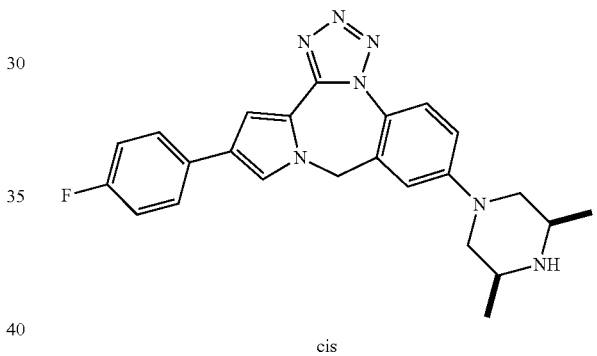

7-(cis-3,5-dimethylpiperazin-1-yl)-12-(4-fluorophenyl)-9H-benzo[e]pyrrolo[1,2-a]tetrazolo[5,1-c][1,4]diazepine, 395. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with cis-2,6-dimethylpiperazine. $^1$HNMR (400 MHz, METHANOL-d$_4$) δ=7.88 (d, J=9.3 Hz, 1H), 7.56 (dd, J=5.5, 8.2 Hz, 2H), 7.49 (s, 1H), 7.31 (br. s., 1H), 7.28-7.20 (m, 2H), 7.07 (t, J=8.6 Hz, 2H), 5.26 (s, 2H), 4.08 (d, J=13.2 Hz, 2H), 3.53 (br. s., 2H), 2.82 (t, J=12.3 Hz, 2H), 1.42 (d, J=6.6 Hz, 6H). ESI [M+H]=430.2

Scheme 33

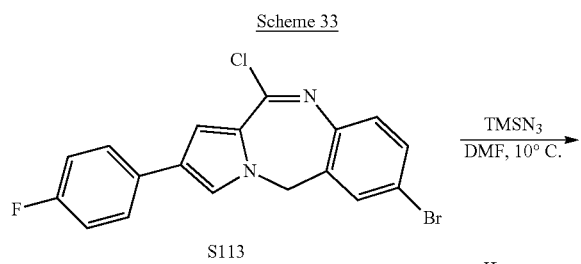

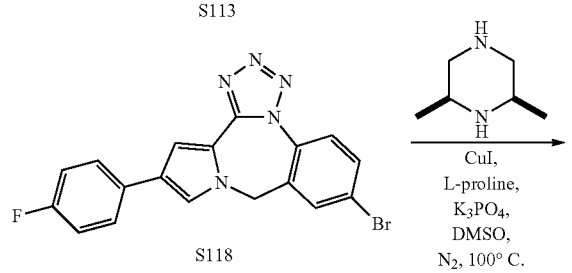

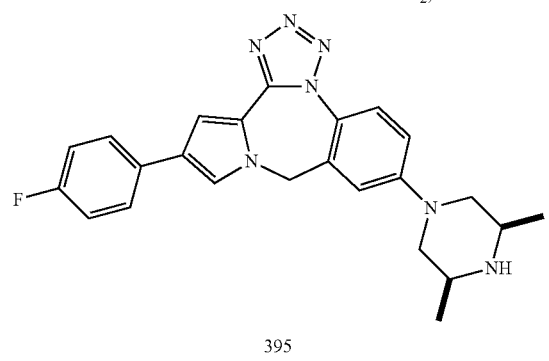

Scheme 34

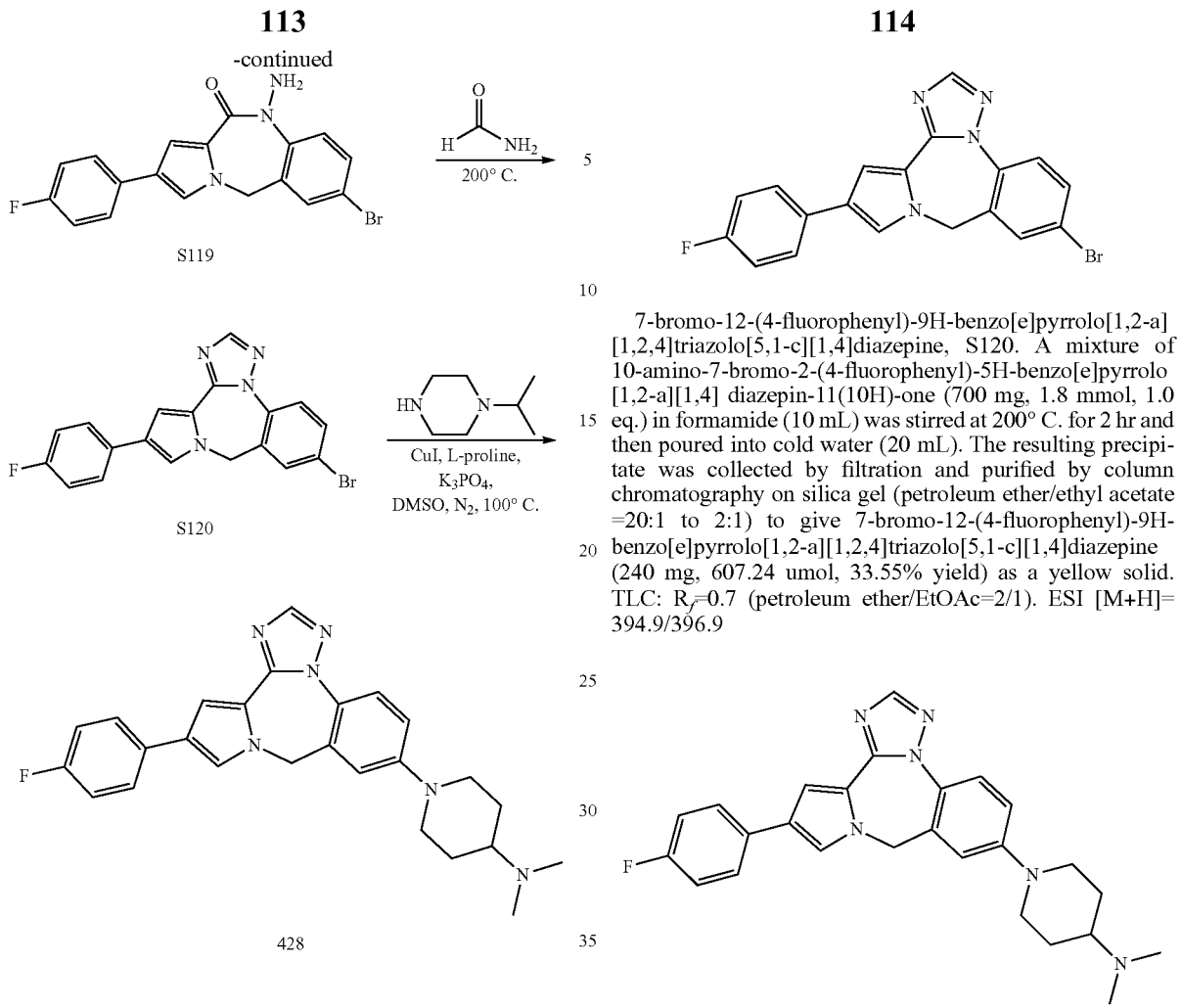

7-bromo-12-(4-fluorophenyl)-9H-benzo[e]pyrrolo[1,2-a][1,2,4]triazolo[5,1-c][1,4]diazepine, S120. A mixture of 10-amino-7-bromo-2-(4-fluorophenyl)-5H-benzo[e]pyrrolo[1,2-a][1,4] diazepin-11(10H)-one (700 mg, 1.8 mmol, 1.0 eq.) in formamide (10 mL) was stirred at 200° C. for 2 hr and then poured into cold water (20 mL). The resulting precipitate was collected by filtration and purified by column chromatography on silica gel (petroleum ether/ethyl acetate =20:1 to 2:1) to give 7-bromo-12-(4-fluorophenyl)-9H-benzo[e]pyrrolo[1,2-a][1,2,4]triazolo[5,1-c][1,4]diazepine (240 mg, 607.24 umol, 33.55% yield) as a yellow solid. TLC: $R_f$=0.7 (petroleum ether/EtOAc=2/1). ESI [M+H]= 394.9/396.9

1-(12-(4-fluorophenyl)-9H-benzo[e]pyrrolo[1,2-a][1,2,4]triazolo[5,1-c][1,4]diazepin-7-yl)-N,N-dimethylpiperidin-4-amine, 428. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4]diazepine and replacing tert-butyl piperazine-1-carboxylate with N,N-dimethylpiperidin-4-amine. $^1$H NMR (400 MHz, METHANOL-$d_4$) δ=8.19 (s, 1H), 7.72 (d, J=9.3 Hz, 1H), 7.54 (dd, J=5.3, 8.4 Hz, 2H), 7.41 (s, 1H), 7.20-7.01 (m, 5H), 5.17 (s, 2H), 4.04 (d, J=13.2 Hz, 2H), 3.47-3.35 (m, 1H), 2.96-2.90 (m, 2H), 2.89 (s, 6H), 2.18 (d, J=11.5 Hz, 2H), 1.82 (dq, J=3.7, 12.1 Hz, 2H). ESI [M+H]=443.2

Chemistry Experimental Methods:

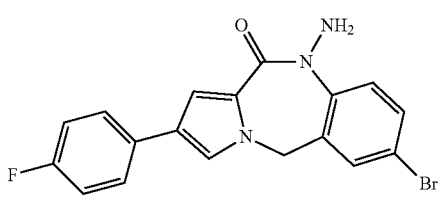 [SMILES: NN1C(=O)c2cc(-c3ccc(F)cc3)cn2Cc2cc(Br)ccc21]

10-amino-7-bromo-2-(4-fluorophenyl)-5H-benzo[e]pyrrolo[1,2-a][1,4]diazepin-11(10H)-one, S119. To a solution of 7-bromo-2-(4-fluorophenyl)-5H-benzo[e]pyrrolo[1,2-a][1,4]diazepin-11(10H)-one (1.0 g, 2.69 mmol, 1.0 eq.) in DMF (20 mL) was added NaH (161.64 mg, 4.04 mmol, 60% purity, 1.5 eq.) at 0° C. After stirred for 1 hr, (aminooxy)diphenylphosphine oxide (753.88 mg, 3.23 mmol, 1.2 eq.) was added. The reaction mixture was stirred at 30° C. for 1 hr, and then quenched by sat.NH$_4$Cl solution (100 mL). The resulting mixture was extracted with EtOAc (30 mL×3). The combined organic layers were washed with brine (30 mL), dried over MgSO$_4$ and concentrated. The residue solid was washed with TBME (20 mL) and dried to give 10-amino-7-bromo-2-(4-fluorophenyl)-5H-benzo[e]pyrrolo[1,2-a][1,4]diazepin-11(10H)-one (700 mg, 1.81 mmol, 67.29% yield) as a yellow solid. ESI [M+H]=386.1/388.1

Scheme 35

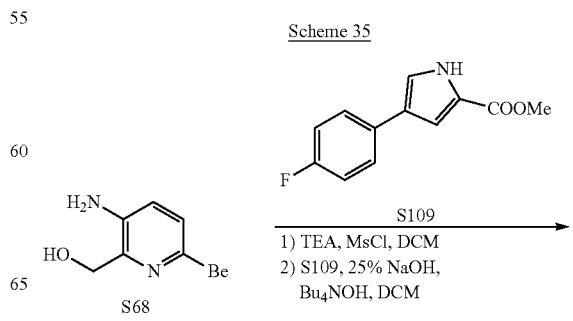

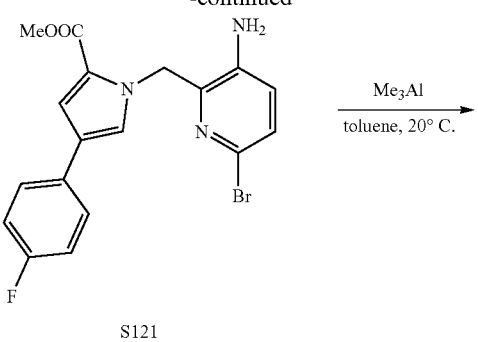

S121

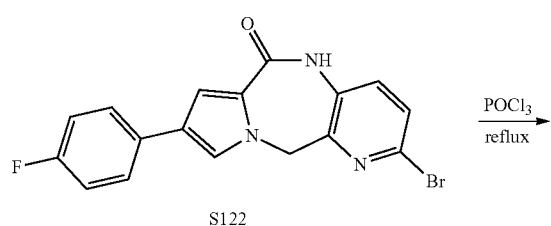

S122

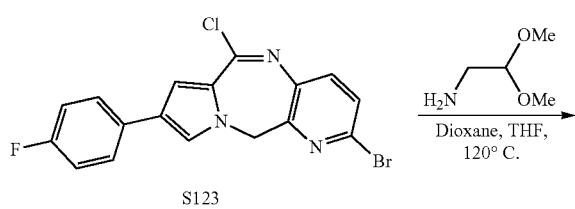

S123

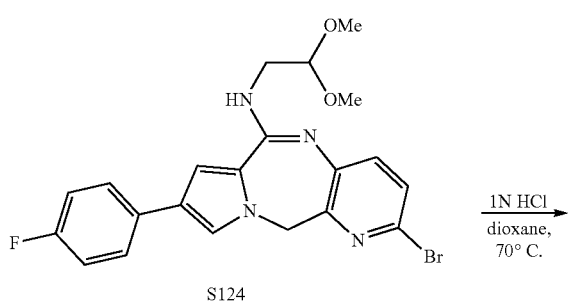

S124

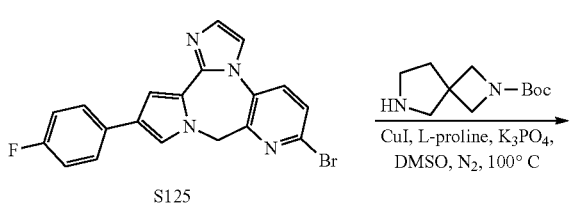

S125

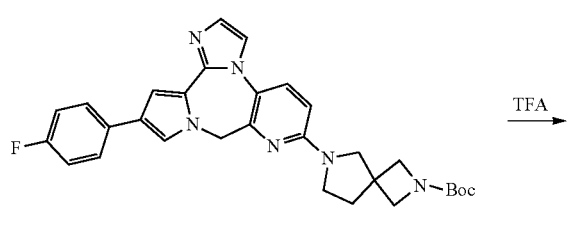

S126

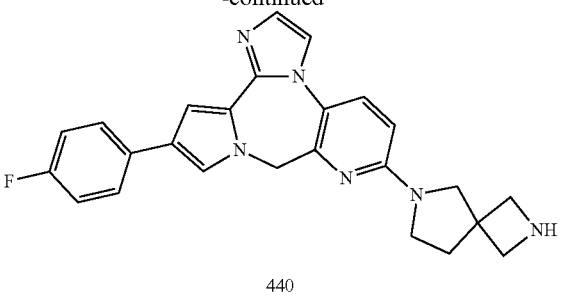

440

Chemistry Experimental Methods:

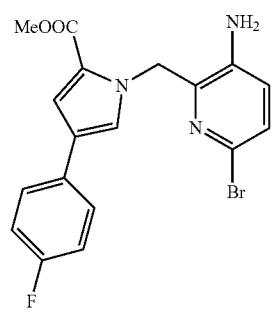 [SMILES: COC(=O)c1cc(-c2ccc(F)cc2)cn1Cc1nc(Br)ccc1N]

Methyl 1-((3-amino-6-bromopyridin-2-yl)methyl)-4-(4-fluorophenyl)-1H-pyrrole-2-carboxylate, S121. To a mixture of (3-amino-6-bromopyridin-2-yl)methanol (8.0 g, 39.40 mmol, 1.0 eq.) and Et$_3$N (12.00 g, 118.59 mmol, 16.44 mL, 3.01 eq.) in dry DCM (1.60 L) and dry THF (160 mL) was added MsCl (6.0 g, 52.40 mmol, 4.05 mL, 1.33 eq.) dropwise at −70° C. under N$_2$ atmosphere. The mixture was allowed to warm to 20° C. slowly and stirred for 30 min. Then the mixture was cooled to 0° C. again and added methyl 4-(4-fluorophenyl)-1H-pyrrole-2-carboxylate (5.5 g, 25.09 mmol, 0.64 eq.), Bu$_4$NOH (5.0 g, 4.82 mmol, 6.25 mL, 25% in H$_2$O, 0.12 eq.), NaOH solution (25% in H$_2$O, 30 g, 187.54 mmol, 4.76 eq.) in turn. The reaction mixture was warmed to 25° C. slowly and stirred for another 15.5 hr. The mixture was washed with water (1 L) and brine (1 L), dried over Na$_2$SO$_4$ and concentrated. The residue was purified by column chromatography on silica gel (petroleum ether/THF=30/1 to 5/1) to give methyl 1-((3-amino-6-bromopyridin-2-yl)methyl)-4-(4-fluorophenyl)-1H-pyrrole-2-carboxylate (3.3 g, 6.94 mmol, 17.61% yield, 90% purity) as a yellow solid. TLC: R$_f$=0.35 (petroleum ether/THF=5/1). $^1$H NMR (400 MHz, DMSO-d$_6$) δ=7.64-7.60 (m, 2H), 7.55 (br. s, 1H), 7.27 (br. s, 1H), 7.17-7.14 (m, 3H), 6.99-6.97 (m, 1H), 5.56 (s, 2H), 5.43 (s, 2H), 3.71 (s, 3H). ESI [M+H] =404.0/406.0

2-bromo-8-(4-fluorophenyl)-5H-pyrido[3,2-e]pyrrolo[1,2-a][1,4]diazepin-6(11H)-one, S122. To a suspension of methyl 1-((3-amino-6-bromopyridin-2-yl)methyl)-4-(4-fluorophenyl)-1H-pyrrole-2-carboxylate (3.3 g, 8.16 mmol, 1.0 eq.) in dry toluene (150 mL) was added AlMe₃ (2 M in toluene, 20 mL, 4.9 eq.) dropwise at 0° C. under N₂ atmosphere. The reaction mixture was warmed to 25° C. and stirred for 16 hour. The mixture was poured into cold aqueous NH₄Cl (200 mL) and extracted with hot EtOAc/THF (4:1, 100 mL×3). The combined organic layers were washed with brine (100 mL), dried over Na₂SO₄ and concentrated. The residue solid was washed with EtOH (10 mL×2) and dried to give 2-bromo-8-(4-fluorophenyl)-5H-pyrido[3,2-e]pyrrolo[1,2-a][1,4]diazepin-6(11H)-one (1.80 g, 4.05 mmol, 49.68% yield, 83.82% purity) as a light yellow solid. ¹H NMR (400 MHz, DMSO-d₆) δ=10.35 (s, 1H), 7.69-7.64 (m, 2H), 7.59-7.54 (m, 3H), 7.19-7.14 (m, 3H), 5.34 (s, 2H). ESI [M+H]=372.0/374.0

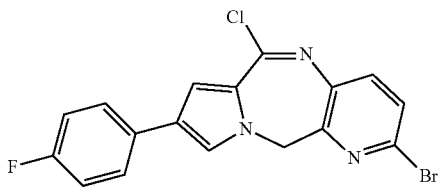 [SMILES: Fc1ccc(-c2cc3n(c2)Cc2nc(Br)ccc2N=C3Cl)cc1]

2-bromo-6-chloro-8-(4-fluorophenyl)-11H-pyrido[3,2-e]pyrrolo[1,2-a][1,4]diazepine, S123.

To a suspension of 2-bromo-8-(4-fluorophenyl)-5H-pyrido[3,2-e]pyrrolo[1,2-a][1,4]diazepin-6 (11H)-one (600 mg, 1.61 mmol, 1.0 eq.) in dry dioxane (20 mL) was added POCl₃ (1.0 g, 6.52 mmol, 600 uL, 4.0 eq.) dropwise at 25° C. under N₂ atmosphere. The mixture was stirred at 85° C. for 4 hour and then concentrated to dryness. The crude product was used directly without purification.

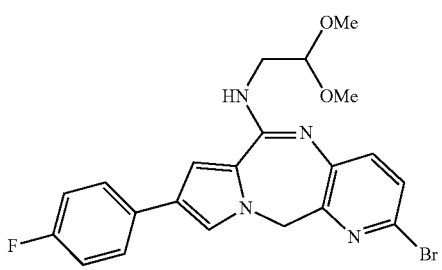 [SMILES: COC(CNC1=Nc2ccc(Br)nc2Cn2cc(-c3ccc(F)cc3)cc21)OC]

2-bromo-N-(2,2-dimethoxyethyl)-8-(4-fluorophenyl)-11H-pyrido[3,2-e] pyrrolo[1,2-a][1,4] diazepin-6-amine, S124. To a solution of 2-bromo-6-chloro-8-(4-fluorophenyl)-11H-pyrido[3,2-e]pyrrolo[1,2-a][1,4]diazepine (600 mg, 1.6 mmol, 1.0 eq.) in dry dioxane (50 mL) was added 2,2-dimethoxyethanamine (7 g, 66 mmol, 7.2 mL, 41 eq.) dropwise at 0° C. under N₂ atmosphere. The mixture was stirred at 100° C. for 8 hour and concentrated. The residue was purified by column chromatography on silica gel with petroleum/THF=40:1 to 10:1 to give 2-bromo-N-(2,2-dimethoxyethyl)-8-(4-fluorophenyl)-11H-pyrido[3,2-e]pyrrolo[1,2-a][1,4]diazepin-6-amine (600 mg, 1.09 mmol, 67.6% yield, 83.4% purity) as a light yellow solid, which was used directly without further purification. TLC: R_f=0.6, petroleum ether/THF=2/1. ESI [M+H]=459.1/461.1

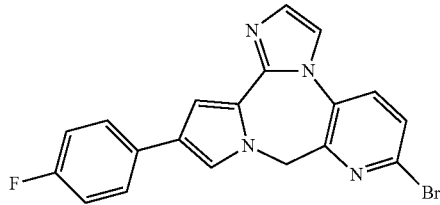 [SMILES: Fc1ccc(-c2cc3n(c2)Cc2nc(Br)ccc2-n2ccnc2-3)cc1]

7-bromo-12-(4-fluorophenyl)-9H-imidazo[2,1-c]pyrido[3,2-e]pyrrolo[1,2-a][1,4]diazepine, S125. A mixture of 2-bromo-N-(2,2-dimethoxyethyl)-8-(4-fluorophenyl)-11H-pyrido[3,2-e]pyrrolo[1,2-a][1,4]diazepin-6-amine (700 mg, 1.27 mmol, 1.00 eq.) in dioxane (30 mL) and 1M HCl (30 mL) was heated to 70° C. for 16 hr and then concentrated. The residue solid was washed with THF (10 mL×2) and dried in vacuum to give 7-bromo-12-(4-fluorophenyl)-9H-imidazo[2,1-c]pyrido[3,2-e]pyrrolo[1,2-a][1,4]diazepine (500 mg, crude) as a light yellow solid, which was used directly without further purification. ESI [M+H]=395.0/397.0

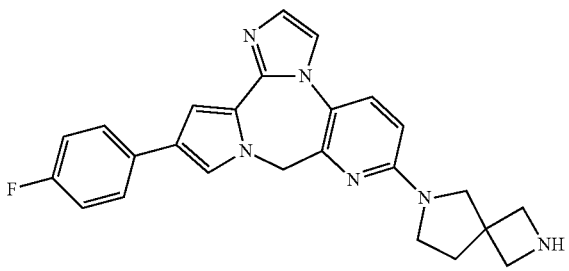 [SMILES: Fc1ccc(-c2cc3n(c2)Cc2nc(N4CCC5(CNC5)C4)ccc2-n2ccnc2-3)cc1]

12-(4-fluorophenyl)-7-(2,6-diazaspiro[3.4]octan-6-yl)-9H-imidazo[2,1-c]pyrido[3,2-e] pyrrolo[1,2-a][1,4]diazepine, 440. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-imidazo[2,1-c]pyrido[3,2-e]pyrrolo[1,2-a][1,4]diazepine and replacing tert-butyl piperazine-1-carboxylate with tert-butyl 2,6-diazaspiro[3.4]octane-2-carboxylate. ¹H NMR (400 MHz, METHANOL-d4) δ=8.01 (s, 1H), 7.88 (d, J=8.8 Hz, 1H), 7.78 (s, 1H), 7.64 (s, 1H), 7.59 (t, J=6.2 Hz, 2H), 7.24 (s, 1H), 7.10 (t, J=8.1 Hz, 2H), 6.68 (d, J=9.0 Hz, 1H), 5.32 (s, 2H), 4.23-4.15 (m, 2H), 4.13-4.05 (m, 2H), 3.85 (br. s., 2H), 3.70-3.56 (m, 2H), 2.40 (t, J=6.7 Hz, 2H). ESI [M+H]=427.1

Scheme 36

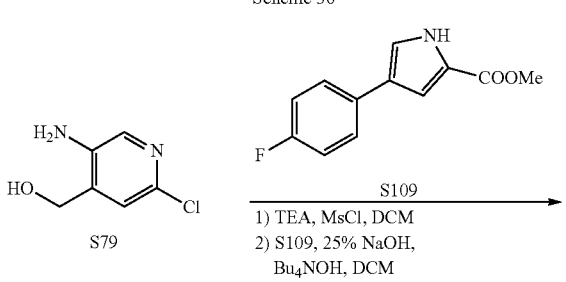

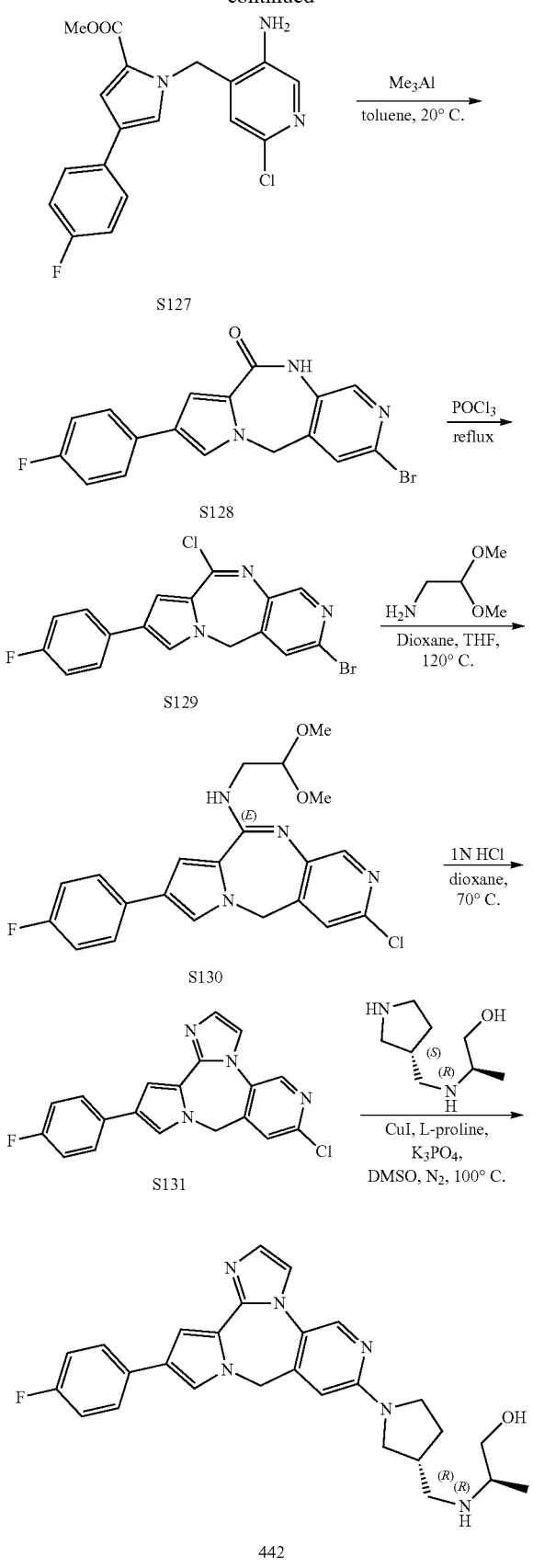

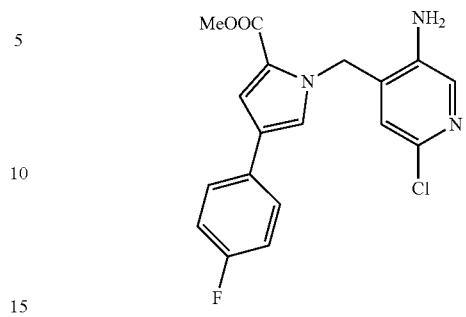

Chemistry Experimental Methods:

Methyl 1-((5-amino-2-chloropyridin-4-yl)methyl)-4-(4-fluorophenyl)-1H-pyrrole-2-carboxylate, S127. To a solution of (5-amino-2-chloropyridin-4-yl)methanol (4.0 g, 25 mmol, 1.0 eq.) and TEA (7.6 g, 75.6 mmol, 10.4 mL, 3.0 eq.) in DCM (400 mL) was added methanesulfonyl chloride (3.4 g, 30.2 mmol, 2.3 mL, 1.2 eq.) at −78° C. under $N_2$. The mixture was warmed to 26° C. and stirred at 26° C. for 1 hr under $N_2$. To the solution was added methyl 4-(4-fluorophenyl)-1H-pyrrole-2-carboxylate (4.4 g, 20.1 mmol, 0.8 eq.), NaOH (25%, 6.00 eq.) and TBAOH (2.62 g, 2.52 mmol, 3.28 mL, 25% purity, 0.10 eq.) at 0° C. The mixture was stirred at 26° C. for 16 hr, diluted with water (500 mL) and extracted with DCM (500 mL*2). The combined organic layer was dried over anhydrous $MgSO_4$, filtered and concentrated to give a residue. The residue was purified by silica gel chromatography (Petroleum ether/Ethyl acetate=5/1 to 1/1) to afford methyl 1-((5-amino-2-chloropyridin-4-yl)methyl)-4-(4-fluorophenyl)-1H-pyrrole-2-carboxylate (1.9 g, 5.28 mmol, 20.94% yield) as a yellow solid. TLC: Rf=0.22 (Petroleum ether/Ethyl acetate=1/1). ESI [M+H]=360.0

3-chloro-8-(4-fluorophenyl)-5H-pyrido[3,4-e]pyrrolo[1,2-a][1,4]diazepin-10(11H)-one, S128. To a solution of methyl 1-((5-amino-2-chloropyridin-4-yl)methyl)-4-(4-fluorophenyl)-1H-pyrrole-2-carboxylate (1.8 g, 5.2 mmol, 1.0 eq.) in toluene (100 mL) was added $AlMe_3$ (2 M, 12.85 mL, 5.0 eq.) dropwise at 0° C. under $N_2$. Then the mixture was stirred at 20° C. for 16 hr, quenched with ice-water (200 mL) and extracted with hot EtOAc/THF (1/1, 200 mL*2). The combined organic layer was washed with brine (100 mL), dried over $Na_2SO_4$ and concentrated. The residue solid was washed with MeOH (20 mL). After filtration, the filter cake was collected to give 3-chloro-8-(4-fluorophenyl)-5H-pyrido[3,4-e]pyrrolo[1,2-a][1,4] diazepin-10(11H)-one (1.60 g, crude) as a yellow solid. 1H NMR (400 MHz, METHANOL-d4) δ=8.13 (s, 1H), 7.49-7.39 (m, 3H), 7.28 (d, J=1.8 Hz, 1H), 7.14 (d, J=1.8 Hz, 1H), 6.96 (t, J=8.8 Hz, 2H), 5.16 (s, 2H). ESI [M+H]=327.9

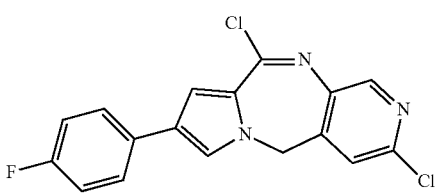 [SMILES: Fc1ccc(-c2cc3n(c2)Cc2cc(Cl)ncc2N=C3Cl)cc1]

3,10-dichloro-8-(4-fluorophenyl)-5H-pyrrolo[1,2-a][1,4]diazepine, S129. A solution of 3-chloro-8-(4-fluorophenyl)-5H-pyrido[3,4-e]pyrrolo[1,2-a][1,4]diazepin-10(11H)-one (300 mg, 806 umol, 1.0 eq.) in POCl$_3$ (5 mL) was stirred at 90° C. for 1 hr. The reaction mixture was concentrated under reduced pressure, diluted with THF (5 mL), adjusted to pH 7-8 with TEA and concentrated under reduced pressure to give crude 3,10-dichloro-8-(4-fluorophenyl)-5H-pyrido[3,4-e]pyrrolo[1,2-a][1,4]diazepine (310 mg) without further purification.

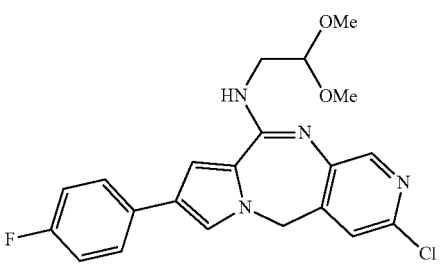 [SMILES: COC(CNC1=Nc2cnc(Cl)cc2Cn2cc(-c3ccc(F)cc3)cc21)OC]

3-chloro-N-(2,2-dimethoxyethyl)-8-(4-fluorophenyl)-5H-pyrido[3,4-e]pyrrolo[1,2-a][1,4] diazepin-10-amine, S130. A solution of 3,10-dichloro-8-(4-fluorophenyl)-5H-pyrido[3,4-e] pyrrolo[1,2-a][1,4]diazepine (310 mg, 793 umol, 1.0 eq.) and 2,2-dimethoxyethanamine (834 mg, 7.94 mmol, 860 uL, 10 eq.) in THF (10 mL)/1,4-dioxane (10 mL) was stirred at 130° C. for 16 hr in sealing tube. The reaction mixture was concentrated under reduced pressure, diluted with THF/EtOAc (50 mL/50 mL) and washed with 1 M HCl (20 mL). The combined organic layer was washed with brine, dried over Na$_2$SO$_4$, filtered and concentrated under reduced pressure to give crude 3-chloro-N-(2,2-dimethoxyethyl)-8-(4-fluorophenyl)-5H-pyrido[3,4-e]pyrrolo[1,2-a][1,4]diazepin-10-amine (360.00 mg, crude) as a black brown oil without further purification.

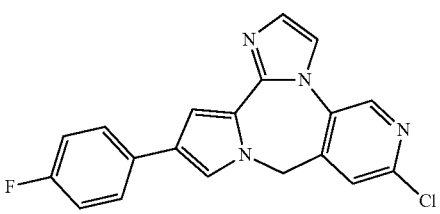 [SMILES: Fc1ccc(-c2cc3n(c2)Cc2cc(Cl)ncc2-n2ccnc2-3)cc1]

7-chloro-12-(4-fluorophenyl)-9H-imidazo[2,1-c]pyrido[3,4-e]pyrrolo[1,2-a][1,4]diazepine, S131. A solution of 3-chloro-N-(2,2-dimethoxyethyl)-8-(4-fluorophenyl)-5H-pyrido[3,4-e] pyrrolo[1,2-a][1,4]diazepin-10-amine (360 mg, 867 umol, 1.0 eq.) in dioxane (10 mL) and 1M HCl (10 mL) was stirred at 70° C. for 16 hr and concentrated under reduced pressure. The residue solid was washed with THF (5 mL) and filtered to give crude 7-chloro-12-(4-fluorophenyl)-9H-imidazo[2,1-c]pyrido[3,4-e]pyrrolo[1,2-a][1,4]diazepine (250 mg, crude) as a black brown solid without further purification. ESI [M+H]=350.9

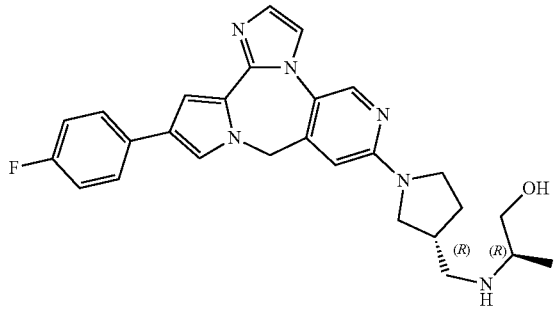

(R)-2-((((R)-1-(12-(4-fluorophenyl)-9H-imidazo[2,1-c]pyrido[3,4-e]pyrrolo[1,2-a][1,4] diazepin-7-yl)pyrrolidin-3-yl)methyl)amino)propan-1-ol, 442. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-chloro-12-(4-fluorophenyl)-9H-imidazo[2,1-c]pyrido[3,4-e]pyrrolo[1,2-a][1,4]diazepine and replacing tert-butyl piperazine-1-carboxylate with (R)-2-(((S)-pyrrolidin-3-ylmethyl)amino)propan-1-ol. 1H NMR (400 MHz, METHANOL-d4) δ=8.43 (s, 1H), 8.09 (br. s., 1H), 7.78 (br. s., 1H), 7.65-7.53 (m, 3H), 7.24 (br. s., 1H), 7.10 (t, J=8.0 Hz, 2H), 6.76 (s, 1H), 5.33 (s, 2H), 3.94-3.79 (m, 2H), 3.72 (br. s., 1H), 3.65-3.50 (m, 2H), 3.41 (br. s., 2H), 3.26-3.16 (m, 2H), 2.81-2.67 (m, 1H), 2.36 (br. s., 1H), 2.02-1.86 (m, 1H), 1.35 (d, J=6.7 Hz, 3H). ESI [M+H]=473.1

Scheme 37

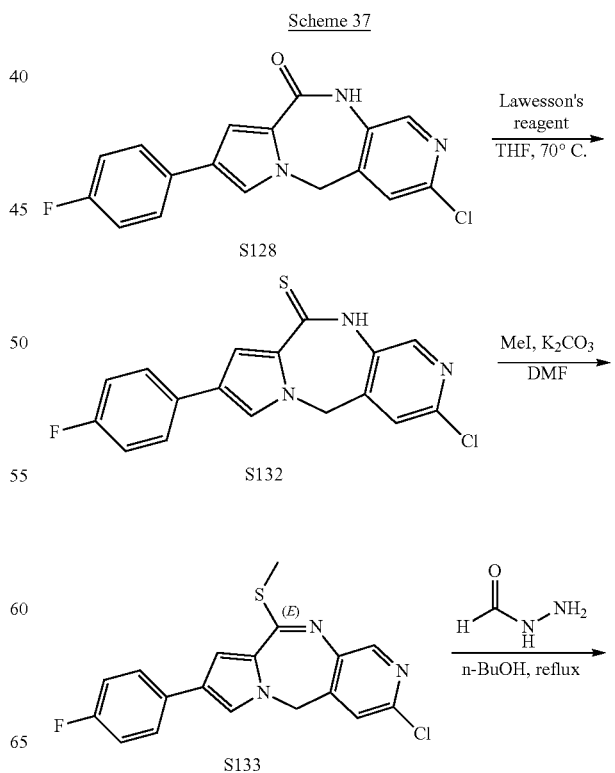

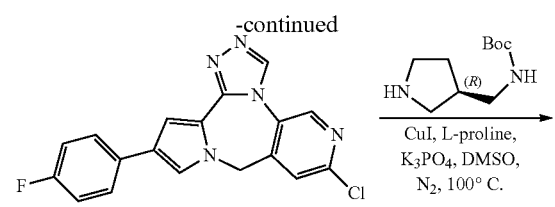

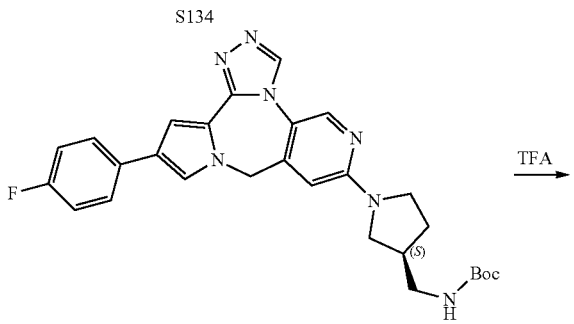

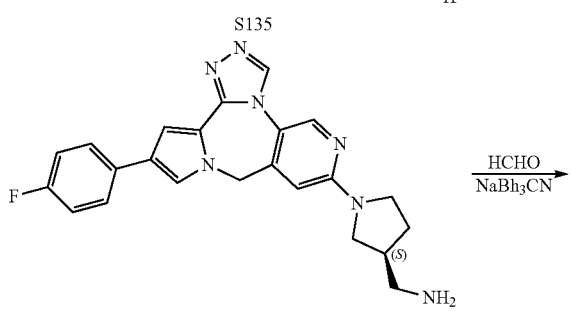

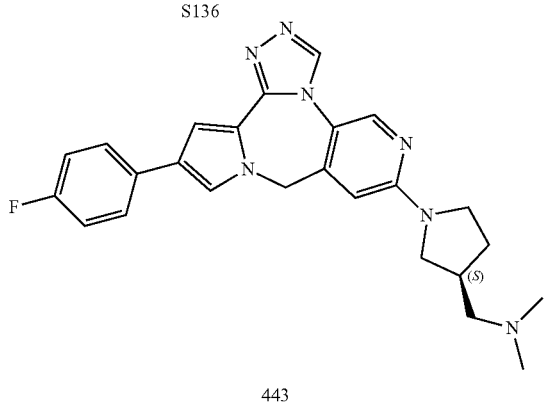

443

Chemistry Experimental Methods:

3-chloro-8-(4-fluorophenyl)-5H-pyrido[3,4-e]pyrrolo[1,2-a][1,4]diazepine-10(11H)-thione, S132. To a solution of 3-chloro-8-(4-fluorophenyl)-5H-pyrido[3,4-e]pyrrolo[1,2-a][1,4] diazepin-10(11H)-one (1.3 g, 3.9 mmol, 1.0 eq.) in THF (30 mL) was added Lawesson's reagent (2.1 g, 5.2 mmol, 1.3 eq.) and the mixture was stirred at 70° C. for 1 hr. The mixture was concentrated and the residue solid was washed with methanol (10 mL) to give 3-chloro-8-(4-fluorophenyl)-5H-pyrido[3,4-e]pyrrolo[1,2-a][1,4]diazepine-10(11H)-thione (1.0 g, 2.9 mmol, 73.5% yield) as a yellow solid, which was used without any purification. ESI [M+H]= 344.1

3-chloro-8-(4-fluorophenyl)-10-(methylthio)-5H-pyrido[3,4-e]pyrrolo[1,2-a][1,4]diazepine, S133. To a solution of 3-chloro-8-(4-fluorophenyl)-5H-pyrido[3,4-e]pyrrolo[1,2-a][1,4] diazepine-10(11H)-thione (1.0 g, 2.9 mmol, 1.0 eq.) in DMF (8.0 mL) was added $K_2CO_3$ (1.2 g, 8.7 mmol, 3.0 eq.) and iodomethane (2.0 g, 14 mmol, 905 uL, 5.0 eq.). The mixture was stirred at 26° C. for 1 hr and filtered. The filtrate was concentrated under reduced pressure to give 3-chloro-8-(4-fluorophenyl)-10-(methylthio)-5H-pyrido[3,4-e] pyrrolo[1,2-a][1,4]diazepine (1.0 g, 2.8 mmol, 96% yield) as a yellow solid, which was used directly without any purification. ESI [M+H]=358.1

7-chloro-12-(4-fluorophenyl)-9H-pyrido[3,4-e]pyrrolo[1,2-a][1,2,4]triazolo[3,4-c][1,4] diazepine, S134. To a solution of 3-chloro-8-(4-fluorophenyl)-10-(methylthio)-5H-pyrido[3,4-e]pyrrolo[1,2-a][1,4]diazepine (1.0 g, 2.8 mmol, 1.0 eq.) in n-BuOH (30 mL) was added formohydrazide (837 mg, 14 mmol, 5.0 eq.) and the mixture was stirred at 120° C. for 16 hr. The mixture was concentrated and the residue solid was washed with 1N HCl (20 mL) to give the 7-chloro-12-(4-fluorophenyl)-9H-pyrido[3,4-e]pyrrolo[1,2-a][1,2,4]triazolo[3,4-c][1,4]diazepine (650 mg, 1.85 mmol, 66.23% yield) as a yellow solid. ESI [M+H]=352.2

(S)-1-(1-(12-(4-fluorophenyl)-9H-pyrido[3,4-e]pyrrolo[1,2-a][1,2,4]triazolo[3,4-c][1,4] diazepin-7-yl)pyrrolidin-3-yl)-N,N-dimethylmethanamine, 443. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-chloro-12-(4-fluorophenyl)-9H-pyrido[3,4-e]pyrrolo[1,2-a][1,2,4] triazolo[3,4-c][1,4]diazepine and replacing tert-butyl (azetidin-3-ylmethyl)(methyl)carbamate with (R)-tert-butyl (pyrrolidin-3-ylmethyl)carbamate. $^1$H NMR (400 MHz, METHANOL-d4) δ=9.04 (br. s., 1H), 8.35 (br. s., 1H), 7.61-7.51 (m, 2H), 7.42 (s, 1H), 7.17 (br. s., 1H), 7.06 (t, J=8.6 Hz, 2H), 6.76 (s, 1H), 5.18 (br. s., 2H), 3.94-3.82 (m, 1H), 3.69 (d, J=6.7 Hz, 1H), 3.58-3.47 (m, 1H), 3.37-3.32 (m, 2H), 2.96 (s, 6H), 2.90-2.76 (m, 1H), 2.70 (s, 1H), 2.34 (br. s., 1H), 1.96-1.83 (m, 1H). ESI [M+H]=444.2

Scheme 38

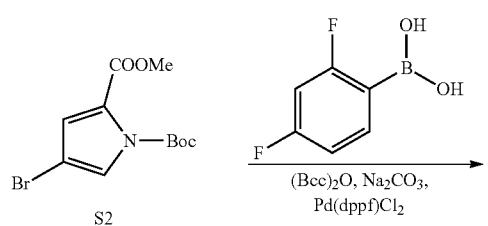

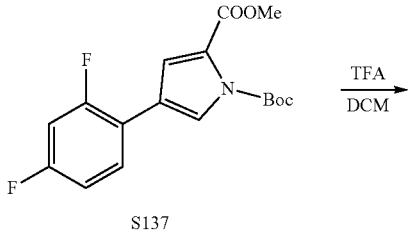

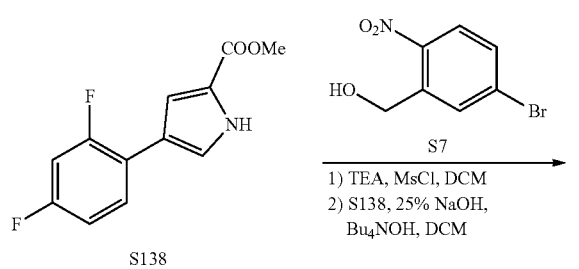

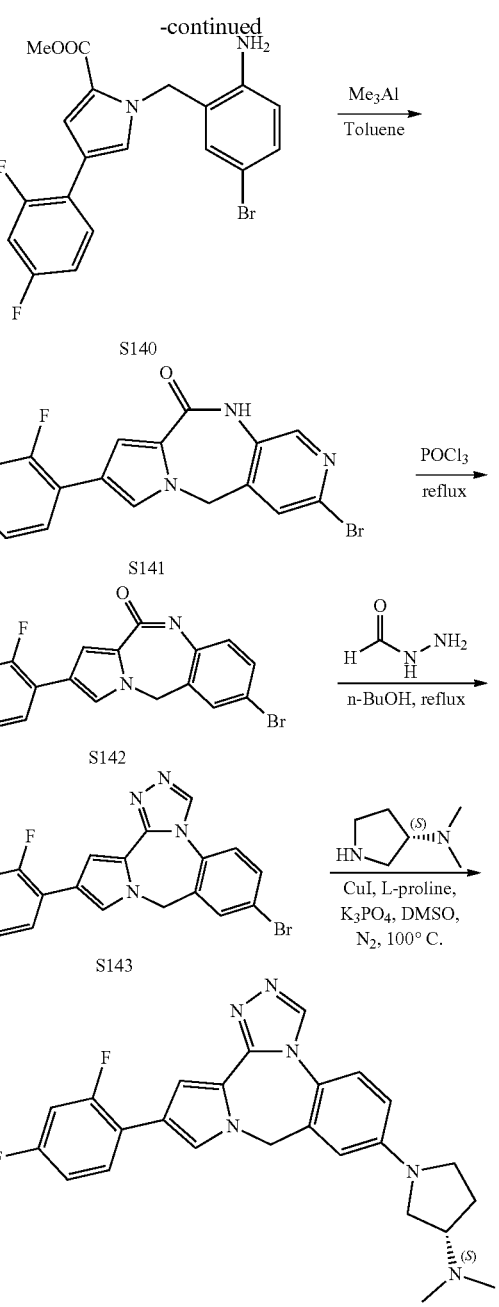

Chemistry Experimental Methods 1-tert-butyl 2-methyl 4-(2,4-difluorophenyl)-1H-pyrrole-1,2-dicarboxylate, S137. To a mixture of 1-tert-butyl 2-methyl 4-bromo-1H-pyrrole-1,2-dicarboxylate (34 g, 111 mmol, 1.0 eq.), (2,4-difluorophenyl)boronic acid (26 g, 164 mmol, 1.47 eq.), Boc₂O (38 g, 174 mmol, 40 mL, 1.56 eq.) and Na₂CO₃ (24 g, 226 mmol, 2.0 eq.) in dioxane (1.0 L) and H₂O (100 mL) was added Pd(dppf)Cl₂ (4 g, 5.4 mmol, 0.05 eq.) at 25° C. under N₂ atmosphere. The mixture was stirred at 100° C. for 16 hr and concentrated. The residue was diluted with EtOAc/THF (400 mL/100 mL) and washed with brine (400 mL). The aqueous layer was separated and extracted with EtOAc (150 mL×2). The combined organic layers were dried over Na₂SO₄ and concentrated to give a mixture of 1-tert-butyl 2-methyl 4-(2,4-difluorophenyl)-1H-pyrrole-1,2-dicarboxylate (40 g, crude) as a black brown oil, which was used directly. ESI [M+H]=338.0

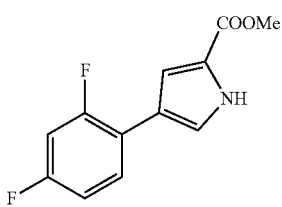 [SMILES: COC(=O)c1cc(-c2ccc(F)cc2F)c[nH]1]

Methyl 4-(2,4-difluorophenyl)-1H-pyrrole-2-carboxylate, S138. To a solution of 1-tert-butyl 2-methyl 4-(2,4-difluorophenyl)-1H-pyrrole-1,2-dicarboxylate (40 g, crude) in DCM (50 mL) was added TFA (100 mL) dropwise. The reaction mixture was stirred at 25° C. for 1.0 hr and concentrated. The residue was added with MeOH (50 mL) and stirred for 1.0 hr. The solid was collected by filtration to give methyl 4-(2,4-difluorophenyl)-1H-pyrrole-2-carboxylate (15 g, 56.91 mmol, 56.41% yield over all 2 steps) as a dark brown solid, which was used directly. ¹H NMR (400 MHz, CDCl₃) δ=9.21, (br. s, 1H), 7.54-7.48, (m, 1H), 7.38 (s, 1H), 7.22 (s, 1H), 6.92-6.85 (m, 2H), 3.90 (s, 3H). ESI [M+H]=238.0

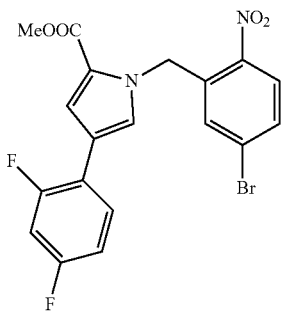 [SMILES: COC(=O)c1cc(-c2ccc(F)cc2F)cn1Cc1cc(Br)ccc1[N+](=O)[O-]]

Methyl 1-(5-bromo-2-nitrobenzyl)-4-(2,4-difluorophenyl)-1H-pyrrole-2-carboxylate, S139. To a solution of (5-bromo-2-nitrophenyl)methanol (9.0 g, 38.7 mmol, 1.0 eq.) and Et₃N (6.0 g, 59.2 mmol, 8.20 mL, 1.5 eq.) in dry DCM (300 mL) was added MsCl (5.2 g, 45.5 mmol, 3.5 mL, 1.2 eq.) dropwise at 0° C. under N₂ atmosphere. The reaction mixture was stirred at 0° C. for 1.0 hr, then methyl 4-(2,4-difluorophenyl)-1H-pyrrole-2-carboxylate (9.0 g, 37.9 mmol, 1.0 eq.), Bu₄NOH (25% in H₂O, 4.0 g, 3.8 mmol, 0.1 eq.) and NaOH aq. (25%, 35 g, 218.9 mmol, 5.7 eq.) were added in turn. The reaction mixture was warmed to 25° C. and stirred for another 16 hr. The mixture was washed with brine (200 mL), dried over Na₂SO₄ and concentrated. The residue solid was washed with EtOAc/petroleum ether (1:1, 50 mL×2), filtered and dried to give methyl 1-(5-bromo-2-nitrobenzyl)-4-(2,4-difluorophenyl)-1H-pyrrole-2-carboxylate (14.50 g, crude) as a yellow solid, which was used directly. ESI [M+H]=450.9/452.9

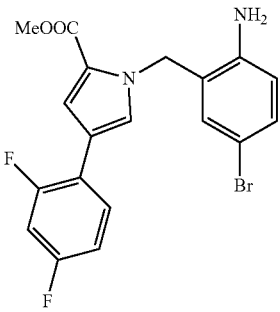 [SMILES: COC(=O)c1cc(-c2ccc(F)cc2F)cn1Cc1cc(Br)ccc1N]

Methyl 1-(2-amino-5-bromobenzyl)-4-(2,4-difluorophenyl)-1H-pyrrole-2-carboxylate, S140. A mixture of methyl 1-(5-bromo-2-nitrobenzyl)-4-(2,4-difluorophenyl)-1H-pyrrole-2-carboxylate (14.5 g, 32.1 mmol, 1.0 eq.), Fe (9.0 g, 161 mmol, 5.0 eq.) and NH₄Cl (5.0 g, 93.5 mmol, 3.27 mL, 2.9 eq.) in THF (100 mL), EtOH (100 mL) and H₂O (50 mL) was stirred at 100° C. for 2.5 hr and then concentrated. The residue was dissolved with hot THF (2 L), filtered and the filtrate was concentrated to give methyl 1-(2-amino-5-bromobenzyl)-4-(2,4-difluorophenyl)-1H-pyrrole-2-carboxylate (13 g, crude) as a yellow solid, which was used directly. ESI [M+H]=420.9/422.9

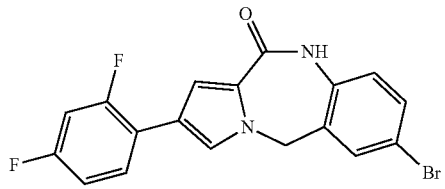 [SMILES: O=C1Nc2ccc(Br)cc2Cn2cc(-c3ccc(F)cc3F)cc21]

7-bromo-2-(2,4-difluorophenyl)-5H-benzo[e]pyrrolo[1,2-a][1,4]diazepin-11(10H)-one, S141. To a suspension of methyl 1-(2-amino-5-bromobenzyl)-4-(2,4-difluorophenyl)-1H-pyrrole-2-carboxylate (13 g, 30.8 mmol, 1.0 eq.) in dry toluene (150 mL) was added AlMe₃ (2 M in toluene, 75 mL, 4.8 eq.) dropwise at 0° C. under N₂ atmosphere. The reaction mixture was stirred at 25° C. for 16 hr and then poured into cold 0.5 M HCl (100 mL) slowly. The aqueous layer was separated and extracted with EtOAc/THF (8:1, 100 mL×3). The combined organic layers were washed with brine (150 mL), dried over Na₂SO₄ and concentrated. The residue solid was washed with petroleum ether/EtOAc (3:1, 50 mL×2) and dried in vacuo to give 7-bromo-2-(2,4-difluorophenyl)-5H-benzo[e]pyrrolo[1,2-a][1,4]diazepin-11(10H)-one (7.5 g, crude) as a light yellow solid, which was used directly without further purification. ESI [M+H]=388.9/390.9

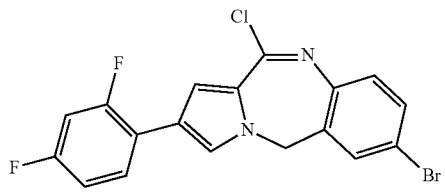 [SMILES: Fc1ccc(-c2cc3n(c2)Cc2cc(Br)ccc2N=C3Cl)c(F)c1]

7-bromo-11-chloro-2-(2,4-difluorophenyl)-5H-benzo[e]pyrrolo[1,2-a][1,4]diazepine, S142. A solution of 7-bromo-2-(2,4-difluorophenyl)-5H-benzo[e]pyrrolo[1,2-a][1,4]diazepin-11(10H)-one (1.5 g, 3.8 mmol, 1.0 eq.) in POCl₃ (50 mL) was heated to 90° C. for 6 hr and then concentrated in vacuum to give the crude product, which was used directly without purification.

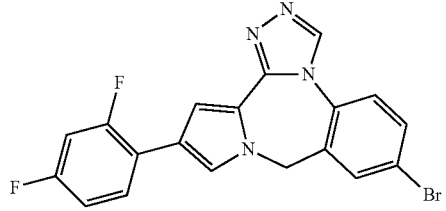 [SMILES: Fc1ccc(-c2cc3n(c2)Cc2cc(Br)ccc2-n2cnnc2-3)c(F)c1]

7-bromo-12-(2,4-difluorophenyl)-9H-benzo[e]pyrrolo[1,2-a][1,2,4]triazolo[3,4-c][1,4] diazepine, S143. To a mixture of 7-bromo-11-chloro-2-(2,4-difluorophenyl)-5H-benzo[e]pyrrolo[1,2-a][1,4]diazepine (1.6 g, 3.9 mmol, 1.0 eq.) in dry dioxane (50 mL) was added formohydrazide (2.4 g, 39.9 mmol, 10.1 eq.) and the reaction mixture was stirred at 110° C. 16 hr. Then the mixture was cooled to 25° C. and poured into ice-cold water (150 mL), extracted with hot EtOAc/THF (4:1, 100 mL×4). The combined organic layers were washed with brine (100 mL), dried over Na₂SO₄ and concentrated. The residue solid was washed with EtOAc (50 mL×2) and dried in vacuum to give 7-bromo-12-(2,4-difluorophenyl)-9H-benzo[e] pyrrolo[1,2-a][1,2,4]triazolo[3,4-c][1,4]diazepine (1.0 g, crude) as an off-white solid, which was used directly. ESI [M+H]=412.9/414.9

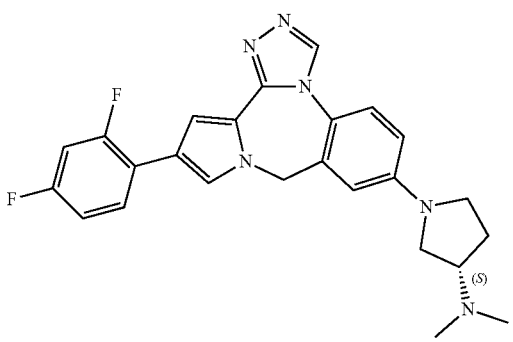

(S)-1-(12-(2,4-difluorophenyl)-9H-benzo[e]pyrrolo[1,2-a][1,2,4]triazolo[3,4-c][1,4]diazepin-7-yl)-N,N-dimethylpyrrolidin-3-amine, 449. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(2,4-difluorophenyl)-9H-benzo[e]pyrrolo[1,2-a][1,2,4]triazolo[3,4-c][1,4]diazepine and replacing tert-butyl piperazine-1-carboxylate with (S)—N,N-dimethylpyrrolidin-3-amine. ¹H NMR (400 MHz, METHANOL-d₄) δ=8.97 (s, 1H), 7.68-7.60 (m, 1H), 7.51-7.46 (m, 2H), 7.15 (s, 1H), 6.99-6.90 (m, 2H), 6.88 (d, J=2.6 Hz, 1H), 6.76 (dd, J=2.4, 8.6 Hz, 1H), 5.16 (s, 2H), 3.91 (br. s., 1H), 3.79-3.72 (m, 1H), 3.65 (dt, J=3.1, 9.0 Hz, 1H), 3.55 (dd, J=6.6, 10.1 Hz, 1H), 3.46-3.37 (m, 1H), 2.88 (s, 6H), 2.73-2.65 (m, 1H), 2.26 (dd, J=7.9, 12.8 Hz, 1H). ESI [M+H]=447.1

Scheme 39

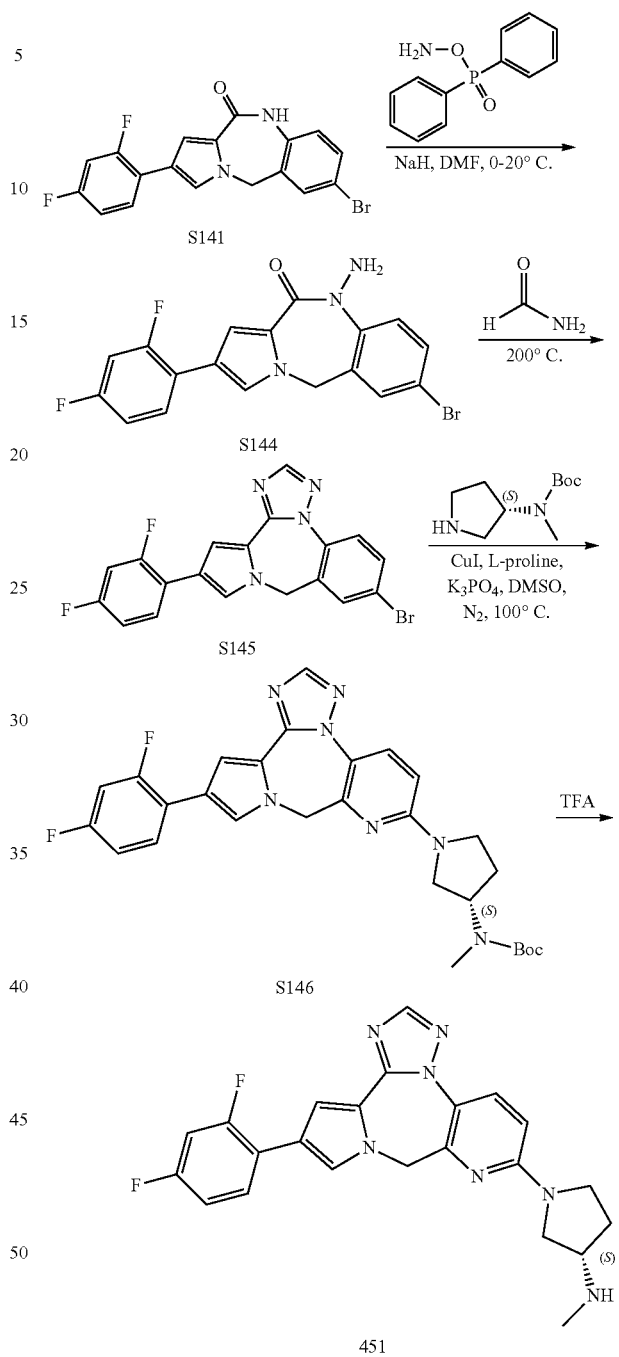

Chemistry Experimental Methods:

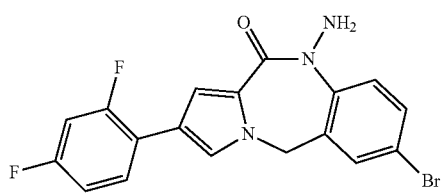 [SMILES: NN1C(=O)c2cc(-c3ccc(F)cc3F)cn2Cc2cc(Br)ccc21]

10-amino-7-bromo-2-(2,4-difluorophenyl)-5H-benzo[e]pyrrolo[1,2-a][1,4]diazepin-11(10H)-one, S144. To a solution of 7-bromo-2-(2,4-difluorophenyl)-5H-benzo[e]pyrrolo[1,2-a][1,4]diazepin-11(10H)-one (1.0 g, 2.5 mmol, 1.0 eq.) in dry DMF (15 mL) was added NaH (260 mg, 6.50 mmol, 60% purity, 2.53 eq.) and the mixture was stirred for 30 min at 0° C. Then (aminooxy)diphenylphosphine oxide (797.1 mg, 3.4 mmol, 1.3 eq.) was added portionwise and the reaction mixture was stirred at 25° C. for another 2.5 hr. The mixture was quenched with ice-cold sat.aq.NH₄Cl (50 mL) and extracted with EtOAc (50 mL×3). The combined organic layers were washed with brine (50 mL), dried over Na₂SO₄ and concentrated. The residue was purified by column chromatography on silica gel with petroleum/EtOAc (10:1 to 1:1) to give 10-amino-7-bromo-2-(2,4-difluorophenyl)-5H-benzo[e]pyrrolo[1,2-a][1,4]diazepin-11(10H)-one (600 mg, 1.34 mmol, 52.14% yield, 90.2% purity) as an off-white solid. TLC: R_f=0.55 (petroleum ether/EtOAc=1/1). ESI [M+H]=404.0/406.0

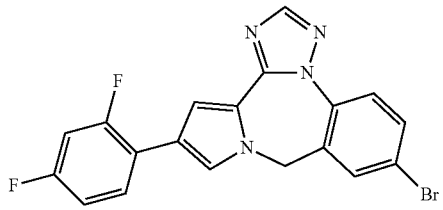 [SMILES: Fc1ccc(-c2cc3n(c2)Cc2cc(Br)ccc2-n2ncnc2-3)c(F)c1]

7-bromo-12-(2,4-difluorophenyl)-9H-benzo[e]pyrrolo[1,2-a][1,2,4]triazolo[5,1-c][1,4] diazepine, S145. A mixture of 10-amino-7-bromo-2-(2,4-difluorophenyl)-5H-benzo[e]pyrrolo[1,2-a][1,4]diazepin-11(10H)-one (250 mg, 618 umol, 1.0 eq.) and ZnCl₂ (250 mg, 1.8 mmol, 85.9 uL, 2.9 eq.) in NH₂CHO (5.0 mL) was stirred at 200° C. for 1 hr and then the mixture was poured into water (50 mL). The resulting precipitate was collected by filtration and then purified by prep-TLC (petroleum ether/EtOAc=2:1) to give 7-bromo-12-(2,4-difluorophenyl)-9H-benzo[e]pyrrolo[1,2-a][1,2,4]triazolo[5,1-c][1,4]diazepine (125 mg, 453 umol, 36% yield, 75% purity) as a light yellow solid, which was used directly. ESI [M+H]=413.0/415.0

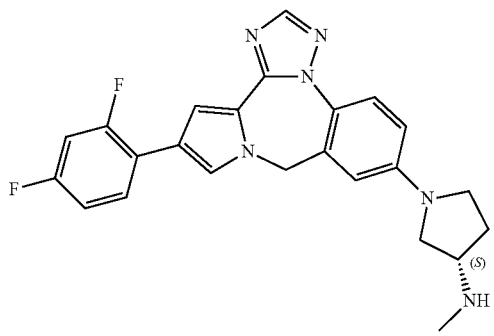

(S)-1-(12-(2,4-difluorophenyl)-9H-benzo[e]pyrrolo[1,2-a][1,2,4]triazolo[5,1-c][1,4]diazepin-7-yl)-N-methylpyrrolidin-3-amine, 451. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(2,4-difluorophenyl)-9H-benzo[e]pyrrolo[1,2-a][1,2,4]triazolo[5,1-c][1,4] diazepine and replacing tert-butyl piperazine-1-carboxylate with (S)-tert-butyl methyl(pyrrolidin-3-yl)carbamate. ¹H NMR (400 MHz, METHANOL-d₄) δ=8.16 (s, 1H), 7.73 (d, J=8.8 Hz, 1H), 7.70-7.60 (m, 1H), 7.50 (s, 1H), 7.17 (s, 1H), 7.03-6.92 (m, 2H), 6.89-6.78 (m, 2H), 5.25-5.17 (m, 2H), 4.05-3.94 (m, 1H), 3.75-3.56 (m, 3H), 3.46 (dt, J=5.7, 9.0 Hz, 1H), 2.86-2.74 (m, 3H), 2.55 (dt, J=6.7, 14.4 Hz, 1H), 2.28 (dt, J=5.3, 13.3 Hz, 1H). ESI [M+H]=433.1

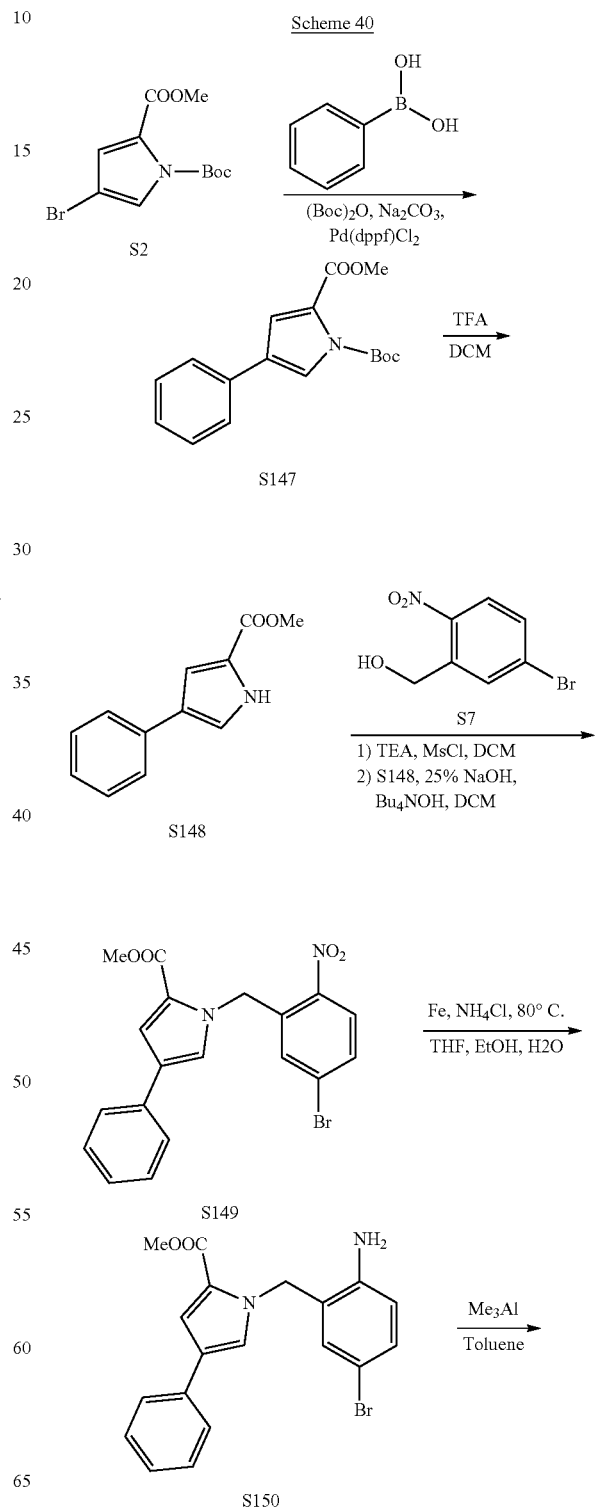

Scheme 40

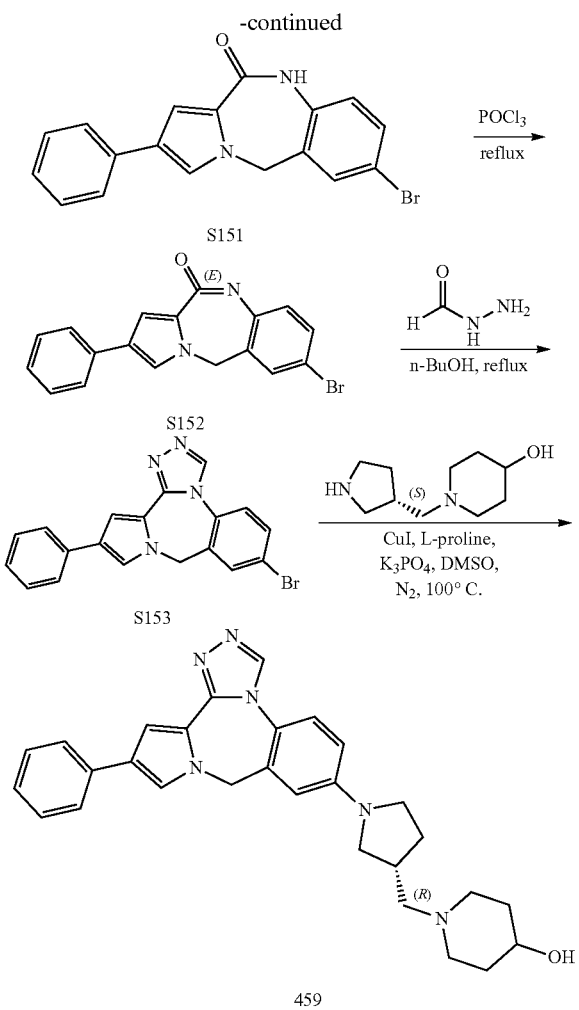

S151

S152

S153

459

Chemistry Experimental Methods:

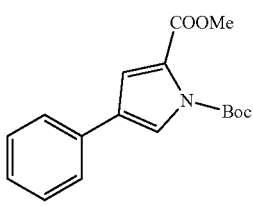 [SMILES: COC(=O)c1cc(-c2ccccc2)cn1C(=O)OC(C)(C)C]

1-tert-butyl 2-methyl 4-phenyl-1H-pyrrole-1,2-dicarboxylate, S147. A suspension of 1-tert-butyl 2-methyl 4-bromo-1H-pyrrole-1,2-dicarboxylate (44 g, 144 mmol, 1.0 eq.), phenyl boronic acid (26.4 g, 217 mmol, 1.5 eq.), $Na_2CO_3$ (30.6 g, 289 mmol, 12 mL, 2.0 eq.) and (Boc)$_2$O (47.3 g, 217 mmol, 49.8 mL, 1.5 eq.), Pd(dppf)Cl$_2$ (5.3 g, 7.2 mmol, 0.05 eq.) in dioxane/H$_2$O (1.5 L, 10:1) was de-gassed and then heated to 80~100° C. for 12 hr under N$_2$. The mixture was concentrated under reduced pressure and the residue was portioned between ethyl acetate (1.0 L) and brine (200 mL). The organic layer was dried over anhydrous Na$_2$SO$_4$, filtered and concentrated to give crude 1-tert-butyl 2-methyl 4-phenyl-1H-pyrrole-1,2-dicarboxylate (43.00 g, crude) as a off-white solid, which was used into the next step without further purification. ESI [M+H]=302.2

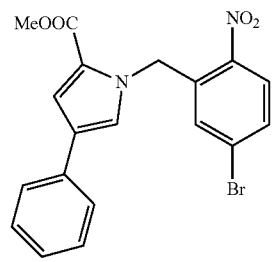 [SMILES: COC(=O)c1cc(-c2ccccc2)cn1Cc1cc(Br)ccc1[N+](=O)[O-]]

Methyl 4-phenyl-1H-pyrrole-2-carboxylate, S148. A solution of 1-tert-butyl 2-methyl 4-phenyl-1H-pyrrole-1,2-dicarboxylate (43 g, 142.7 mmol, 1.0 eq.) in TFA (300 mL) was stirred for 2 hr at 50° C. and then concentrated under reduced pressure. The residue was added MeOH (200 mL) and stirred for 1 hr. The precipitate was collected by filtration to give methyl 4-phenyl-1H-pyrrole-2-carboxylate (20 g, crude) as a white solid. $^1$H NMR (400 MHz, DMSO-d$_6$) δ=7.60 (d, J=7.4 Hz, 2H), 7.49 (dd, J=1.6, 2.7 Hz, 1H), 7.30 (t, J=7.6 Hz, 2H), 7.19-7.11 (m, 2H), 3.77 (s, 3H). ESI [M+H]=202.2

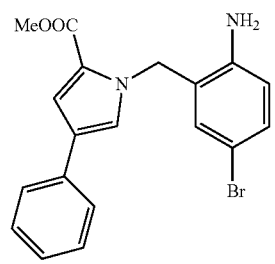

Methyl 1-(5-bromo-2-nitrobenzyl)-4-phenyl-1H-pyrrole-2-carboxylate, S149. To a solution of (5-bromo-2-nitrophenyl)methanol (12.0 g, 51.7 mmol, 1.00 eq.) and TEA (10.4 g, 103.4 mmol, 14.3 mL, 2.0 eq.) in DCM (300 mL) was added MsCl (6.5 g, 56.8 mmol, 4.4 mL, 1.1 eq.) at 0° C. and the mixture was stirred for 0.5 hr at 0° C. Then methyl 4-phenyl-1H-pyrrole-2-carboxylate (10.4 g, 51.7 mmol, 1.0 eq) was added to the solution, followed by tetrabutylammonium hydroxide (5.37 g, 5.2 mmol, 6.7 mL, 25% w %, 0.10 eq.) and a solution of NaOH (25%, 5.0 eq.) at 0° C. The mixture was stirred for 11 hr at 20° C. and then diluted with ice-water (200 mL) and DCM (800 mL). The organic layer was separated, dried over anhydrous Na$_2$SO$_4$, filtered and concentrated. The residue was added EtOH (50 mL) and stirred for 1 hr. The precipitate was collected by filtration to give methyl 1-(5-bromo-2-nitrobenzyl)-4-phenyl-1H-pyrrole-2-carboxylate (20 g) as a off-white solid. $^1$H NMR (400 MHz, CHLOROFORM-d) δ=8.01 (d, J=8.8 Hz, 1H), 7.54 (d, J=7.5 Hz, 3H), 7.41-7.34 (m, 3H), 7.25 (s, 1H), 7.22 (d, J=1.8 Hz, 1H), 6.73 (s, 1H), 5.92 (s, 2H), 3.75 (s, 3H)

Methyl 1-(2-amino-5-bromobenzyl)-4-phenyl-1H-pyrrole-2-carboxylate, S150. A suspension of methyl 1-(5-bromo-2-nitrobenzyl)-4-phenyl-1H-pyrrole-2-carboxylate (17 g, 40.9 mmol, 1.0 eq.), Fe (11.43 g, 204.70 mmol, 5.00 eq.) and NH₄Cl (10.9 g, 204.7 mmol, 7.1 mL, 5.0 eq.) in EtOH (80 mL), H₂O (40 mL) and THF (80 mL) was heated to 80° C. for 5 hr. The mixture was concentrated to dryness and the residue was added hot THF (2 L). The mixture was filtered and the filtrate was concentrated. The residue was added EtOH (100 mL) and stirred for 1 hr. The precipitate was collected by filtration to give methyl 1-(2-amino-5-bromobenzyl)-4-phenyl-1H-pyrrole-2-carboxylate (13.00 g) as a yellow solid. ESI [M+H]=385.1/387.1

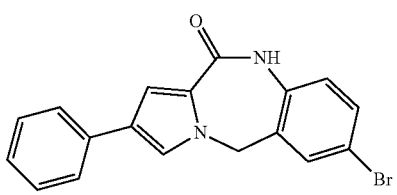 [SMILES: O=C1Nc2ccc(Br)cc2Cn2cc(-c3ccccc3)cc21]

7-bromo-2-phenyl-5H-benzo[e]pyrrolo[1,2-a][1,4]diazepin-11(10H)-one, S151. To a suspension of methyl 1-(2-amino-5-bromobenzyl)-4-phenyl-1H-pyrrole-2-carboxylate (13 g, 33.74 mmol, 1.0 eq.) in toluene (150 mL) was added Me₃Al (2 M in toluene, 85 mL, 5.0 eq.) at 0° C. and the mixture was stirred for 10 hr at 30° C. The mixture was poured into 1M ice-HCl (300 mL) and extracted with hot EtOAc/THF(1:1, 300 mL*4). The organic layer was dried over anhydrous Na₂SO₄, filtered and concentrated. The residue was added MeOH (50 mL) and stirred for 1 hr. The precipitate was collected by filtration to give 7-bromo-2-phenyl-5H-benzo[e] pyrrolo[1,2-a][1,4]diazepin-11(10H)-one (10 g) as a white solid. ¹H NMR (400 MHz, DMSO-d₆) δ=10.29 (s, 1H), 7.73 (s, 1H), 7.63-7.52 (m, 4H), 7.39 (t, J=7.5 Hz, 2H), 7.26-7.17 (m, 3H), 5.27 (s, 2H)

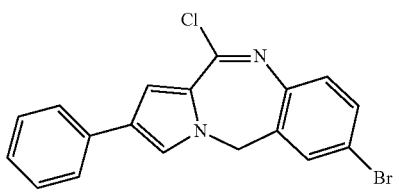 [SMILES: ClC1=Nc2ccc(Br)cc2Cn2cc(-c3ccccc3)cc21]

7-bromo-11-chloro-2-phenyl-5H-benzo[e]pyrrolo[1,2-a][1,4]diazepine, S152. A solution of 7-bromo-2-phenyl-5H-benzo[e]pyrrolo[1,2-a][1,4]diazepin-11(10H)-one (1.0 g, 2.83 mmol, 1.0 eq.) in POCl₃ (50 mL) was stirred for 2 hr at 90° C. The solution was concentrated under reduced pressure to give 7-bromo-11-chloro-2-phenyl-5H-benzo[e] pyrrolo[1,2-a][1,4]diazepine (1.2 g, crude) as a black oil, which was used for next step further purification.

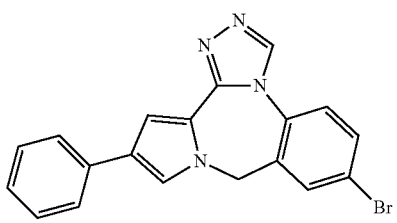 [SMILES: Brc1ccc2c(c1)Cn1cc(-c3ccccc3)cc1-c1nncn1-2]

7-bromo-12-phenyl-9H-benzo[e]pyrrolo[1,2-a][1,2,4]triazolo[3,4-c][1,4]diazepine, S153. A solution of 7-bromo-11-chloro-2-phenyl-5H-benzo[e]pyrrolo[1,2-a][1,4]diazepine (670 mg, 1.75 mmol, 1.0 eq.) and formohydrazide (525 mg, 8.75 mmol, 5.0 eq.) in dioxane (20 mL) was stirred at 130° C. for 12 hours in sealing tube. The mixture was concentrated and the residue was partitioned between hot EtOAc/THF (1:1, 200 mL) and HCl (3 M, 50 mL). The organic phase was washed with brine (15 mL), dried with anhydrous Na₂SO₄, filtered and concentrated in vacuum. The residue was added MeOH (10 mL) and stirred for 1 hr. The precipitate was collected by filtration to give 7-bromo-12-phenyl-9H-benzo[e]pyrrolo[1,2-a][1,2,4]triazolo[3,4-c][1,4]diazepine (500 mg, 1.19 mmol, 68.16% yield) as a white solid. ¹H NMR (400 MHz, DMSO-d₆) δ=9.21 (s, 1H), 7.94 (br. s., 1H), 7.78 (d, J=8.2 Hz, 1H), 7.67 (d, J=8.6 Hz, 1H), 7.59-7.52 (m, 3H), 7.33 (t, J=7.0 Hz, 2H), 7.16 (t, J=7.2 Hz, 1H), 7.11 (s, 1H), 5.28 (s, 2H).

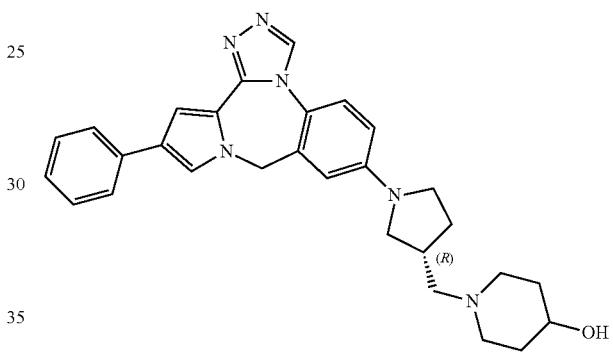

(R)-1-((1-(12-phenyl-9H-benzo[e]pyrrolo[1,2-a][1,2,4]triazolo[3,4-c][1,4]diazepin-7-yl) pyrrolidin-3-yl)methyl)piperidin-4-ol, 459. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-phenyl-9H-benzo[e]pyrrolo[1,2-a][1,2,4]triazolo[3,4-c][1,4]diazepine, replacing tert-butyl piperazine-1-carboxylate with (S)-1-(pyrrolidin-3-ylmethyl)piperidin-4-ol. 1H NMR (400 MHz, METHANOL-d4) δ=9.14 (br. s., 1H), 7.59-7.39 (m, 4H), 7.32 (t, J=7.5 Hz, 2H), 7.24-7.12 (m, 2H), 6.74 (br. s., 1H), 6.65 (d, J=8.4 Hz, 1H), 5.08 (s, 2H), 4.11 (br. s., 1H), 3.84 (br. s., 1H), 3.76-3.58 (m, 2H), 3.54-3.42 (m, 2H), 3.42-3.32 (m, 2H), 3.17-3.02 (m, 2H), 2.93-2.76 (m, 1H), 2.33 (d, J=5.3 Hz, 1H), 2.15 (d, J=13.2 Hz, 1H), 2.11-1.69 (m, 5H). ESI [M+H]=481.2

Scheme 41

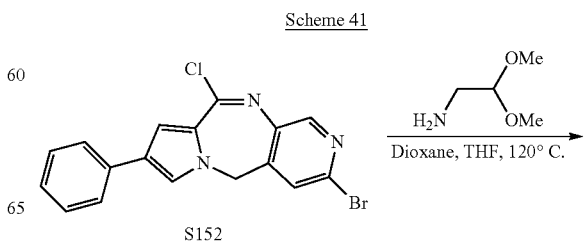

S152

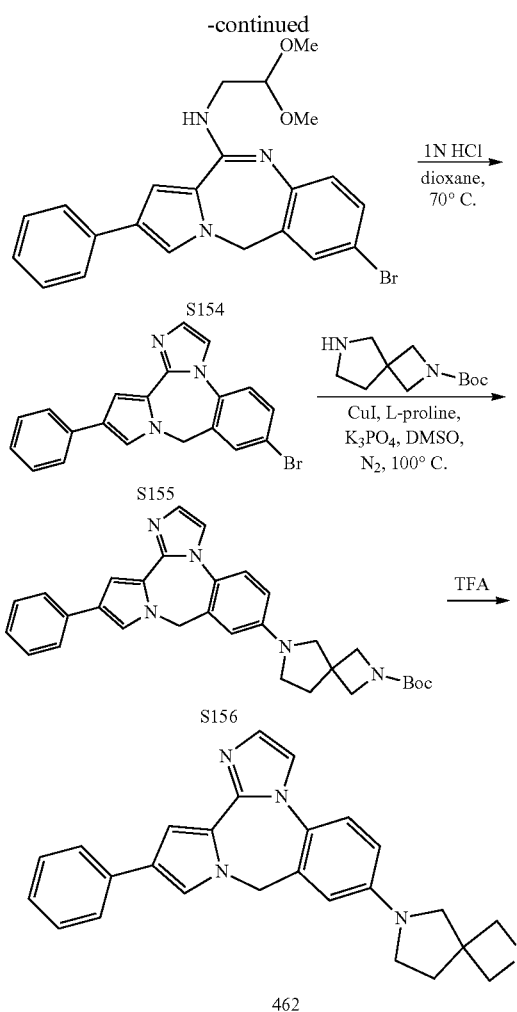

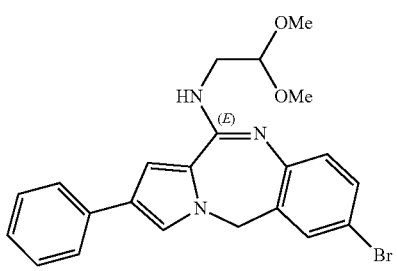 [SMILES: COC(CNC1=Nc2ccc(Br)cc2Cn2cc(-c3ccccc3)cc21)OC]

Chemistry Experimental Methods:

7-bromo-N-(2,2-dimethoxyethyl)-2-phenyl-5H-benzo[e]pyrrolo[1,2-a][1,4]diazepin-11-amine, S154. To a solution of 7-bromo-11-chloro-2-phenyl-5H-benzo[e]pyrrolo[1,2-a][1,4] diazepine (1.05 g, 2.83 mmol, 1.0 eq.) in dioxane (30 mL) and THF (30 mL) was added TEA (1.4 g, 14.1 mmol, 1.9 mL, 5.0 eq.) and 2,2-dimethoxyethanamine (5.9 g, 56.6 mmol, 6.1 mL, 20.0 eq.). The mixture was stirred at 130° C. for 16 hr in sealing tube and concentrated. The residue was diluted with solvent EtOAc (300 mL) and THF (100 mL), washed with 0.5 M HCl (100 mL), sat.NaHCO₃ (100 mL) and brine (100 mL), dried over Na₂SO₄, filtered and concentrated to give crude 7-bromo-N-(2,2-dimethoxyethyl)-2-phenyl-5H-benzo[e]pyrrolo[1,2-a][1,4]diazepin-11-amine (1.25 g, crude) as a black brown oil. ESI [M+H]=440.0/442.0

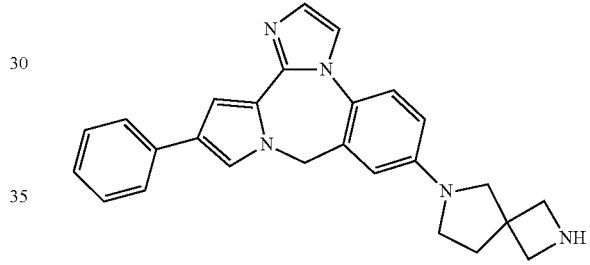

7-bromo-12-phenyl-9H-benzo[e]imidazo[2,1-c]pyrrolo[1,2-a][1,4]diazepine, S155. A mixture of 7-bromo-N-(2,2-dimethoxyethyl)-2-phenyl-5H-benzo[e]pyrrolo[1,2-a][1,4]diazepin-11-amine (1.25 g, 2.84 mmol, 1.0 eq.) in dioxane (20 mL) and 1M HCl (20 mL) was stirred at 80° C. for 16 hr. After the reaction was complete, the mixture was concentrated and the residue was added THF (15 mL) and ethanol (1 mL). After stirred for 1 hr, the precipitate was collected by filtration to give 7-bromo-12-phenyl-9H-benzo[e]imidazo[2,1-c]pyrrolo[1,2-a][1,4]diazepine (1.5 g, crude) as a black brown solid. ESI [M+H]=376.0/378.0

12-phenyl-7-(2,6-diazaspiro[3.4]octan-6-yl)-9H-benzo[e]imidazo[2,1-c]pyrrolo[1,2-a][1,4]diazepine, 462. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-phenyl-9H-benzo[e]imidazo[2,1-c]pyrrolo[1,2-a][1,4]diazepine and replacing tert-butyl piperazine-1-carboxylate with tert-butyl 2,6-diazaspiro[3.4]octane-2-carboxylate. 1H NMR (400 MHz, METHANOL-d4) δ=7.56-7.48 (m, 3H), 7.38-7.25 (m, 4H), 7.17 (s, 1H), 7.15-7.08 (m, 1H), 6.93 (s, 1H), 6.73 (br. s., 1H), 6.65 (d, J=6.8 Hz, 1H), 5.04 (s, 2H), 3.86-3.69 (m, 2H), 3.54 (s, 2H), 3.49-3.34 (m, 4H), 2.35-2.24 (m, 2H). ESI [M+H]=408.1

Amine Synthesis

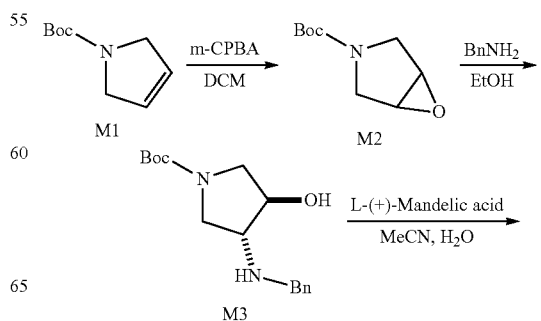

-continued

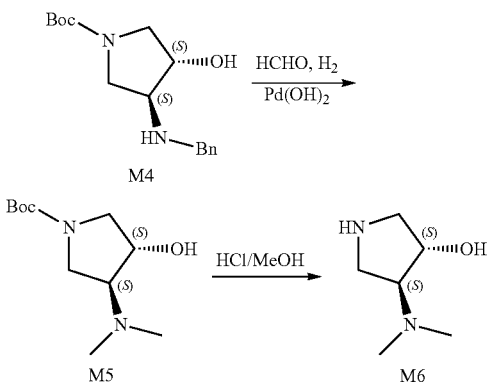

Chemistry Experimental Methods:

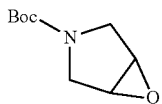

Tert-butyl 6-oxa-3-azabicyclo[3.1.0]hexane-3-carboxylate, M2. To a solution of tert-butyl 2,5-dihydropyrrole-1-carboxylate (100 g, 590.9 mmol, 1.0 eq.) in DCM (1.2 L) was added m-CPBA (180 g, 886.43 mmol, 85% purity, 1.50 eq.) portionwise at 0° C. and the mixture was stirred for 16 hr at 25° C. The mixture was washed with 10% aq.NaHSO$_3$ (600 mL×2), sat. aq.NaHCO$_3$ (600 mL×2) and brine (600 mL), dried over Na$_2$SO$_4$ and concentrated to give tert-butyl 6-oxa-3-azabicyclo[3.1.0]hexane-3-carboxylate (220 g, crude) as a yellow oil. 1H NMR (400 MHz, CHLOROFORM-d) δ=3.75 (d, J=12.8 Hz, 1H), 3.67 (d, J=12.8 Hz, 1H), 3.60 (d, J=3.3 Hz, 2H), 3.24 (dd, J=5.0, 12.7 Hz, 2H), 1.43-1.31 (m, 9H)

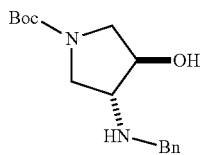 [SMILES: CC(C)(C)OC(=O)N1C[C@@H](O)[C@H](NCc2ccccc2)C1]

Trans-tert-butyl 3-(benzylamino)-4-hydroxypyrrolidine-1-carboxylate, M3. To a solution of tert-butyl 6-oxa-3-azabicyclo[3.1.0]hexane-3-carboxylate (135 g, 728.8 mmol, 1.0 eq.) in EtOH (1.3 L) was added BnNH$_2$ (160 g, 1.49 mol, 163.27 mL, 2.05 eq.) portionwise at 25° C. The reaction mixture was heated to reflux (oil bath 95° C.) for 16 hr and then concentrated. The residue was added EtOAc/petroleum ether (1:1, 400 mL) and stirred for 1.0 hr. The precipitate was collected by filtration to give trans-tert-butyl 3-(benzylamino)-4-hydroxypyrrolidine-1-carboxylate (137 g, 421.7 mmol, 57.8% yield, 90% purity) as a white solid. 1H NMR (400 MHz, CHLOROFORM-d) δ=7.37-7.18 (m, 5H), 4.09 (d, J=4.0 Hz, 1H), 3.88-3.73 (m, 2H), 3.73-3.56 (m, 2H), 3.31-3.07 (m, 3H), 1.48-1.37 (m, 9H)

General Procedure K

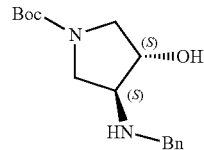

(3S,4S)-tert-butyl 3-(benzylamino)-4-hydroxypyrrolidine-1-carboxylate, M4. To a suspension of trans-tert-butyl 3-(benzylamino)-4-hydroxypyrrolidine-1-carboxylate (151 g, 516.4 mmol, 1.0 eq.) in MeCN (4.20 L) and H$_2$O (280.00 mL) was added (2S)-2-hydroxy-2-phenyl-acetic acid (85.6 mL, 562.9 mmol, 1.1 eq.). The mixture was heated to 85° C. for 2 hr and the solid was dissolved slowly. The solution was cooled to 20° C. for 11 hr and the precipitate was collected by filtration. The filter cake was re-crystallized again from MeCN/H$_2$O (3L, 20:1) get another batch solid. The solid was added to aq.K$_2$CO$_3$ (3%, 1.0 L) and extracted with EtOAc (500 mL*3). The organic layer was dried over Na$_2$SO$_4$ and concentrated to give (3S,4S)-tert-butyl 3-(benzylamino)-4-hydroxypyrrolidine-1-carboxylate (50 g, 168 mmol, 32.7% yield, 98.7% purity) as a white solid. [α]$_D^{22}$=+63.8°, ee %=97.5% by SFC.

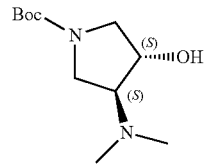

(3S,4S)-tert-butyl 3-(dimethylamino)-4-hydroxypyrrolidine-1-carboxylate, M5. To a solution of (3S,4S)-tert-butyl 3-(benzylamino)-4-hydroxypyrrolidine-1-carboxylate (30 g, 102 mmol, 1.0 eq.) and HCHO (102.7 g, 1.0 mol, 94.2 mL, 10 eq.) in MeOH (1.0 L) was added Pd(OH)$_2$ (2.8 g, 10.2 mmol, 50% purity, 0.1 eq.) and the mixture was heated to 50° C. for 5 hr under 50 psi hydrogen. The mixture was filtered and concentrated to give (3S,4S)-tert-butyl 3-(dimethyl amino)-4-hydroxypyrrolidine-1-carboxylate (23.5 g, 102 mmol, 99.4% yield) as a yellow oil. 1H NMR (400 MHz, CHLOROFORM-d) δ=4.23-4.20 (m, 1H), 3.75-3.50 (m, 2H), 3.26-3.14 (m, 2H), 2.75 (m, 1H), 2.29 (s, 6H), 1.42 (s, 9H)

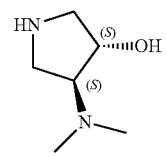

(3S,4S)-4-(dimethylamino)pyrrolidin-3-ol, M6. A solution of (3S,4S)-tert-butyl 3-(dimethyl amino)-4-hydroxypyrrolidine-1-carboxylate (23.5 g, 102 mmol, 1.0 eq.) in HCl/MeOH (4 M, 200 mL) was stirred at 40° C. for 2 hr. The mixture was concentrated to dryness. Then 100 mL MeOH was added to the residue and the solution was added basic resin. The mixture was stirred for 1 hour and pH of the solution was adjusted to 7~8. The mixture was filtered and the filtrate was concentrated. 100 mL THF was added to the residue and the suspension was stirred overnight. The solid was collected by filtration to give (3S,4S)-4-(dimethylamino)pyrrolidin-3-ol (13 g, 99 mmol, 97.8% yield) as a yellow solid. 1H NMR (400 MHz, CHLOROFORM-d) δ=4.35 (br. s., 3H), 3.41-3.44 (m, 1H), 3.29-3.32 (m, 1H), 3.13-3.18 (m, 2H), 2.85 (m, 1H), 2.27 (s, 6H)

filtered and the filtrate was concentrated to give (3S,4S)-tert-butyl 3-amino-4-hydroxypyrrolidine-1-carboxylate (17.9 g, 68.3 mmol, 100% yield, AcOH salt) as a yellow oil. ESI [M+H]=203.1

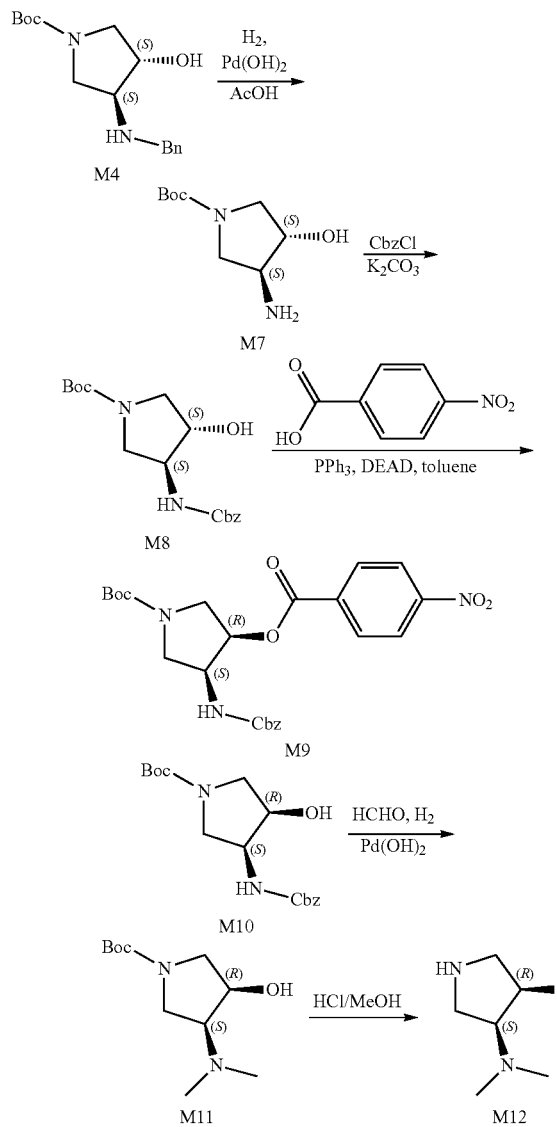

(3S,4S)-tert-butyl 3-(((benzyloxy)carbonyl)amino)-4-hydroxypyrrolidine-1-carboxylate, M8. To a solution of (3S, 4S)-tert-butyl 3-amino-4-hydroxypyrrolidine-1-carboxylate (29.0 g, 110.5 mmol, 1.0 eq., AcOH salt) in THF (290 mL) and $H_2O$ (290 mL) was added $K_2CO_3$ (45.8 g, 331 mmol, 3.0 eq.) and CbzCl (24.5 g, 143.7 mmol, 20.4 mL, 1.3 eq.) at 0° C. The reaction was stirred at 25° C. for 1 hr and extracted with EtOAc (500 mL*3). The organic layer was washed with brine (500 mL), dried over $MgSO_4$ and concentrated. The residue was purified by column chromatography ($SiO_2$, Petroleum ether/Ethyl acetate=10:1 to 1:1) to give (3S,4S)-tert-butyl 3-(((benzyloxy)carbonyl)amino)-4-hydroxypyrrolidine-1-carboxylate (18.3 g, 54.4 mmol, 49.2% yield) as a colorless oil. 1H NMR (400 MHz, METHANOL-d4) δ=7.32-7.26 (m, 5H), 5.06 (s, 2H), 4.08 (s, 1H), 4.07-3.89 (s, 1H), 3.65-3.61 (s, 1H), 3.50-3.48 (s, 1H), 3.29-3.22 (m, 2H), 1.43 (s, 9H). ESI [M+H]=336.9

(3S,4R)-tert-butyl 3-(((benzyloxy)carbonyl)amino)-4-((4-nitrobenzoyl)oxy)pyrrolidine-1-carboxylate, M9. To a solution of (3 S,4 S)-tert-butyl 3-(((benzyloxy)carbonyl)amino)-4-hydro xypyrrolidine-1-carboxylate (8.0 g, 23.7 mmol, 1.0 eq.), 4-nitrobenzoic acid (5.9 g, 35.6 mmol, 1.5 eq.) and $PPh_3$ (11.2 g, 42.8 mmol, 1.8 eq.) in toluene (200 mL) was added DEAD (7.4 g, 42.8 mmol, 7.7 mL, 1.8 eq.) in one portion at 0° C. under $N_2$. After stirred for 10 min, the mixture was heated to 80° C. for 16 hr. The solution was concentrated and purified by silica gel chromatography (Petroleum ether/Ethyl acetate=3:1) to give (3 S,4R)-tert-butyl 3-(((benzyloxy) carbonyl)amino)-4-((4-nitrobenzoyl) oxy)pyrrolidine-1-carboxylate (14 g, crude) as a yellow solid. ESI [M+H]=486.2

General Procedure L (3S,4S)-tert-butyl 3-amino-4-hydroxypyrrolidine-1-carboxylate, M7. To a solution of (3S,4S)-tert-butyl 3-(benzylamino)-4-hydroxypyrrolidine-1-carboxylate (20 g, 68.4 mmol, 1.0 eq) in AcOH (300 mL) was added $Pd(OH)_2$ (5.0 g, 3.56 mmol, 10% purity, 0.05 eq.) and the mixture was stirred for 1 hr at 50° C. under 50 psi $H_2$. The mixture was (3S,4R)-tert-butyl 3-(((benzyloxy)carbonyl)amino)-4-hydroxypyrrolidine-1-carboxylate, M10. To a solution of (3 S,4R)-tert-butyl 3-(((benzyloxy)carbonyl)amino)-4-((4-nitrobenzoyl) oxy)pyrrolidine-1-carboxylate (6.0 g, 12.3 mmol, 1.0 eq.) in MeOH (20 mL) was added K$_2$CO$_3$ (2.0 g, 14.8 mmol, 1.2 eq.) in one portion and the mixture was stirred at 20° C. for 10 min. The mixture was filtered and the filtrate was adjusted to pH=3 with 1M HCl. The filtrate was concentrated and purified by column chromatography to give (3S,4R)-tert-butyl 3-(((benzyloxy) carbonyl)amino)-4-hydroxypyrrolidine-1-carboxylate (4.1 g, crude) as a yellow oil.

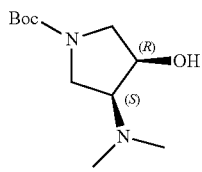

(3S,4R)-tert-butyl 3-(dimethylamino)-4-hydroxypyrrolidine-1-carboxylate, M11. To a solution of tert-butyl (3S,4R)-3-(benzyloxycarbonylamino)-4-hydroxy-pyrrolidine-1-carboxylate (3.6 g, 10.7 mmol, 1.0 eq.) and formaldehyde (6.4 g, 214 mmol, 5.9 mL, 20 eq.) in MeOH (30 mL) was added Pd(OH)$_2$ (20.5 g, 14.6 mmol, 10% purity, 1.3 eq.) and the mixture was stirred under 50 psi H$_2$ at 20° C. for 16 hr. The mixture was filtered and the filtrate was concentrated. The residue was purified by silica gel chromatography (DCM:MeOH=20:1) to give (3S,4R)-tert-butyl 3-(dimethylamino)-4-hydroxypyrrolidine-1-carboxylate (2.0 g, crude) as a yellow oil. 1H NMR (400 MHz, METHANOL-d4) δ=4.22 (br. s., 1H), 3.65-3.54 (m, 1H), 3.48-3.37 (m, 2H), 3.27-3.16 (m, 1H), 2.61-2.45 (m, 1H), 2.29 (d, J=2.4 Hz, 6H), 1.56-1.36 (m, 9H). ESI [M+H]=231.1

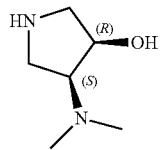

(3R,4S)-4-(dimethylamino)pyrrolidin-3-ol, M12. A solution of (3S,4R)-tert-butyl 3-(dimethyl amino)-4-hydroxypyrrolidine-1-carboxylate (1 g, 4.3 mmol, 1.0 eq.) in HCl/MeOH (4 M, 20 mL) was stirred at 20° C. for 30 min. The solution was concentrated to give (3R,4S)-4-(dimethylamino) pyrrolidin-3-ol (600 mg , HCl salt) as a yellow oil. 1H NMR (400 MHz, METHANOL-d4) δ=4.70 (br. s., 1H), 4.13-4.01 (m, 1H), 3.88 (t, J=10.2 Hz, 1H), 3.57-3.43 (m, 3H), 3.11-2.90 (m, 6H). ESI [M+H]=131.1

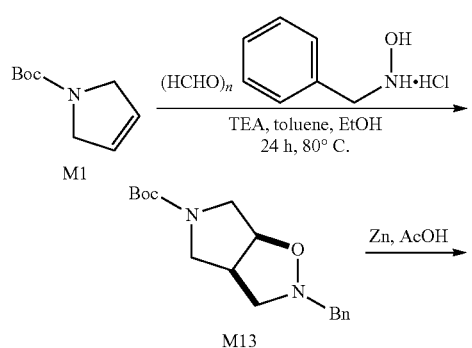

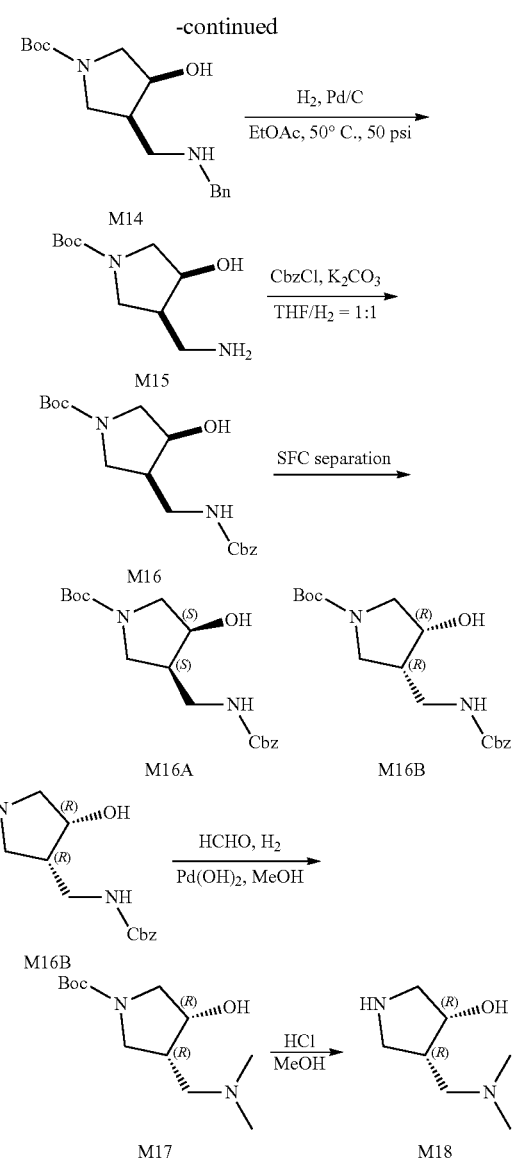

Chemistry Experimental Methods:

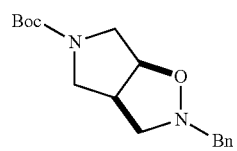

Cis-tert-butyl 2-benzyltetrahydro-2H-pyrrolo[3,4-d]isoxazole-5(3H)-carboxylate, M13. To a solution of tert-butyl 2,5-dihydropyrrole-1-carboxylate (70.6 g, 417.6 mmol, 1.0 eq.) in toluene (2.1 L) and EtOH (700 mL) was added (HCHO)$_n$ (62.8 g, 697 mmol, 1.6 eq.), N-benzyl hydroxyl amine (100 g, 626 mmol, 1.5 eq., HCl salt) and TEA (63.4 g, 626 mmol, 86 mL, 1.5 eq.). The mixture was stirred at 80° C. for 24 hr and then concentrated under reduced pressure. The residue was diluted with hexane/EtOAc(1.5 L/1.5 L), filtered and the filtrate was concentrated under reduced pressure to give cis-tert-butyl 2-benzyltetrahydro-2H-pyrrolo[3,4-d]isoxazole-5(3H)-carboxylate (230 g, crude) as a yellow oil, which was used into the next step without further purification. ESI [M+H]=305.1

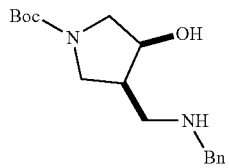

Cis-tert-butyl 3-((benzylamino)methyl)-4-hydroxypyrrolidine-1-carboxylate, M14. Cis-tert-butyl 2-benzyltetrahydro-2H-pyrrolo[3,4-d]isoxazole-5(3H)-carboxylate (229 g, 752 mmol, 1.0 eq.) was dissolved in AcOH (2.5 L). The solution was heated to 70° C. and then Zn powder (245 g, 3.7 mol, 5.0 eq.) was added portionwise with vigorous stirring followed by another batch of Zn powder (80 g) after 30 min. The mixture was stirred at 70° C. for 1.5 hr, diluted with water (1.5 L) and extracted with DCM (2 L*3). The combined organic layer was dried over MgSO$_4$, filtered and concentrated under reduced pressure. The residue was purified by column chromatography (SiO$_2$, DCM:MeOH=1/0 to 10:1) to give cis-tert-butyl 3-((benzylamino) methyl)-4-hydroxypyrrolidine-1-carboxylate (107 g, 272 mmol, 36.2% yield, 78% purity) as a light orange solid. 1H NMR (400 MHz, CHLOROFORM-d) δ=7.31-7.17 (m, 5H), 4.40-4.32 (m, 1H), 3.78-3.67 (m, 2H), 3.46-3.35 (m, 2H), 3.34-3.09 (m, 2H), 2.99-2.84 (m, 2H), 2.20 (br. s., 1H), 1.48-1.31 (s, 9H). ESI [M+H]=307.0

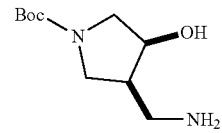

Cis-tert-butyl 3-(aminomethyl)-4-hydroxypyrrolidine-1-carboxylate, M15. To a solution of cis-tert-butyl 3-((benzylamino)methyl)-4-hydroxypyrrolidine-1-carboxylate (20 g, 65.2 mmol, 1.0 eq.) in MeOH (500 mL) was added Pd(OH)$_2$ (13.9 g, 99 mmol, 1.5 eq.) and the mixture was stirred at 70° C. for 36 hr under 50 psi H$_2$. The reaction mixture was filtered and the filtrate was concentrated under reduced pressure to give crude cis-tert-butyl 3-(aminomethyl)-4-hydroxy pyrrolidine-1-carboxylate (11 g, crude) as a colorless oil, which was used into the next step without further purification. ESI [M+H]=217.1

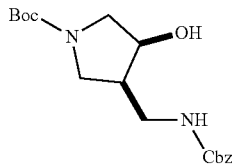

Cis-tert-butyl 3-((((benzyloxy)carbonyl)amino)methyl)-4-hydroxypyrrolidine-1-carboxylate, M16. To a solution of cis-tert-butyl 3-(aminomethyl)-4-hydroxypyrrolidine-1-carboxylate (11 g, 50.8 mmol, 1.0 eq.) in H$_2$O (50 mL) and THF (50 mL) was added K$_2$CO$_3$ (14 g, 101.7 mmol, 2.0 eq.) and CbzCl (10.4 g, 61 mmol, 8.6 mL, 1.2 eq.). The reaction was stirred at 20° C. for 12 hr and then concentrated under reduced pressure. The residue was diluted with H$_2$O (50 mL) and extracted with DCM (50 mL*3). The combined organic layer was concentrated and purified by column chromatography (SiO$_2$, Dichloromethane/Ethyl acetate=10/1 to 1/1 to DCM/Methanol=20/1) to give cis-tert-butyl 3-((((benzyloxy)carbonyl)amino)methyl)-4-hydroxypyrrolidine-1-carboxylate (10 g) as a white solid.

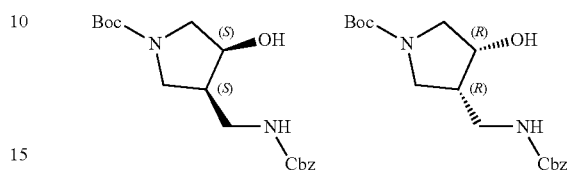

(3S,4S)-tert-butyl 3-((((benzyloxy)carbonyl)amino)methyl)-4-hydroxypyrrolidine-1-carboxylate and (3R,4R)-tert-butyl 3-((((benzyloxy)carbonyl)amino)methyl)-4-hydroxypyrrolidine-1-carboxylate, M16A and M16B. Cis-tert-butyl 3-((((benzyloxy)carbonyl)amino) methyl)-4-hydroxypyrrolidine-1-carboxylate was separated by SFC to give tert-butyl (3S,4S)-3-(benzyloxycarbonylaminomethyl)-4-hydroxy-pyrrolidine-1-carboxylate (4.0 g, 10.7 mmol, 21% yield, 93.7% purity) as a white solid ([α]$_D^{22}$=+17.62°±0.29°, ee %=100% by SFC) and tert-butyl (3R,4R)-3-(benzyloxycarbonylaminomethyl)-4-hydroxy-pyrrolidine-1-carboxyl ate (4.0 g, 10.10 mmol, 19.8% yield, 88% purity) as a white solid ([α]$_D^{22}$=−18.13°±0.24°, ee %=99.5% by SFC).

General Procedure M

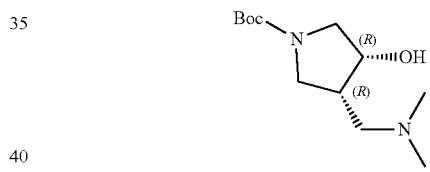

(3R,4R)-tert-butyl 3-((dimethylamino)methyl)-4-hydroxypyrrolidine-1-carboxylate, M17. A mixture of tert-butyl (3R,4R)-3-(benzyloxycarbonylaminomethyl)-4-hydroxy-pyrrolidine-1-carboxylate (2.0 g, 5.71 mmol, 1.0 eq.), HCHO (4.5 g, 57.1 mmol, 4.14 mL, 10 eq.) and Pd(OH)$_2$ (1.6 g, 5.7 mmol, 50% purity, 1.0 eq.) in MeOH (50 mL) was stirred under 50 psi H$_2$ at 50° C. for 50 hr. The reaction mixture was filtered and the filtrate was concentrated under reduced pressure. The residue was purified by column chromatography (SiO$_2$, DCM/MeOH=100/1 to 20:1) to give (3R,4R)-tert-butyl 3-((dimethylamino)methyl)-4-hydroxypyrrolidine-1-carboxylate (1.2 g, 4.9 mmol, 86% yield) as a white solid. 1H NMR (400 MHz, CHLOROFORM-d) δ=4.43 (d, J=5.5 Hz, 1H), 3.72-3.57 (m, 1H), 3.50-3.38 (m, 1H), 3.35-3.20 (m, 1H), 3.16-3.00 (m, 1H), 2.81 (q, J=11.6 Hz, 1H), 2.45-2.27 (m, 8H), 1.44 (s, 9H). ESI [M+H]=245.0

(3R, 4S)-4-((dimethylamino)methyl)pyrrolidin-3-ol, M18. A solution of (3R,4R)-tert-butyl 3-((dimethylamino)methyl)-4-hydroxypyrrolidine-1-carboxylate (1.2 g, 4.9 mmol, 1.0 eq.) in HCl/MeOH (4 M, 20 mL) was stirred at 45° C. for 1 hr. The reaction mixture was concentrated under reduced pressure. The residue was diluted with H₂O (10 mL) and basified by basic resin. The mixture was filtered and the filtrate was lyophilized to give (3R,4S)-4-[(dimethylamino)methyl]pyrrolidin-3-ol (700 mg, crude) as a light yellow solid. 1H NMR (400 MHz, METHANOL-d4) δ=4.46 (t, J=3.1 Hz, 1H), 3.53 (dd, J=8.6, 11.3 Hz, 1H), 3.39-3.31 (m, 2H), 3.28 (br. s., 1H), 3.14-3.03 (m, 2H), 2.90 (dd, J=6.7, 12.9 Hz, 1H), 2.63 (s, 6H). ESI [M+H]=145.0

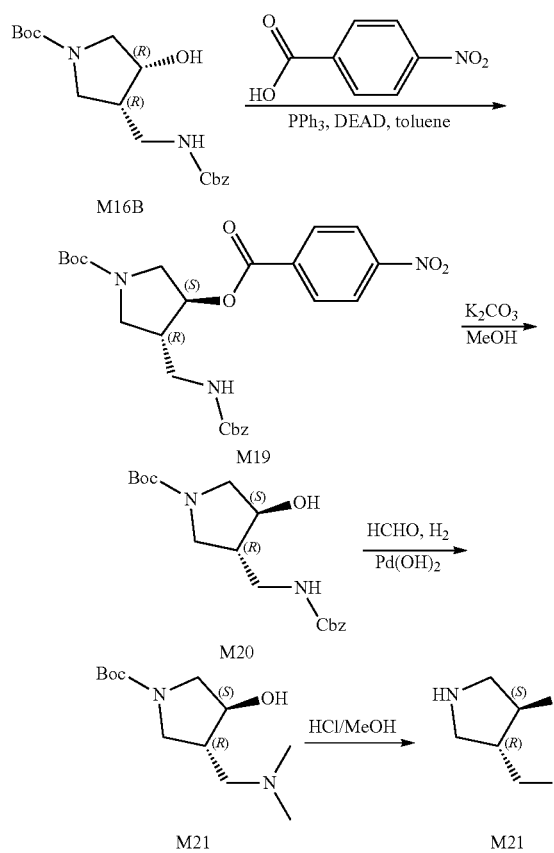

General Procedure N

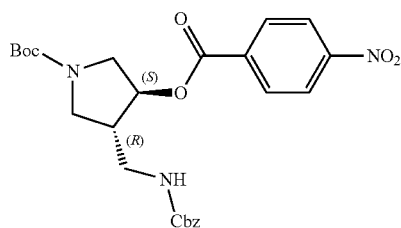

(3R,4S)-tert-butyl 3-((((benzyloxy)carbonyl)amino)methyl)-4-((4-nitrobenzoyl)oxy)pyrrolidine-1-carboxylate, M19. To a solution of tert-butyl (3R,4R)-3-(benzyloxycarbonylamino methyl)-4-hydroxy-pyrrolidine-1-carboxylate (1.0 g, 2.8 mmol, 1.0 eq.) in toluene (20 mL) was added 4-nitrobenzoic acid (714 mg, 4.2 mmol, 1.5 eq.) and PPh₃ (1.5 g, 5.7 mmol, 2.0 eq.) at 25° C. under N₂. Then DEAD (992 mg, 5.7 mmol, 1.0 mL, 2.0 eq.) was added at 0° C. and the mixture was heated to 80° C. for 16 hrs under N₂. The reaction mixture was concentrated and the residue was purified by column chromatography (SiO₂, Petroleum ether/Ethyl acetate=20/1 to 3:1) to give (3R,4S)-tert-butyl 3-((((benzyloxy)carbonyl)amino)methyl)-4-((4-nitrobenzoyl)oxy) pyrrolidine-1-carboxylate (2.2 g, crude) as a yellow oil. ESI [M+H]=500.1

(3R,4S)-tert-butyl 3-((((benzyloxy)carbonyl)amino)methyl)-4-hydroxypyrrolidine-1-carboxylate, M20. To a solution of (3R,4S)-tert-butyl 3-((((benzyloxy)carbonyl)amino)methyl)-4-((4-nitrobenzoyl)oxy) pyrrolidine-1-carboxylate (2.2 g, 4.4 mmol, 1.0 eq.) in MeOH (30 mL) was added K₂CO₃ (1.2 g, 8.8 mmol, 2.0 eq.) and the mixture was stirred at 25° C. for 30 min. The mixture was concentrated in vacuum. The residue was dissolved in water (30 mL) and extracted with DCM (20 mL*3). The organic layer was dried over MgSO₄ and concentrated. The residue was purified by column chromatography (SiO₂, Petroleum ether/Ethyl acetate=20/1 to 1:1) to give tert-butyl (3R,4S)-3-(benzyloxycarbonylaminomethyl)-4-hydroxy-pyrrolidine-1-carboxylate (900 mg, crude) as a yellow oil. ¹H NMR (400 MHz, METHANOL-d₄) δ=7.38-7.29 (m, 4H), 7.27 (d, J=4.9 Hz, 1H), 5.06 (s, 2H), 4.08-3.99 (m, 1H), 3.57-3.46 (m, 2H), 3.21-3.10 (m, 3H), 3.07-2.98 (m, 1H), 2.23 (dd, J=4.0, 7.1 Hz, 1H), 1.43 (s, 9H). ESI [M+H]=351.2

(3R,4S)-tert-butyl 3-((dimethylamino)methyl)-4-hydroxypyrrolidine-1-carboxylate, M21. To a solution of tert-butyl (3R,4 S)-3-(benzyloxycarbonylaminomethyl)-4-hydroxy-pyrrolidine-1-carboxylate (900 mg, 2.5 mmol, 1.0 eq.) in MeOH (50 mL) was added Pd(OH)₂ (0.5 g) and the mixture was stirred under 50 psi H₂ at 60° C. for 16 hr. After filtration, the filtrate was concentrated. The residue was acidified by cold 0.5M HCl (30 mL) and extracted with EtOAC (10 mL*2). The aqueous phase was adjusted to pH=11 with sat.K₂CO₃ solution and extracted with DCM (50 mL*4). The organic layer was dried over MgSO₄ and concentrated to give (3R,4S)-tert-butyl 3-((dimethylamino)methyl)-4-hydroxypyrrolidine-1-carboxylate (250 mg, crude) as a yellow oil, which was used into the next step without further purification. ¹H NMR (400 MHz, METHANOL-d₄) δ=4.07-3.97 (m, 1H), 3.60 (dd, J=5.3, 10.1 Hz, 1H), 3.52 (dd, J=6.0, 11.2 Hz, 1H), 3.19-3.05 (m, 2H), 2.46-2.33 (m, 1H), 2.31-2.18 (m, 8H), 1.44 (s, 9H). ESI [M+H]=245.1

General Procedure O

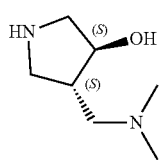

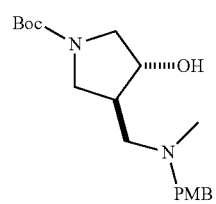

(3S,4S)-4-((dimethylamino)methyl)pyrrolidin-3-ol, M22. To a solution of tert-butyl (3R,4S)-3-[(dimethylamino) methyl]-4-hydroxy-pyrrolidine-1-carboxylate (250 mg, 1.02 mmol, 1.0 eq.) in MeOH (5.0 mL) was added HCl/MeOH (4M, 10 mL) and the mixture was stirred at 25° C. for 30 min. The reaction was concentrated in vacuum. The residue was dissolved in MeOH (10 mL) and basified to pH=7~8 by anion exchange resin. After filtration, the filtrate was concentrated to give (3S,4S)-4-[(dimethylamino)methyl]pyrrolidin-3-ol (150 mg, crude) as a yellow oil, which was used into the next step without further purification. $^1$H NMR (400 MHz, METHANOL-d$_4$) δ=4.23 (td, J=2.6, 5.0 Hz, 1H), 3.54 (dd, J=7.1, 11.9 Hz, 1H), 3.33 (dd, J=4.9, 12.3 Hz, 1H), 3.15 (dd, J=2.6, 12.3 Hz, 1H), 3.06 (dd, J=4.9, 11.9 Hz, 1H), 2.51-2.41 (m, 2H), 2.40-2.35 (m, 1H), 2.33 (s, 6H). ESI [M+H]=145.1

Trans-tert-butyl-3-hydroxy-4-(((4-methoxybenzyl) (methyl)amino)methyl)pyrrolidine-1-carboxylate, M24. To a solution of tert-butyl-trans-3-(aminomethyl)-4-hydroxy-pyrrolidine-1-carboxylate (2.0 g, 9.2 mmol, 1.0 eq.) in MeOH (40 mL) was added AcOH (666 mg, 11 mmol, 1.2 eq.) and 4-methoxybenzaldehyde (1.5 g, 11 mmol, 1.2 eq.). The mixture was stirred at 26° C. for 0.5 hour and then added NaBH$_3$CN (1.4 g, 23.1 mmol, 2.5 eq) followed by HCHO (3.7 g, 46.2 mmol, 5.0 eq) after 1.0 hr. The mixture was stirred at 26° C. for 16 hours and concentrated under reduced pressure. The residue was purified by acidic prep-HPLC to give trans-tert-butyl-3-hydroxy-4-(((4-methoxybenzyl)(methyl)amino)methyl)pyrrolidine-1-carboxylate (3.0 g, 8.5 mmol, 92.5% yield) as a colorless oil. ESI [M+H]=351.1

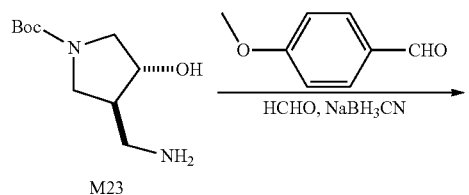

M23

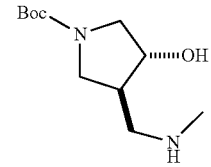 [SMILES: CNC[C@H]1CN(C(=O)OC(C)(C)C)C[C@@H]1O]

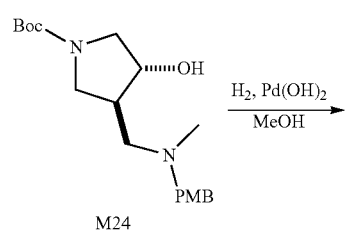

M24

Trans-tert-butyl 3-hydroxy-4-((methylamino)methyl)pyrrolidine-1-carboxylate, M25. To a solution of trans-tert-butyl-3-hydroxy-4-(((4-methoxybenzyl)(methyl)amino) methyl)pyrrolidine-1-carboxylate (1.8 g, 5.1 mmol, 1.0 eq) in MeOH (25 mL) was added Pd(OH)$_2$ (72.1 mg, 513 umol, 0.1 eq.) and the mixture was stirred at 26° C. for 16 hours under 50 psi H$_2$. The mixture was filtered and the filtrate was concentrated under reduced pressure to give trans-tert-butyl 3-hydroxy-4-((methylamino)methyl)pyrrolidine-1-carboxylate (1.1 g, 4.7 mmol, 92.9% yield) as a yellow oil, which was used directly without any purification. ESI [M+H]=231.1

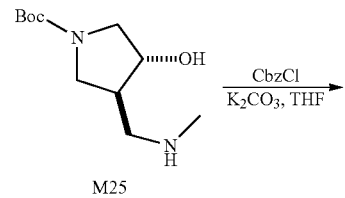

M25

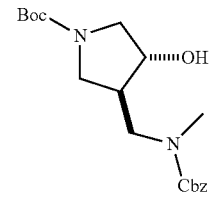 [SMILES: CN(C[C@H]1CN(C(=O)OC(C)(C)C)C[C@@H]1O)C(=O)OCc1ccccc1]

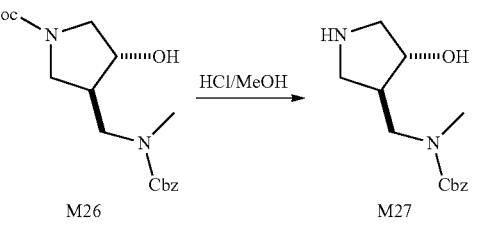

M26    M27

Trans-tert-butyl-3-((((benzyloxy)carbonyl)(methyl) amino)methyl)-4-hydroxypyrrolidine-1-carboxylate, M26. To a solution of trans-tert-butyl-3-hydroxy-4-((methylamino)methyl) pyrrolidine-1-carboxylate (1.1 g, 4.7 mmol, 1.0 eq) in THF (15 mL) and H$_2$O (15 mL) was added K$_2$CO$_3$ (1.3 g, 9.5 mmol, 2.0 eq) and CbzCl (1.2 g, 7.1 mmol, 1.5 eq.) at 0° C. The mixture was stirred at 26° C. for 16 hr and concentrated under reduced pressure. The residue was purified by basic prep-HPLC to give trans-tert-butyl-3-((((benzyloxy)carbonyl) (methyl)amino)methyl)-4-hydroxypyrrolidine-1-carboxylate (800 mg, 2.2 mmol, 45.9% yield) as a yellow oil. ESI [M+H]=365.1

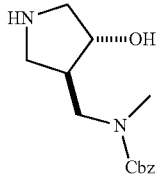

Benzyl ((trans-4-hydroxypyrrolidin-3-yl)methyl)(methyl) carbamate, M27. Trans-tert-butyl-3-(((((benzyloxy)carbonyl) (methyl)amino)methyl)-4-hydroxypyrrolidine-1-carboxylate (400 mg, 1.1 mmol, 1.0 eq) was dissolved into HCl/MeOH (4M, 10 mL) and the mixture was stirred at 26° C. for 1 hour. The mixture was concentrated under reduced pressure and then dissolved into MeOH (15 mL). The pH was adjusted to 8-9 by basic resin and the mixture was filtered. The filtrate was concentrated to give benzyl ((trans-4-hydroxypyrrolidin-3-yl)methyl)(methyl) carbamate (120 mg, 454 umol, 41.2% yield) as a yellow oil. [M+H]=264.9

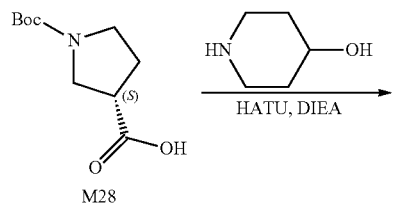

M28

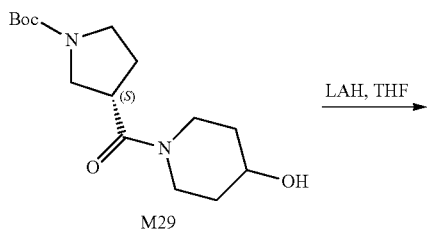

M29

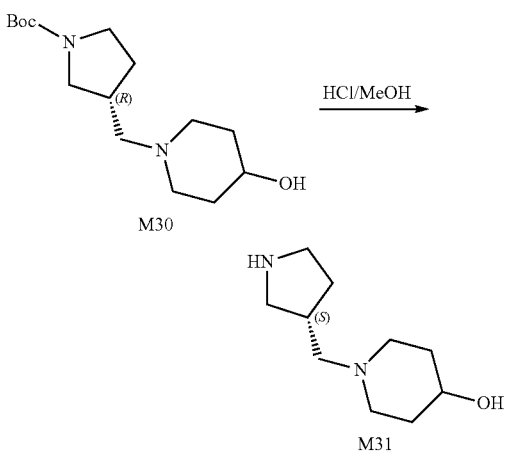

M30

M31

General Procedure P

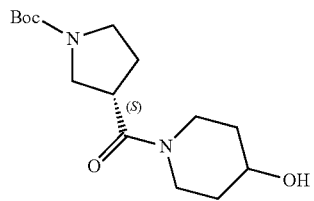

(S)-tert-butyl 3-(4-hydroxypiperidine-1-carbonyl)pyrrolidine-1-carboxylate, M29. To a solution of (3S)-1-tert-butoxycarbonylpyrrolidine-3-carboxylic acid (1.0 g, 4.6 mmol, 1.0 eq.) and piperidin-4-ol (1.4 g, 13.9 mmol, 3.0 eq) in DCM (20 mL) was added HATU (2.3 g, 6.0 mmol, 1.3 eq) and DIEA (1.5 g, 11.6 mmol, 2.0 mL, 2.5 eq). The mixture was stirred at 20° C. for 1 hour and diluted with DCM (100 mL). The organic layer was washed with brine (20 mL), dried with anhydrous Na$_2$SO$_4$, filtered and concentrated in vacuum to give (S)-tert-butyl 3-(4-hydroxy piperidine-1-carbonyl)pyrrolidine-1-carboxylate (1.2 g, crude) as a yellow oil, which was used into the next step without further purification. $^1$H NMR (400 MHz, CHLOROFORM-d) δ=3.69-3.62 (m, 1H), 3.48-3.31 (m, 1H), 3.20 (br. s., 1H), 2.90 (d, J=7.1 Hz, 1H), 2.71 (d, J=5.3 Hz, 2H), 2.28 (br. s., 2H), 2.13 (br. s., 2H), 1.92-1.79 (m, 3H), 1.52 (d, J=8.8 Hz, 3H), 1.46-1.35 (m, 9H). ESI [M+H]=299.0

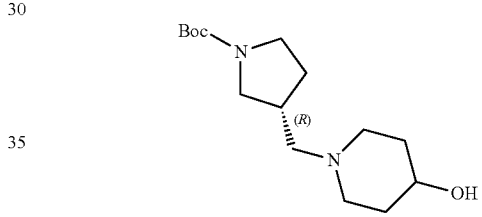

(R)-tert-butyl 3-((4-hydroxypiperidin-1-yl)methyl)pyrrolidine-1-carboxylate, M30. To a solution of (S)-tert-butyl 3-(4-hydroxy piperidine-1-carbonyl)pyrrolidine-1-carboxylate (1.2 g, 4.0 mmol, 1.0 eq.) in THF (30 mL) was added LiAlH$_4$ (183 mg, 4.8 mmol, 1.2 eq.) at 0° C. The mixture was stirred at 20° C. for 1 hour, quenched with sat.aq.MgSO$_4$ (20 mL) and filtered. The filtrate was concentrated and purified by silica gel chromatography (DCM:MeOH=10:1) to give (R)-tert-butyl 3-((4-hydroxypiperidin-1-yl)methyl)pyrrolidine-1-carboxylate (600 mg, crude) as a yellow oil. ESI [M+H]=285.2

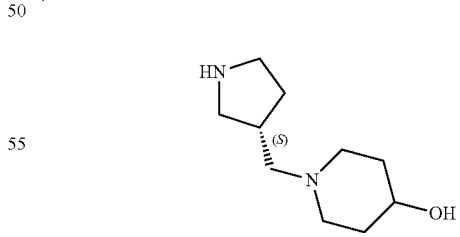

(S)-1-(pyrrolidin-3-ylmethyl)piperidin-4-ol, M31. A solution of (R)-tert-butyl 3-((4-hydroxypiperidin-1-yl)methyl) pyrrolidine-1-carboxylate (600 mg, 2.1 mmol, 1.0 eq.) in HCl/MeOH (4M, 10 mL) was stirred at 20° C. for 0.5 hour and then concentrated under reduced pressure. The residue was diluted with MeOH (20 mL), basified to pH=7~8 by basic resin and filtered. The filtrate was concentrated to give (S)-1-(pyrrolidin-3-ylmethyl) piperidin-4-ol (400 mg, crude) as a light yellow oil, which was used into the next step without further purification. ESI [M+H]=184.9

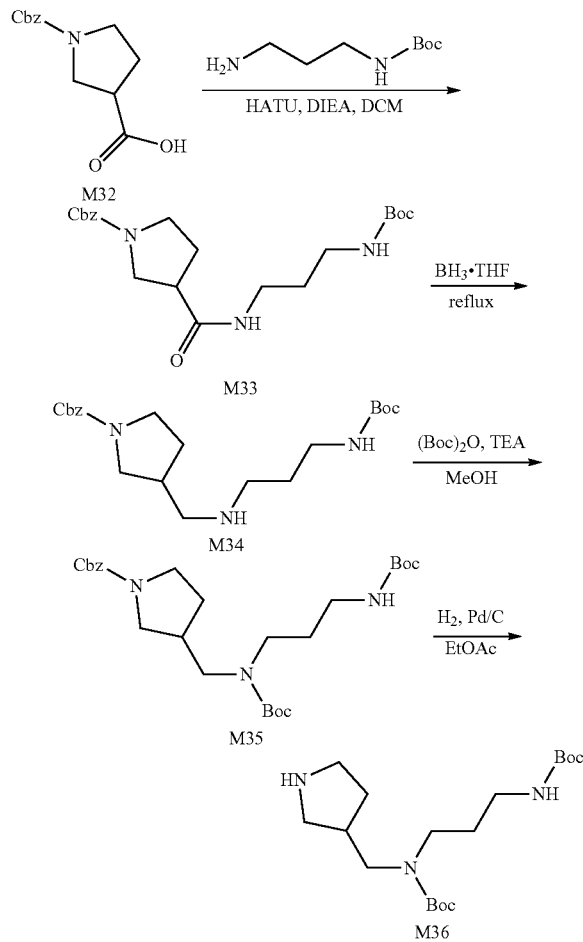

General Procedure Q

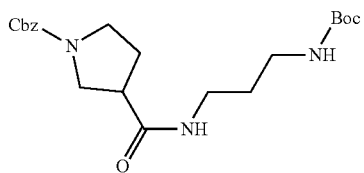 [SMILES: CC(C)(C)OC(=O)NCCCNC(=O)C1CCN(C(=O)OCc2ccccc2)C1]

Benzyl 3-((3-((tert-butoxycarbonyl)amino)propyl)carbamoyl)pyrrolidine-1-carboxylate, M33. To a mixture of 1-benzyloxycarbonylpyrrolidine-3-carboxylic acid (300 mg, 1.2 mmol, 1.0 eq), DIEA (466 mg, 3.6 mmol, 3.0 eq) and HATU (686 mg, 1.8 mmol, 1.5 eq) in DCM (20 mL) was added tert-butyl N-(3-aminopropyl)carbamate (418 mg, 2.4 mmol, 2.0 eq) in one portion at 20° C. The mixture was stirred at 20° C. for 0.5 hour and then poured into ice-water (50 mL). The aqueous phase was extracted with ethyl acetate (20 mL*3). The combined organic phase was washed with brine (10 mL*2), dried with anhydrous Na$_2$SO$_4$, filtered and concentrated in vacuum. The residue was purified by prep-TLC (SiO$_2$, Ethyl acetate) to give benzyl 3-((3-((tert-butoxycarbonyl)amino)propyl)carbamoyl)pyrrolidine-1-carboxylate (450 mg, 654 umol, 54.5% yield, 59% purity) as a colorless oil. ESI [M+H]=406.1

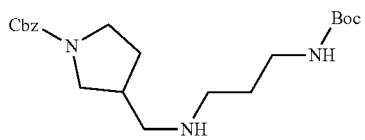 [SMILES: CC(C)(C)OC(=O)NCCCNCC1CCN(C(=O)OCc2ccccc2)C1]

Benzyl 3-(((3-((tert-butoxycarbonyl)amino)propyl)amino)methyl)pyrrolidine-1-carboxylate, M34. To a solution of benzyl 3-((3-((tert-butoxycarbonyl)amino)propyl)carbamoyl)pyrrolidine-1-carboxylate (400 mg, 986 umol, 1.0 eq) in THF (5 mL) was added BH$_3$.THF (1 M, 9.8 mL, 10 eq.) and the reaction mixture was warmed to 70° C. for 1 hr. The reaction was quenched with methanol (100 mL) slowly and concentrated under reduced pressure at 40° C. to give crude benzyl 3-[[3-(tert-butoxycarbonylamino)propylamino]methyl]pyrrolidine-1-carboxylate (400 mg, crude) as a colorless oil. ESI [M+H]=392.1

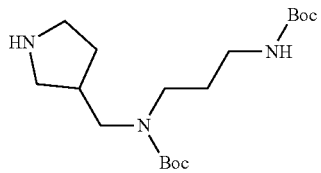

Benzyl 3-(((tert-butoxycarbonyl)(3-((tert-butoxycarbonyl)amino)propyl)amino)methyl) pyrrolidine-1-carboxylate, M35. To a solution of benzyl 3-[[3-(tert-butoxycarbonylamino) propylamino]methyl] pyrrolidine-1-carboxylate (400 mg, 1.0 mmol, 1.0 eq) and tert-butoxy carbonyl tert-butyl carbonate (1.3 g, 6.1 mmol, 6.0 eq) in MeOH (50 mL) was added TEA (309 mg, 3.0 mmol, 3.0 eq) in one portion an the mixture was stirred at 20° C. for 10 hours. The mixture was concentrated and purified by prep-HPLC (neutral condition) to give benzyl 3-(((tert-butoxycarbonyl)(3-((tert-butoxycarbonyl)amino)propyl)amino)methyl)pyrrolidine-1-carboxylate (200 mg, 227 umol, 22.3% yield, 56% purity) as a colorless oil. ESI [M+H]=492.4

Tert-butyl (3-((tert-butoxycarbonyl)amino)propyl)(pyrrolidin-3-ylmethyl)carbamate, M36. To a solution of benzyl 3-(((tert-butoxycarbonyl)(3-((tert-butoxycarbonyl)amino) propyl)amino) methyl)pyrrolidine-1-carboxylate (100 mg, 203 umol, 1.0 eq.) in EtOAc (30 mL) was added Pd/C (100 mg, 203 umol, 1.0 eq) and the mixture was stirred at 20° C. for 1 hr under 50 psi H$_2$. The mixture was filtered and the filtrate was concentrated in vacuum to give tert-butyl (3-((tert-butoxycarbonyl)amino)propyl)(pyrrolidin-3-ylmethyl)carbamate (70 mg, crude) as a colorless oil. ESI [M+H]=358.2

Amine Synthesis

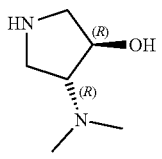

(3R,4R)-4-(dimethylamino)pyrrolidin-3-ol, M37. Synthesized using General Procedure K, replacing (2S)-2-hydroxy-2-phenyl-acetic acid with (2R)-2-hydroxy-2-phenyl-acetic acid. ESI [M+H]=130.8

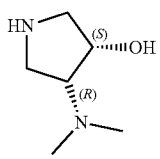

(3S,4R)-4-(dimethylamino)pyrrolidin-3-ol, M38. Synthesized using General Procedure L, replacing (3S,4S)-tert-butyl 3-amino-4-hydroxypyrrolidine-1-carboxylate with (3R,4R)-tert-butyl 3-amino-4-hydroxypyrrolidine-1-carboxylate. 1H NMR (400 MHz, METHANOL-d4) δ=4.60 (br. s., 1H), 3.81-3.63 (m, 2H), 3.48-3.37 (m, 3H), 2.82 (s, 6H). ESI [M+H]=130.8

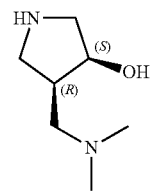

(3S,4R)-4-((dimethylamino)methyl)pyrrolidin-3-ol, M39. Synthesized using General Procedure M, replacing (3R,4R)-tert-butyl 3-((((benzyloxy)carbonyl)amino)methyl)-4-hydroxypyrrolidine-1-carboxylate with (3S,4S)-tert-butyl 3-((((benzyloxy)carbonyl)amino)methyl)-4-hydroxypyrrolidine-1-carboxylate. 1H NMR (400 MHz, METHANOL-d4) δ=4.44 (t, J=3.3 Hz, 1H), 3.50 (dd, J=8.6, 11.3 Hz, 1H), 3.40-3.31 (m, 2H), 3.27 (s, 1H), 3.08 (t, J=11.3 Hz, 1H), 2.96 (dd, J=6.8, 12.7 Hz, 1H), 2.83-2.75 (m, 1H), 2.54 (s, 6H). ESI [M+H]=145.0

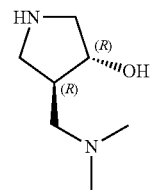

(3R,4R)-4-((dimethylamino)methyl)pyrrolidin-3-ol, M40. Synthesized using General Procedure N, replacing (3R,4R)-tert-butyl 3-((((benzyloxy)carbonyl)amino) methyl)-4-hydroxypyrrolidine-1-carboxylate with (3S,4S)-tert-butyl 3-((((benzyloxy)carbonyl)amino)methyl)-4-hydroxypyrrolidine-1-carboxylate. 1H NMR (400 MHz, METHANOL-d4) δ=4.29-4.19 (m, 1H), 3.55 (dd, J=6.8, 11.7 Hz, 1H), 3.34 (dd, J=4.9, 12.3 Hz, 1H), 3.15 (dd, J=3.1, 12.3 Hz, 1H), 3.06 (dd, J=4.9, 11.9 Hz, 1H), 2.54-2.39 (m, 3H), 2.39-2.28 (s, 6H). ESI [M+H]=145.0

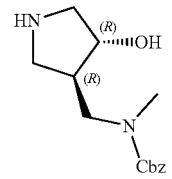

Benzyl (((3R,4R)-4-hydroxypyrrolidin-3-yl)methyl)(methyl)carbamate, M41. Synthesized using General Procedure O, replacing tert-butyl-trans-3-(aminomethyl)-4-hydroxy-pyrrolidine-1-carboxylate with (3S,4R)-tert-butyl 3-(aminomethyl)-4-hydroxypyrrolidine-1-carboxylate. 1H NMR (400 MHz, CHLOROFORM-d) δ=7.38-7.26 (m, 5H), 5.16-5.04 (m, 2H), 4.16-3.91 (m, 1H), 3.35 (d, J=7.5 Hz, 1H), 3.17 (br. s., 2H), 3.00-2.73 (m, 4H), 2.25 (br. s., 1H), 2.11 (br. s., 2H). ESI [M+H]=265.1

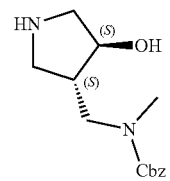

Benzyl (((3S,4S)-4-hydroxypyrrolidin-3-yl)methyl)(methyl)carbamate, M42. Synthesized using General Procedure O, replacing tert-butyl-trans-3-(aminomethyl)-4-hydroxy-pyrrolidine-1-carboxylate with (3R,4S)-tert-butyl 3-(aminomethyl)-4-hydroxypyrrolidine-1-carboxylate. ESI [M+H]=265.1

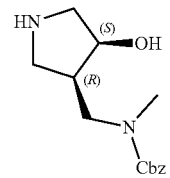

Benzyl (((3R,4S)-4-hydroxypyrrolidin-3-yl)methyl)(methyl)carbamate, M43. Synthesized using General Procedure O, replacing tert-butyl-trans-3-(aminomethyl)-4-hydroxy-pyrrolidine-1-carboxylate with (3S,4S)-tert-butyl-3-(aminomethyl)-4-hydroxypyrrolidine-1-carboxylate. ESI [M+H]=265.1

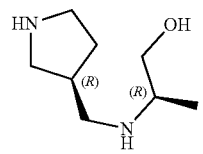

(R)-2-(((R)-pyrrolidin-3-ylmethyl)amino)propan-1-ol, M44. Synthesized using General Procedure P, replacing (3S)-1-tert-butoxycarbonylpyrrolidine-3-carboxylic acid with (3R)-1-tert-butoxycarbonylpyrrolidine-3-carboxylic acid, replacing piperidin-4-ol with (R)-2-aminopropan-1-ol. ESI [M+H]=159.1

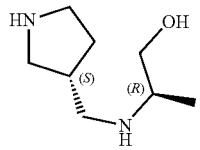

(R)-2-(((S)-pyrrolidin-3-ylmethyl)amino)propan-1-ol, M45. Synthesized using General Procedure P, replacing piperidin-4-ol with (R)-2-aminopropan-1-ol. $^1$H NMR (400 MHz, METHANOL-d$_4$) δ=3.84 (dd, J=3.7, 12.1 Hz, 1H), 3.67-3.54 (m, 2H), 3.52-3.37 (m, 2H), 3.34 (s, 1H), 3.28-3.20 (m, 2H), 3.11 (dd, J=9.0, 11.7 Hz, 1H), 2.85-2.73 (m, 1H), 2.35 (dd, J=4.6, 13.0 Hz, 1H), 1.85 (qd, J=8.7, 13.2 Hz, 1H), 1.35 (d, J=6.6 Hz, 3H). ESI [M+H]=159.1

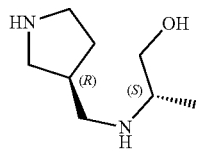

(S)-2-(((R)-pyrrolidin-3-ylmethyl)amino)propan-1-ol, M46. Synthesized using General Procedure P, replacing (5)-1-(tert-butoxycarbonyl)pyrrolidine-3-carboxylic acid with (R)-1-(tert-butoxycarbonyl)pyrrolidine-3-carboxylic acid, replacing piperidin-4-ol with (S)-2-amino propan-1-ol. ESI [M+H]=159.1

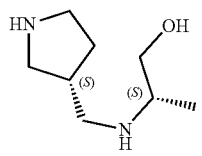

(S)-2-(((S)-pyrrolidin-3-ylmethyl)amino)propan-1-ol, M47. Synthesized using General Procedure P, replacing piperidin-4-ol with (S)-2-aminopropan-1-ol. ESI [M+H]=159.1

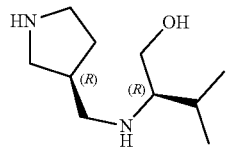

(R)-3-methyl-2-(((R)-pyrrolidin-3-ylmethyl)amino)butan-1-ol, M48. Synthesized using General Procedure P, replacing (S)-1-(tert-butoxycarbonyl) pyrrolidine-3-carboxylic acid with (R)-1-(tert-butoxycarbonyl)pyrrolidine-3-carboxylic acid, replacing piperidin-4-ol with (R)-2-amino-3-methylbutan-1-ol. ESI [M+H]=187.1

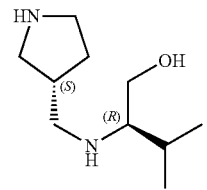

(R)-3-methyl-2-(((S)-pyrrolidin-3-ylmethyl)amino)butan-1-ol, M49. Synthesized using General Procedure P, replacing piperidin-4-ol with (R)-2-amino-3-methylbutan-1-ol. ESI [M+H]=187.1

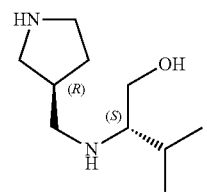

(S)-3-methyl-2-(((R)-pyrrolidin-3-ylmethyl)amino)butan-1-ol, M50. Synthesized using General Procedure P, replacing (S)-1-(tert-butoxycarbonyl)pyrrolidine-3-carboxylic acid with (R)-1-(tert-butoxycarbonyl)pyrrolidine-3-carboxylic acid and replacing piperidin-4-ol with (S)-2-amino-3-methylbutan-1-ol. ESI [M+H]=187.1

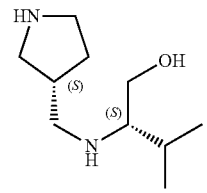

(S)-3-methyl-2-(((S)-pyrrolidin-3-ylmethyl)amino)butan-1-ol, M51. Synthesized using General Procedure P, replacing piperidin-4-ol with (S)-2-amino-3-methylbutan-1-ol. ESI [M+H]=187.1

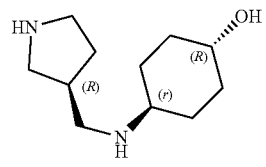

(1R,4r)-4-(((R)-pyrrolidin-3-ylmethyl)amino)cyclohexanol, M52. Synthesized using General Procedure P, replacing (S)-1-(tert-butoxycarbonyl)pyrrolidine-3-carboxylic acid with (R)-1-(tert-butoxycarbonyl)pyrrolidine-3-carboxylic acid and replacing piperidin-4-ol with (1r,4r)-4-amino cyclohexanol. 1H NMR (400 MHz, METHANOL-d4) δ=3.52-3.46 (m, 2H), 3.43-3.42 (m, 1H), 3.32-3.22 (m, 1H), 2.96-2.90 (m, 3H), 2.88-2.86 (m, 1H), 2.54-2.52 (m, 1H), 2.02-2.01 (m, 1H), 1.98-1.96 (m, 4H), 1.73-1.71 (m, 1H), 1.31-1.26 (m, 4H). ESI [M+H]=199.1

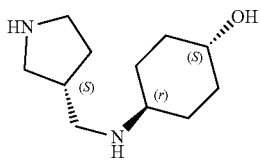

(1S,4r)-4-(((S)-pyrrolidin-3-ylmethyl)amino)cyclohexanol, M53. Synthesized using General Procedure P, replacing piperidin-4-ol with (1r,4r)-4-aminocyclohexanol. 1H NMR (400 MHz, METHANOL-d4) δ=3.56-3.51 (m, 2H), 3.07-3.01 (m, 4H), 2.66-2.62 (m, 1H), 2.31-2.28 (m, 1H), 2.13-2.02 (m, 4H), 1.80-1.77 (m, 1H), 1.44-1.28 (m, 6H). ESI [M+H]=199.1

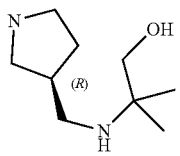

(R)-2-methyl-2-((pyrrolidin-3-ylmethyl)amino)propan-1-ol, M54. Synthesized using General Procedure P, replacing (S)-1-(tert-butoxycarbonyl)pyrrolidine-3-carboxylic acid with (R)-1-(tert-butoxycarbonyl)pyrrolidine-3-carboxylic acid, replacing piperidin-4-ol with 2-amino-2-methyl propan-1-ol. 1H NMR (400 MHz, METHANOL-d4) δ=3.57-3.53 (m, 3H), 3.41-3.38 (m, 1H), 3.09-3.02 (m, 3H), 2.93 (s, 1H), 2.67-2.64 (m, 1H), 2.32-2.31 (m, 1H), 1.82-.177 (m, 1H), 1.30 (s, 6H). ESI [M+H]=173.2

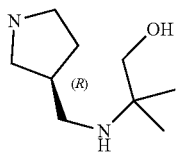

(S)-2-methyl-2-((pyrrolidin-3-ylmethyl)amino)propan-1-ol, M55. Synthesized using General Procedure P, replacing piperidin-4-ol with 2-amino-2-methylpropan-1-ol. 1H NMR (400 MHz, METHANOL-d4) δ=3.46-3.41 (m, 3H), 3.33-3.30 (m, 1H), 3.22 (m, 1H), 2.97-2.96 (m, 1H), 2.88-2.86 (m, 2H), 2.54-2.50 (m, 1H), 2.25-2.23 (m, 1H), 1.76-1.71 (m, 1H), 1.19 (s, 6H). ESI [M+H]=173.2

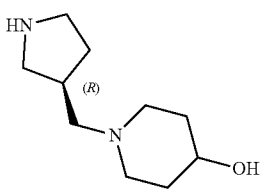

(R)-1-(pyrrolidin-3-ylmethyl)piperidin-4-ol, M56. Synthesized using General Procedure P, replacing (S)-1-(tert-butoxycarbonyl)pyrrolidine-3-carboxylic acid with (R)-1-(tert-butoxycarbonyl)pyrrolidine-3-carboxylic acid. ESI [M+H]=185.1

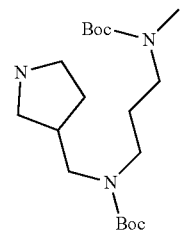 [SMILES: CN(CCCN(CC1CCNC1)C(=O)OC(C)(C)C)C(=O)OC(C)(C)C]

Tert-butyl(3-((tert-butoxycarbonyl)(methyl)amino)propyl)(pyrrolidin-3-ylmethyl)carbamate, M57. Synthesized using General Procedure Q, replacing tert-butyl N-(3-aminopropyl)carbamate with tert-butyl (3-aminopropyl)(methyl)carbamate. ESI [M+H]=372.2

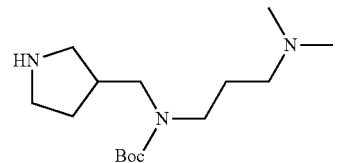 [SMILES: CN(C)CCCN(CC1CCNC1)C(=O)OC(C)(C)C]

Tert-butyl (3-(dimethylamino)propyl)(pyrrolidin-3-ylmethyl)carbamate, M58. Synthesized using General Procedure Q, replacing tert-butyl N-(3-aminopropyl)carbamate with N,N-dimethyl propane-1,3-diamine. ESI [M+H]=286.1

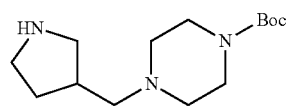 [SMILES: CC(C)(C)OC(=O)N1CCN(CC2CCNC2)CC1]

Tert-butyl 4-(pyrrolidin-3-ylmethyl)piperazine-1-carboxylate, M59. Synthesized using General Procedure Q, replacing tert-butyl N-(3-aminopropyl)carbamate with tert-butyl piperazine-1-carboxylate. ESI [M+H]=270.0

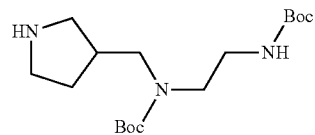 [SMILES: CC(C)(C)OC(=O)NCCN(CC1CCNC1)C(=O)OC(C)(C)C]

Tert-butyl (2-((tert-butoxycarbonyl)amino)ethyl)(pyrrolidin-3-ylmethyl)carbamate, M60. Synthesized using General Procedure Q, replacing tert-butyl N-(3-aminopropyl)carbamate with tert-butyl (2-aminoethyl)carbamate. ESI [M+H]=344.1

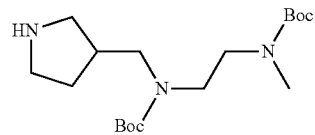

Tert-butyl (2-((tert-butoxycarbonyl)amino)ethyl)(pyrrolidin-3-ylmethyl)carbamate, M61. Synthesized using General Procedure Q, replacing tert-butyl N-(3-aminopropyl)carbamate with tert-butyl (2-aminoethyl)(methyl)carbamate. ESI [M+H]=358.1

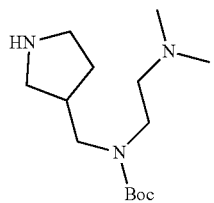 [SMILES: CN(C)CCN(CC1CCNC1)C(=O)OC(C)(C)C]

Tert-butyl (2-(dimethylamino)ethyl)(pyrrolidin-3-ylmethyl)carbamate, M62. Synthesized using General Procedure Q, replacing tert-butyl N-(3-aminopropyl)carbamate with $N^1,N^1$-dimethylethane-1,2-diamine. ESI [M+H]=272.1

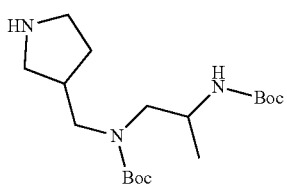 [SMILES: CC(CN(CC1CCNC1)C(=O)OC(C)(C)C)NC(=O)OC(C)(C)C]

Tert-butyl (2-((tert-butoxycarbonyl)amino)propyl)(pyrrolidin-3-ylmethyl) carbamate, M63. Synthesized using General Procedure Q, replacing tert-butyl N-(3-aminopropyl)carbamate with tert-butyl (1-aminopropan-2-yl)carbamate. ESI [M+H]=358.1

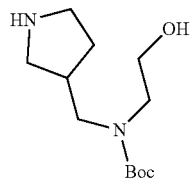

Tert-butyl (2-hydroxyethyl)(pyrrolidin-3-ylmethyl)carbamate, M64. Synthesized using General Procedure Q, replacing tert-butyl N-(3-aminopropyl)carbamate with 2-aminoethanol. ESI [M+H]=245.1

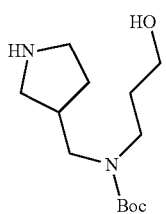 [SMILES: CC(C)(C)OC(=O)N(CCCO)CC1CCNC1]

Tert-butyl (3-hydroxypropyl)(pyrrolidin-3-ylmethyl)carbamate, M65. Synthesized using General Procedure Q, replacing tert-butyl N-(3-aminopropyl)carbamate with 3-aminopropan-1-ol. ESI [M+H]=259.1

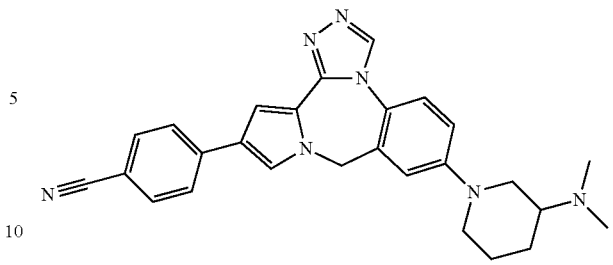

4-(7-(3-(dimethylamino)piperidin-1-yl)-9H-benzo[e]pyrrolo[1,2-a][1,2,4]triazolo[3,4-c][1,4] diazepin-12-yl)benzonitrile, 2. Synthesized using General Procedure A, replacing tert-butyl piperazine-1-carboxylate with N,N-dimethylpiperidin-3-amine. $^1$H NMR (400 MHz, METHANOL-$d_4$) δ=9.13 (br. s., 1H), 7.85-7.64 (m, 5H), 7.61 (d, J=8.8 Hz, 1H), 7.33 (d, J=2.3 Hz, 1H), 7.28 (br. s., 1H), 7.24-7.18 (m, 1H), 5.26 (s, 2H), 3.90 (d, J=11.8 Hz, 1H), 3.63 (d, J=12.5 Hz, 1H), 3.48 (br. s., 1H), 3.11 (t, J=9.5 Hz, 2H), 3.01 (d, J=3.8 Hz, 6H), 2.18 (br. s., 1H), 2.01 (d, J=9.3 Hz, 1H), 1.93-1.80 (m, 2H). ESI [M+H]=450.2

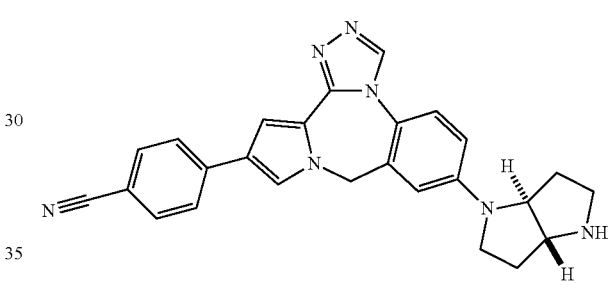

racemic 4-(7-(trans-hexahydropyrrolo[3,2-b]pyrrol-1(2H)-yl)-9H-benzo[e]pyrrolo[1,2-a][1,2,4] triazolo[3,4-c][1,4]diazepin-12-yl)benzonitrile, 3. Synthesized using General Procedure A, replacing tert-butyl piperazine-1-carboxylate with trans-tert-butyl hexahydropyrrolo[3,2-b]pyrrole-1(2H)-carboxylate. $^1$H NMR (400 MHz, METHANOL-$d_4$) δ=9.06 (br. s., 1H), 7.77-7.70 (m, 2H), 7.70-7.61 (m, 3H), 7.54 (d, J=8.8 Hz, 1H), 7.25 (s, 1H), 6.95 (d, J=2.2 Hz, 1H), 6.89-6.83 (m, 1H), 5.22 (s, 2H), 4.34-4.19 (m, 1H), 4.13-3.97 (m, 2H), 3.90-3.76 (m, 2H), 3.69 (dt, J=5.5, 11.1 Hz, 1H), 2.79-2.67 (m, 1H), 2.39-2.25 (m, 1H), 2.23-2.10 (m, 1H), 2.08-1.97 (m, 1H). ESI [M+H]=434.2

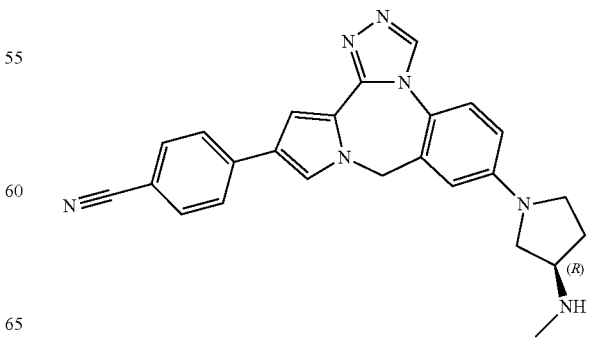

(R)-4-(7-(3-(methylamino)pyrrolidin-1-yl)-9H-benzo[e]pyrrolo[1,2-a][1,2,4]triazolo[3,4-c] [1,4]diazepin-12-yl)benzonitrile, 4. Synthesized using General Procedure A, replacing tert-butyl piperazine-1-carboxylate with (R)-tert-butyl methyl (pyrrolidin-3-yl)carbamate. $^1$H NMR (400 MHz, METHANOL-d4) δ=9.06 (s, 1H), 7.83-7.60 (m, 5H), 7.57 (d, J=8.8 Hz, 1H), 7.26 (d, J=1.5 Hz, 1H), 6.94 (d, J=2.3 Hz, 1H), 6.83 (dd, J=2.6, 8.9 Hz, 1H), 5.24 (s, 2H), 4.03 (br. s., 1H), 3.77-3.60 (m, 3H), 3.53-3.46 (m, 1H), 2.83 (s, 3H), 2.65-2.51 (m, 1H), 2.30 (d, J=5.3 Hz, 1H). ESI [M+H]= 422.2

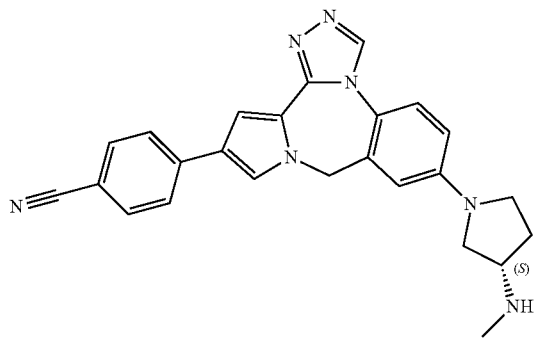

(S)-4-(7-(3-(methylamino)pyrrolidin-1-yl)-9H-benzo[e]pyrrolo[1,2-a][1,2,4]triazolo[3,4-c] [1,4]diazepin-12-yl)benzonitrile, 5. Synthesized using General Procedure A, replacing tert-butyl piperazine-1-carboxylate with (S)-tert-butyl methyl (pyrrolidin-3-yl)carbamate. $^1$H NMR (400 MHz, METHANOL-d$_4$) δ=9.06 (s, 1H), 7.83-7.60 (m, 5H), 7.57 (d, J=8.8 Hz, 1H), 7.26 (d, J=1.5 Hz, 1H), 6.94 (d, J=2.3 Hz, 1H), 6.83 (dd, J=2.6, 8.9 Hz, 1H), 5.24 (s, 2H), 4.03 (br. s., 1H), 3.77-3.60 (m, 3H), 3.53-3.46 (m, 1H), 2.83 (s, 3H), 2.65-2.51 (m, 1H), 2.30 (d, J=5.3 Hz, 1H). ESI [M+H]= 422.2

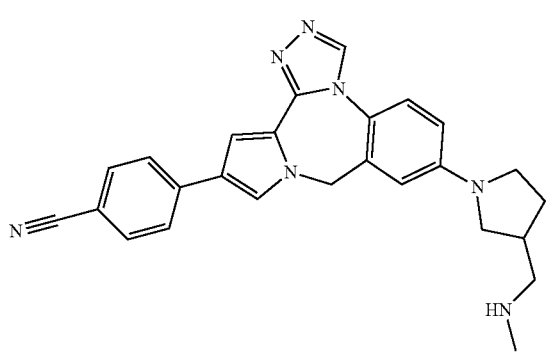 [SMILES: CNCC1CCN(c2ccc3c(c2)Cn2cc(-c4ccc(C#N)cc4)cc2-c2nncn2-3)C1]

4-(7-(3-((methylamino)methyl)pyrrolidin-1-yl)-9H-benzo[e]pyrrolo[1,2-a][1,2,4]triazolo[3,4-c][1,4]diazepin-12-yl)benzonitrile, 18. Synthesized using General Procedure A, replacing tert-butyl piperazine-1-carboxylate with tert-butyl methyl(pyrrolidin-3-ylmethyl)carbamate. $^1$H NMR (400 MHz, METHANOL-d$_4$) δ=9.17 (br. s., 1H), 7.73-7.60 (m, 5H), 7.47 (d, J=7.5 Hz, 1H), 7.26 (br. s., 1H), 6.78 (br. s., 1H), 6.68 (d, J=7.5 Hz, 1H), 5.14 (br. s., 2H), 3.59 (br. s., 1H), 3.55-3.46 (m, 1H), 3.42 (br. s., 1H), 3.15 (br. s., 3H), 2.77 (s, 3H), 2.75-2.66 (m, 1H), 2.32 (d, J=6.2 Hz, 1H), 1.88 (dd, J=8.4, 11.5 Hz, 1H). ESI [M+H]=436.2

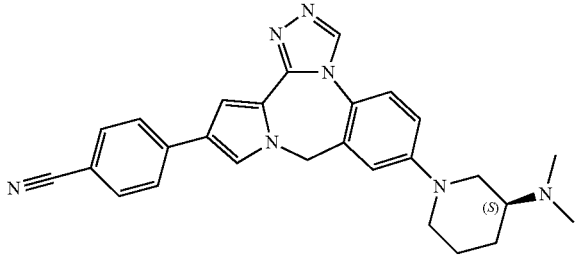

(S)-4-(7-(3-(dimethylamino)piperidin-1-yl)-9H-benzo[e]pyrrolo[1,2-a][1,2,4]triazolo[3,4-c] [1,4]diazepin-12-yl)benzonitrile, 20. Synthesized using General Procedure C, replacing tert-butyl (azetidin-3-ylmethyl)(methyl)carbamate with (S)-tert-butyl piperidin-3-ylcarbamate. $^1$H NMR (400 MHz, METHANOL-d$_4$) δ=9.06 (br. s., 1H), 7.80-7.64 (m, 4H), 7.62 (s, 1H), 7.58 (d, J=8.8 Hz, 1H), 7.31 (d, J=2.6 Hz, 1H), 7.25 (s, 1H), 7.19 (dd, J=2.6, 8.8 Hz, 1H), 5.23 (s, 2H), 3.88 (d, J=11.9 Hz, 1H), 3.66-3.56 (m, 1H), 3.45 (t, J=9.0 Hz, 1H), 3.35 (br. s., 1H), 3.13-3.05 (m, 1H), 3.04-2.86 (m, 6H), 2.24-2.12 (m, 1H), 1.99 (d, J=11.5 Hz, 1H), 1.92-1.77 (m, 2H). ESI [M+H]=450.2

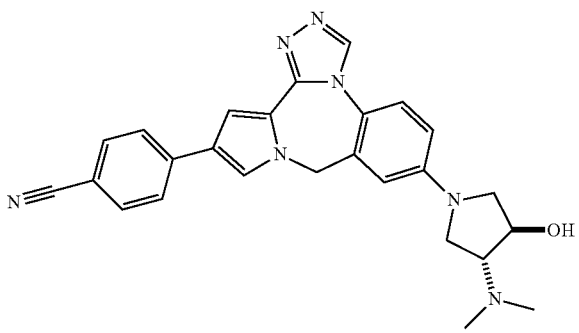

racemic 4-(7-(trans-3-(dimethylamino)-4-hydroxypyrrolidin-1-yl)-9H-benzo[e]pyrrolo[1,2-a][1,2,4]triazolo[3,4-c][1,4]diazepin-12-yl)benzonitrile, 57. Synthesized using General Procedure A, replacing tert-butyl piperazine-1-carboxylate with trans-4-(dimethylamino)pyrrolidin-3-ol. $^1$H NMR (400 MHz, METHANOL-d$_4$) δ=9.07 (s, 1H), 7.75-7.69 (m, 2H), 7.68-7.60 (m, 3H), 7.54 (d, J=8.8 Hz, 1H), 7.23 (s, 1H), 6.89 (d, J=2.2 Hz, 1H), 6.79 (dd, J=2.4, 8.6 Hz, 1H), 5.20 (s, 2H), 4.72 (q, J=6.6 Hz, 1H), 3.96-3.82 (m, 3H), 3.59 (dd, J=6.8, 9.5 Hz, 1H), 3.28-3.22 (m, 1H), 3.14-2.99 (m, 6H). ESI [M+H]=452.2

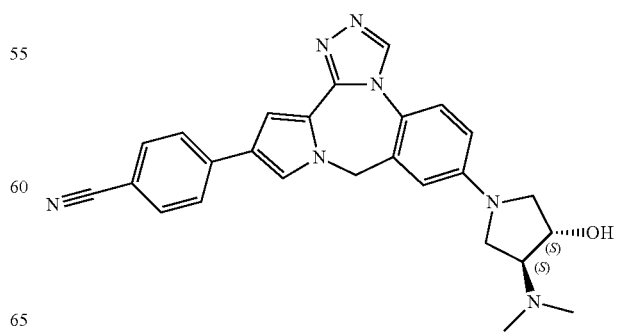

4-(7-((3S,4S)-3-(dimethylamino)-4-hydroxypyrrolidin-1-yl)-9H-benzo[e]pyrrolo[1,2-a][1,2,4] triazolo[3,4-c][1,4]diazepin-12-yl)benzonitrile, 58. Synthesized using General Procedure A, replacing tert-butyl piperazine-1-carboxylate with (3S, 4S)-4-(dimethylamino)pyrrolidin-3-ol. ¹H NMR (400 MHz, METHANOL-d₄) δ=9.07 (br. s., 1H), 7.75-7.58 (m, 5H), 7.53 (d, J=8.8 Hz, 1H), 7.22 (br. s., 1H), 6.88 (br. s., 1H), 6.78 (d, J=8.4 Hz, 1H), 5.18 (br. s., 2H), 4.73 (d, J=6.6 Hz, 1H), 3.99-3.79 (m, 3H), 3.60 (t, J=7.7 Hz, 1H), 3.27 (br. s., 1H), 3.08 (br. s., 6H). ESI [M+H]=452.2

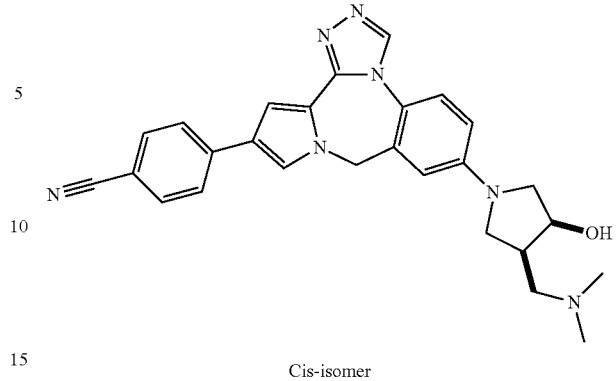

Cis-isomer 4-(7-(Cis-3-((dimethylamino)methyl)-4-hydroxypyrrolidin-1-yl)-9H-benzo[e]pyrrolo[1,2-a] [1,2,4]triazolo[3,4-c][1,4]diazepin-12-yl)benzonitrile, 75. Synthesized using General Procedure A, replacing tert-butyl piperazine-1-carboxylate with cis-4-((dimethylamino)methyl) pyrrolidin-3-ol. 1H NMR (400 MHz, METHANOL-d4) δ=9.10 (s, 1H), 7.79-7.59 (m, 5H), 7.49 (d, J=8.8 Hz, 1H), 7.24 (br. s., 1H), 6.79 (d, J=1.8 Hz, 1H), 6.69 (d, J=8.4 Hz, 1H), 5.17 (s, 2H), 4.57 (br. s., 1H), 3.74-3.53 (m, 4H), 3.44 (d, J=10.6 Hz, 1H), 3.24 (br. s., 1H), 2.98 (s, 6H), 2.86 (br. s., 1H). ESI [M+H]=466.2

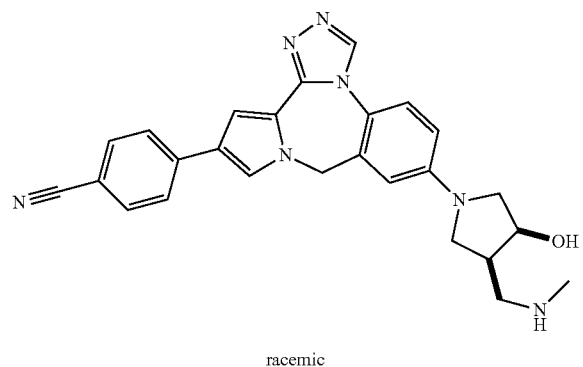 [SMILES: CNC[C@H]1CN(c2ccc3c(c2)Cn2cc(-c4ccc(C#N)cc4)cc2-c2nncn2-3)C[C@H]1O]

racemic 4-(7-(cis-3-hydroxy-4-((methylamino)methyl)pyrrolidin-1-yl)-9H-benzo[e]pyrrolo[1,2-a] [1,2,4] triazolo[3,4-c][1,4] diazepin-12-yl)benzonitrile, 73. Synthesized using General Procedure A, replacing tert-butyl piperazine-1-carboxylate with cis-4-((methylamino) methyl) pyrrolidin-3-ol. 1H NMR (400 MHz, METHANOL-d4) δ=9.02 (br. s., 1H), 7.77-7.60 (m, 5H), 7.50 (d, J=8.8 Hz, 1H), 7.23 (s, 1H), 6.79 (d, J=2.2 Hz, 1H), 6.70 (dd, J=2.6, 8.8 Hz, 1H), 5.18 (s, 2H), 4.57 (br. s., 1H), 3.72-3.56 (m, 2H), 3.49-3.38 (m, 2H), 3.23 (dd, J=5.7, 12.8 Hz, 1H), 3.00 (d, J=11.9 Hz, 1H), 2.78 (s, 3H), 2.71 (br. s., 1H). ESI [M+H]=452.1

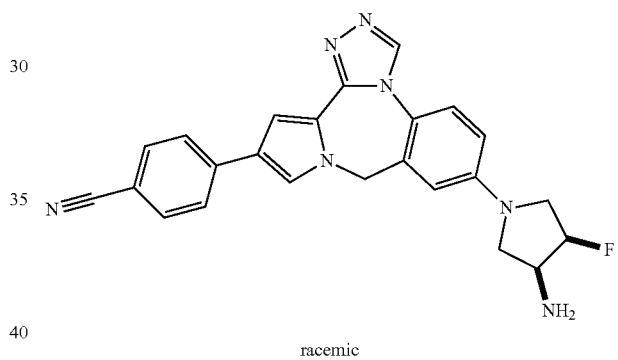

racemic 4-(7-(cis-3-amino-4-fluoropyrrolidin-1-yl)-9H-benzo[e]pyrrolo[1,2-a][1,2,4]triazolo[3,4-c][1,4]diazepin-12-yl)benzonitrile, 76. Synthesized using General Procedure A, replacing tert-butyl piperazine-1-carboxylate with tert-butyl (cis-4-fluoropyrrolidin-3-yl)carbamate. 1H NMR (400 MHz, METHANOL-d4) δ=9.06 (br. s., 1H), 7.77-7.70 (m, 2H), 7.69-7.61 (m, 3H), 7.55 (d, J=8.8 Hz, 1H), 7.24 (s, 1H), 6.89 (d, J=2.6 Hz, 1H), 6.77 (dd, J=2.2, 8.8 Hz, 1H), 5.21 (s, 2H), 4.25-4.11 (m, 1H), 3.91 (t, J=8.8 Hz, 1H), 3.87-3.81 (m, 1H), 3.77 (s, 1H), 3.51 (t, J=9.3 Hz, 1H), 3.41-3.32 (m, 1H). ESI [M+H]=426.1

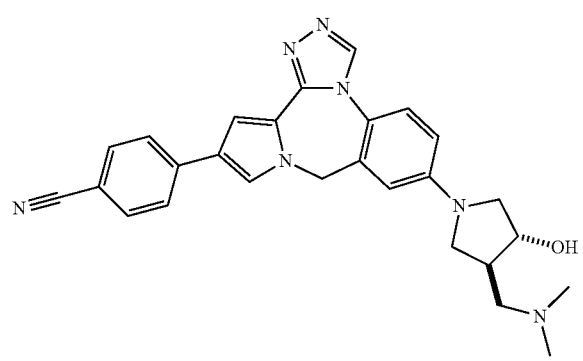

racemic 4-(7-(trans-3-((dimethylamino)methyl)-4-hydroxypyrrolidin-1-yl)-9H-benzo[e]pyrrolo[1,2-a][1,2,4]triazolo[3,4-c][1,4]diazepin-12-yl)benzonitrile, 74. Synthesized using General Procedure A, replacing tert-butyl piperazine-1-carboxylate with trans-4-((dimethylamino) methyl) pyrrolidin-3-ol. 1H NMR (400 MHz, METHANOL-d4) δ=9.15 (br. s., 1H), 7.67-7.51 (m, 5H), 7.42 (d, J=8.4 Hz, 1H), 7.19 (br. s., 1H), 6.71 (br. s., 1H), 6.61 (d, J=7.9 Hz, 1H), 5.10 (br. s., 2H), 4.28-4.15 (m, 1H), 3.74-3.58 (m, 2H), 3.38-3.25 (m, 2H), 3.20-3.07 (m, 2H), 2.97-2.86 (m, 6H), 2.69-2.60 (m, 1H). ESI [M+H]=466.2

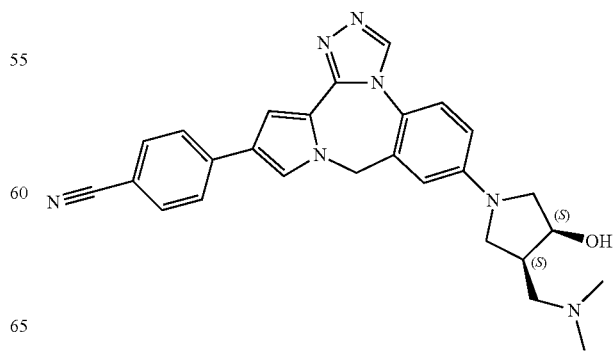

4-(7-((3S,4S)-3-((dimethylamino)methyl)-4-hydroxypyrrolidin-1-yl)-9H-benzo[e]pyrrolo[1,2-a][1,2,4]triazolo[3,4-c][1,4]diazepin-12-yl)benzonitrile, 81. Synthesized using General Procedure A, replacing tert-butyl piperazine-1-carboxylate with (3S, 4R)-4-((dimethylamino) methyl) pyrrolidin-3-ol. 1H NMR (400 MHz, METHANOL-d4) δ=9.02 (s, 1H), 7.74-7.60 (m, 5H), 7.48 (d, J=8.6 Hz, 1H), 7.22 (s, 1H), 6.78 (d, J=2.3 Hz, 1H), 6.69 (dd, J=2.3, 8.6 Hz, 1H), 5.16 (s, 2H), 4.57 (br. s., 1H), 3.72-3.54 (m, 3H), 3.44 (d, J=10.2 Hz, 1H), 3.34 (br. s., 1H), 3.28-3.22 (m, 1H), 2.99 (s, 6H), 2.91-2.81 (m, 1H). ESI [M+H]=466.2

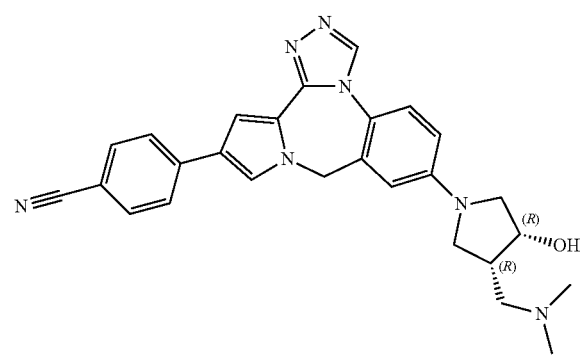

4-(7-((3R,4R)-3-((dimethylamino)methyl)-4-hydroxypyrrolidin-1-yl)-9H-benzo[e]pyrrolo[1,2-a][1,2,4]triazolo[3,4-c][1,4]diazepin-12-yl)benzonitrile, 82. Synthesized using General Procedure A, replacing tert-butyl piperazine-1-carboxylate with (3R, 4S)-4-((dimethylamino) methyl) pyrrolidin-3-ol. 1H NMR (400 MHz, METHANOL-d4) δ=9.01 (br. s., 1H), 7.74-7.60 (m, 5H), 7.48 (d, J=8.6 Hz, 1H), 7.21 (s, 1H), 6.78 (d, J=2.3 Hz, 1H), 6.69 (dd, J=2.3, 9.0 Hz, 1H), 5.16 (s, 2H), 4.57 (br. s., 1H), 3.73-3.55 (m, 3H), 3.44 (d, J=10.6 Hz, 1H), 3.34 (br. s., 1H), 3.29-3.22 (m, 1H), 2.99 (s, 6H), 2.90-2.82 (m, 1H). ESI [M+H]=466.2

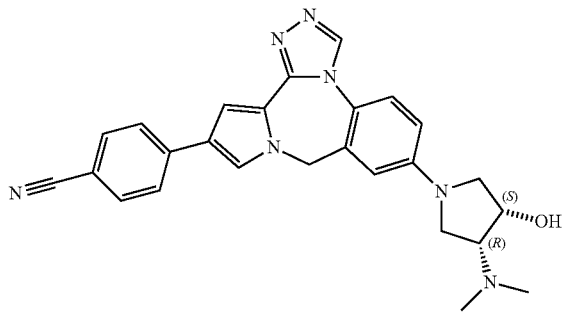

4-(7-((3R,4S)-3-(dimethylamino)-4-hydroxypyrrolidin-1-yl)-9H-benzo[e]pyrrolo[1,2-a][1,2,4]triazolo[3,4-c][1,4]diazepin-12-yl)benzonitrile, 83. Synthesized using General Procedure A, replacing tert-butyl piperazine-1-carboxylate with (3S, 4R)-4-(dimethylamino) pyrrolidin-3-ol. 1H NMR (400 MHz, METHANOL-d4) δ=9.05 (s, 1H), 7.74-7.67 (m, 2H), 7.67-7.60 (m, 3H), 7.52 (d, J=8.8 Hz, 1H), 7.25 (br. s., 1H), 6.86 (d, J=1.8 Hz, 1H), 6.74 (d, J=7.1 Hz, 1H), 5.19 (s, 2H), 4.68 (br. s., 1H), 3.99-3.86 (m, 2H), 3.69 (dd, J=3.3, 11.2 Hz, 1H), 3.61-3.47 (m, 2H), 3.13-2.90 (m, 6H). ESI [M+H]=452.2

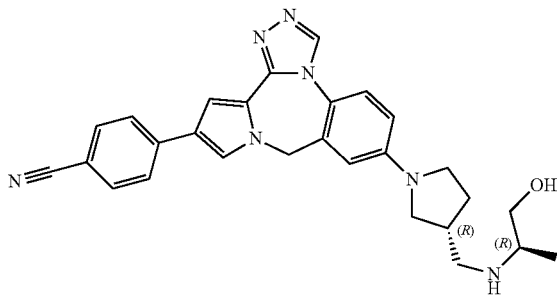

4-(7-((R)-3-((((R)-1-hydroxypropan-2-yl)amino)methyl)pyrrolidin-1-yl)-9H-benzo[e] pyrrolo[1,2-a][1,2,4]triazolo[3,4-c][1,4]diazepin-12-yl)benzonitrile, 85. Synthesized using General Procedure A, replacing tert-butyl piperazine-1-carboxylate with (R)-2-(((S)-pyrrolidin-3-ylmethyl)amino) propan-1-ol. 1H NMR (400 MHz, METHANOL-d4) δ=9.01 (s, 1H), 7.76-7.67 (m, 2H), 7.67-7.57 (m, 3H), 7.46 (d, J=8.8 Hz, 1H), 7.21 (d, J=1.3 Hz, 1H), 6.77 (d, J=2.2 Hz, 1H), 6.68 (dd, J=2.2, 8.8 Hz, 1H), 5.14 (s, 2H), 3.83 (dd, J=3.7, 12.1 Hz, 1H), 3.65-3.55 (m, 2H), 3.51 (dt, J=4.0, 8.8 Hz, 1H), 3.45-3.35 (m, 2H), 3.23-3.14 (m, 3H), 2.73 (td, J=7.3, 14.9 Hz, 1H), 2.39-2.29 (m, 1H), 1.90 (qd, J=8.2, 12.3 Hz, 1H), 1.33 (d, J=7.1 Hz, 3H). ESI [M+H]=480.2

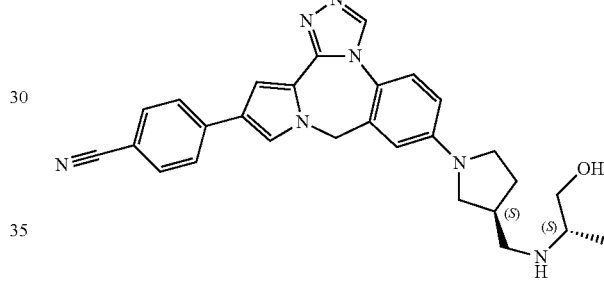

4-(7-((S)-3-((((S)-1-hydroxypropan-2-yl)amino)methyl)pyrrolidin-1-yl)-9H-benzo[e]pyrrolo[1,2-a][1,2,4]triazolo[3,4-c][1,4]diazepin-12-yl)benzonitrile, 86. Synthesized using General Procedure A, replacing tert-butyl piperazine-1-carboxylate with (S)-2-(((R)-pyrrolidin-3-ylmethyl)amino) propan-1-ol. 1H NMR (400 MHz, METHANOL-d4) δ=9.04 (br. s., 1H), 7.75-7.57 (m, 5H), 7.47 (d, J=8.8 Hz, 1H), 7.22 (br. s., 1H), 6.78 (d, J=2.2 Hz, 1H), 6.68 (dd, J=2.2, 8.8 Hz, 1H), 5.15 (s, 2H), 3.83 (dd, J=3.5, 11.9 Hz, 1H), 3.59 (dd, J=5.7, 11.9 Hz, 2H), 3.55-3.47 (m, 1H), 3.41 (d, J=8.4 Hz, 2H), 3.23-3.13 (m, 3H), 2.80-2.66 (m, 1H), 2.35 (dd, J=4.6, 11.7 Hz, 1H), 1.96-1.85 (m, 1H), 1.33 (d, J=6.6 Hz, 3H). ESI [M+H]=480.2

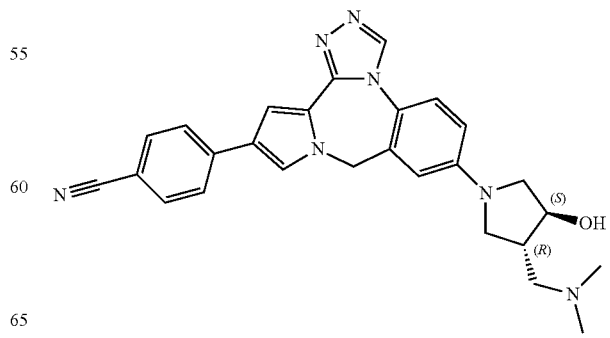

4-(7-((3R,4S)-3-((dimethylamino)methyl)-4-hydroxypyrrolidin-1-yl)-9H-benzo[e]pyrrolo[1,2-a][1,2,4]triazolo[3,4-c][1,4]diazepin-12-yl)benzonitrile, 108. Synthesized using General Procedure A, replacing tert-butyl piperazine-1-carboxylate with (3S, 4S)-4-((dimethylamino) methyl)pyrrolidin-3-ol. ¹H NMR (400 MHz, METHANOL-d₄) δ=8.97 (s, 1H), 7.67-7.73 (m, 2H), 7.57-7.67 (m, 3H), 7.44 (d, J=8.4 Hz, 1H), 7.18 (d, J=1.3 Hz, 1H), 6.77 (d, J=2.2 Hz, 1H), 6.66 (dd, J=8.8, 2.2 Hz, 1H), 5.13 (s, 2H), 4.26 (q, J=6.0 Hz, 1H), 3.62-3.76 (m, 2H), 3.20 (ddd, J=16.3, 9.9, 6.4 Hz, 2H), 2.98-3.07 (m, 1H), 2.86-2.96 (m, 1H), 2.70 (s, 6H), 2.54-2.63 ppm (m, 1H). ESI [M+H]=466.1

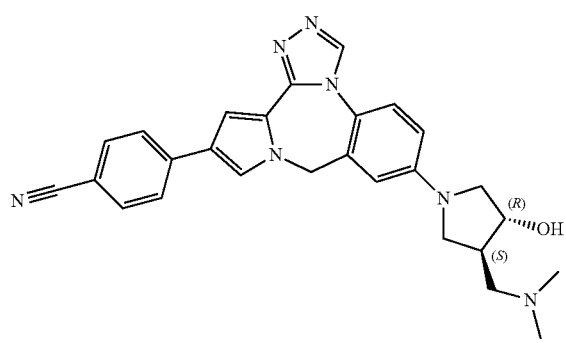

4-(7-((3S,4R)-3-((dimethylamino)methyl)-4-hydroxypyrrolidin-1-yl)-9H-benzo[e]pyrrolo[1,2-a][1,2,4]triazolo[3,4-c][1,4]diazepin-12-yl)benzonitrile, 109. Synthesized using General Procedure A, replacing replacing tert-butyl piperazine-1-carboxylate with (3R, 4R)-4-((dimethylamino)methyl)pyrrolidin-3-ol. ¹H NMR (400 MHz, METHANOL-d₄) δ=8.97 (s, 1H), 7.74-7.68 (m, 2H), 7.67-7.57 (m, 3H), 7.45 (d, J=8.8 Hz, 1H), 7.18 (d, J=1.3 Hz, 1H), 6.77 (d, J=2.2 Hz, 1H), 6.66 (dd, J=2.4, 8.6 Hz, 1H), 5.13 (s, 2H), 4.25 (q, J=6.2 Hz, 1H), 3.74-3.62 (m, 2H), 3.27-3.14 (m, 2H), 3.08-2.95 (m, 1H), 2.94-2.83 (m, 1H), 2.68 (s, 6H), 2.63-2.53 (m, 1H). ESI [M+H]=466.1

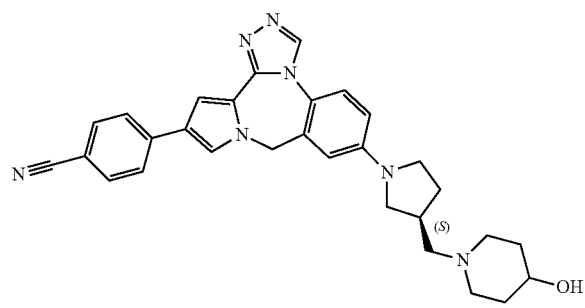

(S)-4-(7-(3-((4-hydroxypiperidin-1-yl)methyl)pyrrolidin-1-yl)-9H-benzo[e]pyrrolo[1,2-a] [1,2,4]triazolo[3,4-c][1,4]diazepin-12-yl)benzonitrile, 110. Synthesized using General Procedure A, replacing tert-butyl piperazine-1-carboxylate with (R)-1-(pyrrolidin-3-ylmethyl) piperidin-4-ol. 1H NMR (400 MHz, METHANOL-d4) δ=9.00 (s, 1H), 7.78-7.60 (m, 5H), 7.49 (d, J=8.6 Hz, 1H), 7.22 (s, 1H), 6.81 (d, J=2.2 Hz, 1H), 6.74-6.68 (m, 1H), 5.18 (s, 2H), 4.11 (br. s., 1H), 3.85 (br. s., 1H), 3.74-3.61 (m, 2H), 3.57-3.41 (m, 3H), 3.17-3.06 (m, 3H), 2.88 (d, J=7.9 Hz, 1H), 2.36 (br. s., 1H), 2.17 (d, J=13.9 Hz, 1H), 2.08-1.86 (m, 4H), 1.77 (d, J=13.7 Hz, 1H). ESI [M+H]=506.2

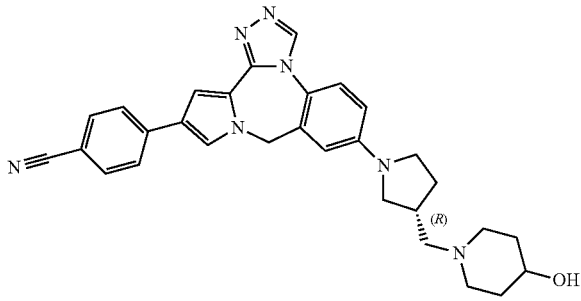

(R)-4-(7-(3-((4-hydroxypiperidin-1-yl)methyl)pyrrolidin-1-yl)-9H-benzo[e]pyrrolo[1,2-a] [1,2,4]triazolo[3,4-c][1,4]diazepin-12-yl)benzonitrile, 111. Synthesized using General Procedure A, replacing tert-butyl piperazine-1-carboxylate with (S)-1-(pyrrolidin-3-ylmethyl) piperidin-4-ol. 1H NMR (400 MHz, METHANOL-d4) δ=9.10 (br. s., 1H), 7.73-7.61 (m, 5H), 7.48 (d, J=8.8 Hz, 1H), 7.28-7.21 (m, 1H), 6.78 (d, J=2.2 Hz, 1H), 6.69 (dd, J=2.6, 8.8 Hz, 1H), 5.17 (s, 2H), 4.10 (br. s., 1H), 3.90-3.76 (m, 1H), 3.65 (t, J=8.2 Hz, 2H), 3.56-3.34 (m, 4H), 3.19-3.03 (m, 2H), 2.85 (td, J=7.6, 14.8 Hz, 1H), 2.34 (br. s., 1H), 2.15 (d, J=13.7 Hz, 1H), 2.07-1.71 (m, 5H). ESI [M+H]=506.2

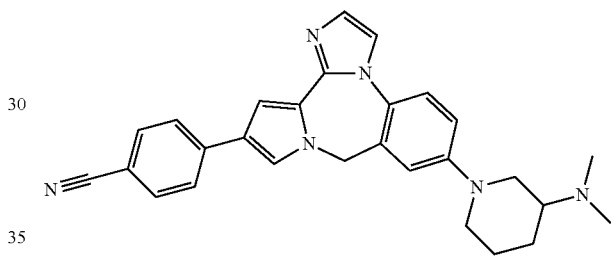

4-(7-(3-(dimethylamino)piperidin-1-yl)-9H-benzo[e]imidazo[2,1-c]pyrrolo[1,2-a][1,4] diazepin-12-yl)benzonitrile, 112. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile, replacing tert-butyl (azetidin-3-ylmethyl)(methyl)carbamate with tert-butyl piperidin-3-ylcarbamate. 1H NMR (400 MHz, METHANOL-d4) δ=8.07 (br. s., 1H), 7.84-7.67 (m, 6H), 7.63 (d, J=8.8 Hz, 1H), 7.38-7.30 (m, 2H), 7.23 (dd, J=2.9, 9.0 Hz, 1H), 5.36 (s, 2H), 3.99 (d, J=12.3 Hz, 1H), 3.70 (s, 1H), 3.50-3.40 (m, 1H), 3.25 (s, 1H), 3.06 (d, J=10.1 Hz, 1H), 2.98 (s, 6H), 2.18 (br. s., 1H), 1.99 (dd, J=4.4, 8.8 Hz, 1H), 1.90-1.79 (m, 2H). ESI [M+H]=449.2

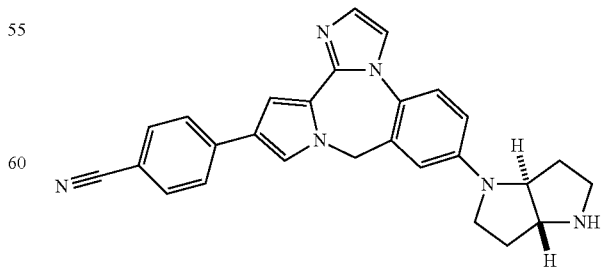

racemic 4-(7-(trans-hexahydropyrrolo[3,2-b]pyrrol-1(2H)-yl)-9H-benzo[e]imidazo[2,1-c]pyrrolo[1,2-a][1,4]diazepin-12-yl)benzonitrile, 113. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-9H-benzo[e]imidazo[2,1-c]pyrrolo[1,2-a][1,4]diazepin-12-yl) benzonitrile, replacing tert-butyl piperazine-1-carboxylate with trans-tert-butyl hexahydropyrrolo[3,2-b]pyrrole-1(2H)-carboxylate. 1H NMR (400 MHz, METHANOL-d4) δ=8.05 (br. s., 1H), 7.89-7.69 (m, 6H), 7.61 (d, J=8.5 Hz, 1H), 7.34 (br. s., 1H), 6.99 (br. s., 1H), 6.96-6.88 (m, 1H), 5.36 (s, 2H), 4.68-4.49 (m, 1H), 4.30 (d, J=7.5 Hz, 1H), 4.14-4.00 (m, 1H), 3.92-3.82 (m, 1H), 3.74 (d, J=5.3 Hz, 1H), 3.45 (d, J=7.8 Hz, 1H), 2.77 (d, J=5.5 Hz, 1H), 2.37 (dd, J=6.1, 10.7 Hz, 1H), 2.22 (d, J=10.5 Hz, 1H), 2.06 (br. s., 1H). ESI [M+H]=433.2

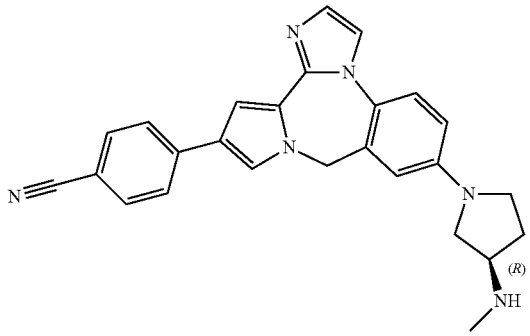

(R)-4-(7-(3-(methylamino)pyrrolidin-1-yl)-9H-benzo[e]imidazo[2,1-c]pyrrolo[1,2-a][1,4] diazepin-12-yl)benzonitrile, 114. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile, replacing tert-butyl piperazine-1-carboxylate with (R)-tert-butyl methyl(pyrrolidin-3-yl)carbamate. 1H NMR (400 MHz, METHANOL-d4) δ=8.06 (s, 1H), 7.84-7.71 (m, 6H), 7.62 (d, J=8.8 Hz, 1H), 7.34 (s, 1H), 6.95 (d, J=2.5 Hz, 1H), 6.91-6.85 (m, 1H), 5.36 (s, 2H), 4.10-4.00 (m, 1H), 3.82-3.58 (m, 3H), 3.51 (d, J=6.0 Hz, 1H), 2.83 (s, 3H), 2.62-2.53 (m, 1H), 2.32 (d, J=5.8 Hz, 1H) ESI [M+H]=421.2

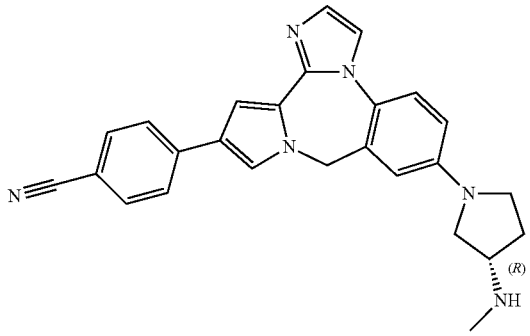

(S)-4-(7-(3-(methylamino)pyrrolidin-1-yl)-9H-benzo[e]imidazo[2,1-c]pyrrolo[1,2-a][1,4] diazepin-12-yl)benzonitrile, 115. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile, replacing tert-butyl piperazine-1-carboxylate with (S)-tert-butyl methyl(pyrrolidin-3-yl)carbamate. 1H NMR (400 MHz, METHANOL-d4) δ=8.06 (s, 1H), 7.84-7.71 (m, 6H), 7.62 (d, J=8.8 Hz, 1H), 7.34 (s, 1H), 6.95 (d, J=2.5 Hz, 1H), 6.91-6.85 (m, 1H), 5.36 (s, 2H), 4.10-4.00 (m, 1H), 3.82-3.58 (m, 3H), 3.51 (d, J=6.0 Hz, 1H), 2.83 (s, 3H), 2.62-2.53 (m, 1H), 2.32 (d, J=5.8 Hz, 1H) ESI [M+H]=421.2

4-(7-(3-(aminomethyl)azetidin-1-yl)-9H-benzo[e]imidazo[2,1-c]pyrrolo[1,2-a][1,4]diazepin-12-yl)benzonitrile, 118. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile, replacing tert-butyl piperazine-1-carboxylate with tert-butyl (azetidin-3-ylmethyl)carbamate. 1H NMR (400 MHz, METHANOL-d4) δ=8.01 (br. s., 1H), 7.85-7.63 (m, 6H), 7.55 (d, J=8.4 Hz, 1H), 7.32 (br. s., 1H), 6.71 (br. s., 1H), 6.64 (d, J=8.4 Hz, 1H), 5.29 (br. s., 2H), 4.14 (t, J=7.5 Hz, 2H), 3.86-3.74 (m, 2H), 3.31-3.26 (m, 2H), 3.07 (br. s., 1H). ESI [M+H]=407.1

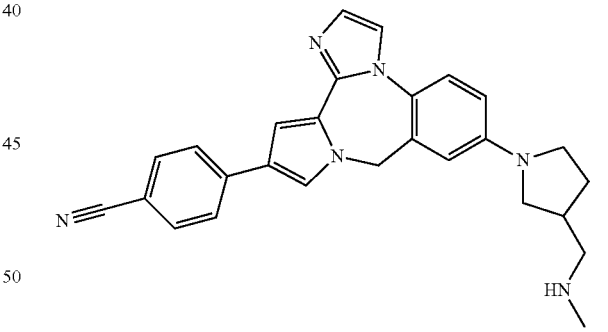

4-(7-(3-((methylamino)methyl)pyrrolidin-1-yl)-9H-benzo[e]imidazo[2,1-c]pyrrolo[1,2-a][1,4] diazepin-12-yl)benzonitrile, 122. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-9H-benzo[e]imidazo[2,1-c]pyrrolo[1,2-a][1,4]diazepin-12-yl)benzonitrile, replacing tert-butyl piperazine-1-carboxylate with tert-butyl methyl(pyrrolidin-3-ylmethyl)carbamate. 1H NMR (400 MHz, METHANOL-d4) δ=8.01 (br. s., 1H), 7.84-7.66 (m, 6H), 7.55 (d, J=8.8 Hz, 1H), 7.31 (s, 1H), 6.82 (br. s., 1H), 6.76 (d, J=8.8 Hz, 1H), 5.30 (s, 2H), 3.64 (br. s., 1H), 3.55 (br. s., 1H), 3.44 (d, J=7.9 Hz, 1H), 3.18 (d, J=7.1 Hz, 3H), 2.78 (s, 3H), 2.75 (br. s., 1H), 2.35 (d, J=6.2 Hz, 1H), 1.98-1.83 (m, 1H). ESI [M+H]=435.2

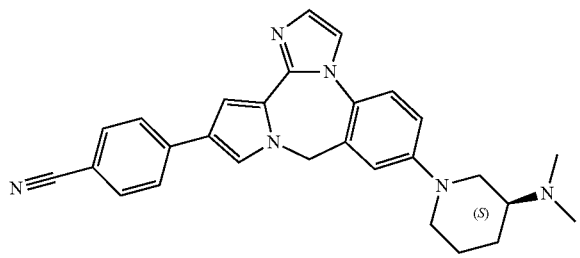

(S)-4-(7-(3-(dimethylamino)piperidin-1-yl)-9H-benzo[e]imidazo[2,1-c]pyrrolo[1,2-a][1,4] diazepin-12-yl)benzonitrile, 123. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl) benzonitrile, replacing tert-butyl(azetidin-3-ylmethyl)(methyl)carbamate with (S)-tert-butyl piperidin-3-ylcarbamate. 1H NMR (400 MHz, METHANOL-d4) δ=8.06 (s, 1H), 7.85-7.68 (m, 6H), 7.63 (d, J=8.8 Hz, 1H), 7.38-7.29 (m, 2H), 7.23 (dd, J=2.6, 8.8 Hz, 1H), 5.35 (s, 2H), 3.99 (d, J=11.9 Hz, 1H), 3.76-3.63 (m, 1H), 3.45 (d, J=3.1 Hz, 1H), 3.25 (br. s., 1H), 3.13-3.03 (m, 1H), 2.98 (s, 6H), 2.27-2.13 (m, 1H), 2.06-1.93 (m, 1H), 1.89-1.78 (m, 2H). ESI [M+H]=449.2

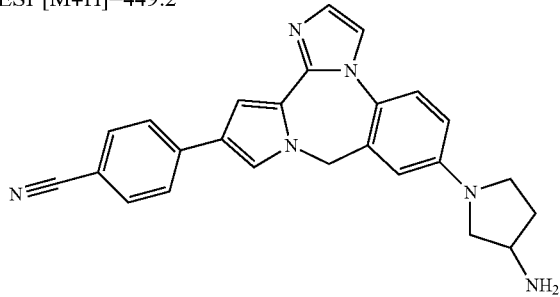

4-(7-(3-aminopyrrolidin-1-yl)-9H-benzo[e]imidazo[2,1-c]pyrrolo[1,2-a][1,4]diazepin-12-yl) benzonitrile, 124. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl) benzonitrile, replacing tert-butyl piperazine-1-carboxylate with tert-butyl pyrrolidin-3-ylcarbamate. 1H NMR (400 MHz, METHANOL-d4) δ=8.02 (d, J=1.8 Hz, 1H), 7.85-7.66 (m, 6H), 7.58 (d, J=9.3 Hz, 1H), 7.32 (s, 1H), 6.90 (d, J=2.6 Hz, 1H), 6.83 (dd, J=2.6, 8.8 Hz, 1H), 5.33 (s, 2H), 4.09 (br. s., 1H), 3.79-3.61 (m, 2H), 3.52 (dd, J=3.7, 10.8 Hz, 2H), 2.58-2.43 (m, 1H), 2.24 (dd, J=4.6, 8.6 Hz, 1H). ESI [M+H]=407.1

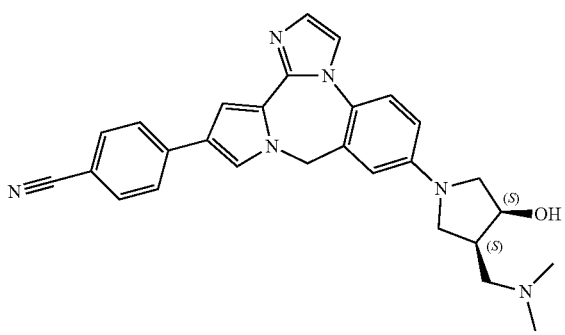

4-(7-((3S,4S)-3-((dimethylamino)methyl)-4-hydroxypyrrolidin-1-yl)-9H-benzo[e]imidazo[2,1-c]pyrrolo[1,2-a][1,4]diazepin-12-yl)benzonitrile, 128. Synthesized using General Procedure A, replacing 4-(7-bromo-9H-benzo[e]pyrrolo[1,2-a][1,2,4]triazolo[3,4-c][1,4] diazepin-12-yl)benzonitrile with 4-(7-bromo-9H-benzo[e]imidazo[2,1-c]pyrrolo[1,2-a][1,4] diazepin-12-yl)benzonitrile, replacing tert-butyl piperazine-1-carboxylate with (3S,4R)-4-((dimethylamino)methyl)pyrrolidin-3-ol. 1H NMR (400 MHz, METHANOL-d4) δ=7.98 (d, J=2.2 Hz, 1H), 7.80-7.64 (m, 6H), 7.53 (d, J=9.3 Hz, 1H), 7.28 (d, J=1.3 Hz, 1H), 6.80 (d, J=2.6 Hz, 1H), 6.74 (dd, J=2.6, 8.8 Hz, 1H), 5.29 (s, 2H), 4.57 (br. s., 1H), 3.70-3.55 (m, 4H), 3.44 (d, J=10.6 Hz, 2H), 2.97 (s, 6H), 2.86 (br. s., 1H). ESI [M+H]=465.1

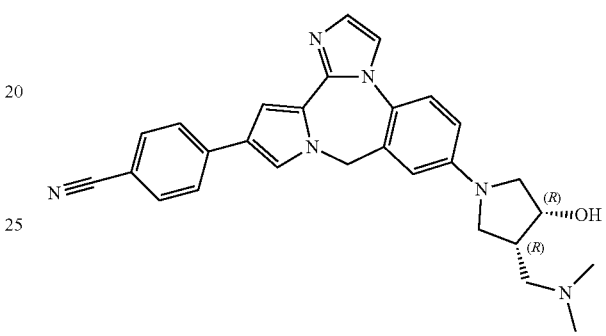

4-(7-((3R,4R)-3-((dimethylamino)methyl)-4-hydroxy-pyrrolidin-1-yl)-9H-benzo[e]imidazo[2,1-c]pyrrolo[1,2-a][1,4]diazepin-12-yl)benzonitrile, 129. Synthesized using General Procedure A, replacing 4-(7-bromo-9H-benzo[e]pyrrolo[1,2-a][1,2,4]triazolo[3,4-c][1,4] diazepin-12-yl)benzonitrile with 4-(7-bromo-9H-benzo[e]imidazo[2,1-c]pyrrolo[1,2-a][1,4] diazepin-12-yl)benzonitrile, replacing tert-butyl piperazine-1-carboxylate with (3R,4S)-4-((dimethylamino)methyl)pyrrolidin-3-ol. 1H NMR (400 MHz, METHANOL-d4) δ=7.98 (s, 1H), 7.79-7.66 (m, 6H), 7.53 (d, J=8.8 Hz, 1H), 7.29 (s, 1H), 6.80 (d, J=2.2 Hz, 1H), 6.74 (dd, J=2.6, 9.3 Hz, 1H), 5.29 (s, 2H), 4.56 (br. s., 1H), 3.71-3.53 (m, 4H), 3.44 (d, J=10.6 Hz, 2H), 2.97 (s, 6H), 2.86 (br. s., 1H). ESI [M+H]=465.1

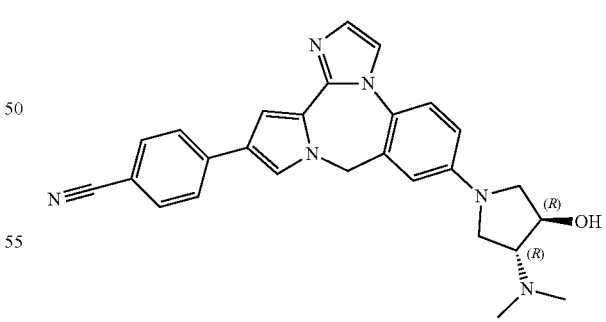

4-(7-((3R,4R)-3-(dimethylamino)-4-hydroxypyrrolidin-1-yl)-9H-benzo[e]imidazo[2,1-c] pyrrolo[1,2-a][1,4]diazepin-12-yl)benzonitrile, 130. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-9H-benzo[e]imidazo[2,1-c]pyrrolo[1,2-a][1,4]diazepin-12-yl) benzonitrile, replacing tert-butyl piperazine-1-carboxylate with (3R,4R)-4-(dimethylamino) pyrrolidin-3-ol. 1H NMR (400 MHz, METHANOL-d4) δ=8.01 (d, J=2.0 Hz, 1H), 7.81-7.67 (m, 6H), 7.59 (d, J=9.0 Hz, 1H), 7.30 (d, J=1.6 Hz, 1H), 6.92 (d, J=2.3 Hz, 1H), 6.85 (dd, J=2.5, 9.0 Hz, 1H), 5.32 (s, 2H), 4.72 (q, J=6.8 Hz, 1H), 4.00-3.82 (m, 3H), 3.60 (dd, J=7.2, 10.2 Hz, 1H), 3.33 (br. s., 1H), 3.15-2.96 (m, 6H). ESI [M+H]=451.1

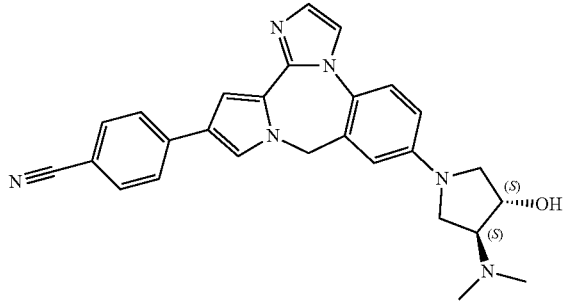

4-(7-((3S,4S)-3-(dimethylamino)-4-hydroxypyrrolidin-1-yl)-9H-benzo[e]imidazo[2,1-c] pyrrolo[1,2-a][1,4]diazepin-12-yl)benzonitrile, 131. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replacing tert-butyl piperazine-1-carboxylate with (3S,4S)-4-(dimethylamino)pyrrolidin-3-ol. ¹H NMR (400 MHz, METHANOL-d₄) δ=7.99 (d, J=1.8 Hz, 1H), 7.79-7.66 (m, 6H), 7.59 (d, J=9.0 Hz, 1H), 7.29 (d, J=1.6 Hz, 1H), 6.92 (d, J=2.5 Hz, 1H), 6.84 (dd, J=2.5, 9.0 Hz, 1H), 5.31 (s, 2H), 4.72 (q, J=7.0 Hz, 1H), 4.00-3.82 (m, 3H), 3.60 (dd, J=7.1, 10.1 Hz, 1H), 3.33 (br. s., 1H), 3.06 (s, 6H). ESI [M+H]=451.1

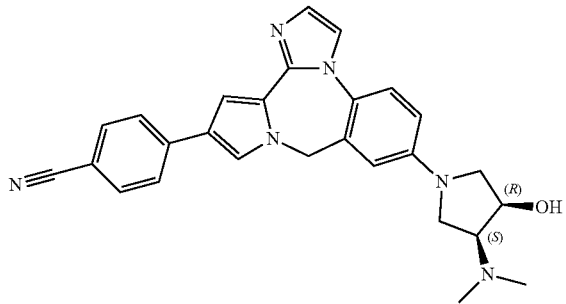

4-(7-((3S,4R)-3-(dimethylamino)-4-hydroxypyrrolidin-1-yl)-9H-benzo[e]imidazo[2,1-c] pyrrolo[1,2-a][1,4]diazepin-12-yl)benzonitrile, 133. Synthesized using General Procedure A, replacing 4-(7-bromo-9H-benzo[e]pyrrolo[1,2-a][1,2,4]triazolo[3,4-c][1,4]diazepin-12-yl)ben-zonitrile with 4-(7-bromo-9H-benzo[e]imidazo[2,1-c]pyrrolo[1,2-a][1,4]diazepin-12-yl)ben-zonitrile and replacing tertbutyl piperazine-1-carboxylate with (3R,4S)-4-(dimethylamino)pyrrolidin-3-ol. ¹H NMR (400 MHz, METHANOL-d₄) δ=7.99 (br. s., 1H), 7.79-7.66 (m, 6H), 7.58 (d, J=7.6 Hz, 1H), 7.29 (br. s., 1H), 6.88 (s, 1H), 6.82 (d, J=8.8 Hz, 1H), 5.31 (s, 2H), 4.70 (br. s., 1H), 3.95 (br. s., 2H), 3.77-3.69 (m, 1H), 3.63-3.52 (m, 2H), 3.03 (d, J=16.0 Hz, 6H). ESI [M+H]=451.1

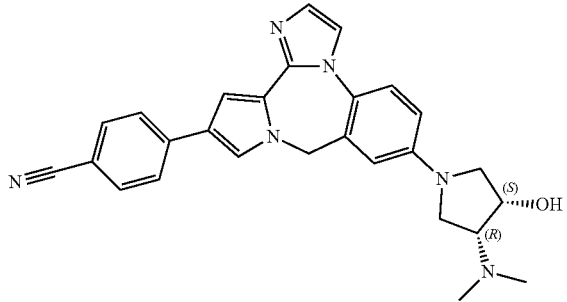

4-(7-((3R,4S)-3-(dimethylamino)-4-hydroxypyrrolidin-1-yl)-9H-benzo[e]imidazo[2,1-c] pyrrolo[1,2-a][1,4]diazepin-12-yl)benzonitrile, 134. Synthesized using General Procedure A, replacing 4-(7-bromo-9H-benzo[e]pyrrolo[1,2-a][1,2,4]triazolo[3,4-c][1,4]diazepin-12-yl)ben-zonitrile with 4-(7-bromo-9H-benzo[e]imidazo[2,1-c]pyrrolo[1,2-a][1,4]diazepin-12-yl)ben-zonitrile and replacing tertbutyl piperazine-1-carboxylate with (3S,4R)-4-(dimethylamino)pyrrolidin-3-ol. ¹H NMR (400 MHz, METHANOL-d₄) δ=8.02 (br. s., 1H), 7.82-7.67 (m, 6H), 7.59 (d, J=8.8 Hz, 1H), 7.31 (br. s., 1H), 6.88 (s, 1H), 6.82 (d, J=8.8 Hz, 1H), 5.32 (s, 2H), 4.70 (br. s., 1H), 3.95 (br. s., 2H), 3.73 (dd, J=3.1, 11.0 Hz, 1H), 3.63-3.51 (m, 2H), 3.03 (br. s., 6H). ESI [M+H]=451.1

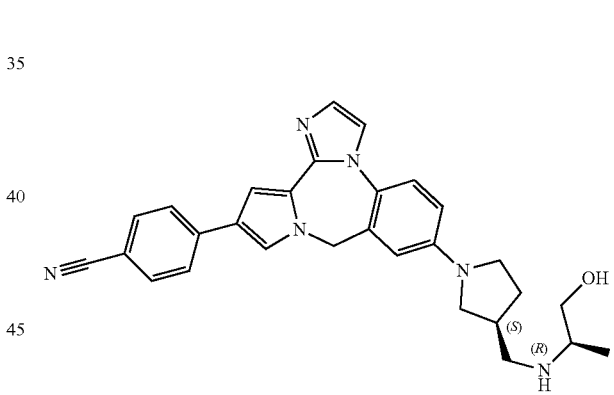

4-(7-((S)-3-((((R)-1-hydroxypropan-2-yl)amino)methyl)pyrrolidin-1-yl)-9H-benzo[e] imidazo[2,1-c]pyrrolo[1,2-a][1,4]diazepin-12-yl)benzonitrile, 135. Synthesized using General Procedure A, replacing 4-(7-bromo-9H-benzo[e]pyrrolo[1,2-a][1,2,4]triazolo[3,4-c][1,4] diazepin-12-yl)benzonitrile with 4-(7-bromo-9H-benzo[e]imidazo[2,1-c]pyrrolo[1,2-a][1,4]di-azepin-12-yl)benzonitrile and replacing tert-butyl piperazine-1-carboxylate with (R)-2-(((R)-pyrrolidin-3-ylmethyl)amino)propan-1-ol. ¹H NMR (400 MHz, METHANOL-d₄) δ=7.98 (d, J=2.0 Hz, 1H), 7.81-7.68 (m, 6H), 7.54 (d, J=9.0 Hz, 1H), 7.29 (d, J=1.6 Hz, 1H), 6.82 (d, J=2.3 Hz, 1H), 6.76 (dd, J=2.5, 9.0 Hz, 1H), 5.29 (s, 2H), 3.84 (dd, J=3.8, 12.0 Hz, 1H), 3.70-3.51 (m, 3H), 3.50-3.37 (m, 2H), 3.26-3.14 (m, 3H), 2.81-2.64 (m, 1H), 2.36 (s, 1H), 1.92 (dd, J=8.6, 12.3 Hz, 1H), 1.35 (d, J=6.8 Hz, 3H). ESI [M+H]=479.2

177

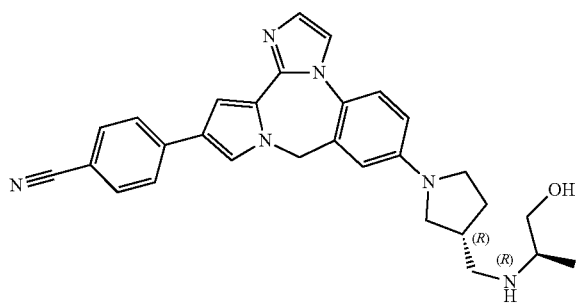

4-(7-((R)-3-((((R)-1-hydroxypropan-2-yl)amino)methyl) pyrrolidin-1-yl)-9H-benzo[e] imidazo[2,1-c]pyrrolo[1,2-a] [1,4]diazepin-12-yl)benzonitrile, 136. Synthesized using General Procedure A, replacing 4-(7-bromo-9H-benzo[e] pyrrolo[1,2-a][1,2,4]triazolo[3,4-c][1,4]di-azepin-12-yl) benzonitrile with 4-(7-bromo-9H-benzo[e]imidazo[2,1-c] pyrrolo[1,2-a][1,4]di-azepin-12-yl)benzonitrile and replacing tert-butyl piperazine-1-carboxylate with (R)-2-(((S)-pyrrolidin-3-ylmethyl)amino)propan-1-ol. $^1$H NMR (400 MHz, METHANOL-d$_4$) δ=7.96 (br. s., 1H), 7.77-7.65 (m, 6H), 7.52 (d, J=8.8 Hz, 1H), 7.27 (br. s., 1H), 6.84-6.71 (m, 2H), 5.27 (s, 2H), 3.83 (dd, J=4.0, 11.9 Hz, 1H), 3.69-3.50 (m, 3H), 3.47-3.36 (m, 2H), 3.23-3.14 (m, 3H), 2.79-2.69 (m, 1H), 2.36 (br. s., 1H), 1.99-1.84 (m, 1H), 1.33 (d, J=6.6 Hz, 3H). ESI [M+H]=479.2

178

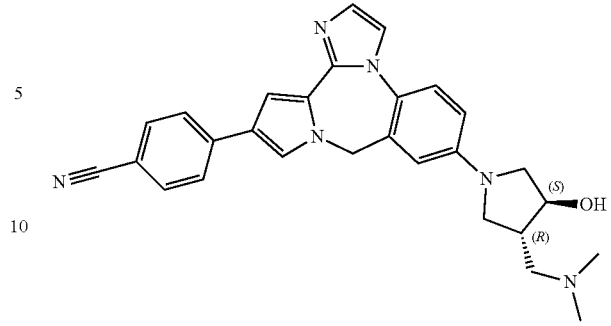

4-(7-((3R,4S)-3-((dimethylamino)methyl)-4-hydroxypyrrolidin-1-yl)-9H-benzo[e]imidazo[2,1-c]pyrrolo[1,2-a][1,4] diazepin-12-yl)benzonitrile, 138. Synthesized using General Procedure A, replacing 4-(7-bromo-9H-benzo[e]pyrrolo[1, 2-a][1,2,4]triazolo[3,4-c][1,4]di-azepin-12-yl)benzonitrile with 4-(7-bromo-9H-benzo[e]imidazo[2,1-c]pyrrolo[1,2-a] [1,4]di-azepin-12-yl)benzonitrile and replacing tert-butyl piperazine-1-carboxylate with (3S,4S)-4-((dimethylamino) methyl)pyrrolidin-3-ol. $^1$H NMR (400 MHz, METHANOL-d$_4$) δ=8.00 (br. s., 1H), 7.83-7.66 (m, 6H), 7.54 (d, J=8.8 Hz, 1H), 7.30 (br. s., 1H), 6.81 (d, J=2.4 Hz, 1H), 6.74 (dd, J=2.4, 8.8 Hz, 1H), 5.29 (s, 2H), 4.29 (q, J=6.6 Hz, 1H), 3.80-3.69 (m, 2H), 3.44-3.33 (m, 2H), 3.26-3.19 (m, 2H), 3.02-2.90 (m, 6H), 2.75-2.61 (m, 1H). ESI [M+H]=465.2

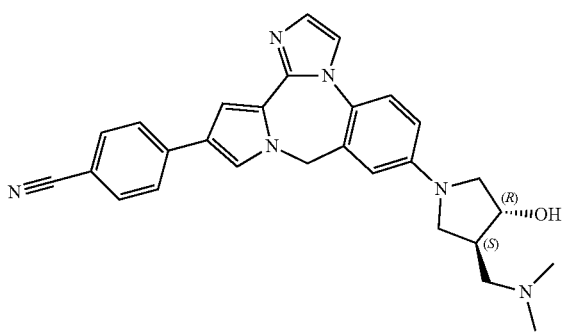

4-(7-((3S,4R)-3-((dimethylamino)methyl)-4-hydroxypyrrolidin-1-yl)-9H-benzo[e]imidazo[2,1-c]pyrrolo[1,2-a][1,4] diazepin-12-yl)benzonitrile, 137. Synthesized using General Procedure A, replacing 4-(7-bromo-9H-benzo[e]pyrrolo[1, 2-a][1,2,4]triazolo[3,4-c][1,4]di-azepin-12-yl)benzonitrile with 4-(7-bromo-9H-benzo[e]imidazo[2,1-c]pyrrolo[1,2-a] [1,4]di-azepin-12-yl)benzonitrile and replacing tert-butyl piperazine-1-carboxylate with (3R,4R)-4-((dimethylamino) methyl)pyrrolidin-3-ol. $^1$H NMR (400 MHz, METHANOL-d$_4$) δ=7.99 (br. s., 1H), 7.79-7.66 (m, 6H), 7.55 (d, J=9.0 Hz, 1H), 7.30 (br. s., 1H), 6.82 (d, J=2.3 Hz, 1H), 6.75 (dd, J=2.3, 8.6 Hz, 1H), 5.29 (s, 2H), 4.30 (q, J=6.7 Hz, 1H), 3.82-3.71 (m, 2H), 3.46-3.34 (m, 2H), 3.27-3.18 (m, 2H), 2.99 (s, 6H), 2.78-2.65 (m, 1H). ESI [M+H]=465.1

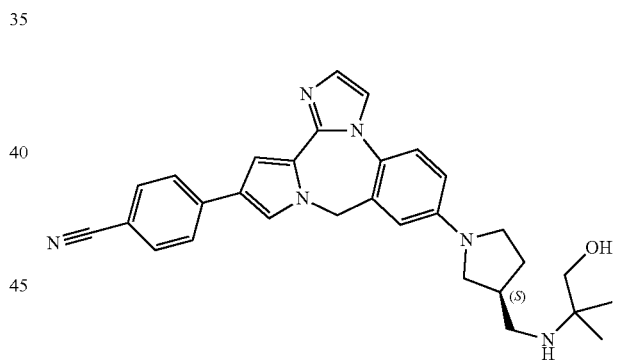

(S)-4-(7-(3-(((1-hydroxy-2-methylpropan-2-yl)amino) methyl)pyrrolidin-1-yl)-9H-benzo[e] imidazo[2,1-c]pyrrolo [1,2-a][1,4]diazepin-12-yl)benzonitrile, 141. Synthesized using General Procedure A, replacing 4-(7-bromo-9H-benzo [e]pyrrolo[1,2-a][1,2,4]triazolo[3,4-c][1,4]di-azepin-12-yl) benzonitrile with 4-(7-bromo-9H-benzo[e]imidazo[2,1-c] pyrrolo[1,2-a][1,4]di-azepin-12-yl)benzonitrile and replacing tert-butyl piperazine-1-carboxylate with (R)-2-methyl-2-((pyrrolidin-3-ylmethyl)amino)propan-1-ol. $^1$H NMR (400 MHz, METHANOL-d$_4$) δ=7.96 (br. s., 1H), 7.72 (dd, J=7.4, 19.1 Hz, 6H), 7.53 (d, J=8.8 Hz, 1H), 7.27 (br. s., 1H), 6.81 (br. s., 1H), 6.76 (d, J=9.0 Hz, 1H), 5.28 (s, 2H), 3.72-3.61 (m, 1H), 3.57 (s, 3H), 3.50-3.41 (m, 1H), 3.26-3.18 (m, 1H), 3.16-3.08 (m, 2H), 2.76-2.64 (m, 1H), 2.38 (d, J=6.6 Hz, 1H), 1.99-1.89 (m, 1H), 1.40-1.27 (m, 6H). ESI [M+H]=493.3

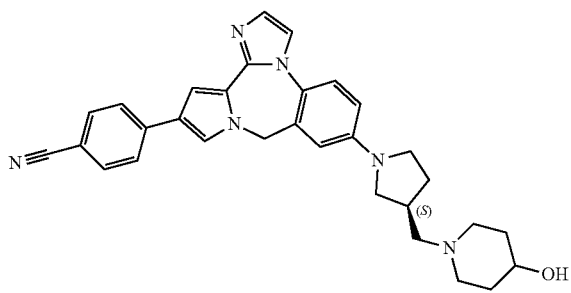

(S)-4-(7-(3-((4-hydroxypiperidin-1-yl)methyl)pyrrolidin-1-yl)-9H-benzo[e]imidazo[2,1-c]pyrrolo[1,2-a][1,4]diazepin-12-yl)benzonitrile, 142. Synthesized using General Procedure A, replacing 4-(7-bromo-9H-benzo[e]pyrrolo[1,2-a][1,2,4]triazolo[3,4-c][1,4]diazepin-12-yl)ben-zonitrile with 4-(7-bromo-9H-benzo[e]imidazo[2,1-c]pyrrolo[1,2-a][1,4]diazepin-12-yl)ben-zonitrile and replacing tert-butyl piperazine-1-carboxylate with (R)-1-(pyrrolidin-3-ylmethyl) piperidin-4-ol. $^1$H NMR (400 MHz, METHANOL-$d_4$) δ=8.02 (br. s., 1H), 7.83-7.66 (m, 6H), 7.54 (d, J=8.8 Hz, 1H), 7.31 (br. s., 1H), 6.82 (s, 1H), 6.76 (d, J=8.8 Hz, 1H), 5.30 (s, 2H), 4.11 (br. s., 1H), 3.84 (br. s., 1H), 3.69 (t, J=8.2 Hz, 2H), 3.61-3.37 (m, 4H), 3.18 (br. s., 1H), 3.09 (br. s., 1H), 2.89 (d, J=6.2 Hz, 1H), 2.36 (br. s., 1H), 2.21-1.99 (m, 2H), 1.99-1.67 (m, 4H). ESI [M+H]=505.3

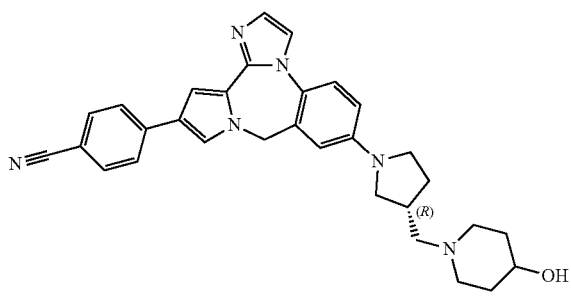

(R)-4-(7-(3-((4-hydroxypiperidin-1-yl)methyl)pyrrolidin-1-yl)-9H-benzo[e]imidazo[2,1-c]pyrrolo[1,2-a][1,4]diazepin-12-yl)benzonitrile, 143. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-9H-benzo[e]imidazo[2,1-c]pyrrolo[1,2-a][1,4]diazepin-12-yl)benzo-nitrile and replacing tert-butyl piperazine-1-carboxylate with (S)-1-(pyrrolidin-3-ylmethyl) piperidin-4-ol. $^1$H NMR (400 MHz, METHANOL-$d_4$) δ=8.01 (d, J=2.2 Hz, 1H), 7.78 (d, J=1.8 Hz, 1H), 7.76-7.67 (m, 5H), 7.53 (d, J=8.8 Hz, 1H), 7.30 (d, J=1.8 Hz, 1H), 6.81 (d, J=2.6 Hz, 1H), 6.75 (dd, J=2.6, 8.8 Hz, 1H), 5.29 (s, 2H), 4.10 (br. s., 1H), 3.73-3.62 (m, 2H), 3.58-3.49 (m, 1H), 3.48-3.38 (m, 2H), 3.32 (br. s., 3H), 3.22-3.01 (m, 2H), 2.94-2.79 (m, 1H), 2.35 (br. s., 1H), 2.15 (d, J=11.0 Hz, 1H), 2.03 (d, J=11.5 Hz, 1H), 1.97-1.84 (m, 2H), 1.77 (d, J=11.0 Hz, 1H). ESI [M+H]=505.2

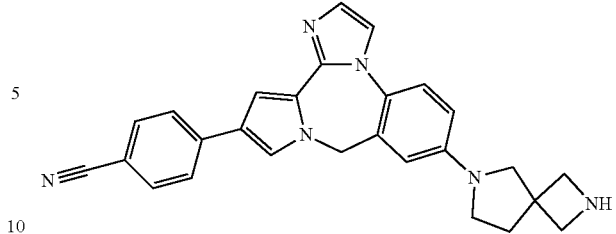

4-(7-(2,6-diazaspiro[3.4]octan-6-yl)-9H-benzo[e]imidazo[2,1-c]pyrrolo[1,2-a][1,4]diazepin-12-yl)benzonitrile, 146. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl) benzonitrile and replacing tert-butyl piperazine-1-carboxylate with tert-butyl 2,6-diazaspiro[3.4]octane-2-carboxylate. $^1$H NMR (400 MHz, METHANOL-$d_4$) δ=7.98 (br. s., 1H), 7.83-7.63 (m, 6H), 7.54 (d, J=8.8 Hz, 1H), 7.29 (br. s., 1H), 6.83 (d, J=2.6 Hz, 1H), 6.76 (dd, J=2.2, 8.8 Hz, 1H), 5.29 (s, 2H), 4.25-4.04 (m, 4H), 3.65 (s, 2H), 3.48 (t, J=6.8 Hz, 2H), 2.40 (t, J=7.1 Hz, 2H). ESI [M+H]=433.2

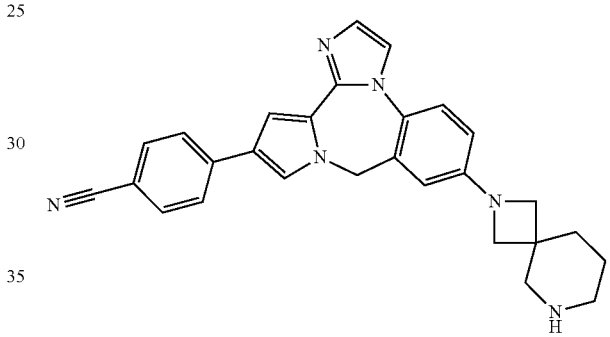

4-(7-(2,6-diazaspiro[3.5]nonan-2-yl)-9H-benzo[e]imidazo[2,1-c]pyrrolo[1,2-a][1,4]diazepin-12-yl)benzonitrile, 149. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl) benzonitrile and replacing tert-butyl piperazine-1-carboxylate with tert-butyl 2,6-diazaspiro[3.5]nonane-6-carboxylate. $^1$H NMR (400 MHz, METHANOL-$d_4$) δ=8.05 (br. s., 1H), 7.86-7.69 (m, 6H), 7.58 (d, J=8.8 Hz, 1H), 7.35 (br. s., 1H), 6.74 (s, 1H), 6.67 (d, J=8.8 Hz, 1H), 5.33 (s, 2H), 3.90 (d, J=7.8 Hz, 2H), 3.80 (d, J=7.5 Hz, 2H), 3.44 (s, 2H), 3.18 (br. s., 2H), 2.02 (d, J=5.3 Hz, 2H), 1.90 (br. s., 2H). ESI [M+H]=447.2

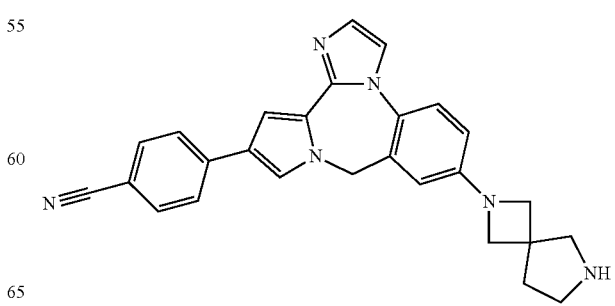

4-(7-(2,6-diazaspiro[3.4]octan-2-yl)-9H-benzo[e]imidazo[2,1-c]pyrrolo[1,2-a][1,4]diazepin-12-yl)benzonitrile, 152. Synthesized using General Procedure A, replacing 4-(7-bromo-9H-benzo[e]pyrrolo[1,2-a][1,2,4]triazolo[3,4-c][1,4]diazepin-12-yl)benzonitrile (S12) with 4-(7-bromo-9H-benzo[e]imidazo[2,1-c]pyrrolo[1,2-a][1,4]diazepin-12-yl)benzonitrile and replacing tert-butyl piperazine-1-carboxylate with tert-butyl 2,6-diazaspiro[3.4]octane-6-carboxylate. $^1$H NMR (400 MHz, METHANOL-$d_4$) δ=8.05 (s, 1H), 7.85-7.70 (m, 6H), 7.59 (d, J=8.8 Hz, 1H), 7.34 (s, 1H), 6.76 (s, 1H), 6.70 (d, J=8.5 Hz, 1H), 5.33 (s, 2H), 4.09-3.99 (m, 4H), 3.56 (s, 2H), 3.42 (t, J=7.3 Hz, 2H), 2.39 (t, J=7.3 Hz, 2H). ESI [M+H]=433.2

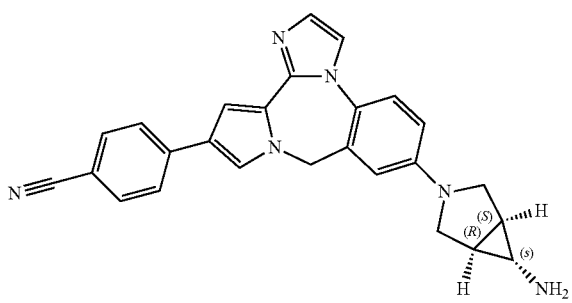

4-(7-((1R,5S,6S)-6-amino-3-azabicyclo[3.1.0]hexan-3-yl)-9H-benzo[e]imidazo[2,1-c]pyrrolo[1,2-a][1,4]diazepin-12-yl)benzonitrile, 153. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-9H-benzo[e]imidazo[2,1-c]pyrrolo[1,2-a][1,4]diazepin-12-yl)benzo-nitrile and replacing tert-butyl piperazine-1-carboxylate with tert-butyl (1R,5S,6S)-3-azabicyclo[3.1.0]hexan-6-ylcarbamate. $^1$H NMR (400 MHz, METHANOL-$d_4$) δ=8.02 (br. s., 1H), 7.86-7.65 (m, 6H), 7.55 (d, J=8.8 Hz, 1H), 7.32 (br. s., 1H), 6.87 (br. s., 1H), 6.80 (d, J=8.8 Hz, 1H), 5.31 (s, 2H), 3.78 (d, J=9.3 Hz, 2H), 3.44 (d, J=9.3 Hz, 2H), 2.53 (br. s., 1H), 2.21 (br. s., 2H). ESI [M+H]=419.2

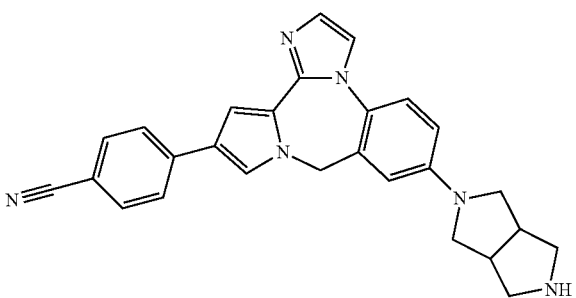 [SMILES: N#Cc1ccc(-c2cc3n(c2)Cc2cc(N4CC5CNCC5C4)ccc2-n2ccnc2-3)cc1]

4-(7-(hexahydropyrrolo[3,4-c]pyrrol-2(1H)-yl)-9H-benzo[e]imidazo[2,1-c]pyrrolo[1,2-a][1,4] diazepin-12-yl)benzonitrile, 154. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replacing tert-butyl piperazine-1-carboxylate with tert-butyl hexahydropyrrolo[3,4-c]pyrrole-2(1H)-carboxylate. $^1$H NMR (400 MHz, METHANOL-$d_4$) δ=8.02 (br. s., 1H), 7.83-7.68 (m, 6H), 7.58 (d, J=8.8 Hz, 1H), 7.31 (br. s., 1H), 6.96 (br. s., 1H), 6.89 (d, J=8.8 Hz, 1H), 5.32 (s, 2H), 3.64 (d, J=4.9 Hz, 2H), 3.53 (br. s., 4H), 3.29-3.20 (m, 4H). ESI [M+H]=433.1

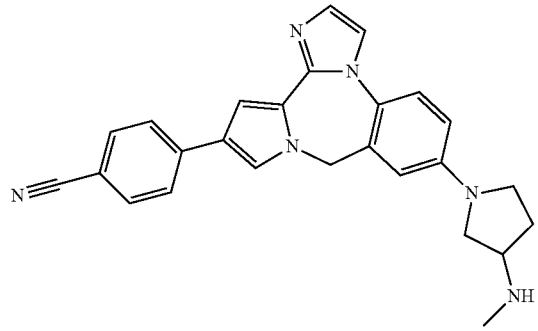 [SMILES: CNC1CCN(c2ccc3c(c2)Cn2cc(-c4ccc(C#N)cc4)cc2-c2nccn2-3)C1]

4-(7-(3-(methylamino)pyrrolidin-1-yl)-9H-benzo[e]imidazo[2,1-c]pyrrolo[1,2-a][1,4]di-azepin-12-yl)benzonitrile, 155. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo -9H-benzo[e]imidazo[2,1-c]pyrrolo[1,2-a][1,4]diazepin-12-yl)benzonitrile and replacing tert-butyl piperazine-1-carboxylate with tert-butyl methyl(pyrrolidin-3-yl)carbamate. $^1$H NMR (400 MHz, METHANOL-$d_4$) δ=8.04 (br. s., 1H), 7.85-7.65 (m, 6H), 7.60 (d, J=8.8 Hz, 1H), 7.33 (br. s., 1H), 6.92 (br. s., 1H), 6.85 (d, J=8.8 Hz, 1H), 5.34 (s, 2H), 4.01 (br. s., 1H), 3.80-3.71 (m, 1H), 3.65 (d, J=4.0 Hz, 2H), 3.54-3.43 (m, 1H), 2.81 (s, 3H), 2.64-2.49 (m, 1H), 2.37-2.24 (m, 1H). ESI [M+H]=421.1

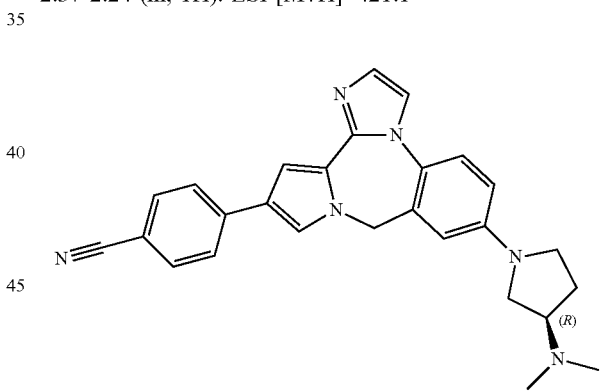

(R)-4-(7-(3-(dimethylamino)pyrrolidin-1-yl)-9H-benzo[e]imidazo[2,1-c]pyrrolo[1,2-a][1,4] diazepin-12-yl)benzonitrile, 156. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replac-ing tert-butyl piperazine-1-carboxylate with (R)—N,N-dimethylpyrrolidin-3-amine. $^1$H NMR (400 MHz, METHANOL-$d_4$) δ=8.01 (d, J=1.8 Hz, 1H), 7.81-7.69 (m, 6H), 7.61 (d, J=8.8 Hz, 1H), 7.31 (d, J=1.5 Hz, 1H), 6.94 (d, J=2.3 Hz, 1H), 6.88 (dd, J=2.5, 8.8 Hz, 1H), 5.34 (s, 2H), 4.16-4.06 (m, 1H), 3.86 (dd, J=7.7, 10.7 Hz, 1H), 3.78-3.70 (m, 1H), 3.66 (dd, J=6.4, 10.7 Hz, 1H), 3.54-3.44 (m, 1H), 3.02 (s, 6H), 2.71-2.59 (m, 1H), 2.35 (dd, J=8.2, 13.2 Hz, 1H). ESI [M+H]=435.2

183

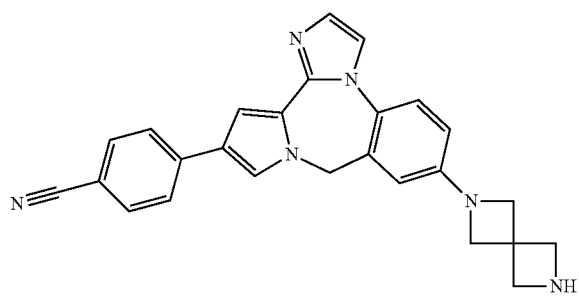 [SMILES: N#Cc1ccc(-c2cc3n(c2)Cc2cc(N4CC5(CNC5)C4)ccc2-n2ccnc2-3)cc1]

4-(7-(2,6-diazaspiro[3.3]heptan-2-yl)-9H-benzo[e]imidazo[2,1-c]pyrrolo[1,2-a][1,4]diazepin-12-yl)benzonitrile, 157. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replacing tert-butyl piperazine-1-carboxylate with tert-butyl 2,6-diazaspiro[3.3]heptane-2-carboxylate. $^1$H NMR (400 MHz, METHANOL-$d_4$) δ=8.03 (br. s., 1H), 7.84-7.65 (m, 6H), 7.55 (d, J=8.8 Hz, 1H), 7.32 (br. s., 1H), 6.73 (br. s., 1H), 6.65 (d, J=8.8 Hz, 1H), 5.30 (s, 2H), 4.33 (s, 4H), 4.18 (s, 4H). ESI [M+H]=419.2

184

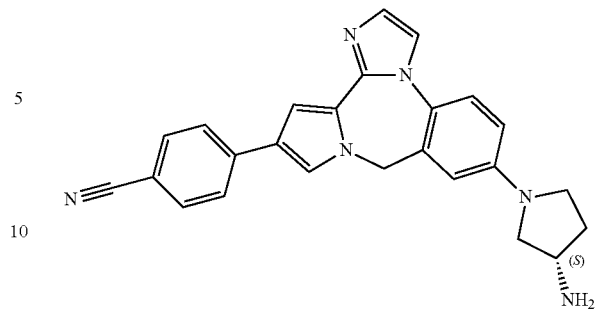

(S)-4-(7-(3-aminopyrrolidin-1-yl)-9H-benzo[e]imidazo[2,1-c]pyrrolo[1,2-a][1,4]diazepin-12-yl)benzonitrile, 159. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replacing tert-butyl piperazine-1-carboxylate with (S)-tert-butyl pyrrolidin-3-ylcarbamate. $^1$H NMR (400 MHz, METHANOL-$d_4$) δ=8.03 (d, J=2.0 Hz, 1H), 7.84-7.69 (m, 6H), 7.61 (d, J=9.0 Hz, 1H), 7.33 (d, J=1.5 Hz, 1H), 6.92 (d, J=2.5 Hz, 1H), 6.85 (dd, J=2.6, 8.9 Hz, 1H), 5.35 (s, 2H), 4.16-4.07 (m, 1H), 3.81-3.63 (m, 2H), 3.59-3.49 (m, 2H), 2.61-2.48 (m, 1H), 2.26 (dd, J=4.4, 8.7 Hz, 1H). ESI [M+H]=407.1

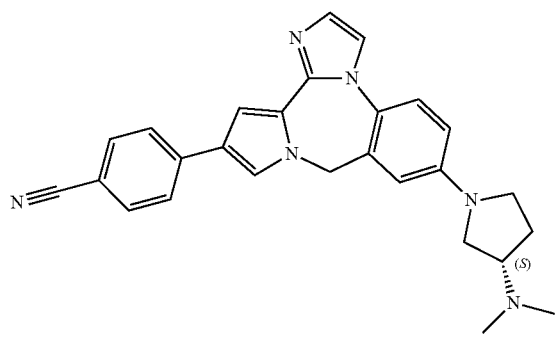

(S)-4-(7-(3-(dimethylamino)pyrrolidin-1-yl)-9H-benzo[e]imidazo[2,1-c]pyrrolo[1,2-a][1,4] diazepin-12-yl)benzonitrile, 158. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replac-ing tert-butyl piperazine-1-carboxylate with (S)—N,N-dimethylpyrrolidin-3-amine. $^1$H NMR (400 MHz, METHANOL-$d_4$) δ=8.01 (d, J=1.8 Hz, 1H), 7.81-7.69 (m, 6H), 7.61 (d, J=8.8 Hz, 1H), 7.31 (d, J=1.5 Hz, 1H), 6.94 (d, J=2.3 Hz, 1H), 6.88 (dd, J=2.5, 8.8 Hz, 1H), 5.34 (s, 2H), 4.16-4.06 (m, 1H), 3.86 (dd, J=7.7, 10.7 Hz, 1H), 3.78-3.70 (m, 1H), 3.66 (dd, J=6.4, 10.7 Hz, 1H), 3.54-3.44 (m, 1H), 3.02 (s, 6H), 2.71-2.59 (m, 1H), 2.35 (dd, J=8.2, 13.2 Hz, 1H). ESI [M+H]=435.2

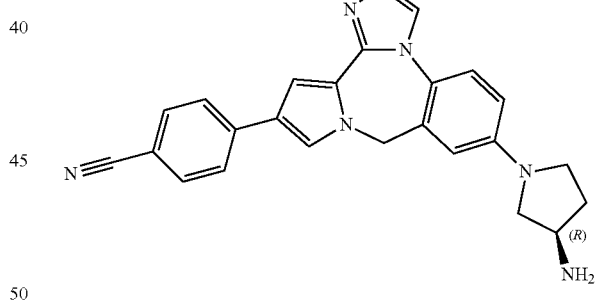

(R)-4-(7-(3-aminopyrrolidin-1-yl)-9H-benzo[e]imidazo[2,1-c]pyrrolo[1,2-a][1,4]diazepin-12-yl)benzonitrile, 161. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]imidazo[2,1-c]pyrrolo[1,2-a][1,4]diazepin-12-yl)benzonitrile and replacing tert-butyl piperazine-1-carboxylate with (R)-tert-butyl pyrrolidin-3-ylcarbamate. $^1$H NMR (400 MHz, METHANOL-$d_4$) δ=8.03 (d, J=2.0 Hz, 1H), 7.84-7.69 (m, 6H), 7.61 (d, J=9.0 Hz, 1H), 7.33 (d, J=1.5 Hz, 1H), 6.92 (d, J=2.5 Hz, 1H), 6.85 (dd, J=2.6, 8.9 Hz, 1H), 5.35 (s, 2H), 4.16-4.07 (m, 1H), 3.81-3.63 (m, 2H), 3.59-3.49 (m, 2H), 2.61-2.48 (m, 1H), 2.26 (dd, J=4.4, 8.7 Hz, 1H). ESI [M+H]=407.1

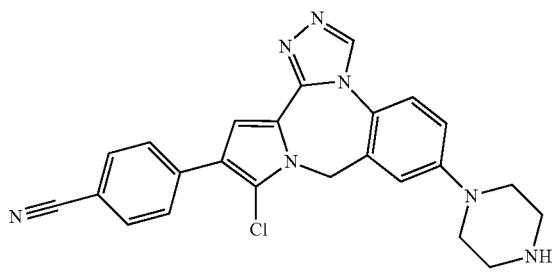 [SMILES: N#Cc1ccc(-c2cc3n(c2Cl)Cc2cc(N4CCNCC4)ccc2-n2cnnc2-3)cc1]

4-(11-chloro-7-(piperazin-1-yl)-9H-benzo[e]pyrrolo[1,2-a][1,2,4]triazolo[3,4-c][1,4]di-azepin-12-yl)benzonitrile, 164. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-11-chloro-9H-benzo[e]pyrrolo[1,2-a][1,2,4]triazolo[3,4-c][1,4]diazepin-12-yl)benzonitrile. $^1$H NMR (400 MHz, METHANOL-$d_4$) δ=9.09 (s, 1H), 7.84-7.71 (m, 4H), 7.63 (d, J=8.8 Hz, 1H), 7.34 (d, J=2.6 Hz, 1H), 7.21 (dd, J=2.9, 9.0 Hz, 1H), 7.15 (s, 1H), 5.31 (s, 2H), 3.61-3.52 (m, 4H), 3.46-3.37 (m, 4H). ESI [M+H]=442.1

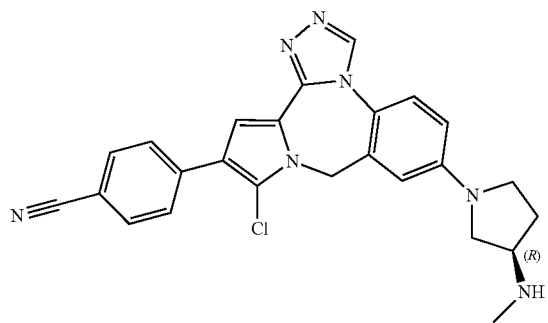

(R)-4-(11-chloro-7-(3-(methylamino)pyrrolidin-1-yl)-9H-benzo[e]pyrrolo[1,2-a][1,2,4]tri-azolo[3,4-c][1,4]diazepin-12-yl)benzonitrile, 166. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-11-chloro-9H-benzo[e]pyrrolo[1,2-a][1,2,4]triazolo[3,4-c][1,4]diazepin-12-yl)benzonitrile and replacing tert-butyl piperazine-1-carboxylate with (R)-tert-butyl methyl(pyrrolidin-3-yl)carbamate. $^1$H NMR (400 MHz, METHANOL-$d_4$) δ=9.06 (br. s., 1H), 7.87-7.79 (m, 2H), 7.78-7.72 (m, 2H), 7.56 (d, J=8.6 Hz, 1H), 7.14 (s, 1H), 6.92 (d, J=2.4 Hz, 1H), 6.82 (dd, J=2.4, 8.8 Hz, 1H), 5.28 (br. s., 2H), 4.00 (br. s., 1H), 3.79-3.58 (m, 3H), 3.52-3.41 (m, 1H), 2.86-2.74 (m, 3H), 2.55 (dt, J=6.7, 14.3 Hz, 1H), 2.34-2.19 (m, 1H). ESI [M+H]=456.1

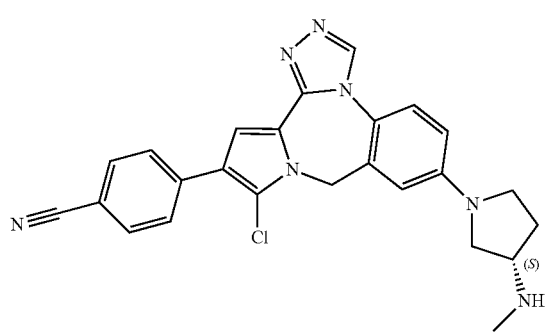

(S)-4-(11-chloro-7-(3-(methylamino)pyrrolidin-1-yl)-9H-benzo[e]pyrrolo[1,2-a][1,2,4]tri-azolo[3,4-c][1,4]diazepin-12-yl)benzonitrile, 167. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-11-chloro-9H-benzo[e]pyrrolo[1,2-a][1,2,4]triazolo[3,4-c][1,4]diazepin-12-yl)benzonitrile and replacing tert-butyl piperazine-1-carboxylate with (S)-tert-butyl methyl(pyrrolidin-3-yl)carbamate. $^1$H NMR (400 MHz, METHANOL-$d_4$) δ=9.04 (br. s., 1H), 7.84-7.76 (m, 2H), 7.75-7.68 (m, 2H), 7.54 (d, J=8.8 Hz, 1H), 7.12 (s, 1H), 6.90 (d, J=2.6 Hz, 1H), 6.80 (dd, J=2.6, 8.8 Hz, 1H), 5.26 (br. s., 2H), 4.04-3.93 (m, 1H), 3.76-3.55 (m, 3H), 3.45 (dt, J=5.7, 9.0 Hz, 1H), 2.85-2.73 (m, 3H), 2.61-2.46 (m, 1H), 2.27 (dt, J=5.4, 13.4 Hz, 1H). ESI [M+H]=456.1

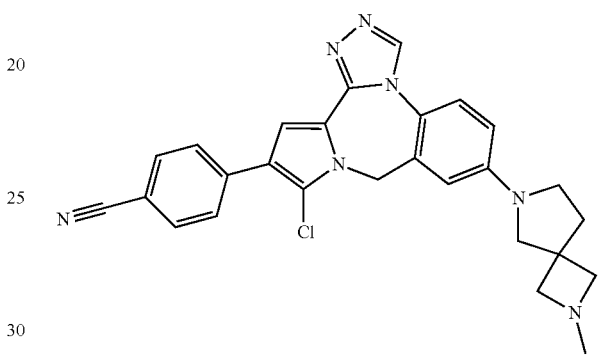

4-(11-chloro-7-(2-methyl-2,6-diazaspiro[3.4] octan-6-yl)-9H-benzo[e]pyrrolo[1,2-a][1,2,4]triazolo[3,4-c][1,4]di-azepin-12-yl)benzonitrile, 168. Synthesized using General Procedure C, replacing 4-(7-bromo-9H-benzo[e]pyrrolo[1,2-a][1,2,4]triazolo[3,4-c][1,4]di-azepin-12-yl)benzonitrile with 4-(7-bromo-11-chloro-9H-benzo[e]pyrrolo[1,2-a][1,2,4]triazolo[3,4-c][1,4]diazepin-12-yl)benzonitrile and replacing tert-butyl (azetidin-3-ylmethyl) (methyl)carbamate with tert-butyl 2,6-diazaspiro[3.4]octane-2-carboxylate. $^1$H NMR (400 MHz, METHANOL-$d_4$) δ=9.03 (s, 1H), 7.83-7.75 (m, 2H), 7.75-7.66 (m, 2H), 7.51 (d, J=8.8 Hz, 1H), 7.11 (s, 1H), 6.80 (d, J=3.5 Hz, 1H), 6.72 (t, J=6.6 Hz, 1H), 5.24 (br. s., 2H), 4.40-4.25 (m, 2H), 4.22-4.07 (m, 2H), 3.70-3.58 (m, 2H), 3.45 (td, J=6.7, 13.1 Hz, 2H), 2.98 (d, J=5.1 Hz, 3H), 2.44-2.33 (m, 2H). ESI [M+H]=482.1

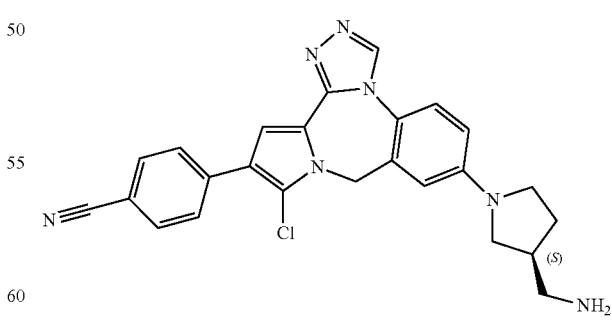

(S)-4-(7-(3-(aminomethyl)pyrrolidin-1-yl)-11-chloro-9H-benzo[e]pyrrolo[1,2-a][1,2,4]tri-azolo[3,4-c][1,4]diazepin-12-yl)benzonitrile, 169. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-11-chloro-9H-benzo[e]pyrrolo[1,2-a][1,2,4]triazolo[3,4-c][1,4]diazepin-12-yl)benzonitrile and replacing tert-butyl piperazine-1-carboxylate with (R)-tert-butyl (pyrrolidin-3-ylmethyl)carbamate. $^1$H NMR (400 MHz, METHANOL-d$_4$) δ=9.04 (br. s., 1H), 7.86-7.79 (m, 2H), 7.78-7.71 (m, 2H), 7.51 (d, J=8.8 Hz, 1H), 7.13 (s, 1H), 6.80 (d, J=2.2 Hz, 1H), 6.73 (dd, J=2.5, 8.7 Hz, 1H), 5.32-5.18 (m, 2H), 3.66-3.50 (m, 2H), 3.47-3.38 (m, 1H), 3.22-3.01 (m, 3H), 2.68 (td, J=7.4, 14.9 Hz, 1H), 2.32 (dt, J=6.9, 11.5 Hz, 1H), 1.88 (qd, J=8.3, 12.4 Hz, 1H). ESI [M+H]=456.1

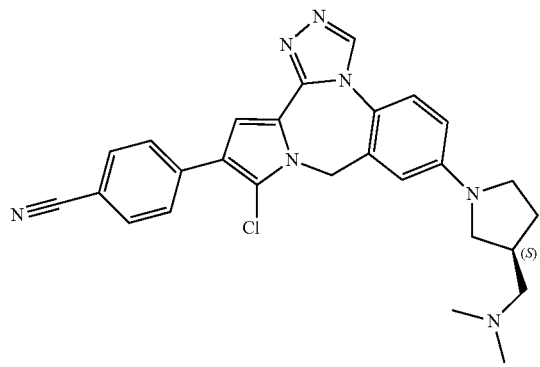

(S)-4-(11-chloro-7-(3-((dimethylamino)methyl)pyrrolidin-1-yl)-9H-benzo[e]pyrrolo[1,2-a][1,2,4]triazolo[3,4-c][1,4]diazepin-12-yl)benzonitrile, 170. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-11-chloro-9H-benzo[e]pyrrolo[1,2-a][1,2,4]triazolo[3,4-c][1,4]diazepin-12-yl)benzonitrile and replacing tert-butyl (azetidin-3-ylmethyl)(methyl) carbamate with (R)-tert-butyl (pyrrolidin-3-ylmethyl)carbamate. $^1$H NMR (400 MHz, METHANOL-d$_4$) δ=9.03 (s, 1H), 7.82-7.69 (m, 4H), 7.49 (d, J=8.8 Hz, 1H), 7.09 (s, 1H), 6.78 (d, J=2.4 Hz, 1H), 6.71 (dd, J=2.4, 8.8 Hz, 1H), 5.30-5.17 (m, 2H), 3.72-3.61 (m, 1H), 3.52 (dt, J=3.1, 8.8 Hz, 1H), 3.46-3.36 (m, 1H), 3.34 (s, 2H), 3.20-3.11 (m, 1H), 2.97 (s, 6H), 2.91-2.80 (m, 1H), 2.40-2.29 (m, 1H), 1.88 (qd, J=8.8, 12.3 Hz, 1H). ESI [M+H]=484.1

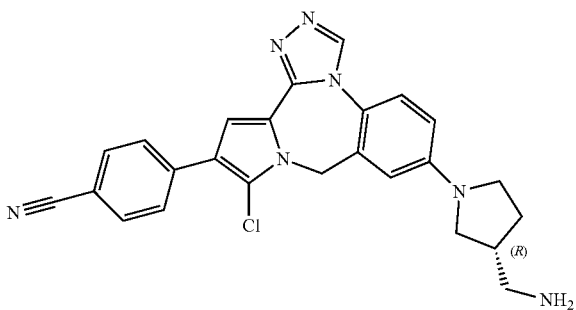

(R)-4-(7-(3-(aminomethyl)pyrrolidin-1-yl)-11-chloro-9H-benzo[e]pyrrolo[1,2-a][1,2,4]tri-azolo[3,4-c][1,4]diazepin-12-yl)benzonitrile, 171. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-11-chloro-9H-benzo[e]pyrrolo[1,2-a][1,2,4]triazolo[3,4-c][1,4]diazepin-12-yl)benzonitrile and replacing tert-butyl piperazine-1-carboxylate with (S)-tert-butyl (pyrrolidin-3-ylmethyl)carbamate. $^1$H NMR (400 MHz, METHANOL-d$_4$)δ=9.04 (br. s., 1H), 7.84-7.78 (m, 2H), 7.77-7.70 (m, 2H), 7.51 (d, J=8.8 Hz, 1H), 7.13 (s, 1H), 6.79 (d, J=2.2 Hz, 1H), 6.72 (dd, J=2.4, 8.8 Hz, 1H), 5.24 (br. s., 2H), 3.65-3.49 (m, 2H), 3.47-3.39 (m, 1H), 3.22-3.02 (m, 3H), 2.74-2.61 (m, 1H), 2.32 (dt, J=6.9, 11.5 Hz, 1H), 1.88 (qd, J=8.3, 12.5 Hz, 1H). ESI [M+H]=456.1

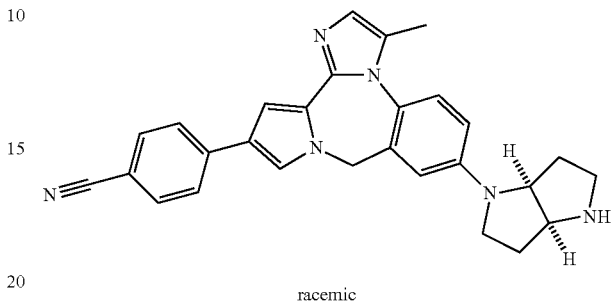

racemic 4-(7-(cis-hexahydropyrrolo[3,2-b]pyrrol-1(2H)-yl)-3-methyl-9H-benzo[e]imidazo[2,1-c] pyrrolo[1,2-a][1,4]diazepin-12-yl)benzonitrile, 184. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-3-methyl-9H-benzo[e]imidazo[2,1-c]pyrrolo[1,2-a][1,4]diazepin-12-yl) benzonitrile and replacing tert-butyl piperazine-1-carboxylate with cis-tert-butyl hexahydro-pyrrolo[3,2-b]pyrrole-1(2H)-carboxylate. $^1$H NMR (400 MHz, METHANOL-d$_4$) δ=7.78 (d, J=8.8 Hz, 1H), 7.76-7.67 (m, 4H), 7.56 (s, 1H), 7.52 (d, J=8.8 Hz, 1H), 7.26 (br. s., 1H), 6.99 (br. s., 1H), 6.86 (d, J=9.3 Hz, 1H), 5.33-5.21 (m, 2H), 4.66-4.48 (m, 2H), 3.72-3.56 (m, 2H), 3.44 (d, J=4.4 Hz, 1H), 3.25 (br. s., 1H), 2.51 (d, J=3.1 Hz, 3H), 2.47-2.34 (m, 2H), 2.17 (d, J=16.8 Hz, 2H). ESI [M+H]=447.2

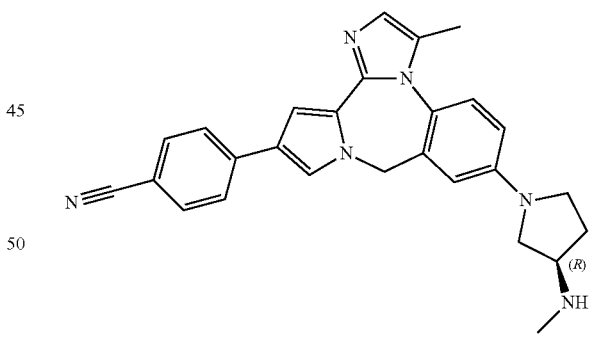

(R)-4-(3-methyl-7-(3-(methylamino)pyrrolidin-1-yl)-9H-benzo[e]imidazo[2,1-c]pyrrolo[1,2-a][1,4]diazepin-12-yl) benzonitrile, 186. Synthesized using General Procedure A, replacing 4-(7-bromo-9H-benzo[e]pyrrolo[1,2-a][1,2,4]tri-azolo[3,4-c][1,4]diazepin-12-yl)benzonitrile with 4-(7-bromo-3-methyl-9H-benzo[e]imidazo[2,1-c]pyrrolo[1,2-a][1,4]diazepin-12-yl)benzo-nitrile and replacing tert-butyl piperazine-1-carboxylate with (R)-tert-butyl methyl(pyrrolidin-3-yl)carbamate. $^1$H NMR (400 MHz, METHANOL-d$_4$) δ=7.81 (s, 1H), 7.74 (q, J=8.2 Hz, 4H), 7.59 (br. s., 1H), 7.53 (d, J=8.8 Hz, 1H), 7.29 (br. s., 1H), 6.97 (br. s., 1H), 6.84 (d, J=8.8 Hz, 1H), 5.28 (br. s., 2H), 4.03 (br. s., 1H), 3.82-3.60 (m, 3H), 3.51 (br. s., 1H), 2.83 (s, 3H), 2.63-2.48 (m, 4H), 2.32 (d, J=5.8 Hz, 1H). ESI [M+H]=435.2

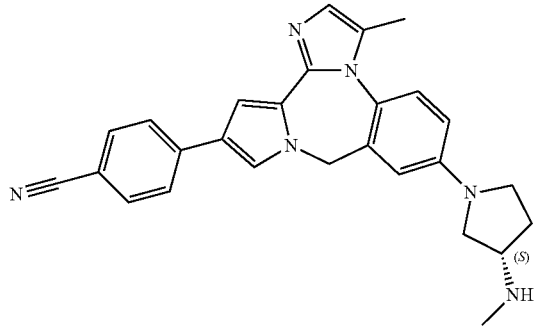

(S)-4-(3-methyl-7-(3-(methylamino)pyrrolidin-1-yl)-9H-benzo[e]imidazo[2,1-c]pyrrolo[1,2-a][1,4]diazepin-12-yl)benzonitrile, 187. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-methyl-9H-benzo[e]imidazo[2,1-c]pyrrolo[1,2-a][1,4]diazepin-12-yl)benzonitrile and replacing tert-butyl piperazine-1-carboxylate with (S)-tert-butyl methyl(pyrrolidin-3-yl)carbamate. $^1$H NMR (400 MHz, METHANOL-d$_4$) δ=7.81 (s, 1H), 7.74 (q, J=8.2 Hz, 4H), 7.59 (br. s., 1H), 7.53 (d, J=8.8 Hz, 1H), 7.29 (br. s., 1H), 6.97 (br. s., 1H), 6.84 (d, J=8.8 Hz, 1H), 5.28 (br. s., 2H), 4.03 (br. s., 1H), 3.82-3.60 (m, 3H), 3.51 (br. s., 1H), 2.83 (s, 3H), 2.63-2.48 (m, 4H), 2.32 (d, J=5.8 Hz, 1H). ESI [M+H]=435.2

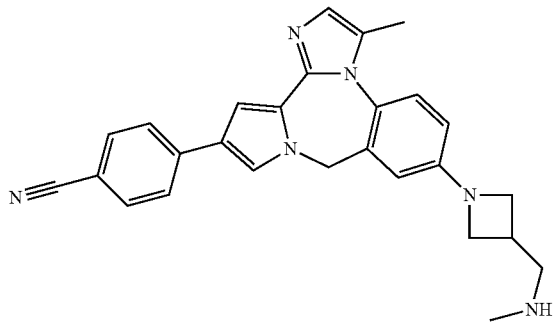 [SMILES: CNCC1CN(c2ccc3c(c2)Cn2cc(-c4ccc(C#N)cc4)cc2-c2ncc(C)n2-3)C1]

4-(3-methyl-7-(3-((methylamino)methyl)azetidin-1-yl)-9H-benzo[e]imidazo[2,1-c]pyrrolo[1,2-a][1,4]diazepin-12-yl)benzonitrile, 190. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 4-(7-bromo-3-methyl-9H-benzo[e]imidazo[2,1-c]pyrrolo[1,2-a][1,4]diazepin-12-yl) benzonitrile and replacing tert-butyl piperazine-1-carboxylate with tert-butyl (azetidin-3-ylmethyl)(methyl)carbamate. $^1$H NMR (400 MHz, METHANOL-d$_4$) δ=7.80 (d, J=1.3 Hz, 1H), 7.78-7.68 (m, 4H), 7.59 (s, 1H), 7.49 (d, J=8.8 Hz, 1H), 7.28 (d, J=1.3 Hz, 1H), 6.76 (d, J=2.3 Hz, 1H), 6.63 (dd, J=2.3, 8.8 Hz, 1H), 5.25 (d, J=4.8 Hz, 2H), 4.19 (dt, J=4.0, 7.8 Hz, 2H), 3.87-3.76 (m, 2H), 3.39 (d, J=7.3 Hz, 2H), 3.22-3.08 (m, 1H), 2.77 (s, 3H), 2.52 (s, 3H). ESI [M+H]=435.2

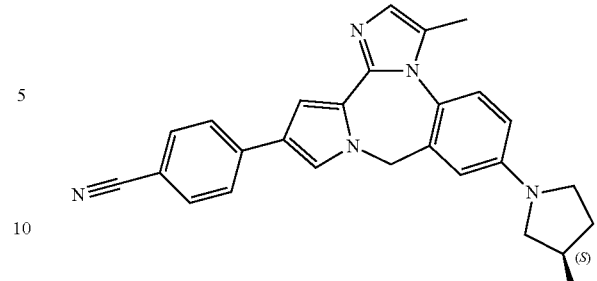

(S)-4-(7-(3-(aminomethyl)pyrrolidin-1-yl)-3-methyl-9H-benzo[e]imidazo[2,1-c]pyrrolo[1,2-a][1,4]diazepin-12-yl) benzonitrile, 196. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-methyl-9H-benzo[e]imidazo[2,1-c]pyrrolo[1,2-a][1,4]diazepin-12-yl)benzonitrile and replacing tert-butyl piperazine-1-carboxylate with (R)-tert-butyl (pyrrolidin-3-ylmethyl) carbamate. $^1$H NMR (400 MHz, METHANOL-d$_4$) δ=7.78 (s, 1H), 7.76-7.66 (m, 4H), 7.56 (s, 1H), 7.46 (d, J=8.8 Hz, 1H), 7.26 (s, 1H), 6.84 (br. s., 1H), 6.73 (d, J=8.8 Hz, 1H), 5.28-5.18 (m, 2H), 3.67-3.51 (m, 2H), 3.44 (d, J=7.9 Hz, 1H), 3.24-3.14 (m, 1H), 3.14-3.03 (m, 2H), 2.69 (td, J=7.1, 14.4 Hz, 1H), 2.50 (s, 3H), 2.33 (d, J=6.2 Hz, 1H), 1.95-1.82 (m, 1H). ESI [M+H]=435.2

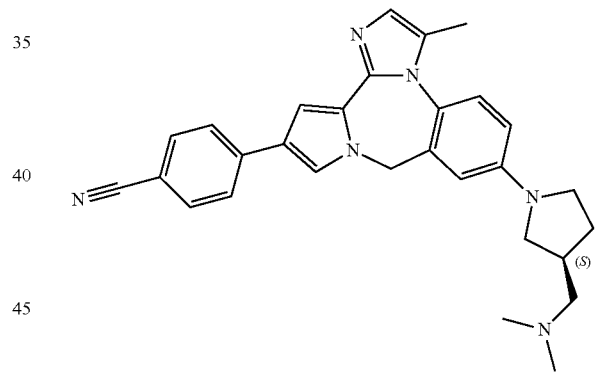

(S)-4-(7-(3-((dimethylamino)methyl)pyrrolidin-1-yl)-3-methyl-9H-benzo[e]imidazo[2,1-c] pyrrolo[1,2-a][1,4]diazepin-12-yl)benzonitrile, 197. Synthesized using General Procedure C, replacing 4-(7-bromo-9H-benzo[e]pyrrolo[1,2-a][1,2,4]triazolo[3,4-c][1,4]diazepin-12-yl)benzo-nitrile with 4-(7-bromo-3-methyl-9H-benzo[e]imidazo[2,1-c]pyrrolo[1,2-a][1,4]diazepin-12-yl) benzonitrile and replacing tert-butyl (azetidin-3-ylmethyl)(methyl)carbamate with (R)-tert-butyl (pyrrolidin-3-ylmethyl)carbamate. $^1$H NMR (400 MHz, METHANOL-d$_4$) δ=7.76 (s, 1H), 7.70 (q, J=8.4 Hz, 4H), 7.55 (s, 1H), 7.45 (d, J=8.8 Hz, 1H), 7.24 (s, 1H), 6.83 (d, J=2.6 Hz, 1H), 6.72 (dd, J=2.4, 9.0 Hz, 1H), 5.27-5.17 (m, 2H), 3.73-3.61 (m, 1H), 3.59-3.50 (m, 1H), 3.48-3.38 (m, 1H), 3.37-3.30 (m, 2H), 3.16 (dt, J=4.2, 8.5 Hz, 1H), 2.96 (s, 6H), 2.90-2.80 (m, 1H), 2.55-2.44 (m, 3H), 2.41-2.29 (m, 1H), 1.94-1.81 (m, 1H). ESI [M+H]=463.2

191

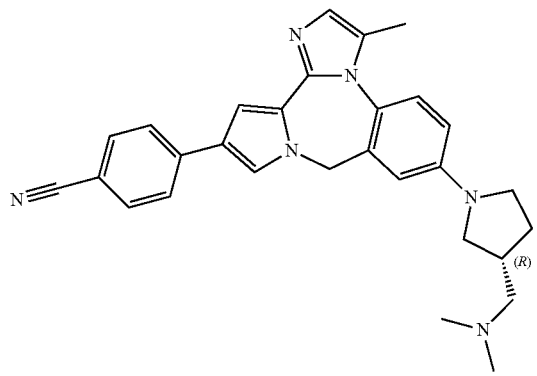

(R)-4-(7-(3-((dimethylamino)methyl)pyrrolidin-1-yl)-3-methyl-9H-benzo[e]imidazo[2,1-c] pyrrolo[1,2-a][1,4]diazepin-12-yl)benzonitrile, 198. Synthesized using General Procedure C, replacing 4-(7-bromo-9H-benzo[e]pyrrolo[1,2-a][1,2,4]triazolo[3,4-c][1,4]diazepin-12-yl)benzo-nitrile with 4-(7-bromo-3-methyl-9H-benzo[e]imidazo[2,1-c]pyrrolo[1,2-a][1,4]diazepin-12-yl) benzonitrile and replacing tert-butyl (azetidin-3-ylmethyl)(methyl)carbamate with (S)-tert-butyl (pyrrolidin-3-ylmethyl)carbamate. $^1$H NMR (400 MHz, METHANOL-d$_4$) δ=7.77 (s, 1H), 7.72 (q, J=7.9 Hz, 4H), 7.56 (s, 1H), 7.47 (d, J=8.8 Hz, 1H), 7.26 (s, 1H), 6.85 (br. s., 1H), 6.73 (d, J=8.8 Hz, 1H), 5.23 (s, 2H), 3.73-3.62 (m, 1H), 3.56 (br. s., 1H), 3.45 (d, J=8.4 Hz, 1H), 3.34 (br. s., 2H), 3.17 (br. s., 1H), 2.97 (s, 6H), 2.92-2.82 (m, 1H), 2.50 (s, 3H), 2.35 (br. s., 1H), 1.96-1.83 (m, 1H). ESI [M+H]=463.2

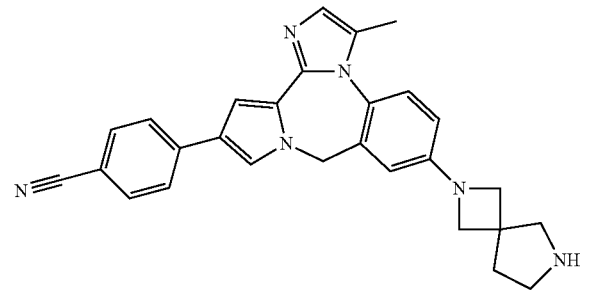 [SMILES: Cc1cnc2n1-c1ccc(N3CC4(CCNC4)C3)cc1Cn1cc(-c3ccc(C#N)cc3)cc1-2]

4-(3-methyl-7-(2,6-diazaspiro[3.4]octan-2-yl)-9H-benzo[e]imidazo[2,1-c]pyrrolo[1,2-a][1,4] diazepin-12-yl)benzonitrile, 203. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-methyl-9H-benzo[e]imidazo[2,1-c] pyrrolo-[1,2-a][1,4]diazepin-12-yl)benzonitrile, replacing tert-butyl piperazine-1-carboxylate with tert-butyl 2,6-diazaspiro[3.4]octane-6-carboxylate. 1H NMR (400 MHz, METHANOL-d4) δ=7.80 (s, 1H), 7.74 (q, J=8.4 Hz, 4H), 7.59 (s, 1H), 7.50 (d, J=8.8 Hz, 1H), 7.29 (s, 1H), 6.79 (d, J=2.5 Hz, 1H), 6.66 (dd, J=2.4, 8.7 Hz, 1H), 5.25 (d, J=2.8 Hz, 2H), 4.10-3.97 (m, 4H), 3.56 (s, 2H), 3.42 (t, J=7.3 Hz, 2H), 2.52 (s, 3H), 2.38 (t, J=7.3 Hz, 2H). ESI [M+H]=447.2

192

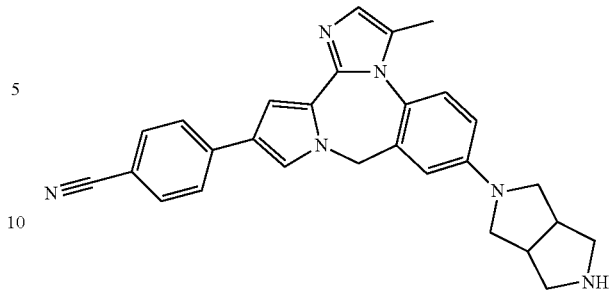

4-(7-(hexahydropyrrolo[3,4-c]pyrrol-2(1H)-yl)-3-methyl-9H-benzo[e]imidazo[2,1-c]pyrrolo[1,2-a][1,4]diazepin-12-yl)benzonitrile, 204. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-methyl-9H-benzo[e]imidazo[2,1-c]pyrrolo-[1,2-a][1,4]diazepin-12-yl) benzonitrile, replacing tert-butyl piperazine-1-carboxylate with tert-butyl hexahydropyrrolo[3,4-c]pyrrole-2(1H)-carboxylate. 1H NMR (400 MHz, METHANOL-d4) δ=7.76 (s, 1H), 7.72 (q, J=8.1 Hz, 4H), 7.54 (s, 1H), 7.49 (d, J=8.8 Hz, 1H), 7.25 (s, 1H), 6.98 (br. s., 1H), 6.86 (d, J=8.8 Hz, 1H), 5.24 (s, 2H), 3.64 (d, J=4.9 Hz, 2H), 3.52 (br. s., 4H), 3.29-3.21 (m, 4H), 2.50 (s, 3H). ESI [M+H]=447.2

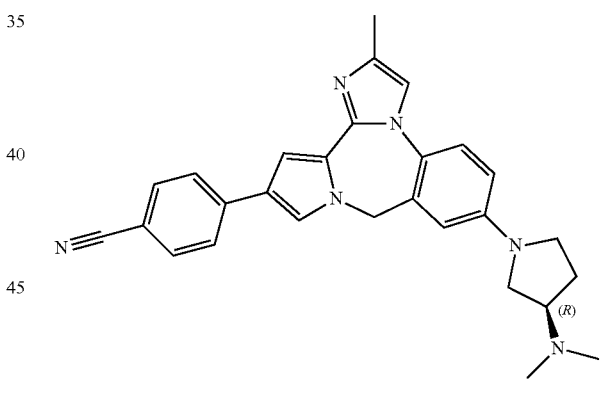

(R)-4-(7-(3-(dimethylamino)pyrrolidin-1-yl)-2-methyl-9H-benzo[e]imidazo[2,1-c]pyrrolo[1,2-a][1,4]diazepin-12-yl)benzonitrile, 218. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-2-methyl-9H-benzo[e]imidazo[2,1-c]pyrrolo[1,2-a][1,4]diazepin-12-yl) benzonitrile, replacing tert-butyl piperazine-1-carboxylate with (R)—N,N-dimethylpyrrolidin-3-amine. 1H NMR (400 MHz, METHANOL-d4) δ=7.81-7.68 (m, 6H), 7.57 (d, J=8.8 Hz, 1H), 7.29 (d, J=1.8 Hz, 1H), 6.92 (d, J=2.4 Hz, 1H), 6.85 (dd, J=2.5, 8.9 Hz, 1H), 5.32 (s, 2H), 4.10 (quin, J=7.2 Hz, 1H), 3.84 (dd, J=7.6, 10.7 Hz, 1H), 3.74-3.60 (m, 2H), 3.51-3.41 (m, 1H), 3.00 (s, 6H), 2.68-2.57 (m, 1H), 2.49 (s, 3H), 2.40-2.27 (m, 1H). ESI [M+H]=449.2

193

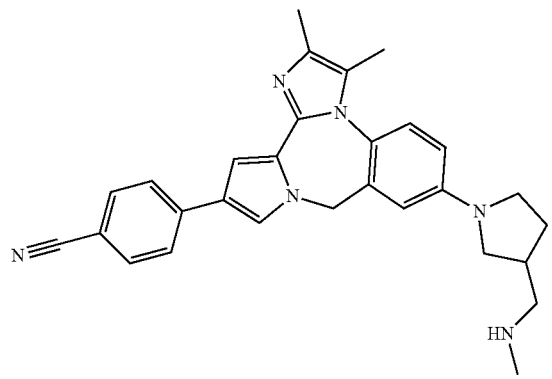 [SMILES: CNCC1CCN(c2ccc3c(c2)Cn2cc(-c4ccc(C#N)cc4)cc2-c2nc(C)c(C)n2-3)C1]

4-(2,3-dimethyl-7-(3-((methylamino)methyl)pyrrolidin-1-yl)-9H-benzo[e]imidazo[2,1-c] pyrrolo[1,2-a][1,4]diazepin-12-yl)benzonitrile, 220. Synthesized using General Procedure A, replacing 4-(7-bromo-9H-benzo[e]pyrrolo[1,2-a][1,2,4]triazolo[3,4-c]-[1,4]diazepin-12-yl) benzonitrile with 4-(7-bromo-2,3-dimethyl-9H-benzo[e]imidazo[2,1-c] pyrrolo[1,2-a][1,4] diazepin-12-yl)benzonitrile, replacing tert-butyl piperazine-1-carboxylate with tert-butyl methyl (pyrrolidin-3-ylmethyl)carbamate. 1H NMR (400 MHz, METHANOL-d4) δ=7.75-7.67 (m, 5H), 7.41 (d, J=8.8 Hz, 1H), 7.21 (d, J=1.3 Hz, 1H), 6.81 (d, J=2.6 Hz, 1H), 6.71 (dd, J=2.4, 9.0 Hz, 1H), 5.20 (s, 2H), 3.66-3.50 (m, 2H), 3.48-3.37 (m, 1H), 3.18-3.13 (m, 3H), 2.75 (s, 3H), 2.74-2.67 (m, 1H), 2.41 (d, J=7.1 Hz, 6H), 2.32 (dd, J=5.1, 11.2 Hz, 1H), 1.88 (dd, J=8.4, 12.3 Hz, 1H). ESI [M+H]=463.2

194

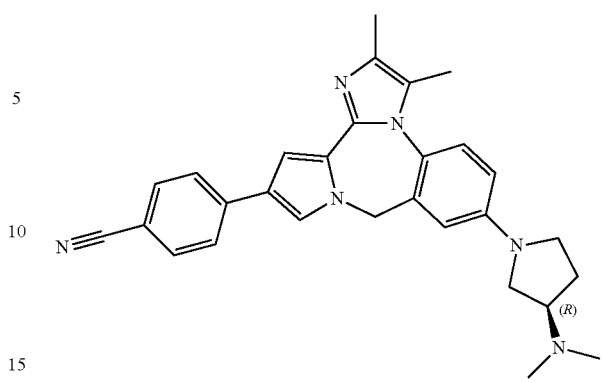

4-(7-((R)-3-(dimethylamino)pyrrolidin-1-yl)-2,3-dimethyl-9H-benzo[e]imidazo[2,1-c] pyrrolo[1,2-a][1,4]diazepin-12-yl)benzonitrile, 223. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-2,3-dimethyl-9H-benzo[e]imidazo[2,1-c] pyrrolo[1,2-a][1,4] diazepin-12-yl)benzonitrile, replacing tert-butyl piperazine-1-carboxylate with (R)—N,N-dimethylpyrrolidin-3-amine. 1H NMR (400 MHz, METHANOL-d4) δ=7.79-7.65 (m, 5H), 7.46 (d, J=8.8 Hz, 1H), 7.23 (s, 1H), 6.94 (br. s., 1H), 6.81 (d, J=8.4 Hz, 1H), 5.30-5.17 (m, 2H), 4.09 (t, J=6.8 Hz, 1H), 3.87-3.77 (m, 1H), 3.74-3.58 (m, 2H), 3.46 (d, J=6.6 Hz, 1H), 2.98 (s, 6H), 2.60 (br. s., 1H), 2.42 (d, J=6.2 Hz, 6H), 2.34 (dd, J=7.9, 13.2 Hz, 1H). ESI [M+H]=463.2

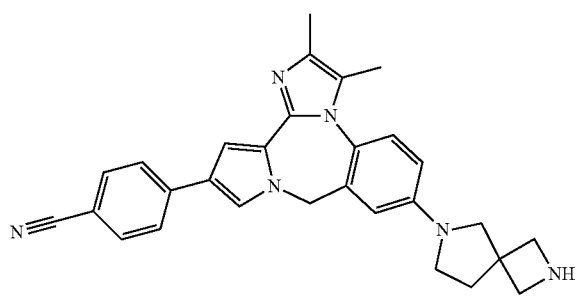 [SMILES: Cc1nc2n(c1C)-c1ccc(N3CCC4(CNC4)C3)cc1Cn1cc(-c3ccc(C#N)cc3)cc1-2]

4-(2,3-dimethyl-7-(2,6-diazaspiro[3.4]octan-6-yl)-9H-benzo[e]imidazo[2,1-c]pyrrolo[1,2-a] [1,4]diazepin-12-yl)benzonitrile, 222. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-2,3-dimethyl-9H-benzo[e]imidazo[2,1-c]pyrrolo[1,2-a][1,4]diazepin-12-yl) benzonitrile, replacing tert-butyl piperazine-1-carboxylate with tert-butyl 2,6-diazaspiro[3.4]octane-2-carboxylate. 1H NMR (400 MHz, METHANOL-d4) δ=7.76-7.66 (m, 5H), 7.41 (d, J=8.8 Hz, 1H), 7.21 (d, J=1.8 Hz, 1H), 6.83 (d, J=2.2 Hz, 1H), 6.71 (dd, J=2.6, 8.8 Hz, 1H), 5.26-5.15 (m, 2H), 4.20-4.03 (m, 4H), 3.66-3.60 (m, 2H), 3.46 (t, J=7.1 Hz, 2H), 2.45-2.35 (m, 8H). ESI [M+H]=461.2

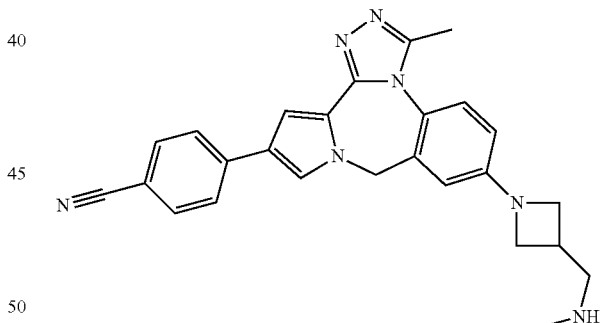

4-(3-methyl-7-(3-((methylamino)methyl)azetidin-1-yl)-9H-benzo[e]pyrrolo[1,2-a][1,2,4] triazolo[3,4-c][1,4]diazepin-12-yl)benzonitrile, 225. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-3-methyl-9H-benzo[e]pyrrolo[1,2-a][1,2,4]triazolo[3,4-c][1,4] diazepin-12-yl)benzonitrile, replacing tert-butyl piperazine-1-carboxylate with tert-butyl (azetidin-3-ylmethyl)(methyl) carbamate. 1H NMR (400 MHz, METHANOL-d4) δ=7.74-7.62 (m, 5H), 7.44 (d, J=8.8 Hz, 1H), 7.25 (d, J=17.6 Hz, 1H), 6.72 (br. s., 1H), 6.59 (d, J=8.4 Hz, 1H), 5.16 (br. s., 2H), 4.15 (d, J=3.1 Hz, 2H), 3.78 (d, J=4.9 Hz, 2H), 3.37 (d, J=7.1 Hz, 2H), 3.12 (d, J=5.7 Hz, 1H), 2.77-2.64 (m, 6H). ESI [M+H]=436.2

195

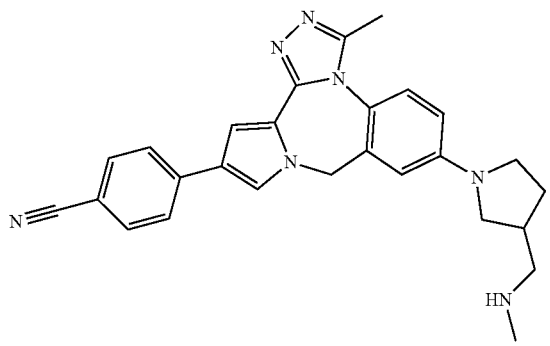 [SMILES: CNCC1CCN(c2ccc3c(c2)Cn2cc(-c4ccc(C#N)cc4)cc2-c2nnc(C)n2-3)C1]

4-(3-methyl-7-(3-((methylamino)methyl)pyrrolidin-1-yl)-9H-benzo[e]pyrrolo[1,2-a][1,2,4] triazolo[3,4-c][1,4]diazepin-12-yl)benzonitrile, 226. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-3-methyl-9H-benzo[e]pyrrolo[1,2-a][1,2,4]triazolo[3,4-c][1,4] diazepin-12-yl)benzonitrile, replacing tert-butyl piperazine-1-carboxylate with tert-butyl methyl (pyrrolidin-3-ylmethyl) carbamate. 1H NMR (400 MHz, METHANOL-d4) δ=7.72-7.68 (m, 2H), 7.64 (d, J=7.5 Hz, 3H), 7.41 (d, J=8.8 Hz, 1H), 7.19 (br. s., 1H), 6.81 (d, J=2.6 Hz, 1H), 6.68 (dd, J=2.4, 9.0 Hz, 1H), 5.12 (s, 2H), 3.64-3.48 (m, 2H), 3.41 (d, J=7.5 Hz, 1H), 3.21-3.10 (m, 3H), 2.77-2.70 (m, 4H), 2.67 (s, 3H), 2.31 (dd, J=4.4, 11.5 Hz, 1H), 1.93-1.82 (m, 1H). ESI [M+H]=450.2

196

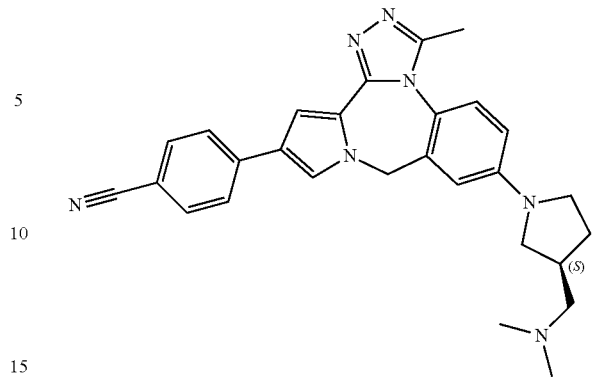

4-(7-((S)-3-((dimethylamino)methyl)pyrrolidin-1-yl)-3-methyl-9H-benzo[e]pyrrolo[1,2-a] [1,2,4]triazolo[3,4-c][1,4]diazepin-12-yl)benzonitrile, 228. Synthesized using General Procedure C, replacing 4-(7-bromo-9H-benzo[e]pyrrolo[1,2-a][1,2,4]triazolo[3,4-c][1,4] diazepin-12-yl) benzonitrile with 4-(7-bromo-3-methyl-9H-benzo[e]pyrrolo[1,2-a][1,2,4]triazolo[3,4-c][1,4]diazepin-12-yl) benzonitrile, replacing tert-butyl(azetidin-3-ylmethyl)(methyl) carbamate with (R)-tert-butyl(pyrrolidin-3-ylmethyl)carbamate. 1H NMR (400 MHz, METHANOL-d4) δ=7.74-7.61 (m, 5H), 7.41 (d, J=8.8 Hz, 1H), 7.17 (s, 1H), 6.83 (d, J=2.2 Hz, 1H), 6.70 (dd, J=2.6, 8.8 Hz, 1H), 5.12 (s, 2H), 3.70-3.61 (m, 1H), 3.54 (br. s., 1H), 3.49-3.39 (m, 1H), 3.33 (br. s., 2H), 3.20-3.12 (m, 1H), 2.97 (s, 6H), 2.91-2.80 (m, 1H), 2.66 (s, 3H), 2.34 (d, J=4.0 Hz, 1H), 1.94-1.83 (m, 1H). ESI [M+H]=464.2

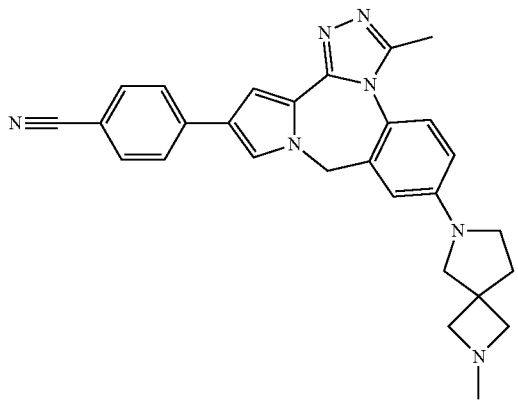 [SMILES: Cc1nnc2n1-c1ccc(N3CCC4(CN(C)C4)C3)cc1Cn1cc(-c3ccc(C#N)cc3)cc1-2]

4-(3-methyl-7-(2-methyl-2,6-diazaspiro[3.4]octan-6-yl)-9H-benzo[e]pyrrolo[1,2-a][1,2,4] triazolo[3,4-c][1,4]diazepin-12-yl)benzonitrile, 227. Synthesized using General Procedure C, replacing 4-(7-bromo-9H-benzo[e]pyrrolo[1,2-a][1,2,4]triazolo[3,4-c][1,4]diazepin-12-yl) benzonitrile with 4-(7-bromo-3-methyl-9H-benzo[e]pyrrolo[1,2-a][1,2,4]triazolo[3,4-c][1,4] diazepin-12-yl)benzonitrile, replacing tert-butyl (azetidin-3-ylmethyl)(methyl)carbamate with tert-butyl 2,6-diazaspiro[3.4] octane-2-carboxylate. 1H NMR (400 MHz, METHANOL-d4) δ=7.74-7.62 (m, 5H), 7.43 (d, J=8.8 Hz, 1H), 7.20 (s, 1H), 6.83 (br. s., 1H), 6.70 (d, J=6.2 Hz, 1H), 5.14 (s, 2H), 4.40-4.27 (m, 2H), 4.19-4.09 (m, 2H), 3.70-3.59 (m, 2H), 3.51-3.41 (m, 2H), 2.99 (d, J=4.4 Hz, 3H), 2.68 (s, 3H), 2.44-2.34 (m, 2H). ESI [M+H]=462.2

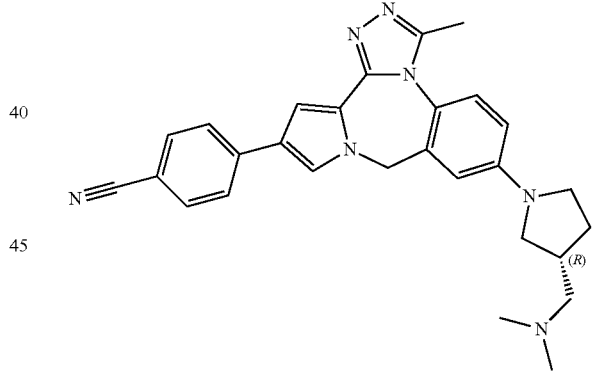

4-(7-((R)-3-((dimethylamino)methyl)pyrrolidin-1-yl)-3-methyl-9H-benzo[e]pyrrolo[1,2-a] [1,2,4]triazolo[3,4-c][1,4]diazepin-12-yl)benzonitrile, 229. Synthesized using General Procedure C, replacing 4-(7-bromo-9H-benzo[e]pyrrolo[1,2-a][1,2,4]triazolo[3,4-c][1,4] diazepin-12-yl) benzonitrile with 4-(7-bromo-3-methyl-9H-benzo[e]pyrrolo[1,2-a][1,2,4]triazolo[3,4-c][1,4]diazepin-12-yl) benzonitrile, replacing tert-butyl(azetidin-3-ylmethyl) (methyl) carbamate with (S)-tert-butyl(pyrrolidin-3-ylmethyl)carbamate. 1H NMR (400 MHz, METHANOL-d4) δ=7.73-7.65 (m, 5H), 7.44 (d, J=8.8 Hz, 1H), 7.26 (br. s., 1H), 6.84 (d, J=2.2 Hz, 1H), 6.71 (dd, J=2.2, 8.8 Hz, 1H), 5.17 (d, J=3.5 Hz, 2H), 3.71-3.62 (m, 1H), 3.54 (d, J=4.4 Hz, 1H), 3.48-3.39 (m, 1H), 3.20-3.11 (m, 1H), 3.01-2.92 (m, 8H), 2.91-2.81 (m, 1H), 2.72 (br. s., 3H), 2.40-2.31 (m, 1H), 1.94-1.83 (m, 1H). ESI [M+H]=464.2

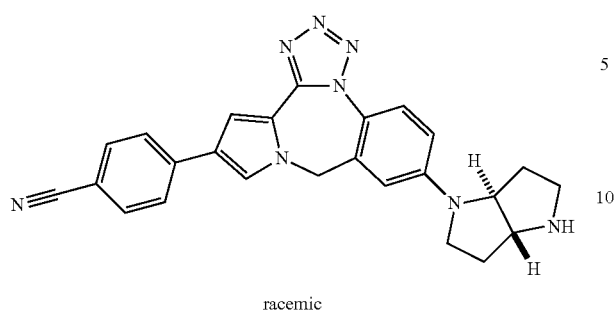

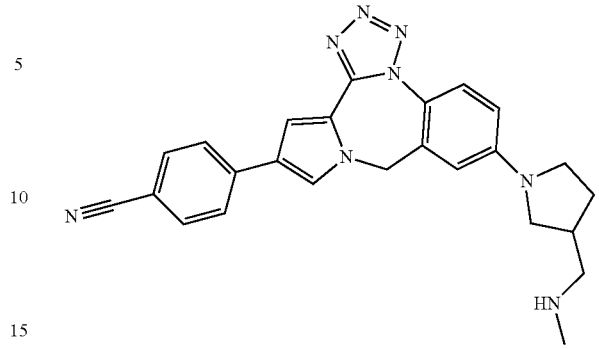

4-(7-(trans-hexahydropyrrolo[3,2-b]pyrrol-1(2H)-yl)-9H-benzo[e]pyrrolo[1,2-a]tetrazolo[5,1-c][1,4]diazepin-12-yl)benzonitrile, 232. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c][1,4]diazepin-12-yl)benzonitrile, replacing tert-butyl piperazine-1-carboxylate with trans-tert-butyl hexahydropyrrolo[3,2-b]pyrrole-1(2H)-carboxylate. 1H NMR (400 MHz, METHANOL-d4) δ=7.83 (d, J=8.8 Hz, 1H), 7.78-7.64 (m, 5H), 7.37 (d, J=1.8 Hz, 1H), 6.97-6.88 (m, 2H), 5.28 (s, 2H), 4.28 (d, J=7.5 Hz, 1H), 4.09-3.96 (m, 2H), 3.84 (d, J=9.7 Hz, 2H), 3.75-3.65 (m, 1H), 2.76 (d, J=5.3 Hz, 1H), 2.37-2.29 (m, 1H), 2.17 (d, J=11.0 Hz, 1H), 2.08-2.00 (m, 1H). ESI [M+H]=435.1

4-(7-(3-((methylamino)methyl)pyrrolidin-1-yl)-9H-benzo[e]pyrrolo[1,2-a]tetrazolo[5,1-c] [1,4]diazepin-12-yl) benzonitrile, 239. Synthesized using General Procedure A, replacing 4-(7-bromo-9H-benzo[e]pyrrolo[1,2-a][1,2,4]triazolo[3,4-c][1,4] diazepin-12-yl)benzonitrile with 4-(7-bromo-9H-benzo[e]pyrrolo[1,2-a]tetrazolo[5,1-c][1,4]diazepin-12-yl)benzonitrile, replacing tert-butyl piperazine-1-carboxylate with tert-butyl methyl(pyrrolidin-3-ylmethyl)carbamate. 1H NMR (400 MHz, METHANOL-d4) δ=7.75 (s, 3H), 7.70 (d, J=4.9 Hz, 3H), 7.36 (s, 1H), 6.84-6.74 (m, 2H), 5.24 (s, 2H), 3.64 (br. s., 1H), 3.60-3.51 (m, 1H), 3.46 (d, J=8.4 Hz, 1H), 3.24-3.14 (m, 3H), 2.78 (s, 3H), 2.75-2.65 (m, 1H), 2.35 (d, J=7.5 Hz, 1H), 1.91 (dd, J=8.4, 12.3 Hz, 1H). ESI [M+H]=437.2

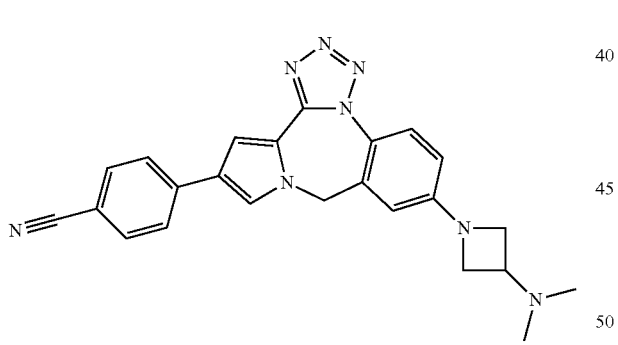

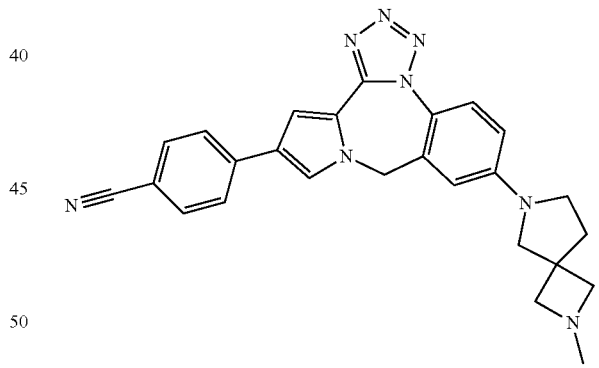

4-(7-(3-(dimethylamino)azetidin-1-yl)-9H-benzo[e]pyrrolo[1,2-a]tetrazolo[5,1-c][1,4] diazepin-12-yl)benzonitrile, 235. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c][1,4]diazepin-12-yl)benzonitrile, replacing tert-butyl piperazine-1-carboxylate with N,N-dimethylazetidin-3-amine. 1H NMR (400 MHz, METHANOL-d4) δ=7.85 (d, J=8.8 Hz, 1H), 7.78-7.73 (m, 2H), 7.73-7.66 (m, 3H), 7.38 (d, J=1.8 Hz, 1H), 6.81 (d, J=2.2 Hz, 1H), 6.76 (dd, J=2.4, 8.8 Hz, 1H), 5.27 (s, 2H), 4.40-4.24 (m, 3H), 4.16 (dd, J=4.0, 9.0 Hz, 2H), 2.98 (s, 6H). ESI [M+H]=423.1

4-(7-(2-methyl-2,6-diazaspiro[3.4]octan-6-yl)-9H-benzo[e]pyrrolo[1,2-a]tetrazolo[5,1-c] [1,4]diazepin-12-yl)benzonitrile, 240. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c][1,4]diazepin-12-yl)benzonitrile, replacing tert-butyl(azetidin-3-ylmethyl)(methyl)carbamate with tert-butyl 2,6-diazaspiro[3.4]octane-2-carboxylate. 1H NMR (400 MHz, METHANOL-d4) δ=7.81-7.72 (m, 3H), 7.71-7.65 (m, 3H), 7.35 (d, J=1.3 Hz, 1H), 6.83-6.74 (m, 2H), 5.24 (s, 2H), 4.31 (br. s., 1H), 4.18 (br. s., 1H), 3.77-3.60 (m, 4H), 3.48 (br. s., 2H), 3.00 (s, 3H), 2.41 (t, J=6.6 Hz, 2H). ESI [M+H]=449.2

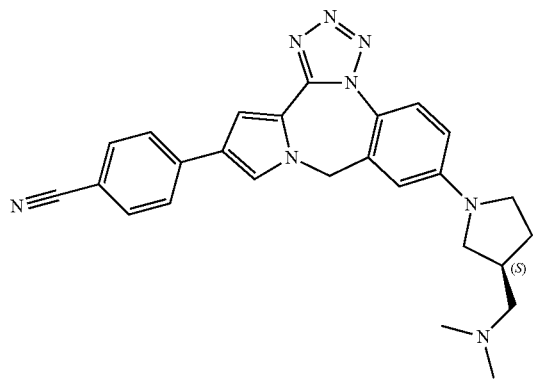

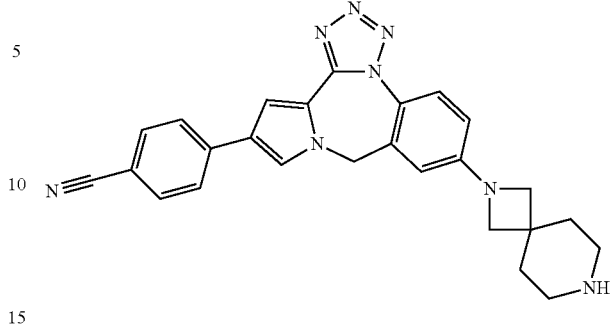

(S)-4-(7-(3-((dimethylamino)methyl)pyrrolidin-1-yl)-9H-benzo[e]pyrrolo[1,2-a]tetrazolo[5,1-c][1,4]diazepin-12-yl)benzonitrile, 241. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c][1,4]diazepin-12-yl)benzonitrile, replacing tert-butyl(azetidin-3-ylmethyl)(methyl)carbamate with (R)-tert-butyl(pyrrolidin-3-ylmethyl) carbamate. 1H NMR (400 MHz, METHANOL-d4) δ=7.83-7.71 (m, 3H), 7.71-7.64 (m, 3H), 7.35 (d, J=0.9 Hz, 1H), 6.83-6.73 (m, 2H), 5.23 (s, 2H), 3.68 (t, J=8.4 Hz, 1H), 3.56 (d, J=6.2 Hz, 1H), 3.46 (d, J=8.4 Hz, 1H), 3.34 (d, J=7.1 Hz, 2H), 3.18 (t, J=8.6 Hz, 1H), 2.98 (s, 6H), 2.88 (br. s., 1H), 2.36 (d, J=5.7 Hz, 1H), 1.90 (dd, J=8.8, 11.9 Hz, 1H). ESI [M+H]=451.2

4-(7-(2,7-diazaspiro[3.5]nonan-2-yl)-9H-benzo[e]pyrrolo[1,2-a]tetrazolo[5,1-c][1,4] diazepin-12-yl)benzonitrile, 245. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c][1,4] diazepin-12-yl) benzonitrile, replacing tert-butyl piperazine-1-carboxylate with tert-butyl 2,7-diazaspiro[3.5]nonane-7-carboxylate. 1H NMR (400 MHz, METHANOL-d4) δ=7.80-7.72 (m, 3H), 7.71-7.64 (m, 3H), 7.37-7.33 (m, 1H), 6.71-6.62 (m, 2H), 5.23 (s, 2H), 3.81 (s, 4H), 3.25-3.10 (m, 4H), 2.12-2.05 (m, 4H). ESI [M+H]=449.2

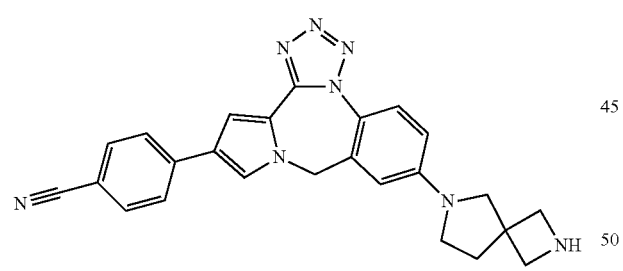

4-(7-(2,6-diazaspiro[3.4]octan-6-yl)-9H-benzo[e]pyrrolo[1,2-a]tetrazolo[5,1-c][1,4]diazepin-12-yl)benzonitrile, 244. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a]tetrazolo[5,1-c]-[1,4]diazepin-12-yl)benzonitrile, replacing tert-butyl piperazine-1-carboxylate with tert-butyl 2,6-diazaspiro[3.4]octane-2-carboxylate. 1H NMR (400 MHz, METHANOL-d4) δ=7.86-7.60 (m, 6H), 7.37 (br. s., 1H), 6.84-6.76 (m, 2H), 5.26 (s, 2H), 4.23-4.15 (m, 2H), 4.14-4.06 (m, 2H), 3.66 (br. s., 2H), 3.49 (d, J=7.1 Hz, 2H), 2.49-2.33 (m, 2H). ESI [M+H]=435.2

4-(7-(trans-hexahydropyrrolo[3,2-b]pyrrol-1(2H)-yl)-9H-benzo[e]pyrrolo[1,2-a][1,2,4] triazolo[5,1-c][1,4]diazepin-12-yl)benzonitrile, 249. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-9H-benzo[e]pyrrolo[1,2-a][1,2,4]triazolo[5,1-c][1,4]diazepin-12-yl) benzonitrile, replacing tert-butyl piperazine-1-carboxylate with trans-tert-butyl hexahydropyrrolo[3,2-b]pyrrole-1(2H)-carboxylate. 1H NMR (400 MHz, METHANOL-d4) δ=8.16 (s, 1H), 7.75-7.70 (m, 3H), 7.68-7.63 (m, 2H), 7.60 (d, J=1.5 Hz, 1H), 7.20 (d, J=1.3 Hz, 1H), 6.93-6.82 (m, 2H), 5.21 (s, 2H), 4.33-4.21 (m, 1H), 4.13-3.93 (m, 2H), 3.87-3.75 (m, 2H), 3.66 (dt, J=5.5, 11.0 Hz, 1H), 2.79-2.67 (m, 1H), 2.38-2.26 (m, 1H), 2.22-1.95 (m, 2H). ESI [M+H]=434.2

201

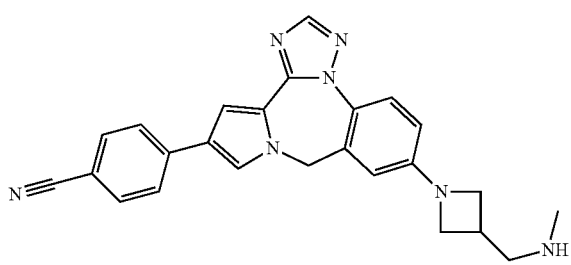 [SMILES: CNCC1CN(c2ccc3c(c2)Cn2cc(-c4ccc(C#N)cc4)cc2-c2ncnn2-3)C1]

4-(7-(3-((methylamino)methyl)azetidin-1-yl)-9H-benzo[e]pyrrolo[1,2-a][1,2,4]triazolo[5,1-c] [1,4]diazepin-12-yl)benzonitrile, 250. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile, replacing tert-butyl piperazine-1-carboxylate with tert-butyl (azetidin-3-ylmethyl)(methyl)carbamate. 1H NMR (400 MHz, METHANOL-d4) δ=8.14 (s, 1H), 7.76-7.55 (m, 6H), 7.19 (s, 1H), 6.69-6.53 (m, 2H), 5.21-5.11 (m, 2H), 4.12 (t, J=7.7 Hz, 2H), 3.75 (dd, J=5.3, 7.5 Hz, 2H), 3.36 (d, J=7.3 Hz, 2H), 3.15-3.01 (m, 1H), 2.79-2.66 (m, 3H). ESI [M+H]=422.2

202

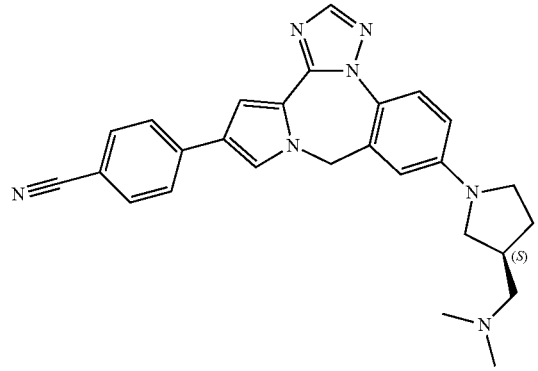

(S)-4-(7-(3-((dimethylamino)methyl)pyrrolidin-1-yl)-9H-benzo[e]pyrrolo[1,2-a][1,2,4] triazolo[5,1-c][1,4]diazepin-12-yl)benzonitrile, 254. Synthesized using General Procedure C, replacing 4-(7-bromo-9H-benzo[e]pyrrolo[1,2-a][1,2,4]triazolo[3,4-c][1,4]diazepin-12-yl) enzonitrile with 4-(7-bromo-9H-benzo[e]pyrrolo[1,2-a][1,2,4] triazolo[5,1-c][1,4]diazepin-12-yl)benzonitrile, replacing tert-butyl (azetidin-3-ylmethyl) (methyl)carbamate with (R)-tert-butyl (pyrrolidin-3-ylmethyl)carbamate. 1H NMR (400 MHz, METHANOL-d4) δ=8.20 (br. s., 1H), 7.78-7.57 (m, 6H), 7.24 (br. s., 1H), 6.80-6.68 (m, 2H), 5.18 (s, 2H), 3.65 (t, J=8.4 Hz, 1H), 3.59-3.51 (m, 1H), 3.49-3.39 (m, 1H), 3.34 (s, 2H), 3.16 (t, J=8.6 Hz, 1H), 2.98 (s, 6H), 2.91-2.78 (m, 1H), 2.41-2.28 (m, 1H), 1.95-1.81 (m, 1H). ESI [M+H]=450.2

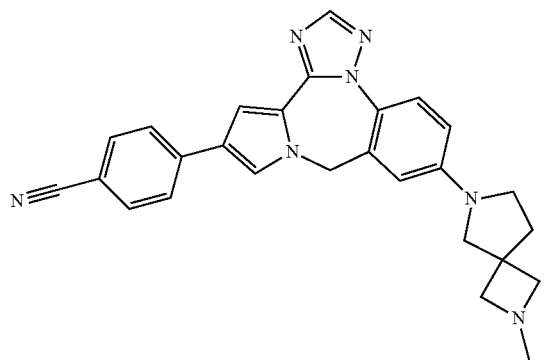 [SMILES: CN1CC2(CCN(c3ccc4c(c3)Cn3cc(-c5ccc(C#N)cc5)cc3-c3ncnn3-4)C2)C1]

4-(7-(2-methyl-2,6-diazaspiro[3.4]octan-6-yl)-9H-benzo[e]pyrrolo[1,2-a][1,2,4]triazolo[5,1-c][1,4]diazepin-12-yl)benzonitrile, 253. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile, replacing tert-butyl(azetidin-3-ylmethyl) (methyl)carbamate with tert-butyl 2,6-diazaspiro[3.4] octane-2-carboxylate. 1H NMR (400 MHz, METHANOL-d4) δ=8.16 (s, 1H), 7.81-7.58 (m, 6H), 7.20 (s, 1H), 6.80-6.69 (m, 2H), 5.19 (s, 2H), 4.42-4.25 (m, 2H), 4.22-4.06 (m, 2H), 3.64 (d, J=19.8 Hz, 2H), 3.52-3.41 (m, 2H), 3.06-2.94 (m, 3H), 2.47-2.33 (m, 2H). ESI [M+H]=448.2

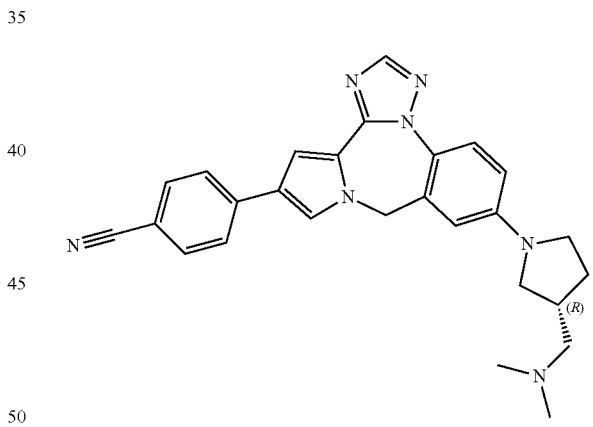

(R)-4-(7-(3-((dimethylamino)methyl)pyrrolidin-1-yl)-9H-benzo[e] pyrrolo[1,2-a][1,2,4] riazolo[5,1-c][1,4]diazepin-12-yl)benzonitrile, 255. Synthesized using General Procedure C, replacing 4-(7-bromo-9H-benzo[e]pyrrolo[1,2-a][1,2,4]triazolo[3,4-c][1,4]diazepin-12-yl) enzonitrile with 4-(7-bromo-9H-benzo[e]pyrrolo[1,2-a][1,2,4] triazolo [5,1-c][1,4]diazepin-12-yl) enzonitrile, replacing tert-butyl (azetidin-3-ylmethyl)(methyl)carbamate with (S)-tert-butyl (pyrrolidin-3-ylmethyl)carbamate. 1H NMR (400 MHz, METHANOL-d4) δ=8.22 (br. s., 1H), 7.84-7.47 (m, 6H), 7.24 (br. s., 1H), 6.83-6.55 (m, 2H), 5.14 (s, 2H), 3.69-3.59 (m, 1H), 3.58-3.47 (m, 1H), 3.46-3.36 (m, 2H), 3.20-3.10 (m, 1H), 3.09-3.02 (m, 1H), 3.00-2.76 (m, 6H), 2.73-2.61 (m, 1H), 2.46-2.26 (m, 1H), 1.96-1.78 (m, 1H). ESI [M+H]=450.2

203

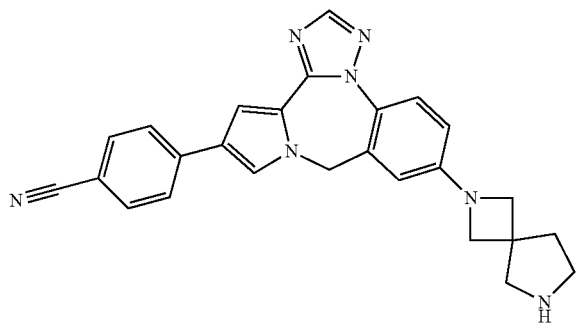 [SMILES: N#Cc1ccc(-c2cc3n(c2)Cc2cc(N4CC5(CCNC5)C4)ccc2-n2ncnc2-3)cc1]

4-(7-(2,6-diazaspiro[3.4]octan-2-yl)-9H-benzo[e]pyrrolo[1,2-a][1,2,4]triazolo[5,1-c][1,4] diazepin-12-yl)benzonitrile, 258. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile, replacing tert-butyl piperazine-1-carboxylate with tert-butyl 2,6-diazaspiro[3.4]octane-6-carboxylate. 1H NMR (400 MHz, METHANOL-d4) δ=8.15 (s, 1H), 7.75-7.62 (m, 5H), 7.59 (s, 1H), 7.19 (s, 1H), 6.69-6.60 (m, 2H), 5.17 (s, 2H), 4.01-3.92 (m, 4H), 3.51 (s, 2H), 3.37 (t, J=7.5 Hz, 2H), 2.34 (t, J=7.3 Hz, 2H). ESI [M+H]=434.1

204

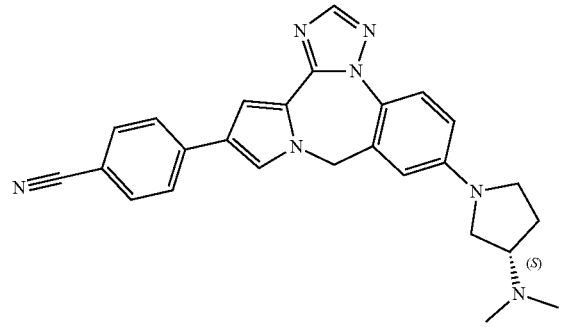

(S)-4-(7-(3-(dimethylamino)pyrrolidin-1-yl)-9H-benzo[e]pyrrolo[1,2-a][1,2,4]triazolo[5,1-c][1,4]diazepin-12-yl)benzonitrile, 260. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile, replacing tert-butyl(azetidin-3-ylmethyl) (methyl)carbamate with (S)-tert-butyl pyrrolidin-3-ylcarbamate. 1H NMR (400 MHz, METHANOL-d4) δ=8.17 (s, 1H), 7.75-7.63 (m, 5H), 7.60 (s, 1H), 7.20 (br. s., 1H), 6.92-6.77 (m, 2H), 5.20 (s, 2H), 4.07 (quin, J=7.1 Hz, 1H), 3.79 (dd, J=7.4, 10.7 Hz, 1H), 3.73-3.55 (m, 2H), 3.49-3.39 (m, 1H), 3.04-2.89 (m, 6H), 2.65-2.52 (m, 1H), 2.37-2.21 (m, 1H). ESI [M+H]=436.2

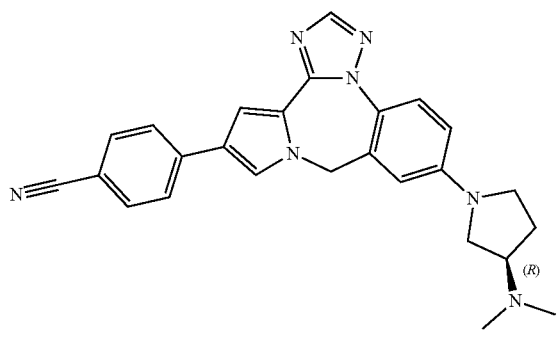

(R)-4-(7-(3-(dimethylamino)pyrrolidin-1-yl)-9H-benzo[e]pyrrolo[1,2-a][1,2,4]triazolo[5,1-c][1,4]diazepin-12-yl)benzonitrile, 259. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile, replacing tert-butyl(azetidin-3-ylmethyl) (methyl)carbamate with (R)-tert-butyl pyrrolidin-3-ylcarbamate. 1H NMR (400 MHz, METHANOL-d4) δ=8.18 (br. s., 1H), 7.79-7.56 (m, 6H), 7.22 (br. s., 1H), 6.88-6.79 (m, 2H), 5.21 (s, 2H), 4.09 (td, J=7.2, 13.9 Hz, 1H), 3.80 (dd, J=7.5, 10.6 Hz, 1H), 3.74-3.57 (m, 2H), 3.50-3.39 (m, 1H), 3.06-2.94 (m, 6H), 2.67-2.55 (m, 1H), 2.38-2.23 (m, 1H). ESI [M+H]=436.2

(S)-4-(7-(3-((methylamino)methyl)pyrrolidin-1-yl)-9H-benzo[e]pyrrolo[1,2-a][1,2,4]triazolo[5,1-c][1,4]diazepin-12-yl)benzonitrile, 262. Synthesized using General Procedure I, replacing 4-(7-bromo-11-chloro-9H-benzo[e]pyrrolo[1,2-a][1,2,4]triazolo[3,4-c][1,4]diazepin-12-yl)benzonitrile with 4-(7-bromo-9H-benzo[e]pyrrolo[1,2-a][1,2,4]triazolo[5,1-c][1,4]diazepin-12-yl)benzonitrile. 1H NMR (400 MHz, METHANOL-d4) δ=8.13 (s, 1H), 7.76-7.62 (m, 5H), 7.60 (d, J=1.3 Hz, 1H), 7.18 (d, J=1.8 Hz, 1H), 6.74-6.61 (m, 2H), 5.14 (s, 2H), 3.53 (t, J=8.4 Hz, 1H), 3.44 (dd, J=3.3, 8.6 Hz, 1H), 3.40-3.33 (m, 1H), 3.10-3.01 (m, 1H), 2.69 (d, J=7.1 Hz, 2H), 2.60-2.50 (m, 1H), 2.44 (s, 3H), 2.29-2.17 (m, 1H), 1.78 (dd, J=8.4, 12.3 Hz, 1H). ESI [M+H]=436.1

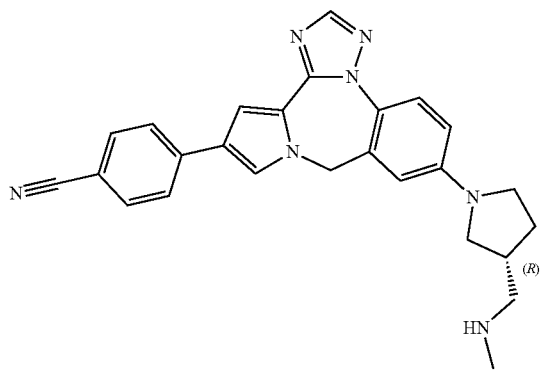

(R)-4-(7-(3-((methylamino)methyl)pyrrolidin-1-yl)-9H-benzo[e]pyrrolo[1,2-a][1,2,4]triazolo[5,1-c][1,4]diazepin-12-yl)benzonitrile, 263. Synthesized using General Procedure I, replacing 4-(7-bromo-11-chloro-9H-benzo[e]pyrrolo[1,2-a][1,2,4]triazolo[3,4-c][1,4]diazepin-12-yl) benzonitrile with 4-(7-bromo-9H-benzo[e]pyrrolo[1,2-a][1,2,4]triazolo[5,1-c][1,4]diazepin-12-yl)benzonitrile, replacing (R)-tert-butyl (pyrrolidin-3-ylmethyl)carbamate with (S)-tert-butyl (pyrrolidin-3-ylmethyl)carbamate. 1H NMR (400 MHz, METHANOL-d4) δ=8.13 (s, 1H), 7.76-7.57 (m, 6H), 7.18 (d, J=1.8 Hz, 1H), 6.73-6.64 (m, 2H), 5.14 (s, 2H), 3.53 (s, 1H), 3.45 (d, J=3.1 Hz, 1H), 3.35 (d, J=8.4 Hz, 1H), 3.06 (t, J=8.6 Hz, 1H), 2.70 (d, J=7.1 Hz, 2H), 2.61-2.50 (m, 1H), 2.45 (s, 3H), 2.23 (dd, J=3.7, 11.7 Hz, 1H), 1.78 (dd, J=8.4, 12.3 Hz, 1H). ESI [M+H]=436.2

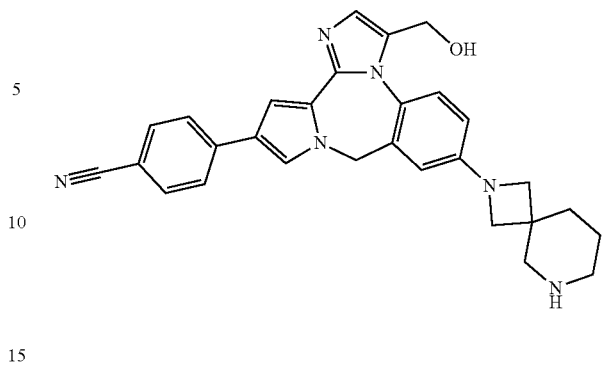

4-(3-(hydroxymethyl)-7-(2,6-diazaspiro[3.5]nonan-2-yl)-9H-benzo[e]imidazo[2,1-c]pyrrolo[1,2-a][1,4]diazepin-12-yl)benzonitrile, 273. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-3-(hydroxymethyl)-9H-benzo[e]imidazo[2,1-c]pyrrolo[1,2-a][1,4] diazepin-12-yl)benzonitrile, replacing tert-butyl piperazine-1-carboxylate with tert-butyl 2,6-diazaspiro[3.5]nonane-6-carboxylate. 1H NMR (400 MHz, METHANOL-d4) δ=7.77 (d, J=7.9 Hz, 3H), 7.75-7.71 (m, 2H), 7.70-7.66 (m, 2H), 7.28 (d, J=0.9 Hz, 1H), 6.72 (d, J=2.6 Hz, 1H), 6.60 (dd, J=2.2, 8.8 Hz, 1H), 5.26-5.17 (m, 2H), 4.79 (s, 1H), 4.62 (d, J=14.1 Hz, 1H), 3.86 (dd, J=3.1, 7.5 Hz, 2H), 3.76 (dd, J=4.4, 7.5 Hz, 2H), 3.39 (s, 2H), 3.13 (t, J=5.3 Hz, 2H), 1.97 (d, J=5.7 Hz, 2H), 1.85 (br. s., 2H). ESI [M+H]=477.2

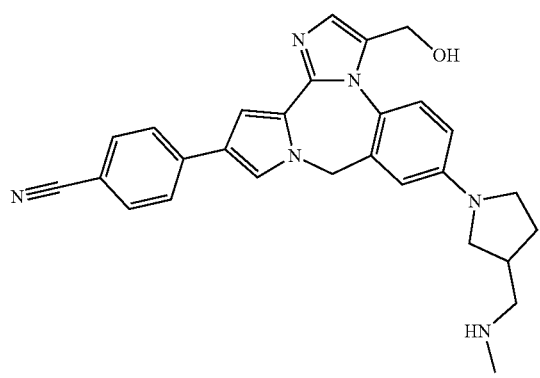 [SMILES: CNCC1CCN(c2ccc3c(c2)Cn2cc(-c4ccc(C#N)cc4)cc2-c2ncc(CO)n2-3)C1]

4-(3-(hydroxymethyl)-7-(3-((methylamino)methyl)pyrrolidin-1-yl)-9H-benzo[e]imidazo[2,1-c]pyrrolo[1,2-a][1,4]diazepin-12-yl)benzonitrile, 272. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-3-(hydroxymethyl)-9H-benzo[e]imidazo[2,1-c]pyrrolo[1,2-a][1,4] diazepin-12-yl)benzonitrile and replacing tert-butyl piperazine-1-carboxylate with tert-butyl methyl(pyrrolidin-3-ylmethyl)carbamate. 1H NMR (400 MHz, METHANOL-d4) δ=7.78 (br. s., 1H), 7.74 (d, J=8.8 Hz, 4H), 7.71-7.67 (m, 2H), 7.28 (s, 1H), 6.84 (br. s., 1H), 6.72 (d, J=8.8 Hz, 1H), 5.28-5.17 (m, 2H), 4.80 (br. s., 1H), 4.65 (d, J=14.1 Hz, 1H), 3.62 (br. s., 1H), 3.55 (br. s., 1H), 3.44 (q, J=7.9 Hz, 1H), 3.25-3.09 (m, 3H), 2.83-2.68 (m, 4H), 2.34 (d, J=6.2 Hz, 1H), 1.97-1.85 (m, 1H). ESI [M+H]=465.2

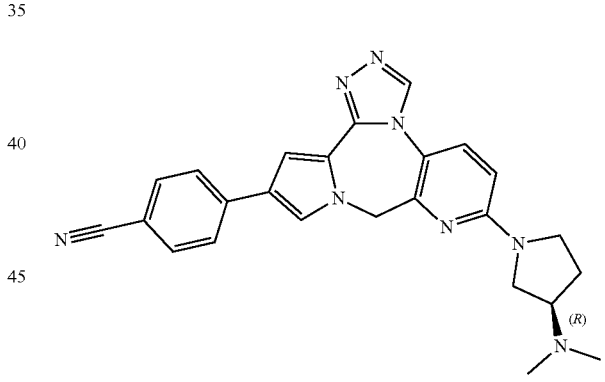

(R)-4-(7-(3-(dimethylamino)pyrrolidin-1-yl)-9H-pyrido[3,2-e]pyrrolo[1,2-a][1,2,4]triazolo[3,4-c][1,4]diazepin-12-yl)benzonitrile, 291. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-pyrido[3,2-e]pyrrolo[1,2-a][1,2,4]triazolo[3,4-c][1,4]diazepin-12-yl) benzonitrile, replacing tert-butyl piperazine-1-carboxylate with (R)—N,N-dimethyl pyrrolidin-3-amine. 1H NMR (400 MHz, METHANOL-d4) δ=9.06 (s, 1H), 7.89 (d, J=8.8 Hz, 1H), 7.76-7.70 (m, 2H), 7.68-7.66 (m, 3H), 7.27 (d, J=1.3 Hz, 1H), 6.71 (d, J=9.0 Hz, 1H), 5.25 (s, 2H), 4.13-4.03 (m, 2H), 3.89-3.80 (m, 1H), 3.79-3.70 (m, 1H), 3.62-3.52 (m, 1H), 3.01 (s, 6H), 2.68-2.57 (m, 1H), 2.38-2.26 (m, 1H). ESI [M+H]=437.2

207

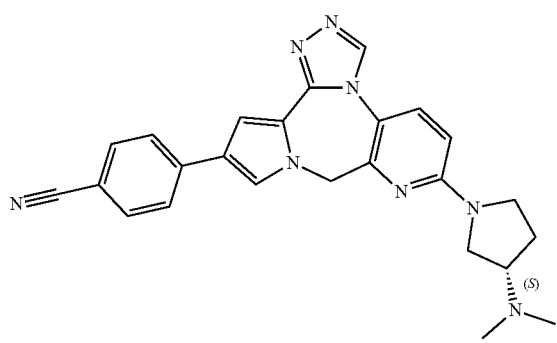

(S)-4-(7-(3-(dimethylamino)pyrrolidin-1-yl)-9H-pyrido[3,2-e]pyrrolo[1,2-a][1,2,4]triazolo[3,4-c][1,4]diazepin-12-yl)benzonitrile, 292. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-9H-pyrido[3,2-e]pyrrolo[1,2-a][1,2,4]triazolo[3,4-c][1,4]diazepin-12-yl)benzonitrile, replacing tert-butyl piperazine-1-carboxylate with (S)—N,N-dimethyl pyrrolidin-3-amine. 1H NMR (400 MHz, METHANOL-d4) δ=9.07 (s, 1H), 7.91 (d, J=9.0 Hz, 1H), 7.78-7.72 (m, 2H), 7.71-7.65 (m, 3H), 7.28 (d, J=1.5 Hz, 1H), 6.73 (d, J=8.8 Hz, 1H), 5.27 (s, 2H), 4.16-4.01 (m, 2H), 3.85 (t, J=8.0 Hz, 1H), 3.75-3.74 (m, 1H), 3.63-3.53 (m, 1H), 3.01 (s, 6H), 2.66-2.62 (m, 1H), 2.37-2.27 (m, 1H). ESI [M+H]=437.2

208

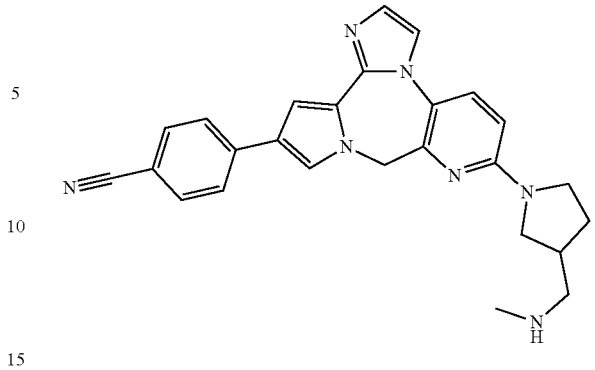

4-(7-(3-((methylamino)methyl)pyrrolidin-1-yl)-9H-imidazo[2,1-c]pyrido[3,2-e]pyrrolo[1,2-a][1,4]diazepin-12-yl)benzonitrile, 296. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with tert-butyl methyl(pyrrolidin-3-ylmethyl)carbamate. 1H NMR (400 MHz, METHANOL-d4) δ=7.95 (br. s., 1H), 7.84 (d, J=8.8 Hz, 1H), 7.80-7.67 (m, 6H), 7.31 (br. s., 1H), 6.66 (d, J=9.3 Hz, 1H), 5.29 (s, 2H), 3.91-3.82 (m, 1H), 3.73 (br. s., 1H), 3.60-3.50 (m, 1H), 3.42-3.33 (m, 1H), 3.17 (dd, J=2.9, 7.3 Hz, 2H), 2.77 (s, 3H), 2.75-2.67 (m, 1H), 2.33 (dd, J=4.6, 11.2 Hz, 1H), 1.97-1.82 (m, 1H). ESI [M+H]=436.2

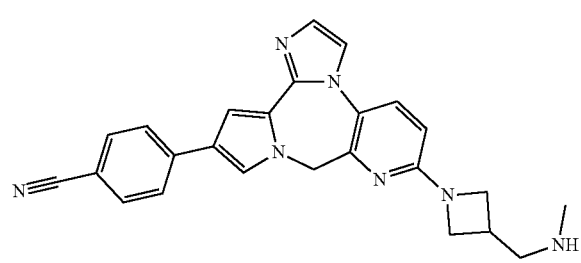 [SMILES: CNCC1CN(c2ccc3c(n2)Cn2cc(-c4ccc(C#N)cc4)cc2-c2nccn2-3)C1]

4-(7-(3-((methylamino)methyl)azetidin-1-yl)-9H-imidazo[2,1-c]pyrido[3,2-e]pyrrolo[1,2-a][1,4]diazepin-12-yl)benzonitrile, 295. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with tert-butyl (azetidin-3-ylmethyl)(methyl)carbamate. 1H NMR (400 MHz, METHANOL-d4) δ=7.96 (s, 1H), 7.86 (d, J=9.3 Hz, 1H), 7.79 (s, 1H), 7.76-7.73 (m, 2H), 7.72-7.67 (m, 3H), 7.30 (s, 1H), 6.56 (d, J=8.8 Hz, 1H), 5.30 (s, 2H), 4.29 (t, J=8.4 Hz, 2H), 3.91 (dd, J=5.3, 8.8 Hz, 2H), 3.36 (d, J=7.5 Hz, 2H), 3.18-3.06 (m, 1H), 2.79-2.70 (m, 3H). ESI [M+H]=422.2

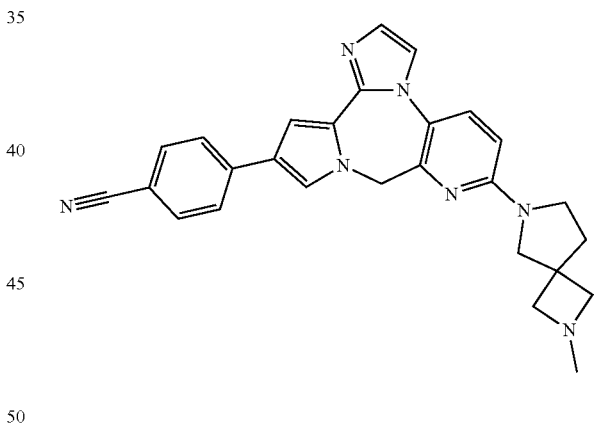

4-(7-(2-methyl-2,6-diazaspiro[3.4]octan-6-yl)-9H-imidazo[2,1-c]pyrido[3,2-e]pyrrolo[1,2-a][1,4]diazepin-12-yl)benzonitrile, 297. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile and replacing tert-butyl (azetidin-3-ylmethyl)(methyl)carbamate with tert-butyl 2,6-diazaspiro[3.4]octane-2-carboxylate. 1H NMR (400 MHz, METHANOL-d4) δ=7.73-7.60 (m, 5H), 7.56 (s, 1H), 7.52 (d, J=1.8 Hz, 1H), 7.21 (s, 1H), 7.03 (d, J=1.8 Hz, 1H), 6.54 (d, J=8.8 Hz, 1H), 5.10 (s, 2H), 3.64 (s, 2H), 3.51 (t, J=6.8 Hz, 2H), 3.42-3.36 (m, 4H), 2.44 (s, 3H), 2.24-2.17 (m, 2H). ESI [M+H]=448.1

209

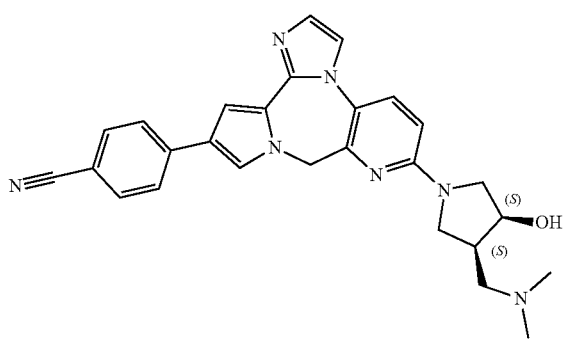

4-(7-((3S,4S)-3-((dimethylamino)methyl)-4-hydroxypyrrolidin-1-yl)-9H-imidazo[2,1-c] pyrido[3,2-e]pyrrolo[1,2-a][1,4]diazepin-12-yl)benzonitrile, 298. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3S,4R)-4-((dimethylamino) methyl)pyrrolidin-3-ol. 1H NMR (400 MHz, METHANOL-d4) δ=8.00 (s, 1H), 7.87 (d, J=9.0 Hz, 1H), 7.82 (d, J=1.2 Hz, 1H), 7.79-7.73 (m, 3H), 7.72-7.67 (m, 2H), 7.34 (s, 1H), 6.67 (d, J=9.0 Hz, 1H), 5.33 (s, 2H), 4.56 (br. s., 1H), 3.90 (br. s., 1H), 3.81-3.65 (m, 2H), 3.58 (dd, J=8.0, 13.1 Hz, 1H), 3.44-3.32 (m, 2H), 2.99 (s, 6H), 2.86 (d, J=3.9 Hz, 1H). ESI [M+H]=466.2

210

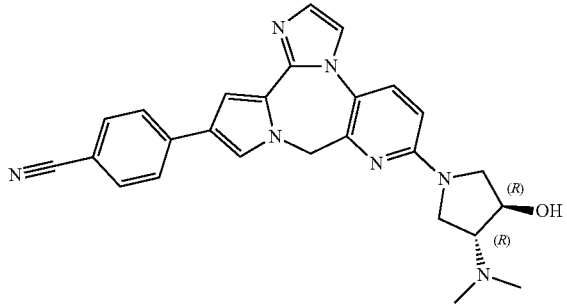

4-(7-((3R,4R)-3-(dimethylamino)-4-hydroxypyrrolidin-1-yl)-9H-imidazo[2,1-c]pyrido[3,2-e] pyrrolo[1,2-a][1,4]diazepin-12-yl)benzonitrile, 300. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3R,4R)-4-(dimethylamino) pyrrolidin-3-ol. 1H NMR (400 MHz, METHANOL-d4) δ=8.03 (br. s., 1H), 7.92 (d, J=9.3 Hz, 1H), 7.83 (s, 1H), 7.80-7.72 (m, 3H), 7.71-7.66 (m, 2H), 7.36 (br. s., 1H), 6.75 (d, J=9.3 Hz, 1H), 5.36 (s, 2H), 4.72 (q, J=7.4 Hz, 1H), 4.19 (dd, J=8.2, 11.2 Hz, 1H), 4.09 (dd, J=7.9, 10.6 Hz, 1H), 3.85 (q, J=7.6 Hz, 1H), 3.72 (dd, J=7.9, 11.5 Hz, 1H), 3.39 (dd, J=6.8, 10.8 Hz, 1H), 3.05 (s, 6H). ESI [M+H]=452.1

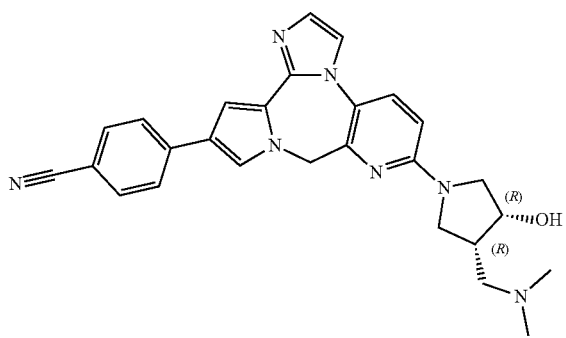

4-(7-((3R,4R)-3-((dimethylamino)methyl)-4-hydroxypyrrolidin-1-yl)-9H-imidazo[2,1-c] pyrido[3,2-e]pyrrolo[1,2-a][1,4]diazepin-12-yl)benzonitrile, 299. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3R,4S)-4-((dimethylamino) methyl)pyrrolidin-3-ol. 1H NMR (400 MHz, METHANOL-d4) δ=8.01 (br. s., 1H), 7.90-7.80 (m, 2H), 7.80-7.71 (m, 3H), 7.71-7.65 (m, 2H), 7.35 (br. s., 1H), 6.66 (d, J=9.0 Hz, 1H), 5.38-5.25 (m, 2H), 4.55 (br. s., 1H), 3.89 (br. s., 1H), 3.80-3.62 (m, 2H), 3.57 (dd, J=7.9, 13.0 Hz, 1H), 3.44-3.30 (m, 2H), 3.05-2.92 (m, 6H), 2.89-2.75 (m, 1H). ESI [M+H]=466.1

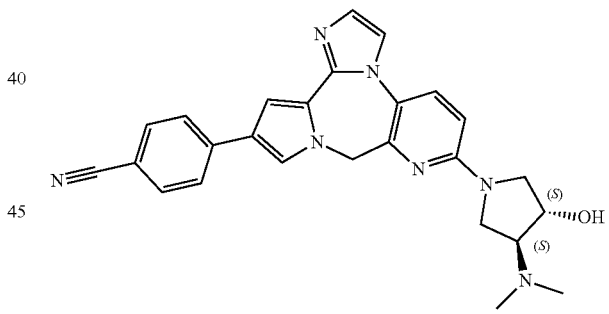

4-(7-((3S,4S)-3-(dimethylamino)-4-hydroxypyrrolidin-1-yl)-9H-imidazo[2,1-c]pyrido[3,2-e] pyrrolo[1,2-a][1,4]diazepin-12-yl)benzonitrile, 301. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3S,4S)-4-(dimethylamino) pyrrolidin-3-ol. 1H NMR (400 MHz, METHANOL-d4) δ=8.02 (s, 1H), 7.92 (d, J=9.3 Hz, 1H), 7.83 (s, 1H), 7.79-7.66 (m, 5H), 7.35 (s, 1H), 6.75 (d, J=9.3 Hz, 1H), 5.36 (s, 2H), 4.72 (d, J=7.1 Hz, 1H), 4.23-4.14 (m, 1H), 4.09 (d, J=3.1 Hz, 1H), 3.85 (d, J=7.5 Hz, 1H), 3.72 (dd, J=7.9, 11.5 Hz, 1H), 3.39 (dd, J=7.1, 10.6 Hz, 1H), 3.05 (s, 6H). ESI [M+H]=452.1

211

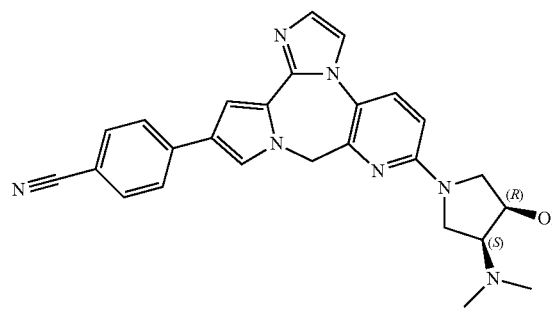

4-(7-((3S,4R)-3-(dimethylamino)-4-hydroxypyrrolidin-1-yl)-9H-imidazo[2,1-c]pyrido[3,2-e] pyrrolo[1,2-a][1,4]diazepin-12-yl)benzonitrile, 302. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3R,4S)-4-(dimethylamino)pyrrolidin-3-ol. 1H NMR (400 MHz, METHANOL-d4) δ=8.05 (br. s., 1H), 7.94 (d, J=9.0 Hz, 1H), 7.88-7.67 (m, 6H), 7.37 (s, 1H), 6.76 (d, J=8.8 Hz, 1H), 5.38 (s, 2H), 4.69 (br. s., 1H), 4.23 (br. s., 1H), 3.94 (br. s., 1H), 3.88-3.73 (m, 2H), 3.66 (t, J=9.9 Hz, 1H), 3.11-2.92 (m, 6H). ESI [M+H]=452.1

212

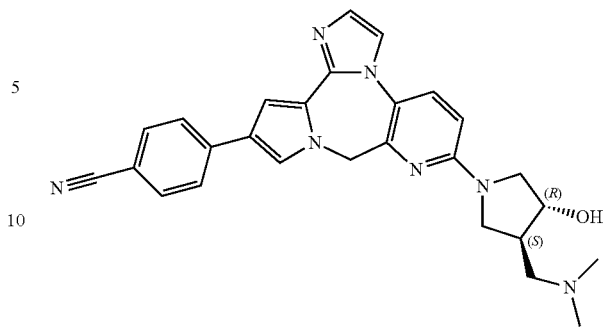

4-(7-((3S,4R)-3-((dimethylamino)methyl)-4-hydroxypyrrolidin-1-yl)-9H-imidazo[2,1-c] pyrido[3,2-e]pyrrolo[1,2-a][1,4]diazepin-12-yl)benzonitrile, 306. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3R,4R)-4-((dimethylamino)methyl)pyrrolidin-3-ol. 1H NMR (400 MHz, METHANOL-d4) δ=8.00 (br. s., 1H), 7.87 (d, J=9.0 Hz, 1H), 7.81 (s, 1H), 7.78-7.66 (m, 5H), 7.34 (br. s., 1H), 6.67 (d, J=9.0 Hz, 1H), 5.32 (s, 2H), 4.29 (q, J=6.7 Hz, 1H), 4.04-3.89 (m, 2H), 3.45-3.32 (m, 4H), 3.05-2.95 (m, 6H), 2.77-2.65 (m, 1H). ESI [M+H]=466.2

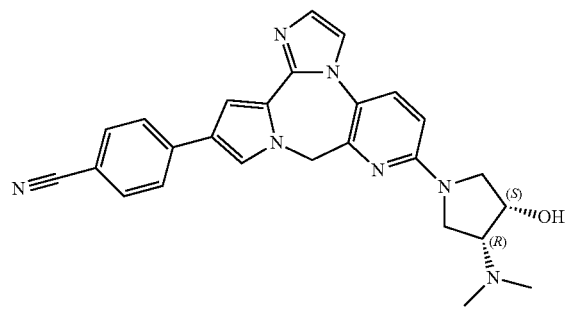

4-(7-((3R,4S)-3-(dimethylamino)-4-hydroxypyrrolidin-1-yl)-9H-imidazo[2,1-c]pyrido[3,2-e] pyrrolo[1,2-a][1,4]diazepin-12-yl)benzonitrile, 303. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3S,4R)-4-(dimethylamino)pyrrolidin-3-ol. 1H NMR (400 MHz, METHANOL-d4) δ=8.04 (br. s., 1H), 7.93 (d, J=8.8 Hz, 1H), 7.85 (s, 1H), 7.82-7.66 (m, 5H), 7.37 (s, 1H), 6.76 (d, J=8.8 Hz, 1H), 5.37 (s, 2H), 4.69 (br. s., 1H), 4.23 (br. s., 1H), 4.01-3.90 (m, 1H), 3.85-3.71 (m, 2H), 3.66 (t, J=9.9 Hz, 1H), 3.03 (br. s., 6H). ESI [M+H]=452.1

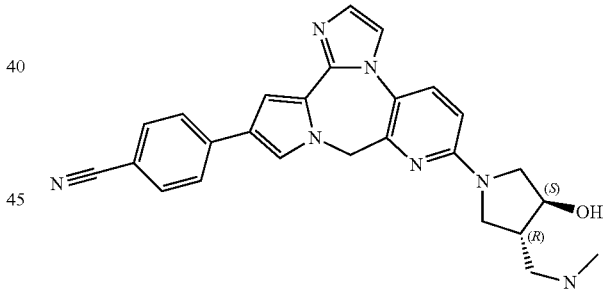

4-(7-((3R,4S)-3-((dimethylamino)methyl)-4-hydroxypyrrolidin-1-yl)-9H-imidazo[2,1-c] pyrido[3,2-e]pyrrolo[1,2-a][1,4]diazepin-12-yl)benzonitrile, 307. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl)benzonitrile, replacing tert-butyl piperazine-1-carboxylate with (3S,4S)-4-((dimethylamino)methyl)pyrrolidin-3-ol. 1H NMR (400 MHz, METHANOL-d4) δ=7.98 (br. s., 1H), 7.86 (d, J=9.0 Hz, 1H), 7.80 (s, 1H), 7.77-7.67 (m, 5H), 7.32 (s, 1H), 6.66 (d, J=9.0 Hz, 1H), 5.31 (s, 2H), 4.27 (q, J=6.6 Hz, 1H), 4.03-3.89 (m, 2H), 3.45-3.33 (m, 4H), 2.98 (s, 6H), 2.74-2.63 (m, 1H). ESI [M+H]=466.2

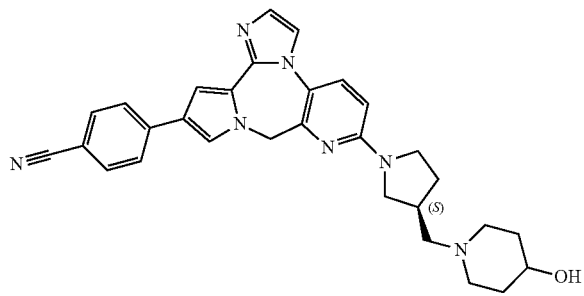

(S)-4-(7-(3-((4-hydroxypiperidin-1-yl)methyl)pyrrolidin-1-yl)-9H-imidazo[2,1-c]pyrido[3,2-e]pyrrolo[1,2-a][1,4]diazepin-12-yl)benzonitrile, 308. Synthesized using General Procedure A, replacing 4-(7-bromo-9H-benzo[e]pyrrolo[1,2-a][1,2,4]triazolo[3,4-c][1,4]diazepin-12-yl) benzonitrile with 4-(7-bromo-9H-imidazo[2,1-c]pyrido[3,2-e]pyrrolo[1,2-a][1,4]diazepin-12-yl) benzonitrile, replacing tert-butyl piperazine-1-carboxylate with (R)-1-(pyrrolidin-3-ylmethyl) piperidin-4-ol. 1H NMR (400 MHz, METHANOL-d4) δ=8.04 (s, 1H), 7.94-7.84 (m, 3H), 7.81 (s, 1H), 7.79-7.75 (m, 2H), 7.74-7.68 (m, 1H), 7.37 (s, 1H), 6.68 (d, J=8.8 Hz, 1H), 5.34 (s, 2H), 4.12 (br. s., 1H), 3.95 (br. s., 1H), 3.85 (t, J=10.1 Hz, 1H), 3.79-3.62 (m, 2H), 3.60-3.43 (m, 3H), 3.34 (br. s., 2H), 3.09 (t, J=12.6 Hz, 1H), 2.96-2.79 (m, 1H), 2.35 (br. s., 1H), 2.22-2.01 (m, 2H), 1.99-1.71 (m, 3H). ESI [M+H]=506.2

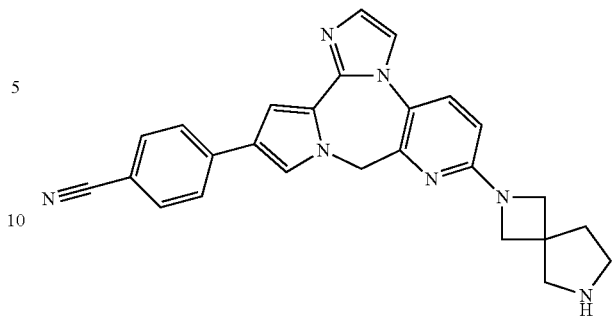

4-(7-(2,6-diazaspiro[3.4]octan-2-yl)-9H-imidazo[2,1-c]pyrido[3,2-e]pyrrolo[1,2-a][1,4] diazepin-12-yl)benzonitrile, 311. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl) benzonitrile, replacing tert-butyl piperazine-1-carboxylate with tert-butyl 2,6-diazaspiro[3.4]octane-6-carboxylate. 1H NMR (400 MHz, METHANOL-d4) δ=8.03 (d, J=2.2 Hz, 1H), 7.89 (d, J=8.8 Hz, 1H), 7.85-7.78 (m, 2H), 7.77-7.73 (m, 2H), 7.73-7.67 (m, 2H), 7.35 (d, J=1.8 Hz, 1H), 6.60 (d, J=8.8 Hz, 1H), 5.34 (s, 2H), 4.20-4.14 (m, 2H), 4.14-4.10 (m, 2H), 3.53 (s, 2H), 3.38 (t, J=7.3 Hz, 2H), 2.35 (t, J=7.3 Hz, 2H). ESI [M+H]=434.2

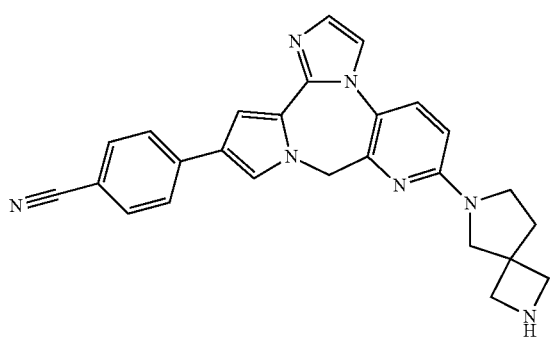 [SMILES: N#Cc1ccc(-c2cc3n(c2)Cc2nc(N4CCC5(CNC5)C4)ccc2-n2ccnc2-3)cc1]

4-(7-(2,6-diazaspiro[3.4]octan-6-yl)-9H-imidazo[2,1-c]pyrido[3,2-e]pyrrolo[1,2-a][1,4] diazepin-12-yl)benzonitrile, 310. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-bromo-9H-imidazo[2,1-c]pyrido[3,2-e]pyrrolo[1,2-a][1,4]diazepin-12-yl) benzonitrile, replacing tert-butyl piperazine-1-carboxylate with tert-butyl 2,6-diazaspiro[3.4]octane-2-carboxylate. 1H NMR (400 MHz, METHANOL-d4) δ=8.04 (d, J=1.8 Hz, 1H), 7.89 (d, J=9.0 Hz, 1H), 7.87-7.79 (m, 2H), 7.79-7.74 (m, 2H), 7.73-7.68 (m, 2H), 7.38 (s, 1H), 6.69 (d, J=9.0 Hz, 1H), 5.35 (s, 2H), 4.24-4.16 (m, 2H), 4.13-4.05 (m, 2H), 3.88-3.81 (m, 2H), 3.63 (t, J=6.7 Hz, 2H), 2.40 (t, J=6.9 Hz, 2H). ESI [M+H]=434.2

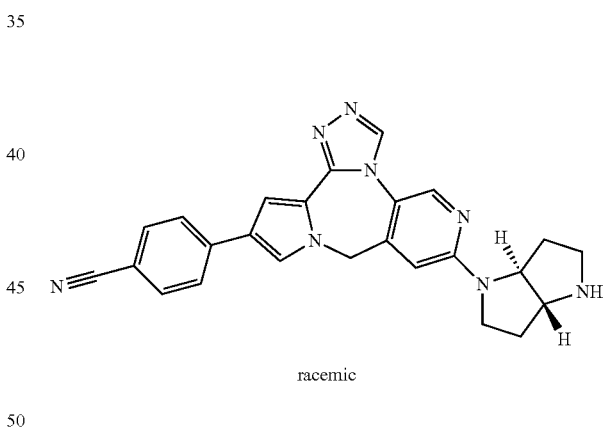

racemic 4-(7-(trans-hexahydropyrrolo[3,2-b]pyrrol-1(2H)-yl)-9H-pyrido[3,4-e]pyrrolo[1,2-a][1,2,4] triazolo[3,4-c][1,4] diazepin-12-yl)benzonitrile, 314. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-chloro-9H-pyrido[3,4-e]pyrrolo[1,2-a][1,2,4]triazolo[3,4-c][1,4]diazepin-12-yl) benzonitrile, replacing tert-butyl piperazine-1-carboxylate with trans-tert-butyl hexahydro pyrrolo[3,2-b]pyrrole-1(2H)-carboxylate. 1H NMR (400 MHz, METHANOL-d4) δ=9.09 (s, 1H), 8.43 (s, 1H), 7.77-7.59 (m, 5H), 7.25 (s, 1H), 6.81 (s, 1H), 5.24 (s, 2H), 4.27-4.12 (m, 1H), 4.07-3.88 (m, 3H), 3.85-3.66 (m, 2H), 2.79 (d, J=6.6 Hz, 1H), 2.42-2.26 (m, 1H), 2.23-2.10 (m, 1H), 2.02 (quin, J=10.5 Hz, 1H). ESI [M+H]=435.1

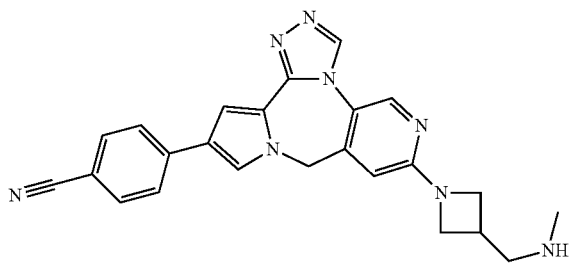 [SMILES: CNCC1CN(c2cc3c(cn2)-n2cnnc2-c2cc(-c4ccc(C#N)cc4)cn2C3)C1]

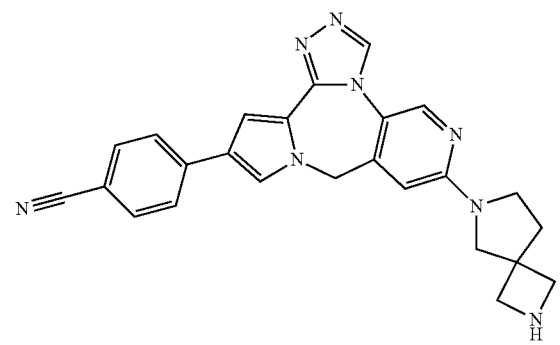

4-(7-(3-((methylamino)methyl)azetidin-1-yl)-9H-pyrido[3,4-e]pyrrolo[1,2-a][1,2,4]triazolo[3,4-c][1,4]diazepin-12-yl)benzonitrile, 315. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-chloro-9H-pyrido[3,4-e]pyrrolo[1,2-a][1,2,4]triazolo[3,4-c][1,4]diazepin-12-yl) benzonitrile, replacing tert-butyl piperazine-1-carboxylate with tert-butyl (azetidin-3-ylmethyl)(methyl)carbamate. 1H NMR (400 MHz, METHANOL-d4) δ=9.16 (br. s., 1H), 8.36 (s, 1H), 7.73-7.55 (m, 5H), 7.25 (s, 1H), 6.74-6.63 (m, 1H), 5.30-5.19 (m, 2H), 4.37-4.27 (m, 2H), 3.95 (dd, J=5.3, 8.8 Hz, 2H), 3.37 (d, J=7.5 Hz, 2H), 3.24-3.09 (m, 1H), 2.79-2.71 (m, 3H). ESI [M+H]=423.1

4-(7-(2,6-diazaspiro[3.4]octan-6-yl)-9H-pyrido[3,4-e]pyrrolo[1,2-a][1,2,4]triazolo[3,4-c][1,4] diazepin-12-yl)benzonitrile, 318. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-chloro-9H-pyrido[3,4-e]pyrrolo[1,2-a][1,2,4]triazolo[3,4-c][1,4]diazepin-12-yl)benzonitrile, replacing tert-butyl piperazine-1-carboxylate with tert-butyl 2,6-diazaspiro[3.4]octane-2-carboxylate. 1H NMR (400 MHz, METHANOL-d4) δ=9.19 (br. s., 1H), 8.38 (s, 1H), 7.77-7.60 (m, 5H), 7.27 (br. s., 1H), 6.78 (s, 1H), 5.24 (s, 2H), 4.24-4.01 (m, 4H), 3.82 (s, 2H), 3.60 (t, J=6.9 Hz, 2H), 2.47-2.32 (m, 2H). ESI [M+H]=435.1

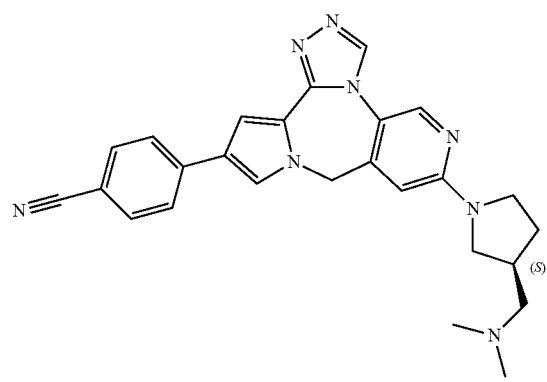

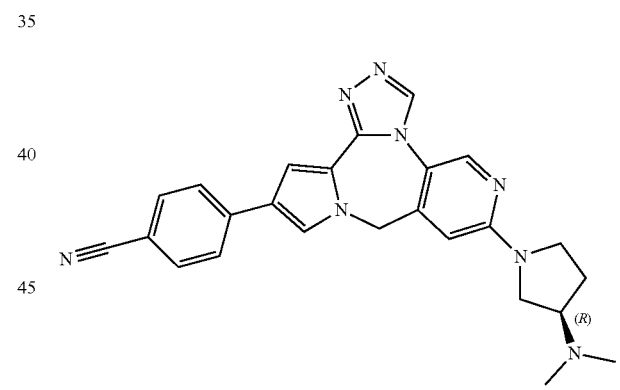

(S)-4-(7-(3-((dimethylamino)methyl)pyrrolidin-1-yl)-9H-pyrido[3,4-e]pyrrolo[1,2-a][1,2,4] triazolo[3,4-c][1,4]diazepin-12-yl)benzonitrile, 317. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-chloro-9H-pyrido[3,4-e]pyrrolo[1,2-a][1,2,4]triazolo[3,4-c][1,4]diazepin-12-yl) benzonitrile and replacing tert-butyl (azetidin-3-ylmethyl)(methyl)carbamate with (R)-tert-butyl (pyrrolidin-3-ylmethyl)carbamate. 1H NMR (400 MHz, METHANOL-d4) δ=9.09 (s, 1H), 8.35 (br. s., 1H), 7.78-7.56 (m, 5H), 7.30 (s, 1H), 6.78 (s, 1H), 5.21 (br. s., 2H), 3.88 (dd, J=7.7, 10.1 Hz, 1H), 3.70 (t, J=7.8 Hz, 1H), 3.60-3.45 (m, 1H), 3.32 (d, J=7.1 Hz, 2H), 3.25 (d, J=10.6 Hz, 1H), 3.02-2.90 (m, 6H), 2.88-2.75 (m, 1H), 2.34 (td, J=2.8, 6.0 Hz, 1H), 1.97-1.79 (m, 1H). ESI [M+H]=451.2

(R)-4-(7-(3-(dimethylamino)pyrrolidin-1-yl)-9H-pyrido[3,4-e]pyrrolo[1,2-a][1,2,4]triazolo[3,4-c][1,4]diazepin-12-yl)benzonitrile, 319. Synthesized using General Procedure A, replacing 4-(7-bromo-9H-benzo[e]pyrrolo[1,2-a][1,2,4]triazolo[3,4-c][1,4]diazepin-12-yl)benzonitrile with 4-(7-chloro-9H-pyrido[3,4-e]pyrrolo[1,2-a][1,2,4]triazolo[3,4-c][1,4]diazepin-12-yl) benzonitrile, replacing tert-butyl piperazine-1-carboxylate with (R)—N,N-dimethyl pyrrolidin-3-amine. 1H NMR (400 MHz, METHANOL-d4) δ=9.16 (br. s., 1H), 8.42 (s, 1H), 7.80-7.56 (m, 5H), 7.27 (br. s., 1H), 6.87-6.74 (m, 1H), 5.23 (s, 2H), 4.05 (d, J=7.3 Hz, 2H), 3.87-3.67 (m, 2H), 3.63-3.50 (m, 1H), 3.02-2.89 (m, 6H), 2.62 (d, J=12.6 Hz, 1H), 2.38-2.24 (m, 1H). ESI [M+H]=437.1

217

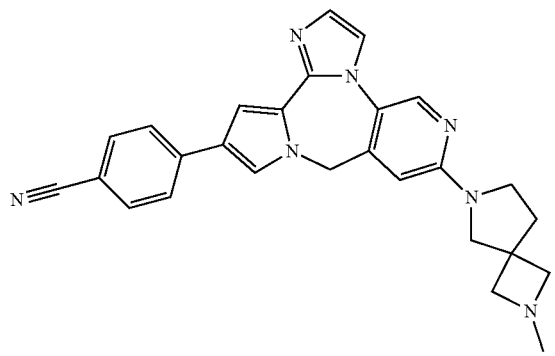 [SMILES: CN1CC2(CCN(c3cc4c(cn3)-n3ccnc3-c3cc(-c5ccc(C#N)cc5)cn3C4)C2)C1]

4-(7-(2-methyl-2,6-diazaspiro[3.4]octan-6-yl)-9H-imidazo[2,1-c]pyrido[3,4-e]pyrrolo[1,2-a] [1,4]diazepin-12-yl)benzonitrile, 322. Synthesized using General Procedure C, replacing 4-(7-bromo-9H-benzo[e]pyrrolo[1,2-a][1,2,4]triazolo[3,4-c][1,4]diazepin-12-yl)benzonitrile with 4-(7-chloro-9H-imidazo[2,1-c]pyrido[3,4-e]pyrrolo[1,2-a][1,4]diazepin-12-yl)benzonitrile and replacing tert-butyl (azetidin-3-ylmethyl)(methyl)carbamate with tert-butyl 2,6-diazaspiro[3.4] octane-2-carboxylate. 1H NMR (400 MHz, METHANOL-d4) δ=8.43 (s, 1H), 8.09 (d, J=1.3 Hz, 1H), 7.84-7.66 (m, 6H), 7.35 (s, 1H), 6.77 (br. s., 1H), 5.36 (s, 2H), 4.44-4.26 (m, 2H), 4.21-4.07 (m, 2H), 3.92-3.76 (m, 2H), 3.67-3.55 (m, 2H), 2.98 (br. s., 3H), 2.42 (br. s., 2H). ESI [M+H]=448.2

218

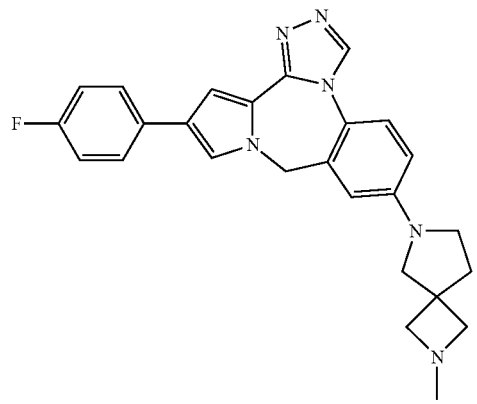

12-(4-fluorophenyl)-7-(2-methyl-2,6-diazaspiro[3.4]octan-6-yl)-9H-benzo[e]pyrrolo[1,2-a] [1,2,4]triazolo[3,4-c][1,4]diazepine, 332. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e] pyrrolo[1,2-a] [1,2,4]triazolo[3,4-c][1,4]diazepine and replacing tert-butyl (azetidin-3-ylmethyl)(methyl)carbamate with tert-butyl 2,6-diazaspiro[3.4] octane-2-carboxylate. 1H NMR (400 MHz, METHANOL-d4) δ=9.14 (br. s., 1H), 7.57-7.46 (m, 4H), 7.16 (br. s., 1H), 7.05 (t, J=8.8 Hz, 2H), 6.80 (d, J=4.9 Hz, 1H), 6.74-6.67 (m, 1H), 5.17 (s, 2H), 4.39-4.27 (m, 2H), 4.18-4.08 (m, 2H), 3.68-3.58 (m, 2H), 3.44 (td, J=6.8, 13.3 Hz, 2H), 2.98 (d, J=5.3 Hz, 3H), 2.43-2.34 (m, 2H). ESI [M+H]=441.2

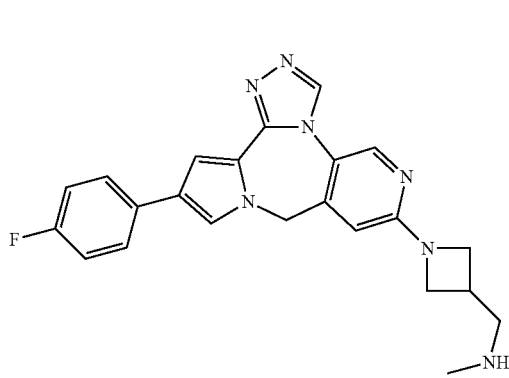 [SMILES: CNCC1CN(c2cc3c(cn2)-n2cnnc2-c2cc(-c4ccc(F)cc4)cn2C3)C1]

1-(1-(12-(4-fluorophenyl)-9H-benzo[e]pyrrolo[1,2-a][1,2,4]triazolo[3,4-c][1,4]diazepin-7-yl) azetidin-3-yl)-N-methylmethanamine, 330. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[3,4-c][1,4]diazepine, replacing tert-butyl piperazine-1-carboxylate with tert-butyl (azetidin-3-ylmethyl)(methyl) carbamate. 1H NMR (400 MHz, METHANOL-d4) δ=9.14 (br. s., 1H), 7.58-7.43 (m, 4H), 7.15 (br. s., 1H), 7.04 (t, J=8.8 Hz, 2H), 6.67 (d, J=2.6 Hz, 1H), 6.57 (dd, J=2.4, 8.6 Hz, 1H), 5.14 (s, 2H), 4.12 (t, J=7.7 Hz, 2H), 3.75 (dd, J=5.3, 7.9 Hz, 2H), 3.35 (d, J=7.5 Hz, 2H), 3.15-3.04 (m, 1H), 2.74 (s, 3H). ESI [M+H]=415.1

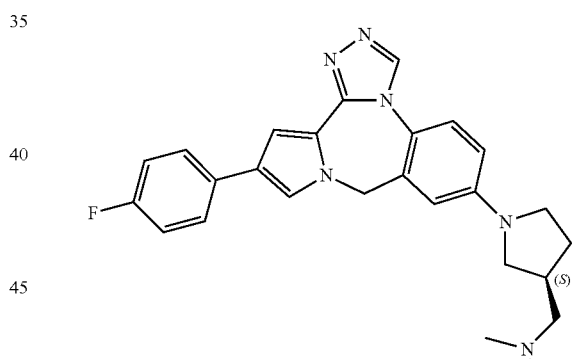

(S)-1-(1-(12-(4-fluorophenyl)-9H-benzo[e]pyrrolo[1,2-a][1,2,4]triazolo[3,4-c][1,4]diazepin-7-yl)pyrrolidin-3-yl)-N,N-dimethylmethanamine, 333. Synthesized using General Procedure C, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[3,4-c] [1,4]diazepine and replacing tert-butyl (azetidin-3-ylmethyl)(methyl)carbamate with (R)-tert-butyl (pyrrolidin-3-ylmethyl) carbamate. 1H NMR (400 MHz, METHANOL-d4) δ=9.06 (br. s., 1H), 7.55 (dd, J=5.3, 8.8 Hz, 2H), 7.48 (d, J=8.8 Hz, 1H), 7.43 (s, 1H), 7.13 (br. s., 1H), 7.06 (t, J=8.8 Hz, 2H), 6.79 (s, 1H), 6.70 (d, J=8.8 Hz, 1H), 5.14 (s, 2H), 3.64 (d, J=7.9 Hz, 1H), 3.53 (d, J=5.7 Hz, 1H), 3.43 (d, J=8.4 Hz, 1H), 3.34 (s, 2H), 3.19-3.11 (m, 1H), 3.03-2.94 (m, 6H), 2.87 (d, J=7.1 Hz, 1H), 2.35 (dd, J=3.1, 12.3 Hz, 1H), 1.88 (dd, J=8.8, 12.3 Hz, 1H). ESI [M+H]=443.1

219

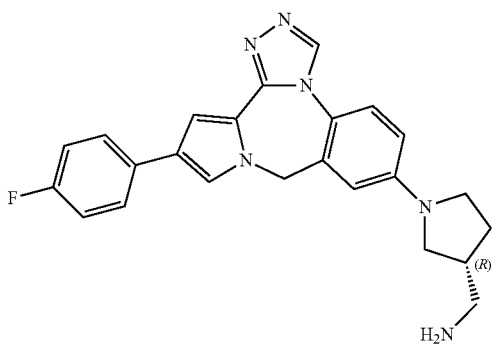

(R)-(1-(12-(4-fluorophenyl)-9H-benzo[e]pyrrolo[1,2-a][1,2,4]triazolo[3,4-c][1,4]diazepin-7-yl)pyrrolidin-3-yl)methanamine, 334. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo [e]pyrrolo[1,2-a][1,2,4]triazolo[3,4-c][1,4]diazepine and replacing tert-butyl piperazine-1-carboxylate with (S)-tert-butyl (pyrrolidin-3-ylmethyl) carbamate. 1H NMR (400 MHz, METHANOL-d4) δ=9.06 (s, 1H), 7.54 (dd, J=5.3, 8.4 Hz, 2H), 7.50-7.39 (m, 2H), 7.12 (d, J=1.3 Hz, 1H), 7.05 (t, J=8.8 Hz, 2H), 6.77 (d, J=2.6 Hz, 1H), 6.68 (dd, J=2.6, 8.8 Hz, 1H), 5.13 (s, 2H), 3.63-3.46 (m, 2H), 3.40 (d, J=8.8 Hz, 1H), 3.20-2.99 (m, 3H), 2.74-2.60 (m, 1H), 2.31 (dd, J=4.4, 11.5 Hz, 1H), 1.95-1.80 (m, 1H). ESI [M+H]=415.1

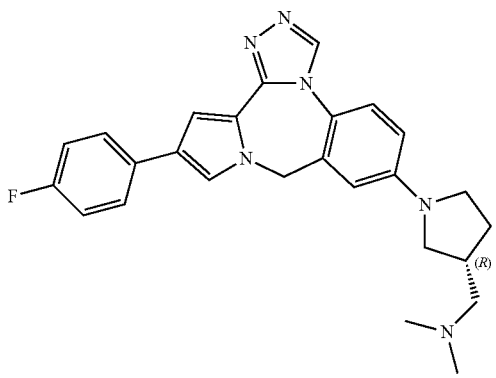

(R)-1-(1-(12-(4-fluorophenyl)-9H-benzo[e]pyrrolo[1,2-a][1,2,4]triazolo[3,4-c][1,4]diazepin-7-yl)pyrrolidin-3-yl)-N,N-dimethylmethanamine, 335. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[3,4-c][1,4]diazepine and replacing tert-butyl (azetidin-3-ylmethyl)(methyl)carbamate with (S)-tert-butyl (pyrrolidin-3-ylmethyl) carbamate. 1H NMR (400 MHz, METHANOL-d4) δ=9.15 (br. s., 1H), 7.59-7.48 (m, 2H), 7.41 (s, 2H), 7.14 (br. s., 1H), 7.04 (t, J=8.6 Hz, 2H), 6.75 (s, 1H), 6.66 (d, J=7.1 Hz, 1H), 5.09 (s, 2H), 3.66-3.57 (m, 1H), 3.50 (d, J=2.6 Hz, 1H), 3.39 (d, J=8.4 Hz, 1H), 3.31 (s, 2H), 3.12 (t, J=8.6 Hz, 1H), 2.96 (s, 6H), 2.89-2.76 (m, 1H), 2.39-2.26 (m, 1H), 1.86 (dd, J=8.8, 12.3 Hz, 1H). ESI [M+H]=443.1

220

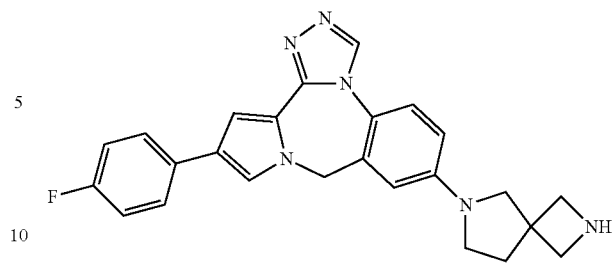

12-(4-fluorophenyl)-7-(2,6-diazaspiro[3.4]octan-6-yl)-9H-benzo[e]pyrrolo[1,2-a][1,2,4] triazolo[3,4-c][1,4]diazepine, 336. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[3,4-c][1,4]diazepine and replacing tert-butyl piperazine-1-carboxylate with tert-butyl 2,6-diazaspiro[3.4]octane-2-carboxylate. 1H NMR (400 MHz, METHANOL-d4) δ=9.08 (s, 1H), 7.58-7.41 (m, 4H), 7.14 (s, 1H), 7.06 (t, J=8.7 Hz, 2H), 6.80 (d, J=2.2 Hz, 1H), 6.70 (dd, J=2.4, 8.8 Hz, 1H), 5.21-5.12 (m, 2H), 4.22-4.14 (m, 2H), 4.13-4.04 (m, 2H), 3.62 (s, 2H), 3.45 (t, J=6.8 Hz, 2H), 2.43-2.35 (m, 2H). ESI [M+H]=427.2

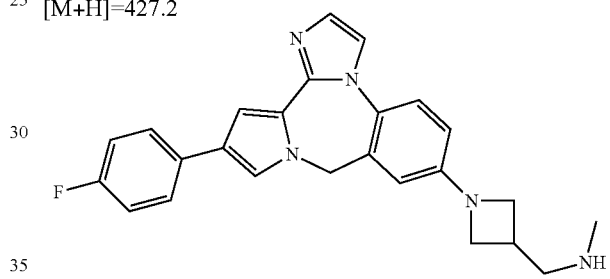

1-(1-(12-(4-fluorophenyl)-9H-benzo[e]imidazo[2,1-c]pyrrolo[1,2-a][1,4]diazepin-7-yl)azetidin-3-yl)-N-methylmethanamine, 341. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and and replacing tert-butyl piperazine-1-carboxylate with tert-butyl (azetidin-3-ylmethyl)(methyl) carbamate. 1H NMR (400 MHz, METHANOL-d4) δ=7.93 (d, J=1.8 Hz, 1H), 7.66 (d, J=1.8 Hz, 1H), 7.59-7.47 (m, 4H), 7.14 (d, J=1.8 Hz, 1H), 7.07 (t, J=8.8 Hz, 2H), 6.69 (d, J=2.2 Hz, 1H), 6.62 (dd, J=2.6, 8.8 Hz, 1H), 5.26-5.20 (m, 2H), 4.14 (t, J=7.7 Hz, 2H), 3.77 (dd, J=5.1, 7.7 Hz, 2H), 3.36 (d, J=7.5 Hz, 2H), 3.15-3.04 (m, 1H), 2.74 (s, 3H). ESI [M+H]=414.2

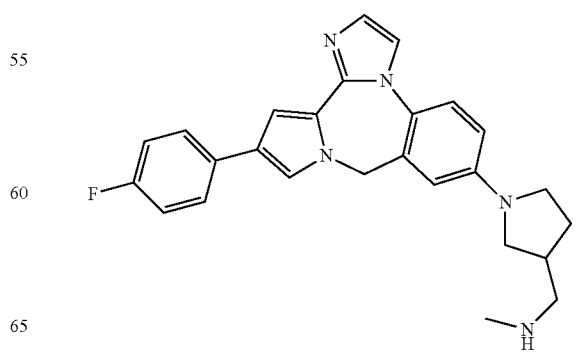

1-(1-(12-(4-fluorophenyl)-9H-benzo[e]imidazo[2,1-c]pyrrolo[1,2-a][1,4]diazepin-7-yl)pyrrolidin-3-yl)-N-methylmethanamine, 342. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine and and replacing tert-butyl piperazine-1-carboxylate with tert-butyl methyl(pyrrolidin-3-ylmethyl)carbamate. 1H NMR (400 MHz, METHANOL-d4) δ=7.99 (br. s., 1H), 7.72 (br. s., 1H), 7.60-7.51 (m, 4H), 7.19 (br. s., 1H), 7.09 (t, J=8.7 Hz, 2H), 6.81 (d, J=2.4 Hz, 1H), 6.75 (dd, J=2.5, 8.9 Hz, 1H), 5.27 (s, 2H), 3.67-3.60 (m, 1H), 3.55 (dt, J=3.6, 8.9 Hz, 1H), 3.48-3.41 (m, 1H), 3.22-3.12 (m, 3H), 2.82-2.69 (m, 4H), 2.40-2.29 (m, 1H), 1.90 (qd, J=8.3, 12.5 Hz, 1H). ESI [M+H]=428.1

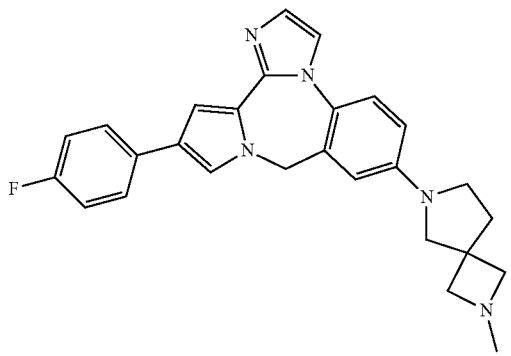 [SMILES: CN1CC2(CCN(c3ccc4c(c3)Cn3cc(-c5ccc(F)cc5)cc3-c3nccn3-4)C2)C1]

12-(4-fluorophenyl)-7-(2-methyl-2,6-diazaspiro[3.4]octan-6-yl)-9H-benzo[e]imidazo[2,1-c] pyrrolo[1,2-a][1,4]diazepine, 344. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl (azetidin-3-ylmethyl)(methyl) carbamate with tert-butyl 2,6-diazaspiro[3.4]octane-2-carboxylate. NMR (400 MHz, METHANOL-d$_4$) δ=7.55-7.46 (m, 3H), 7.32 (d, J=8.8 Hz, 1H), 7.26 (s, 1H), 7.16 (s, 1H), 7.01 (t, J=8.6 Hz, 2H), 6.87 (d, J=1.8 Hz, 1H), 6.69 (br. s., 1H), 6.62 (d, J=8.8 Hz, 1H), 5.01 (br. s., 2H), 4.61 (br. s., 1H), 3.45 (s, 2H), 3.35 (br. s., 5H), 2.40 (s, 3H), 2.21 (t, J=6.6 Hz, 2H). ESI [M+H]=440.1

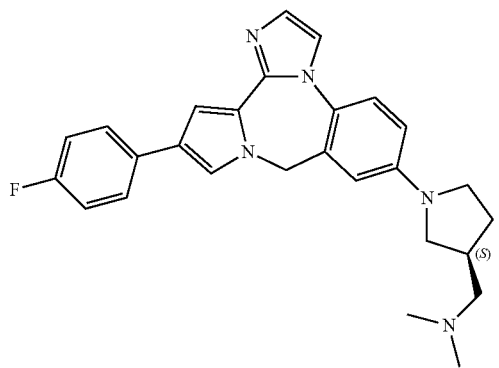

(S)-1-(1-(12-(4-fluorophenyl)-9H-benzo[e]imidazo[2,1-c]pyrrolo[1,2-a][1,4]diazepin-7-yl) pyrrolidin-3-yl)-N,N-dimethylmethanamine, 345. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl (azetidin-3-ylmethyl)(methyl)carbamate with (R)-tert-butyl (pyrrolidin-3-ylmethyl)carbamate. $^1$H NMR (400 MHz, METHANOL-d$_4$) δ=8.00 (br. s., 1H), 7.74 (br. s., 1H), 7.63-7.48 (m, 4H), 7.20 (br. s., 1H), 7.09 (t, J=8.8 Hz, 2H), 6.85-6.72 (m, 2H), 5.28 (s, 2H), 3.73-3.63 (m, 1H), 3.56 (dt, J=3.1, 8.8 Hz, 1H), 3.49-3.39 (m, 1H), 3.34 (s, 2H), 3.22-3.12 (m, 1H), 2.97 (s, 6H), 2.92-2.80 (m, 1H), 2.35 (ddd, J=3.3, 6.1, 9.2 Hz, 1H), 1.89 (qd, J=8.7, 12.3 Hz, 1H). ESI [M+H]=442.2

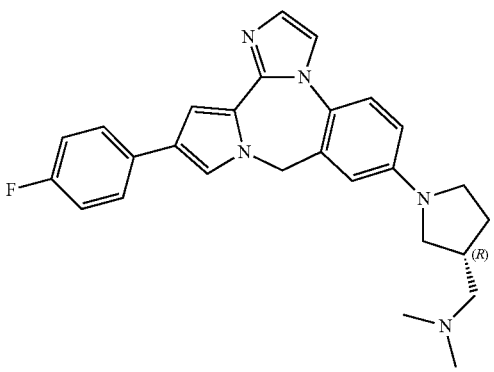

(R)-1-(1-(12-(4-fluorophenyl)-9H-benzo[e]imidazo[2,1-c]pyrrolo[1,2-a][1,4]diazepin-7-yl) pyrrolidin-3-yl)-N,N-dimethylmethanamine, 346. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl (azetidin-3-ylmethyl)(methyl)carbamate with (S)-tert-butyl(pyrrolidin-3-ylmethyl)carbamate. $^1$H NMR (400 MHz, METHANOL-d$_4$) δ=8.00 (br. s., 1H), 7.74 (br. s., 1H), 7.62-7.49 (m, 4H), 7.19 (br. s., 1H), 7.09 (t, J=8.6 Hz, 2H), 6.82 (d, J=2.2 Hz, 1H), 6.76 (dd, J=2.6, 8.8 Hz, 1H), 5.28 (s, 2H), 3.67 (t, J=8.6 Hz, 1H), 3.56 (dt, J=3.1, 8.8 Hz, 1H), 3.49-3.39 (m, 1H), 3.33 (d, J=7.5 Hz, 2H), 3.21-3.12 (m, 1H), 2.97 (s, 6H), 2.92-2.80 (m, 1H), 2.36 (dd, J=3.3, 12.1 Hz, 1H), 1.95-1.81 (m, 1H). ESI [M+H]=442.2

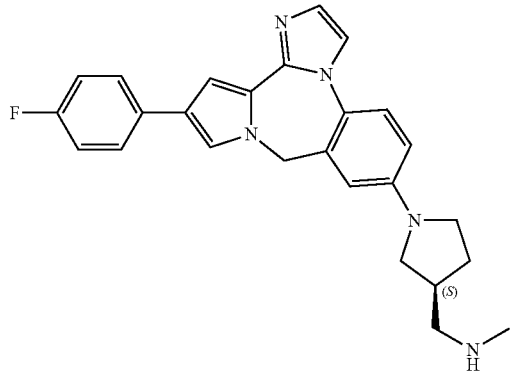

(S)-1-(1-(12-(4-fluorophenyl)-9H-benzo[e]imidazo[2,1-c]pyrrolo[1,2-a][1,4]diazepin-7-yl) pyrrolidin-3-yl)-N-methylmethanamine, 347. Synthesized using General Procedure I, replacing 4-(7-bromo-11-chloro-9H-benzo[e]

pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine. ¹H NMR (400 MHz, METHANOL-d₄) δ=7.98 (d, J=2.2 Hz, 1H), 7.72 (d, J=1.8 Hz, 1H), 7.60-7.48 (m, 4H), 7.18 (d, J=1.8 Hz, 1H), 7.07 (t, J=8.8 Hz, 2H), 6.79 (d, J=2.6 Hz, 1H), 6.73 (dd, J=2.4, 9.0 Hz, 1H), 5.25 (s, 2H), 3.61 (dd, J=7.5, 9.7 Hz, 1H), 3.53 (dt, J=3.7, 8.9 Hz, 1H), 3.47-3.38 (m, 1H), 3.21-3.07 (m, 3H), 2.82-2.65 (m, 4H), 2.39-2.24 (m, 1H), 1.88 (qd, J=8.4, 12.3 Hz, 1H). ESI [M+H]=428.1

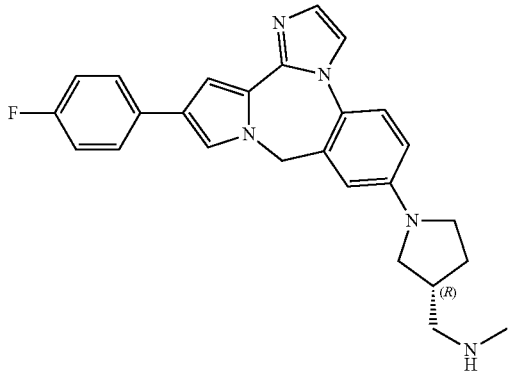

(R)-1-(1-(12-(4-fluorophenyl)-9H-benzo[e]imidazo[2,1-c]pyrrolo[1,2-a][1,4]diazepin-7-yl) pyrrolidin-3-yl)-N-methylmethanamine, 348. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4] diazepine and replacing tert-butyl piperazine-1-carboxylate with (S)-tert-butyl(pyrrolidin-3-yl methyl)carbamate. 1H NMR (400 MHz, METHANOL-d4) δ=7.78 (s, 1H), 7.59-7.51 (m, 2H), 7.46 (d, J=10.6 Hz, 3H), 7.12-7.00 (m, 3H), 6.78 (br. s., 1H), 6.72 (d, J=8.8 Hz, 1H), 5.16 (s, 2H), 3.61 (br. s., 1H), 3.53 (br. s., 1H), 3.42 (d, J=8.4 Hz, 1H), 3.17 (br. s., 3H), 2.84-2.66 (m, 4H), 2.32 (br. s., 1H), 1.97-1.81 (m, 1H). ESI [M+H]=428.1

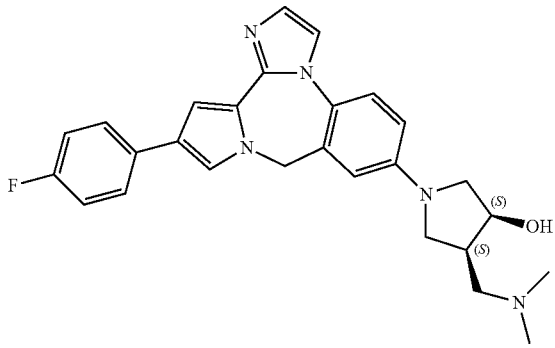

(3S,4S)-4-((dimethylamino)methyl)-1-(12-(4-fluorophenyl)-9H-benzo[e]imidazo[2,1-c] pyrrolo[1,2-a][1,4]diazepin-7-yl)pyrrolidin-3-ol, 349. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine and replacing tert-butyl piperazine-1-carboxylate with (3S,4R)-4-((dimethylamino) methyl)pyrrolidin-3-ol. 1H NMR (400 MHz, METHANOL-d4) δ=7.98 (s, 1H), 7.71 (s, 1H), 7.62-7.50 (m, 4H), 7.18 (s, 1H), 7.08 (t, J=8.8 Hz, 2H), 6.80 (d, J=2.2 Hz, 1H), 6.74 (dd, J=2.4, 9.0 Hz, 1H), 5.26 (s, 2H), 4.58 (br. s., 1H), 3.73-3.63 (m, 2H), 3.58 (dd, J=7.9, 13.2 Hz, 1H), 3.45 (d, J=11.0 Hz, 1H), 3.33 (d, J=6.2 Hz, 1H), 3.29-3.24 (m, 1H), 2.98 (s, 6H), 2.86 (d, J=7.5 Hz, 1H). ESI [M+H]=458.1

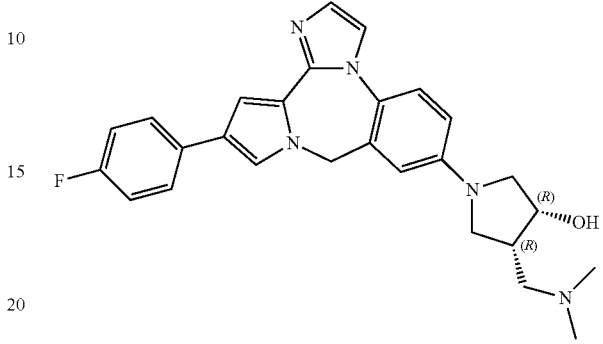

(3R,4R)-4-((dimethylamino)methyl)-1-(12-(4-fluorophenyl)-9H-benzo[e]imidazo[2,1-c] pyrrolo[1,2-a][1,4]diazepin-7-yl)pyrrolidin-3-ol, 350. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine and replacing tert-butyl piperazine-1-carboxylate with (3R,4S)-4-((dimethylamino) methyl)pyrrolidin-3-ol. 1H NMR (400 MHz, METHANOL-d4) δ=7.99 (s, 1H), 7.72 (s, 1H), 7.63-7.50 (m, 4H), 7.19 (s, 1H), 7.08 (t, J=8.8 Hz, 2H), 6.80 (d, J=2.2 Hz, 1H), 6.74 (dd, J=2.2, 8.8 Hz, 1H), 5.27 (s, 2H), 4.58 (br. s., 1H), 3.72-3.63 (m, 2H), 3.58 (dd, J=7.9, 13.2 Hz, 1H), 3.45 (d, J=10.6 Hz, 1H), 3.33 (d, J=5.7 Hz, 1H), 3.29-3.24 (m, 1H), 2.98 (s, 6H), 2.86 (d, J=7.5 Hz, 1H). ESI [M+H]=458.1

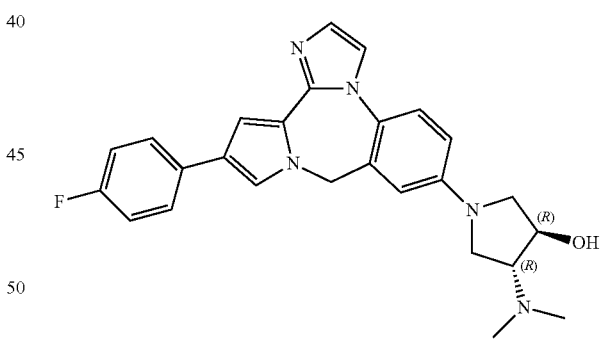

(3R,4R)-4-(dimethylamino)-1-(12-(4-fluorophenyl)-9H-benzo[e]imidazo[2,1-c]pyrrolo[1,2-a] [1,4]diazepin-7-yl) pyrrolidin-3-ol, 351. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (3R,4R)-4-(dimethylamino)pyrrolidin-3-ol. 1H NMR (400 MHz, METHANOL-d4) δ=7.98 (s, 1H), 7.70 (s, 1H), 7.61-7.52 (m, 4H), 7.18 (s, 1H), 7.09 (t, J=8.8 Hz, 2H), 6.91 (d, J=2.3 Hz, 1H), 6.84 (dd, J=2.5, 8.8 Hz, 1H), 5.28 (s, 2H), 4.72 (q, J=7.0 Hz, 1H), 4.00-3.80 (m, 3H), 3.60 (dd, J=7.2, 10.2 Hz, 1H), 3.33 (br. s., 1H), 3.06 (s, 6H). ESI [M+H]=444.2

225

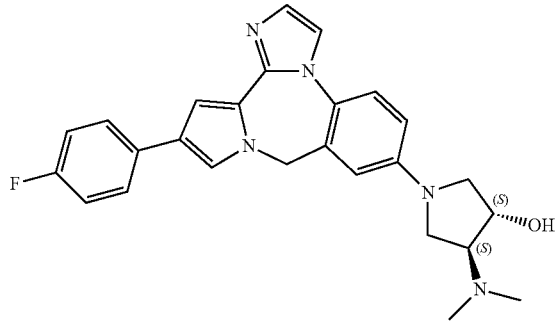

(3S,4S)-4-(dimethylamino)-1-(12-(4-fluorophenyl)-9H-benzo[e]imidazo[2,1-c]pyrrolo[1,2-a] [1,4]diazepin-7-yl)pyrrolidin-3-ol, 352. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (3S,4S)-4-(dimethylamino)pyrrolidin-3-ol. 1H NMR (400 MHz, METHANOL-d4) δ=8.00 (d, J=1.5 Hz, 1H), 7.72 (d, J=1.8 Hz, 1H), 7.62-7.52 (m, 4H), 7.19 (s, 1H), 7.08 (t, J=8.7 Hz, 2H), 6.91 (d, J=2.2 Hz, 1H), 6.83 (dd, J=2.3, 8.9 Hz, 1H), 5.29 (s, 2H), 4.77-4.68 (m, 1H), 3.98-3.82 (m, 3H), 3.61 (dd, J=7.3, 9.9 Hz, 1H), 3.36-3.31 (m, 1H), 3.06 (s, 6H). ESI [M+H]=444.2

226

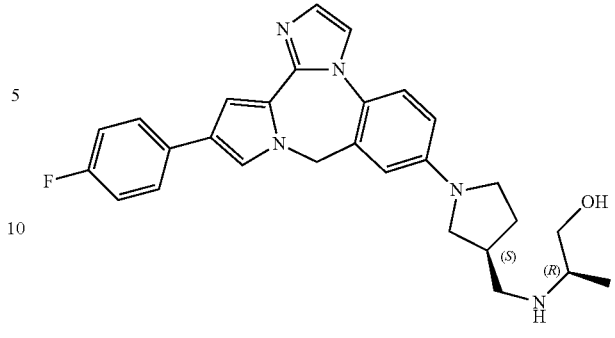

(R)-2-((((S)-1-(12-(4-fluorophenyl)-9H-benzo[e]imidazo[2,1-c]pyrrolo[1,2-a][1,4]diazepin-7-yl)pyrrolidin-3-yl)methyl)amino)propan-1-ol, 354. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (R)-2(((R)-pyrrolidin-3-yl methyl) amino)propan-1-ol. 1H NMR (400 MHz, METHANOL-d4) δ=7.98 (d, J=1.8 Hz, 1H), 7.71 (d, J=2.0 Hz, 1H), 7.61-7.49 (m, 4H), 7.18 (d, J=1.5 Hz, 1H), 7.08 (t, J=8.7 Hz, 2H), 6.81 (d, J=2.2 Hz, 1H), 6.75 (dd, J=2.4, 8.8 Hz, 1H), 5.33-5.20 (m, 2H), 3.89-3.77 (m, 1H), 3.71-3.50 (m, 3H), 3.48-3.34 (m, 2H), 3.25-3.08 (m, 3H), 2.75 (td, J=7.3, 14.9 Hz, 1H), 2.36 (dt, J=6.8, 11.4 Hz, 1H), 1.96-1.86 (m, 1H), 1.41-1.26 (m, 3H). ESI [M+H]=472.2

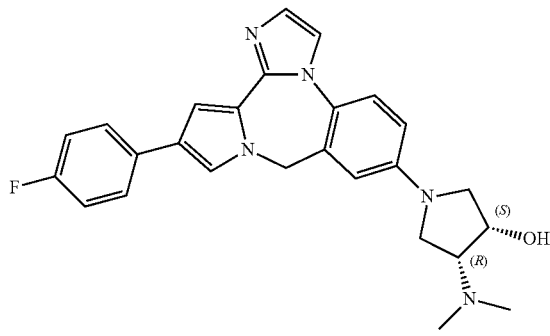

(3S,4R)-4-(dimethylamino)-1-(12-(4-fluorophenyl)-9H-benzo[e]imidazo[2,1-c]pyrrolo[1,2-a] [1,4]diazepin-7-yl)pyrrolidin-3-ol, 353. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (3S,4R)-4-(dimethylamino)pyrrolidin-3-ol. 1H NMR (400 MHz, METHANOL-d4) δ=8.01 (br. s., 1H), 7.73 (br. s., 1H), 7.63-7.52 (m, 4H), 7.20 (br. s., 1H), 7.09 (t, J=8.8 Hz, 2H), 6.88 (br. s., 1H), 6.82 (d, J=8.8 Hz, 1H), 5.29 (s, 2H), 4.70 (br. s., 1H), 3.95 (d, J=3.5 Hz, 2H), 3.72 (dd, J=3.1, 11.0 Hz, 1H), 3.64-3.52 (m, 2H), 3.03 (br. s., 6H). ESI [M+H]=444.1

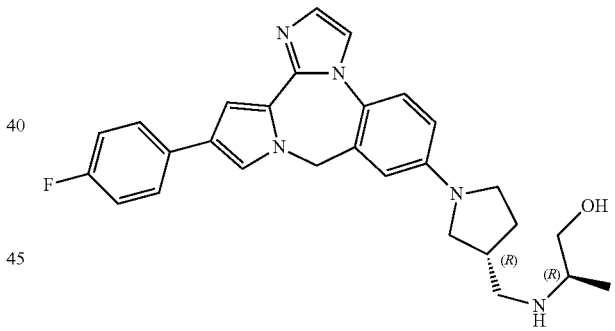

(R)-2-((((R)-1-(12-(4-fluorophenyl)-9H-benzo[e]imidazo[2,1-c]pyrrolo[1,2-a][1,4]diazepin-7-yl)pyrrolidin-3-yl)methyl)amino)propan-1-ol, 355. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (R)-2-(((S)-pyrrolidin-3-ylmethyl) amino)propan-1-ol. 1H NMR (400 MHz, METHANOL-d4) δ=7.98 (s, 1H), 7.71 (s, 1H), 7.62-7.50 (m, 4H), 7.18 (s, 1H), 7.09 (t, J=8.8 Hz, 2H), 6.81 (d, J=2.3 Hz, 1H), 6.75 (dd, J=2.3, 9.0 Hz, 1H), 5.26 (s, 2H), 3.84 (dd, J=3.7, 11.9 Hz, 1H), 3.68-3.52 (m, 3H), 3.49-3.37 (m, 2H), 3.27-3.16 (m, 3H), 2.76 (td, J=7.3, 14.8 Hz, 1H), 2.37 (dd, J=4.3, 11.7 Hz, 1H), 1.99-1.87 (m, 1H), 1.35 (d, J=7.0 Hz, 3H). ESI [M+H]=472.2

227

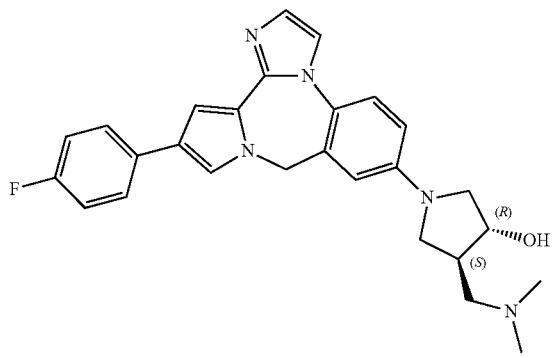

(3R,4S)-4-((dimethylamino)methyl)-1-(12-(4-fluorophenyl)-9H-benzo[e]imidazo[2,1-c] pyrrolo[1,2-a][1,4]diazepin-7-yl)pyrrolidin-3-ol, 356. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine and replacing tert-butyl piperazine-1-carboxylate with (3R,4R)-4-((dimethylamino) methyl)pyrrolidin-3-ol. 1H NMR (400 MHz, METHANOL-d4) δ=8.00 (d, J=1.8 Hz, 1H), 7.75 (s, 1H), 7.62-7.53 (m, 4H), 7.19 (s, 1H), 7.09 (t, J=8.6 Hz, 2H), 6.82 (s, 2H), 5.28 (s, 2H), 4.34-4.26 (m, 1H), 3.81-3.73 (m, 2H), 3.44-3.35 (m, 2H), 3.28-3.16 (m, 2H), 3.00 (br. s., 6H), 2.78-2.66 (m, 1H). ESI [M+H]=458.1

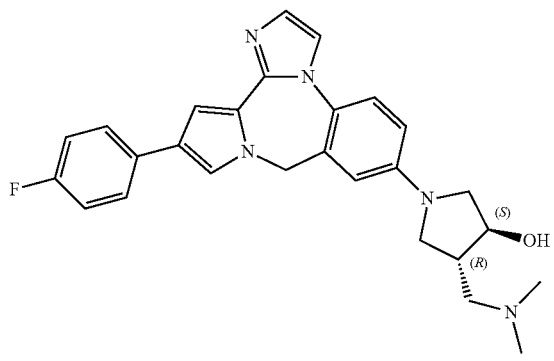

(3S,4R)-4-((dimethylamino)methyl)-1-(12-(4-fluorophenyl)-9H-benzo[e]imidazo[2,1-c] pyrrolo[1,2-a][1,4]diazepin-7-yl)pyrrolidin-3-ol 357. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine and replacing tert-butyl piperazine-1-carboxylate with (3S,4S)-4-((dimethylamino) methyl)pyrrolidin-3-ol. 1H NMR (400 MHz, METHANOL-d4) δ=8.00 (s, 1H), 7.74 (d, J=1.3 Hz, 1H), 7.62-7.53 (m, 4H), 7.19 (s, 1H), 7.09 (t, J=8.6 Hz, 2H), 6.82 (s, 1H), 6.76 (d, J=8.8 Hz, 1H), 5.28 (s, 2H), 4.30 (q, J=6.6 Hz, 1H), 3.81-3.72 (m, 2H), 3.45-3.33 (m, 2H), 3.28-3.19 (m, 2H), 2.99 (s, 6H), 2.77-2.67 (m, 1H). ESI [M+H]=458.1

228

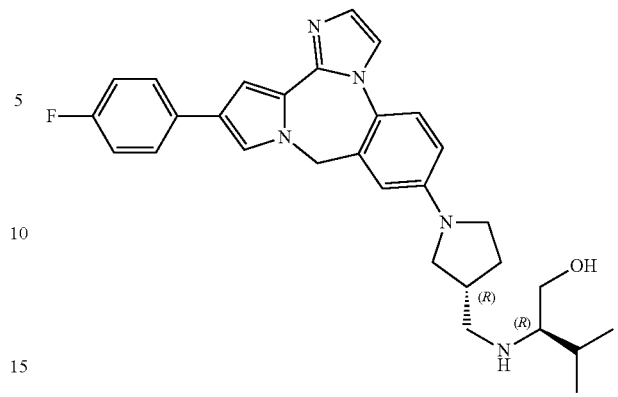

(R)-2-((((R)-1-(12-(4-fluorophenyl)-9H-benzo[e]imidazo[2,1-c]pyrrolo[1,2-a][1,4]diazepin-7-yl)pyrrolidin-3-yl) methyl)amino)-3-methylbutan-1-ol, 358. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a] [1,4]diazepine and replacing tert-butyl piperazine-1-carboxylate with (R)-3-methyl-2-(((S)-pyrrolidin-3-ylmethyl) amino)butan-1-ol. 1H NMR (400 MHz, METHANOL-d4) δ=7.93 (br. s., 1H), 7.66 (br. s., 1H), 7.60-7.48 (m, 4H), 7.15 (br. s., 1H), 7.08 (t, J=8.6 Hz, 2H), 6.81 (br. s., 1H), 6.75 (d, J=8.8 Hz, 1H), 5.24 (s, 2H), 3.91 (dd, J=3.5, 12.1 Hz, 1H), 3.76 (dd, J=6.6, 12.1 Hz, 1H), 3.70-3.62 (m, 1H), 3.54 (d, J=4.9 Hz, 1H), 3.49-3.39 (m, 2H), 3.25-3.17 (m, 2H), 3.11 (d, J=4.0 Hz, 1H), 2.85-2.74 (m, 1H), 2.39 (d, J=6.4 Hz, 1H), 2.15 (dt, J=6.9, 13.5 Hz, 1H), 2.00-1.89 (m, 1H), 1.11 (d, J=6.8 Hz, 3H), 1.05 (d, J=6.6 Hz, 3H). ESI [M+H]=500.3

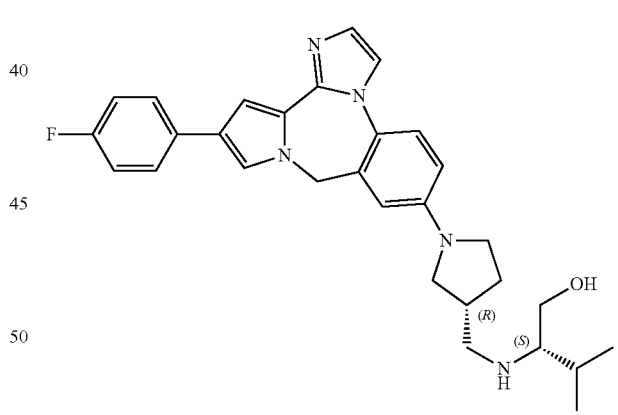

(S)-2-((((R)-1-(12-(4-fluorophenyl)-9H-benzo[e]imidazo[2,1-c]pyrrolo[1,2-a][1,4]diazepin-7-yl)pyrrolidin-3-yl) methyl)amino)-3-methylbutan-1-ol, 359. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a] [1,4]diazepine and replacing tert-butyl piperazine-1-carboxylate with (S)-3-methyl-2-(((S)-pyrrolidin-3-ylmethyl)amino)butan-1-ol. 1H NMR (400 MHz, METHANOL-d4) δ=7.98 (br. s., 1H), 7.71 (s, 1H), 7.64-7.50 (m, 4H), 7.19 (s, 1H), 7.09 (t, J=8.4 Hz, 2H), 6.84 (br. s., 1H), 6.75 (d, J=8.6 Hz, 1H), 5.28 (br. s., 2H), 3.91 (d, J=12.1 Hz, 1H), 3.78 (dd, J=6.8, 11.9 Hz, 1H), 3.69

(t, J=8.4 Hz, 1H), 3.54 (br. s., 1H), 3.49-3.35 (m, 2H), 3.29-3.19 (m, 2H), 3.13 (br. s., 1H), 2.88-2.75 (m, 1H), 2.38 (d, J=6.7 Hz, 1H), 2.23-2.10 (m, 1H), 2.01-1.87 (m, 1H), 1.22-0.96 (m, 6H). ESI [M+H]=500.2

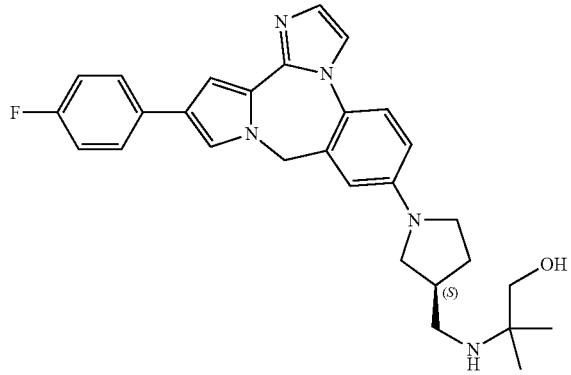

(S)-2-(((1-(12-(4-fluorophenyl)-9H-benzo[e]imidazo[2,1-c]pyrrolo[1,2-a][1,4]diazepin-7-yl) pyrrolidin-3-yl)methyl)amino)-2-methylpropan-1-ol, 360. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (R)-2-methyl-2-((pyrrolidin-3-ylmethyl) amino)propan-1-ol. 1H NMR (400 MHz, METHANOL-d4) δ=7.95 (br. s., 1H), 7.67 (br. s., 1H), 7.62-7.49 (m, 4H), 7.16 (br. s., 1H), 7.08 (t, J=8.6 Hz, 2H), 6.81 (br. s., 1H), 6.75 (d, J=8.8 Hz, 1H), 5.25 (s, 2H), 3.71-3.62 (m, 1H), 3.57 (s, 2H), 3.49-3.39 (m, 1H), 3.25-3.18 (m, 2H), 3.17-3.08 (m, 2H), 2.74-2.64 (m, 1H), 2.38 (d, J=6.6 Hz, 1H), 1.94 (dd, J=8.3, 12.2 Hz, 1H), 1.35 (s, 6H). ESI [M+H]=486.2

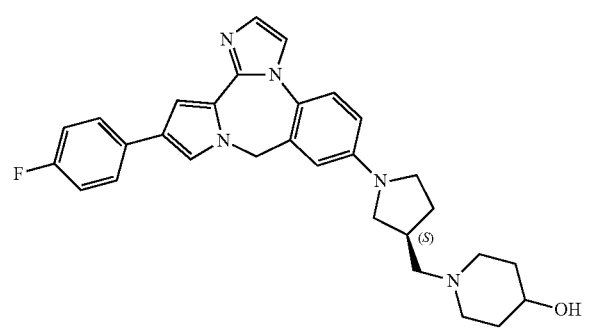

(S)-1-((1-(12-(4-fluorophenyl)-9H-benzo[e]imidazo[2,1-c]pyrrolo[1,2-a][1,4]diazepin-7-yl) pyrrolidin-3-yl)methyl)piperidin-4-ol, 361. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (R)-1-(pyrrolidin-3-ylmethyl)piperidin-4-ol. ¹H NMR (400 MHz, METHANOL-d₄) δ=8.01 (d, J=2.2 Hz, 1H), 7.74 (d, J=1.8 Hz, 1H), 7.63 (s, 1H), 7.61-7.51 (m, 3H), 7.20 (s, 1H), 7.09 (t, J=8.8 Hz, 2H), 6.85 (d, J=2.2 Hz, 1H), 6.76 (dd, J=2.2, 8.8 Hz, 1H), 5.29 (s, 2H), 4.11 (br. s., 1H), 3.91-3.80 (m, 1H), 3.77-3.63 (m, 1H), 3.60-3.39 (m, 3H), 3.33 (br. s., 2H), 3.25-3.17 (m, 1H), 3.11 (t, J=12.3 Hz, 1H), 2.90 (td, J=7.6, 14.8 Hz, 1H), 2.36 (br. s., 1H), 2.21-2.05 (m, 2H), 1.99-1.74 (m, 3H). ESI [M+H]=498.2

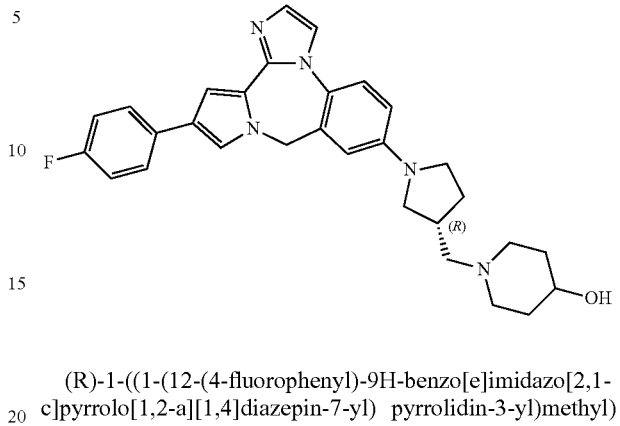

(R)-1-((1-(12-(4-fluorophenyl)-9H-benzo[e]imidazo[2,1-c]pyrrolo[1,2-a][1,4]diazepin-7-yl) pyrrolidin-3-yl)methyl)piperidin-4-ol, 362. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (S)-1-(pyrrolidin-3-ylmethyl)piperidin-4-ol. 1H NMR (400 MHz, METHANOL-d4) δ=7.98 (d, J=1.8 Hz, 1H), 7.72 (d, J=2.2 Hz, 1H), 7.60-7.50 (m, 4H), 7.18 (d, J=1.3 Hz, 1H), 7.07 (t, J=8.6 Hz, 2H), 6.80 (d, J=2.2 Hz, 1H), 6.74 (dd, J=2.4, 9.0 Hz, 1H), 5.26 (s, 2H), 4.10 (br. s., 1H), 3.83 (br. s., 1H), 3.68 (t, J=8.6 Hz, 2H), 3.57-3.49 (m, 1H), 3.48-3.37 (m, 2H), 3.35 (br. s., 2H), 3.22-3.01 (m, 2H), 2.87 (br. s., 1H), 2.34 (br. s., 1H), 2.21-1.99 (m, 2H), 1.97-1.71 (m, 3H). ESI [M+H]=498.2

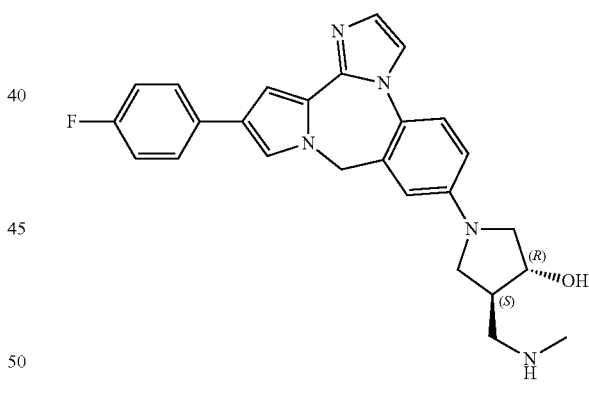

(3R,4S)-1-(12-(4-fluorophenyl)-9H-benzo[e]imidazo[2,1-c]pyrrolo[1,2-a][1,4]diazepin-7-yl)-4-((methylamino)methyl)pyrrolidin-3-ol, 363. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine. ¹H NMR (400 MHz, METHANOL-d₄) δ=7.97 (d, J=1.8 Hz, 1H), 7.71 (d, J=1.8 Hz, 1H), 7.61-7.49 (m, 4H), 7.17 (d, J=1.8 Hz, 1H), 7.07 (t, J=8.8 Hz, 2H), 6.80 (d, J=2.6 Hz, 1H), 6.73 (dd, J=2.6, 8.8 Hz, 1H), 5.26 (s, 2H), 4.30 (q, J=6.3 Hz, 1H), 3.78-3.65 (m, 2H), 3.26-3.09 (m, 4H), 2.76 (s, 3H), 2.64-2.52 (m, 1H). ESI [M+H]=444.1

231

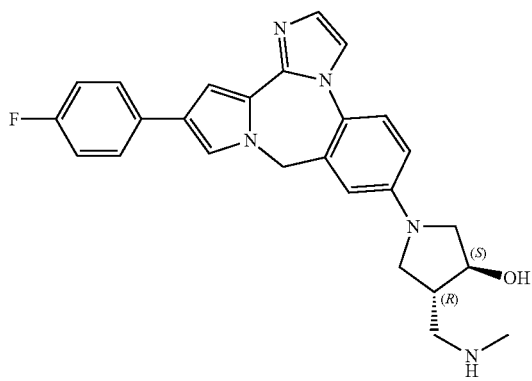

232

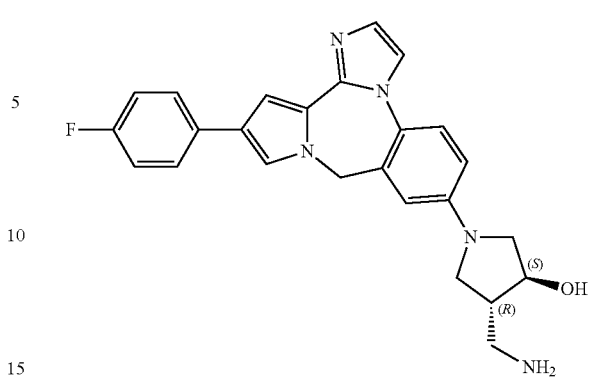

(3S,4R)-1-(12-(4-fluorophenyl)-9H-benzo[e]imidazo[2,1-c]pyrrolo[1,2-a][1,4]diazepin-7-yl)-4-((methylamino)methyl)pyrrolidin-3-ol, 364. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((3R,4R)-4-hydroxypyrrolidin-3-yl)methyl)(methyl)carbamate with benzyl (((3S,4S)-4-hydroxy pyrrolidin-3-yl)methyl)(methyl)carbamate. 1H NMR (400 MHz, METHANOL-d4) δ=7.98 (d, J=1.8 Hz, 1H), 7.72 (d, J=1.8 Hz, 1H), 7.60-7.51 (m, 4H), 7.17 (d, J=1.8 Hz, 1H), 7.08 (t, J=8.6 Hz, 2H), 6.80 (d, J=2.2 Hz, 1H), 6.73 (dd, J=2.2, 8.8 Hz, 1H), 5.26 (s, 2H), 4.30 (q, J=6.5 Hz, 1H), 3.77-3.66 (m, 2H), 3.26-3.12 (m, 4H), 2.75 (s, 3H), 2.61-2.54 (m, 1H). ESI [M+H]=444.1

(3S,4R)-4-(aminomethyl)-1-(12-(4-fluorophenyl)-9H-benzo[e]imidazo[2,1-c]pyrrolo[1,2-a][1,4]diazepin-7-yl)pyrrolidin-3-ol, 366. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((3R,4R)-4-hydroxypyrrolidin-3-yl)methyl)(methyl)carbamate with benzyl (((3S,4S)-4-hydroxypyrrolidin-3-yl)methyl)carbamate. 1H NMR (400 MHz, METHANOL-d4) δ=7.99 (s, 1H), 7.73 (s, 1H), 7.64-7.50 (m, 4H), 7.19 (s, 1H), 7.09 (t, J=8.4 Hz, 2H), 6.82 (br. s., 1H), 6.75 (d, J=9.0 Hz, 1H), 5.28 (s, 2H), 4.32 (d, J=6.1 Hz, 1H), 3.78-3.66 (m, 2H), 3.28-2.99 (m, 4H), 2.59-2.49 (m, 1H). ESI [M+H]=430.1

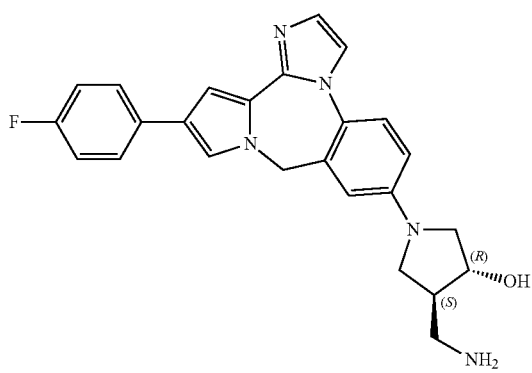

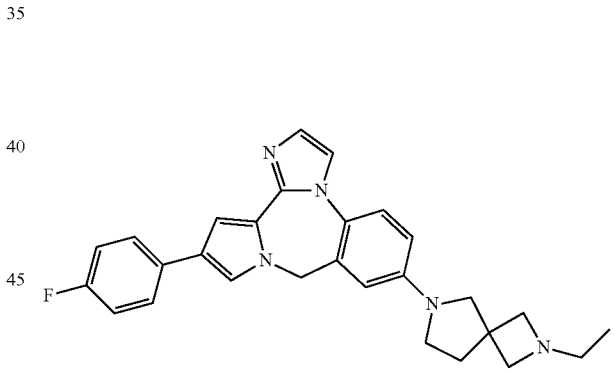

(3R,4S)-4-(aminomethyl)-1-(12-(4-fluorophenyl)-9H-benzo[e]imidazo[2,1-c]pyrrolo[1,2-a][1,4]diazepin-7-yl)pyrrolidin-3-ol, 365. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((3R,4R)-4-hydroxypyrrolidin-3-yl)methyl)(methyl)carbamate with benzyl (((3R,4R)-4-hydroxypyrrolidin-3-yl)methyl) carbamate. 1H NMR (400 MHz, METHANOL-d4) δ=7.93 (br. s., 1H), 7.65 (br. s., 1H), 7.62-7.46 (m, 4H), 7.15 (br. s., 1H), 7.08 (t, J=8.7 Hz, 2H), 6.82 (br. s., 1H), 6.74 (d, J=9.0 Hz, 1H), 5.25 (s, 2H), 4.32 (d, J=6.0 Hz, 1H), 3.73 (dd, J=7.3, 17.0 Hz, 2H), 3.48 (s, 2H), 3.09 (dd, J=12.3, 19.8 Hz, 2H), 2.54 (d, J=6.6 Hz, 1H). ESI [M+H]=430.1

7-(2-ethyl-2,6-diazaspiro[3.4]octan-6-yl)-12-(4-fluorophenyl)-9H-benzo[e]imidazo[2,1-c]pyrrolo[1,2-a][1,4]diazepine, 367. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl (azetidin-3-ylmethyl)(methyl)carbamate with tert-butyl 2,6-diazaspiro[3.4]octane-2-carboxylate and replacing formaldehyde with acetaldehyde. 1H NMR (400 MHz, METHANOL-d4) δ=7.58-7.48 (m, 3H), 7.35 (d, J=8.6 Hz, 1H), 7.27 (s, 1H), 7.17 (s, 1H), 7.03 (t, J=8.1 Hz, 2H), 6.89 (s, 1H), 6.72 (br. s., 1H), 6.64 (d, J=8.8 Hz, 1H), 5.04 (s, 2H), 3.48 (s, 2H), 3.40-3.33 (m, 6H), 2.61 (d, J=7.0 Hz, 2H), 2.24 (t, J=6.5 Hz, 2H), 1.02 (t, J=6.7 Hz, 3H). ESI [M+H]=454.1

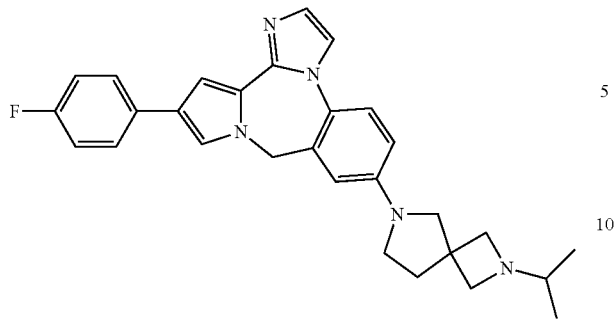

12-(4-fluorophenyl)-7-(2-isopropyl-2,6-diazaspiro[3.4]octan-6-yl)-9H-benzo[e]imidazo[2,1-c]pyrrolo[1,2-a][1,4]diazepine, 368. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl (azetidin-3-ylmethyl)(methyl)carbamate with tert-butyl 2,6-diazaspiro[3.4]octane-2-carboxylate and replacing formaldehyde with propan-2-one. 1H NMR (400 MHz, METHANOL-d4) δ=7.56-7.47 (m, 3H), 7.35 (d, J=8.8 Hz, 1H), 7.27 (s, 1H), 7.17 (s, 1H), 7.03 (t, J=8.1 Hz, 2H), 6.89 (s, 1H), 6.71 (br. s., 1H), 6.64 (d, J=8.8 Hz, 1H), 5.03 (s, 2H), 3.48 (br. s., 6H), 3.39 (t, J=6.5 Hz, 2H), 2.70 (br. s., 1H), 2.25 (t, J=6.3 Hz, 2H), 1.04 (d, J=5.7 Hz, 6H). ESI [M+H]=468.2

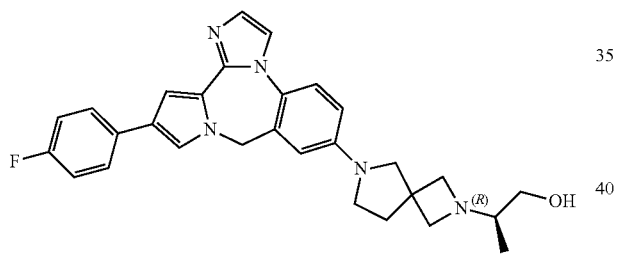

(R)-2-(6-(12-(4-fluorophenyl)-9H-benzo[e]imidazo[2,1-c]pyrrolo[1,2-a][1,4]diazepin-7-yl)-2,6-diazaspiro[3.4]octan-2-yl)propan-1-ol, 370. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl (azetidin-3-ylmethyl)(methyl)carbamate with tert-butyl 2,6-diazaspiro[3.4]octane-2-carboxylate and replacing formaldehyde with 1-hydroxypropan-2-one. SFC separation using General Procedure E, replacing 4-(7-(2-((dimethylamino)methyl) morpholino)-9H-benzo[e]pyrrolo[1,2-a][1,2,4]triazolo[3,4-c][1,4]diazepin-12-yl)benzonitrile with 2-(6-(12-(4-fluorophenyl)-9H-benzo[e]imidazo[2, 1-c]pyrrolo[1,2-a] [1,4] diazepin-7-yl)-2,6-diazaspiro[3.4] octan-2-yl) propan-1-ol. 1H NMR (400 MHz, METHANOL-d4) δ=7.54-7.46 (m, 3H), 7.32 (d, J=8.8 Hz, 1H), 7.26 (d, J=1.8 Hz, 1H), 7.15 (d, J=1.1 Hz, 1H), 7.01 (t, J=8.8 Hz, 2H), 6.87 (d, J=1.8 Hz, 1H), 6.69 (d, J=2.4 Hz, 1H), 6.61 (dd, J=2.6, 8.8 Hz, 1H), 5.00 (s, 2H), 3.48-3.36 (m, 10H), 2.55 (br. s., 1H), 2.27-2.16 (m, 2H), 0.98 (d, J=6.4 Hz, 3H). ESI [M+H]=484.2

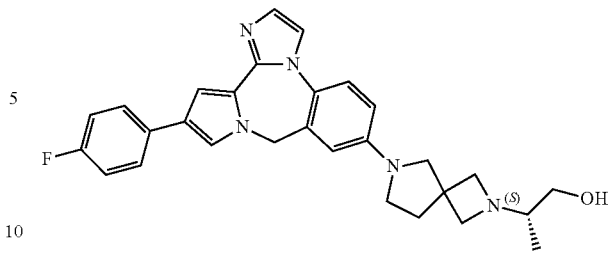

(S)-2-(6-(12-(4-fluorophenyl)-9H-benzo[e]imidazo[2,1-c]pyrrolo[1,2-a][1,4]diazepin-7-yl)-2,6-diazaspiro[3.4]octan-2-yl)propan-1-ol, 371. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4] diazepine, replacing tert-butyl (azetidin-3-ylmethyl)(methyl)carbamate with tert-butyl 2,6-diazaspiro[3.4]octane-2-carboxylate and replacing formaldehyde with 1-hydroxypropan-2-one. SFC separation using General Procedure E, replacing 4-(7-(2-((dimethylamino)methyl) morpholino)-9H-benzo[e]pyrrolo[1,2-a][1,2,4]triazolo[3,4-c][1,4]diazepin-12-yl)benzonitrile with 2-(6-(12-(4-fluorophenyl)-9H-benzo[e]imidazo[2,1-c]pyrrolo[1,2-a][1,4]diazepin-7-yl)-2,6-diazaspiro[3.4]octan-2-yl) propan-1-ol. 1H NMR (400 MHz, METHANOL-d4) δ=7.55-7.48 (m, 3H), 7.32 (d, J=8.6 Hz, 1H), 7.26 (d, J=1.8 Hz, 1H), 7.16 (s, 1H), 7.01 (t, J=8.8 Hz, 2H), 6.87 (d, J=1.5 Hz, 1H), 6.69 (d, J=2.4 Hz, 1H), 6.61 (dd, J=2.4, 8.8 Hz, 1H), 5.03-4.98 (m, 2H), 3.47-3.42 (m, 2H), 3.38-3.31 (m, 8H), 2.45 (d, J=6.0 Hz, 1H), 2.21 (t, J=6.7 Hz, 2H), 0.96 (d, J=6.4 Hz, 3H). ESI [M+H]=484.1

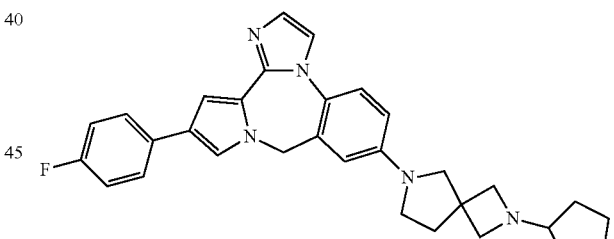

7-(2-cyclopentyl-2,6-diazaspiro[3.4]octan-6-yl)-12-(4-fluorophenyl)-9H-benzo[e]imidazo[2,1-c]pyrrolo[1,2-a][1,4]diazepine, 375. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl (azetidin-3-ylmethyl)(methyl)carbamate with tert-butyl 2,6-diazaspiro[3.4]octane-2-carboxylate and replacing formaldehyde with cyclopentanone. 1H NMR (400 MHz, METHANOL-d4) δ=7.59-7.47 (m, 3H), 7.37-7.24 (m, 2H), 7.17 (s, 1H), 7.02 (t, J=8.6 Hz, 2H), 6.89 (s, 1H), 6.68 (br. s., 1H), 6.61 (d, J=8.6 Hz, 1H), 5.00 (s, 2H), 3.43 (s, 2H), 3.28 (br. s., 6H), 2.85 (d, J=5.7 Hz, 1H), 2.20 (t, J=6.5 Hz, 2H), 1.80-1.49 (m, 6H), 1.32 (d, J=5.3 Hz, 2H). ESI [M+H]=494.2

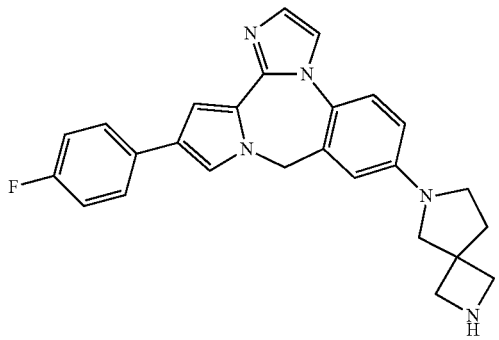 [SMILES: Fc1ccc(-c2cc3n(c2)Cc2cc(N4CCC5(CNC5)C4)ccc2-n2ccnc2-3)cc1]

12-(4-fluorophenyl)-7-(2,6-diazaspiro[3.4]octan-6-yl)-9H-benzo[e]imidazo[2,1-c]pyrrolo[1,2-a][1,4]diazepine, 376. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with tert-butyl 2,6-diazaspiro[3.4]octane-2-carboxylate. 1H NMR (400 MHz, CHLOROFORM-d) δ=7.42 (dd, J=5.5, 8.6 Hz, 2H), 7.30 (s, 1H), 7.24-7.18 (m, 2H), 7.05-6.92 (m, 4H), 6.57-6.46 (m, 2H), 4.93 (br. s., 2H), 3.70-3.54 (m, 4H), 3.50 (s, 2H), 3.34 (t, J=6.6 Hz, 2H), 2.24 (t, J=6.6 Hz, 2H). ESI [M+H]=426.1

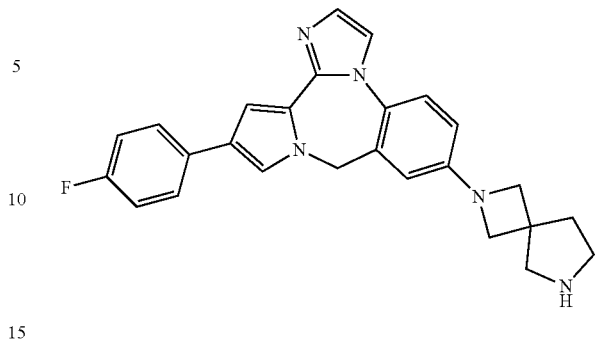

12-(4-fluorophenyl)-7-(2,6-diazaspiro[3.4]octan-2-yl)-9H-benzo[e]imidazo[2,1-c]pyrrolo[1,2-a][1,4]diazepine, 378. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with tert-butyl 2,6-diazaspiro[3.4]octane-6-carboxylate. 1H NMR (400 MHz, METHANOL-d4) δ=8.01 (d, J=2.0 Hz, 1H), 7.79-7.72 (m, 1H), 7.63-7.50 (m, 4H), 7.20 (d, J=1.5 Hz, 1H), 7.09 (t, J=8.8 Hz, 2H), 6.74 (d, J=2.4 Hz, 1H), 6.66 (dd, J=2.4, 8.8 Hz, 1H), 5.34-5.20 (m, 2H), 4.08-3.94 (m, 4H), 3.58-3.49 (m, 2H), 3.43-3.34 (m, 2H), 2.36 (t, J=7.4 Hz, 2H). ESI [M+H]=426.2

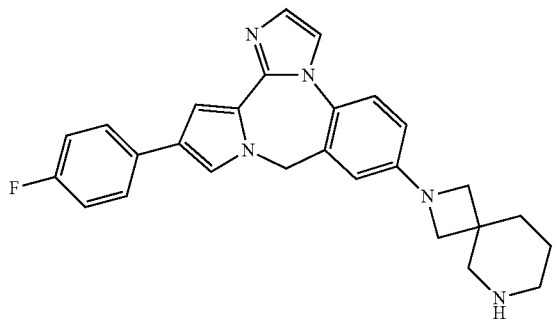 [SMILES: Fc1ccc(-c2cc3n(c2)Cc2cc(N4CC5(CCCNC5)C4)ccc2-n2ccnc2-3)cc1]

12-(4-fluorophenyl)-7-(2,6-diazaspiro[3.5]nonan-2-yl)-9H-benzo[e]imidazo[2,1-c]pyrrolo[1,2-a][1,4]diazepine, 377. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with tert-butyl 2,6-diazaspiro[3.5]nonane-6-carboxylate. ¹H NMR (400 MHz, METHANOL-d₄) δ=7.99 (d, J=2.2 Hz, 1H), 7.73 (d, J=2.2 Hz, 1H), 7.61-7.49 (m, 4H), 7.18 (d, J=1.8 Hz, 1H), 7.08 (t, J=8.6 Hz, 2H), 6.70 (d, J=2.6 Hz, 1H), 6.63 (dd, J=2.6, 8.8 Hz, 1H), 5.26 (s, 2H), 3.86 (d, J=7.5 Hz, 2H), 3.76 (d, J=7.5 Hz, 2H), 3.40 (s, 2H), 3.14 (t, J=5.5 Hz, 2H), 2.04-1.93 (m, 2H), 1.86 (d, J=4.9 Hz, 2H). ESI [M+H]=440.2

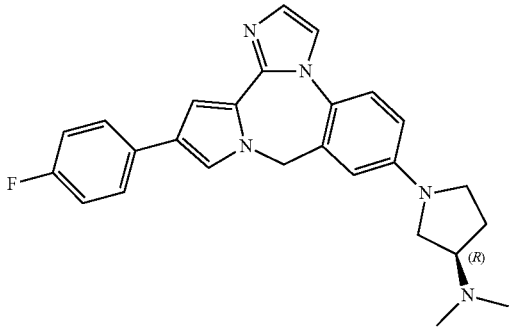

(R)-1-(12-(4-fluorophenyl)-9H-benzo[e]imidazo[2,1-c]pyrrolo[1,2-a][1,4]diazepin-7-yl)-N,N-dimethylpyrrolidin-3-amine, 379. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl piperazine-1-carboxylate with (R)—N,N-dimethylpyrrolidin-3-amine. ¹H NMR (400 MHz, METHANOL-d₄) δ=8.02 (br. s., 1H), 7.75 (br. s., 1H), 7.65-7.49 (m, 4H), 7.21 (s, 1H), 7.09 (t, J=8.6 Hz, 2H), 6.91 (d, J=2.2 Hz, 1H), 6.84 (dd, J=2.2, 8.8 Hz, 1H), 5.30 (s, 2H), 4.09 (quin, J=7.3 Hz, 1H), 3.83 (dd, J=7.5, 10.6 Hz, 1H), 3.74-3.58 (m, 2H), 3.52-3.41 (m, 1H), 2.99 (s, 6H), 2.67-2.54 (m, 1H), 2.41-2.24 (m, 1H). ESI [M+H]=428.2

237

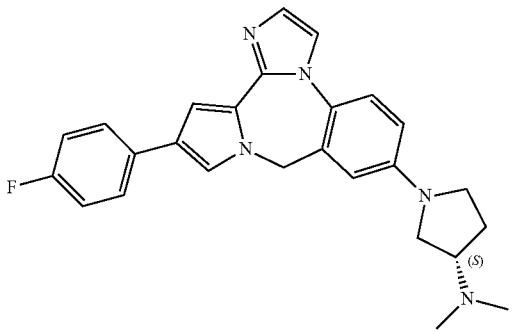

(S)-1-(12-(4-fluorophenyl)-9H-benzo[e]imidazo[2,1-c]pyrrolo[1,2-a][1,4]diazepin-7-yl)-N,N-dimethylpyrrolidin-3-amine, 380. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl piperazine-1-carboxylate with (S)—N,N-dimethylpyrrolidin-3-amine. $^1$H NMR (400 MHz, METHANOL-d$_4$) δ=8.02 (d, J=2.2 Hz, 1H), 7.75 (d, J=2.2 Hz, 1H), 7.63-7.51 (m, 4H), 7.21 (d, J=1.3 Hz, 1H), 7.08 (t, J=8.6 Hz, 2H), 6.92 (d, J=2.2 Hz, 1H), 6.84 (dd, J=2.4, 9.0 Hz, 1H), 5.30 (s, 2H), 4.09 (quin, J=7.2 Hz, 1H), 3.83 (dd, J=7.5, 10.6 Hz, 1H), 3.75-3.60 (m, 2H), 3.51-3.40 (m, 1H), 2.99 (s, 6H), 2.67-2.56 (m, 1H), 2.42-2.29 (m, 1H). ESI [M+H]=428.2

238

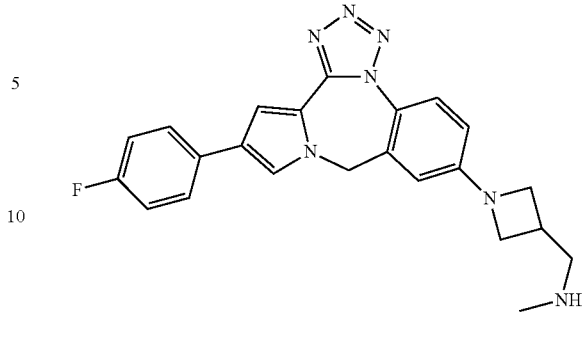

1-(1-(12-(4-fluorophenyl)-9H-benzo[e]pyrrolo[1,2-a]tetrazolo[5,1-c][1,4]diazepin-7-yl) azetidin-3-yl)-N-methylmethanamine, 386. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine, replacing tert-butyl piperazine-1-carboxylate with tert-butyl (azetidin-3-ylmethyl)(methyl)carbamate. 1H NMR (400 MHz, METHANOL-d4) δ=7.79 (d, J=8.8 Hz, 1H), 7.57 (dd, J=5.3, 8.8 Hz, 2H), 7.49 (d, J=1.8 Hz, 1H), 7.24 (d, J=1.8 Hz, 1H), 7.08 (t, J=8.8 Hz, 2H), 6.69 (d, J=2.2 Hz, 1H), 6.65 (dd, J=2.5, 8.7 Hz, 1H), 5.23 (s, 2H), 4.17 (t, J=7.8 Hz, 2H), 3.80 (dd, J=5.3, 7.7 Hz, 2H), 3.39 (d, J=7.3 Hz, 2H), 3.12 (ddd, J=5.2, 7.5, 12.7 Hz, 1H), 2.77 (s, 3H). ESI [M+H]=416.1

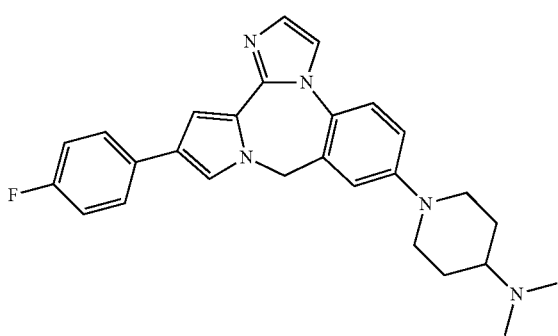 [SMILES: CN(C)C1CCN(c2ccc3c(c2)Cn2cc(-c4ccc(F)cc4)cc2-c2nccn2-3)CC1]

1-(12-(4-fluorophenyl)-9H-benzo[e]imidazo[2,1-c]pyrrolo[1,2-a][1,4]diazepin-7-yl)-N,N-dimethylpiperidin-4-amine, 381. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl (azetidin-3-ylmethyl)(methyl) carbamate with tert-butyl piperidin-4-ylcarbamate. 1H NMR (400 MHz, METHANOL-d4) δ=8.01 (d, J=1.8 Hz, 1H), 7.74 (s, 1H), 7.60-7.52 (m, 4H), 7.25 (d, J=2.2 Hz, 1H), 7.21-7.14 (m, 2H), 7.08 (t, J=8.8 Hz, 2H), 5.29 (s, 2H), 4.08 (d, J=13.2 Hz, 2H), 3.42 (t, J=12.1 Hz, 1H), 2.99-2.92 (m, 2H), 2.90-2.87 (m, 6H), 2.18 (d, J=11.5 Hz, 2H), 1.88-1.74 (m, 2H). ESI [M+H]=442.2

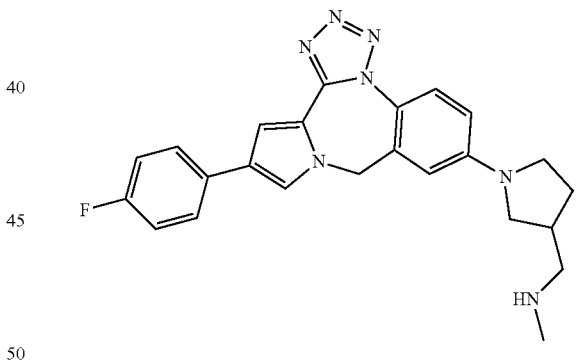

1-(1-(12-(4-fluorophenyl)-9H-benzo[e]pyrrolo[1,2-a]tetrazolo[5,1-c][1,4]diazepin-7-yl) pyrrolidin-3-yl)-N-methylmethanamine, 388. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4] diazepine and replacing tert-butyl piperazine-1-carboxylate with tert-butyl methyl(pyrrolidin-3-ylmethyl) carbamate. 1H NMR (400 MHz, METHANOL-d4) δ=7.78 (d, J=8.8 Hz, 1H), 7.57 (dd, J=5.4, 8.7 Hz, 2H), 7.49 (d, J=1.8 Hz, 1H), 7.23 (d, J=1.5 Hz, 1H), 7.07 (t, J=8.8 Hz, 2H), 6.81-6.72 (m, 2H), 5.19 (s, 2H), 3.67-3.61 (m, 2H), 3.56-3.46 (m, 1H), 3.23-3.13 (m, 3H), 2.82-2.69 (m, 4H), 2.41-2.29 (m, 1H), 1.91 (m, 1H). ESI [M+H]=430.2

239

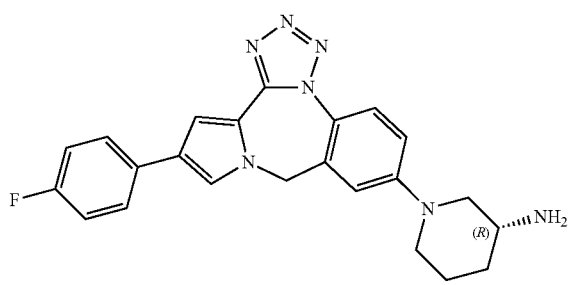

(R)-1-(12-(4-fluorophenyl)-9H-benzo[e]pyrrolo[1,2-a]tetrazolo[5,1-c][1,4]diazepin-7-yl) piperidin-3-amine, 389. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with (R)-tert-butyl piperidin-3-ylcarbamate. 1H NMR (400 MHz, METHANOL-d4) δ=7.84 (d, J=8.8 Hz, 1H), 7.55 (dd, J=5.3, 8.4 Hz, 2H), 7.48 (d, J=1.8 Hz, 1H), 7.26-7.21 (m, 2H), 7.18 (dd, J=2.6, 8.8 Hz, 1H), 7.05 (t, J=8.8 Hz, 2H), 5.23 (s, 2H), 3.67 (dd, J=2.9, 12.6 Hz, 1H), 3.52-3.41 (m, 2H), 3.27-3.19 (m, 2H), 2.13-2.03 (m, 1H), 2.01-1.91 (m, 1H), 1.86-1.69 (m, 2H). ESI [M+H]=416.2

240

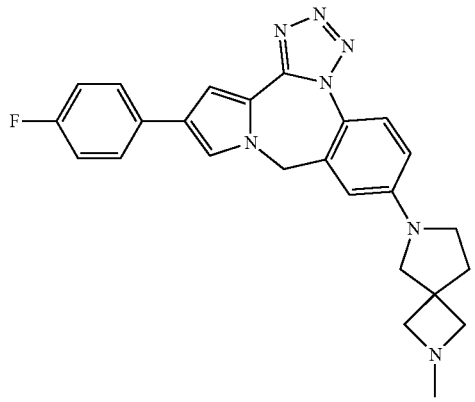

12-(4-fluorophenyl)-7-(2-methyl-2,6-diazaspiro[3.4]octan-6-yl)-9H-benzo[e]pyrrolo[1,2-a] tetrazolo[5,1-c][1,4]diazepine, 392. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine, replacing tert-butyl (azetidin-3-ylmethyl)(methyl)carbamate with tert-butyl 2,6-diazaspiro[3.4]octane-2-carboxylate. 1H NMR (400 MHz, METHANOL-d4) δ=7.78 (d, J=8.4 Hz, 1H), 7.56 (dd, J=5.3, 8.4 Hz, 2H), 7.49 (s, 1H), 7.22 (s, 1H), 7.06 (t, J=8.8 Hz, 2H), 6.83-6.72 (m, 2H), 5.20 (s, 2H), 3.65 (br. s., 2H), 3.52-3.44 (m, 2H), 3.34 (br. s., 4H), 2.99 (s, 3H), 2.40 (t, J=6.8 Hz, 2H). ESI [M+H]=442.2

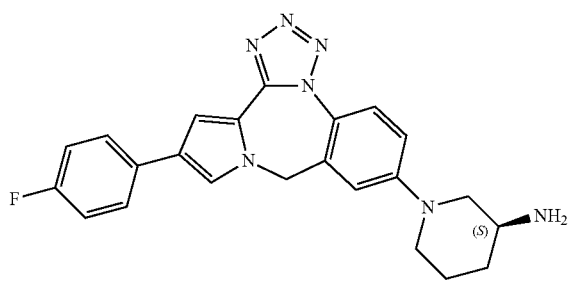

(S)-1-(12-(4-fluorophenyl)-9H-benzo[e]pyrrolo[1,2-a]tetrazolo[5,1-c][1,4]diazepin-7-yl) piperidin-3-amine, 390. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with (S)-tert-butyl piperidin-3-ylcarbamate. 1H NMR (400 MHz, METHANOL-d4) δ=7.83 (d, J=9.3 Hz, 1H), 7.55 (dd, J=5.3, 8.8 Hz, 2H), 7.49 (d, J=1.8 Hz, 1H), 7.23 (s, 2H), 7.18 (dd, J=2.4, 9.0 Hz, 1H), 7.06 (t, J=8.6 Hz, 2H), 5.26-5.19 (m, 2H), 3.69 (d, J=10.1 Hz, 1H), 3.54-3.44 (m, 1H), 3.40 (br. s., 1H), 3.25-3.14 (m, 2H), 2.05 (dd, J=4.2, 8.2 Hz, 1H), 1.94 (dd, J=3.7, 6.8 Hz, 1H), 1.79 (ddd, J=4.9, 8.8, 13.2 Hz, 2H). ESI [M+H]=416.2

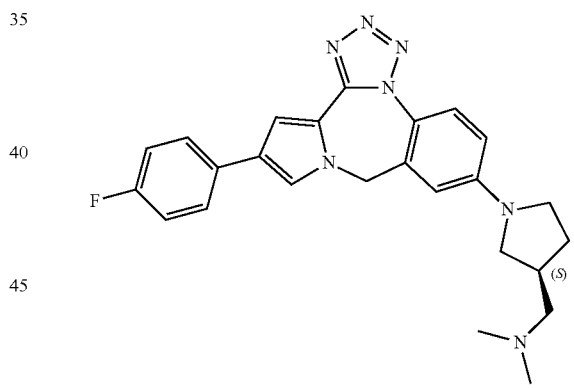

(S)-1-(1-(12-(4-fluorophenyl)-9H-benzo[e]pyrrolo[1,2-a]tetrazolo[5,1-c][1,4]diazepin-7-yl) pyrrolidin-3-yl)-N,N-dimethylmethanamine, 393. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4] diazepine, replacing tert-butyl (azetidin-3-ylmethyl)(methyl)carbamate with (S)-tert-butyl (pyrrolidin-3-ylmethyl)carbamate. 1H NMR (400 MHz, METHANOL-d4) δ=7.78 (d, J=8.8 Hz, 1H), 7.60-7.53 (m, 2H), 7.49 (s, 1H), 7.22 (d, J=1.8 Hz, 1H), 7.06 (t, J=8.6 Hz, 2H), 6.81-6.74 (m, 2H), 5.21 (s, 2H), 3.71-3.64 (m, 1H), 3.57 (s, 1H), 3.50-3.42 (m, 1H), 3.34 (br. s., 3H), 3.20-3.08 (m, 1H), 2.97 (s, 6H), 2.90-2.80 (m, 1H), 1.92-1.76 (m, 1H). ESI [M+H]=444.2

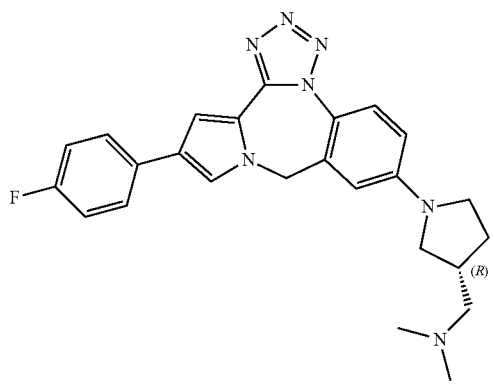

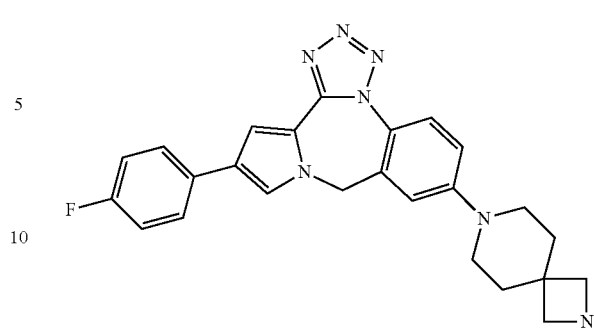

(R)-1-(1-(12-(4-fluorophenyl)-9H-benzo[e]pyrrolo[1,2-a]tetrazolo[5,1-c][1,4]diazepin-7-yl) pyrrolidin-3-yl)-N,N-dimethylmethanamine, 394. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4] diazepine, replacing tert-butyl (azetidin-3-ylmethyl)(methyl)carbamate with (R)-tert-butyl (pyrrolidin-3-ylmethyl)carbamate. 1H NMR (400 MHz, METHANOL-d4) δ=7.77 (d, J=8.8 Hz, 1H), 7.56 (dd, J=5.5, 8.6 Hz, 2H), 7.49 (d, J=1.3 Hz, 1H), 7.22 (d, J=1.8 Hz, 1H), 7.06 (t, J=8.8 Hz, 2H), 6.81-6.73 (m, 2H), 5.20 (s, 2H), 3.71-3.63 (m, 1H), 3.59-3.52 (m, 1H), 3.49-3.39 (m, 1H), 3.33 (s, 3H), 3.21-3.12 (m, 1H), 2.97 (s, 6H), 2.91-2.81 (m, 1H), 1.95-1.83 (m, 1H). ESI [M+H]=444.2

12-(4-fluorophenyl)-7-(2,7-diazaspiro[3.5]nonan-7-yl)-9H-benzo[e]pyrrolo[1,2-a]tetrazolo[5,1-c][1,4]diazepine, 402. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with tert-butyl 2,7-diazaspiro[3.5]nonane-2-carboxylate. 1H NMR (400 MHz, METHANOL-d4) δ=7.73 (d, J=9.3 Hz, 1H), 7.51 (dd, J=5.3, 8.8 Hz, 2H), 7.44 (d, J=1.3 Hz, 1H), 7.16 (dd, J=2.0, 12.1 Hz, 2H), 7.08 (dd, J=2.6, 8.8 Hz, 1H), 7.03 (t, J=8.8 Hz, 2H), 5.13 (s, 2H), 3.90 (s, 4H), 3.34-3.29 (m, 4H), 2.06-1.93 (m, 4H). ESI [M+H]= 442.2

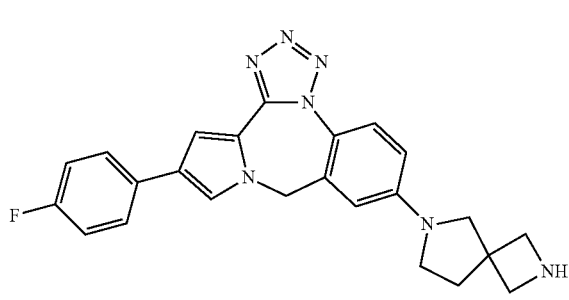 [SMILES: Fc1ccc(-c2cc3n(c2)Cc2cc(N4CCC5(CNC5)C4)ccc2-n2nnnc2-3)cc1]

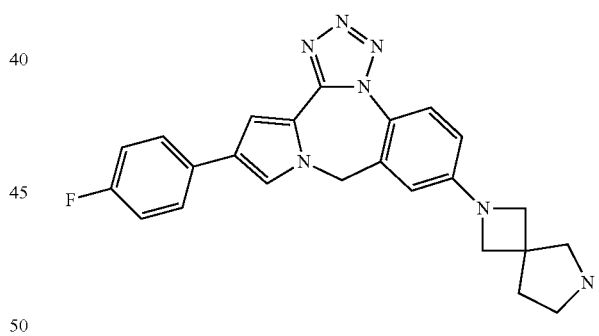

12-(4-fluorophenyl)-7-(2,6-diazaspiro[3.4]octan-6-yl)-9H-benzo[e]pyrrolo[1,2-a]tetrazolo[5,1-c][1,4]diazepine, 398. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with tert-butyl 2,6-diazaspiro[3.4]octane-2-carboxylate. 1H NMR (400 MHz, METHANOL-d4) δ=7.80 (d, J=8.6 Hz, 1H), 7.58 (dd, J=5.3, 8.8 Hz, 2H), 7.51 (d, J=1.8 Hz, 1H), 7.24 (d, J=1.8 Hz, 1H), 7.08 (t, J=8.8 Hz, 2H), 6.84-6.76 (m, 2H), 5.22 (s, 2H), 4.24-4.16 (m, 2H), 4.14-4.05 (m, 2H), 3.66 (s, 2H), 3.50 (t, J=6.8 Hz, 2H), 2.41 (t, J=6.9 Hz, 2H). ESI [M+H]=428.1

12-(4-fluorophenyl)-7-(2,6-diazaspiro[3.4]octan-2-yl)-9H-benzo[e]pyrrolo[1,2-a]tetrazolo[5,1-c][1,4]diazepine, 403. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with tert-butyl 2,6-diazaspiro[3.4]octane-6-carboxylate. 1H NMR (400 MHz, METHANOL-d4) δ=7.79 (d, J=8.8 Hz, 1H), 7.60-7.54 (m, 2H), 7.49 (d, J=1.8 Hz, 1H), 7.23 (d, J=1.8 Hz, 1H), 7.08 (t, J=8.7 Hz, 2H), 6.71 (d, J=2.2 Hz, 1H), 6.67 (dd, J=2.5, 8.7 Hz, 1H), 5.20 (s, 2H), 4.05-3.99 (m, 4H), 3.55 (s, 2H), 3.40 (t, J=7.4 Hz, 2H), 2.38 (t, J=7.4 Hz, 2H). ESI [M+H]=428.1

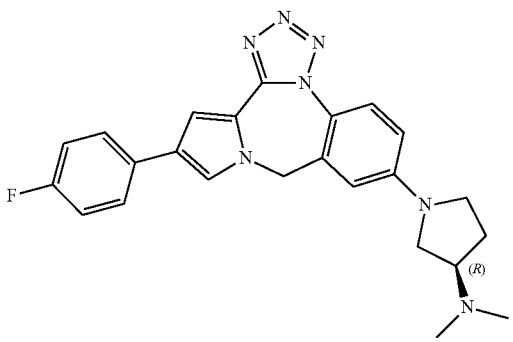

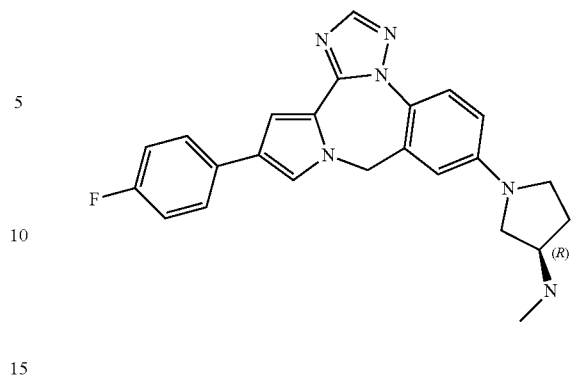

(R)-1-(12-(4-fluorophenyl)-9H-benzo[e]pyrrolo[1,2-a]tetrazolo[5,1-c][1,4]diazepin-7-yl)-N,N-dimethylpyrrolidin-3-amine, 406. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl piperazine-1-carboxylate with (R)—N,N-dimethylpyrrolidin-3-amine. 1H NMR (400 MHz, METHANOL-d4) δ=7.81 (d, J=8.8 Hz, 1H), 7.55 (dd, J=5.3, 8.8 Hz, 2H), 7.48 (d, J=1.8 Hz, 1H), 7.22 (d, J=1.8 Hz, 1H), 7.06 (t, J=8.6 Hz, 2H), 6.90-6.82 (m, 2H), 5.21 (s, 2H), 4.08 (quin, J=7.2 Hz, 1H), 3.83 (dd, J=7.5, 10.6 Hz, 1H), 3.70 (dt, J=3.5, 9.3 Hz, 1H), 3.63 (dd, J=6.4, 10.8 Hz, 1H), 3.52-3.42 (m, 1H), 3.03-2.96 (m, 6H), 2.67-2.55 (m, 1H), 2.38-2.26 (m, 1H). ESI [M+H]=430.2

(R)-1-(12-(4-fluorophenyl)-9H-benzo[e]pyrrolo[1,2-a][1,2,4]triazolo[5,1-c][1,4]diazepin-7-yl)-N-methylpyrrolidin-3-amine, 409. Synthesized using General Procedure I, replacing 4-(7-bromo-11-chloro-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4] diazepine and replacing (R)-tert-butyl (pyrrolidin-3-ylmethyl)carbamate with (R)-tert-butyl pyrrolidin-3-ylcarbamate. 1H NMR (400 MHz, METHANOL-d4) δ=8.14 (s, 1H), 7.72 (d, J=8.8 Hz, 1H), 7.55 (dd, J=5.3, 8.8 Hz, 2H), 7.41 (d, J=1.8 Hz, 1H), 7.10-7.00 (m, 3H), 6.88-6.77 (m, 2H), 5.18 (s, 2H), 4.04-3.94 (m, 1H), 3.74-3.59 (m, 3H), 3.45 (dt, J=5.7, 9.0 Hz, 1H), 2.80 (s, 3H), 2.61-2.48 (m, 1H), 2.34-2.22 (m, 1H). ESI [M+H]=415.1

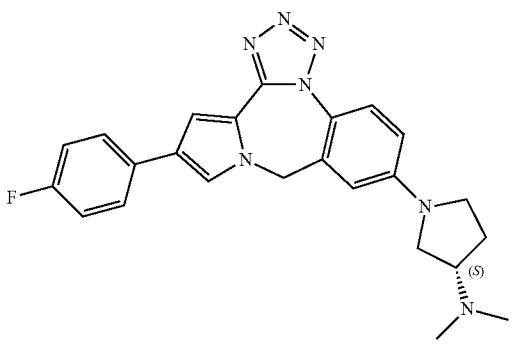

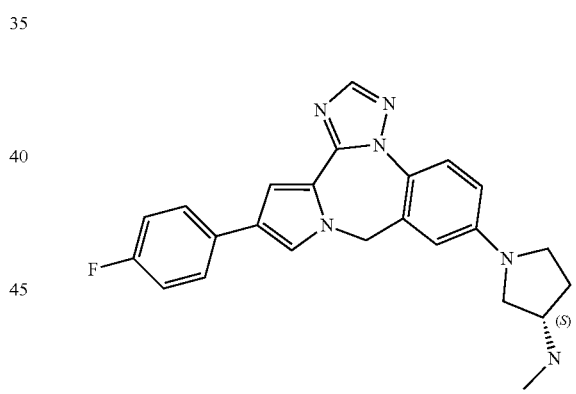

(S)-1-(12-(4-fluorophenyl)-9H-benzo[e]pyrrolo[1,2-a]tetrazolo[5,1-c][1,4]diazepin-7-yl)-N,N-dimethylpyrrolidin-3-amine, 407. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a]tetrazolo[5,1-c][1,4]diazepine and replacing tert-butyl (azetidin-3-ylmethyl)(methyl)carbamate with (S)-tert-butyl pyrrolidin-3-ylcarbamate. 1H NMR (400 MHz, METHANOL-d4) δ=7.84 (d, J=8.8 Hz, 1H), 7.57 (dd, J=5.3, 8.8 Hz, 2H), 7.50 (d, J=1.8 Hz, 1H), 7.24 (d, J=1.8 Hz, 1H), 7.08 (t, J=8.6 Hz, 2H), 6.94-6.84 (m, 2H), 5.24 (s, 2H), 4.05 (d, J=6.2 Hz, 1H), 3.84 (dd, J=7.5, 10.6 Hz, 1H), 3.76-3.68 (m, 1H), 3.62 (dd, J=6.2, 10.6 Hz, 1H), 3.54-3.42 (m, 1H), 2.98 (s, 6H), 2.63 (d, J=14.6 Hz, 1H), 2.38-2.26 (m, 1H). ESI [M+H]=430.2

(S)-1-(12-(4-fluorophenyl)-9H-benzo[e]pyrrolo[1,2-a][1,2,4]triazolo[5,1-c][1,4]diazepin-7-yl)-N-methylpyrrolidin-3-amine, 410. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4]diazepine and replacing tert-butyl piperazine-1-carboxylate with (S)-tert-butyl methyl(pyrrolidin-3-yl)carbamate. 1H NMR (400 MHz, METHANOL-d4) δ=8.14 (s, 1H), 7.71 (d, J=8.6 Hz, 1H), 7.53 (dd, J=5.3, 8.6 Hz, 2H), 7.39 (s, 1H), 7.10-7.00 (m, 3H), 6.84-6.76 (m, 2H), 5.23-5.12 (m, 2H), 4.04-3.92 (m, 1H), 3.74-3.55 (m, 3H), 3.44 (dt, J=5.7, 9.2 Hz, 1H), 2.83-2.74 (m, 3H), 2.53 (dt, J=6.6, 14.3 Hz, 1H), 2.26 (dt, J=5.3, 13.3 Hz, 1H). ESI [M+H]=415.1

245

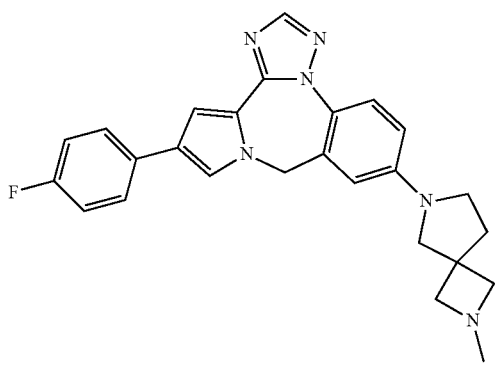 [SMILES: CN1CC2(CCN(c3ccc4c(c3)Cn3cc(-c5ccc(F)cc5)cc3-c3ncnn3-4)C2)C1]

12-(4-fluorophenyl)-7-(2-methyl-2,6-diazaspiro[3.4]octan-6-yl)-9H-benzo[e]pyrrolo[1,2-a][1,2,4]triazolo[5,1-c][1,4]diazepine, 412. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4]diazepine and replacing tert-butyl (azetidin-3-ylmethyl)(methyl)carbamate with tert-butyl 2,6-diazaspiro[3.4]octane-2-carboxylate. 1H NMR (400 MHz, METHANOL-d4) δ=8.19 (br. s., 1H), 7.68 (d, J=8.4 Hz, 1H), 7.55 (dd, J=5.3, 8.4 Hz, 2H), 7.41 (s, 1H), 7.12 (br. s., 1H), 7.06 (t, J=8.6 Hz, 2H), 6.80-6.70 (m, 2H), 5.16 (s, 2H), 4.40-4.27 (m, 2H), 4.21-4.08 (m, 2H), 3.70-3.60 (m, 2H), 3.51-3.40 (m, 2H), 2.99 (d, J=5.3 Hz, 3H), 2.44-2.34 (m, 2H). ESI [M+H]=441.1

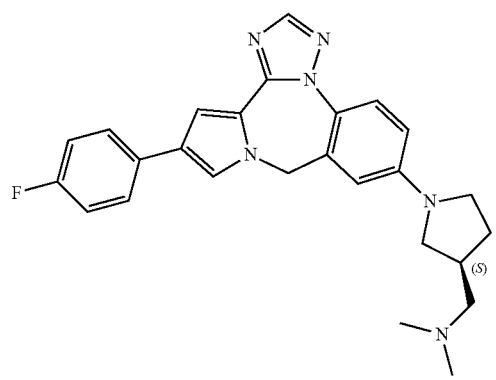

(S)-1-(1-(12-(4-fluorophenyl)-9H-benzo[e]pyrrolo[1,2-a][1,2,4]triazolo[5,1-c][1,4]diazepin-7-yl)pyrrolidin-3-yl)-N,N-dimethylmethanamine, 413. Synthesized using General Procedure C, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[5,1-c] [1,4]diazepine and replacing tert-butyl (azetidin-3-ylmethyl)(methyl)carbamate with (R)-tert-butyl (pyrrolidin-3-ylmethyl)carbamate. 1H NMR (400 MHz, METHANOL-d4) δ=8.18 (br. s., 1H), 7.68 (d, J=8.6 Hz, 1H), 7.55 (dd, J=5.4, 8.5 Hz, 2H), 7.40 (s, 1H), 7.15-7.00 (m, 3H), 6.77-6.66 (m, 2H), 5.22-5.08 (m, 2H), 3.71-3.60 (m, 1H), 3.54 (dt, J=3.1, 8.8 Hz, 1H), 3.47-3.38 (m, 1H), 3.33 (s, 2H), 3.15 (t, J=8.6 Hz, 1H), 2.97 (s, 6H), 2.85 (td, J=7.5, 15.4 Hz, 1H), 2.40-2.30 (m, 2H), 1.88 (qd, J=8.7, 12.2 Hz, 1H). ESI [M+H]=443.2

246

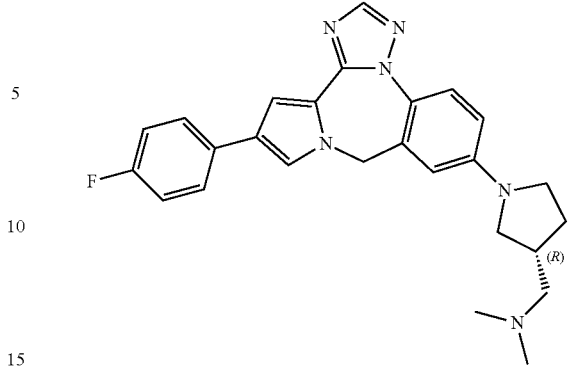

(R)-1-(1-(12-(4-fluorophenyl)-9H-benzo[e]pyrrolo[1,2-a][1,2,4]triazolo[5,1-c][1,4]diazepin-7-yl)pyrrolidin-3-yl)-N,N-dimethylmethanamine, 414. Synthesized using General Procedure C, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[5,1-c] [1,4]diazepine and replacing tert-butyl piperazine-1-carboxylate with (S)-tert-butyl (pyrrolidin-3-ylmethyl)carbamate. 1H NMR (400 MHz, METHANOL-d4) δ=8.22 (br. s., 1H), 7.67 (d, J=9.0 Hz, 1H), 7.54 (dd, J=5.4, 8.3 Hz, 2H), 7.39 (s, 1H), 7.22-6.98 (m, 3H), 6.75-6.64 (m, 2H), 5.19-5.07 (m, 2H), 3.64 (t, J=8.5 Hz, 1H), 3.57-3.49 (m, 1H), 3.47-3.36 (m, 1H), 3.33 (s, 2H), 3.14 (t, J=8.5 Hz, 1H), 2.97 (s, 6H), 2.85 (tt, J=8.0, 15.4 Hz, 1H), 2.39-2.29 (m, 1H), 1.87 (qd, J=8.6, 12.3 Hz, 1H). ESI [M+H]=443.2

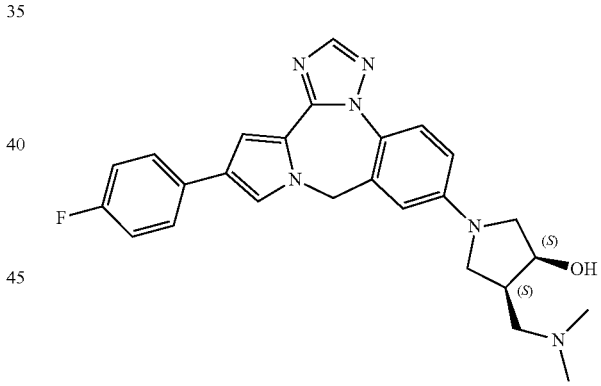

(3S,4S)-4-((dimethylamino)methyl)-1-(12-(4-fluorophenyl)-9H-benzo[e]pyrrolo[1,2-a][1,2,4] triazolo[5,1-c][1,4] diazepin-7-yl)pyrrolidin-3-ol, 415. Synthesized using General Procedure A, replacing 4-(7-bromo-9H-benzo[e]pyrrolo [1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[5,1-c][1,4] diazepine and replacing tert-butyl piperazine-1-carboxylate with (3S,4R)-4-((dimethylamino) methyl)pyrrolidin-3-ol. 1H NMR (400 MHz, METHANOL-d4) δ=8.13 (s, 1H), 7.67 (d, J=8.8 Hz, 1H), 7.54 (dd, J=5.5, 8.6 Hz, 2H), 7.39 (s, 1H), 7.10-7.00 (m, 3H), 6.74-6.67 (m, 2H), 5.14 (s, 2H), 4.57 (br. s., 1H), 3.72-3.52 (m, 3H), 3.44 (d, J=10.6 Hz, 1H), 3.32 (d, J=5.7 Hz, 2H), 2.97 (br. s., 6H), 2.84 (dd, J=5.3, 13.2 Hz, 1H). ESI [M+H]=459.2

247

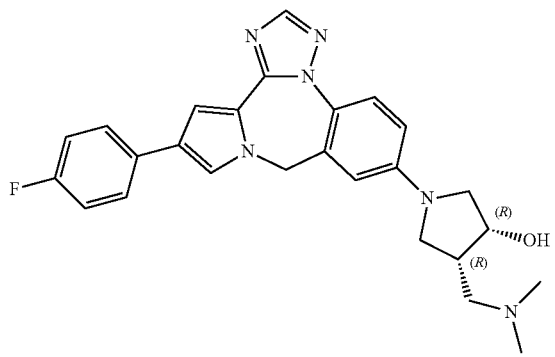

(3R,4R)-4-((dimethylamino)methyl)-1-(12-(4-fluorophenyl)-9H-benzo[e]pyrrolo[1,2-a][1,2,4] triazolo[5,1-c][1,4]diazepin-7-yl)pyrrolidin-3-ol, 416. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[5,1-c][1,4] diazepine and replacing tert-butyl piperazine-1-carboxylate with (3R,4S)-4-((dimethylamino) methyl)pyrrolidin-3-ol. 1H NMR (400 MHz, METHANOL-d4) δ=8.12 (s, 1H), 7.68 (d, J=8.8 Hz, 1H), 7.54 (dd, J=5.5, 8.6 Hz, 2H), 7.39 (d, J=1.8 Hz, 1H), 7.11-6.99 (m, 3H), 6.76-6.65 (m, 2H), 5.15 (s, 2H), 4.56 (d, J=1.8 Hz, 1H), 3.74-3.53 (m, 3H), 3.48-3.40 (m, 1H), 3.36-3.30 (m, 2H), 2.97 (d, J=3.1 Hz, 6H), 2.88-2.80 (m, 1H). ESI [M+H]=459.1

248

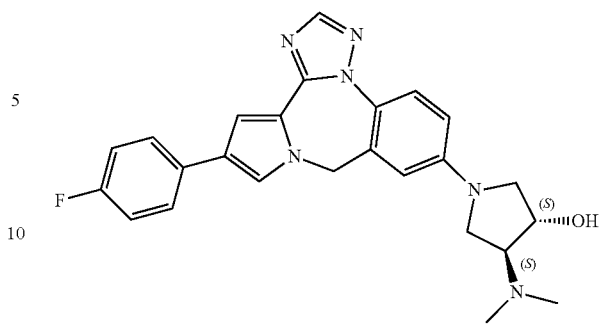

(3S,4S)-4-(dimethylamino)-1-(12-(4-fluorophenyl)-9H-benzo[e]pyrrolo[1,2-a][1,2,4]triazolo[5,1-c][1,4]diazepin-7-yl)pyrrolidin-3-ol, 418. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[5,1-c][1,4] diazepine and replacing tert-butyl piperazine-1-carboxylate with (3R,4R)-4-((dimethylamino)methyl)pyrrolidin-3-ol. 1H NMR (400 MHz, METHANOL-d4) δ=8.14 (s, 1H), 7.72 (d, J=8.4 Hz, 1H), 7.53 (dd, J=5.5, 8.6 Hz, 2H), 7.39 (d, J=1.8 Hz, 1H), 7.09-7.01 (m, 3H), 6.84-6.76 (m, 2H), 5.16 (s, 2H), 4.69 (q, J=6.9 Hz, 1H), 3.94-3.80 (m, 4H), 3.57 (dd, J=6.6, 9.7 Hz, 1H), 3.05 (br. s., 6H). ESI [M+H]=445.2

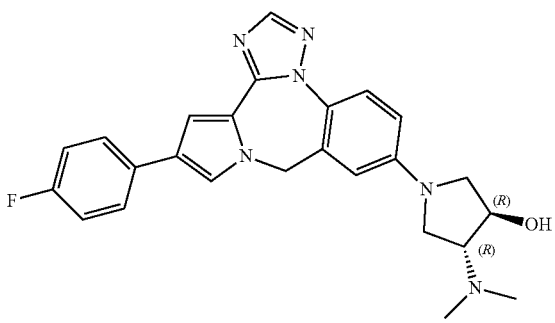

(3R,4R)-4-(dimethylamino)-1-(12-(4-fluorophenyl)-9H-benzo[e]pyrrolo[1,2-a][1,2,4]triazolo[5,1-c][1,4]diazepin-7-yl)pyrrolidin-3-ol, 417. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]pyrrolo[1,2-a][1,2,4]triazolo[5,1-c][1,4] diazepine and replacing tert-butyl piperazine-1-carboxylate with (3S,4S)-4-((dimethylamino) methyl)pyrrolidin-3-ol. 1H NMR (400 MHz, METHANOL-d4) δ=8.16 (s, 1H), 7.72 (d, J=8.6 Hz, 1H), 7.54 (dd, J=5.5, 8.6 Hz, 2H), 7.40 (d, J=1.6 Hz, 1H), 7.11-7.01 (m, 3H), 6.86-6.76 (m, 2H), 5.16 (s, 2H), 4.70 (q, J=7.0 Hz, 1H), 3.96-3.81 (m, 3H), 3.58 (dd, J=6.7, 9.8 Hz, 1H), 3.28 (d, J=7.0 Hz, 1H), 3.07 (br. s., 6H). ESI [M+H]=445.1

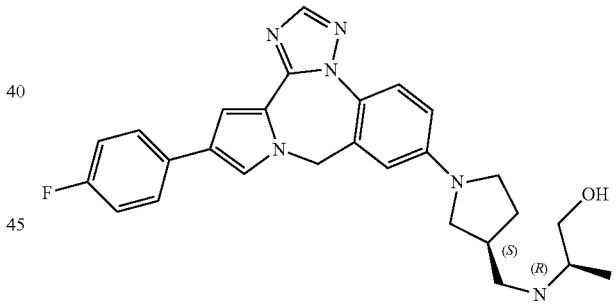

(R)-2-((((S)-1-(12-(4-fluorophenyl)-9H-benzo[e]pyrrolo[1,2-a][1,2,4]triazolo[5,1-c][1,4] diazepin-7-yl)pyrrolidin-3-yl)methyl)amino)propan-1-ol, 419. Synthesized using General Procedure A, replacing 4-(7-bromo-9H-benzo[e]pyrrolo[1,2-a][1,2,4]triazolo[3,4-c][1,4] diazepin-12-yl) benzonitrile with 7-bromo-12-(4-fluorophenyl)-9H-benzo[e]pyrrolo[1,2-a][1,2,4] triazolo[5,1-c][1,4]diazepine and replacing tert-butyl piperazine-1-carboxylate with (R)-2-(((R)-pyrrolidin-3-ylmethyl)amino)propan-1-ol. 1H NMR (400 MHz, METHANOL-d4) δ=8.15 (s, 1H), 7.67 (d, J=9.4 Hz, 1H), 7.54 (dd, J=5.1, 8.6 Hz, 2H), 7.39 (s, 1H), 7.12-7.00 (m, 3H), 6.75-6.67 (m, 2H), 5.13 (s, 2H), 3.84 (dd, J=3.7, 11.9 Hz, 1H), 3.67-3.57 (m, 2H), 3.57-3.48 (m, 1H), 3.45-3.37 (m, 2H), 3.26-3.15 (m, 3H), 2.74 (td, J=7.3, 14.8 Hz, 1H), 2.40-2.30 (m, 1H), 1.91 (qd, J=8.1, 12.5 Hz, 1H), 1.35 (d, J=6.7 Hz, 3H). ESI [M+H]=473.2

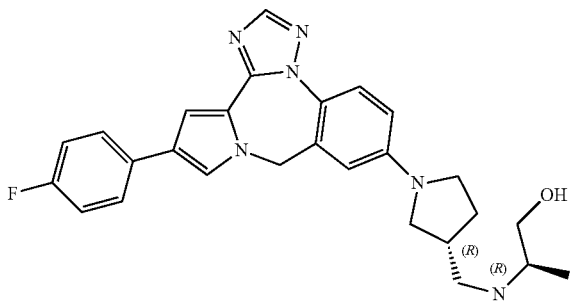

(R)-2-((((R)-1-(12-(4-fluorophenyl)-9H-benzo[e]pyrrolo[1,2-a][1,2,4]triazolo[5,1-c][1,4] diazepin-7-yl)pyrrolidin-3-yl)methyl)amino)propan-1-ol, 420. Synthesized using General Procedure A, replacing 4-(7-bromo-9H-benzo[e]pyrrolo[1,2-a][1,2,4]triazolo[3,4-c][1,4] diazepin-12-yl)benzonitrile with 7-bromo-12-(4-fluorophenyl)-9H-benzo[e]pyrrolo[1,2-a][1,2,4] triazolo[5,1-c][1,4]diazepine and replacing tert-butyl piperazine-1-carboxylate with (R)-2-(((S)-pyrrolidin-3-ylmethyl)amino)propan-1-ol. 1H NMR (400 MHz, METHANOL-d4) δ=8.15 (s, 1H), 7.66 (d, J=8.8 Hz, 1H), 7.54 (dd, J=5.3, 8.4 Hz, 2H), 7.39 (s, 1H), 7.11-7.00 (m, 3H), 6.75-6.67 (m, 2H), 5.12 (s, 2H), 3.84 (dd, J=3.5, 11.9 Hz, 1H), 3.67-3.57 (m, 2H), 3.52 (dt, J=3.7, 8.7 Hz, 1H), 3.46-3.35 (m, 2H), 3.26-3.12 (m, 3H), 2.74 (td, J=7.3, 14.6 Hz, 1H), 2.42-2.28 (m, 1H), 1.95-1.85 (m, 1H), 1.34 (d, J=6.6 Hz, 3H). ESI [M+H]=473.1

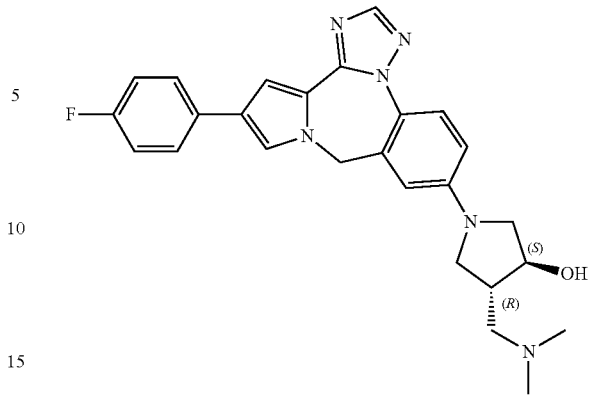

(3S,4R)-4-((dimethylamino)methyl)-1-(12-(4-fluorophenyl)-9H-benzo[e]pyrrolo[1,2-a][1,2,4] triazolo[5,1-c][1,4] diazepin-7-yl)pyrrolidin-3-ol, 422. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4] diazepine and replacing tert-butyl piperazine-1-carboxylate with (3S,4S)-4-((dimethylamino) methyl)pyrrolidin-3-ol. 1H NMR (400 MHz, METHANOL-d4) δ=8.14 (br. s., 1H), 7.67 (d, J=8.8 Hz, 1H), 7.53 (dd, J=5.3, 8.8 Hz, 2H), 7.39 (s, 1H), 7.05 (q, J=8.7 Hz, 3H), 6.75-6.67 (m, 2H), 5.14 (s, 2H), 4.28 (q, J=6.6 Hz, 1H), 3.77-3.69 (m, 2H), 3.42-3.32 (m, 2H), 3.26-3.16 (m, 2H), 2.98 (br. s., 6H), 2.73-2.65 (m, 1H). ESI [M+H]=459.3

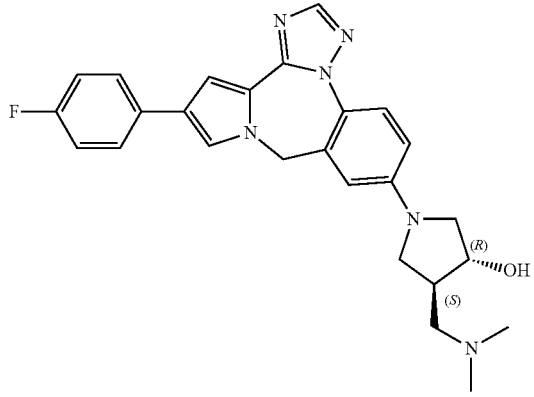

(3R,4S)-4-((dimethylamino)methyl)-1-(12-(4-fluorophenyl)-9H-benzo[e]pyrrolo[1,2-a][1,2,4] triazolo[5,1-c][1,4] diazepin-7-yl)pyrrolidin-3-ol, 421. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4] diazepine and replacing tert-butyl piperazine-1-carboxylate with (3R,4R)-4-((dimethylamino) methyl)pyrrolidin-3-ol. 1H NMR (400 MHz, METHANOL-d4) δ=8.17 (s, 1H), 7.68 (d, J=8.4 Hz, 1H), 7.59-7.50 (m, 2H), 7.40 (s, 1H), 7.11-7.01 (m, 3H), 6.75-6.67 (m, 2H), 5.14 (s, 2H), 4.28 (q, J=6.6 Hz, 1H), 3.74 (t, J=8.4 Hz, 2H), 3.46-3.33 (m, 2H), 3.28-3.15 (m, 2H), 2.99 (br. s., 6H), 2.76-2.64 (m, 1H). ESI [M+H]=459.3

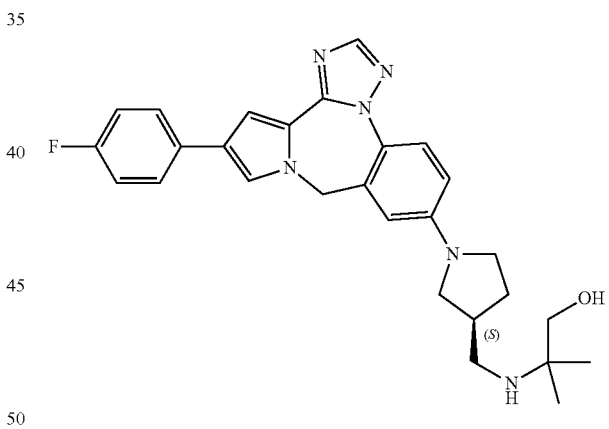

(S)-2-(((1-(12-(4-fluorophenyl)-9H-benzo[e]pyrrolo[1,2-a][1,2,4]triazolo[5,1-c][1,4]diazepin-7-yl)pyrrolidin-3-yl)methyl)amino)-2-methylpropan-1-ol, 425. Synthesized using General Procedure A, replacing 4-(7-bromo-9H-benzo[e]pyrrolo[1,2-a][1,2,4]triazolo[3,4-c][1,4] diazepin-12-yl)benzonitrile with 7-bromo-12-(4-fluorophenyl)-9H-benzo[e]pyrrolo[1,2-a][1,2,4] triazolo[5,1-c][1,4]diazepine and replacing tert-butyl piperazine-1-carboxylate with (R)-2-methyl-2-((pyrrolidin-3-ylmethyl)amino)propan-1-ol. 1H NMR (400 MHz, METHANOL-d4) δ=8.17 (br. s., 1H), 7.67 (d, J=8.8 Hz, 1H), 7.54 (dd, J=5.4, 8.5 Hz, 2H), 7.39 (s, 1H), 7.17-6.99 (m, 3H), 6.76-6.67 (m, 2H), 5.13 (s, 2H), 3.68-3.59 (m, 1H), 3.58-3.48 (m, 3H), 3.46-3.37 (m, 1H), 3.19 (dd, J=6.8, 9.5 Hz, 1H), 3.15-3.07 (m, 1H), 2.72-2.62 (m, 1H), 2.35 (dd, J=4.7, 11.8 Hz, 1H), 1.97-1.85 (m, 1H), 1.39-1.28 (m, 6H). ESI [M+H]=487.3

251

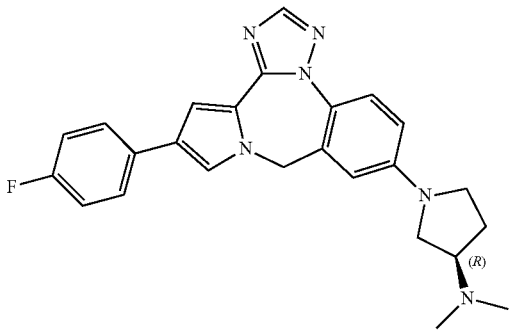

(R)-1-(12-(4-fluorophenyl)-9H-benzo[e]pyrrolo[1,2-a][1,2,4]triazolo[5,1-c][1,4]diazepin-7-yl)-N,N-dimethylpyrrolidin-3-amine, 426. Synthesized using General Procedure C, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4]diazepine and replacing tert-butyl (azetidin-3-ylmethyl)(methyl)carbamate with (R)-tert-butyl pyrrolidin-3-ylcarbamate. 1H NMR (400 MHz, METHANOL-d4) δ=8.15 (s, 1H), 7.72 (d, J=8.8 Hz, 1H), 7.54 (dd, J=5.5, 8.6 Hz, 2H), 7.40 (d, J=1.3 Hz, 1H), 7.11-7.01 (m, 3H), 6.86-6.78 (m, 2H), 5.17 (s, 2H), 4.13-4.03 (m, 1H), 3.80 (dd, J=7.5, 10.6 Hz, 1H), 3.72-3.59 (m, 2H), 3.48-3.39 (m, 1H), 2.99 (s, 6H), 2.67-2.55 (m, 1H), 2.38-2.27 (m, 1H). ESI [M+H]=429.1

252

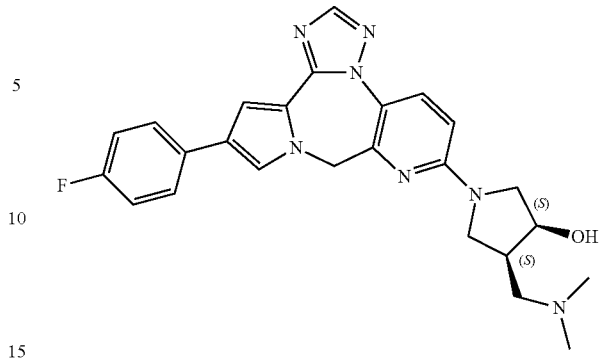

(3S,4S)-4-((dimethylamino)methyl)-1-(12-(4-fluorophenyl)-9H-imidazo[2,1-c]pyrido[3,2-e]pyrrolo[1,2-a][1,4]diazepin-7-yl)pyrrolidin-3-ol, 429. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a] [1,4]diazepine and replacing tert-butyl piperazine-1-carboxylate with (3S,4R)-4-((dimethylamino) methyl)pyrrolidin-3-ol. 1H NMR (400 MHz, METHANOL-d4) δ=8.00 (d, J=2.2 Hz, 1H), 7.86 (d, J=9.3 Hz, 1H), 7.76 (d, J=1.8 Hz, 1H), 7.62 (d, J=1.3 Hz, 1H), 7.57 (dd, J=5.3, 8.8 Hz, 2H), 7.23 (d, J=1.8 Hz, 1H), 7.08 (t, J=8.8 Hz, 2H), 6.66 (d, J=8.8 Hz, 1H), 5.29 (s, 2H), 4.55 (br. s., 1H), 3.89 (br. s., 1H), 3.78-3.62 (m, 2H), 3.56 (dd, J=7.9, 13.2 Hz, 1H), 3.43-3.30 (m, 2H), 3.01-2.92 (m, 6H), 2.89-2.78 (m, 1H). ESI [M+H]=459.1

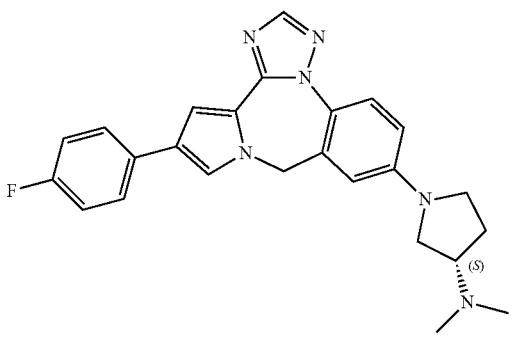

(S)-1-(12-(4-fluorophenyl)-9H-benzo[e]pyrrolo[1,2-a][1,2,4]triazolo[5,1-c][1,4]diazepin-7-yl)-N,N-dimethylpyrrolidin-3-amine, 427. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4]diazepine and replacing tert-butyl piperazine-1-carboxylate with ((S)—N,N-dimethylpyrrolidin-3-amine. 1H NMR (400 MHz, METHANOL-d4) δ=8.13 (s, 1H), 7.71 (d, J=8.8 Hz, 1H), 7.53 (dd, J=5.3, 8.8 Hz, 2H), 7.39 (s, 1H), 7.09-7.00 (m, 3H), 6.85-6.78 (m, 2H), 5.16 (s, 2H), 4.06 (t, J=6.4 Hz, 1H), 3.83-3.75 (m, 1H), 3.72-3.64 (m, 1H), 3.61 (dd, J=6.2, 10.1 Hz, 1H), 3.48-3.39 (m, 1H), 2.98 (s, 6H), 2.61 (d, J=19.8 Hz, 1H), 2.36-2.24 (m, 1H). ESI [M+H]=429.2

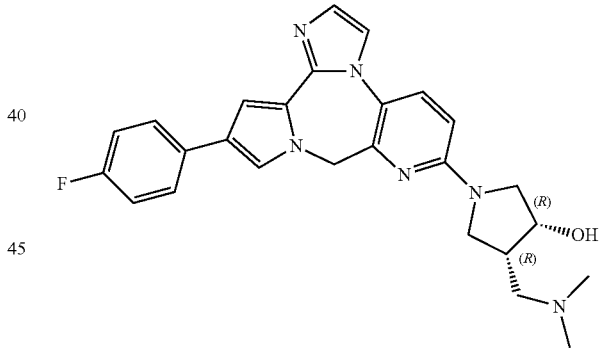

(3R,4R)-4-((dimethylamino)methyl)-1-(12-(4-fluorophenyl)-9H-imidazo[2,1-c]pyrido[3,2-e]pyrrolo[1,2-a][1,4]diazepin-7-yl)pyrrolidin-3-ol, 430. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a] [1,4]diazepine and replacing tert-butyl piperazine-1-carboxylate with (3R,4S)-4-((dimethylamino) methyl)pyrrolidin-3-ol. 1H NMR (400 MHz, METHANOL-d4) δ=8.00 (d, J=1.8 Hz, 1H), 7.86 (d, J=9.3 Hz, 1H), 7.76 (d, J=1.8 Hz, 1H), 7.62 (d, J=1.3 Hz, 1H), 7.57 (dd, J=5.3, 8.8 Hz, 2H), 7.24 (d, J=1.8 Hz, 1H), 7.07 (t, J=8.8 Hz, 2H), 6.65 (d, J=9.3 Hz, 1H), 5.29 (s, 2H), 4.55 (br. s., 1H), 3.97-3.83 (m, 1H), 3.78-3.62 (m, 2H), 3.56 (dd, J=7.9, 12.8 Hz, 1H), 3.43-3.31 (m, 2H), 3.02-2.92 (m, 6H), 2.88-2.78 (m, 1H). ESI [M+H]=459.1

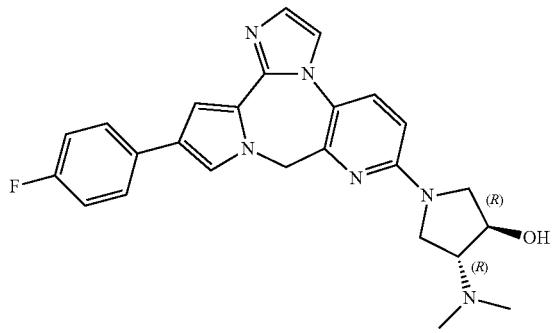
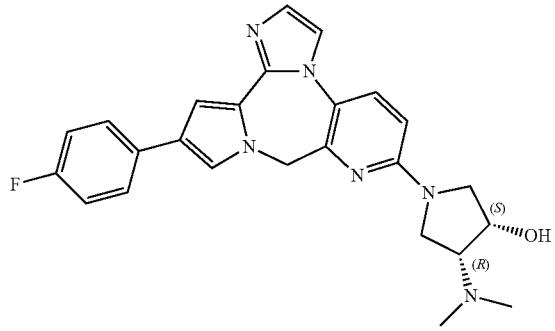

(3R,4R)-4-(dimethylamino)-1-(12-(4-fluorophenyl)-9H-imidazo[2,1-c]pyrido[3,2-e]pyrrolo[1,2-a][1,4]diazepin-7-yl)pyrrolidin-3-ol, 431. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a][1,4] diazepine and replacing tert-butyl piperazine-1-carboxylate with (3R,4R)-4-(dimethylamino)pyrrolidin-3-ol. 1H NMR (400 MHz, METHANOL-d4) δ=8.01 (s, 1H), 7.92 (d, J=8.8 Hz, 1H), 7.77 (s, 1H), 7.63 (s, 1H), 7.57 (dd, J=5.3, 8.8 Hz, 2H), 7.23 (s, 1H), 7.08 (t, J=8.8 Hz, 2H), 6.75 (d, J=9.3 Hz, 1H), 5.33 (s, 2H), 4.72 (q, J=7.2 Hz, 1H), 4.19 (dd, J=8.2, 11.2 Hz, 1H), 4.09 (dd, J=7.9, 10.6 Hz, 1H), 3.85 (q, J=7.8 Hz, 1H), 3.72 (dd, J=7.9, 11.5 Hz, 1H), 3.39 (dd, J=7.1, 10.6 Hz, 1H), 3.05 (s, 6H). ESI [M+H]=445.1

(3S,4R)-4-(dimethylamino)-1-(12-(4-fluorophenyl)-9H-imidazo[2,1-c]pyrido[3,2-e]pyrrolo[1,2-a][1,4]diazepin-7-yl)pyrrolidin-3-ol, 433. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a][1,4] diazepine and replacing tert-butyl piperazine-1-carboxylate with (3S,4R)-4-(dimethylamino)pyrrolidin-3-ol. 1H NMR (400 MHz, METHANOL-d4) δ=8.00 (d, J=1.8 Hz, 1H), 7.91 (d, J=9.3 Hz, 1H), 7.76 (d, J=2.2 Hz, 1H), 7.63 (d, J=1.8 Hz, 1H), 7.57 (dd, J=5.3, 8.8 Hz, 2H), 7.23 (d, J=1.8 Hz, 1H), 7.08 (t, J=8.8 Hz, 2H), 6.74 (d, J=8.8 Hz, 1H), 5.32 (s, 2H), 4.68 (br. s., 1H), 4.22 (br. s., 1H), 4.00-3.88 (m, 1H), 3.82-3.71 (m, 2H), 3.65 (t, J=9.9 Hz, 1H), 3.02 (br. s., 6H). ESI [M+H]=445.1

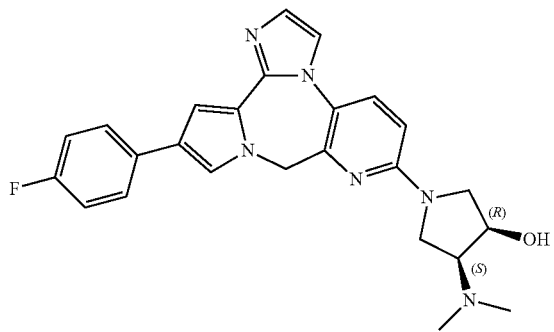

(3R,4S)-4-(dimethylamino)-1-(12-(4-fluorophenyl)-9H-imidazo[2,1-c]pyrido[3,2-e]pyrrolo[1,2-a][1,4]diazepin-7-yl)pyrrolidin-3-ol, 432. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a][1,4] diazepine and replacing tert-butyl piperazine-1-carboxylate with (3R,4S)-4-(dimethylamino)pyrrolidin-3-ol. 1H NMR (400 MHz, METHANOL-d4) δ=8.01 (d, J=1.8 Hz, 1H), 7.91 (d, J=9.3 Hz, 1H), 7.77 (d, J=1.8 Hz, 1H), 7.63 (d, J=1.3 Hz, 1H), 7.57 (dd, J=5.3, 8.8 Hz, 2H), 7.25 (d, J=1.3 Hz, 1H), 7.08 (t, J=8.8 Hz, 2H), 6.74 (d, J=8.8 Hz, 1H), 5.33 (s, 2H), 4.68 (br. s., 1H), 4.22 (br. s., 1H), 3.98-3.89 (m, 1H), 3.84-3.70 (m, 2H), 3.65 (t, J=9.9 Hz, 1H), 3.01 (d, J=15.0 Hz, 6H). ESI [M+H]=445.1

(R)-2-((((R)-1-(12-(4-fluorophenyl)-9H-imidazo[2,1-c]pyrido[3,2-e]pyrrolo[1,2-a][1,4] diazepin-7-yl)pyrrolidin-3-yl)methyl)amino)propan-1-ol, 434. Synthesized using General Procedure A, replacing 4-(7-bromo-9H-benzo[e]pyrrolo[1,2-a][1,2,4]triazolo[3,4-c][1,4] diazepin-12-yl) benzonitrile with 7-bromo-12-(4-fluorophenyl)-9H-imidazo[2,1-c]pyrido[3,2-e] pyrrolo[1,2-a][1,4]diazepine and replacing tert-butyl piperazine-1-carboxylate with (R)-2-(((S)-pyrrolidin-3-ylmethyl)amino)propan-1-ol. 1H NMR (400 MHz, METHANOL-d4) δ=8.00 (d, J=1.8 Hz, 1H), 7.86 (d, J=8.8 Hz, 1H), 7.77 (d, J=2.2 Hz, 1H), 7.63-7.53 (m, 3H), 7.23 (d, J=1.3 Hz, 1H), 7.08 (t, J=8.6 Hz, 2H), 6.65 (d, J=9.3 Hz, 1H), 5.29 (s, 2H), 3.95-3.78 (m, 2H), 3.73 (br. s., 1H), 3.63-3.47 (m, 2H), 3.44-3.32 (m, 2H), 3.21 (d, J=7.5 Hz, 2H), 2.73 (td, J=7.3, 14.9 Hz, 1H), 2.34 (dd, J=4.6, 11.2 Hz, 1H), 1.99-1.83 (m, 1H), 1.33 (d, J=6.6 Hz, 3H). ESI [M+H]=473.1

255

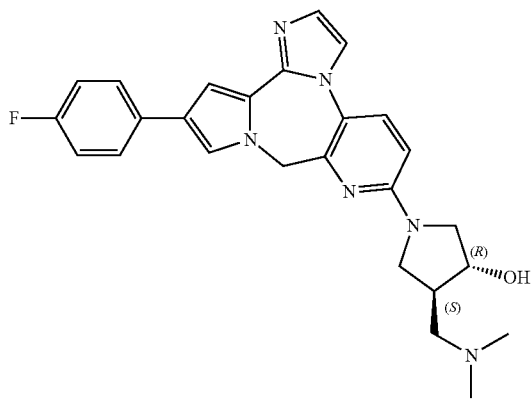

(3R,4S)-4-((dimethylamino)methyl)-1-(12-(4-fluorophenyl)-9H-imidazo[2,1-c]pyrido[3,2-e]pyrrolo[1,2-a][1,4]diazepin-7-yl)pyrrolidin-3-ol, 435. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a] [1,4]diazepine and replacing tert-butyl piperazine-1-carboxylate with (3R,4R)-4-((dimethyl amino)methyl)pyrrolidin-3-ol. 1H NMR (400 MHz, METHANOL-d4) δ=7.97 (br. s., 1H), 7.87 (d, J=8.8 Hz, 1H), 7.73 (br. s., 1H), 7.64-7.53 (m, 3H), 7.22 (br. s., 1H), 7.09 (t, J=8.2 Hz, 2H), 6.66 (d, J=8.8 Hz, 1H), 5.29 (s, 2H), 4.29 (d, J=6.6 Hz, 1H), 3.97 (d, J=8.4 Hz, 2H), 3.45-3.32 (m, 4H), 2.99 (s, 6H), 2.79-2.62 (m, 1H). ESI [M+H]=459.3

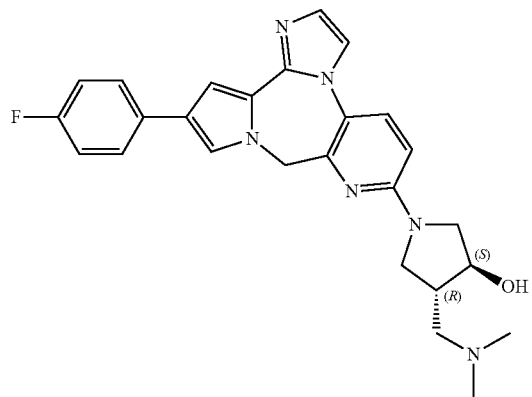

(3S,4R)-4-((dimethylamino)methyl)-1-(12-(4-fluorophenyl)-9H-imidazo[2,1-c]pyrido[3,2-e]pyrrolo[1,2-a][1,4]diazepin-7-yl)pyrrolidin-3-ol, 436. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-imidazo[2,1-c]pyrido[3,2-e]pyrrolo[1,2-a] [1,4]diazepine and replacing tert-butyl piperazine-1-carboxylate with ((3S,4S)-4-((dimethyl amino)methyl)pyrrolidin-3-ol. 1H NMR (400 MHz, METHANOL-d4) δ=7.98 (br. s., 1H), 7.86 (d, J=9.3 Hz, 1H), 7.74 (br. s., 1H), 7.62-7.53 (m, 3H), 7.21 (s, 1H), 7.08 (t, J=8.8 Hz, 2H), 6.66 (d, J=9.3 Hz, 1H), 5.29 (s, 2H), 4.27 (q, J=6.6 Hz, 1H), 4.02-3.89 (m, 2H), 3.42-3.31 (m, 4H), 2.98 (s, 6H), 2.73-2.64 (m, 1H). ESI [M+H]=459.2

256

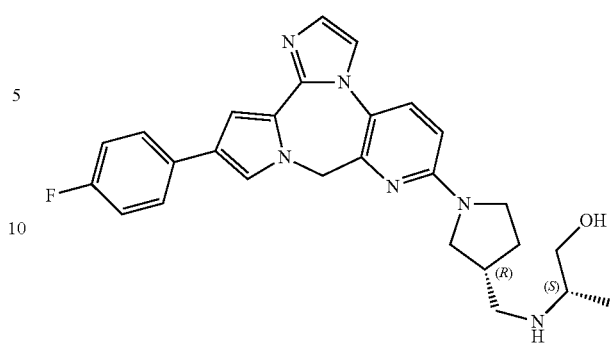

(S)-2-((((R)-1-(12-(4-fluorophenyl)-9H-imidazo[2,1-c]pyrido[3,2-e]pyrrolo[1,2-a][1,4] diazepin-7-yl)pyrrolidin-3-yl)methyl)amino)propan-1-ol, 437. Synthesized using General Procedure A, replacing 4-(7-bromo-9H-benzo[e]pyrrolo[1,2-a][1,2,4]triazolo[3,4-c][1,4] diazepin-12-yl) benzonitrile with 7-bromo-12-(4-fluorophenyl)-9H-imidazo[2,1-c]pyrido[3,2-e] pyrrolo[1,2-a][1,4]diazepine and replacing tert-butyl piperazine-1-carboxylate with (S)-2-(((S)-pyrrolidin-3-ylmethyl)amino)propan-1-ol. 1H NMR (400 MHz, METHANOL-d4) δ=8.01 (d, J=1.3 Hz, 1H), 7.86 (d, J=8.8 Hz, 1H), 7.78 (d, J=1.3 Hz, 1H), 7.66-7.53 (m, 3H), 7.25 (s, 1H), 7.09 (t, J=8.6 Hz, 2H), 6.66 (d, J=8.8 Hz, 1H), 5.30 (s, 2H), 3.95-3.80 (m, 2H), 3.74 (br. s., 1H), 3.67-3.50 (m, 2H), 3.46-3.33 (m, 2H), 3.27-3.18 (m, 2H), 2.74 (td, J=7.2, 14.8 Hz, 1H), 2.35 (dd, J=4.9, 11.0 Hz, 1H), 1.98-1.84 (m, 1H), 1.35 (d, J=6.6 Hz, 3H). ESI [M+H]= 473.1

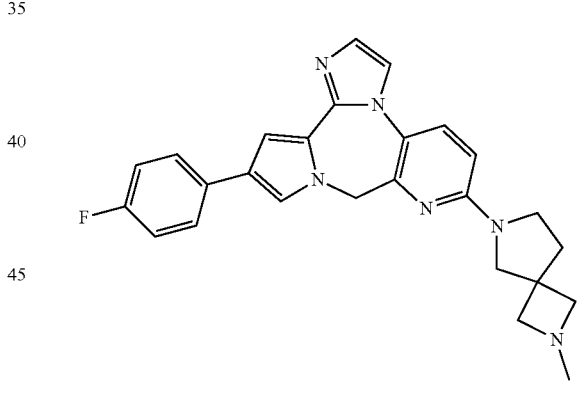

12-(4-fluorophenyl)-7-(2-methyl-2,6-diazaspiro[3.4]octan-6-yl)-9H-imidazo[2,1-c]pyrido[3,2-e]pyrrolo[1,2-a][1,4]diazepine, 441. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-imidazo[2,1-c]pyrido[3,2-e]pyrrolo[1,2-a][1,4]diazepine and replacing tert-butyl (azetidin-3-ylmethyl)(methyl)carbamate with tert-butyl 2,6-diazaspiro[3.4] octane-2-carboxylate. 1H NMR (400 MHz, METHANOL-d4) δ=8.02 (s, 1H), 7.89 (d, J=9.0 Hz, 1H), 7.78 (s, 1H), 7.64 (s, 1H), 7.59 (t, J=6.3 Hz, 2H), 7.24 (s, 1H), 7.10 (t, J=8.3 Hz, 2H), 6.68 (d, J=8.8 Hz, 1H), 5.32 (s, 2H), 4.42-4.27 (m, 1H), 4.22-4.05 (m, 3H), 3.93-3.80 (m, 2H), 3.64 (d, J=6.3 Hz, 2H), 3.00 (br. s., 3H), 2.41 (d, J=6.1 Hz, 2H). ESI [M+H]=441.1

Scheme 42:

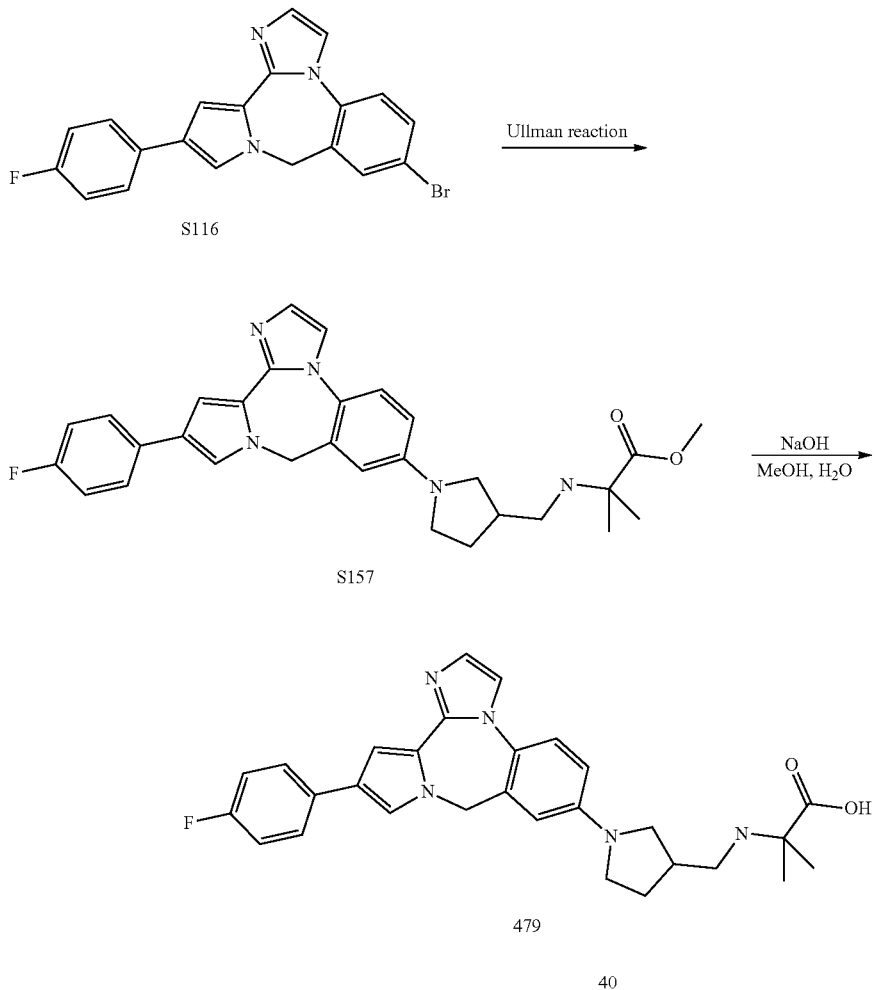

Chemistry Experimental Methods:
General Procedure R as below.

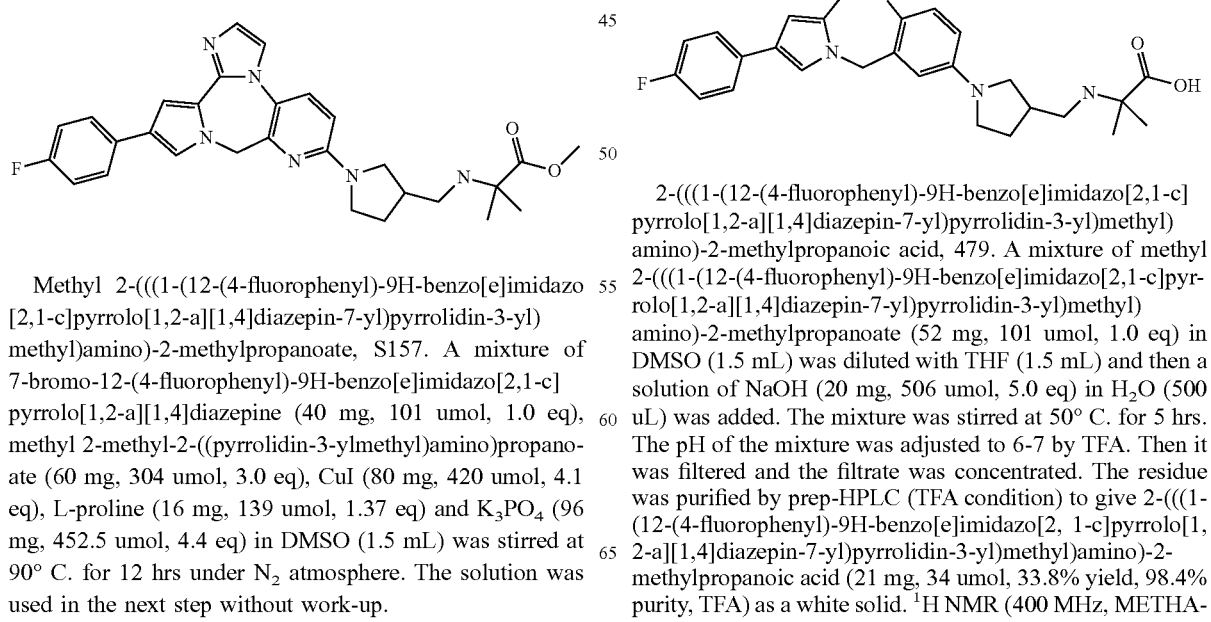

Methyl 2-(((1-(12-(4-fluorophenyl)-9H-benzo[e]imidazo[2,1-c]pyrrolo[1,2-a][1,4]diazepin-7-yl)pyrrolidin-3-yl)methyl)amino)-2-methylpropanoate, S157. A mixture of 7-bromo-12-(4-fluorophenyl)-9H-benzo[e]imidazo[2,1-c]pyrrolo[1,2-a][1,4]diazepine (40 mg, 101 umol, 1.0 eq), methyl 2-methyl-2-((pyrrolidin-3-ylmethyl)amino)propanoate (60 mg, 304 umol, 3.0 eq), CuI (80 mg, 420 umol, 4.1 eq), L-proline (16 mg, 139 umol, 1.37 eq) and $K_3PO_4$ (96 mg, 452.5 umol, 4.4 eq) in DMSO (1.5 mL) was stirred at 90° C. for 12 hrs under $N_2$ atmosphere. The solution was used in the next step without work-up.

2-(((1-(12-(4-fluorophenyl)-9H-benzo[e]imidazo[2,1-c]pyrrolo[1,2-a][1,4]diazepin-7-yl)pyrrolidin-3-yl)methyl)amino)-2-methylpropanoic acid, 479. A mixture of methyl 2-(((1-(12-(4-fluorophenyl)-9H-benzo[e]imidazo[2,1-c]pyrrolo[1,2-a][1,4]diazepin-7-yl)pyrrolidin-3-yl)methyl)amino)-2-methylpropanoate (52 mg, 101 umol, 1.0 eq) in DMSO (1.5 mL) was diluted with THF (1.5 mL) and then a solution of NaOH (20 mg, 506 umol, 5.0 eq) in $H_2O$ (500 uL) was added. The mixture was stirred at 50° C. for 5 hrs. The pH of the mixture was adjusted to 6-7 by TFA. Then it was filtered and the filtrate was concentrated. The residue was purified by prep-HPLC (TFA condition) to give 2-(((1-(12-(4-fluorophenyl)-9H-benzo[e]imidazo[2, 1-c]pyrrolo[1, 2-a][1,4]diazepin-7-yl)pyrrolidin-3-yl)methyl)amino)-2-methylpropanoic acid (21 mg, 34 umol, 33.8% yield, 98.4% purity, TFA) as a white solid. $^1$H NMR (400 MHz, METHA- NOL-d$_4$) δ=8.00 (d, J=1.3 Hz, 1H), 7.74 (d, J=1.8 Hz, 1H), 7.66-7.49 (m, 4H), 7.20 (s, 1H), 7.09 (t, J=8.6 Hz, 2H), 6.81 (br. s., 1H), 6.76 (d, J=9.3 Hz, 1H), 5.28 (s, 2H), 3.72-3.61 (m, 1H), 3.54 (dd, J=4.0, 8.4 Hz, 1H), 3.50-3.38 (m, 1H), 3.28-3.13 (m, 3H), 2.75 (td, J=7.1, 14.1 Hz, 1H), 2.38 (dd, J=4.9, 11.5 Hz, 1H), 2.03-1.90 (m, 1H), 1.63 (s, 6H). ESI [M+H]=500.2

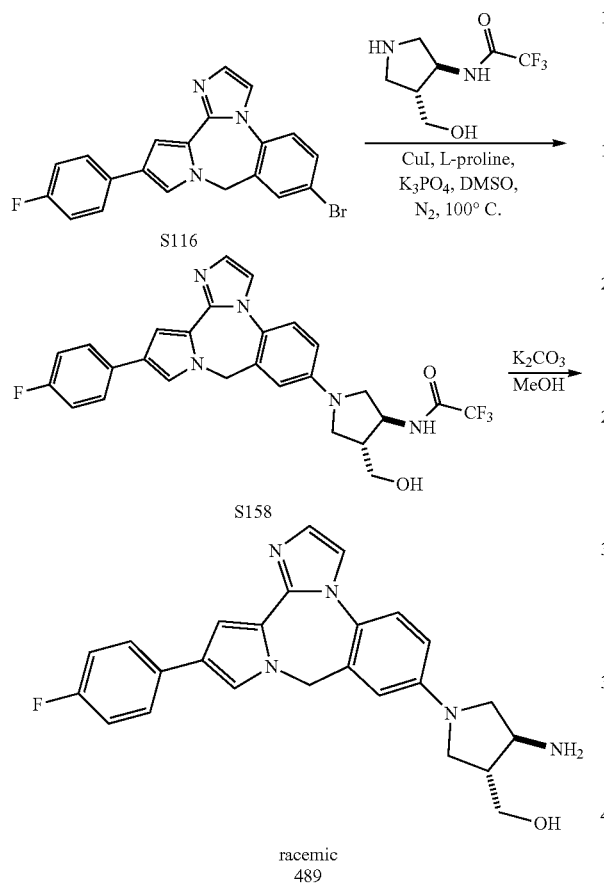

Chemistry Experimental Methods:
General Procedure S as below.

2,2,2-trifluoro-N-((trans)-1-(12-(4-fluorophenyl)-9H-benzo[e]imidazo[2,1-c]pyrrolo[1,2-a][1,4]diazepin-7-yl)-4-(hydroxymethyl)pyrrolidin-3-yl)acetamide, S158. To a solution of 7-bromo-12-(4-fluorophenyl)-9H-benzo[e]imidazo[2,1-c]pyrrolo[1,2-a][1,4]diazepine (70 mg, 177 umol, 1.0 eq) in DMSO (3.0 mL) was added 2,2,2-trifluoro-N-((trans)-4-(hydroxymethyl) pyrrolidin-3-yl)acetamide (289.6 mg, 887.8 umol, 5.0 eq, TFA), CuI (101 mg, 532.7 umol, 3.0 eq), L-proline (10.2 mg, 88.8 umol, 0.5 eq) and K$_3$PO$_4$ (188.4 mg, 887.8 umol, 5.0 eq) and the mixture was stirred at 90° C. for 16 hrs under N$_2$ atmosphere. The mixture was poured into water (50 mL) and the aqueous phase was extracted with DCM (50 mL×3). The combined organic phases were dried, filtered and concentrated. The residue was purified by prep-HPLC (column: Boston Green ODS 150*30 5 u; mobile phase: [water(0.1% TFA)-ACN]; B %: 1%-40%, 15 min) to give 2,2,2-trifluoro-N-((trans)-1-(12-(4-fluorophenyl)-9H-benzo[e]imidazo[2,1-c]pyrrolo[1,2-a] [1,4]diazepin-7-yl)-4-(hydroxymethyl)pyrrolidin-3-yl)acetamide (60 mg, crude) as a yellow solid.

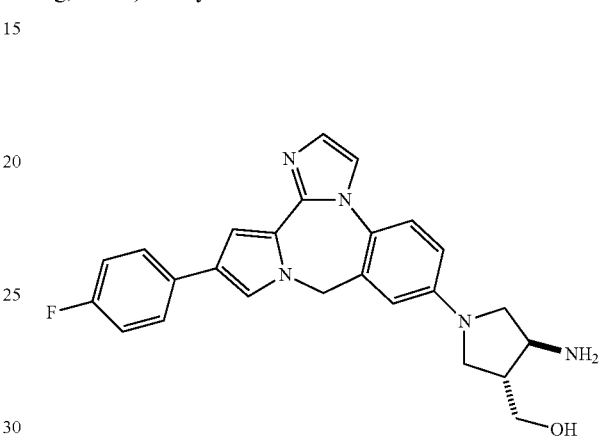

((trans)-4-amino-1-(12-(4-fluorophenyl)-9H-benzo[e] imidazo[2,1-c]pyrrolo[1,2-a][1,4] diazepin-7-yl)pyrrolidin-3-yl)methanol, 489. To a solution of 2,2,2-trifluoro-N-((trans)-1-(12-(4-fluorophenyl)-9H-benzo[e]imidazo[2,1-c] pyrrolo[1,2-a][1,4]diazepin-7-yl)-4-(hydroxymethyl) pyrrolidin-3-yl)acetamide (60 mg, 114 umol, 1.0 eq) in MeOH (5.0 mL) was added K$_2$CO$_3$ (47.3 mg, 342.5 umol, 3.0 eq) and the mixture was stirred at 60° C. for 16 hrs. The mixture was concentrated and the residue was purified by acidic prep-HPLC (column: Boston Green ODS 150*30 5 u; mobile phase: [water(0.1% TFA)-ACN]; B %: 1%-40%, 15 min) to give ((trans)-4-amino-1-(12-(4-fluorophenyl)-9H-benzo[e]imidazo[2,1-c]pyrrolo[1,2-a][1,4]diazepin-7-yl) pyrrolidin-3-yl)methanol (40.7 mg, 92 umol, 80.6% yield, 97% purity) as a yellow solid. $^1$H NMR (400 MHz, METHANOL-d$_4$) δ=8.01 (d, J=2.2 Hz, 1H), 7.74 (d, J=2.2 Hz, 1H), 7.64-7.50 (m, 4H), 7.19 (d, J=1.8 Hz, 1H), 7.07 (t, J=8.7 Hz, 2H), 6.88 (d, J=2.4 Hz, 1H), 6.80 (dd, J=2.5, 8.9 Hz, 1H), 5.29 (s, 2H), 3.97-3.89 (m, 1H), 3.83-3.70 (m, 3H), 3.64 (dd, J=7.3, 10.8 Hz, 1H), 3.51 (dd, J=4.3, 10.9 Hz, 1H), 3.27-3.22 (m, 1H), 2.71-2.60 (m, 1H). ESI [M+H]=430.1

Scheme 44:

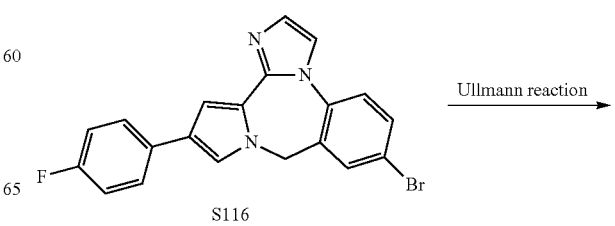

-continued

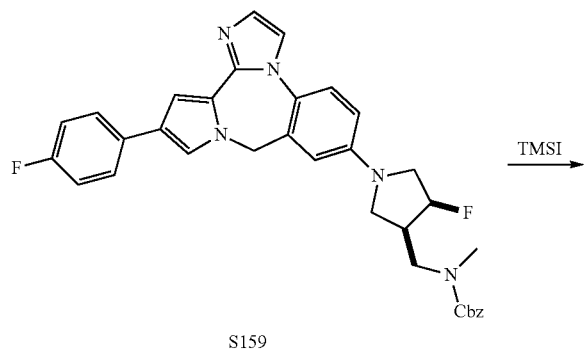

S159

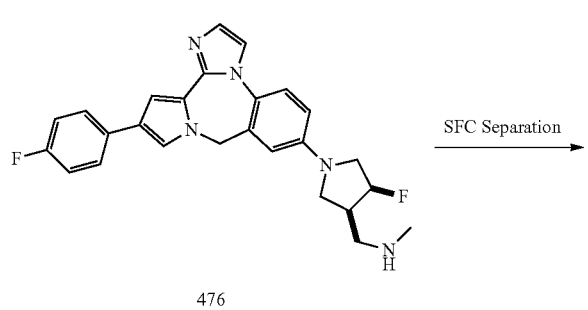

476

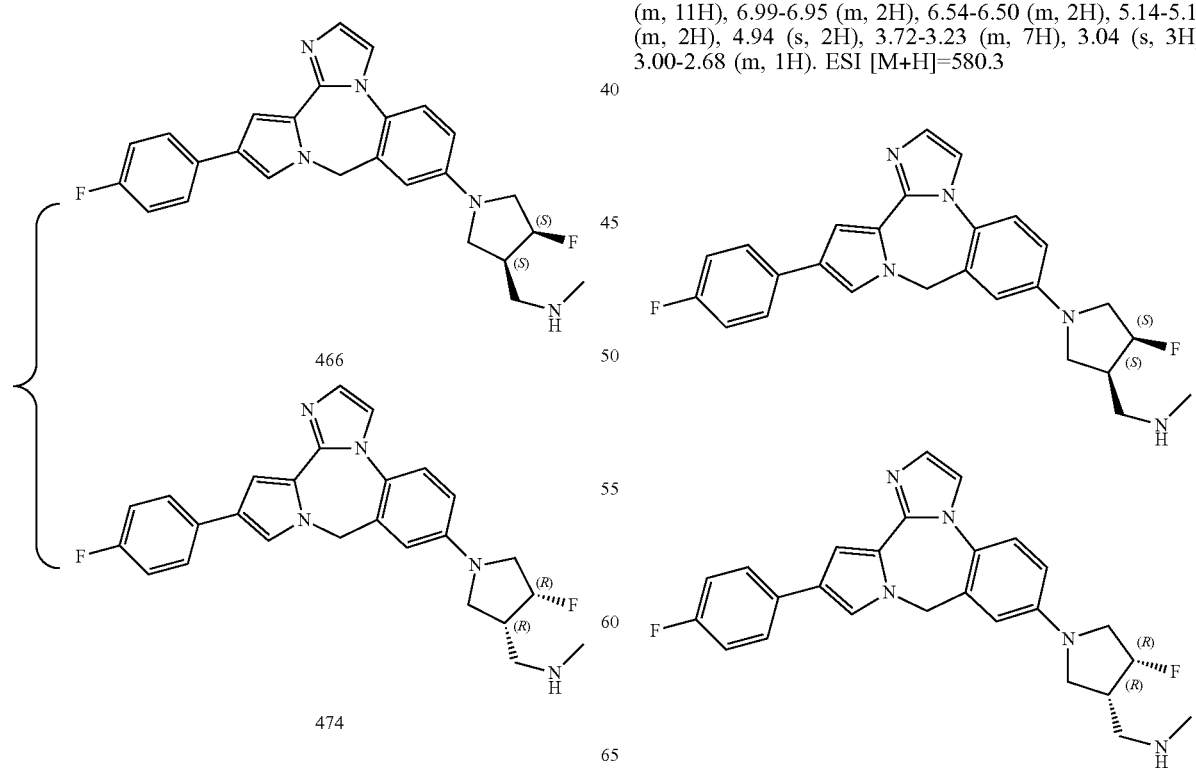

466

474

Chemistry Experimental Methods:
General Procedure T as below.

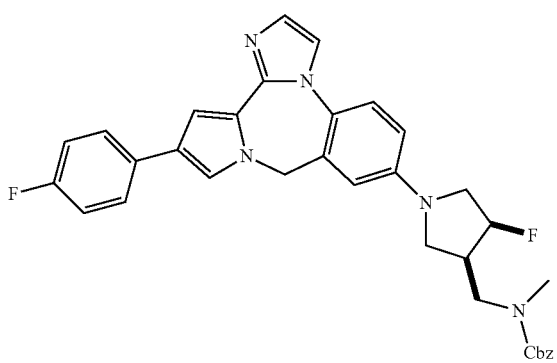 [SMILES: CN(C[C@H]1CN(c2ccc3c(c2)Cn2cc(-c4ccc(F)cc4)cc2-c2nccn2-3)C[C@H]1F)C(=O)OCc1ccccc1]

Benzyl (((cis)-4-fluoro-1-(12-(4-fluorophenyl)-9H-benzo[e]imidazo[2,1-c]pyrrolo[1,2-a][1,4] diazepin-7-yl)pyrrolidin-3-yl)methyl)(methyl)carbamate, S159. A mixture of 7-bromo-12-(4-fluorophenyl)-9H-benzo[e]imidazo[2,1-c]pyrrolo[1,2-a][1,4]diazepine (300 mg, 761 umol, 1.0 eq), benzyl (((cis)-4-fluoropyrrolidin-3-yl)methyl)(methyl)carbamate (810 mg, 3 mmol, 4.0 eq), CuI (144.9 mg, 760.9 umol, 1.0 eq), K₃PO₄ (484.6 mg, 2.3 mmol, 3.0 eq) and L-proline (26.3 mg, 228.3 umol, 0.3 eq) in DMSO (5.0 mL) was stirred at 100° C. under N₂ atmosphere for 12 hrs. The mixture was diluted with THF (20 mL) and TMT (5 mL), stirred at 60° C. for 30 mins and then filtered. The filtrate was concentrated in vacuum. The residue was purified by prep-HPLC (column: Boston Green ODS 150*30 5 u; mobile phase: [water(0.1% TFA)-ACN]; B %: 45%-75%, 10 min) to give benzyl (((cis)-4-fluoro-1-(12-(4-fluorophenyl)-9H-benzo[e]imidazo [2,1-c]pyrrolo[1,2-a][1,4]diazepin-7-yl)pyrrolidin-3-yl)methyl)(methyl)carbamate (110 mg, 170 umol, 22.4% yield, 90% purity) as a yellow solid. ¹H NMR (400 MHz, CHLOROFORM-d) δ=7.55 (s, 1H), 7.40-7.22 (m, 11H), 6.99-6.95 (m, 2H), 6.54-6.50 (m, 2H), 5.14-5.11 (m, 2H), 4.94 (s, 2H), 3.72-3.23 (m, 7H), 3.04 (s, 3H), 3.00-2.68 (m, 1H). ESI [M+H]=580.3

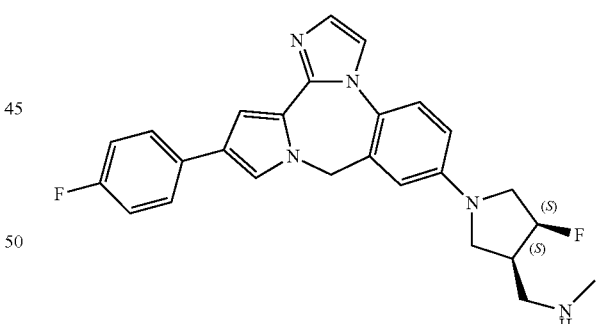

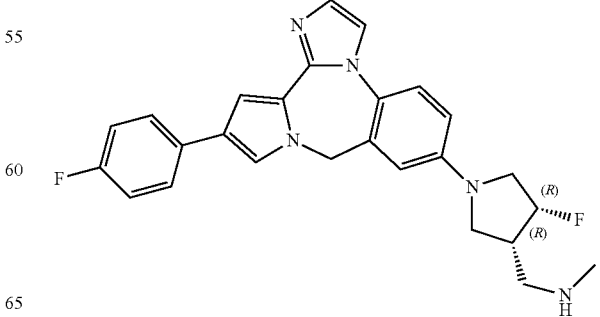

1-((3S,4S)-4-fluoro-1-(12-(4-fluorophenyl)-9H-benzo[e]
imidazo[2,1-c]pyrrolo[1,2-a][1,4]diazepin-7-yl)pyrrolidin-
3-yl)-N-methylmethanamine, 466.

1-((3R,4R)-4-fluoro-1-(12-(4-fluorophenyl)-9H-benzo[e]
imidazo[2,1-c]pyrrolo[1,2-a][1,4]diazepin-7-yl)pyrrolidin-
3-yl)-N-methylmethanamine, 474. To a solution of benzyl
(((cis)-4-fluoro-1-(12-(4-fluorophenyl)-9H-benzo[e]imi-
dazo[2,1-c]pyrrolo[1,2-a][1,4]diazepin-7-yl)pyrrolidin-3-
yl)methyl)(methyl)carbamate (500 mg, 862 umol, 1.0 eq) in
DCM (5.0 mL) and ACN (5.0 mL) was added TMSI (345
mg, 1.7 mmol, 234.8 uL, 2.0 eq) dropwise, then stirred at
35° C. for 0.5 hr and concentrated. The residue was purified
by acidic prep-HPLC to afford 1-(cis-4-fluoro-1-(12-(4-
fluorophenyl)-9H-benzo[e]imidazo[2, 1-c]pyrrolo[1,2-a][1,
4]diazepin-7-yl)pyrrolidin-3-yl)-N-methylmethanamine
(476) (300 mg). Then the cis-compound 476 was separated
by SFC to give two homo-chiral compounds. 1-((3S,4S)-4-
fluoro-1-(12-(4-fluorophenyl)-9H-benzo[e]imidazo[2,1-c]
pyrrolo[1,2-a][1,4]diazepin-7-yl)pyrrolidin-3-yl)-N-methyl-
methanamine (466) (100 mg, 177 umol, 20.6% yield, 99.4%
purity, TFA, ee %=100%) was obtained as a white solid,
which was assigned randomly as the left peak in the SFC. $^1$H
NMR (400 MHz, METHANOL-$d_4$) δ=δ=8.01 (d, J=2.2 Hz,
1H), 7.74 (d, J=1.8 Hz, 1H), 7.62-7.51 (m, 4H), 7.19 (d,
J=1.8 Hz, 1H), 7.08 (t, J=8.6 Hz, 2H), 6.83 (d, J=2.6 Hz,
1H), 6.77 (dd, J=2.6, 8.8 Hz, 1H), 5.53-5.33 (m, 1H), 5.28
(s, 2H), 3.87-3.81 (m, 1H), 3.80-3.71 (m, 2H), 3.71-3.66 (m,
1H), 3.44 (dd, J=7.7, 13.0 Hz, 1H), 3.26 (br. s., 1H), 2.88 (d,
J=15.0 Hz, 1H), 2.80 (s, 3H). ESI [M+H]=446.2

1-((3R,4R)-4-fluoro-1-(12-(4-fluorophenyl)-9H-benzo[e]
imidazo[2,1-c]pyrrolo[1,2-a][1,4] diazepin-7-yl)pyrrolidin-
3-yl)-N-methylmethanamine (474) (3.41 mg, 6.97 umol,
3.67% yield, 91% purity, ee %=96.6%) was obtained as a
yellow solid, which was assigned randomly as the right peak
in the SFC. 1H NMR (400 MHz, METHANOL-d4) δ=7.56-
7.49 (m, 3H), 7.37 (d, J=8.8 Hz, 1H), 7.27 (s, 1H), 7.18 (s,
1H), 7.03 (t, J=8.7 Hz, 2H), 6.90 (s, 1H), 6.74 (s, 1H), 6.66
(dd, J=2.2, 8.8 Hz, 1H), 5.44-5.26 (m, 1H), 5.05 (s, 2H),
3.78-3.56 (m, 3H), 3.24-3.13 (m, 1H), 3.04 (dd, J=7.4, 12.0
Hz, 1H), 2.87 (br dd, J=7.1, 11.9 Hz, 1H), 2.76-2.57 (m, 1H),
2.52 (s, 3H). ESI [M+H]=446.1

Scheme 45:

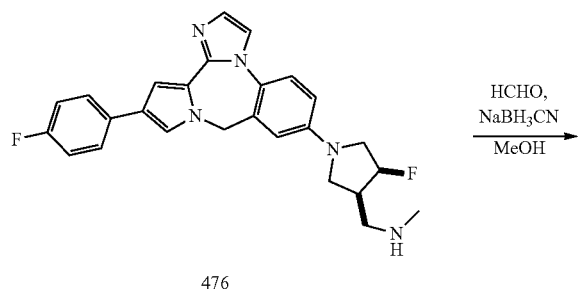

476

-continued

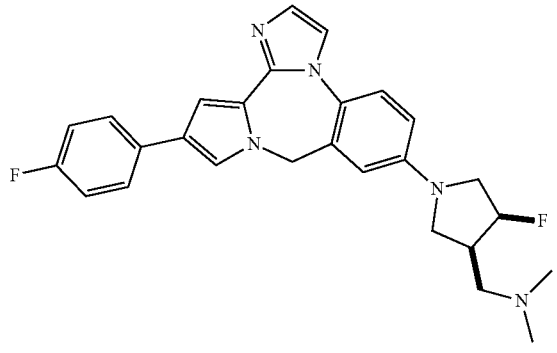

477

Chemistry Experimental Methods:
General Procedure U as below.

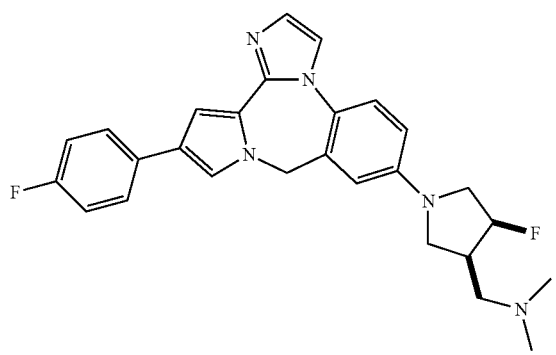 [SMILES: CN(C)C[C@H]1CN(c2ccc3c(c2)Cn2cc(-c4ccc(F)cc4)cc2-c2nccn2-3)C[C@H]1F]

1-((cis)-4-fluoro-1-(12-(4-fluorophenyl)-9H-benzo[e]
imidazo[2,1-c]pyrrolo[1,2-a][1,4]diazepin-7-yl)pyrrolidin-
3-yl)-N,N-dimethylmethanamine, 477. A mixture of
1-((cis)-4-fluoro-1-(12-(4-fluorophenyl)-9H-benzo[e]imi-
dazo[2,1-c]pyrrolo[1,2-a][1,4]diazepin-7-yl)pyrrolidin-3-
yl)-N-methylmethanamine (5.0 mg, 11.2 umol, 1.0 eq) and
formaldehyde (9.1 mg, 112 umol, 8.3 uL, 10 eq) in MeOH
(3.0 mL) was stirred at 25° C. for 10 mins, then NaBH$_3$CN
(2.1 mg, 33.6 umol, 3.0 eq) was added and stirred at 25° C.
for 5 mins. The mixture was concentrated and the residue
was purified by prep-HPLC (column: Boston Green ODS
150*30 5 u; mobile phase: [water(0.1% TFA)-ACN]; B %:
17%-47%, 10 min) to give the product 1-((cis)-4-fluoro-1-
(12-(4-fluorophenyl)-9H-benzo[e]imidazo[2,1-c]pyrrolo[1,
2-a][1,4]diazepin-7-yl)pyrrolidin-3-yl)-N,N-dimethylmeth-
anamine (1.0 mg, 1.7 umol, 15.2% yield, 95% purity, TFA)
as a yellow solid. 1H NMR (400 MHz, METHANOL-d4)
δ=8.03 (s, 1H), 7.77 (s, 1H), 7.63-7.53 (m, 4H), 7.21 (s, 1H),
7.10 (t, J=8.6 Hz, 2H), 6.85 (s, 1H), 6.80 (d, J=8.8 Hz, 1H),
5.56-5.37 (m, 1H), 5.30 (s, 2H), 3.89-3.82 (m, 1H), 3.80 (d,
J=11.0 Hz, 1H), 3.73 (d, J=11.8 Hz, 1H), 3.63 (dd, J=7.0,
13.6 Hz, 1H), 3.43 (dd, J=6.8, 13.4 Hz, 1H), 3.37-3.32 (m,
1H), 3.08-2.97 (m, 7H). ESI [M+H]=460.2

Scheme 46:

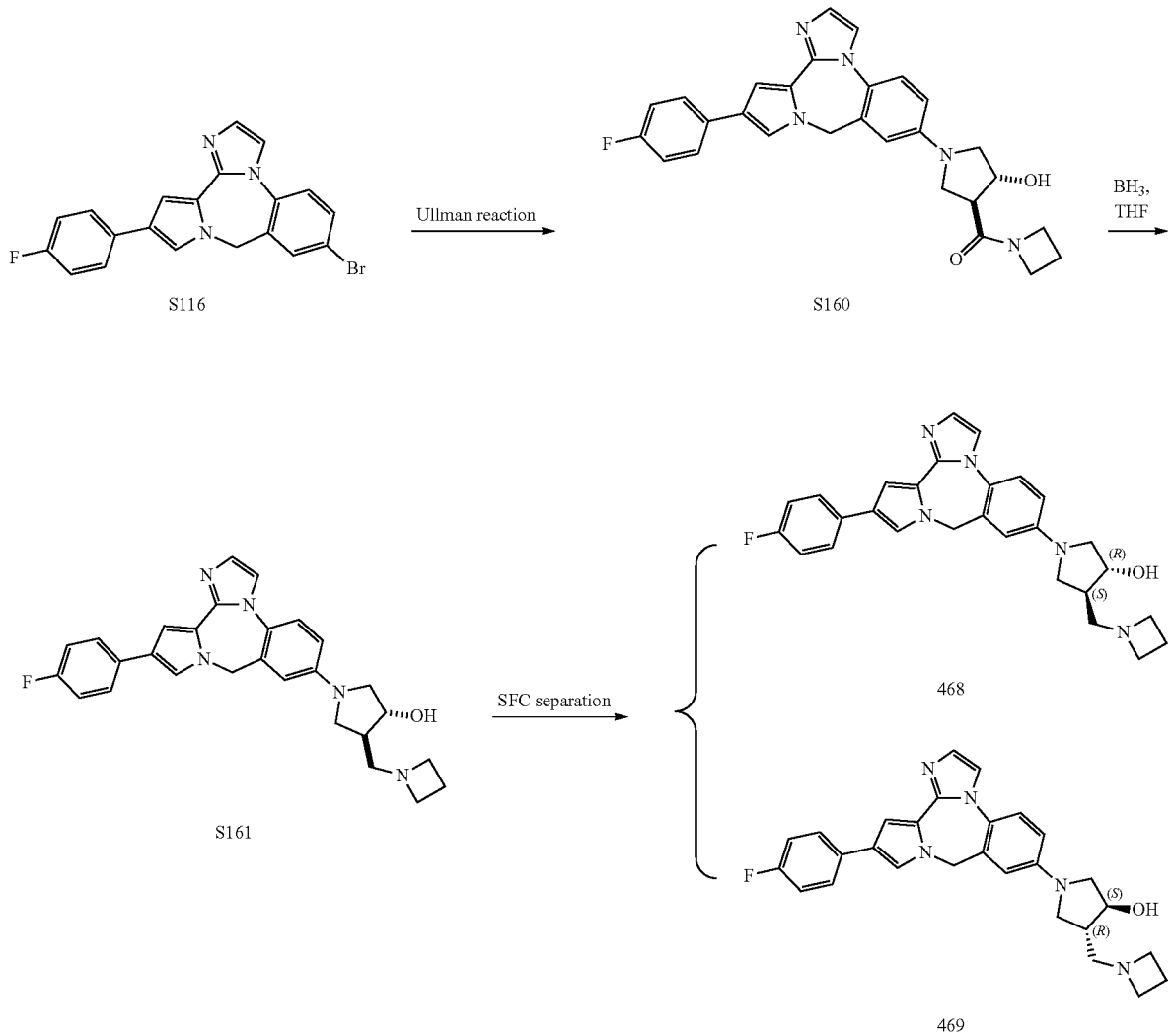

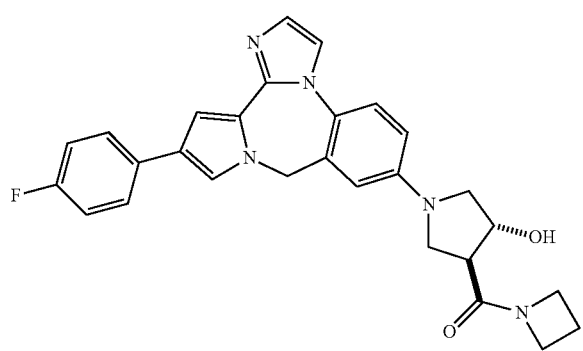 [SMILES: O=C([C@H]1CN(c2ccc3c(c2)Cn2cc(-c4ccc(F)cc4)cc2-c2nccn2-3)C[C@@H]1O)N1CCC1]

Chemistry Experimental Methods:
General Procedure V as below.

Azetidin-1-yl((trans)-1-(12-(4-fluorophenyl)-9H-benzo[e]imidazo[2,1-c]pyrrolo[1,2-a][1,4] diazepin-7-yl)-4-hydroxypyrrolidin-3-yl)methanone, S160. A mixture of 7-bromo-12-(4-fluorophenyl)-9H-benzo[e]imidazo[2,1-c]pyrrolo[1,2-a][1,4]diazepine (100 mg, 253 umol, 1.0 eq), azetidin-1-yl((trans)-4-hydroxypyrrolidin-3-yl)methanone (86.4 mg, 507 umol, 2.0 eq), CuI (144.9 mg, 760.9 umol, 3.0 eq), $K_3PO_4$ (26.9 mg, 126.8 umol, 0.5 eq) and L-proline (87.6 mg, 760.9 umol, 3.0 eq) in DMSO (5.0 mL) was stirred at 100° C. under $N_2$ for 2 hrs. The mixture was diluted with THF (20 mL) and TMT (2 mL) and stirred at 60° C. for 30 mins. The mixture was filtered and the filtrate was concentrated. The residue was purified by prep-HPLC (column: Boston Green ODS 150*30 5 u; mobile phase: [water(0.1% TFA)-ACN]; B %: 23%-53%, 10 min) to give azetidin-1-yl((trans)-1-(12-(4-fluorophenyl)-9H-benzo[e]imidazo[2,1-c]pyrrolo[1,2-a][1,4] diazepin-7-yl)-4-hydroxypyrrolidin-3-yl)methanone (40 mg, 82 umol, 32.6% yield) as a white solid. ESI [M+H]=484.3

267

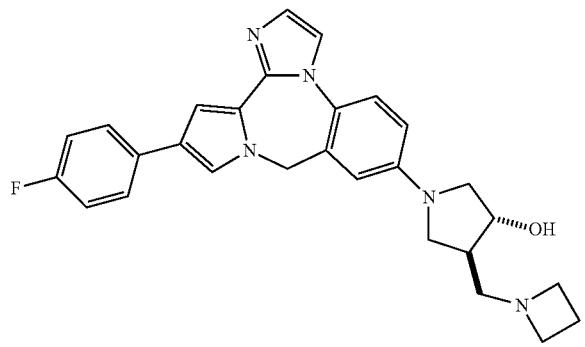 [SMILES: O[C@H]1CN(c2ccc3c(c2)Cn2cc(-c4ccc(F)cc4)cc2-c2nccn2-3)C[C@@H]1CN1CCC1]

Trans-4-(azetidin-1-ylmethyl)-1-(12-(4-fluorophenyl)-9H-benzo[e]imidazo[2,1-c]pyrrolo[1,2-a][1,4]diazepin-7-yl)pyrrolidin-3-ol, S161. A solution of azetidin-1-yl((trans)-1-(12-(4-fluorophenyl)-9H-benzo[e]imidazo[2,1-c]pyrrolo[1,2-a][1,4]diazepin-7-yl)-4-hydroxypyrrolidin-3-yl)methanone (70 mg, 144 umol, 1.0 eq) in $BH_3 \cdot THF$ (1 M, 20 mL, 138 eq) was stirred at 65° C. for 30 mins. The mixture was quenched with methanol (100 mL) at 0° C. and then concentrated. The residue was dissolved with ethanol (50 mL) and stirred at 80° C. for 10 hrs. The mixture was concentrated and the residue was purified by prep-HPLC (column: Boston Green ODS 150*30 5 u; mobile phase: [water(0.1% TFA)-ACN]; B %: 15%-45%, 10 min) to give (trans)-4-(azetidin-1-ylmethyl)-1-(12-(4-fluorophenyl)-9H-benzo[e]imidazo[2,1-c]pyrrolo[1,2-a][1,4]diazepin-7-yl)pyrrolidin-3-ol (45 mg, 77 umol, 53% yield, 100% purity, TFA) as a yellow solid. $^1$H NMR (400 MHz, METHANOL-d$_4$) δ=7.98 (d, J=1.6 Hz, 1H), 7.71 (d, J=2.4 Hz, 1H), 7.58-7.52 (m, 4H), 7.17 (d, J=1.6 Hz, 1H), 7.10-7.05 (m, 2H), 6.78 (d, J=2.4 Hz, 1H), 6.75-6.65 (m, 1H), 5.26 (s, 2H), 4.30-4.14 (m, 5H), 3.73-3.67 (m, 2H), 3.41-3.38 (m, 2H), 3.24-3.16 (m, 2H), 2.65-2.43 (m, 3H). ESI [M+H]=470.1

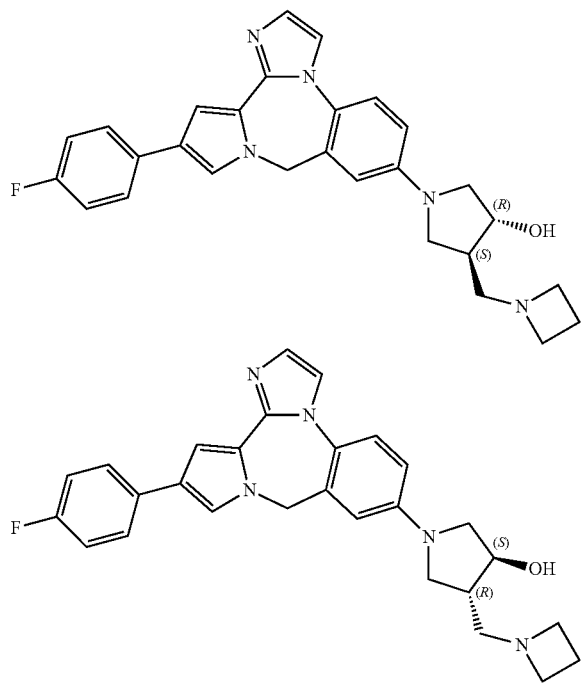

268

(3R,4S)-4-(azetidin-1-ylmethyl)-1-(12-(4-fluorophenyl)-9H-benzo[e]imidazo[2,1-c]pyrrolo[1,2-a][1,4]diazepin-7-yl)pyrrolidin-3-ol, 468

(3S,4R)-4-(azetidin-1-ylmethyl)-1-(12-(4-fluorophenyl)-9H-benzo[e]imidazo[2,1-c]pyrrolo[1,2-a][1,4]diazepin-7-yl)pyrrolidin-3-ol, 469 The racemic compound 5161 was separated by SFC.

The left peak was assigned randomly as (3R,4S)-4-(azetidin-1-ylmethyl)-1-(12-(4-fluorophenyl)-9H-benzo[e]imidazo[2,1-c]pyrrolo[1,2-a][1,4]diazepin-7-yl)pyrrolidin-3-ol (17 mg, 29 umol, 30% yield, 100% purity, TFA, ee %=99.78%), which was obtained as a yellow solid. 1H NMR (400 MHz, METHANOL-d4) δ=8.01 (d, J=2.0 Hz, 1H), 7.74 (d, J=2.0 Hz, 1H), 7.62-7.52 (m, 4H), 7.20 (d, J=1.5 Hz, 1H), 7.09 (t, J=8.7 Hz, 2H), 6.81 (d, J=2.4 Hz, 1H), 6.74 (dd, J=2.6, 8.8 Hz, 1H), 5.28 (s, 2H), 4.40-4.09 (m, 5H), 3.77-3.66 (m, 2H), 3.46-3.35 (m, 2H), 3.28-3.15 (m, 2H), 2.70-2.56 (m, 1H), 2.53-2.40 (m, 2H). ESI [M+H]=470.1

The right peak was assigned randomly as (3S,4R)-4-(azetidin-1-ylmethyl)-1-(12-(4-fluorophenyl)-9H-benzo[e]imidazo[2,1-c]pyrrolo[1,2-a][1,4]diazepin-7-yl)pyrrolidin-3-ol (21 mg, 36 umol, 37.9% yield, 97% purity, TFA, ee %=94.62%) which was obtained as a yellow solid. 1H NMR (400 MHz, METHANOL-d4) δ=8.01 (d, J=2.0 Hz, 1H), 7.74 (d, J=2.0 Hz, 1H), 7.62-7.53 (m, 4H), 7.20 (d, J=1.8 Hz, 1H), 7.10 (t, J=8.8 Hz, 2H), 6.81 (d, J=2.6 Hz, 1H), 6.74 (dd, J=2.5, 8.9 Hz, 1H), 5.28 (s, 2H), 4.40-4.09 (m, 5H), 3.72 (ddd, J=7.4, 9.6, 16.9 Hz, 2H), 3.47-3.36 (m, 2H), 3.27-3.15 (m, 2H), 2.63 (br d, J=9.5 Hz, 1H), 2.54-2.40 (m, 2H). ESI [M+H]=470.2

Scheme 47:

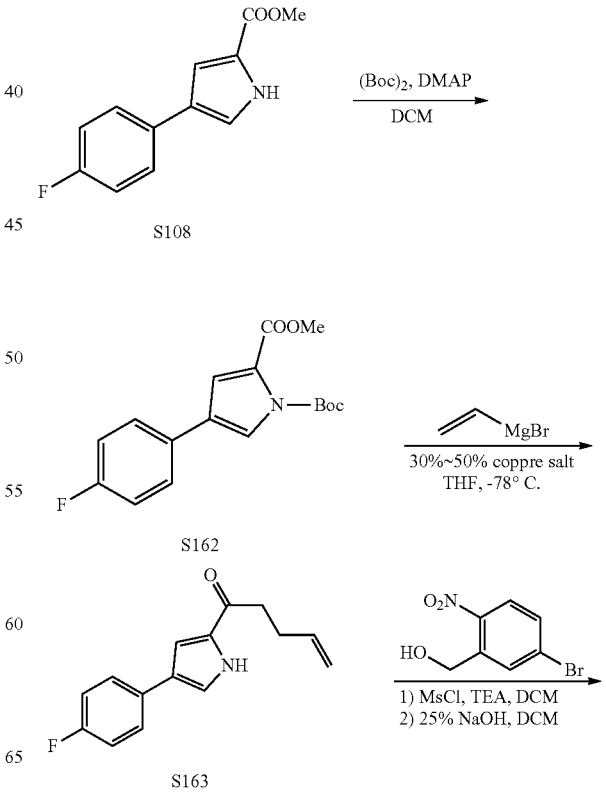

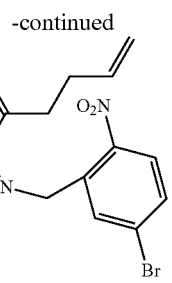

S164

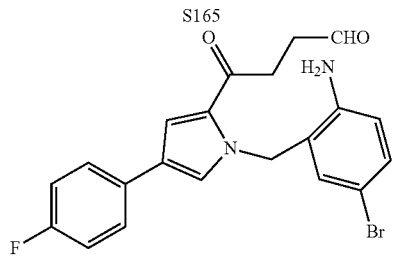

S165

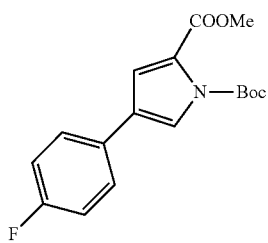 [SMILES: COC(=O)c1cc(-c2ccc(F)cc2)cn1C(=O)OC(C)(C)C]

S166

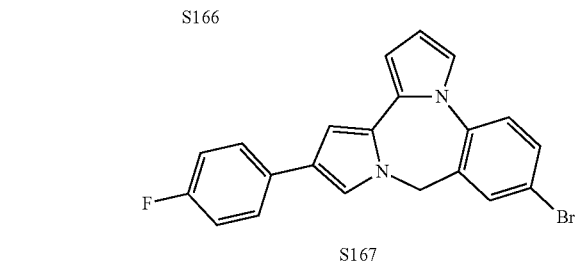

S167

Chemistry Experimental Methods:

[structure: 1-tert-butyl 2-methyl 4-(4-fluorophenyl)-1H-pyrrole-1,2-dicarboxylate]

1-tert-butyl 2-methyl 4-(4-fluorophenyl)-1H-pyrrole-1,2-dicarboxylate, S162. To a mixture of methyl 4-(4-fluorophenyl)-1H-pyrrole-2-carboxylate (5.5 g, 25 mmol, 1.0 eq) and (Boc)$_2$O (6.5 g, 30.1 mmol, 6.9 mL, 1.2 eq) in THF (200 mL) was added DMAP (306 mg, 2.5 mmol, 0.1 eq) in one portion. The mixture was stirred at 20° C. for 1 hr, and then concentrated. The residue was purified by silica gel chromatography (petroleum ether/ethyl acetate=5:1) to give 1-tert-butyl 2-methyl 4-(4-fluorophenyl)-1H-pyrrole-1,2-dicarboxylate (17 g, 47.9 mmol, 95.5% yield, 90% purity) as yellow oil. $^1$H NMR (400 MHz, CHLOROFORM-d) δ=7.50-7.49 (m, 1H), 7.45-7.42 (m, 2H), 7.06-7.04 (m, 3H), 3.86 (s, 3H), 1.58 (s, 9H).

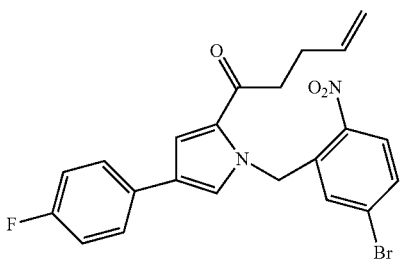 [SMILES: C=CCCC(=O)c1cc(-c2ccc(F)cc2)cn1Cc1cc(Br)ccc1[N+](=O)[O-]]

1-(4-(4-fluorophenyl)-1H-pyrrol-2-yl)pent-4-en-1-one, S163. To a solution of 1-tert-butyl 2-methyl 4-(4-fluorophenyl)-1H-pyrrole-1,2-dicarboxylate (4.7 g, 14.8 mmol, 1.0 eq) in THF (90 mL) was added CuCN (799 mg, 8.9 mmol, 1.9 mL, 0.6 eq) and the mixture was cooled to −78° C., then bromo(vinyl)magnesium (1M, 89.2 mmol, 89.2 mL, 6.0 eq) was added dropwise under N$_2$. The reaction mixture was stirred at −78° C. for 1 hr, then warmed to 0° C. and stirred for another 1 hr. The mixture was quenched by sat.NH$_4$Cl solution (100 mL) at 0° C. and was extracted with EtOAc (100 mL×3). The combined organic phase was dried and concentrated. The residue was purified by silica gel chromatography eluted with petroleum ether/ethyl acetate=10:1 to give 1-(4-(4-fluorophenyl)-1H-pyrrol-2-yl)pent-4-en-1-one (1.5 g, 4.3 mmol, crude) as a yellow solid. ESI [M+H]=243.9

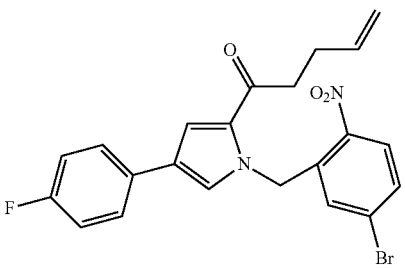 [SMILES: C=CCCC(=O)c1cc(-c2ccc(F)cc2)cn1Cc1cc(Br)ccc1[N+](=O)[O-]]

1-(1-(5-bromo-2-nitrobenzyl)-4-(4-fluorophenyl)-1H-pyrrol-2-yl)pent-4-en-1-one, S164. To a mixture of (5-bromo-2-nitrophenyl)methanol (1.9 g, 8.3 mmol, 1.5 eq) and TEA (648 mg, 6.4 mmol, 888 uL, 1.2 eq) in DCM (20 mL) was added MsCl (1.2 g, 10.6 mmol, 826 uL, 2.0 eq) at 0° C. The mixture was warmed to 10° C. and stirred for 2 hrs. Then 1-[4-(4-fluorophenyl)-1H-pyrrol-2-yl]pent-4-en-1-one (1.3 g, 5.3 mmol, 1.0 eq), 25% NaOH solution (4.2 g, 26.7 mmol, 5.0 eq) and tetrabutylammonium;hydroxide (25%, 138 mg, 534 umol, 173.31 uL, 0.1 eq) were added into the mixture and it was stirred at 10° C. for 16 hrs. The mixture was diluted with water (50 mL) and extracted with DCM (30 mL×3). The combined organic phase was dried, filtered and concentrated. The residue was purified by silica gel chromatography eluted with petroleum ether/ethyl acetate=20:1 to give the product 1-[1-[(5-bromo-2-nitrophenyl)methyl]-4-(4-fluorophenyl)pyrrol-2-yl]pent-4-en-1-one (1.4 g, crude) as a yellow oil. ESI [M+H]=457.0/459.0

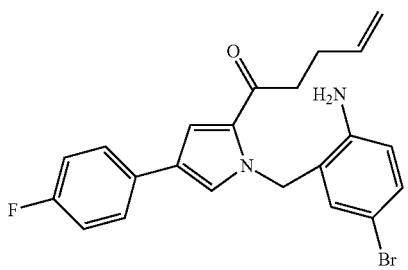

1-(1-(2-amino-5-bromobenzyl)-4-(4-fluorophenyl)-1H-pyrrol-2-yl)pent-4-en-1-one, S165. To a solution of 1-(1-(5-bromo-2-nitrobenzyl)-4-(4-fluorophenyl)-1H-pyrrol-2-yl)pent-4-en-1-one (700 mg, 1.5 mmol, 1.0 eq) in THF (10 mL), EtOH (10 mL) and H$_2$O (3 mL) was added Fe (256 mg, 4.5 mmol, 3.0 eq) and NH$_4$Cl (122 mg, 2.3 mmol, 80.2 uL, 1.5 eq) and the mixture was stirred at 90° C. for 1 hr. Then it was filtered and the aqueous layer was extracted with EtOAc/THF (1:1, 20 mL×3). The combined organic layers were washed with sat. NaHCO$_3$ (20 mL), dried, filtered and concentrated. The residue was purified by prep-HPLC (column: Phenomenex luna C18 250*50 mm*10 um; mobile phase: [water(10 mM NH$_4$HCO3)-ACN]; B %: 45%-75%, 20 min) to give 1-(1-(2-amino-5-bromobenzyl)-4-(4-fluorophenyl)-1H-pyrrol-2-yl)pent-4-en-1-one (220 mg, 514 umol, 33.6% yield) as a white solid. $^1$H NMR (400 MHz, CHLOROFORM-d) δ=7.42-7.39 (m, 2H), 7.25-7.21 (m, 2H), 7.10-7.02 (m, 4H), 6.56-6.54 (m, 1H), 5.90-5.83 (m, 1H), 5.45 (s, 2H), 5.09-4.98 (m, 2H), 2.97-2.93 (m, 2H), 2.49-2.44 (m, 2H). ESI [M+H]=427.1/429.1

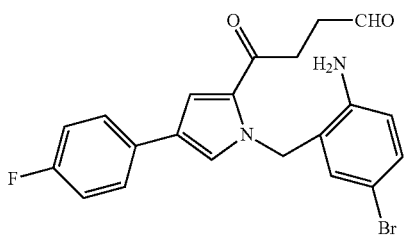 [SMILES: Nc1ccc(Br)cc1Cn1cc(-c2ccc(F)cc2)cc1C(=O)CCC=O]

4-(1-(2-amino-5-bromobenzyl)-4-(4-fluorophenyl)-1H-pyrrol-2-yl)-4-oxobutanal, S166. To a solution of 1-(1-(2-amino-5-bromobenzyl)-4-(4-fluorophenyl)-1H-pyrrol-2-yl)pent-4-en-1-one (220 mg, 514 umol, 1.0 eq) in dioxane (30 mL) and H$_2$O (8 mL) were added NaIO4 (440 mg, 2 mmol, 114 uL, 4.0 eq), OsO$_4$ (2.6 mg, 10.3 umol, 0.53 uL, 0.02 eq) and 2,6-lutidine (110 mg, 1.0 mmol, 119.9 uL, 2.0 eq). The mixture was stirred at 10° C. for 16 hrs. The mixture was diluted with water (20 mL) then extracted with DCM (50 mL×2). The combined organic phases were dried, filtered and concentrated to give 4-(1-(2-amino-5-bromobenzyl)-4-(4-fluorophenyl)-1H-pyrrol-2-yl)-4-oxobutanal (250 mg, crude) as a black brown solid, which was used directly for next step without further purification.

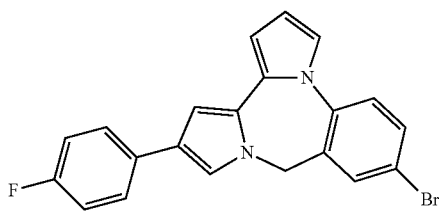

7-bromo-12-(4-fluorophenyl)-9H-benzo[e]dipyrrolo[1,2-a:2',1'-c][1,4]diazepine, S167. 4-(1-(2-amino-5-bromobenzyl)-4-(4-fluorophenyl)-1H-pyrrol-2-yl)-4-oxobutanal (150 mg, 349 umol, 1.0 eq) was dissolved in ACN (5.0 mL), then AcONa (28.6 mg, 349.4 umol, 1.0 eq), AcOH (20.9 mg, 349.4 umol, 19.9 uL, 1.0 eq) and ammonium formate (22 mg, 349 umol, 1.0 eq) were added into the mixture. The mixture was stirred at 65° C. for 16 hrs, then filtered and the filtrate was concentrated. The residue was purified by prep-HPLC (column: Daiso 250*50 mm, 10 um; mobile phase: [water(0.1% TFA)-ACN]; B %: 55%-85%, 20 min) to give 7-bromo-12-(4-fluorophenyl)-9H-benzo[e]dipyrrolo[1,2-a:2',1'-c][1,4]diazepine (80 mg, 203 umol, 58.2% yield) as a black brown solid. $^1$H NMR (400 MHz, CHLOROFORM-d) δ=7.57-7.52 (m, 2H), 7.44 (dd, J=5.3, 8.8 Hz, 2H), 7.29 (d, J=8.4 Hz, 1H), 7.12-7.07 (m, 1H), 7.05-6.97 (m, 3H), 6.57 (d, J=1.8 Hz, 1H), 6.52 (dd, 3.5 Hz, 1H), 6.45 (t, J=3.1 Hz, 1H), 5.03 (s, 2H).

Scheme 48:

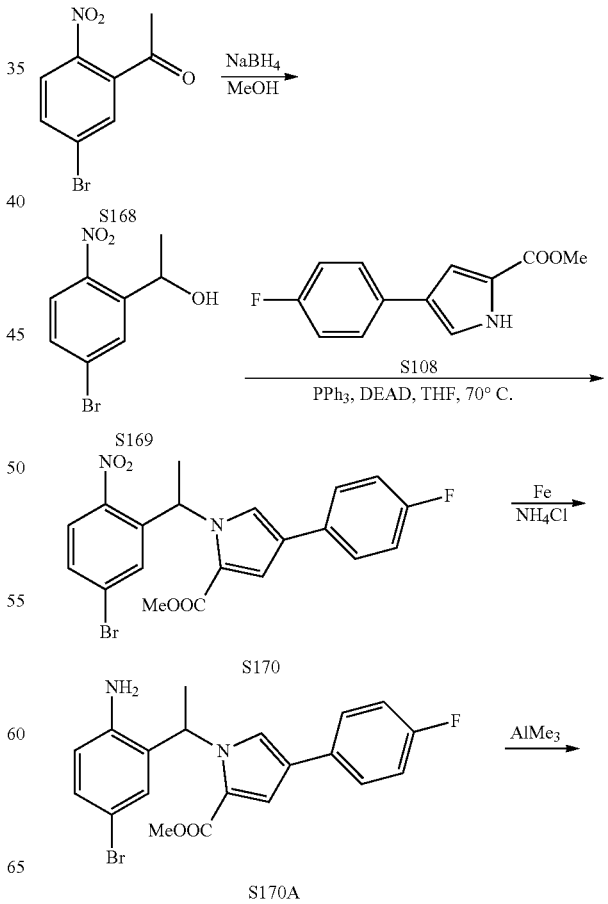

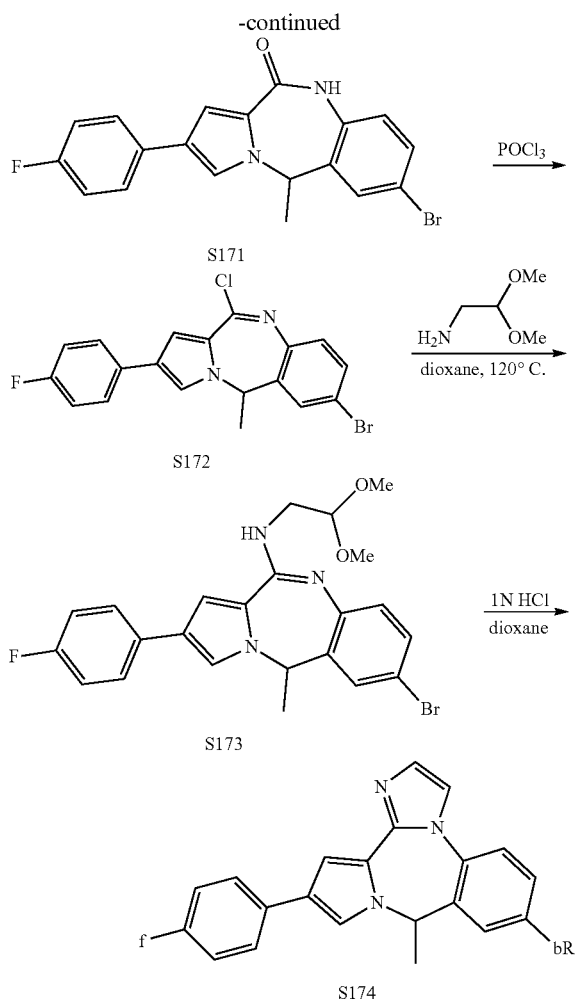

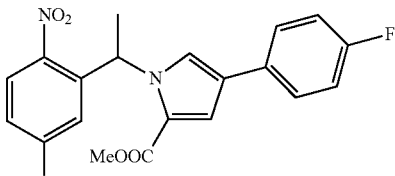

Methyl 1-(1-(5-bromo-2-nitrophenyl)ethyl)-4-(4-fluorophenyl)-1H-pyrrole-2-carboxylate, S170. A mixture of methyl 4-(4-fluorophenyl)-1H-pyrrole-2-carboxylate (2.2 g, 10 mmol, 1.0 eq), 1-(5-bromo-2-nitrophenyl)ethanol (2.99 g, 12 mmol, 1.2 eq) and PPh$_3$ (4.7 g, 18 mmol, 1.8 eq) in THF (20 mL) was degassed and purged with N$_2$ for 3 times, and then DEAD (3.15 g, 18 mmol, 3.3 mL, 1.8 eq) was added dropwise into the solution. The mixture was stirred at 70° C. under N$_2$ atmosphere for 1 hr and then concentrated. The residue was purified by column chromatography (SiO$_2$, petroleum ether/ethyl acetate=100:1 to 50:1) to give methyl 1-(1-(5-bromo-2-nitrophenyl)ethyl)-4-(4-fluorophenyl)-1H-pyrrole-2-carboxylate (1.05 g, 2.1 mmol, 21% yield, 90% purity) as a light red solid. $^1$H NMR (400 MHz, CHLOROFORM-d) δ=7.79 (d, J=8.8 Hz, 1H), 7.49-7.40 (m, 4H), 7.17 (d, J=1.8 Hz, 1H), 7.02 (t, J=8.6 Hz, 2H), 6.96 (d, J=1.8 Hz, 1H), 6.72 (q, J=6.8 Hz, 1H), 3.60 (s, 3H), 1.91 (d, J=7.1 Hz, 3H). ESI [M+H]=447.0/449.0

Chemistry Experimental Methods:

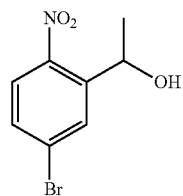

1-(5-bromo-2-nitrophenyl)ethanol, S169. To a solution of 1-(5-bromo-2-nitrophenyl)ethanone (4.9 g, 20.4 mmol, 1.0 eq) in MeOH (100 mL) was added NaBH$_4$ (1.5 g, 40 mmol, 2.0 eq) portionwise at 0° C. The mixture was warmed to 15° C. and stirred for 2 hrs. The reaction mixture was quenched with water (50 mL), and then concentrated to remove MeOH. The aqueous phase was extracted with DCM (50 mL×3). The combined organic layers were washed brine (50 mL), dried over Na$_2$SO$_4$, filtered and concentrated to give 1-(5-bromo-2-nitrophenyl)ethanol (4.9 g, 90% purity) as a yellow solid, which was used in the next step without purification. $^1$H NMR (400 MHz, CHLOROFORM-d) δ=8.00 (d, J=2.4 Hz, 1H), 7.81 (d, J=8.4 Hz, 1H), 7.61 (dd, J=2.4, 8.4 Hz, 2H), 5.29 (q, J=6.4 Hz, 1H), 1.44 (d, J=6.4 Hz, 3H).

Methyl 1-(1-(2-amino-5-bromophenyl)ethyl)-4-(4-fluorophenyl)-1H-pyrrole-2-carboxylate, S170A. To a mixture of methyl 1-(1-(5-bromo-2-nitrophenyl)ethyl)-4-(4-fluorophenyl)-1H-pyrrole-2-carboxylate (1.0 g, 2.2 mmol, 1.0 eq) in H$_2$O (2.0 mL), THF (6.0 mL) and MeOH (6.0 mL) was added Fe (1.25 g, 22.4 mmol, 10.0 eq) and NH$_4$Cl (5.0 g, 93.5 mmol, 3.3 mL, 41.7 eq). The mixture was stirred at 80° C. for 1 hr, then filtered and the filtrate was concentrated to give methyl 1-(1-(2-amino-5-bromophenyl)ethyl)-4-(4-fluorophenyl)-1H-pyrrole-2-carboxylate (1.1 g, crude) as a light yellow solid, which was used in the next step without purification.

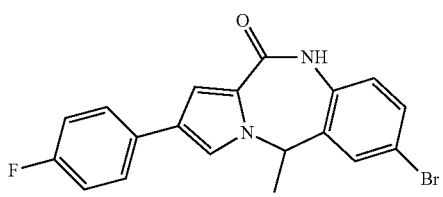 [SMILES: CC1c2cc(Br)ccc2NC(=O)c2cc(-c3ccc(F)cc3)cn21]

7-bromo-2-(4-fluorophenyl)-5-methyl-5H-benzo[e]pyrrolo[1,2-a][1,4]diazepin-11(10H)-one, S171. To a mixture of methyl 1-(1-(2-amino-5-bromophenyl)ethyl)-4-(4-fluorophenyl)-1H-pyrrole-2-carboxylate (1.1 g, 2.6 mmol, 1.0 eq) in toluene (30 mL) was added AlMe$_3$ (2M, 6.6 mL, 13.2 mmol, 5.0 eq) dropwise and the mixture was stirred at 15°

C. for 12 hrs. The mixture was quenched by cooled 1N HCl (30 mL) and extracted with ethyl acetate/THF (2:1, 100 mL×3). The organic layer was washed with brine (50 mL), dried over MgSO$_4$ and concentrated to give 7-bromo-2-(4-fluorophenyl)-5-methyl-5H-benzo[e]pyrrolo[1,2-a][1,4]diazepin-11(10H)-one (1.05 g, crude) as light yellow solid, which was used in the next step without purification. ESI [M+H]=385.0/387.0

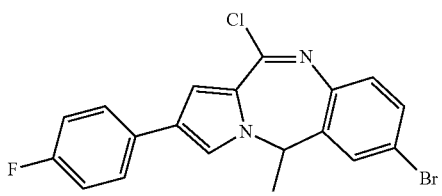 [SMILES: CC1c2cc(Br)ccc2N=C(Cl)c2cc(-c3ccc(F)cc3)cn21]

7-bromo-11-chloro-2-(4-fluorophenyl)-5-methyl-5H-benzo[e]pyrrolo[1,2-a][1,4]diazepine, S172. A mixture of 7-bromo-2-(4-fluorophenyl)-5-methyl-5H-benzo[e]pyrrolo[1,2-a][1,4] diazepin-11(10H)-one (300 mg, 778 umol, 1.0 eq) in POCl$_3$ (30 mL) was stirred at 70° C. for 2 hrs. The reaction mixture was concentrated to give 7-bromo-11-chloro-2-(4-fluorophenyl)-5-methyl-5H-benzo[e]pyrrolo[1,2-a][1,4]diazepine (1.50 g, crude) as yellow oil, which was used in the next step without purification.

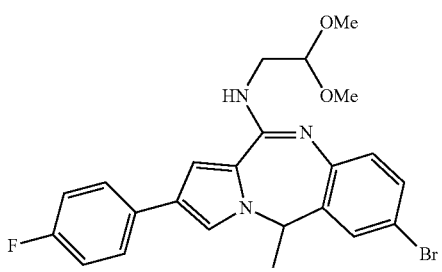 [SMILES: COC(CNC1=Nc2ccc(Br)cc2C(C)n2cc(-c3ccc(F)cc3)cc21)OC]

7-bromo-N-(2,2-dimethoxyethyl)-2-(4-fluorophenyl)-5-methyl-5H-benzo[e]pyrrolo[1,2-a] [1,4]diazepin-11-amine, S173. To a mixture of 7-bromo-11-chloro-2-(4-fluorophenyl)-5-methyl-5H-benzo[e]pyrrolo[1,2-a][1,4]diazepine (1.5 g, 3.7 mmol, 1.0 eq) in THF (5 mL) and dioxane (5 mL) was added Et$_3$N until the pH=9. Then 2,2-dimethoxyethanamine (2.3 g, 22.3 mmol, 2.4 mL, 6.0 eq) was added and the mixture was stirred at 120° C. for 12 hrs. The reaction mixture was concentrated and the residue was purified by column chromatography (SiO$_2$, petroleum ether/ethyl acetate=10/1 to 6/1) to give 7-bromo-N-(2,2-dimethoxyethyl)-2-(4-fluorophenyl)-5-methyl-5H-benzo[e]pyrrolo[1,2-a][1,4]diazepin-11-amine (305 mg, 368 umol, 9.9% yield, 57% purity) as a light yellow oil. ESI [M+H]=472.2/474.2

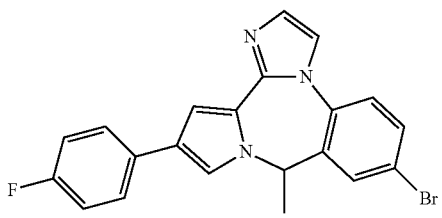 [SMILES: CC1c2cc(Br)ccc2-n2ccnc2-c2cc(-c3ccc(F)cc3)cn21]

7-bromo-12-(4-fluorophenyl)-9-methyl-9H-benzo[e]imidazo[2,1-c]pyrrolo[1,2-a][1,4] diazepine, S174. A mixture of 7-bromo-N-(2,2-dimethoxyethyl)-2-(4-fluorophenyl)-5-methyl-5H-benzo[e]pyrrolo[1,2-a][1,4]diazepin-11-amine (305 mg, 645 umol, 1.0 eq) in 1M HCl (5 mL) and dioxane (5 mL) was stirred at 80° C. for 12 hrs and then concentrated. The residue solid was washed with THF (2 mL×2), and dried to give 7-bromo-12-(4-fluorophenyl)-9-methyl-9H-benzo[e]imidazo[2,1-c]pyrrolo[1,2-a][1,4]diazepine (150 mg, crude) as a brown solid. ESI [M+H]=407.9/409.9

Scheme 49:

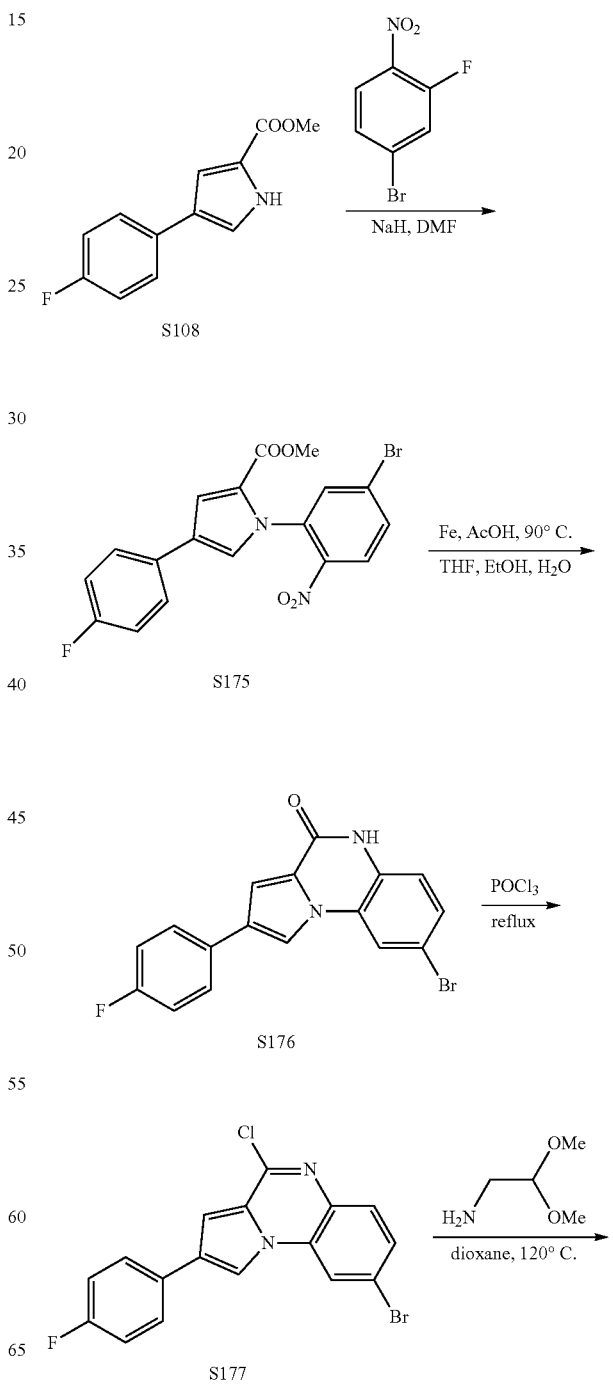

277
-continued
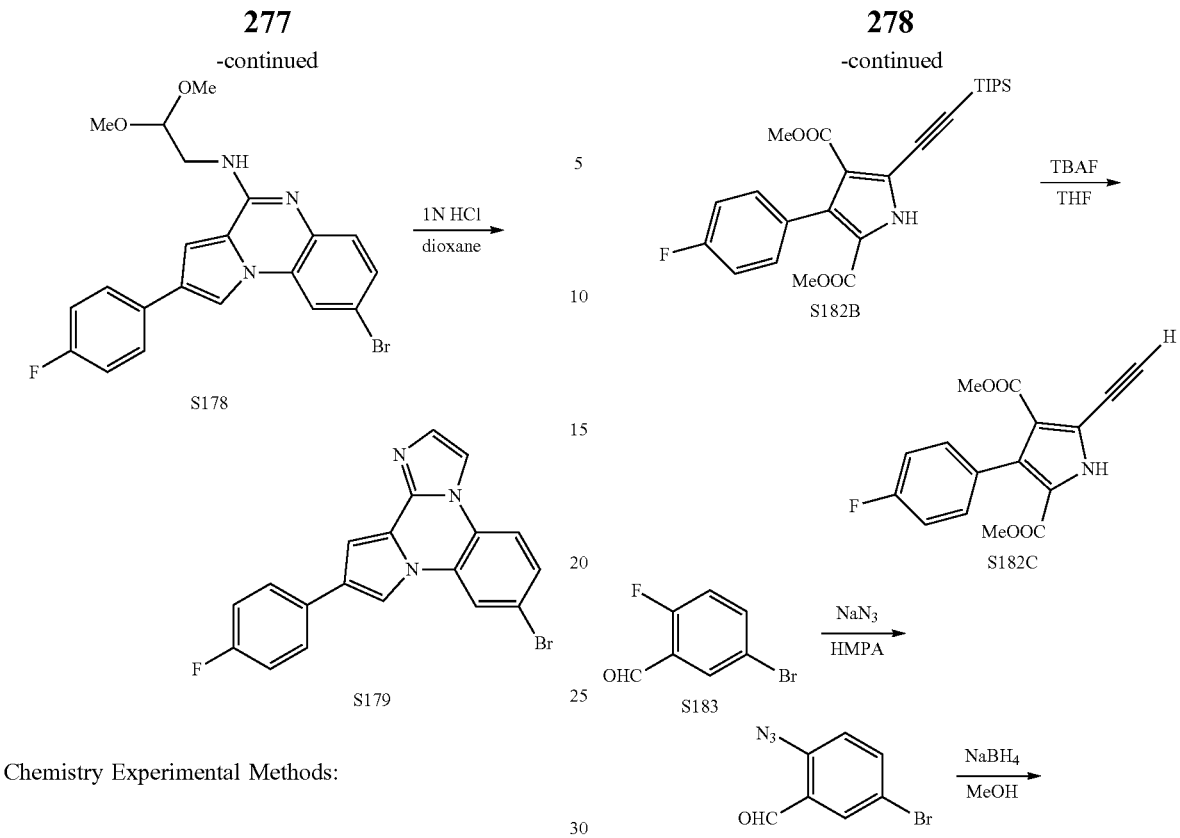
Chemistry Experimental Methods:
Scheme 50:
278
-continued
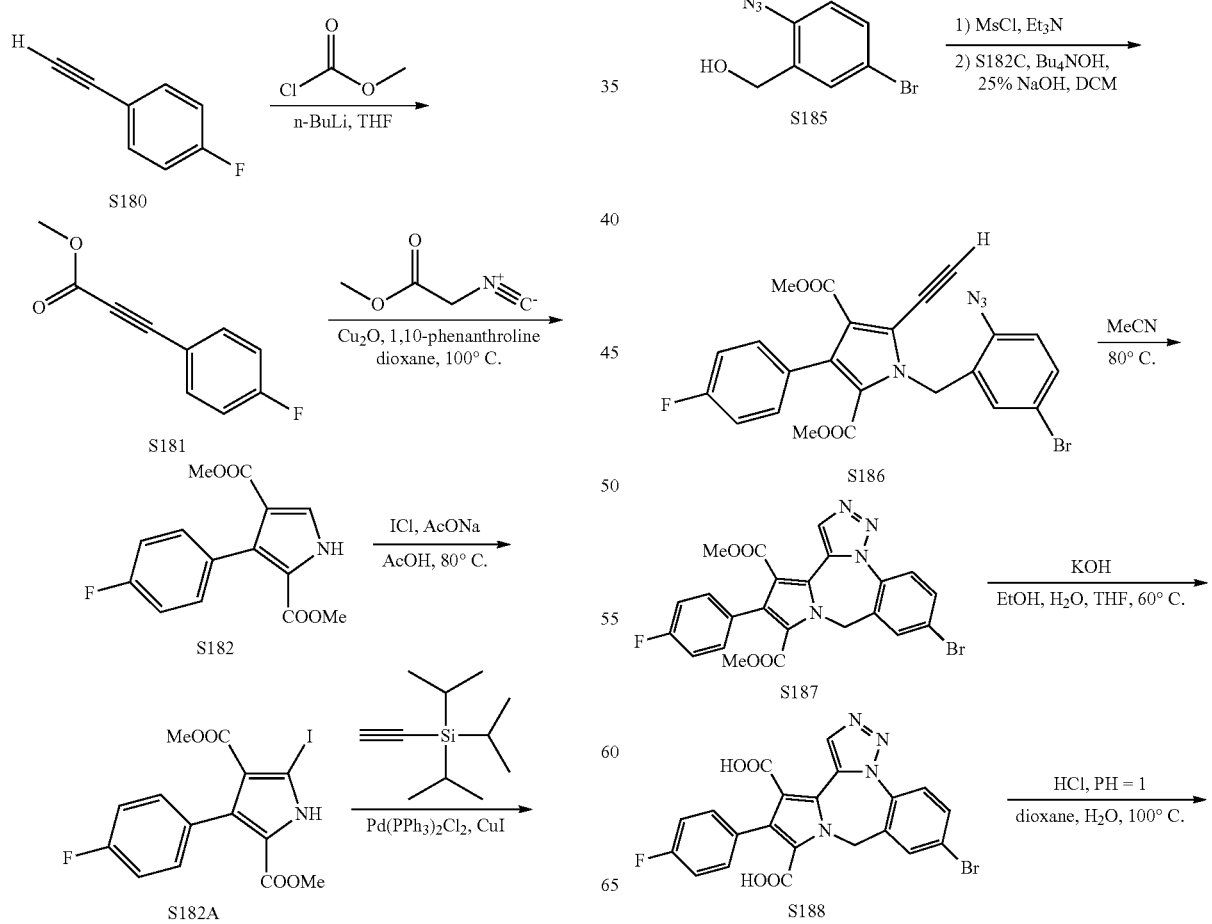

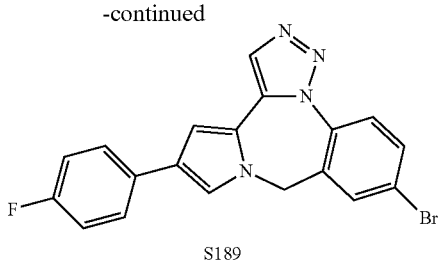

S189

Chemistry Experimental Methods:

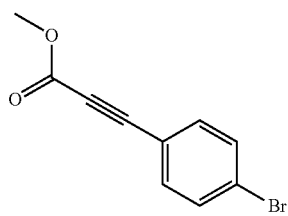

Methyl 3-(4-fluorophenyl)propiolate, S181. To a solution of 1-ethynyl-4-fluorobenzene (22.5 g, 187.3 mmol, 21.4 mL, 1.0 eq) in dry THF (400 mL) was added n-BuLi (2.5 M, 88 mL, 1.17 eq) dropwise at −70° C. under $N_2$ atmosphere. After stirred for 1 hr at −70° C., methyl carbonochloridate (20 g, 211 mmol, 16 mL, 1.13 eq) was added dropwise and the mixture was stirred at −70° C. for 0.5 hr, then warmed to 15° C. for 1.5 hrs. The mixture was cooled to −5° C., quenched with sat.$NH_4Cl$ aq. (200 mL) and extracted with EtOAc (100 mL×3). The combined organic layers were dried over $Na_2SO_4$, and concentrated to dryness. The residue solid was washed with EtOAc/petroleum ether (1:80, 100 mL×2) and filtered. The filter cake was dried in vacuum to give methyl 3-(4-fluorophenyl)propiolate (23 g, 122 mmol, 65.5% yield, 95% purity) as a white solid. 1H NMR (400 MHz, CHLOROFORM-d) d=7.60 (dd, J=5.6, 8.4 Hz, 2H), 7.09 (t, J=8.6 Hz, 2H), 3.85 (s, 3H)

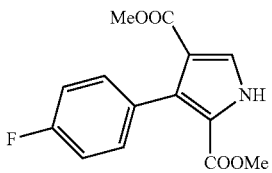 [SMILES: COC(=O)c1c[nH]c(C(=O)OC)c1-c1ccc(F)cc1]

Dimethyl 3-(4-fluorophenyl)-1H-pyrrole-2,4-dicarboxylate, S182. To a mixture of $Cu_2O$ (915 mg, 6.4 mmol, 654 uL, 0.06 eq), 1,10-phenanthroline (2.3 g, 12.8 mmol, 0.12 eq) and methyl 3-(4-fluorophenyl)propiolate (19 g, 106 mmol, 1.0 eq) in dioxane (300 mL) was added methyl 2-isocyanoacetate (13 g, 131 mmol, 11.9 mL, 1.2 eq) dropwise under $N_2$ atmosphere. The mixture was stirred at 100° C. 16 hrs, filtered and the filtrate was concentrated. The residue solid was washed with petroleum ether/EtOAc (1:1, 150 mL), then dried to give dimethyl 3-(4-fluorophenyl)-1H-pyrrole-2,4-dicarboxylate (25 g, 63 mmol, 59.5% yield, 70.4% purity) as a light brown solid. 1H NMR (400 MHz, CHLOROFORM-d) d=7.59 (d, J=3.5 Hz, 1H), 7.35-7.28 (m, 2H), 7.07 (t, J=8.8 Hz, 2H), 3.70 (s, 3H), 3.69 (s, 3H). ESI [M+H]=277.9

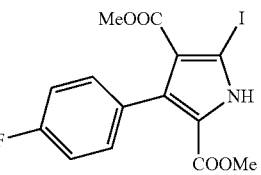

Dimethyl 3-(4-fluorophenyl)-5-iodo-1H-pyrrole-2,4-dicarboxylate, S182A. To a solution of dimethyl 3-(4-fluorophenyl)-1H-pyrrole-2,4-dicarboxylate (5.0 g, 18 mmol, 1.0 eq.) in AcOH (200 mL) was added AcONa (8.9 g, 108 mmol, 6.0 eq.) and the mixture was heated to 80° C. Then ICl (8.8 g, 54 mmol, 2.7 mL, 3.0 eq.) solution in AcOH (200 mL) was added and the mixture was stirred at 80° C. for 16 hrs. The mixture was cooled and sodium thiosulfate was added to the mixture until the color turned yellow. Then water was added until a yellow precipitate formed. The yellow solid was filtered off, washed with water and dried to give dimethyl 3-(4-fluorophenyl)-5-iodo-1H-pyrrole-2,4-dicarboxylate (4.3 g, crude) as a yellow solid. 1H NMR (400 MHz, CHLOROFORM-d) δ=9.38 (br. s., 1H), 7.23-7.17 (m, 2H), 7.07-6.99 (m, 2H), 3.67 (s, 3H), 3.60 (s, 3H).

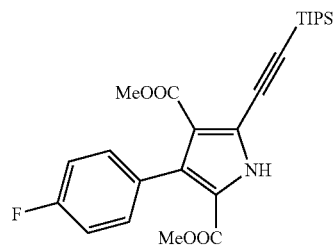

Dimethyl 3-(4-fluorophenyl)-5-((triisopropylsilyl)ethynyl)-1H-pyrrole-2,4-dicarboxylate, S182B. To a solution of dimethyl 3-(4-fluorophenyl)-5-iodo-1H-pyrrole-2,4-dicarboxylate (4.3 g, 10.7 mmol, 1.0 eq.) in THF (100 mL) was added ethynyl(triisopropyl)silane (2.9 g, 16 mmol, 3.6 mL, 1.5 eq.), $Pd(PPh_3)_2Cl_2$ (748 mg, 1.07 mmol, 0.1 eq.), CuI (406 mg, 2.1 mmol, 0.2 eq.) and TEA (3.2 g, 32 mmol, 4.4 mL, 3.0 eq.) and the mixture was stirred at 70° C. for 16 hrs under $N_2$. The mixture was concentrated and the residue was purified by silica gel chromatography (petroleum ether/ethyl acetate=50:1 to 5:1) to afford dimethyl 3-(4-fluorophenyl)-5-((triisopropylsilyl)ethynyl)-1H-pyrrole-2,4-dicarboxylate (4.0 g, crude) as a yellow solid. ESI [M+H]=458.3

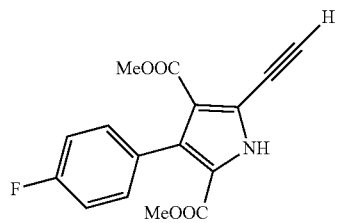 [SMILES: C#Cc1[nH]c(C(=O)OC)c(-c2ccc(F)cc2)c1C(=O)OC]

Dimethyl 5-ethynyl-3-(4-fluorophenyl)-1H-pyrrole-2,4-dicarboxylate, S182C. To a solution of dimethyl 3-(4-fluorophenyl)-5-((triisopropyl silyl)ethynyl)-1H-pyrrole-2,4-dicarboxylate (1.0 g, 2.2 mmol, 1.0 eq.) in THF (20 mL) was added TBAF (1 M, 6.6 mL, 3.0 eq.) and the mixture was stirred at 26° C. for 0.5 hr. The mixture was concentrated and the residue was purified by silica gel chromatography (petroleum ether/ethyl acetate=5:1 to 1:1) to afford dimethyl 5-ethynyl-3-(4-fluorophenyl)-1H-pyrrole-2,4-dicarboxylate (650 mg, crude) as a light red solid. 1H NMR (400 MHz, CHLOROFORM-d) δ=9.49 (br. s., 1H), 7.27-7.24 (m, 1H), 7.24-7.20 (m, 1H), 7.04 (t, J=8.8 Hz, 2H), 3.68 (s, 3H), 3.65 (s, 3H), 3.48 (s, 1H).

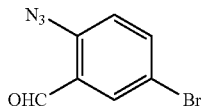 [SMILES: [N-]=[N+]=Nc1ccc(Br)cc1C=O]

2-azido-5-bromobenzaldehyde, S184. To a solution of 5-bromo-2-fluoro-benzaldehyde (5.0 g, 24.6 mmol, 1.0 eq.) in HMPA (100 mL) was added azidosodium (4.8 g, 73.9 mmol, 2.6 mL, 3.0 eq.) and the mixture was stirred at 50° C. for 2 hrs. The mixture was diluted with water (100 mL), extracted with EtOAc (150 mL×3), dried and concentrated. The residue was purified by silica gel chromatography (petroleum ether/ethyl acetate=50:1 to 5:1) to afford 2-azido-5-bromobenzaldehyde (5.0 g, crude) as a yellow solid. 1H NMR (400 MHz, CHLOROFORM-d) δ=10.21 (s, 1H), 7.93 (s, 1H), 7.65 (d, J=8.4 Hz, 1H), 7.11 (d, J=8.4 Hz, 1H).

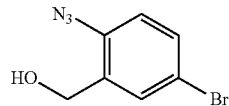 [SMILES: [N-]=[N+]=Nc1ccc(Br)cc1CO]

(2-azido-5-bromophenyl)methanol, S185. To a solution of 2-azido-5-bromobenzaldehyde (1.0 g, 4.4 mmol, 1.0 eq.) in MeOH (50 mL) was added NaBH$_4$ (501 mg, 13 mmol, 3.0 eq.) slowly and the mixture was stirred at 26° C. for 0.5 hr. The mixture was concentrated, diluted with ethyl acetate (30 mL) and washed with H$_2$O (15 mL×2). The aqueous phase was extracted with ethyl acetate (15 mL×3). The combined organic layers were dried over anhydrous MgSO$_4$, filtered and concentrated to give (2-azido-5-bromophenyl)methanol (980 mg, crude) as yellow oil, which was used into next step without further purification.

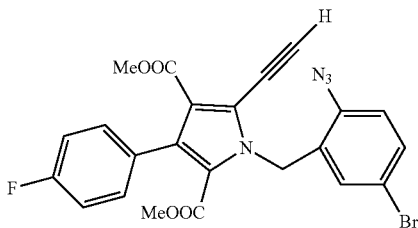 [SMILES: C#Cc1c(C(=O)OC)c(-c2ccc(F)cc2)c(C(=O)OC)n1Cc1cc(Br)ccc1N=[N+]=[N-]]

Dimethyl 1-(2-azido-5-bromobenzyl)-5-ethynyl-3-(4-fluorophenyl)-1H-pyrrole-2,4-dicarboxylate, S186. To a solution of (2-azido-5-bromophenyl)methanol (S185) (417 mg, 1.8 mmol, 1.0 eq.) in DCM (5 mL) were added TEA (554 mg, 5.5 mmol, 759 uL, 3.0 eq.) and MsCl (251 mg, 2.2 mmol, 170 uL, 1.2 eq.) at 0° C. The mixture was stirred at 20° C. for 0.5 hr, and then cooled to 0° C. Dimethyl 5-ethynyl-3-(4-fluorophenyl)-1H-pyrrole-2,4-dicarboxylate (S182C) (550 mg, 1.8 mmol, 1.0 eq.) was added to the mixture, followed by tetrabutylammonium hydroxide (189 mg, 182 umol, 236 uL, 25% purity, 0.1 eq.) and NaOH (1.7 g, 10.9 mmol, 25% purity, 6.0 eq.). The mixture was stirred at 40° C. for 3 hrs, poured into H$_2$O (5 mL) and extracted with DCM (10 mL×5). The combined organic layers were washed with brine (10 mL), dried over anhydrous Na$_2$SO$_4$, filtered and concentrated to give dimethyl 1-(2-azido-5-bromobenzyl)-5-ethynyl-3-(4-fluorophenyl)-1H-pyrrole-2,4-dicarboxylate (1.0 g, crude) as a yellow solid, which was used into next step without further purification. ESI [M+H] =511.0/513.1

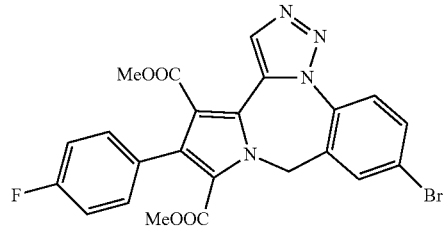 [SMILES: COC(=O)c1c(-c2ccc(F)cc2)c(C(=O)OC)n2c1-c1cnnn1-c1ccc(Br)cc1C2]

Dimethyl 10-bromo-5-(4-fluorophenyl)-8H-benzo[e]pyrrolo[1,2-a][1,2,3]triazolo[5,1-c][1,4] diazepine-4,6-dicarboxylate, S187. A solution of dimethyl 1-(2-azido-5-bromobenzyl)-5-ethynyl-3-(4-fluorophenyl)-1H-pyrrole-2,4-dicarboxylate (990 mg, 815 umol, 1.0 eq.) in MeCN (10 mL) was stirred at 80° C. for 20 mins. The mixture was filtered and the filtrate was concentrated to give dimethyl 10-bromo-5-(4-fluorophenyl)-8H-benzo[e]pyrrolo[1,2-a][1,2,3] triazolo[5,1-c][1,4] diazepine-4,6-dicarboxylate (379 mg, crude) as a light yellow solid, which was used into the next step without further purification. 1H NMR (400 MHz, CHLOROFORM-d) δ=8.41 (s, 1H), 7.94-7.87 (m, 2H), 7.74 (dd, J=2.2, 8.8 Hz, 1H), 7.21-7.11 (m, 2H), 7.09-6.97 (m, 2H), 6.44 (br s, 1H), 4.63 (br s, 1H), 3.61 (s, 3H), 3.54 (s, 3H). ESI [M+H]=511.0/513.1

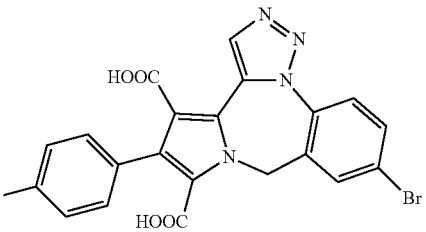

10-bromo-5-(4-fluorophenyl)-8H-benzo[e]pyrrolo[1,2-a][1,2,3]triazolo[5,1-c][1,4]diazepine-4,6-dicarboxylic acid, S188. To a solution of dimethyl 10-bromo-5-(4-fluorophenyl)-8H-benzo[e]pyrrolo[1,2-a][1,2,3 ]triazolo[5,1-c][1,4] diazepine-4,6-dicarboxylate (150 mg, 293 umol, 1.0 eq.) in EtOH (2 mL)/THF (1 mL) was added KOH (82 mg, 1.5 mmol, 5.0 eq.) aqueous solution (2.0 mL). The resulting mixture was stirred at 60° C. for 20 hrs, and then cooled to 0° C. The pH of the mixture was adjusted to pH 6-7 with 6M HCl and concentrated to remove EtOH and THF. Then it was used directly for the next step as a solution in water (2 mL). ESI [M+H]=482.9/484.9

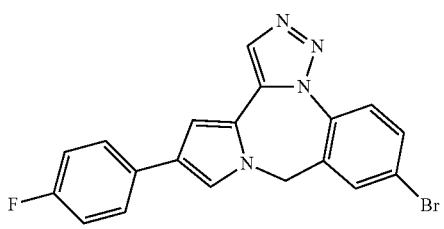 [SMILES: Fc1ccc(-c2cc3n(c2)Cc2cc(Br)ccc2-n2nncc2-3)cc1]

10-bromo-5-(4-fluorophenyl)-8H-benzo[e]pyrrolo[1,2-a][1,2,3]triazolo[5,1-c][1,4]diazepine, S189. To a suspension of 10-bromo-5-(4-fluorophenyl)-8H-benzo[e]pyrrolo[1,2-a][1,2,3]triazolo[5,1-c][1,4]diazepine-4,6-dicarboxylic acid (141 mg, 291 umol, 1.0 eq.) in $H_2O$ (2 mL)/dioxane (2 mL) was added HCl (2 M, 4.5 mL, 31.2 eq.) until the pH=1. The resulting mixture was stirred at 100° C. for 10 hrs. Then the pH was adjusted to 8 by sat.$Na_2CO_3$ solution. The mixture was concentrated, diluted with 5 mL water and extracted with EtOAc/THF (5:1, 6 mL*3). The combined organic layers were concentrated and the residue was purified by prep-HPLC (TFA condition) to give 10-bromo-5-(4-fluorophenyl)-8H-benzo[e]pyrrolo[1,2-a][1,2,3] triazolo[5,1-c][1,4]diazepine (42 mg, 95 umol, 32.8% yield, 90% purity) as a light brown solid. 1H NMR (400 MHz, DMSO-d6) δ=8.17 (s, 1H), 8.00 (d, J=2.1 Hz, 1H), 7.94-7.89 (m, 1H), 7.87-7.81 (m, 1H), 7.62-7.53 (m, 3H), 7.19 (t, J=8.9 Hz, 2H), 7.02 (d, J=1.9 Hz, 1H), 5.30 (s, 2H). ESI [M+H]=394.9/396.9

Scheme 51:

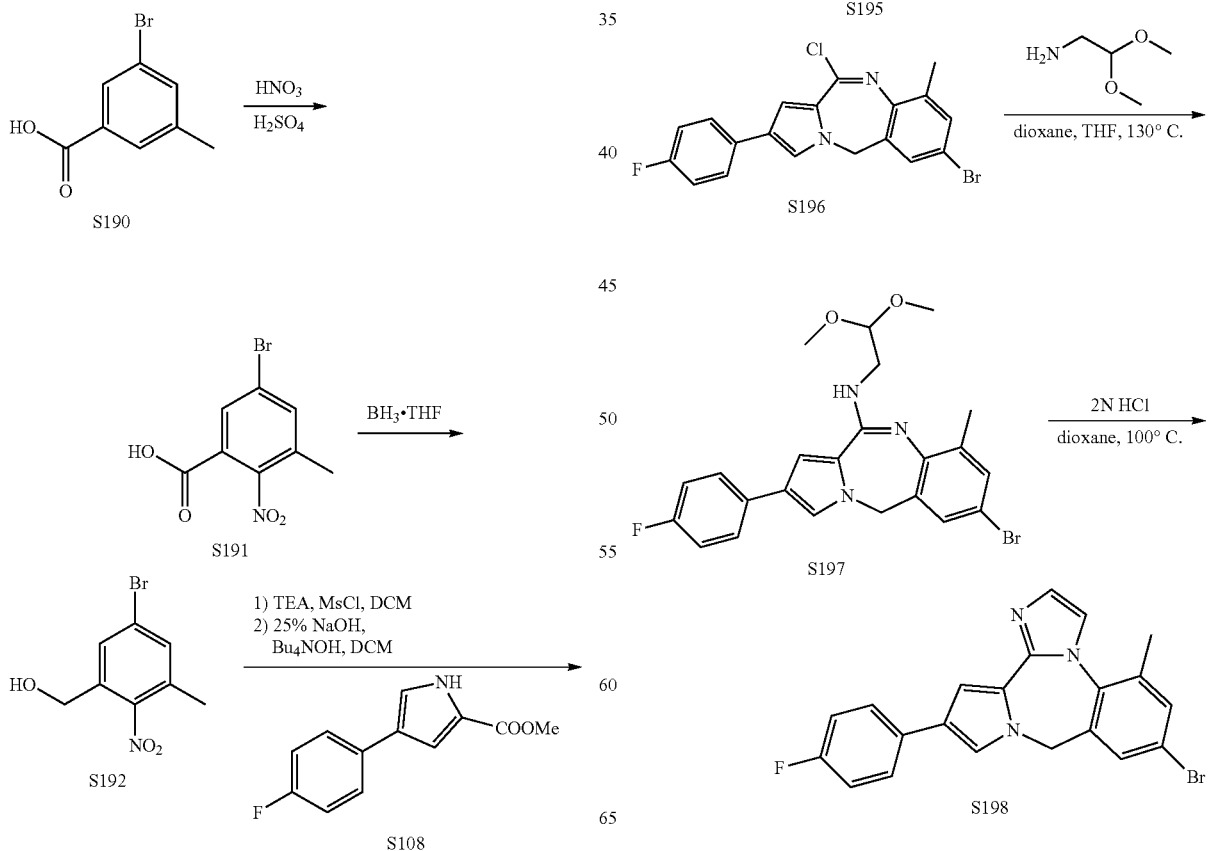

Chemistry Experimental Methods:

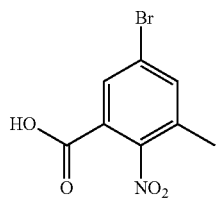

5-bromo-3-methyl-2-nitrobenzoic acid, S191. To a solution of 3-bromo-5-methyl-benzoic acid (9.5 g, 44.2 mmol, 1.0 eq.) in H$_2$SO$_4$ (50 mL) was added HNO$_3$ (2.8 g, 44 mmol, 1.99 mL, 1.0 eq.) at 0° C. Then the mixture was stirred at 20° C. for 1 hr. The solution was poured into ice (500 g) slowly while vigorous stirring. Some white solid was formed. The mixture was extracted with ethyl acetate (300 mL*3), dried, filtered and concentrated. A mixture of 5-bromo-3-methyl-2-nitrobenzoic acid (S191) and 3-bromo-5-methyl-2-nitrobenzoic acid (10 g, mixture) was got as a yellow solid.

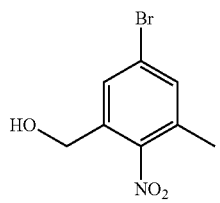

(5-bromo-3-methyl-2-nitrophenyl)methanol, S192. To a solution of 5-bromo-3-methyl-2-nitrobenzoic acid (S191) and 3-bromo-5-methyl-2-nitrobenzoic acid (9.9 g, 38 mmol, 1.0 eq.) in THF (50 mL) was added BH$_3$.THF (1 M, 190 mL, 5.0 eq.) and the mixture was stirred at 70° C. for 1 hr. The mixture was cooled to 0° C., quenched by MeOH (20 mL), and then concentrated. The residue was purified by silica gel chromatography (Petroleum ether/Ethyl acetate=20:1 to 5:1) to afford the product (5-bromo-3-methyl-2-nitrophenyl)methanol (2.1 g) as a white solid. 1H NMR (400 MHz, CHLOROFORM-d) δ=7.56-7.52 (m, 1H), 7.36 (d, J=1.5 Hz, 1H), 4.60 (d, J=6.4 Hz, 2H), 2.29 (s, 3H)

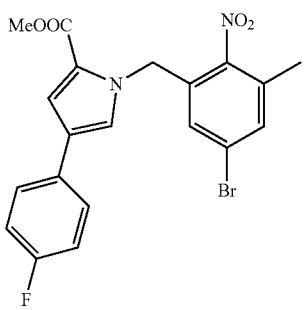

Methyl 1-(5-bromo-3-methyl-2-nitrobenzyl)-4-(4-fluorophenyl)-1H-pyrrole-2-carboxylate, S193. To a solution of (5-bromo-3-methyl-2-nitrophenyl)methanol (2.0 g, 8.1 mmol, 1.0 eq.) and Et$_3$N (1.6 g, 15.7 mmol, 2.2 mL, 1.9 eq.) in dry DCM (50 mL) was added MsCl (1.1 g, 9.6 mmol, 743 uL, 1.2 eq.) dropwise at 0° C. under N$_2$ atmosphere. The mixture was stirred at 0° C. for 1 hr. Then methyl 4-(4-fluorophenyl)-1H-pyrrole-2-carboxylate (S108) (1.6 g, 7.3 mmol, 0.9 eq.) was added, followed by tetrabutylammonium hydroxide (800 mg, 770 umol, 1.0 mL, 25% purity, 0.09 eq.) and NaOH aqueous solution (8.0 g, 50 mmol, 25% purity, 6.1 eq.). The mixture was warmed to 25° C. and stirred for 16 hrs. The mixture was washed with water (50 mL) and brine (30 mL), dried over Na$_2$SO$_4$, filtered and concentrated to give methyl 1-(5-bromo-3-methyl-2-nitrobenzyl)-4-(4-fluorophenyl)-1H-pyrrole-2-carboxylate (3.5 g, crude) as a brown solid, which was used directly. ESI [M+H]=447.0/449.0

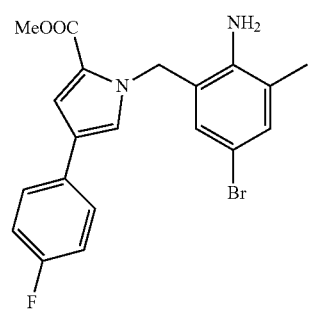 [SMILES: COC(=O)c1cc(-c2ccc(F)cc2)cn1Cc1cc(Br)cc(C)c1N]

Methyl 1-(2-amino-5-bromo-3-methylbenzyl)-4-(4-fluorophenyl)-1H-pyrrole-2-carboxylate, S194. To a solution of methyl 1-(5-bromo-3-methyl-2-nitrobenzyl)-4-(4-fluorophenyl)-1H-pyrrole-2-carboxylate (3.4 g, 7.6 mmol, 1.0 eq.) in EtOH (100 mL), THF (50 mL) and H$_2$O (50 mL) were added NH$_4$Cl (406 mg, 7.6 mmol, 265 uL, 1.0 eq.) and Fe (2.1 g, 38 mmol, 5.0 eq.) and the mixture was stirred at 90° C. for 2 hrs. The mixture was filtered and the filtrate was concentrated to removed THF and EtOH. The aqueous phase was extracted with ethyl acetate (100 mL*3). The combined organic phase was washed with brine (100 mL), dried over anhydrous Na$_2$SO$_4$, filtered and concentrated in vacuum to afford methyl 1-(2-amino-5-bromo-3-methylbenzyl)-4-(4-fluorophenyl)-1H-pyrrole-2-carboxylate (3.0 g, crude) as a yellow solid, which was used without purification. ESI [M+H]=417.0/419.0

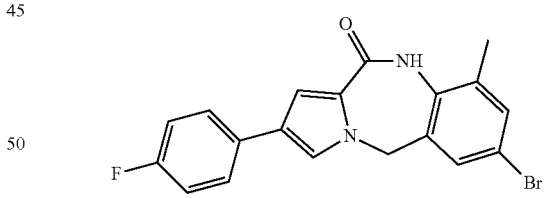

7-bromo-2-(4-fluorophenyl)-9-methyl-5H-benzo[e]pyrrolo[1,2-a][1,4]diazepin-11(10H)-one, S195. To a solution of methyl 1-(2-amino-5-bromo-3-methylbenzyl)-4-(4-fluorophenyl)-1H-pyrrole-2-carboxylate (2.9 g, 6.9 mmol, 1.0 eq.) in toluene (100 mL) was added AlMe$_3$ (2 M, 17 mL, 5.0 eq.) at 0° C. dropwise and the mixture was stirred at 26° C. for 6 hrs under N$_2$. The mixture was quenched by sat.NH$_4$Cl (100 mL) and extracted with ethyl acetate (100 mL*3). The combined organic phase was washed with brine (100 mL), dried over anhydrous Na$_2$SO$_4$, filtered and concentrated in vacuum. The residue was added petroleum ether: ethyl acetate (20 mL, 4:1) and stirred for 2 hrs. The solid was collected by filtration to give 7-bromo-2-(4-fluorophenyl)-9-methyl-5H-benzo[e]pyrrolo[1,2-a][1,4]diazepin-11(10H)- one (1.6 g, crude) as a light yellow solid. 1H NMR (400 MHz, DMSO-d6) δ=9.45 (s, 1H), 7.61-7.48 (m, 3H), 7.44 (s, 2H), 7.20-7.00 (m, 3H), 5.17 (s, 2H), 2.33 (s, 3H). ESI [M+H]=385.1/387.1

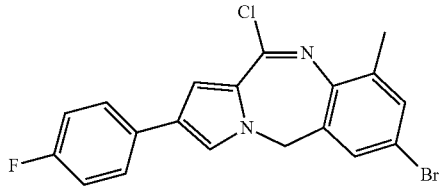 [SMILES: Cc1cc(Br)cc2c1N=C(Cl)c1cc(-c3ccc(F)cc3)cn1C2]

7-bromo-11-chloro-2-(4-fluorophenyl)-9-methyl-5H-benzo[e]pyrrolo[1,2-a][1,4]diazepine, S196. 7-bromo-2-(4-fluorophenyl)-9-methyl-5H-benzo[e]pyrrolo[1,2-a][1,4]diazepin-11(10H)-one (300 mg, 778 umol, 1.0 eq.) was dissolved into POCl₃ (5 mL), stirred at 80° C. for 1 hr and concentrated to give 7-bromo-11-chloro-2-(4-fluorophenyl)-9-methyl-5H-benzo[e]pyrrolo[1,2-a][1,4]diazepine (300 mg, crude) as a yellow solid, which can be used without any purification.

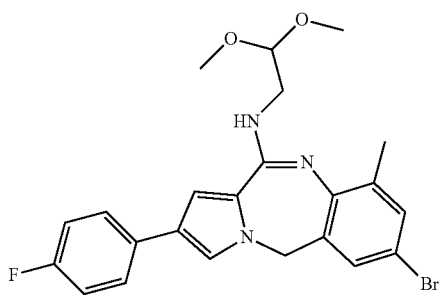 [SMILES: COC(CNC1=Nc2c(C)cc(Br)cc2Cn2cc(-c3ccc(F)cc3)cc21)OC]

7-bromo-N-(2,2-dimethoxyethyl)-2-(4-fluorophenyl)-9-methyl-5H-benzo[e]pyrrolo[1,2-a] [1,4]diazepin-11-amine, S197. To a solution of 7-bromo-11-chloro-2-(4-fluorophenyl)-9-methyl-5H-benzo[e]pyrrolo[1,2-a][1,4]diazepine (300 mg, 743 umol, 1.0 eq.) in THF (15 mL) and dioxane (15 mL) was added 2,2-dimethoxyethanamine (781 mg, 7.4 mmol, 805 uL, 10 eq.) and the mixture was stirred at 130° C. for 16 hrs in a sealed tube. The mixture was poured into ice-water (150 mL) and extracted with ethyl acetate (100 mL*3). The combined organic phase was washed with brine (100 mL), dried over anhydrous Na₂SO₄, filtered and concentrated to give 7-bromo-N-(2,2-dimethoxyethyl)-2-(4-fluorophenyl)-9-methyl-5H-benzo[e]pyrrolo[1,2-a][1,4]diazepin-11-amine (350 mg) as a black brown solid, which can be used without any purification. ESI [M+H]=472.1/474.1

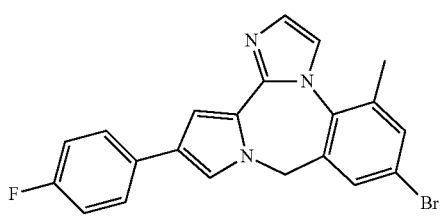

7-bromo-12-(4-fluorophenyl)-5-methyl-9H-benzo[e]imidazo[2,1-c]pyrrolo[1,2-a][1,4] diazepine, S198. To a solution of 7-bromo-N-(2,2-dimethoxyethyl)-2-(4-fluorophenyl)-9-methyl-5H-benzo[e]pyrrolo[1,2-a][1,4]diazepin-11-amine (350 mg, 741 umol, 1.0 eq.) in dioxane (10 mL) was added 2 M HCl (7.4 mL, 20 eq.) and the mixture was stirred at 100° C. for 16 hrs. The mixture was concentrated and the residue was purified by acidic prep-HPLC to give 7-bromo-12-(4-fluorophenyl)-5-methyl-9H-benzo[e]imidazo[2,1-c]pyrrolo[1,2-a][1,4]diazepine (100 mg, 232 umol, 31.4% yield, 95% purity) as a yellow solid. 1H NMR (400 MHz, DMSO-d6) δ=8.03 (s, 1H), 7.81-7.63 (m, 3H), 7.60-7.49 (m, 3H), 7.22-7.10 (m, 2H), 7.03 (s, 1H), 5.31-5.07 (m, 2H), 2.36 (s, 3H). ESI [M+H]=408.0/410.0

Scheme 52:

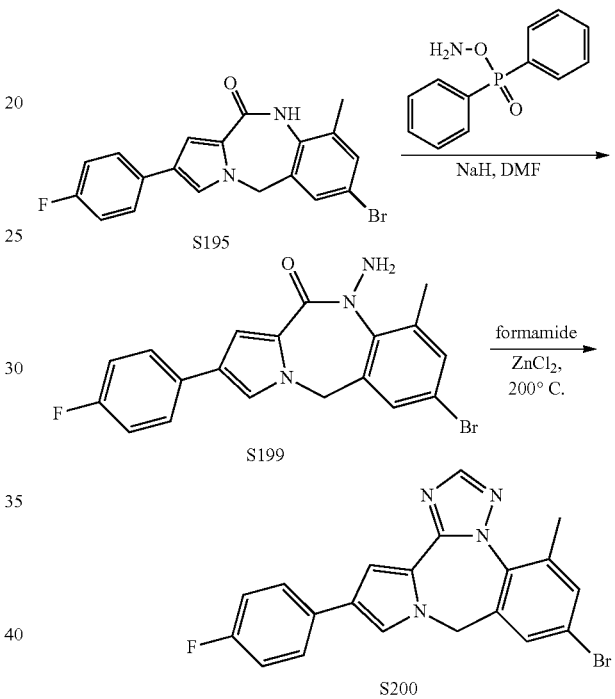

Chemistry Experimental Methods:

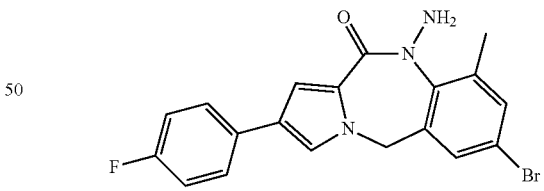

10-amino-7-bromo-2-(4-fluorophenyl)-9-methyl-5H-benzo[e] pyrrolo[1,2-a][1,4]diazepin-11(10H)-one, S199. To a solution of 7-bromo-2-(4-fluorophenyl)-9-methyl-5H-benzo[e] pyrrolo[1,2-a][1,4]diazepin-11(10H)-one (S195) (500 mg, 1.3 mmol, 1.0 eq.) in DMF (10 mL) was added NaH (100 mg, 2.5 mmol, 60% purity, 1.9 eq.) at 0° C. After stirring 30 mins at 0° C., (aminooxy)diphenylphosphine oxide (400 mg, 1.7 mmol, 1.3 eq.) was added, warmed to 20° C. and stirred for 1 hr. The mixture was quenched with ice-cold sat.NH₄Cl aq. (100 mL) and extracted with ethyl acetate (50 mL*3). The combined organic layers were washed with brine (50 mL), dried over Na₂SO₄ and concentrated to give 10-amino-7-bromo-2-(4-fluorophenyl)-9-methyl-5H-benzo[e]pyrrolo[1,2-a][1,4]diazepin-11(10H)-one (400 mg) as a light brown solid, which was used directly. ESI [M+H]=400.0/402.0

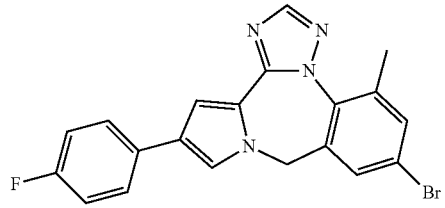 [SMILES: Cc1cc(Br)cc2c1-n1ncnc1-c1cc(-c3ccc(F)cc3)cn1C2]

7-bromo-12-(4-fluorophenyl)-5-methyl-9H-benzo[e]pyrrolo[1,2-a][1,2,4]triazolo[5,1-c][1,4] diazepine, S200. To a mixture of ZnCl$_2$ (50 mg, 366 umol, 17 uL, 2.9 eq.) in NH$_2$CHO (1.0 mL) was added 10-amino-7-bromo-2-(4-fluorophenyl)-9-methyl-5H-benzo[e]pyrrolo[1,2-a][1,4] diazepin-11(10H)-one (50 mg, 124 umol, 1.0 eq.) at 200° C. and the mixture was stirred for 1 hr. Then the mixture was diluted with water (50 mL), extracted with ethyl acetate/THF (5:1, 30 mL*3). The organic layers were dried over Na$_2$SO$_4$, filtered and concentrated. The residue was purified by acidic prep-HPLC to afford 7-bromo-12-(4-fluorophenyl)-5-methyl-9H-benzo[e] pyrrolo[1,2-a][1,2,4]triazolo[5,1-c][1,4]diazepine (20 mg, 44 umol, 35% yield, 90.9% purity) as a white solid. 1H NMR (400 MHz, DMSO-d6) δ=8.33 (s, 1H), 7.77 (d, J=2.0 Hz, 1H), 7.68 (d, J=2.0 Hz, 1H), 7.63-7.56 (m, 2H), 7.54 (d, J=1.8 Hz, 1H), 7.16 (t, J=8.9 Hz, 2H), 7.08 (d, J=1.8 Hz, 1H), 5.37-5.24 (m, 1H), 5.10-4.98 (m, 1H), 2.39 (s, 3H). ESI [M+H]=409.0/411.0

The General method of Amines.

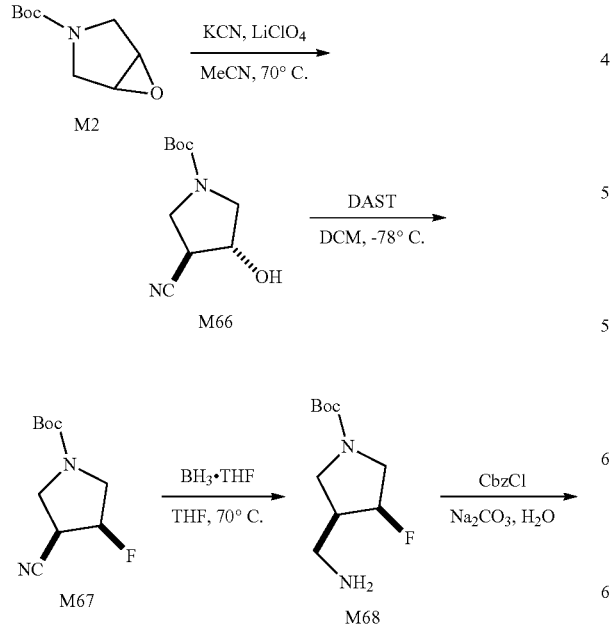

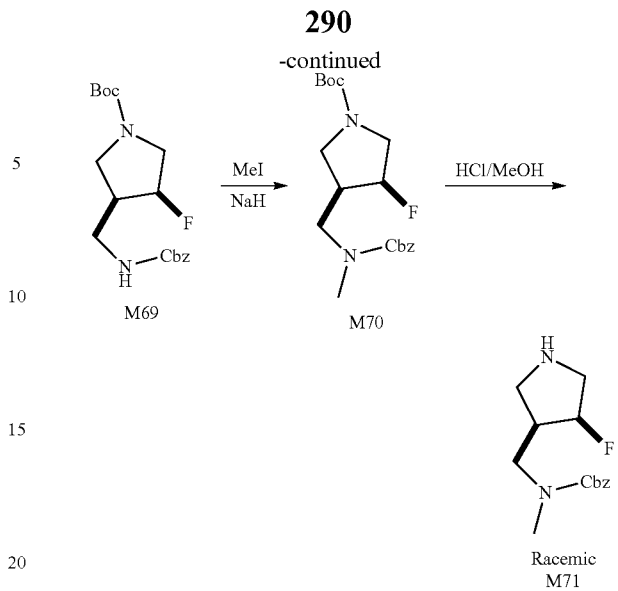

Chemistry Experimental Methods:
General Procedure A1 as below.

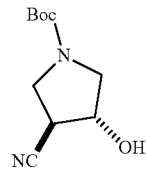 [SMILES: CC(C)(C)OC(=O)N1C[C@H](O)[C@@H](C#N)C1]

(Trans)-tert-butyl 3-cyano-4-hydroxypyrrolidine-1-carboxylate, M66. To a mixture of tert-butyl 6-oxa-3-azabicyclo[3.1.0]hexane-3-carboxylate (43.00 g, 232.16 mmol, 1.00 eq) and LiClO$_4$ (37.05 g, 348.24 mmol, 15.31 mL, 1.50 eq) in CH$_3$CN (1.00 L) was added KCN (30.24 g, 464.32 mmol, 19.89 mL, 2.00 eq) in one portion. The mixture was stirred at 70° C. for 20 hrs. The mixture was concentrated in reduced pressure at 40° C. The residue was poured into ice-water (300 mL), and extracted with ethyl acetate (150 mL×3). The combined organic phases were washed with brine (100 mL), dried over Na$_2$SO$_4$, filtered and concentrated in vacuum. The residue was purified by column chromatography on silica gel with petroleum ether: ethyl acetate (20:1 to 5:1). (trans)-tert-butyl 3-cyano-4-hydroxy-pyrrolidine-1-carboxylate (31.00 g, 131.45 mmol, 56.62% yield, 90% purity based on HNMR) was obtained as yellow oil. $^1$H NMR (400 MHz, CHLOROFORM-d) δ=4.65-4.52 (m, 1H), 3.76 (br. s., 3H), 3.45-3.28 (m, 1H), 3.04 (br. s., 1H), 2.83 (br. s., 1H), 1.46-1.41 (m, 9H).

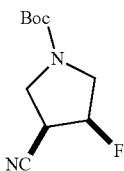

(Cis)-tert-butyl 3-cyano-4-fluoropyrrolidine-1-carboxylate, M67. To a solution of tert-butyl (trans)-3-cyano-4-hydroxy-pyrrolidine-1-carboxylate (10.0 g, 47.11 mmol, 1.0 eq) in DCM (100 mL) was added DAST (15.19 g, 94.23 mmol, 12.45 mL, 2.0 eq) dropwise at −78° C. under N₂ atmosphere. The reaction mixture was stirred at −78° C. for 2 hrs, and then quenched with saturated Na₂CO₃ solution (100 mL). The mixture was extracted with DCM (100 mL×3). The combined organic phases were dried over Na₂SO₄, then filtered and concentrated. The residue was purified by silica gel column chromatography with petroleum ether: ethyl acetate (20:1 to 10:1) to afford (cis)-tert-butyl 3-cyano-4-fluoropyrrolidine-1-carboxylate (9.0 g, 42 mmol, 89% yield) as light yellow oil. ¹H NMR (400 MHz, METHANOL-d₄) δ=5.42-5.22 (m, 1H), 3.97-3.87 (m, 1H), 3.73-3.55 (m, 2H), 3.53-3.43 (m, 2H), 1.56-1.38 (m, 9H).

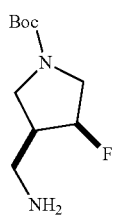

(Cis)-tert-butyl 3-(aminomethyl)-4-fluoropyrrolidine-1-carboxylate, M68. To a solution of (cis)-tert-butyl 3-cyano-4-fluoropyrrolidine-1-carboxylate (11.0 g, 51.34 mmol, 1.0 eq.) in THF (15.00 mL) was added BH₃.THF (1M, 250 mL, 5.0 eq.) dropwise at 10° C. and the reaction mixture was refluxed at 70° C. for 2 hrs. The reaction mixture was cooled to 0° C. and added EtOH dropwise until no gas was formed. The mixture was concentrated, dissolved in EtOH (30 mL) and refluxed for 16 hrs. The mixture was concentrated to afford (cis)-tert-butyl 3-(aminomethyl)-4-fluoropyrrolidine-1-carboxylate (11.0 g, crude) as colorless oil, which was used without purification. ESI [M+H]=219.1

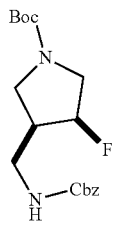

(Cis)-tert-butyl 3-((((benzyloxy)carbonyl)amino)methyl)-4-fluoropyrrolidine-1-carboxylate, M69. To a mixture of (cis)-tert-butyl 3-(aminomethyl)-4-fluoropyrrolidine-1-carboxylate (11 g, 50.40 mmol, 1.0 eq) and Na₂CO₃ (10.68 g, 100.8 mmol, 2.0 eq) in THF (100 mL) and H₂O (100 mL) was added CbzCl (17.19 g, 100.8 mmol, 2.0 eq) dropwise at 10° C. The reaction mixture was stirred for 2 hrs and extracted with EtOAc (100 mL×2). The combined organic phases were dried over Na₂SO₄, filtered and concentrated. The residue was purified by silica gel column chromatography with petroleum ether: ethyl acetate (8:1) to afford (cis)-tert-butyl 3-((((benzyloxy)carbonyl)amino)methyl)-4-fluoropyrrolidine-1-carboxylate (9.0 g, 25.54 mmol, 50% yield) as colorless oil. ¹H NMR (400 MHz, CHLOROFORM-d) δ=7.33 (d, J=4.4 Hz, 4H), 7.24 (d, J=4.4 Hz, 1H), 5.17-5.05 (m, 2H), 4.99 (br. s., 1H), 3.81-3.64 (m, 2H), 3.63-3.52 (m, 1H), 3.47-3.32 (m, 2H), 3.11 (d, J=7.5 Hz, 1H), 2.63-2.43 (m, 1H), 1.44 (d, J=4.0 Hz, 9H). ESI [M+H]=353.2

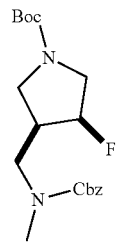 [SMILES: CN(C[C@H]1CN(C(=O)OC(C)(C)C)C[C@H]1F)C(=O)OCc1ccccc1]

(Cis)-tert-butyl 3-((((benzyloxy)carbonyl)(methyl)amino)methyl)-4-fluoropyrrolidine-1-carboxylate, M70. To a solution of (cis)-tert-butyl 3-((((benzyloxy)carbonyl)amino)methyl)-4-fluoropyrrolidine-1-carboxylate (9.0 g, 25.5 mmol, 1.0 eq) and MeI (7.25 g, 51 mmol, 3.18 mL, 2.0 eq) in DMF (80 mL) was added NaH (2.04 g, 51.08 mmol, 60% purity, 2.0 eq) portionwise at 0° C. and the mixture was warmed to 10° C. and stirred for 0.5 hr. The reaction mixture was cooled to 0° C. and quenched with sat.ice-NH₄Cl solution (500 mL). The resulting mixture was extracted with EtOAc: THF (1:1, 200 mL×2). The combined organic phases were dried over Na₂SO₄, filtered and concentrated. The residue was purified by silica gel chromatography eluted with petroleum ether: ethyl acetate (15:1 to 4:1) to afford (cis)-tert-butyl 3-((((benzyloxy) carbonyl)(methyl)amino)methyl)-4-fluoropyrrolidine-1-carboxylate (9.0 g, 24.56 mmol, 96% yield) as colorless oil. ¹H NMR (400 MHz, METHANOL-d₄) δ=7.39-7.24 (m, 5H), 5.19-5.01 (m, 3H), 3.56 (br. s., 5H), 3.14-3.03 (m, 1H), 2.96 (d, J=11.0 Hz, 3H), 2.59 (br. s., 1H), 1.44 (s, 9H). ESI [M+H]=367.2

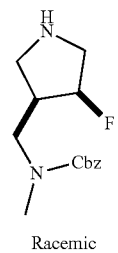

Racemic

Benzyl (((cis)-4-fluoropyrrolidin-3-yl)methyl)(methyl)carbamate, M71. A solution of (cis)-tert-butyl 3-((((benzyloxy)carbonyl)(methyl)amino)methyl)-4-fluoropyrrolidine-1-carboxylate (9.0 g, 24.56 mmol, 1.0 eq) in HCl/MeOH (4 M, 150 mL) was stirred at 30° C. for 0.5 hr. The reaction mixture was concentrated, dissolved in MeOH (50 mL) and basified with basic resin to pH=7-8. The mixture was filtered and the filtrate was concentrated to dryness. Benzyl (((cis)-4-fluoropyrrolidin-3-yl)methyl)(methyl)carbamate (6.0 g, 22.5 mmol, 91.7% yield) was obtained as light yellow oil. ¹H NMR (400 MHz, METHANOL-d₄) δ=7.44-7.19 (m, 5H), 5.34-5.13 (m, 1H), 5.11 (s, 2H), 3.71-3.62 (m, 1H), 3.52-3.34 (m, 4H), 3.10-2.91 (m, 4H), 2.74-2.53 (m, 1H). ESI [M+H]=267.1

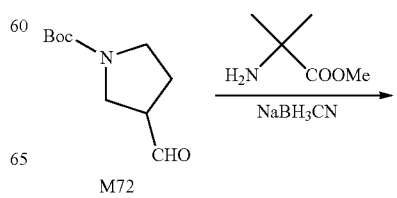

-continued

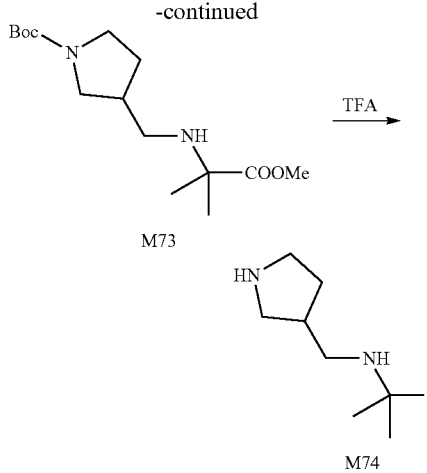

Chemistry Experimental Methods:
General Procedure A2 as below.

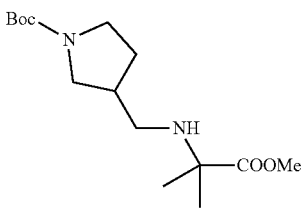 [SMILES: COC(=O)C(C)(C)NCC1CCN(C(=O)OC(C)(C)C)C1]

Tert-butyl 3-(((1-methoxy-2-methyl-1-oxopropan-2-yl)amino)methyl)pyrrolidine-1-carboxylate, M73. To a solution of tert-butyl 3-formylpyrrolidine-1-carboxylate (500 mg, 2.5 mmol, 1.0 eq) and methyl 2-amino-2-methyl-propanoate (352 mg, 3.0 mmol, 1.2 eq) in MeOH (20 mL) was added NaBH₃CN (315 mg, 5 mmol, 2.0 eq). The mixture was stirred for 12 hrs at 20° C. The mixture was purified by pre-HPLC (column: Luna C18 100*30 5 u; mobile phase: [water(0.1% TFA)-ACN]; B %: 5%-35%, 12 min) to afford tert-butyl 3-(((1-methoxy-2-methyl-1-oxopropan-2-yl)amino)methyl)pyrrolidine-1-carboxy late (300 mg, 998 umol, 39.79% yield) as yellow oil. ESI [M+H]=301.2

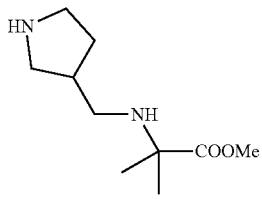

Methyl 2-methyl-2-((pyrrolidin-3-ylmethyl)amino)propanoate, M74. To a solution of tert-butyl 3-(((1-methoxy-2-methyl-1-oxopropan-2-yl)amino)methyl)pyrrolidine-1-carboxylate (300 mg, 998.7 umol, 1.0 eq) in CH₂Cl₂ (10 mL) was added TFA (1.14 g, 9.99 mmol, 739 uL, 10 eq). The mixture was stirred at 45° C. for 15 mins and concentrated in reduced pressure at 40° C. The residue was dissolved in MeOH (50 mL) and basified with basic resin to pH=9. The mixture was filtered and the filtrate was concentrated to dryness. Methyl 2-methyl-2-((pyrrolidin-3-ylmethyl)amino) propanoate (200 mg, crude) was obtained as yellow oil, which was used directly without purification. ¹H NMR (400 MHz, METHANOL-d₄) δ=3.71 (s, 3H), 3.45-3.42 (m, 1H), 3.36-3.33 (m, 1H), 3.25-3.15 (m, 1H), 3.03-2.98 (m, 1H), 2.61-2.57 (m, 2H), 2.44-2.35 (m, 1H), 2.25-2.15 (m, 1H), 1.76-1.71 (m, 1H), 1.32 (s, 6H). ESI [M+H]=201.1

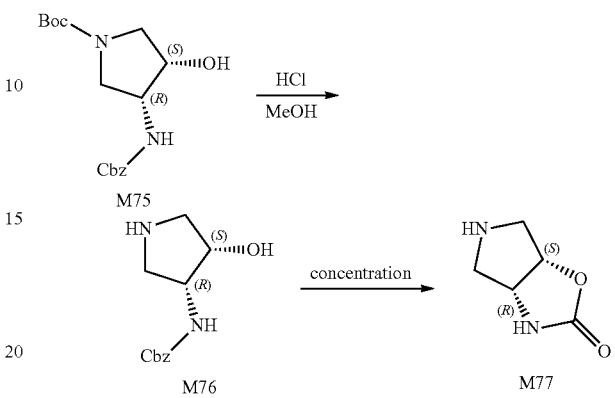

Chemistry Experimental Methods:
General Procedure A3 as below.

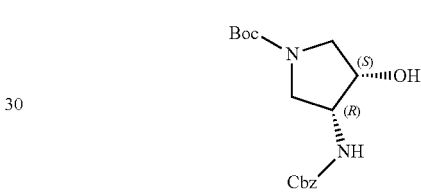

(3R,4S)-tert-butyl 3-(((benzyloxy)carbonyl)amino)-4-hydroxypyrrolidine-1-carboxylate, M75. Synthesized using General Procedure L, replacing (3S,4S)-tert-butyl 3-(benzylamino)-4-hydroxypyrrolidine-1-carboxylate with (3R,4R)-tert-butyl 3-(benzylamino)-4-hydroxypyrrolidine-1-carboxylate. ESI [M+Na]=359.0

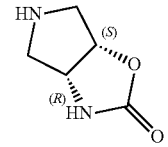

(3aR,6aS)-hexahydro-2H-pyrrolo[3,4-d]oxazol-2-one, M77. (3R,4S)-tert-butyl 3-(((benzyl oxy)carbonyl)amino)-4-hydroxypyrrolidine-1-carboxylate (700 mg, 2.08 mmol, 1.0 eq) was dissolved into HCl/MeOH (4M, 20 mL). The mixture was stirred at 26° C. for 16 hrs and concentrated under reduced pressure. The residue was purified by prep-HPLC (column: Boston Green ODS 150*30 5 u; mobile phase: [water(0.1% TFA)-ACN]; B %: 12%-42%, 10 min) and lyophilized. The product was dissolved into MeOH (10 mL) and pH was adjusted to 8-9 with basic resin. The mixture was filtered and filtrate was concentrated under reduced pressure. Benzyl ((3R,4S)-4-hydroxypyrrolidin-3-yl)carbamate (M76) (300 mg, crude) was obtained as a yellow solid. HNMR (¹H NMR (400 MHz, CHLOROFORM-d) δ=7.30-7.25 (m, 3H), 7.24-7.20 (m, 2H), 5.00 (br. s., 2H), 4.26 (br. s., 2H), 3.48 (br. s., 1H), 3.40-3.18 (m, 2H), 3.07 (br. s., 1H)) showed the structure was correct, but not pure enough. ESI [M+H]=237.1

It was purified again by prep-HPLC (column: Gemini 150*25 5 u; mobile phase: [water(10 mM NH₄HCO₃)-ACN]; B %: 1%-30%, 15 min). During the concentration at 50 degree under reduced pressure, benzyl ((3R,4S)-4-hydroxypyrrolidin-3-yl)carbamate (M76) turned into (3aR,6aS)-hexahydro-2H-pyrrolo[3,4-d]oxazol-2-one (M77). (3aR,6aS)-hexahydro-2H-pyrrolo[3,4-d]oxazol-2-one (M77) (50 mg, 234 umol, 22% yield, about 60% purity based on HNMR) was obtained as a white solid. $^1$H NMR (400 MHz, CHLOROFORM-d) δ=5.05-5.02 (m, 1H), 4.26-4.26 (m, 1H), 3.32-3.28 (m, 1H), 3.04-3.00 (m, 1H), 2.72-2.67 (m, 2H). ESI [M+H]=129.1

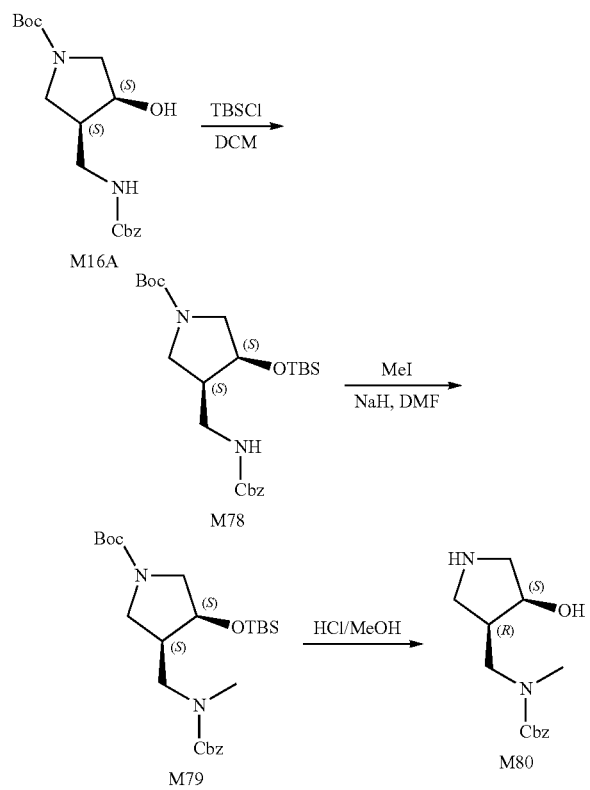

Chemistry Experimental Methods:
General Procedure A4 as below.

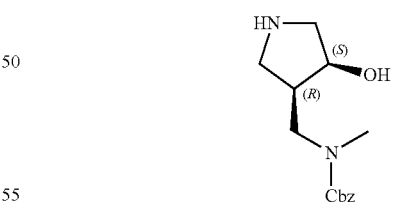

(3S,4S)-tert-butyl 3-((((benzyloxy)carbonyl)amino)methyl)-4-((tert-butyldimethylsilyl)oxy)pyrrolidine-1-carboxylate, M78. To a solution of (3 S,4S)-tert-butyl 3-((((benzyloxy)carbonyl)amino) methyl)-4-hydroxypyrrolidine-1-carboxylate (500 mg, 1.43 mmol, 1.0 eq) in DCM (10 mL), were added DMAP (522.9 mg, 4.28 mmol, 3.0 eq) and TBSCl (1.08 g, 7.1 mmol, 874 uL, 5.0 eq) and the mixture was stirred at 26° C. for 32 hrs. The mixture was poured into ice-cold sat.KHSO₄ solution (100 mL) and extracted with DCM (50 mL×3). The combined organic phases were dried over anhydrous Na₂SO₄, filtered and concentrated in vacuum. The residue was purified by silica gel chromatography with petroleum ether: ethyl acetate (20:1 to 1:1) to afford (3 S,4S)-tert-butyl 3-((((benzyloxy)carbonyl)amino) methyl)-4-((tert-butyldimethylsilyl)oxy)pyrrolidine-1-carboxylate (580 mg, crude) as a yellow oil. ESI [M+Na]= 487.2

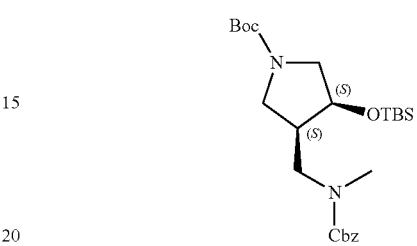

(3S,4S)-tert-butyl 3-((((benzyloxy)carbonyl)(methyl)amino)methyl)-4-((tert-butyldimethyl silyl)oxy)pyrrolidine-1-carboxylate, M79. To a solution of (3 S,4S)-tert-butyl 3-((((benzyloxy) carbonyl)amino)methyl)-4-((tert-butyldimethylsilyl)oxy)pyrrolidine-1-carboxylate (580 mg, 1.25 mmol, 1.0 eq) in DMF (10 mL) was added NaH (75.2 mg, 1.88 mmol, 60% purity, 1.5 eq) at 0° C. After stirring at 26° C. for 0.2 hr, MeI (532 mg, 3.7 mmol, 233 uL, 3.0 eq) was added and the mixture was stirred at 26° C. for 0.3 hr. The mixture was quenched by sat. NH₄Cl solution (20 mL) at 0° C., poured into ice-cold water (100 mL) and extracted with ethyl acetate (50 mL×3). The combined organic phases were washed with brine (50 mL), dried over anhydrous Na₂SO₄, filtered and concentrated in vacuum. The residue was purified by silica gel chromatography (petroleum ether: ethyl acetate 20:1 to 2:1) to afford (3S,4S)-tert-butyl 3-((((benzyloxy)carbonyl) (methyl)amino)methyl)-4-((tert-butyldimethylsilyl)oxy)pyrrolidine-1-carboxylate (550 mg, crude) as yellow oil. $^1$H NMR (400 MHz, CHLOROFORM-d) δ=7.28 (br. s., 5H), 5.15-4.96 (m, 2H), 4.18 (d, J=18.4 Hz, 1H), 3.64-3.04 (m, 6H), 2.88 (d, J=5.1 Hz, 3H), 2.49-2.16 (m, 1H), 1.39 (s, 9H), 0.81 (br. s., 9H), 0.00 (br. s., 6H). ESI [M+Na]=501.2

Benzyl (((3R,4S)-4-hydroxypyrrolidin-3-yl)methyl)(methyl)carbamate, M80. (3S,4S)-tert-butyl 3-((((benzyloxy)carbonyl)(methyl)amino)methyl)-4-((tert-butyldimethylsilyl)oxy) pyrrolidine-1-carboxylate (550 mg, 1.15 mmol, 1.0 eq) was dissolved in HCl/MeOH (4M, 20 mL). The mixture was stirred at 40° C. for 2 hrs, and then concentrated under reduced pressure. The residue was purified by prep-HPLC (TFA condition) to give benzyl (((3R,4S)-4-hydroxypyrrolidin-3-yl)methyl)(methyl)carbamate (420 mg, crude, TFA) as yellow oil. ESI [M+H]=265.1

Chemistry Experimental Methods:
General Procedure A5 as below.

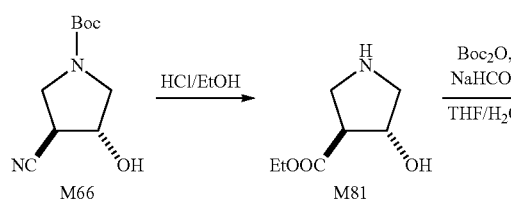
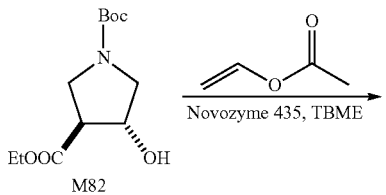
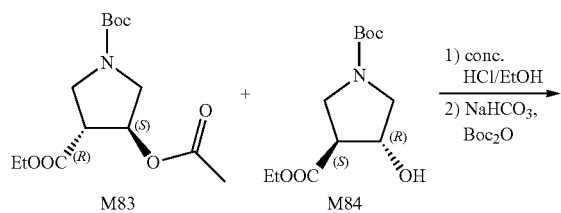
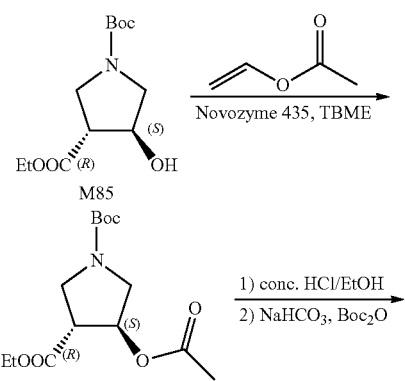
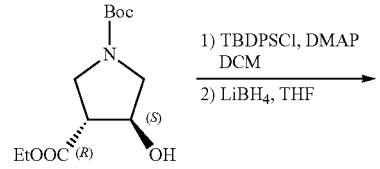
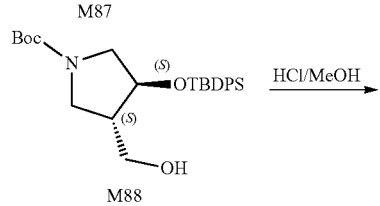
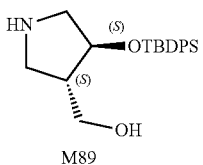

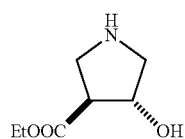

(Trans)-ethyl 4-hydroxypyrrolidine-3-carboxylate, M81. To a mixture of (trans)-tert-butyl 3-cyano-4-hydroxypyrrolidine-1-carboxylate (70 g, 329 mmol, 1.0 eq) in dry EtOH (50 mL) was added HCl/EtOH (dry, 5M, 1.0 L) dropwise at 15° C. The mixture was stirred at 15° C. for 4 days, and then concentrated to give (trans)-ethyl 4-hydroxypyrrolidine-3-carboxylate (70 g, crude, HCl salt), which was used directly for next step without further purification.

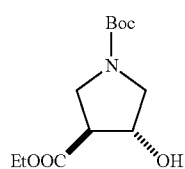

(Trans)-1-tert-butyl 3-ethyl 4-hydroxypyrrolidine-1,3-dicarboxylate, M82. To a solution of (trans)-ethyl 4-hydroxypyrrolidine-3-carboxylate (64.5 g, 329 mmol, 1.0 eq, HCl) in $H_2O$ (400 mL) was added solid $NaHCO_3$ portionwise at 0° C. until the pH was adjusted to about 7, then more $NaHCO_3$ (45 g, 535 mmol, 1.6 eq) was added. To the mixture above, a solution of $Boc_2O$ (85 g, 389 mmol, 89.4 mL, 1.18 eq) in THF (400 mL) was added dropwise. The mixture was warmed to 15° C. and stirred for 16 hrs. The aqueous layer was separated and extracted with EtOAc (200 mL×3). The combined organic layers were dried over $Na_2SO_4$, filtered and concentrated. The residue was purified by column chromatography on silica gel with petroleum ether: ethyl acetate (10:1 to 3:1). (trans)-1-tert-butyl 3-ethyl 4-hydroxypyrrolidine-1,3-dicarboxylate (50 g, 173.7 mmol, 52.7% yield, 90% purity) was got as yellow oil. $^1$H NMR (400 MHz, CHLOROFORM-d) δ=4.55 (q, J=5.7 Hz, 1H), 4.20 (quin, J=7.3 Hz, 2H), 3.71 (br s, 2H), 3.61-3.51 (m, 1H), 3.28 (br s, 1H), 2.99 (br s, 1H), 2.74 (br s, 1H), 1.45 (s, 9H), 1.34-1.24 (m, 3H).

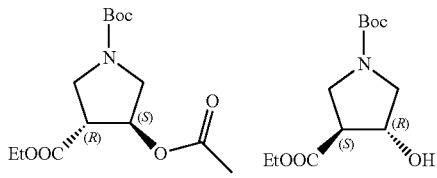

(3R,4S)-1-tert-butyl 3-ethyl 4-acetoxypyrrolidine-1,3-dicarboxylate, M83.

(3S,4R)-1-tert-butyl 3-ethyl 4-hydroxypyrrolidine-1,3-dicarboxylate, M84. To a mixture of (trans)-1-tert-butyl 3-ethyl 4-hydroxypyrrolidine-1,3-dicarboxylate (27 g, 104.13 mmol, 1.0 eq) and vinyl acetate (27 g, 313.6 mmol, 29 mL, 3.01 eq) in MTBE (1.3 L) was added Novozyme 435 (11 g) portionwise. The reaction mixture was stirred at 20° C. for 20 hrs (two batches). The two batches mixture was filtered through Celite and the solid was washed with EtOAc (300 mL×2). The combined filtrates were washed with sat.$NaHCO_3$ aq. (1 L) and brine (500 mL), dried over Na$_2$SO$_4$, filtered and concentrated. The residue was purified by column chromatography on silica gel with petroleum ether: ethyl acetate (10:1 to 2:1). (3R,4S)-1-tert-butyl 3-ethyl 4-acetoxypyrrolidine-1,3-dicarboxylate, M83 (26 g, 83 mmol, 39.9% yield, 96.3% purity) was got as yellow oil. (3S,4R)-1-tert-butyl 3-ethyl 4-hydroxypyrrodine-1,3-dicarboxylate, M84 (31 g, 100 mmol, 48.2% yield, 83.9% purity, ee %:95.58%) was got as yellow oil.

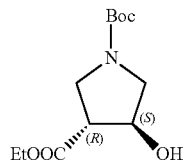

(3R,4S)-1-tert-butyl 3-ethyl 4-hydroxypyrrolidine-1,3-dicarboxylate, M85. To a solution of (3R,4S)-1-tert-butyl 3-ethyl 4-acetoxypyrrolidine-1,3-dicarboxylate (30 g, 99.6 mmol, 1.0 eq) in EtOH (300 mL) was added conc.HCl (12 M, 15 mL, 4.2 eq) portionwise. The reaction mixture was heated to 60° C. and stirred for 10 hrs. The reaction mixture was cooled to 0° C. and H$_2$O (200 mL) was added. The pH was adjusted to about 7 with solid NaHCO$_3$, then more NaHCO$_3$ (15 g, 178 mmol, 6.9 mL, 1.79 eq) was added, followed by Boc$_2$O (25 g, 114.5 mmol, 26.3 mL, 1.15 eq). The mixture was warmed to 15° C. and stirred for 16 hrs. The mixture was extracted with EtOAc (300 mL×3). The combined organic layers were washed brine (200 mL), dried over Na$_2$SO$_4$, filtered and concentrated. The residue was purified by column chromatography on silica gel with petroleum ether: ethyl acetate (10:1 to 3:1). (3R,4S)-1-tert-butyl 3-ethyl 4-hydroxypyrrolidine-1,3-dicarboxylate (22 g, 80 mmol, 80.4% yield, 94.3% purity, ee %=89%) was got as yellow oil. $^1$H NMR (400 MHz, CHLOROFORM-d) δ=4.54 (q, J=5.5 Hz, 1H), 4.23-4.13 (m, 2H), 3.80-3.62 (m, 2H), 3.56 (d, J=6.6 Hz, 1H), 3.27 (t, J=10.5 Hz, 1H), 2.97 (dd, J=6.8, 13.6 Hz, 2H), 1.45 (s, 9H), 1.32-1.24 (m, 3H). ESI [M+Na]=282.1

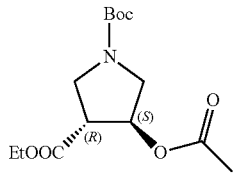

(3R,4S)-1-tert-butyl 3-ethyl 4-acetoxypyrrolidine-1,3-dicarboxylate, M86. To a mixture of (3R,4S)-1-tert-butyl 3-ethyl 4-hydroxypyrrolidine-1,3-dicarboxylate (22 g, 80.4 mmol, 1.0 eq, ee %=89%) and vinyl acetate (40 g, 464.6 mmol, 43 mL, 5.8 eq) in MTBE (1.0 L) was added Novozyme 435 (12 g). The reaction mixture was stirred at 10° C. for 20 hrs. The mixture was filtered and the solid was washed with EtOAc (300 mL×2). The combined filtrate was washed with sat.aq.NaHCO$_3$ (1 L) and brine (500 mL), dried over Na$_2$SO$_4$, then filtered and concentrated. The residue was purified by column chromatography on silica gel with petroleum ether: ethyl acetate (10:1 to 2:1). (3R,4S)-1-tert-butyl 3-ethyl 4-acetoxypyrrolidine-1,3-dicarboxylate (20 g, 59.7 mmol, 74.3% yield, 90% purity based on HNMR) was got as yellow oil. $^1$HNMR (400 MHz, CHLOROFORM-d) δ=5.45 (br. s., 1H), 4.18 (q, J=7.1 Hz, 2H), 3.72 (br. s., 3H), 3.51-3.31 (m, 1H), 3.14-3.05 (m, 1H), 2.08 (s, 3H), 1.46 (s, 9H), 1.27 (t, 1=7.2 Hz, 3H). ESI [M+H]=302.1

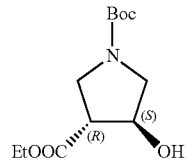

(3R,4S)-1-tert-butyl 3-ethyl 4-hydroxypyrrolidine-1,3-dicarboxylate, M87. To a solution of (3R,4S)-1-tert-butyl 3-ethyl 4-acetoxypyrrolidine-1,3-dicarboxylate (20 g, 66.3 mmol, 1.0 eq) in EtOH (200 mL) was added conc.HCl (12 M, 20 mL, 3.6 eq) portionwise. The reaction mixture was heated to 65° C. and stirred for 6 hrs. The reaction mixture was cooled to 0° C. and H$_2$O (200 mL) was added. The pH was adjusted to about 7 with solid NaHCO$_3$, then more NaHCO$_3$ (10 g, 119 mmol, 1.8 eq) was added followed by Boc$_2$O (16 g, 73.3 mmol, 16.8 mL, 1.1 eq). The reaction mixture was warmed to 15° C. and stirred for 16 hrs. The mixture was extracted with EtOAc (300 mL×3). The combined organic layers were washed brine (200 mL), dried over Na$_2$SO$_4$, then filtered and concentrated. The residue was purified by column chromatography on silica gel with petroleum ether: ethyl acetate (10:1 to 3:1). (3R,4S)-1-tert-butyl 3-ethyl 4-hydroxypyrrolidine-1,3-dicarboxylate (13.0 g, 50.1 mmol, 75.6% yield, 100% purity, ee %: 99.86%) was got as yellow oil. $^1$H NMR (400 MHz, CHLOROFORM-d) δ=4.54-4.44 (m, 1H), 4.17-4.08 (m, 2H), 3.73-3.58 (m, 2H), 3.50 (d, J=4.4 Hz, 1H), 3.21 (br. s., 1H), 2.93 (br. s., 1H), 2.78 (br. s., 1H), 1.39 (s, 9H), 1.25-1.18 (m, 3H). ESI [M+Na]=282.1

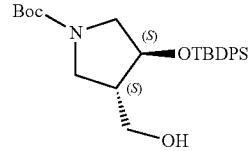

(3S,4S)-tert-butyl 3-((tert-butyldiphenylsilyl)oxy)-4-(hydroxymethyl)pyrrolidine-1-carboxylate, M88. To a mixture of (3R,4S)-1-tert-butyl 3-ethyl 4-hydroxypyrrolidine-1,3-dicarboxylate (200 mg, 771.3 umol, 1.0 eq) and DMAP (150 mg, 1.23 mmol, 1.59 eq) in DCM (10 mL) was added TBDPSCl (220 mg, 800 umol, 205.6 uL, 1.04 eq). The reaction mixture was stirred at 15° C. for 16 hrs, washed with HCl aq. (0.5 M, 10 mL) and brine (10 mL), dried over Na$_2$SO$_4$, filtered and concentrated. To a solution of the residue and MeOH (40 mg, 1.25 mmol, 2.07 eq) in dry THF (4.0 mL) was added LiBH$_4$ (40 mg, 1.8 mmol, 3.05 eq). The mixture was stirred at 30° C. for 16 hrs. The mixture was quenched with sat.NaHCO$_3$ (20 mL) and extracted with EtOAc (20 mL×3). The combined organic layers were washed with brine (20 mL), dried over Na$_2$SO$_4$, then filtered and concentrated. The residue was purified by prep-TLC with petroleum ether: ethyl acetate (4:1). (3S,4S)-tert-butyl 3-((tert-butyldiphenylsilyl)oxy)-4-(hydroxymethyl) pyrrolidine-1-carboxylate (160 mg, 316 umol, 52.4% yield, 90% purity based on HNMR) was got as light yellow oil. $^1$H NMR (400 MHz, CHLOROFORM-d) δ=7.73-7.59 (m, 4H), 7.51-7.33 (m, 6H), 4.27-4.06 (m, 1H), 3.68-3.09 (m, 7H), 2.28 (d, J=5.3 Hz, 1H), 1.45 (br. s., 9H), 1.08 (s, 9H). ESI [M+Na]=478.2

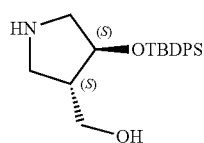

((3S,4S)-4-(((tert-butyldiphenylsilyl)oxy)pyrrolidin-3-yl)methanol, M89. (3 S,4 S)-tert-butyl 3-((tert-butyldiphenylsilyl)oxy)-4-(hydroxymethyl)pyrrolidine-1-carboxylate (160 mg, 351 umol, 1.0 eq) was dissolved in HCl/MeOH (4M, 20 mL) and stirred at 30° C. for 0.5 hr. The reaction mixture was concentrated and dissolved with MeOH (20 mL). The mixture was basified with basic resin to pH =7-8, then filtered and concentrated. ((3S,4S)-4-((tert-butyldiphenylsilyl)oxy) pyrrolidin-3-yl)methanol (120 mg, 337.5 umol, 96.1% yield) was obtained as light yellow oil. $^1$H NMR (400 MHz, METHANOL-d$_4$) δ=7.74-7.57 (m, 4H), 7.49-7.31 (m, 6H), 4.26-4.13 (m, 1H), 3.62-3.51 (m, 1H), 3.31 (br. s., 1H), 3.21-3.07 (m, 1H), 2.97-2.78 (m, 3H), 2.33-2.19 (m, 1H), 1.06 (s, 5H), 1.01-0.98 (m, 4H). ESI [M+H]=356.4

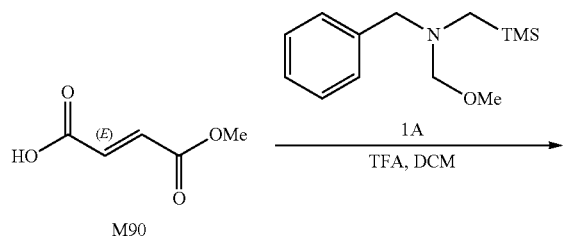

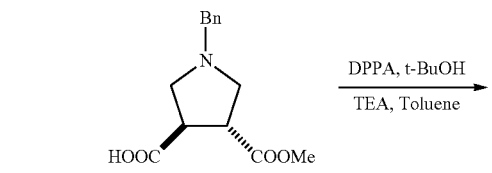

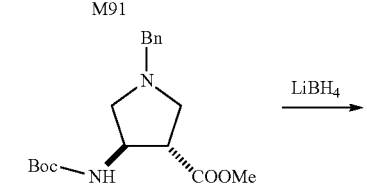

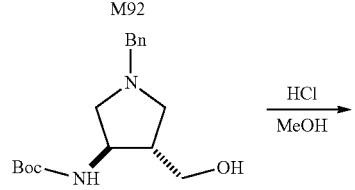

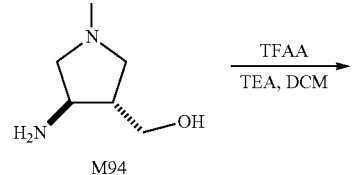

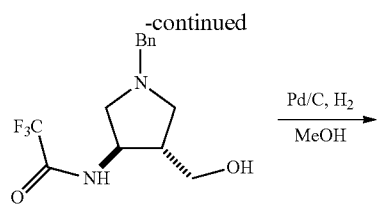

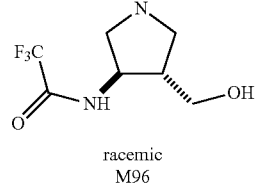

Chemistry Experimental Methods:
General Procedure A6 as below.

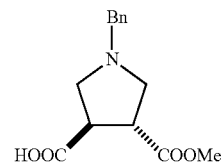 [SMILES: COC(=O)[C@H]1CN(Cc2ccccc2)C[C@@H]1C(=O)O]

Trans-1-benzyl-4-(methoxycarbonyl)pyrrolidine-3-carboxylic acid, M91. To a mixture of (E)-4-methoxy-4-oxobut-2-enoic acid (50 g, 384 mmol, 1.0 eq.) and TFA (4.4 g, 38 mmol, 2.8 mL, 0.1 eq.) in dry DCM (1.0 L) was added N-(methoxymethyl)-1-phenyl-N-(trimethylsilyl methyl)methanamine (183.4 g, 772 mmol, 2.0 eq.) dropwise at 0° C. under N$_2$ atmosphere. The reaction mixture was stirred at 0° C. for 30 mins, then warmed to 20° C. and stirred for another 48 hrs. The mixture was concentrated and purified by column chromatography on silica gel with DCM/MeOH (100:1 to 15:1) to obtain (trans)-1-benzyl-4-methoxycarbonyl-pyrrolidine-3-carboxylic acid (60 g, 205.1 mmol, 53.4% yield, 90% purity) as a light yellow solid. 1H NMR (400 MHz, DMSO-d6) δ=12.44 (s, 1H), 7.36-7.21 (m, 5H), 3.66-3.50 (m, 5H), 3.36-3.28 (m, 1H), 3.26-3.18 (m, 1H), 2.85-2.75 (m, 2H), 2.72-2.62 (m, 2H). ESI [M+H]=264.1

Trans-methyl 1-benzyl-4-((tert-butoxycarbonyl)amino)pyrrolidine-3-carboxylate, M92. A mixture of (trans)-1-benzyl-4-methoxycarbonyl-pyrrolidine-3-carboxylic acid (20 g, 75.9 mmol, 1.0 eq.), TEA (9.99 g, 98 mmol, 13.7 mL, 1.3 eq.), DPPA (25.09 g, 91.15 mmol, 19.75 mL, 1.20 eq.), t-BuOH (28 g, 379.8 mmol, 36.1 mL, 5.0 eq.) in toluene (200 mL) was refluxed at 110° C. for 16 hrs. The reaction was concentrated and then washed with saturated NaHCO$_3$ solution (300 mL), extracted with DCM (200 mL*3), dried, filtered and concentrated. The residue was purified by silica gel column chromatography (Petroleum ether: Ethyl acetate=20:1) to obtain trans-methyl 1-benzyl-4-((tert-butoxycarbonyl)amino)pyrrolidine-3-carboxylate (14 g, 41.8 mmol, 55% yield) as a yellow oil. ¹H NMR (400 MHz, CHLOROFORM-d) δ=7.33-7.18 (m, 5H), 5.00 (br s, 1H), 4.37 (br s, 1H), 3.70-3.64 (m, 3H), 3.61-3.52 (m, 2H), 3.09 (t, J=9.0 Hz, 1H), 2.82 (dt, J=4.0, 8.0 Hz, 1H), 2.70-2.58 (m, 2H), 2.45 (dd, J=7.8, 9.2 Hz, 1H), 1.45-1.34 (m, 9H). ESI [M+H]=335.1

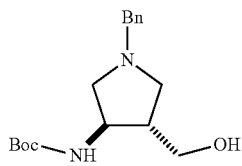 [SMILES: CC(C)(C)OC(=O)N[C@H]1CN(Cc2ccccc2)C[C@@H]1CO]

Tert-butyl (trans-1-benzyl-4-(hydroxymethyl)pyrrolidin-3-yl)carbamate, M93. Trans-methyl 1-benzyl-4-((tert-butoxycarbonyl)amino)pyrrolidine-3-carboxylate (14 g, 41.8 mmol, 1.0 eq.) was dissolved in THF (100 mL), then MeOH (2.35 g, 73.3 mmol, 1.75 eq.) and LiBH₄ (1.37 g, 62.8 mmol, 1.5 eq.) were added into the reaction mixture. The mixture was stirred at 30° C. for 0.5 hr and quenched by MeOH (50 mL). It was concentrated and diluted with saturated NaHCO₃ solution (200 mL), extracted with DCM (300 mL*3), dried, filtered and concentrated. The residue was purified by silica gel column chromatography (petroleum ether: Ethyl acetate=5:1 to dichloromethane: methanol=40:1) and purified by prep-HPLC(neutral condition) to obtain tert-butyl (trans-1-benzyl-4-(hydroxymethyl)pyrrolidin-3-yl)carbamate (8.0 g, 26.1 mmol, 62% yield) as a light yellow oil. 1H NMR (400 MHz, CHLOROFORM-d) δ=7.36-7.19 (m, 5H), 5.04 (d, J=6.6 Hz, 1H), 3.83 (td, J=3.5, 7.1 Hz, 1H), 3.64-3.42 (m, 4H), 2.90 (t, J=8.6 Hz, 1H), 2.74-2.63 (m, 1H), 2.47 (dd, J=2.9, 9.9 Hz, 1H), 2.22-2.10 (m, 1H), 2.06-1.97 (m, 1H), 1.51-1.31 (m, 9H). ESI [M+H]=307.4

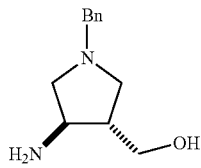

Trans-4-amino-1-benzylpyrrolidin-3-yl)methanol, M94. To a solution of tert-butyl(trans-1-benzyl-4-(hydroxymethyl)pyrrolidin-3-yl)carbamate (1.5 g, 4.9 mmol, 1.0 eq.) in MeOH (5 mL) was added HCl/MeOH (4M, 50 mL) portionwise. The reaction mixture was heated to 40° C. and stirred for 2 hrs. The mixture was concentrated to give trans-4-amino-1-benzylpyrrolidin-3-yl)methanol (1.4 g, crude, 2HCl) as an off-white solid, which was used directly. ESI [M+H]=207.1

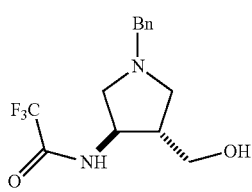 [SMILES: O=C(N[C@H]1CN(Cc2ccccc2)C[C@@H]1CO)C(F)(F)F]

N-(trans-1-benzyl-4-(hydroxymethyl)pyrrolidin-3-yl)-2,2,2-trifluoroacetamide, M95. To a solution of trans-4-amino-1-benzylpyrrolidin-3-yl)methanol (300 mg, 1.45 mmol, 1.0 eq.) in DCM (15 mL) were added TEA (880 mg, 8.7 mmol, 1.2 mL, 6.0 eq.) and (2,2,2-trifluoroacetyl) 2,2,2-trifluoroacetate (1.07 g, 5.07 mmol, 705.9 uL, 3.5 eq.) at 0° C. Then the mixture was stirred at 26° C. for 2 hrs. The mixture was concentrated and purified by acidic prep-HPLC to give N-(trans-1-benzyl-4-(hydroxymethyl)pyrrolidin-3-yl)-2,2,2-trifluoroacetamide (550 mg, crude, TFA) as a yellow oil. ESI [M+H]=303.1

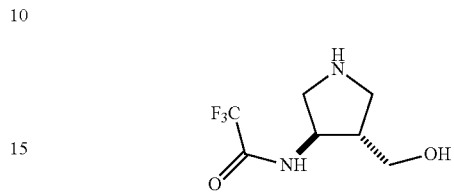

2,2,2-trifluoro-N-(trans-4-(hydroxymethyl)pyrrolidin-3-yl)acetamide, M96. To a solution of N-(trans-1-benzyl-4-(hydroxymethyl)pyrrolidin-3-yl)-2,2,2-trifluoroacetamide (740 mg, 1.78 mmol, 1.0 eq., TFA) in MeOH (20 mL) was added Pd/C (1.0 g, 1.78 mmol, 10% purity), then stirred at 50° C. for 16 hrs under 50 Psi hydrogen. The mixture was filtered and the filtrate was concentrated to give 2,2,2-trifluoro-N-(trans-4-(hydroxymethyl)pyrrolidin-3-yl)acetamide (520 mg, crude, TFA) as a colorless oil. 1H NMR (400 MHz, METHANOL-d4) δ=3.76-3.52 (m, 6H), 3.27-3.21 (m, 1H), 2.61-2.48 (m, 1H). ESI [M+H]=212.9

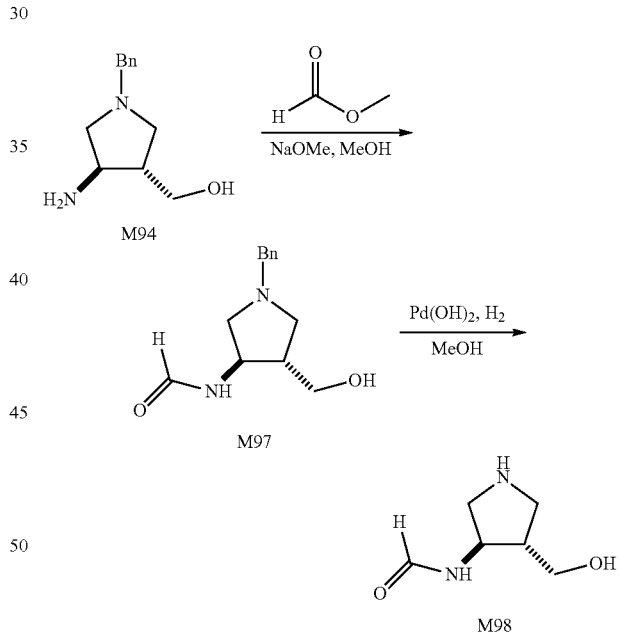

Chemistry Experimental Methods:
General Procedure A7 as below.

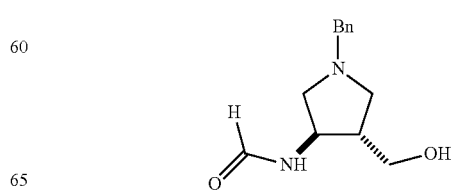

N-(trans-1-benzyl-4-(hydroxymethyl)pyrrolidin-3-yl)formamide, M97. To a mixture of trans-4-amino-1-benzylpyrrolidin-3-yl)methanol (1.0 g, 3.6 mmol, 1.0 eq., 2HCl) in dry MeOH (20 mL) was added NaOMe in MeOH (1.6 g, 7.4 mmol, 25% purity, 2.07 eq.) dropwise, followed by methyl formate (1.0 g, 16.6 mmol, 1 mL, 4.6 eq.). The mixture was warmed to 40° C. and stirred for 3 hrs. The mixture was concentrated and purified by prep-HPLC (neutral condition) to give N-(trans-1-benzyl-4-(hydroxymethyl)pyrrolidin-3-yl)formamide (550 mg, 2.1 mmol, 58.9% yield, 90% purity) as a colorless oil. 1H NMR (400 MHz, METHANOL-d4) δ=7.96 (s, 1H), 7.34-7.19 (m, 5H), 4.12-4.02 (m, 1H), 3.65-3.46 (m, 5H), 2.91-2.82 (m, 1H), 2.77 (dd, J=7.2, 9.8 Hz, 1H), 2.53-2.46 (m, 1H), 2.33 (dd, J=6.8, 9.7 Hz, 1H), 2.19-2.10 (m, 1H). ESI [M+H]=234.9

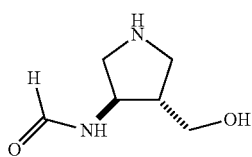

N-(trans-4-(hydroxymethyl)pyrrolidin-3-yl)formamide, M98. A solution of N-[(trans)-1-benzyl-4-(hydroxymethyl)pyrrolidin-3-yl]formamide (550 mg, 2.35 mmol, 1.0 eq.) in dry MeOH (20 mL) was hydrogenated over Pd(OH)$_2$ (200 mg, 1.42 mmol, 0.61 eq.) under H$_2$ (50 Psi) at 50° C. for 3 hrs. The mixture was filtered and the filtrate was concentrated to give N-(trans-4-(hydroxymethyl)pyrrolidin-3-yl)formamide (320 mg, crude) as a gray oil, which was used directly. 1H NMR (400 MHz, METHANOL-d4) δ=8.03 (s, 1H), 4.11-4.02 (m, 1H), 3.67-3.59 (m, 1H), 3.57-3.48 (m, 1H), 3.21-3.06 (m, 2H), 2.78-2.63 (m, 2H), 2.19-2.08 (m, 1H). ESI [M+H]=145.1

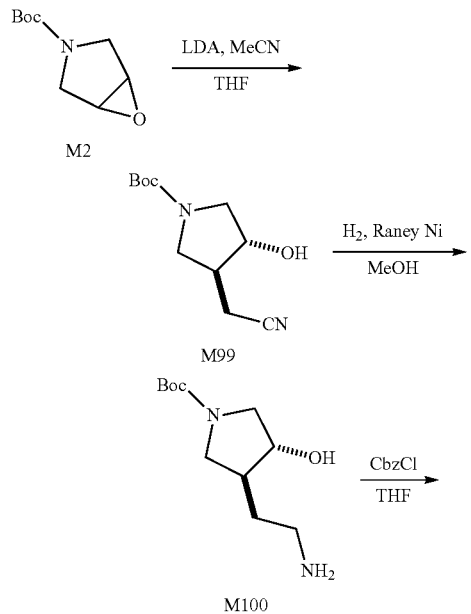

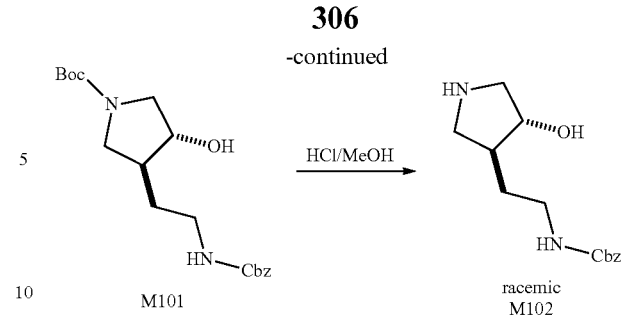

Chemistry Experimental Methods:
General Procedure A8 as below.

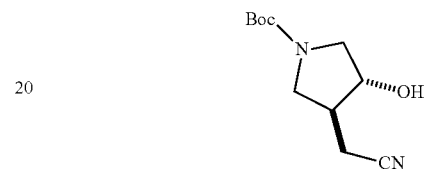

Trans-tert-butyl 3-(cyanomethyl)-4-hydroxypyrrolidine-1-carboxylate, M99. To a mixture of LDA (2 M, 80 mL, 1.48 eq.) in dry THF (350 mL) was added MeCN (8.0 g, 195 mmol, 10.3 mL, 1.8 eq.) dropwise under N$_2$ atmosphere at −70° C. After addition, the mixture was warmed to 20° C. and stirred for 30 mins. The mixture was cooled to −5° C., and added dropwise a solution of tert-butyl 6-oxa-3-azabicyclo[3.1.0]hexane-3-carboxylate (20 g, 108 mmol, 1.0 eq.) in dry THF (50 mL). The reaction mixture was warmed to 15° C. and stirred for 16 hrs. The mixture was poured into ice-cold sat.aq.NH$_4$Cl (500 mL) and concentrated to remove THF. The aqueous layer was extracted with EtOAc (200 mL×3). The combined organic layers were washed with brine (300 mL), dried over Na$_2$SO$_4$, filtered and concentrated. The residue was purified by column chromatography on silica gel with petroleum ether: ethyl acetate (10:1 to 2:1) to give trans-tert-butyl 3-(cyanomethyl)-4-hydroxypyrrolidine-1-carboxylate (10 g, 42 mmol, 38.88% yield, 95% purity) as a pale yellow oil. 1H NMR (400 MHz, CHLOROFORM-d) δ=4.22-4.17 (m, 1H), 3.71 (br. s., 2H), 3.31-3.17 (m, 2H), 2.68-2.36 (m, 4H), 1.47 (s, 9H).

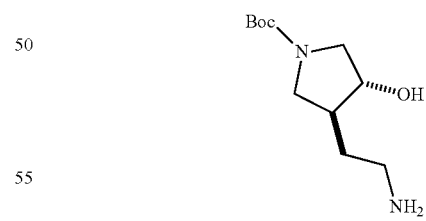

Trans-tert-butyl 3-(2-aminoethyl)-4-hydroxypyrrolidine-1-carboxylate, M100. A mixture of trans-tert-butyl 3-(cyanomethyl)-4-hydroxypyrrolidine-1-carboxylate (7.5 g, 33 mmol, 1.0 eq.) in MeOH (150 mL) and NH$_3$H$_2$O (30 mL) was hydrogenated over Ni (3.0 g, 51 mmol, 1.5 eq.) under 35 Psi H$_2$ atmosphere at 30° C. for 4 hrs. The mixture was filtered and the filtrate was concentrated to give trans-tert-butyl 3-(2-aminoethyl)-4-hydroxypyrrolidine-1-carboxylate (8.0 g, crude) as dark yellow oil which was used directly.

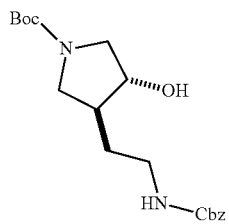 [SMILES: CC(C)(C)OC(=O)N1C[C@H](CCNC(=O)OCc2ccccc2)[C@@H](O)C1]

Trans-tert-butyl 3-(2-(((benzyloxy)carbonyl)amino)ethyl)-4-hydroxypyrrolidine-1-carboxylate, M101. To a mixture of trans-tert-butyl 3-(2-aminoethyl)-4-hydroxypyrrolidine-1-carboxylate (7.6 g, 33.1 mmol, 1.0 eq.) and $K_2CO_3$ (10 g, 72.3 mmol, 2.2 eq.) in $H_2O$ (60 mL) and THF (60 mL) was added CbzCl (10 g, 58.6 mmol, 8.3 mL, 1.8 eq.) dropwise at 0° C. The mixture was warmed to 15° C. and stirred for 2 hrs. The aqueous layer was separated and extracted with EtOAc (50 mL×3). The combined organic layers were washed with brine (50 mL), dried over $Na_2SO_4$, filtered and concentrated. The residue was purified by column chromatography on silica gel with petroleum ether: ethyl acetate (8:1 to 1:1) to give trans-tert-butyl 3-(2-(((benzyloxy)carbonyl)amino)ethyl)-4-hydroxypyrrolidine-1-carboxylate (10 g, 26 mmol, 78.7% yield, 95% purity) as a pale yellow oil. 1H NMR (400 MHz, CHLOROFORM-d) δ=7.42-7.30 (m, 5H), 5.10 (s, 2H), 4.03 (br. s., 1H), 3.63 (d, J=7.9 Hz, 2H), 3.44-3.31 (m, 1H), 3.29-3.11 (m, 2H), 3.01 (d, J=5.7 Hz, 1H), 2.77 (d, J=12.1 Hz, 1H), 2.05 (s, 1H), 1.69-1.50 (m, 2H), 1.46 (s, 9H).

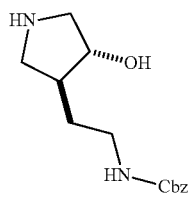

Benzyl (2-(trans-4-hydroxypyrrolidin-3-yl)ethyl)carbamate, M102. To a solution of trans-tert-butyl 3-(2-(((benzyloxy)carbonyl)amino)ethyl)-4-hydroxypyrrolidine-1-carboxylate (1.3 g, 3.6 mmol, 1.0 eq.) in MeOH (5 mL) was added HCl/MeOH (4M, 40 mL) portion-wise. The mixture was stirred at 15° C. for 4 hrs. The mixture was concentrated. The residue was dissolved in MeOH (20 mL) and the pH was adjusted to 10 with basic resin. The mixture was dried over $Na_2SO_4$, filtered and concentrated to give benzyl (2-(trans-4-hydroxypyrrolidin-3-yl)ethyl) carbamate (950 mg, crude) as a yellow oil, which was used directly. 1H NMR (400 MHz, METHANOL-d4) δ=7.41-7.26 (m, 5H), 5.07 (s, 2H), 4.17-4.06 (m, 1H), 3.73 (t, J=6.3 Hz, 1H), 3.50 (dd, J=7.6, 11.3 Hz, 1H), 3.30-3.25 (m, 1H), 3.06 (dd, J=2.0, 12.1 Hz, 1H), 2.97-2.88 (m, 1H), 2.23-2.11 (m, 1H), 1.87 (t, J=6.4 Hz, 1H), 1.69 (qd, J=7.0, 13.8 Hz, 1H), 1.53-1.42 (m, 1H). ESI [M+H]=265.2

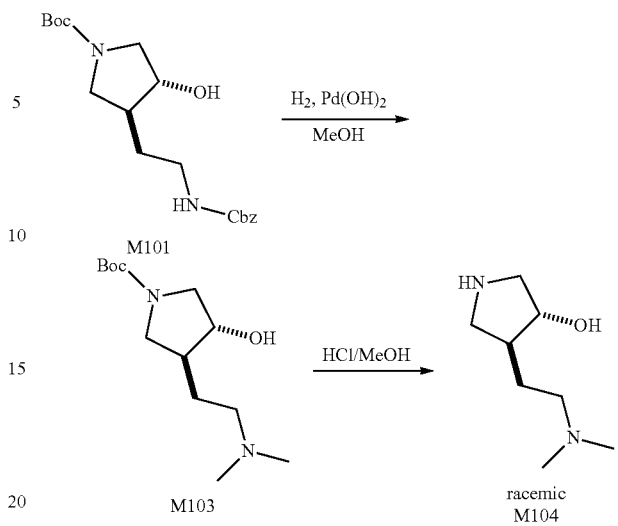

Chemistry Experimental Methods:
General Procedure A9 as below.

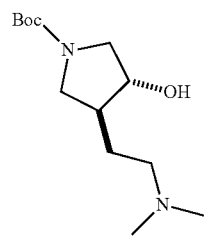 [SMILES: CN(C)CC[C@H]1CN(C(=O)OC(C)(C)C)C[C@@H]1O]

Trans-tert-butyl 3-(2-(dimethylamino)ethyl)-4-hydroxypyrrolidine-1-carboxylate, M103. Trans-tert-butyl 3-(2-(((benzyloxy)carbonyl)amino)ethyl)-4-hydroxypyrrolidine-1-carboxylate (2 g, 5.5 mmol, 1.0 eq.) was dissolved in MeOH (50 mL), then HCHO (164 mg, 5.5 mmol, 151 uL, 1.0 eq.) and $Pd(OH)_2$ (3.0 g, 10.7 mmol, 50% purity, 1.95 eq.) was added and the reaction mixture was stirred at 50° C. under 50 Psi $H_2$ for 2 hrs. The mixture was filtered and concentrated. The residue was purified by silica gel column chromatography (dichloromethane:methanol=40:1 to 10:1) to give trans-tert-butyl 3-(2-(dimethylamino)ethyl)-4-hydroxypyrrolidine-1-carboxylate (1.3 g, 5 mmol, 91.6% yield) as a light yellow oil. 1H NMR (400 MHz, METHANOL-d4) δ=3.90 (q, J=6.3 Hz, 1H), 3.64-3.52 (m, 2H), 3.07 (dd, J=6.2, 10.6 Hz, 1H), 2.98 (q, J=9.3 Hz, 1H), 2.51-2.40 (m, 1H), 2.39-2.29 (m, 1H), 2.26 (s, 6H), 1.99-1.88 (m, 1H), 1.73-1.59 (m, 1H), 1.54-1.39 (m, 10H). ESI [M+H]=259.1

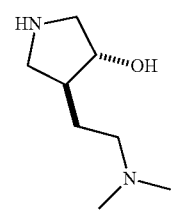

Trans-4-(2-(dimethylamino)ethyl)pyrrolidin-3-ol, M104. Trans-tert-butyl 3-(2-(dimethyl amino)ethyl)-4-hydroxypyrrolidine-1-carboxylate (1.3 g, 5 mmol, 1.0 eq.) was dissolved in HCl/MeOH (50 mL, 4 mol/L). The mixture was stirred at 30° C. for 0.5 hr and concentrated. The residue was dissolved in MeOH (30 mL) and basified by basic resin (800 mg) to pH=7-8. It was filtered and concentrated to give trans-4-(2-(dimethylamino)ethyl)pyrrolidin-3-ol (780 mg, 4.9 mmol, 98% yield) as a yellow oil. 1H NMR (400 MHz, METHANOL-d4) δ=4.18 (q, J=4.4 Hz, 1H), 3.54 (dd, J=7.5, 11.9 Hz, 1H), 3.42 (dd, J=5.3, 12.3 Hz, 1H), 3.11 (dd, J=4.0, 12.3 Hz, 1H), 3.01 (dd, J=7.1, 11.9 Hz, 1H), 2.96-2.77 (m, 2H), 2.62 (s, 6H), 2.24-2.12 (m, 1H), 1.88-1.74 (m, 1H), 1.74-1.61 (m, 1H). ESI [M+H]=159.0

(Trans-4-aminopyrrolidin-3-yl)methanol, M106. A solution of tert-butyl (trans-4-(hydroxyl methyl)pyrrolidin-3-yl) carbamate (270 mg, 1.25 mmol, 1.0 eq.) in HCl/MeOH (20 mL, 4 mol/L), was stirred at 10° C. for 0.5 hr and concentrated. The residue was dissolved in MeOH (30 mL) basified with basic resin (500 mg) to pH=7-8. It was filtered and concentrated to give (trans-4-aminopyrrolidin-3-yl)methanol (140 mg, 1.2 mmol, 96.8% yield) as a light yellow oil. 1H NMR (400 MHz, METHANOL-d4) δ=3.69-3.59 (m, 2H), 3.51-3.36 (m, 3H), 3.12-3.01 (m, 1H), 2.96 (dd, J=6.0, 11.7 Hz, 1H), 2.27-2.16 (m, 1H)

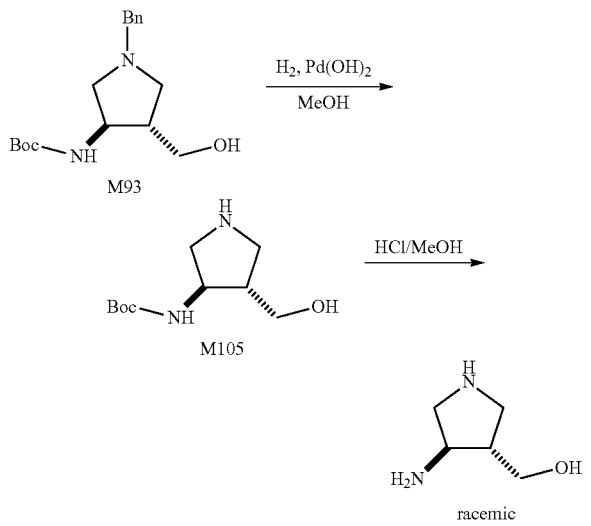

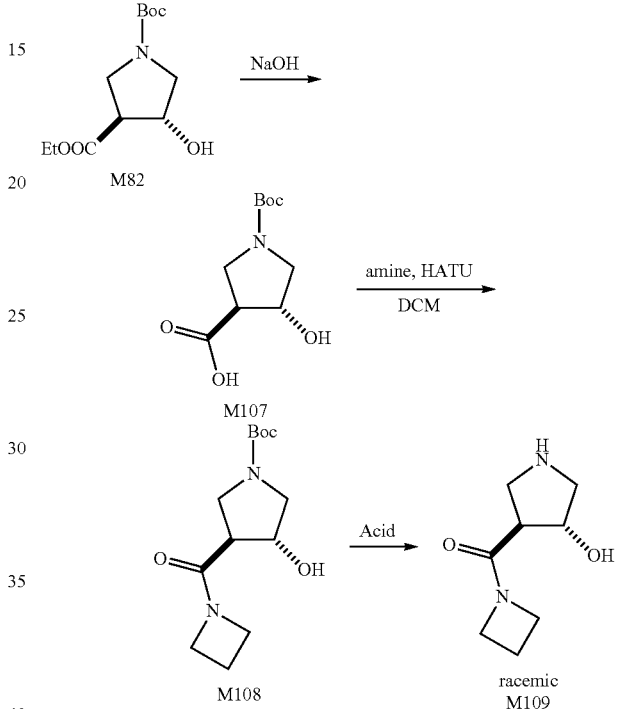

Chemistry Experimental Methods:
General Procedure A10 as below.

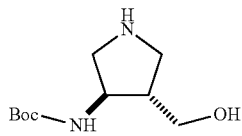 [SMILES: CC(C)(C)OC(=O)N[C@H]1CNC[C@@H]1CO]

Tert-butyl (trans-4-(hydroxymethyl)pyrrolidin-3-yl)carbamate, M105. To a solution of tert-butyl (trans-1-benzyl-4-(hydroxymethyl)pyrrolidin-3-yl)carbamate (900 mg, 2.9 mmol, 1.0 eq.) in MeOH (50 mL) was added Pd(OH)₂ (998 mg, 7.1 mmol, 2.4 eq.) and the reaction mixture was stirred at 30° C. for 1 hr under 50 Psi H2. The reaction mixture was filtered and concentrated to give tert-butyl (trans-4-(hydroxymethyl)pyrrolidin-3-yl)carbamate (600 mg, 2.7 mmol, 94% yield) as a white solid. 1H NMR (400 MHz, METHANOL-d4) δ=3.72 (q, J=5.9 Hz, 1H), 3.62 (dd, J=5.7, 10.8 Hz, 1H), 3.50 (dd, J=7.2, 10.8 Hz, 1H), 3.14-3.03 (m, 2H), 2.73-2.59 (m, 2H), 2.12-2.02 (m, 1H), 1.51-1.38 (m, 9H). ESI [M+H]=217.0

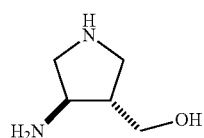

Chemistry Experimental Methods:
General Procedure A11 as below.

Trans-1-(tert-butoxycarbonyl)-4-hydroxypyrrolidine-3-carboxylic acid, M107. To a solution of (trans)-1-tert-butyl 3-ethyl 4-hydroxypyrrolidine-1,3-dicarboxylate (1.4 g, 5.4 mmol, 1.0 eq) in THF (10 mL), H₂O (10 mL) and EtOH (30 mL) was added NaOH (413 mg, 10.8 mmol, 2.0 eq) and the mixture was stirred at 25° C. for 1 hr. The mixture was concentrated and the residue was dissolved into water (50 mL). The aqueous phase was extracted with DCM (50 ml*2). The aqueous phase was adjusted to pH=2 by HCl solution (0.5 M) concentrated to give trans-1-(tert-butoxycarbonyl)-4-hydroxypyrrolidine-3-carboxylic acid (1.25 g, crude) as a white solid, which can be used without any purification. ESI [M+H]=232.1

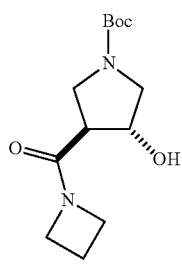 [SMILES: CC(C)(C)OC(=O)N1C[C@H](C(=O)N2CCC2)[C@@H](O)C1]

Trans-tert-butyl 3-(azetidine-1-carbonyl)-4-hydroxypyrrolidine-1-carboxylate, M108. To a solution of (trans)-1-tert-butoxycarbonyl-4-hydroxy-pyrrolidine-3-carboxylic acid (892 mg, 3.8 mmol, 1.0 eq) in DCM (30 mL) was added DIEA (1.7 g, 13.5 mmol, 2.3 mL, 3.5 eq), HATU (1.7 g, 4.6 mmol, 1.2 eq) and azetidine (541 mg, 5.8 mmol, 636 uL, 1.5 eq, HCl). The mixture was stirred at 25° C. for 2 hrs and concentrated in vacuo. The residue was purified by acidic prep-HPLC to give trans-tert-butyl 3-(azetidine-1-carbonyl)-4-hydroxypyrrolidine-1-carboxylate (750 mg, 2.5 mmol, 64.7% yield, 90% purity) as a yellow oil. ESI [M+H]=271.2

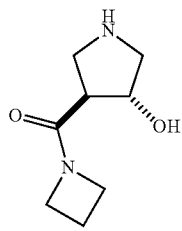 [SMILES: O=C([C@H]1CNC[C@@H]1O)N1CCC1]

Azetidin-1-yl(trans-4-hydroxypyrrolidin-3-yl)methanone, M109. Trans-tert-butyl 3-(azetidine-1-carbonyl)-4-hydroxy-pyrrolidine-1-carboxylate (800 mg, 2.9 mmol, 1.0 eq) was dissolved into TFA (5.0 mL) and the mixture was stirred at 25° C. for 5 mins. The mixture was concentrated and then dissolved into THF (10 mL). The mixture was adjusted to pH=9 by basic resin. It was filtered and concentrated to give azetidin-1-yl(trans-4-hydroxypyrrolidin-3-yl) methanone (450 mg, 2.5 mmol, 84.8% yield, 95% purity) as a yellow oil. ESI [M+H]=171.2

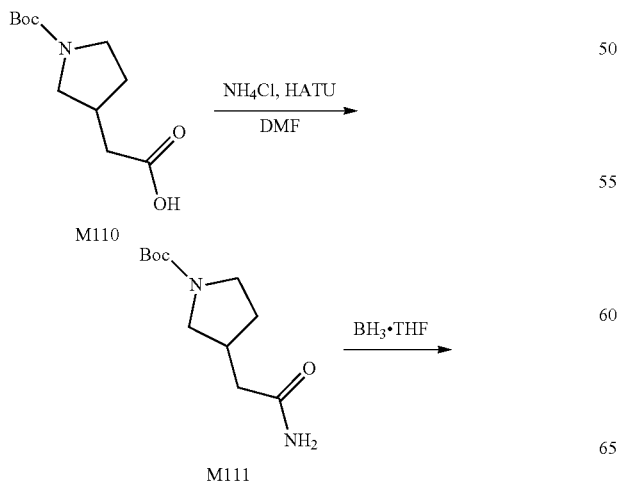

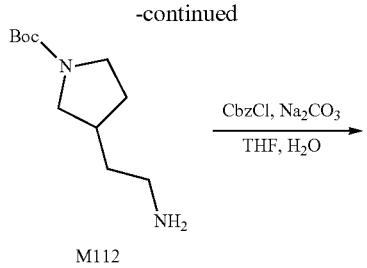

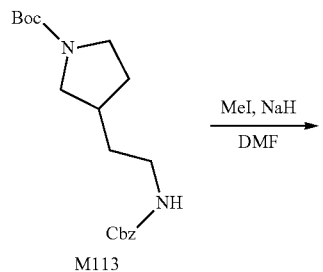

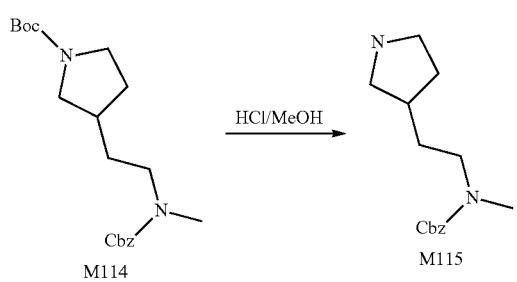

Chemistry Experimental Methods:
General Procedure A12 as below.

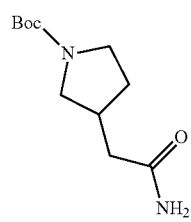 [SMILES: CC(C)(C)OC(=O)N1CCC(CC(N)=O)C1]

Tert-butyl 3-(2-amino-2-oxoethyl)pyrrolidine-1-carboxylate, M111. A mixture of 2-(1-tert-butoxycarbonylpyrrolidin-3-yl)acetic acid (1.4 g, 6.1 mmol, 1.0 eq), NH₄Cl (979 mg, 18 mmol, 3.0 eq) and DIEA (2.7 g, 21.4 mmol, 3.7 mL, 3.5 eq) in DMF (20 mL) was stirred at 20° C. for 10 min, then HATU (2.8 g, 7.3 mmol, 1.2 eq) was added in one portion and the mixture was stirred at 20° C. for 50 min. The mixture was poured into cold water (200 mL) and extracted with ethyl acetate (100 mL*3). The combined organic phase was washed with brine (200 mL), dried over anhydrous Na₂SO₄, filtered and concentrated to give tert-butyl 3-(2-amino-2-oxoethyl) pyrrolidine-1-carboxylate (2.0 g, crude) as a colorless oil, which can be used without any purification. ESI [M+H]=229.1

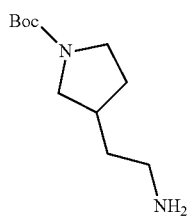 [SMILES: CC(C)(C)OC(=O)N1CCC(CCN)C1]

Tert-butyl 3-(2-aminoethyl)pyrrolidine-1-carboxylate, M112. To a solution of tert-butyl 3-(2-amino-2-oxo-ethyl)pyrrolidine-1-carboxylate (2.0 g, 8.7 mmol, 1.0 eq) in THF (10 mL) was added BH$_3$.THF (1 M, 50 mL, 5.7 eq) dropwise at 0° C. The mixture was stirred at 70° C. for 30 min. The mixture was cooled to 0° C. and quenched by MeOH (50 mL). Then the mixture was stirred at 70° C. for 2 hrs and concentrated to give tert-butyl 3-(2-aminoethyl)pyrrolidine-1-carboxylate (1.8 g, crude) as a yellow oil, which can be used without any purification. ESI [M+H]=215.1

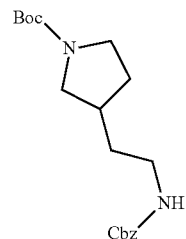

Tert-butyl 3-(2-(((benzyloxy)carbonyl)amino)ethyl)pyrrolidine-1-carboxylate, M113. To a solution of tert-butyl 3-(2-aminoethyl)pyrrolidine-1-carboxylate (1.8 g, 7.8 mmol, 1.0 eq) in THF (30 mL) and water (30 mL) were added Na$_2$CO$_3$ (1.6 g, 15.7 mmol, 2.0 eq) and CbzCl (1.5 g, 8.6 mmol, 1.2 mL, 1.1 eq) in one portion at 0° C. The mixture was stirred at 30° C. for 1 hr, poured into ice-water (50 mL) and extracted with ethyl acetate (200 mL*3). The combined organic phase was washed with brine (200 mL*2), dried over anhydrous Na$_2$SO$_4$, filtered and concentrated to give tert-butyl 3-(2-(((benzyloxy)carbonyl)amino)ethyl)pyrrolidine-1-carboxylate (1.0 g, crude) as a colorless oil, which can be used without any purification. ESI [M+H]=349.2

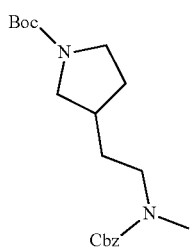

Tert-butyl 3-(2-(((benzyloxy)carbonyl)(methyl)amino)ethyl)pyrrolidine-1-carboxylate, M114. To a solution of tert-butyl 3-(2-(((benzyloxy)carbonyl)amino)ethyl)pyrrolidine-1-carboxylate (500 mg, 1.4 mmol, 1.0 eq) in DMF (10 mL) was added NaH (85 mg, 2.1 mmol, 60% purity, 1.5 eq) at 0° C. The mixture was stirred at 0° C. for 0.1 hr and then added MeI (608 mg, 4.2 mmol, 267 uL, 3.0 eq). The mixture was stirred at 26° C. for 0.4 hr and quenched by cold sat. NH$_4$Cl solution (100 mL). The mixture was extracted with ethyl acetate (50 mL*3). The combined organic phase was washed with brine (50 mL), dried over anhydrous Na$_2$SO$_4$, filtered and concentrated in vacuum. The residue was purified by acidic prep-HPLC to give tert-butyl 3-(2-(((benzyloxy)carbonyl)(methyl)amino)ethyl)pyrrolidine-1-carboxylate (500 mg) as a yellow oil. ESI [M+H]=363.2

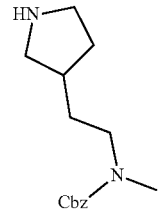

Benzyl methyl(2-(pyrrolidin-3-yl)ethyl)carbamate, M115. A solution of tert-butyl 3-(2-(((benzyloxy) carbonyl)(methyl)amino)ethyl)pyrrolidine-1-carboxylate (400 mg, 1.1 mmol, 1.0 eq) in HCl/MeOH (30 mL, 4 M) was stirred at 30° C. for 0.5 hr and then concentrated. The residue was dissolved in MeOH (30 mL) and basified by basic resin to pH=8-9. It was filtered and concentrated to give benzyl methyl(2-(pyrrolidin-3-yl)ethyl)carbamate (250 mg, 952 umol, 86.6% yield) as a light yellow oil. 1H NMR (400 MHz, METHANOL-d4) δ=7.34 (br. s., 5H), 5.14-5.05 (m, 2H), 3.48-3.30 (m, 3H), 3.22-3.04 (m, 1H), 2.98-2.87 (m, 3H), 2.87-2.70 (m, 1H), 2.19 (br. s., 2H), 1.75-1.51 (m, 3H). ESI [M+H]=263.2

The Synthesis of other Amines.

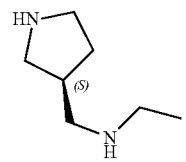

(S)—N-(pyrrolidin-3-ylmethyl)ethanamine, M116. Synthesized using General Procedure A12, replacing 2-(1-(tert-butoxycarbonyl)pyrrolidin-3-yl)acetic acid with (R)-1-(tert-butoxycarbonyl) pyrrolidine-3-carboxylic acid, replacing ammonium chloride with ethanamine. ESI [M+H]=129.1

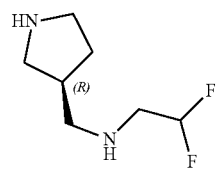

(R)-2,2-difluoro-N-(pyrrolidin-3-ylmethyl)ethanamine, M117. Synthesized using General Procedure A12, replacing 2-(1-(tert-butoxycarbonyl)pyrrolidin-3-yl)acetic acid with (R)-1-(tert-butoxycarbonyl)pyrrolidine-3-carboxylic acid, replacing ammonium chloride with 2,2-difluoro ethanamine. 1H NMR (400 MHz, CHLOROFORM-d) δ=5.88-5.58 (m, 1H), 3.34-3.29 (m, 2H), 3.19 (br. s., 1H), 3.04-3.02 (m, 1H), 2.93-2.89 (m, 2H), 2.74-2.72 (m, 1H), 2.64 (m, 1H), 2.42-2.41 (m, 1H), 2.12-2.10 (m, 1H), 1.72-1.68 (m, 1H). ESI [M+H]=165.0

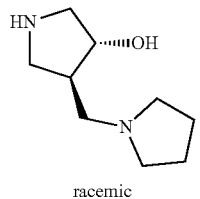 [SMILES: O[C@H]1CNC[C@@H]1CN1CCCC1]

racemic (Trans)-4-(pyrrolidin-1-ylmethyl)pyrrolidin-3-ol, M118. Synthesized using General Procedure Q, replacing 1-((benzyloxy)carbonyl)pyrrolidine-3-carboxylic acid with trans-1-benzyl-4-(benzyloxy)pyrrolidine-3-carboxylic acid, replacing tert-butyl (3-aminopropyl) carbamate with pyrrolidine. 1H NMR (400 MHz, METHANOL-d4) δ=4.29-4.27 (m, 1H), 3.72 (s, 1H), 3.59-3.58 (m, 1H), 3.37-3.34 (m, 1H), 3.16-3.09 (m, 2H), 2.88-2.83 (m, 4H), 2.79-2.76 (m, 1H), 2.50-2.49 (m, 1H), 1.92-1.85 (m, 4H). ESI [M+H]=171.1

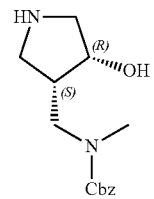

Benzyl (((3S,4R)-4-hydroxypyrrolidin-3-yl)methyl)(methyl)carbamate, M121. Synthesized using General Procedure A4, replacing (3S,4S)-tert-butyl 3-((((benzyloxy)carbonyl)amino) methyl)-4-hydroxypyrrolidine-1-carboxylate with (3R,4R)-tert-butyl 3-((((benzyloxy)carbonyl) amino) methyl)-4-hydroxypyrrolidine-1-carboxylate. 1H NMR (400 MHz, METHANOL-d4) d=7.45-7.21 (m, 5H), 5.12 (s, 2H), 4.28 (br. s., 1H), 3.67 (br. s., 1H), 3.56-3.40 (m, 2H), 3.40-3.30 (m, 2H), 3.08 (t, J=11.4 Hz, 1H), 2.99 (s, 3H), 2.54 (br. s., 1H). ESI [M+H]=265.2

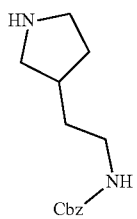

Benzyl (2-(pyrrolidin-3-yl)ethyl)carbamate, M119. Synthesized using General Procedure A12, replacing tert-butyl 3-(2-(((benzyloxy)carbonyl)(methyl)amino)ethyl)pyrrolidine-1-carboxylate with tert-butyl 3-(2-(((benzyloxy)carbonyl)amino)ethyl)pyrrolidine-1-carboxylate. 1H NMR (400 MHz, METHANOL-d4) δ=7.41-7.23 (m, 5H), 5.13-5.01 (m, 2H), 3.48-3.32 (m, 2H), 3.23-3.09 (m, 3H), 2.79 (t, J=10.4 Hz, 1H), 2.36-2.12 (m, 2H), 1.73-1.50 (m, 3H). ESI [M+H]=249.1

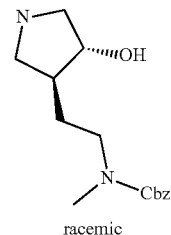

racemic

Benzyl (2-(trans-4-hydroxypyrrolidin-3-yl)ethyl)(methyl)carbamate, M122. Synthesized using General Procedure A4, replacing (3S,4S)-tert-butyl 3-((((benzyloxy)carbonyl)amino) methyl)-4-hydroxypyrrolidine-1-carboxylate with trans-tert-butyl 3-(2-(((benzyloxy)carbonyl) amino) ethyl)-4-hydroxypyrrolidine-1-carboxylate. 1H NMR (400 MHz, METHANOL-d4) d=7.36 (d, J=3.5 Hz, 5H), 5.12 (br. s., 2H), 4.24-4.10 (m, 1H), 3.61-3.33 (m, 3H), 3.29-3.23 (m, 1H), 3.17-2.88 (m, 5H), 2.14 (br. s., 1H), 1.77 (td, J=6.8, 13.6 Hz, 1H), 1.49 (dtd, J=5.6, 8.2, 13.9 Hz, 1H). ESI [M+H]=279.0

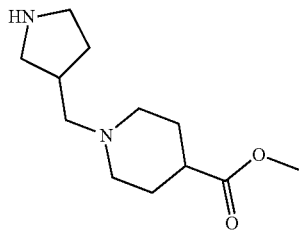 [SMILES: COC(=O)C1CCN(CC2CCNC2)CC1]

Methyl 1-(pyrrolidin-3-ylmethyl)piperidine-4-carboxylate, M120. Synthesized using General Procedure A2, replacing methyl 2-amino-2-methylpropanoate with methyl piperidine-4-carboxylate. 1H NMR (400 MHz, METHANOL-d4) δ=3.72-3.66 (m, 3H), 3.42-3.39 (m, 1H), 3.34 (m, 1H), 3.25 (m, 1H), 3.00-2.95 (m, 3H), 2.49-2.48 (m, 3H), 2.46 (m, 1H), 2.21-2.16 (m, 3H), 1.93-1.90 (m, 2H), 1.74-1.70 (m, 3H). ESI [M+H]=227.0

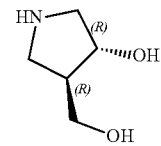

(3R,4R)-4-(hydroxymethyl)pyrrolidin-3-ol, M123. Synthesized using General Procedure A5, replacing (3R,4S)-1-tert-butyl 3-ethyl 4-hydroxypyrrolidine-1,3-dicarboxylate with (3S,4R)-1-tert-butyl 3-ethyl 4-hydroxypyrrolidine-1,3-dicarboxylate. 1H NMR (400 MHz, METHANOL-d4) d=4.24-4.16 (m, 1H), 3.61-3.50 (m, 2H), 3.35 (dd, J=7.9, 11.5 Hz, 1H), 3.16 (dd, J=5.1, 12.1 Hz, 1H), 3.00-2.88 (m, 2H), 2.31-2.22 (m, 1H). ESI [M+H]=117.8

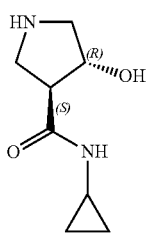

(3S,4R)—N-cyclopropyl-4-hydroxypyrrolidine-3-carboxamide, M124. Synthesized using General Procedure A11, replacing trans-1-tert-butyl 3-ethyl 4-hydroxypyrrolidine-1,3-dicarboxylate with (3S,4R)-1-tert-butyl 3-ethyl 4-hydroxypyrrolidine-1,3-dicarboxylate, replacing azetidine with cyclopropanamine. 1H NMR (400 MHz, METHANOL-d4) d=4.46 (br. s., 1H), 3.52 (d, J=4.4 Hz, 2H), 3.42 (dd, J=3.5, 11.9 Hz, 1H), 3.21 (d, J=11.9 Hz, 1H), 3.02 (br. s., 1H), 2.67 (dd, J=3.5, 7.1 Hz, 1H), 0.73 (d, J=6.6 Hz, 2H), 0.50 (br. s., 2H). ESI [M+H]=171.0

The Synthesis of other Targets.

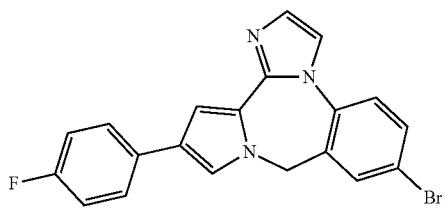 [SMILES: Fc1ccc(-c2cc3n(c2)Cc2cc(Br)ccc2-n2ccnc2-3)cc1]

7-bromo-12-(4-fluorophenyl)-9H-benzo[e]imidazo[2,1-c]pyrrolo[1,2-a][1,4]diazepine, 463. See 5116 in General Procedure J. $^1$H NMR (400 MHz, DMSO-d$_6$) δ=7.91 (dd, J=1.9, 7.2 Hz, 2H), 7.73 (dd, J=2.3, 8.7 Hz, 1H), 7.59-7.51 (m, 3H), 7.46 (d, J=2.0 Hz, 1H), 7.38 (s, 1H), 7.18-7.09 (m, 2H), 6.96 (d, J=1.8 Hz, 1H), 5.23 (s, 2H). ESI [M+H]=394.0/396.0

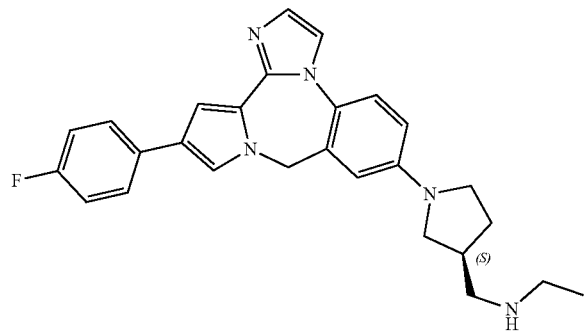

(S)—N-((1-(12-(4-fluorophenyl)-9H-benzo[e]imidazo[2,1-c]pyrrolo[1,2-a][1,4]diazepin-7-yl) pyrrolidin-3-yl) methyl)ethanamine, 464. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (S)—N-(pyrrolidin-3-ylmethyl)ethanamine. $^1$H NMR (400 MHz, METHANOL-d$_4$) δ=8.00-7.99 (m, 1H), 7.74-7.73 (m, 1H), 7.59-7.52 (m, 4H), 7.19-7.18 (m, 1H), 7.10-7.06 (m, 2H), 6.80-6.79 (m, 1H), 6.75-6.65 (m, 1H), 5.27 (s, 2H), 3.64-3.42 (m, 3H), 3.20-3.08 (m, 5H), 2.73-2.69 (m, 1H), 2.34-2.32 (m, 1H), 1.92-1.86 (m, 1H), 1.33 (t, J=7.4 Hz, 3H). ESI [M+H]=442.1

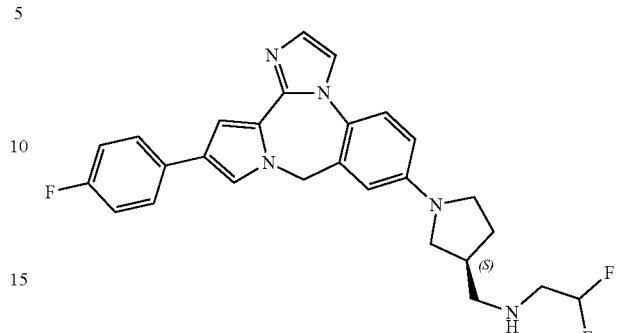

(S)-2,2-difluoro-N-((1-(12-(4-fluorophenyl)-9H-benzo[e]imidazo[2,1-c]pyrrolo[1,2-a][1,4] diazepin-7-yl)pyrrolidin-3-yl)methyl)ethanamine, 465. Synthesized using General Procedure A, replacing 4-(7-bromo-9H-benzo[e]pyrrolo[1,2-a][1,2,4]triazolo[3,4-c][1,4]diazepin-12-yl) benzonitrile with 7-bromo-12-(4-fluorophenyl)-9H-benzo[e]imidazo[2,1-c]pyrrolo[1,2-a][1,4] diazepine and replacing tertbutyl piperazine-1-carboxylate with (R)-2,2-difluoro-N-(pyrrolidin-3-ylmethyl)ethanamine. $^1$H NMR (400 MHz, METHANOL-d$_4$) δ=8.01 (br. s., 1H), 7.75 (br. s., 1H), 7.65-7.52 (m, 4H), 7.20 (s, 1H), 7.09 (t, J=8.6 Hz, 2H), 6.81 (s, 1H), 6.76 (d, J=9.0 Hz, 1H), 6.49-6.18 (m, 1H), 5.28 (s, 2H), 3.70-3.40 (m, 6H), 3.34 (br. s., 1H), 3.21 (t, J=8.6 Hz, 1H), 2.86-2.73 (m, 1H), 2.36 (d, J=6.3 Hz, 1H), 2.00-1.84 (m, 1H). ESI [M+H]=478.1

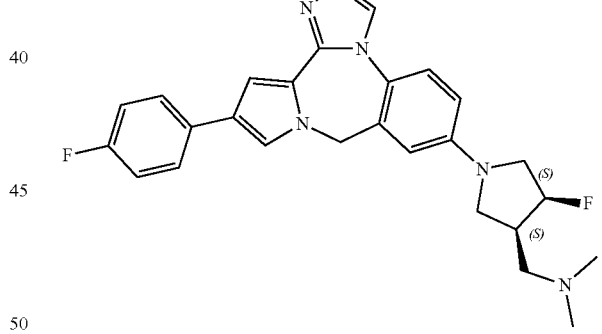

1-((3S,4S)-4-fluoro-1-(12-(4-fluorophenyl)-9H-benzo[e]imidazo[2,1-c]pyrrolo[1,2-a][1,4] diazepin-7-yl)pyrrolidin-3-yl)-N,N-dimethylmethanamine, 467. Synthesized using General Procedure U, replacing 1-((cis)-4-fluoro-1-(12-(4-fluorophenyl)-9H-benzo[e]imidazo[2,1-c] pyrrolo[1,2-a][1,4]diazepin-7-yl)pyrrolidin-3-yl)-N-methylmethanamine with 1-((3S,4S)-4-fluoro-1-(12-(4-fluorophenyl)-9H-benzo[e]imidazo[2,1-c]pyrrolo[1,2-a][1,4]diazepin-7-yl)pyrrolidin-3-yl)-N-methylmethanamine. $^1$H NMR (400 MHz, METHANOL-d$_4$) δ=8.02 (d, J=1.3 Hz, 1H), 7.75 (d, J=1.3 Hz, 1H), 7.62-7.54 (m, 4H), 7.20 (s, 1H), 7.09 (t, J=8.6 Hz, 2H), 6.85 (s, 1H), 6.79 (d, J=8.8 Hz, 1H), 5.55-5.38 (m, 1H), 5.29 (s, 2H), 3.84 (t, J=9.0 Hz, 2H), 3.79-3.67 (m, 2H), 3.63 (dd, J=6.8, 13.5 Hz, 1H), 3.43 (dd, J=6.8, 13.5 Hz, 1H), 3.02 (s, 7H). ESI [M+H]=460.1

319

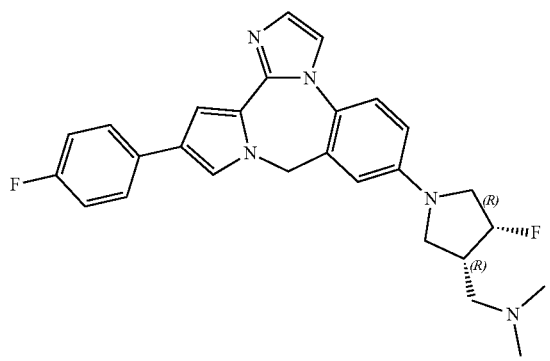

1-((3R,4R)-4-fluoro-1-(12-(4-fluorophenyl)-9H-benzo[e]
imidazo[2,1-c]pyrrolo[1,2-a][1,4] diazepin-7-yl)pyrrolidin-
3-yl)-N,N-dimethylmethanamine, 475. Synthesized using
General Procedure U, replacing 1-((cis)-4-fluoro-1-(12-(4-
fluorophenyl)-9H-benzo[e]imidazo[2,1-c] pyrrolo[1,2-a][1,
4]diazepin-7-yl)pyrrolidin-3-yl)-N-methylmethanamine
with 1-((3R,4R)-4-fluoro-1-(12-(4-fluorophenyl)-9H-benzo
[e]imidazo[2,1-c]pyrrolo[1,2-a][1,4]diazepin-7-yl)pyrroli-
din-3-yl)-N-methylmethanamine. $^1$H NMR (400 MHz,
METHANOL-d$_4$) δ=8.01 (s, 1H), 7.75 (d, J=1.8 Hz, 1H),
7.63-7.54 (m, 4H), 7.20 (s, 1H), 7.09 (t, J=8.6 Hz, 2H), 6.85
(s, 1H), 6.79 (d, J=8.8 Hz, 1H), 5.56-5.37 (m, 1H), 5.29 (s,
2H), 3.84 (t, J=8.8 Hz, 2H), 3.80-3.67 (m, 2H), 3.63 (dd,
J=6.6, 13.2 Hz, 1H), 3.43 (dd, J=6.6, 13.2 Hz, 1H), 3.02 (s,
7H). ESI [M+H]=460.1

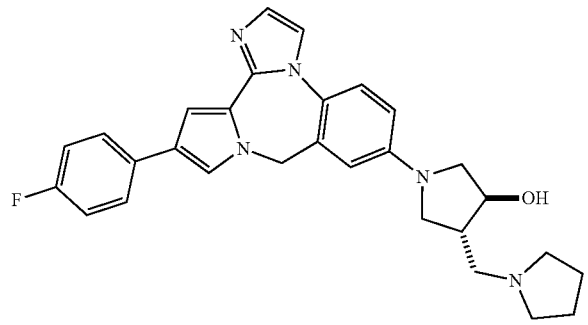 [SMILES: O[C@@H]1CN(c2ccc3c(c2)Cn2cc(-c4ccc(F)cc4)cc2-c2nccn2-3)C[C@H]1CN1CCCC1]

(Trans)-1-(12-(4-fluorophenyl)-9H-benzo[e]imidazo[2,1-
c]pyrrolo[1,2-a][1,4]diazepin-7-yl)-4-(pyrrolidin-1-ylm-
ethyl)pyrrolidin-3-ol, 472. $^1$H NMR (400 MHz, METHA-
NOL-d$_4$) δ=8.00 (d, J=1.6 Hz, 1H), 7.45 (s, 1H), 7.60-7.55
(m, 4H), 7.20 (s, 1H), 7.12-7.03 (m, 2H), 6.82-6.75 (m, 2H),
5.29 (s, 2H), 4.31-4.30 (m, 1H), 3.80-3.76 (m, 3H), 3.47-
3.37 (m, 2H), 3.27-3.16 (m, 4H), 2.69-2.64 (m, 1H), 2.20-
2.07 (s, 4H), 1.33-1.29 (m, 1H). ESI [M+H]=484.1

All three compounds (470,471,472) above were synthe-
sized using General Procedure E, replacing 4-(7-bromo-9H-
benzo[e]pyrrolo[1,2-a][1,2,4]triazolo[3,4-c][1,4]diazepin-
12-yl) benzonitrile with 7-bromo-12-(4-fluorophenyl)-9H-
benzo[e]imidazo[2,1-c]pyrrolo[1,2-a][1,4]diazepine and
replacing N,N-dimethyl-1-(morpholin-2-yl)methanamine
with (trans)-4-(pyrrolidin-1-ylmethyl)pyrrolidin-3-ol.

320

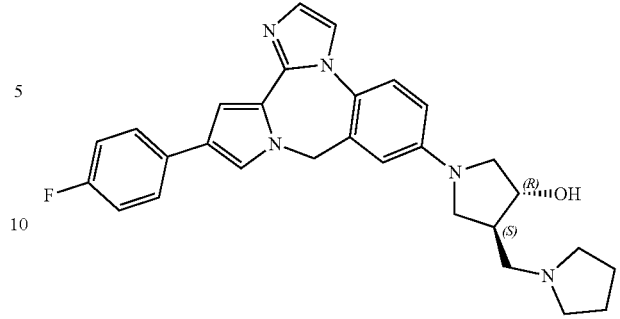

(3R,4S)-1-(12-(4-fluorophenyl)-9H-benzo[e]imidazo[2,
1-c]pyrrolo[1,2-a][1,4]diazepin-7-yl)-4-(pyrrolidin-1-ylm-
ethyl)pyrrolidin-3-ol, 470. $^1$H NMR (400 MHz, DMSO-d$_6$)
δ=7.64 (s, 1H), 7.54 (dd, J=5.5, 8.2 Hz, 2H), 7.39 (s, 1H),
7.31 (d, J=8.8 Hz, 1H), 7.17-7.07 (m, 3H), 6.81 (s, 1H), 6.71
(br. s., 1H), 6.56 (d, J=8.4 Hz, 1H), 5.14-4.98 (m, 3H), 4.07
(br. s., 1H), 3.53-3.41 (m, 2H), 3.15-3.01 (m, 2H), 2.45-2.24
(m, 6H), 1.67 (br. s., 4H). ESI [M+H]=484.2

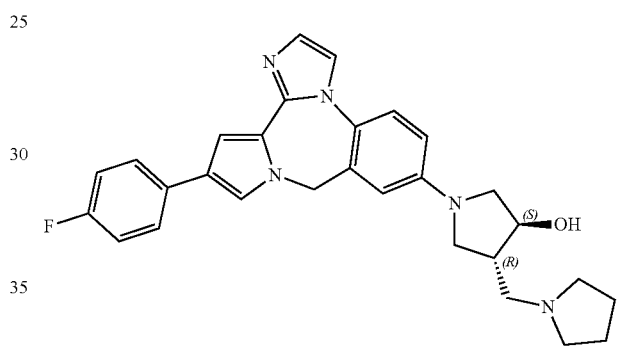

(3S,4R)-1-(12-(4-fluorophenyl)-9H-benzo[e]imidazo[2,
1-c]pyrrolo[1,2-a][1,4]diazepin-7-yl)-4-(pyrrolidin-1-ylm-
ethyl)pyrrolidin-3-ol, 471. $^1$H NMR (400 MHz, METHA-
NOL-d$_4$) δ=7.96 (s, 1H), 7.69 (s, 1H), 7.58-7.54 (m, 4H),
7.16 (s, 1H), 7.11-7.07 (m, 2H), 6.82-6.75 (m, 2H), 5.26 (s,
2H), 4.31-4.30 (m, 1H), 3.77-3.32 (m, 13H), 2.20-2.07 (s,
2H). ESI [M+H]=484.2

(3R,4S)-4-((cyclopropylamino)methyl)-1-(12-(4-fluoro-
phenyl)-9H-benzo[e]imidazo[2,1-c]pyrrolo[1,2-a][1,4]diaz-
epin-7-yl)pyrrolidin-3-ol, 473. Synthesized using General
Procedure V, replacing azetidin-1-yl((trans)-4-hydroxypyrrolidin-3-yl)methanone with (3S,4R)—N-cyclo propyl-4-hydroxypyrrolidine-3-carboxamide. ¹H NMR (400 MHz, METHANOL-$d_4$) δ=8.00 (s, 1H), 7.74 (s, 1H), 7.64-7.51 (m, 4H), 7.19 (s, 1H), 7.09 (t, J=8.6 Hz, 2H), 6.82 (br. s., 1H), 6.75 (d, J=8.8 Hz, 1H), 5.28 (s, 2H), 4.37-4.25 (m, 1H), 3.79-3.69 (m, 2H), 3.49-3.34 (m, 2H), 3.27-3.14 (m, 2H), 2.84 (br. s., 1H), 2.61 (dd, J=7.1, 14.1 Hz, 1H), 0.94 (br. s., 4H). ESI [M+H]=470.1

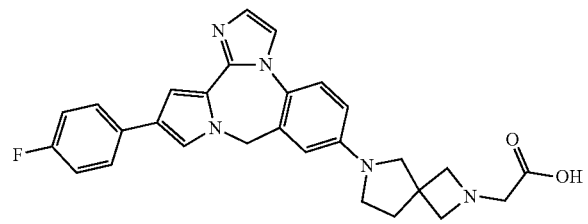 [SMILES: O=C(O)CN1CC2(CCN(c3ccc4c(c3)Cn3cc(-c5ccc(F)cc5)cc3-c3nccn3-4)C2)C1]

2-(6-(12-(4-fluorophenyl)-9H-benzo[e]imidazo[2,1-c]pyrrolo[1,2-a][1,4]diazepin-7-yl)-2,6-diazaspiro[3.4]octan-2-yl)acetic acid, 478. Synthesized using General Procedure J, replacing 2-bromoethanol with 2-bromoacetic acid. 1H NMR (400 MHz, METHANOL-d4) δ=7.57-7.49 (m, 3H), 7.37 (d, J=8.8 Hz, 1H), 7.27 (s, 1H), 7.18 (s, 1H), 7.03 (t, J=8.8 Hz, 2H), 6.90 (s, 1H), 6.75 (s, 1H), 6.68 (br d, J=8.6 Hz, 1H), 5.05 (s, 2H), 4.19 (s, 4H), 3.81 (s, 2H), 3.62 (s, 2H), 3.43 (br t, J=6.8 Hz, 2H), 2.38 (br t, J=7.1 Hz, 2H). ESI [M+H]=484.1

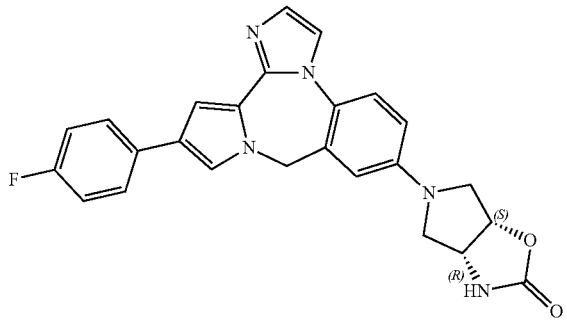

(3aR,6aS)-5-(12-(4-fluorophenyl)-9H-benzo[e]imidazo[2,1-c]pyrrolo[1,2-a][1,4]diazepin-7-yl)hexahydro-2H-pyrrolo[3,4-d]oxazol-2-one, 481. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (3aR,6aS)-hexahydro-2H-pyrrolo[3,4-d]oxazol-2-one. ¹H NMR (400 MHz, METHANOL-$d_4$) δ=8.11 (d, J=1.8 Hz, 1H), 8.04 (d, J=2.2 Hz, 1H), 7.91-7.84 (m, 1H), 7.84-7.76 (m, 2H), 7.63 (d, J=1.3 Hz, 1H), 7.56 (dd, J=5.3, 8.4 Hz, 2H), 7.24 (d, J=1.3 Hz, 1H), 7.08 (t, J=8.8 Hz, 2H), 5.51-5.45 (m, 1H), 5.44-5.37 (m, 3H), 3.88 (d, J=13.7 Hz, 1H), 3.73-3.65 (m, 1H), 3.64-3.53 (m, 2H). ESI [M+H]=442.0

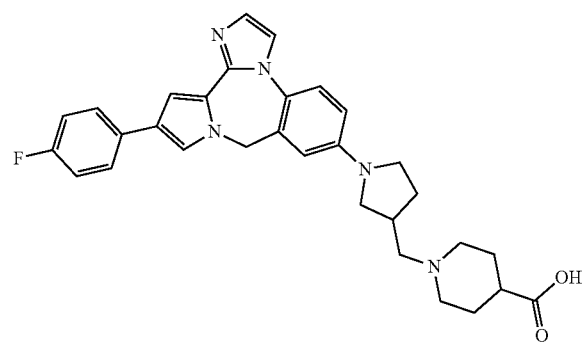 [SMILES: O=C(O)C1CCN(CC2CCN(c3ccc4c(c3)Cn3cc(-c5ccc(F)cc5)cc3-c3nccn3-4)C2)CC1]

1-((1-(12-(4-fluorophenyl)-9H-benzo[e]imidazo[2,1-c]pyrrolo[1,2-a][1,4]diazepin-7-yl)pyrrolidin-3-yl)methyl)piperidine-4-carboxylic acid, 480. Synthesized using General Procedure R, replacing methyl 2-methyl-2-((pyrrolidin-3-ylmethyl)amino)propanoate with methyl 1-(pyrrolidin-3-ylmethyl)piperidine-4-carboxylate. ¹H NMR (400 MHz, METHANOL-$d_4$) δ=8.01 (d, J=1.3 Hz, 1H), 7.74 (d, J=1.8 Hz, 1H), 7.63-7.50 (m, 4H), 7.20 (s, 1H), 7.09 (t, J=8.8 Hz, 2H), 6.81 (br. s., 1H), 6.76 (d, J=8.8 Hz, 1H), 5.27 (s, 2H), 3.79-3.67 (m, 2H), 3.54 (t, J=7.5 Hz, 2H), 3.49-3.38 (m, 1H), 3.18 (t, J=8.6 Hz, 2H), 3.07 (t, J=12.3 Hz, 2H), 2.89 (br. s., 1H), 2.73-2.60 (m, 1H), 2.42-2.21 (m, 3H), 2.13 (br. s., 1H), 2.05-1.83 (m, 3H). ESI [M+H]=526.2

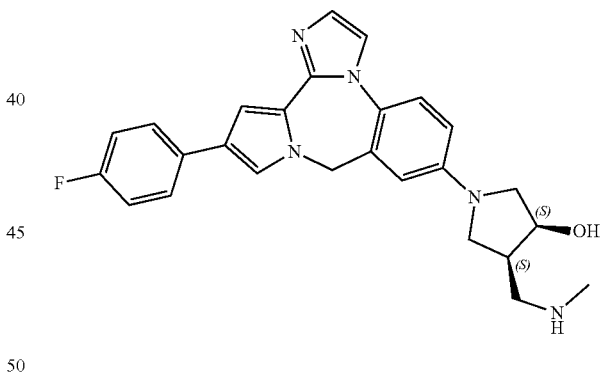

(3S,4S)-1-(12-(4-fluorophenyl)-9H-benzo[e]imidazo[2,1-c]pyrrolo[1,2-a][1,4]diazepin-7-yl)-4-((methylamino)methyl)pyrrolidin-3-ol, 482. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((trans)-4-hydroxypyrrolidin-3-yl)methyl)(methyl)carbamate with benzyl (((3R,4S)-4-hydroxypyrrolidin-3-yl)methyl)(methyl)carbamate. ¹H NMR (400 MHz, METHANOL-$d_4$) δ=7.98 (d, J=2.2 Hz, 1H), 7.72 (d, J=2.2 Hz, 1H), 7.62-7.48 (m, 4H), 7.18 (d, J=1.8 Hz, 1H), 7.07 (t, J=8.8 Hz, 2H), 6.78 (d, J=2.2 Hz, 1H), 6.71 (dd, J=2.4, 9.0 Hz, 1H), 5.25 (s, 2H), 4.56 (t, J=3.5 Hz, 1H), 3.69-3.56 (m, 2H), 3.46-3.36 (m, 2H), 3.32 (br. s., 1H), 3.22 (dd, J=6.2, 12.8 Hz, 1H), 2.81-2.65 (m, 4H). ESI [M+H]=444.1

323

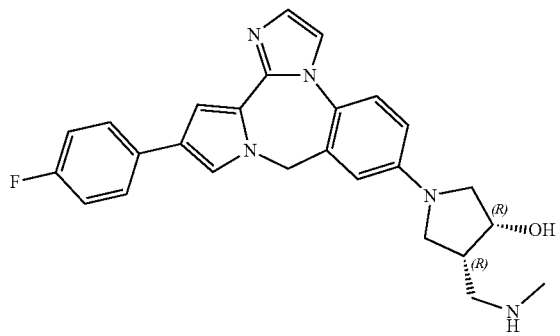

(3R,4R)-1-(12-(4-fluorophenyl)-9H-benzo[e]imidazo[2,1-c]pyrrolo[1,2-a][1,4]diazepin-7-yl)-4-((methylamino)methyl)pyrrolidin-3-ol, 483. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((trans)-4-hydroxypyrrolidin-3-yl)methyl)(methyl)carbamate with benzyl (((3S,4R)-4-hydroxypyrrolidin-3-yl)methyl)(methyl)carbamate. $^1$H NMR (400 MHz, METHANOL-d$_4$) δ=7.99 (d, J=2.0 Hz, 1H), 7.73 (d, J=2.0 Hz, 1H), 7.63-7.50 (m, 4H), 7.18 (d, J=1.8 Hz, 1H), 7.08 (t, J=8.7 Hz, 2H), 6.79 (d, J=2.4 Hz, 1H), 6.73 (dd, J=2.4, 8.8 Hz, 1H), 5.27 (s, 2H), 4.56 (t, J=3.4 Hz, 1H), 3.72-3.57 (m, 2H), 3.47-3.35 (m, 2H), 3.22 (dd, J=6.0, 12.8 Hz, 2H), 2.76 (s, 3H), 2.71 (d, J=5.3 Hz, 1H). ESI [M+H]=444.1

324

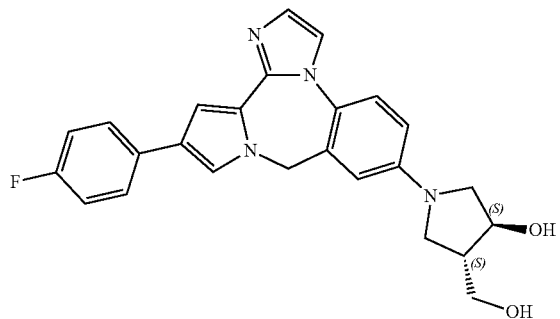

(3S,4S)-1-(12-(4-fluorophenyl)-9H-benzo[e]imidazo[2,1-c] pyrrolo[1,2-a][1,4]diazepin-7-yl)-4-(hydroxymethyl)pyrrolidin-3-ol, 485. Synthesized using General Procedure A, replacing 4-(7-bromo-9H-benzo[e]pyrrolo[1,2-a][1,2,4]triazolo[3,4-c][1,4]diazepin-12-yl)benzo-nitrile with 7-bromo-12-(4-fluorophenyl)-9H-benzo[e]imidazo[2,1-c]pyrrolo[1,2-a][1,4]diazepine and replacing tert-butyl piperazine-1-carboxylate with ((3S,4S)-4-((tert-butyldiphenylsilyl)oxy)pyrrolidin-3-yl)methanol. $^1$H NMR (400 MHz, METHANOL-d$_4$) δ=8.00 (d, J=1.8 Hz, 1H), 7.72 (s, 1H), 7.63-7.54 (m, 3H), 7.51 (d, J=8.8 Hz, 1H), 7.17 (s, 1H), 7.08 (t, J=8.6 Hz, 2H), 6.78 (s, 1H), 6.72 (d, J=8.8 Hz, 1H), 5.26 (s, 2H), 4.33 (br. s., 1H), 3.68-3.58 (m, 3H), 3.55-3.43 (m, 1H), 3.35 (br. s., 2H), 2.44 (br. s., 1H). ESI [M+H]=431.2

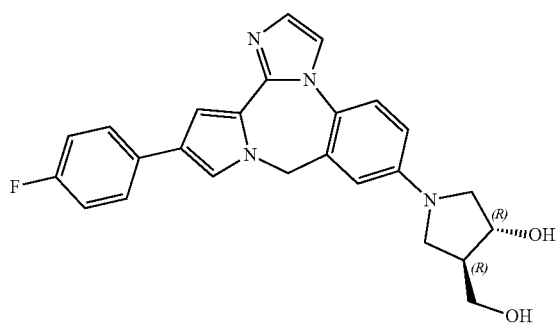

(3R,4R)-1-(12-(4-fluorophenyl)-9H-benzo[e]imidazo[2,1-c]pyrrolo[1,2-a][1,4]diazepin-7-yl)-4-(hydroxymethyl)pyrrolidin-3-ol, 484. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with (3R,4R)-4-(hydroxymethyl)pyrrolidin-3-ol. 1H NMR (400 MHz, METHANOL-d4) δ=7.98 (s, 1H), 7.71 (s, 1H), 7.61-7.53 (m, 3H), 7.50 (d, J=8.8 Hz, 1H), 7.16 (s, 1H), 7.07 (t, J=8.6 Hz, 2H), 6.78 (s, 1H), 6.72 (d, J=8.8 Hz, 1H), 5.25 (s, 2H), 4.33 (d, J=4.9 Hz, 1H), 3.68-3.58 (m, 3H), 3.55-3.44 (m, 1H), 3.27-3.23 (m, 2H), 2.44 (br. s., 1H). ESI[M+H]=431.2

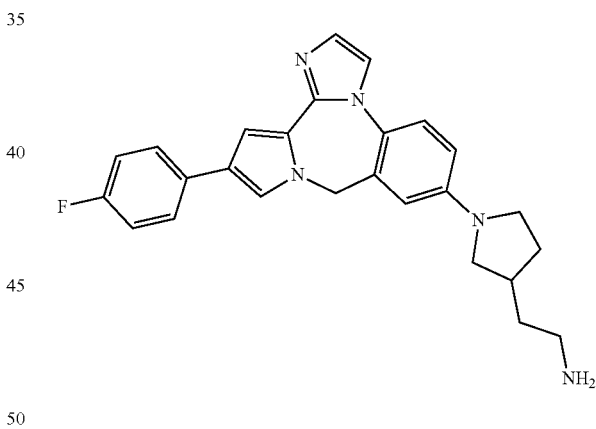

2-(1-(12-(4-fluorophenyl)-9H-benzo[e]imidazo[2,1-c]pyrrolo[1,2-a][1,4]diazepin-7-yl) pyrrolidin-3-yl)ethanamine, 486. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((trans)-4-hydroxypyrrolidin-3-yl)methyl)(methyl)carbamate with benzyl (2-(pyrrolidin-3-yl)ethyl)carbamate. $^1$H NMR (400 MHz, METHANOL-d$_4$) δ=7.99 (d, J=2.2 Hz, 1H), 7.73 (d, J=1.8 Hz, 1H), 7.62-7.47 (m, 4H), 7.18 (d, J=1.3 Hz, 1H), 7.08 (t, J=8.8 Hz, 2H), 6.78 (d, J=2.6 Hz, 1H), 6.72 (dd, J=2.6, 8.8 Hz, 1H), 5.26 (s, 2H), 3.64-3.56 (m, 1H), 3.54-3.45 (m, 1H), 3.43-3.33 (m, 1H), 3.08-2.96 (m, 3H), 2.50-2.35 (m, 1H), 2.34-2.21 (m, 1H), 1.95-1.66 (m, 3H). ESI [M+H]=428.1

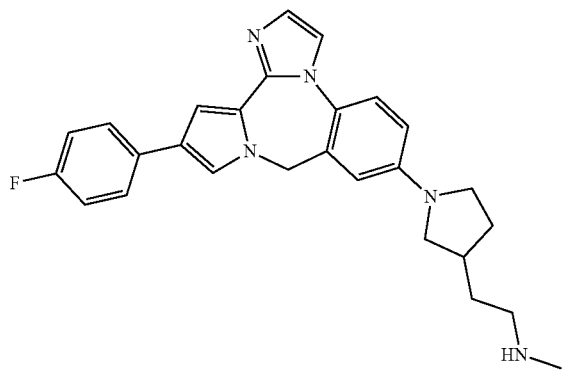 [SMILES: CNCCC1CCN(c2ccc3c(c2)Cn2cc(-c4ccc(F)cc4)cc2-c2nccn2-3)C1]

2-(1-(12-(4-fluorophenyl)-9H-benzo[e]imidazo[2,1-c]pyrrolo[1,2-a][1,4]diazepin-7-yl)pyrrolidin-3-yl)-N-methylethanamine, 487. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing benzyl (((trans)-4-hydroxypyrrolidin-3-yl)methyl)(methyl)carbamate with benzyl methyl(2-(pyrrolidin-3-yl)ethyl)carbamate. $^1$H NMR (400 MHz, METHANOL-$d_4$) δ=7.99 (d, J=2.2 Hz, 1H), 7.73 (d, J=2.2 Hz, 1H), 7.61-7.49 (m, 4H), 7.18 (d, J=1.8 Hz, 1H), 7.08 (t, J=8.8 Hz, 2H), 6.78 (d, J=2.6 Hz, 1H), 6.72 (dd, J=2.6, 8.8 Hz, 1H), 5.26 (s, 2H), 3.64-3.56 (m, 1H), 3.53-3.46 (m, 1H), 3.43-3.36 (m, 1H), 3.14-3.00 (m, 3H), 2.72 (s, 3H), 2.46-2.34 (m, 1H), 2.28 (d, J=12.3 Hz, 1H), 1.92-1.72 (m, 3H). ESI [M+H]=442.2

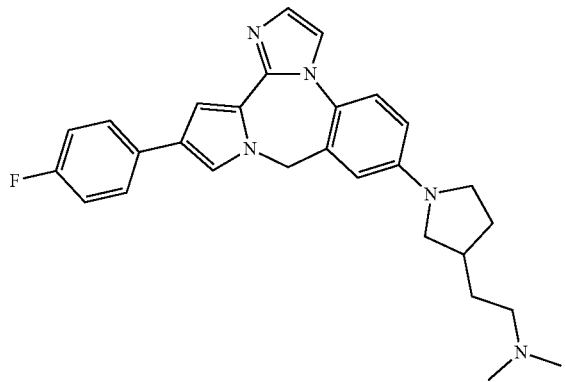 [SMILES: CN(C)CCC1CCN(c2ccc3c(c2)Cn2cc(-c4ccc(F)cc4)cc2-c2nccn2-3)C1]

2-(1-(12-(4-fluorophenyl)-9H-benzo[e]imidazo[2,1-c]pyrrolo[1,2-a][1,4]diazepin-7-yl) pyrrolidin-3-yl)-N,N-dimethylethanamine, 488. Synthesized using General Procedure U, replacing 1-((cis)-4-fluoro-1-(12-(4-fluorophenyl)-9H-benzo[e]imidazo[2,1-c]pyrrolo[1,2-a][1,4]diazepin-7-yl)pyrrolidin-3-yl)-N-methylmethanamine with 2-(1-(12-(4-fluorophenyl)-9H-benzo[e]imidazo[2,1-c]pyrrolo[1,2-a][1,4]diazepin-7-yl)pyrrolidin-3-yl)ethanamine. $^1$H NMR (400 MHz, METHANOL-$d_4$) δ=7.98 (d, J=2.2 Hz, 1H), 7.72 (d, J=2.2 Hz, 1H), 7.62-7.46 (m, 4H), 7.19 (d, J=1.8 Hz, 1H), 7.08 (t, J=8.8 Hz, 2H), 6.78 (d, J=2.6 Hz, 1H), 6.72 (dd, J=2.4, 9.0 Hz, 1H), 5.25 (s, 2H), 3.59 (t, J=8.4 Hz, 1H), 3.54-3.44 (m, 1H), 3.43-3.34 (m, 1H), 3.26-3.15 (m, 2H), 3.10-3.01 (m, 1H), 2.90 (s, 6H), 2.45-2.20 (m, 2H), 1.99-1.71 (m, 3H). ESI [M+H]=456.2

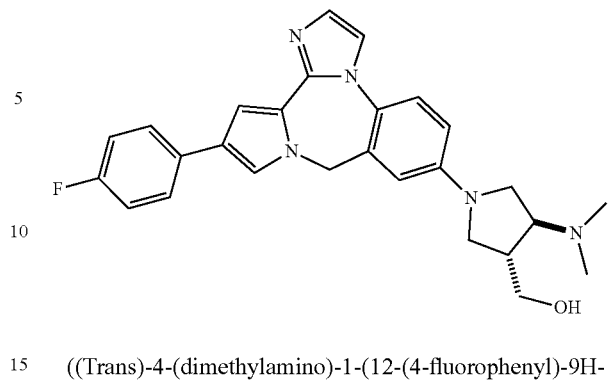

((Trans)-4-(dimethylamino)-1-(12-(4-fluorophenyl)-9H-benzo[e]imidazo[2,1-c]pyrrolo[1,2-a][1,4]diazepin-7-yl)pyrrolidin-3-yl)methanol, 490. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine and replacing tert-butyl piperazine-1-carboxylate with ((trans)-4-(dimethyl amino)pyrrolidin-3-yl)methanol. $^1$H NMR (400 MHz, METHANOL-$d_4$) δ=8.04 (s, 1H), 7.77 (s, 1H), 7.62-7.55 (m, 4H), 7.21 (s, 1H), 7.10 (t, J=8.8 Hz, 2H), 6.97 (s, 1H), 6.91 (d, J=9.0 Hz, 1H), 5.32 (s, 2H), 4.08 (d, J=3.3 Hz, 1H), 3.91-3.81 (m, 2H), 3.80-3.71 (m, 2H), 3.66-3.57 (m, 1H), 3.22 (dd, J=4.8, 10.1 Hz, 1H), 2.95 (s, 7H). ESI [M+H]=458.1

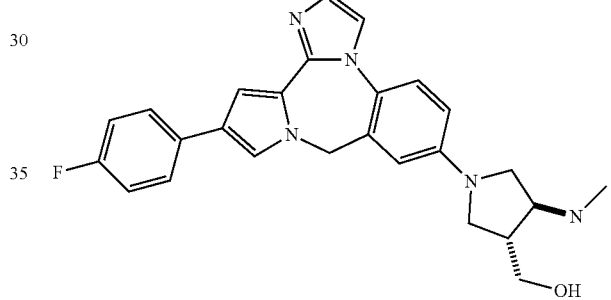

((Trans)-1-(12-(4-fluorophenyl)-9H-benzo[e]imidazo[2,1-c]pyrrolo[1,2-a][1,4]diazepin-7-yl)-4-(methylamino)pyrrolidin-3-yl)methanol, 491. Synthesized using General Procedure V, replacing azetidin-1-yl((trans)-4-hydroxypyrrolidin-3-yl)methanone with N-((trans)-4-(hydroxymethyl)pyrrolidin-3-yl)formamide. 1H NMR (400 MHz, METHANOL-d4) δ=8.03 (br. s., 1H), 7.76 (br. s., 1H), 7.60 (d, J=10.4 Hz, 4H), 7.21 (br. s., 1H), 7.10 (t, J=8.0 Hz, 2H), 6.98-6.79 (m, 2H), 5.31 (br. s., 2H), 3.89 (br. s., 1H), 3.83-3.74 (m, 3H), 3.70-3.60 (m, 2H), 3.25 (br. s., 1H), 2.99-2.90 (m, 1H), 2.86-2.70 (m, 3H). ESI [M+H]=444.1

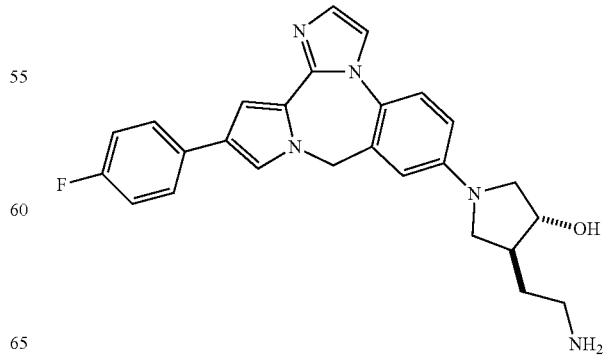

Trans-4-(2-aminoethyl)-1-(12-(4-fluorophenyl)-9H-benzo[e]imidazo[2,1-c]pyrrolo[1,2-a][1,4]diazepin-7-yl)pyrrolidin-3-ol, 492. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e] imidazo[2,1-c]pyrrolo[1,2-a][1,4]diazepine, replacing benzyl ((trans-4-hydroxypyrrolidin-3-yl)methyl)(methyl)carbamate with benzyl (2-((trans)-4-hydroxypyrrolidin-3-yl)ethyl)carbamate. 1H NMR (400 MHz, METHANOL-d4) δ=8.00 (d, J=1.6 Hz, 1H), 7.74 (d, J=1.6 Hz, 1H), 7.63-7.51 (m, 4H), 7.20 (s, 1H), 7.09 (t, J=8.7 Hz, 2H), 6.80 (d, J=2.2 Hz, 1H), 6.74 (dd, J=2.2, 8.8 Hz, 1H), 5.28 (s, 2H), 4.19 (q, J=6.2 Hz, 1H), 3.76-3.65 (m, 2H), 3.25 (dd, J=5.7, 9.8 Hz, 1H), 3.18-3.06 (m, 3H), 2.29 (qd, J=7.1, 14.2 Hz, 1H), 1.97-1.86 (m, 1H), 1.85-1.75 (m, 1H). ESI [M+H]=444.1

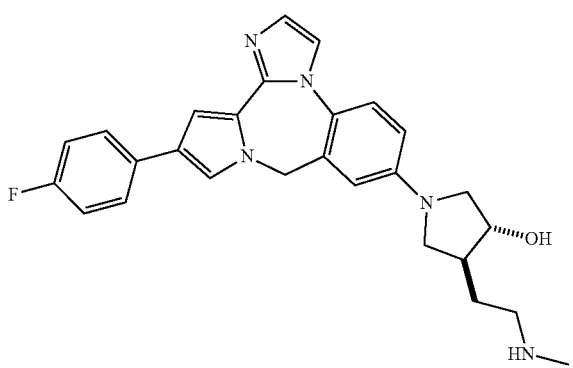 [SMILES: CNCC[C@H]1CN(c2ccc3c(c2)Cn2cc(-c4ccc(F)cc4)cc2-c2nccn2-3)C[C@@H]1O]

Trans-1-(12-(4-fluorophenyl)-9H-benzo[e]imidazo[2,1-c]pyrrolo[1,2-a][1,4]diazepin-7-yl)-4-(2-(methylamino)ethyl)pyrrolidin-3-ol, 493. Synthesized using General Procedure G, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing benzyl ((trans-4-hydroxypyrrolidin-3-yl)methyl)(methyl)carbamate with benzyl (2-(trans-4-hydroxypyrrolidin-3-yl)ethyl)(methyl)carbamate. 1HNMR (400 MHz, METHANOL-d4) δ=8.00 (d, J=1.8 Hz, 1H), 7.74 (d, J=1.8 Hz, 1H), 7.64-7.50 (m, 4H), 7.20 (s, 1H), 7.09 (t, J=8.6 Hz, 2H), 6.80 (d, J=2.0 Hz, 1H), 6.73 (dd, J=2.1, 8.9 Hz, 1H), 5.27 (s, 2H), 4.20 (q, J=6.0 Hz, 1H), 3.76-3.63 (m, 2H), 3.27-3.10 (m, 4H), 2.74 (s, 3H), 2.28 (qd, J=7.0, 14.1 Hz, 1H), 2.01-1.88 (m, 1H), 1.87-1.74 (m, 1H). ESI [M+H]=458.2

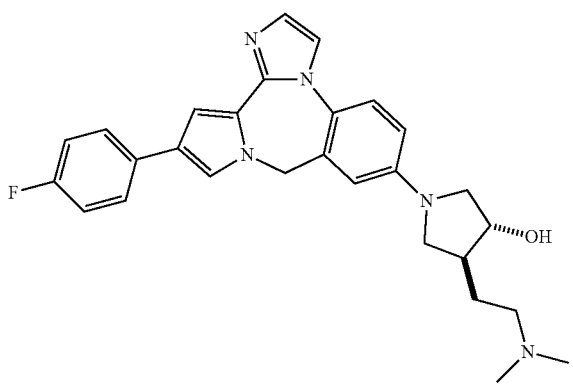 [SMILES: CN(C)CC[C@H]1CN(c2ccc3c(c2)Cn2cc(-c4ccc(F)cc4)cc2-c2nccn2-3)C[C@@H]1O]

Trans-4-(2-(dimethylamino)ethyl)-1-(12-(4-fluorophenyl)-9H-benzo[e]imidazo[2,1-c] pyrrolo[1,2-a][1,4]diazepin-7-yl)pyrrolidin-3-ol, 494. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]imidazo[2,1-c]pyrrolo[1,2-a][1,4]diazepine, replacing tert-butyl piperazine-1-carboxylate with trans-4-(2-(dimethylamino)ethyl) pyrrolidin-3-ol. 1H NMR (400 MHz, METHANOL-d4) δ=8.01 (br. s., 1H), 7.75 (br. s., 1H), 7.64-7.51 (m, 4H), 7.21 (br. s., 1H), 7.10 (t, J=7.9 Hz, 2H), 6.81 (br. s., 1H), 6.75 (d, J=8.8 Hz, 1H), 5.29 (br. s., 2H), 4.23 (d, J=5.3 Hz, 1H), 3.77-3.65 (m, 2H), 3.26 (d, J=8.8 Hz, 2H), 3.16 (t, J=8.2 Hz, 1H), 2.93 (br. s., 7H), 2.26 (d, J=7.1 Hz, 1H), 2.00 (br. s., 1H), 1.87 (br. s., 1H). ESI [M+H]=472.2

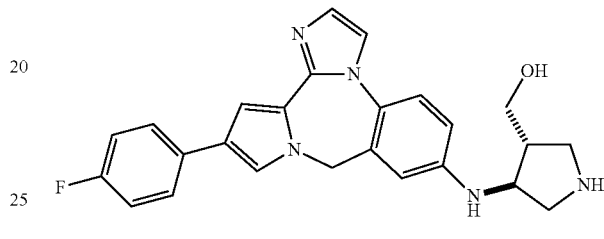

(Trans-4-((12-(4-fluorophenyl)-9H-benzo[e]imidazo[2,1-c]pyrrolo[1,2-a][1,4]diazepin-7-yl)amino)pyrrolidin-3-yl)methanol, 495. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo [e]imidazo[2,1-c]pyrrolo[1,2-a][1,4]diazepine, replacing tert-butyl piperazine-1-carboxylate with (trans-4-aminopyrrolidin-3-yl)methanol. 1H NMR (400 MHz, METHANOL-d4) δ=7.99 (d, J=7.0 Hz, 1H), 7.74 (d, J=7.0 Hz, 1H), 7.65-7.45 (m, 4H), 7.20 (d, J=6.7 Hz, 1H), 7.08 (d, J=7.8 Hz, 2H), 6.96-6.80 (m, 2H), 5.25 (d, J=6.7 Hz, 2H), 4.21 (br. s., 1H), 3.72 (br. s., 3H), 3.60 (d, J=8.6 Hz, 1H), 3.20 (br. s., 2H), 2.52 (br. s., 1H). ESI [M+H]=430.1

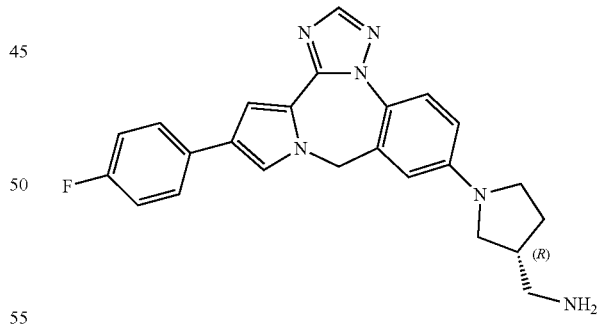

(R)-(1-(12-(4-fluorophenyl)-9H-benzo[e]pyrrolo[1,2-a][1,2,4]triazolo[5,1-c][1,4]diazepin-7-yl)pyrrolidin-3-yl)methanamine, 496. Synthesized using General Procedure A, replacing 4-(7-bromo-9H-benzo[e]pyrrolo[1,2-a][1,2,4]triazolo[3,4-c] [1,4]diazepin-12-yl)benzonitrile with 7-bromo-12-(4-fluorophenyl)-9H-benzo[e]pyrrolo[1,2-a][1,2,4]triazolo[5,1-c][1,4]diazepine, replacing tert-butyl piperazine-1-carboxylate with (S)-tert-butyl (pyrrolidin-3-ylmethyl)carbamate. 1H NMR (400 MHz, METHANOL-d4) δ=8.13 (s, 1H), 7.67-7.65 (m, 1H), 7.57-7.54 (m, 2H), 7.41-7.40 (m, 1H), 7.08-7.04 (m, 3H), 6.72-6.70 (m, 2H), 5.15 (s, 2H), 3.57-3.37 (m, 3H), 3.13-3.09 (m, 1H), 2.84-2.82 (m, 2H), 2.53-2.49 (m, 1H), 2.26-2.24 (m, 1H), 1.84-1.81 (m, 1H). ESI [M+H]=415.1

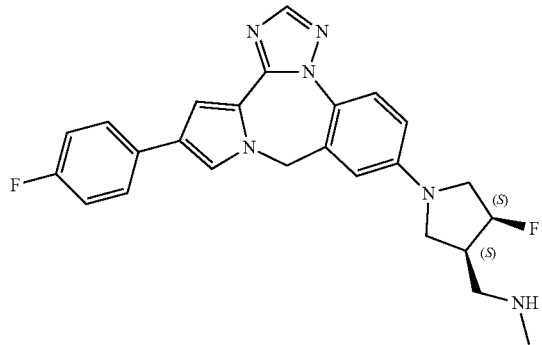

1-((3S,4S)-4-fluoro-1-(12-(4-fluorophenyl)-9H-benzo[e]pyrrolo[1,2-a][1,2,4]triazolo[5,1-c] [1,4]diazepin-7-yl)pyrrolidin-3-yl)-N-methylmethanamine, 497. Synthesized using General Procedure T, replacing 7-bromo-12-(4-fluorophenyl)-9H-benzo[e]imidazo[2,1-c]pyrrolo[1,2-a][1,4]diazepine with 7-bromo-12-(4-fluorophenyl)-9H-benzo[e]pyrrolo[1,2-a][1,2,4]triazolo[5,1-c][1,4]diazepine. 1H NMR (400 MHz, METHANOL-d4) δ=8.16 (s, 1H), 7.71 (d, J=9.0 Hz, 1H), 7.54 (dd, J=5.5, 8.2 Hz, 2H), 7.40 (s, 1H), 7.12-7.02 (m, 3H), 6.78-6.71 (m, 2H), 5.52-5.34 (m, 1H), 5.15 (s, 2H), 3.88-3.79 (m, 1H), 3.79-3.71 (m, 2H), 3.70-3.63 (m, 1H), 3.45 (dd, J=7.2, 12.7 Hz, 1H), 3.26 (br. s., 1H), 2.82 (s, 4H). ESI [M+H]=447.1

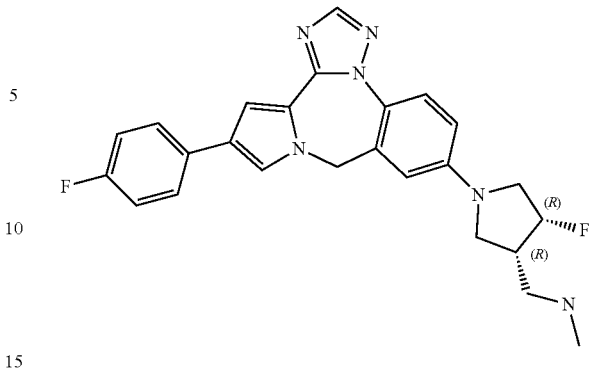

1-((3R,4R)-4-fluoro-1-(12-(4-fluorophenyl)-9H-benzo[e]pyrrolo[1,2-a][1,2,4]triazolo[5,1-c] [1,4]diazepin-7-yl)pyrrolidin-3-yl)-N-methylmethanamine, 499. Synthesized using General Procedure T, replacing 7-bromo-12-(4-fluorophenyl)-9H-benzo[e]imidazo[2,1-c]pyrrolo[1,2-a][1,4]diazepine with 7-bromo-12-(4-fluorophenyl)-9H-benzo[e]pyrrolo[1,2-a][1,2,4]triazolo[5,1-c][1,4]diazepine. 1H NMR (400 MHz, METHANOL-d4) δ=8.13 (s, 1H), 7.69 (d, J=8.8 Hz, 1H), 7.58-7.47 (m, 2H), 7.39 (s, 1H), 7.12-6.98 (m, 3H), 6.79-6.66 (m, 2H), 5.52-5.31 (m, 1H), 5.14 (s, 2H), 3.86-3.78 (m, 1H), 3.78-3.69 (m, 2H), 3.69-3.62 (m, 1H), 3.44 (dd, J=7.1, 12.8 Hz, 1H), 3.25 (br. s., 1H), 2.93-2.77 (m, 4H). ESI [M+H]=447.2

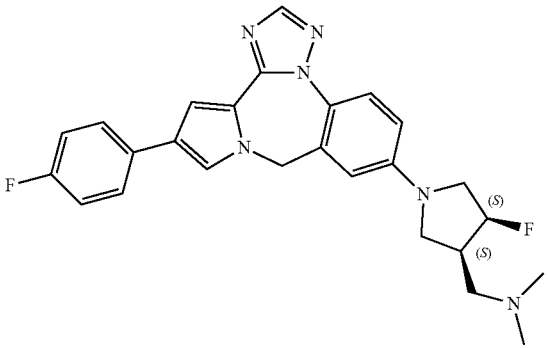

1-((3S,4S)-4-fluoro-1-(12-(4-fluorophenyl)-9H-benzo[e]pyrrolo[1,2-a][1,2,4]triazolo[5,1-c][1,4]diazepin-7-yl)pyrrolidin-3-yl)-N,N-dimethylmethanamine, 498. Synthesized using General Procedure U, replacing 1-(cis-4-fluoro-1-(12-(4-fluorophenyl)-9H-benzo[e]imidazo[2,1-c]pyrrolo[1,2-a][1,4]diazepin-7-yl)pyrrolidin-3-yl)-N-methylmethanamine with 1-((3S,4S)-4-fluoro-1-(12-(4-fluorophenyl)-9H-benzo[e]pyrrolo[1,2-a][1,2,4]triazolo[5,1-c][1,4]diazepin-7-yl)pyrrolidin-3-yl)-N-methylmethanamine. 1H NMR (400 MHz, METHANOL-d4) δ=8.14 (s, 1H), 7.70 (d, J=8.8 Hz, 1H), 7.54 (dd, J=5.3, 8.8 Hz, 2H), 7.39 (d, J=1.3 Hz, 1H), 7.11-7.00 (m, 3H), 6.79-6.71 (m, 2H), 5.53-5.34 (m, 1H), 5.16 (s, 2H), 3.88-3.67 (m, 3H), 3.66-3.58 (m, 1H), 3.46-3.38 (m, 1H), 3.35 (br. s., 1H), 3.09-2.93 (m, 7H). ESI [M+H]=461.1

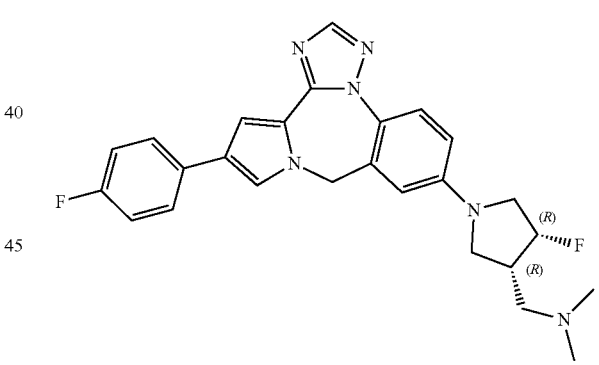

1-((3R,4R)-4-fluoro-1-(12-(4-fluorophenyl)-9H-benzo[e]pyrrolo[1,2-a][1,2,4]triazolo[5,1-c] [1,4]diazepin-7-yl)pyrrolidin-3-yl)-N,N-dimethylmethanamine, 500. Synthesized using General Procedure U, replacing 1-(cis-4-fluoro-1-(12-(4-fluorophenyl)-9H-benzo[e]imidazo[2, 1-c]pyrrolo[1,2-a][1,4]diazepin-7-yl)pyrrolidin-3-yl)-N-methylmethanamine with 1-((3R,4R)-4-fluoro-1-(12-(4-fluorophenyl)-9H-benzo[e]pyrrolo[1,2-a][1,2,4]triazolo[5,1-c][1,4]diazepin-7-yl)pyrrolidin-3-yl)-N-methylmethanamine. 1H NMR (400 MHz, METHANOL-d4) δ=8.11 (s, 1H), 7.65 (d, J=8.6 Hz, 1H), 7.53 (dd, J=5.3, 8.6 Hz, 2H), 7.39 (d, J=1.8 Hz, 1H), 7.09-6.99 (m, 3H), 6.73-6.64 (m, 2H), 5.38-5.20 (m, 1H), 5.12 (s, 2H), 3.77-3.69 (m, 1H), 3.67-3.58 (m, 2H), 3.15 (br t, J=9.6 Hz, 1H), 2.77-2.61 (m, 2H), 2.60-2.53 (m, 1H), 2.33 (s, 6H). ESI [M+H]=461.2

331

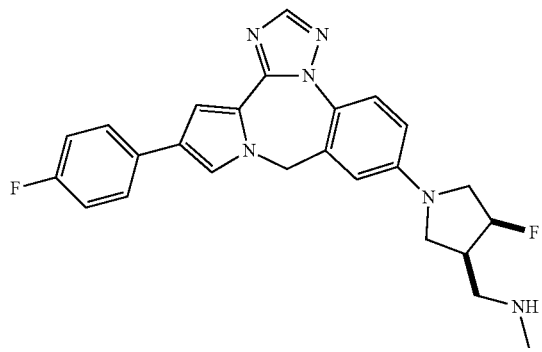 [SMILES: CNC[C@H]1CN(c2ccc3c(c2)Cn2cc(-c4ccc(F)cc4)cc2-c2ncnn2-3)C[C@H]1F]

1-(cis-4-fluoro-1-(12-(4-fluorophenyl)-9H-benzo[e] pyrrolo[1,2-a][1,2,4]triazolo[5,1-c][1,4] diazepin-7-yl)pyrrolidin-3-yl)-N-methylmethanamine, 501. Synthesized using General Procedure T, replacing 7-bromo-12-(4-fluorophenyl)-9H-benzo[e]imidazo[2,1-c]pyrrolo[1,2-a][1,4]diazepine with 7-bromo-12-(4-fluorophenyl)-9H-benzo[e]pyrrolo[1,2-a][1,2,4]triazolo[5,1-c][1,4]diazepine. 1H NMR (400 MHz, METHANOL-d4) δ=8.16 (s, 1H), 7.71 (d, J=8.8 Hz, 1H), 7.59-7.50 (m, 2H), 7.41 (s, 1H), 7.12-7.00 (m, 3H), 6.79-6.72 (m, 2H), 5.50-5.36 (m, 1H), 5.17 (s, 2H), 3.88-3.80 (m, 1H), 3.79-3.71 (m, 2H), 3.71-3.65 (m, 1H), 3.45 (dd, J=7.1, 12.8 Hz, 1H), 3.35-3.32 (m, 1H), 2.94-2.76 (m, 4H). ESI [M+H]=447.2

332

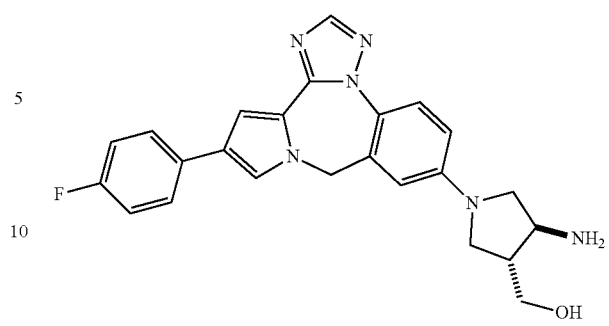

(Trans-4-amino-1-(12-(4-fluorophenyl)-9H-benzo[e]pyrrolo[1,2-a][1,2,4]triazolo[5,1-c][1,4] diazepin-7-yl)pyrrolidin-3-yl)methanol, 503. Synthesized using General Procedure A, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9H-benzo[e]pyrrolo[1,2-a][1,2,4]triazolo[5,1-c][1,4] diazepine, replacing tert-butyl piperazine-1-carboxylate with tert-butyl ((trans)-4-(hydroxymethyl)pyrrolidin-3-yl)carbamate. 1H NMR (400 MHz, METHANOL-d4) δ=8.15 (s, 1H), 7.70 (d, J=8.8 Hz, 1H), 7.53 (dd, J=5.3, 8.4 Hz, 2H), 7.40 (s, 1H), 7.10-7.00 (m, 3H), 6.82-6.75 (m, 2H), 5.16 (s, 2H), 3.92 (d, J=4.9 Hz, 1H), 3.81-3.71 (m, 3H), 3.67-3.60 (m, 1H), 3.48 (dd, J=4.2, 10.8 Hz, 1H), 3.23 (dd, J=5.7, 10.1 Hz, 1H), 2.63 (d, J=5.7 Hz, 1H). ESI [M+H]=431.1

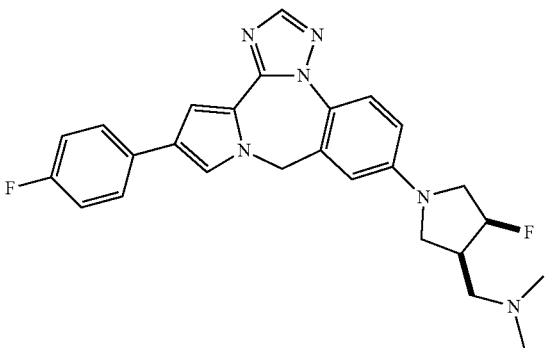 [SMILES: CN(C)C[C@H]1CN(c2ccc3c(c2)Cn2cc(-c4ccc(F)cc4)cc2-c2ncnn2-3)C[C@H]1F]

1-(cis-4-fluoro-1-(12-(4-fluorophenyl)-9H-benzo[e]pyrrolo[1,2-a][1,2,4]triazolo[5,1-c][1,4] diazepin-7-yl)pyrrolidin-3-yl)-N,N-dimethylmethanamine, 502. Synthesized using General Procedure U, replacing 1-(cis-4-fluoro-1-(12-(4-fluorophenyl)-9H-benzo[e]imidazo[2,1-c]pyrrolo[1,2-a][1,4]diazepin-7-yl)pyrrolidin-3-yl)-N-methylmethanamine with 1-(cis-4-fluoro-1-(12-(4-fluorophenyl)-9H-benzo[e]pyrrolo[1,2-a][1,2,4]triazolo[5, 1-c][1,4]diazepin-7-yl)pyrrolidin-3-yl)-N-methylmethanamine. 1H NMR (400 MHz, METHANOL-d4) δ=8.16 (s, 1H), 7.70 (d, J=8.8 Hz, 1H), 7.54 (dd, J=5.3, 8.4 Hz, 2H), 7.40 (s, 1H), 7.11-6.99 (m, 3H), 6.78-6.71 (m, 2H), 5.50-5.37 (m, 1H), 5.16 (s, 2H), 3.85-3.78 (m, 1H), 3.76 (d, J=7.5 Hz, 1H), 3.70 (d, J=15.0 Hz, 1H), 3.66-3.57 (m, 1H), 3.42 (dd, J=6.6, 13.2 Hz, 1H), 3.30 (br s, 1H), 3.06-2.94 (m, 7H). ESI [M+H]=461.2

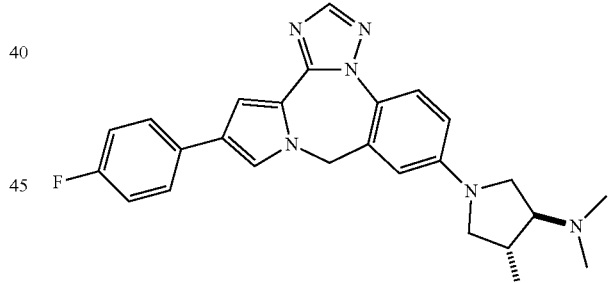

(Trans-4-(dimethylamino)-1-(12-(4-fluorophenyl)-9H-benzo[e]pyrrolo[1,2-a][1,2,4]triazolo[5,1-c][1,4]diazepin-7-yl)pyrrolidin-3-yl)methanol, 504. Synthesized using General Procedure U, replacing 1-(cis-4-fluoro-1-(12-(4-fluorophenyl)-9H-benzo[e]imidazo[2,1-c]pyrrolo[1,2-a][1,4]diazepin-7-yl)pyrrolidin-3-yl)-N-methylmethanamine with (trans-4-amino-1-(12-(4-fluoro phenyl)-9H-benzo[e]pyrrolo[1,2-a][1,2,4]triazolo[5,1-c][1,4]diazepin-7-yl)pyrrolidin-3-yl) methanol. 1H NMR (400 MHz, METHANOL-d4) δ=8.20 (s, 1H), 7.73 (d, J=8.8 Hz, 1H), 7.54 (dd, J=5.3, 8.3 Hz, 2H), 7.41 (s, 1H), 7.13-7.00 (m, 3H), 6.93-6.79 (m, 2H), 5.17 (s, 2H), 4.10-4.00 (m, 1H), 3.87-3.65 (m, 4H), 3.60 (dd, J=7.7, 10.7 Hz, 1H), 3.16 (dd, J=5.0, 9.9 Hz, 1H), 2.94 (s, 7H). ESI [M+H]=459.2

333

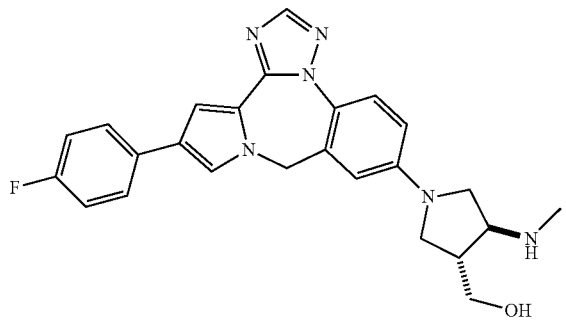 [SMILES: CN[C@@H]1CN(c2ccc3c(c2)Cn2cc(-c4ccc(F)cc4)cc2-c2ncnn2-3)C[C@H]1CO]

(Trans-1-(12-(4-fluorophenyl)-9H-benzo[e]pyrrolo[1,2-a][1,2,4]triazolo[5,1-c][1,4]diazepin-7-yl)-4-(methylamino)pyrrolidin-3-yl)methanol, 505. Synthesized using General Procedure V, replacing 7-bromo-12-(4-fluorophenyl)-9H-benzo[e]imidazo[2,1-c]pyrrolo[1,2-a][1,4]diazepine with 7-bromo-12-(4-fluorophenyl)-9H-benzo[e]pyrrolo[1,2-a][1,2,4]triazolo[5,1-c][1,4]diazepine, replacing azetidin-1-yl(trans-4-hydroxypyrrolidin-3-yl)methanone with N-(trans-4-(hydroxyl methyl)pyrrolidin-3-yl)formamide. 1H NMR (400 MHz, METHANOL-d4) δ=8.11 (s, 1H), 7.66 (d, J=8.6 Hz, 1H), 7.54 (dd, J=5.4, 8.7 Hz, 2H), 7.40 (d, J=1.5 Hz, 1H), 7.07-7.01 (m, 3H), 6.75-6.70 (m, 2H), 5.14 (s, 2H), 3.70-3.56 (m, 4H), 3.21 (dd, J=5.8, 9.8 Hz, 3H), 2.53-2.41 (m, 4H). ESI [M+H]=445.1

334

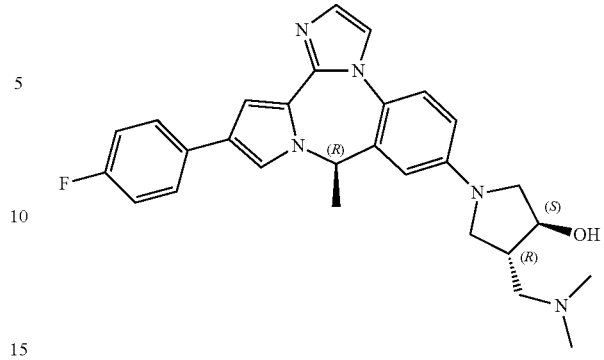

(3S,4R)-4-((dimethylamino)methyl)-1-((R)-12-(4-fluorophenyl)-9-methyl-9H-benzo[e] imidazo[2,1-c]pyrrolo[1,2-a][1,4]diazepin-7-yl)pyrrolidin-3-ol, 508. Synthesized using General Procedure E, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9-methyl-9H-benzo[e] imidazo[2,1-c]pyrrolo[1,2-a][1,4]diazepine, replacing N,N-dimethyl-1-(morpholin-2-yl)methan amine with (3S,4S)-4-((dimethylamino)methyl)pyrrolidin-3-ol. 1H NMR (400 MHz, DMSO-d6) δ=7.62 (s, 1H), 7.58-7.44 (m, 2H), 7.40 (br. s., 1H), 7.36-7.23 (m, 2H), 7.16-7.05 (m, 2H), 6.83 (d, J=1.8 Hz, 1H), 6.63 (br. s., 1H), 6.53 (d, J=8.8 Hz, 1H), 5.53 (q, J=6.9 Hz, 1H), 4.06 (br. S., 1H), 3.47 (d, J=5.7 Hz, 2H), 3.06 (d, J=8.8 Hz, 2H), 2.38-2.08 (m, 9H), 1.28-1.17 (m, 3H). ESI [M+H]=472.2

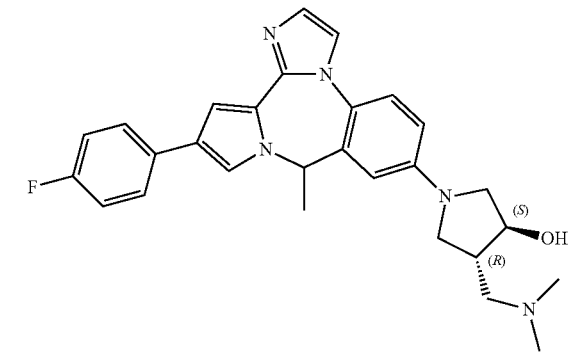

(3S,4R)-4-((dimethylamino)methyl)-1-(12-(4-fluorophenyl)-9-methyl-9H-benzo[e]imidazo[2,1-c]pyrrolo[1,2-a][1,4]diazepin-7-yl)pyrrolidin-3-ol, 507. Synthesized using General Procedure A, replacing 4-(7-bromo-9H-benzo[e]pyrrolo[1,2-a][1,2,4]triazolo[3,4-c][1,4] diazepin-12-yl)benzonitrile with 7-bromo-12-(4-fluorophenyl)-9-methyl-9H-benzo[e] imidazo[2,1-c]pyrrolo[1,2-a][1,4]diazepine, replacing tert-butyl piperazine-1-carboxylate with (3S,4S)-4-((dimethylamino)methyl)pyrrolidin-3-ol. 1H NMR (400 MHz, METHANOL-d4) δ=8.07-7.99 (m, 1H), 7.77 (s, 1H), 7.68-7.62 (m, 1H), 7.61-7.52 (m, 3H), 7.25 (s, 1H), 7.09 (t, J=8.6 Hz, 2H), 6.78-6.69 (m, 2H), 5.69 (d, J=7.1 Hz, 1H), 4.32-4.21 (m, 1H), 3.83-3.68 (m, 2H), 3.43-3.33 (m, 2H), 3.27-3.18 (m, 2H), 2.99 (br. s., 6H), 2.77-2.64 (m, 1H), 1.45 (d, J=7.1 Hz, 3H). ESI [M+H]=472.2

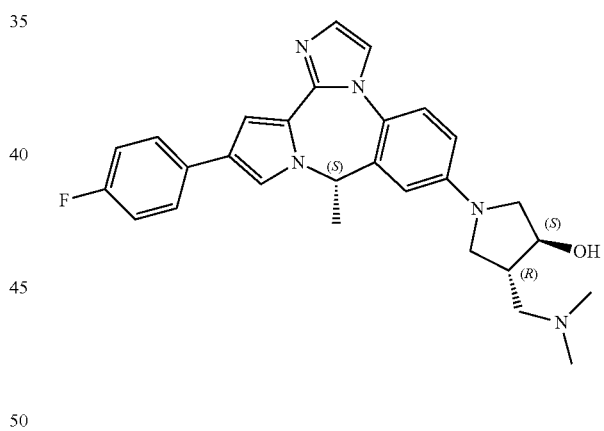

(3S,4R)-4-((dimethylamino)methyl)-1-((S)-12-(4-fluorophenyl)-9-methyl-9H-benzo[e] imidazo[2,1-c]pyrrolo[1,2-a][1,4]diazepin-7-yl)pyrrolidin-3-ol, 509. Synthesized using General Procedure E, replacing 4-(7-bromo-9H-benzo[e]pyrrolo[1,2-a][1,2,4]triazolo[3,4-c][1,4]diazepin-12-yl)benzonitrile with 7-bromo-12-(4-fluorophenyl)-9-methyl-9H-benzo[e] imidazo[2,1-c]pyrrolo[1,2-a][1,4]diazepine, replacing N,N-dimethyl-1-(morpholin-2-yl)methan amine with (3S,4S)-4-((dimethylamino)methyl)pyrrolidin-3-ol. 1H NMR (400 MHz, METHANOL-d4) δ=8.07-7.98 (m, 1H), 7.76 (d, J=1.8 Hz, 1H), 7.68-7.62 (m, 1H), 7.61-7.49 (m, 3H), 7.25 (s, 1H), 7.09 (t, J=8.7 Hz, 2H), 6.79-6.66 (m, 2H), 5.68 (q, J=7.0 Hz, 1H), 4.29 (q, J=6.5 Hz, 1H), 3.79-3.68 (m, 2H), 3.43-3.32 (m, 2H), 3.27-3.17 (m, 2H), 2.98 (br. s., 6H), 2.75-2.59 (m, 1H), 1.44 (d, J=7.1 Hz, 3H). ESI [M+H]=472.2

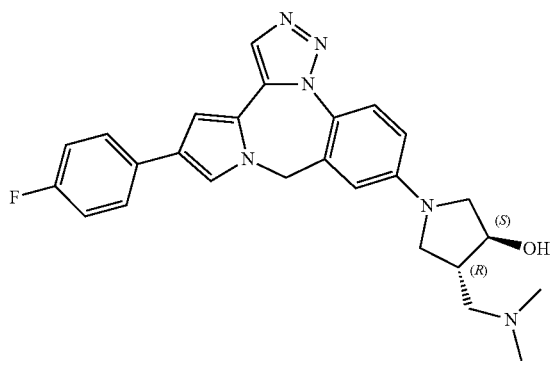

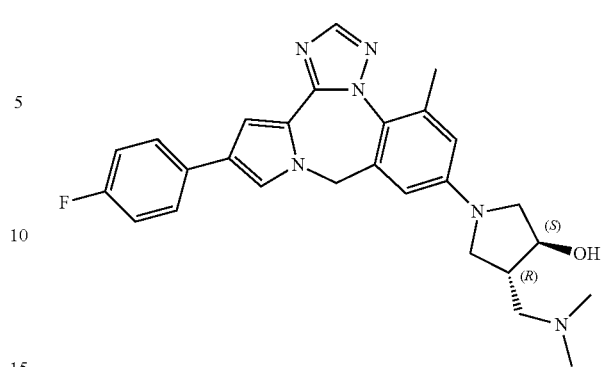

(3S,4R)-4-((dimethylamino)methyl)-1-(5-(4-fluorophenyl)-8H-benzo[e]pyrrolo[1,2-a][1,2,3] triazolo[5,1-c][1,4]diazepin-10-yl)pyrrolidin-3-ol, 511. Synthesized using General Procedure A, replacing 4-(7-bromo-9H-benzo[e]pyrrolo[1,2-a][1,2,4]triazolo[3,4-c][1,4]diazepin-12-yl)benzonitrile with 10-bromo-5-(4-fluorophenyl)-8H-benzo[e]pyrrolo[1,2-a][1,2,3 ]triazolo[5,1-c] [1,4]diazepine, replacing tert-butyl piperazine-1-carboxylate with (3S,4S)-4-((dimethyl amino)methyl)pyrrolidin-3-ol. 1H NMR (400 MHz, METHANOL-d4) δ=7.98 (s, 1H), 7.76 (d, J=8.6 Hz, 1H), 7.55-7.47 (m, 2H), 7.34 (d, J=2.0 Hz, 1H), 7.02 (t, J=8.9 Hz, 2H), 6.86 (d, J=1.8 Hz, 1H), 6.76-6.68 (m, 2H), 5.06 (s, 2H), 4.27 (q, J=6.8 Hz, 1H), 3.79-3.69 (m, 2H), 3.44-3.32 (m, 2H), 3.26-3.13 (m, 2H), 2.99 (br s, 6H), 2.75-2.64 (m, 1H). ESI [M+H]=459.1

(3S,4R)-4-((dimethylamino)methyl)-1-(12-(4-fluorophenyl)-5-methyl-9H-benzo[e]pyrrolo[1,2-a][1,2,4]triazolo[5,1-c][1,4]diazepin-7-yl)pyrrolidin-3-ol, 513. Synthesized using General Procedure A, replacing 4-(7-bromo-9H-benzo[e]pyrrolo[1,2-a][1,2,4]triazolo[3,4-c][1,4] diazepin-12-yl)benzonitrile with 7-bromo-12-(4-fluorophenyl)-5-methyl-9H-benzo[e]pyrrolo[1,2-a][1,2,4]triazolo[5,1-c][1,4]diazepine, replacing tert-butylpiperazine-1-carboxylate with (3S,4S)-4-((dimethylamino) methyl)pyrrolidin-3-ol. 1H NMR (400 MHz, METHANOL-d4) δ=8.17 (s, 1H), 7.58-7.49 (m, 2H), 7.37 (d, J=1.8 Hz, 1H), 7.09-7.00 (m, 3H), 6.60 (d, J=2.6 Hz, 1H), 6.53 (d, J=2.2 Hz, 1H), 5.10-5.00 (m, 1H), 4.92 (br s, 1H), 4.28 (q, J=6.7 Hz, 1H), 3.78-3.69 (m, 2H), 3.44-3.33 (m, 2H), 3.28-3.16 (m, 2H), 3.00 (s, 6H), 2.75-2.64 (m, 1H), 2.38 (s, 3H). ESI [M+H]=473.2

B. Biological Assays

The following assay methods were used to identify and evaluate compounds of Formula (I) or Formula (II) that are effective in inhibiting the MK2 enzyme.

Example: MK2 Enzymatic Assay

Inhibition of MK2 was determined for certain compounds of the invention as listed in Table 4. Briefly, 5 µL of 2× (4 µM) 100% phosphorylation peptide was delivered into the control wells of a 384-well assay plate. 5 µL of 2× (1 nM) MAPKAPK2 and 2× peptide (4 µM) mixture in assay buffer was dispensed to remaining columns of assay plate using Eppendorf electronic multiple channel pipette. The assay plate was incubated for 20 minutes. 5 µL of 2× ATP (6 µM) in assay buffer was dispensed to each well and then the assay plate was lightly centrifuged. The assay plate was incubated for an additional 120 minutes.

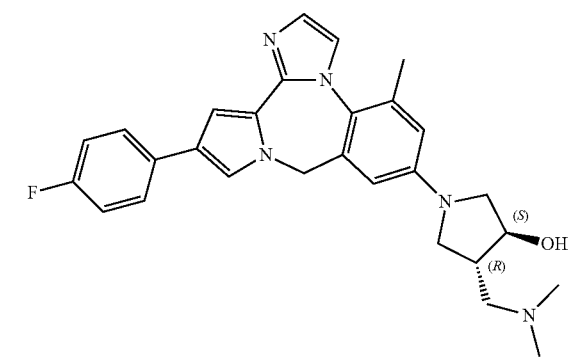

(3S,4R)-4-((dimethylamino)methyl)-1-(12-(4-fluorophenyl)-5-methyl-9H-benzo[e]imidazo[2,1-c]pyrrolo[1,2-a][1,4]diazepin-7-yl)pyrrolidin-3-ol, 512. Synthesized using General Procedure A, replacing 4-(7-bromo-9H-benzo[e]pyrrolo[1,2-a][1,2,4]triazolo[3,4-c][1,4] diazepin-12-yl)benzonitrile with 7-bromo-12-(4-fluorophenyl)-5-methyl-9H-benzo[e]imidazo[2,1-c]pyrrolo[1,2-a][1,4]diazepine, replacing tert-butyl piperazine-1-carboxylate with (3S,4S)-4-((dimethylamino)methyl)pyrrolidin-3-ol. 1H NMR (400 MHz, METHANOL-d4) δ=7.91 (s, 1H), 7.70 (s, 1H), 7.60-7.49 (m, 3H), 7.16-7.03 (m, 3H), 6.68 (d, J=2.4 Hz, 1H), 6.58 (s, 1H), 5.19-5.06 (m, 2H), 4.28 (q, J=6.9 Hz, 1H), 3.81-3.69 (m, 2H), 3.44-3.33 (m, 2H), 3.28-3.17 (m, 2H), 2.99 (s, 6H), 2.75-2.63 (m, 1H), 2.39 (s, 3H). ESI [M+H]=472.1

TABLE 2

| Conditions for MK2 Enzymatic Assay | |
|---|---|
| [MAPKAPK2] | 0.5 nM |
| [ATP] | 3 µM |
| Peptide substrate: | 2 µM Ser/Thr4 |
| Reaction time: | 120 minutes |
| Temperature: | 23° C. |
| Total volume: | 10 µL |

5 µL of development reagent A was dispensed to all wells using Eppendorf electronic multiple channel pipette. After incubating the development reaction for 120 min, plates were read on a Perkin Elmer Envision instrument.

TABLE 3

| Conditions for Development Reaction | |
| --- | --- |
| Reaction system above | 10 μL |
| Development Reagent A | 5 μL (1:1024 dilution in Development buffer) |
| Reaction time: | 60 minutes |
| Temperature: | 23° C. |
| Total volume: | 15 μL reaction |

Percent phosphorylation was calculated using the following formula:

$$\% \text{ phosphorylation} = \left[1 - \frac{\text{Emission Ratio} * F100\% - C100\%}{(C0\% - C100\%) + [\text{Emmision Ratio} * (F100\% - F0\%)]}\right] * 100$$

Where
C100%=Average Coumarin emission signal of the 100% Phos. Control
C0%=Average Coumarin emission signal of the 0% Phos. Control
F100%=Average Fluorescein emission signal of the 100% Phos. Control
F0%=Average Flurescein emission signal of the 0% Phos. Control $$\text{And Emmision Ratio} = \frac{\text{coumarin emission signal intensity @ 445 nm}}{\text{fluorescein emmision signal intensity @ 520 nm}}$$

The ability of compounds Formula (I) or Formula (II) or pharmaceutically acceptable salts thereof to inhibit MK2 was established with the representative compounds of Formula (I) or Formula (II) listed in Table 5 using the assays described above.

TABLE 4

| MK2 assay | |
| --- | --- |
| Compound No. | MK2 Activity |
| 1 | 100-200 nM |
| 9 | 100-200 nM |
| 11 | 50-100 nM |
| 29 | <50 nM |
| 50 | 50-100 nM |
| 56 | 50-100 nM |
| 57 | <50 nM |
| 58 | 50-100 nM |
| 59 | <50 nM |
| 60 | <50 nM |
| 61 | <50 nM |
| 62 | <50 nM |
| 63 | <50 nM |
| 64 | <50 nM |
| 65 | <50 nM |
| 66 | <50 nM |
| 67 | <50 nM |
| 68 | <50 nM |
| 69 | <50 nM |
| 70 | <50 nM |
| 71 | <50 nM |
| 72 | <50 nM |
| 73 | <50 nM |
| 74 | <50 nM |
| 75 | <50 nM |
| 76 | <50 nM |
| 77 | 50-100 nM |
| 78 | 100-200 nM |
| 79 | 50-100 nM |
| 80 | 50-100 nM |
| 81 | <50 nM |
| 82 | <50 nM |
| 83 | 50-100 nM |
| 84 | <50 nM |
| 85 | <50 nM |
| 86 | <50 nM |
| 87 | <50 nM |
| 88 | <50 nM |
| 89 | <50 nM |
| 90 | <50 nM |
| 91 | <50 nM |
| 92 | <50 nM |
| 93 | <50 nM |
| 94 | <50 nM |
| 95 | <50 nM |
| 96 | <50 nM |
| 97 | <50 nM |
| 98 | <50 nM |
| 99 | <50 nM |
| 100 | 50-100 nM |
| 101 | 100-200 nM |
| 102 | 50-100 nM |
| 103 | 100-200 nM |
| 104 | 100-200 nM |
| 105 | <50 nM |
| 106 | 50-100 nM |
| 107 | 100-200 nM |
| 108 | <50 nM |
| 109 | <50 nM |
| 110 | <50 nM |
| 111 | <50 nM |
| 125 | <50 nM |
| 128 | 50-100 nM |
| 129 | <50 nM |
| 130 | <50 nM |
| 131 | <50 nM |
| 133 | <50 nM |
| 134 | <50 nM |
| 135 | <50 nM |
| 136 | <50 nM |
| 137 | <50 nM |
| 138 | <50 nM |
| 139 | <50 nM |
| 140 | <50 nM |
| 141 | <50 nM |
| 142 | <50 nM |
| 143 | <50 nM |
| 165 | 100-200 nM |
| 166 | 100-200 nM |
| 167 | 50-100 nM |
| 168 | 100-200 nM |
| 169 | <50 nM |
| 170 | 50-100 nM |
| 171 | 50-100 nM |
| 172 | 50-100 nM |
| 173 | <50 nM |
| 174 | 50-100 nM |
| 175 | 100-200 nM |
| 176 | <50 nM |
| 177 | 50-100 nM |
| 178 | 100-200 nM |
| 179 | 100-200 nM |
| 180 | 100-200 nM |
| 181 | 100-200 nM |
| 182 | 100-200 nM |
| 224 | <50 nM |
| 228 | 50-100 nM |
| 229 | 50-100 nM |
| 230 | 50-100 nM |
| 231 | 50-100 nM |

TABLE 4-continued

MK2 assay

| Compound No. | MK2 Activity |
|---|---|
| 232 | <50 nM |
| 233 | 50-100 nM |
| 235 | 100-200 nM |
| 236 | <50 nM |
| 237 | <50 nM |
| 238 | 100-200 nM |
| 239 | <50 nM |
| 240 | <50 nM |
| 241 | <50 nM |
| 242 | 50-100 nM |
| 243 | 50-100 nM |
| 245 | 100-200 nM |
| 246 | <50 nM |
| 247 | <50 nM |
| 249 | <50 nM |
| 250 | 50-100 nM |
| 251 | <50 nM |
| 252 | 50-100 nM |
| 253 | <50 nM |
| 254 | 50-100 nM |
| 255 | <50 nM |
| 256 | <50 nM |
| 257 | 50-100 nM |
| 258 | 50-100 nM |
| 259 | <50 nM |
| 260 | <50 nM |
| 261 | 50-100 nM |
| 262 | <50 nM |
| 263 | 100-200 nM |
| 275 | <50 nM |
| 276 | <50 nM |
| 277 | 50-100 nM |
| 278 | <50 nM |
| 295 | <50 nM |
| 297 | 50-100 nM |
| 298 | <50 nM |
| 299 | <50 nM |
| 300 | <50 nM |
| 301 | 100-200 nM |
| 302 | 50-100 nM |
| 303 | 50-100 nM |
| 304 | <50 nM |
| 305 | <50 nM |
| 306 | <50 nM |
| 307 | <50 nM |
| 308 | <50 nM |
| 309 | <50 nM |
| 310 | <50 nM |
| 314 | <50 nM |
| 315 | 100-200 nM |
| 316 | 100-200 nM |
| 317 | 100-200 nM |
| 318 | 100-200 nM |
| 319 | 50-100 nM |
| 320 | 100-200 nM |
| 321 | 100-200 nM |
| 322 | 100-200 nM |
| 323 | 50-100 nM |
| 329 | <50 nM |
| 330 | 50-100 nM |
| 332 | <50 nM |
| 334 | <50 nM |
| 336 | <50 nM |
| 340 | <50 nM |
| 341 | <50 nM |
| 342 | <50 nM |
| 343 | 50-100 nM |
| 344 | <50 nM |
| 345 | <50 nM |
| 346 | <50 nM |
| 347 | <50 nM |
| 348 | <50 nM |
| 349 | <50 nM |
| 350 | <50 nM |
| 351 | <50 nM |
| 352 | <50 nM |
| 353 | <50 nM |
| 354 | <50 nM |
| 355 | <50 nM |
| 356 | <50 nM |
| 357 | <50 nM |
| 358 | <50 nM |
| 359 | <50 nM |
| 360 | <50 nM |
| 361 | <50 nM |
| 362 | <50 nM |
| 363 | <50 nM |
| 364 | <50 nM |
| 365 | 50-100 nM |
| 366 | <50 nM |
| 367 | <50 nM |
| 368 | <50 nM |
| 369 | <50 nM |
| 370 | <50 nM |
| 371 | <50 nM |
| 372 | 100-200 nM |
| 373 | 100-200 nM |
| 374 | <50 nM |
| 375 | <50 nM |
| 376 | <50 nM |
| 377 | <50 nM |
| 378 | <50 nM |
| 379 | <50 nM |
| 380 | <50 nM |
| 381 | <50 nM |
| 382 | 100-200 nM |
| 383 | <50 nM |
| 384 | 100-200 nM |
| 386 | <50 nM |
| 387 | 50-100 nM |
| 388 | <50 nM |
| 389 | <50 nM |
| 390 | 50-100 nM |
| 391 | <50 nM |
| 392 | <50 nM |
| 393 | <50 nM |
| 394 | 50-100 nM |
| 395 | <50 nM |
| 396 | 100-200 nM |
| 397 | 100-200 nM |
| 398 | <50 nM |
| 399 | 50-100 nM |
| 400 | <50 nM |
| 401 | <50 nM |
| 402 | <50 nM |
| 403 | 50-100 nM |
| 404 | 50-100 nM |
| 405 | <50 nM |
| 406 | <50 nM |
| 407 | 50-100 nM |
| 408 | <50 nM |
| 409 | 100-200 nM |
| 410 | 50-100 nM |
| 411 | 100-200 nM |
| 412 | <50 nM |
| 413 | <50 nM |
| 414 | 50-100 nM |
| 415 | 100-200 nM |
| 416 | <50 nM |
| 417 | 50-100 nM |
| 418 | 100-200 nM |
| 419 | <50 nM |
| 420 | <50 nM |
| 421 | <50 nM |
| 422 | <50 nM |
| 423 | <50 nM |
| 424 | <50 nM |
| 425 | 50-100 nM |
| 426 | 50-100 nM |
| 427 | 50-100 nM |
| 428 | 50-100 nM |
| 429 | <50 nM |

TABLE 4-continued

MK2 assay

| Compound No. | MK2 Activity |
|---|---|
| 430 | <50 nM |
| 431 | <50 nM |
| 432 | 100-200 nM |
| 433 | 50-100 nM |
| 434 | <50 nM |
| 435 | <50 nM |
| 436 | <50 nM |
| 437 | <50 nM |
| 438 | <50 nM |
| 439 | <50 nM |
| 440 | <50 nM |
| 441 | <50 nM |
| 442 | 100-200 nM |
| 443 | 100-200 nM |
| 444 | 50-100 nM |
| 445 | 50-100 nM |
| 446 | 100-200 nM |
| 447 | 100-200 nM |
| 448 | 50-100 nM |
| 449 | 100-200 nM |
| 450 | 100-200 nM |
| 451 | 100-200 nM |
| 452 | 50-100 nM |
| 453 | 100-200 nM |
| 454 | 50-100 nM |
| 455 | 100-200 nM |
| 456 | 100-200 nM |
| 457 | 100-200 nM |
| 458 | 100-200 nM |
| 459 | 100-200 nM |
| 460 | 100-200 nM |
| 461 | 50-100 nM |
| 462 | <50 nM |
| 464 | <50 nM |
| 465 | 200-1000 nM |
| 466 | <50 nM |
| 467 | <50 nM |
| 468 | <50 nM |
| 469 | <50 nM |
| 470 | <50 nM |
| 471 | <50 nM |
| 472 | <50 nM |
| 473 | <50 nM |
| 474 | <50 nM |
| 475 | <50 nM |
| 476 | <50 nM |
| 477 | <50 nM |
| 478 | 100-200 nM |
| 479 | 100-200 nM |
| 480 | 50-100 nM |
| 481 | 200-1000 nM |
| 482 | <50 nM |
| 483 | <50 nM |
| 484 | 50-100 nM |
| 485 | 100-200 nM |
| 486 | <50 nM |
| 487 | <50 nM |
| 488 | <50 nM |
| 489 | <50 nM |
| 490 | <50 nM |
| 491 | <50 nM |
| 492 | <50 nM |
| 493 | <50 nM |
| 494 | <50 nM |
| 495 | 100-200 nM |
| 496 | 50-100 nM |
| 497 | <50 nM |
| 498 | <50 nM |
| 499 | <50 nM |
| 500 | 100-200 nM |
| 501 | <50 nM |
| 502 | <50 nM |
| 503 | 100-200 nM |
| 504 | 100-200 nM |
| 505 | 50-100 nM |
| 507 | <50 nM |
| 508 | <50 nM |
| 509 | <50 nM |
| 511 | <50 nM |
| 512 | 500-1000 nM |
| 513 | 100-200 nM |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of treating a disorder, comprising administering to a subject a compound having a structure of Formula I or a pharmaceutically acceptable salt thereof:

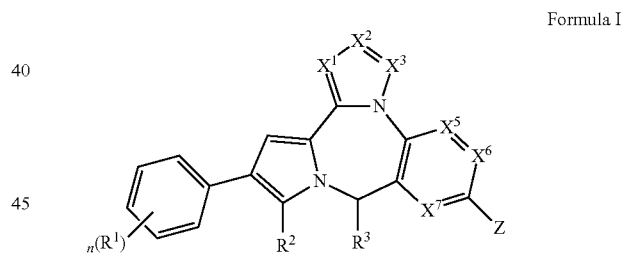

Formula I wherein
X$^1$, X$^2$, and X$^3$ are, independently for each occurrence, CR$^5$ or N;
X$^5$, X$^6$, and X$^7$ are, independently for each occurrence, CR$^7$ or N;
R$^1$ is, independently for each occurrence, H, halo, —OH, —CN, or optionally substituted alkyl, alkoxy, —O—R$^{31}$, —O—C(O)—NR$^{31}$R$^{32}$, or —C(O)—OR$^{31}$;
R$^2$ is H, halo, —CN, alkyl, or —C(O)—OR$^{41}$;
R$^3$ is H, alkyl, or cycloalkyl;
R$^5$ is H, halo, —CN or optionally substituted alkyl, alkoxy, aryl, heteroaryl, O—C(O)—NR$^{61}$R$^{62}$, or —C(O)—OR$^{61}$;
R$^7$ is H, halo, —OH, —CN, or optionally substituted alkyl, alkoxy, —O—C(O)—NR$^{71}{}_2$, or —C(O)—OR$^{71}$;
R$^{31}$ and R$^{32}$ are, independently for each occurrence, optionally substituted alkyl, alkenyl, alkynyl, cycloalkyl, (cycloalkyl)alkyl, aryl, or aralkyl;

$R^{41}$ is optionally substituted alkyl, alkenyl, alkynyl, cycloalkyl, (cycloalkyl)alkyl, aryl, or aralkyl;

$R^{61}$ and $R^{62}$ are, independently for each occurrence, optionally substituted alkyl, alkenyl, alkynyl, cycloalkyl, (cycloalkyl)alkyl, aryl, or aralkyl;

$R^{71}$ is optionally substituted alkyl, alkenyl, alkynyl, cycloalkyl, (cycloalkyl)alkyl, aryl, or aralkyl;

Z is halo or optionally substituted amino, alkylamino, heteroalkylamino, cycloalkylamino, or heterocycloalkylamino; and n is an integer from 0-5; and wherein the disorder is a cancer selected from Acute Lymphoblastic Leukemia (ALL), Acute Myeloid Leukemia (AML), bladder cancer, chronic myeloid leukemia (CML), colorectal cancer, gastric cancer, liver cancer, lung cancer, and non-small cell lung cancer.

2. The method of claim 1, further comprising conjointly administering one or more additional chemotherapeutic agents selected from ABT-263, aminoglutethimide, amsacrine, anastrozole, asparaginase, AZD5363, Bacillus Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil and 5-fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, LY2603618, mechlorethamine, medroxyprogesterone, megestrol, melphalan, mercaptopurine, mesna, metformin, methotrexate, miltefosine, mitomycin, mitotane, mitoxantrone, MK2206, nilutamide, nocodazole, octreotide, oxaliplatin, paclitaxel, pamidronate, pentostatin, pazopanib, perifosine, PF-04691502, PF477736, plicamycin, pomalidomide, porfimer, procarbazine, raltitrexed, rituximab, romidepsin, selumetinib, sorafenib, streptozocin, sunitinib, suramin, tamoxifen, temozolomide, temsirolimus, teniposide, testosterone, thalidomide, thioguanine, thiotepa, titanocene dichloride, topotecan, trametinib, trastuzumab, tretinoin, vinblastine, vincristine, vindesine, vinorelbine, and vorinostat (SAHA) or a combination therapy.

3. The method of claim 2, wherein the additional chemotherapeutic agent is cisplatin.

4. The method of claim 2, wherein the additional chemotherapeutic agent is PF477736 or LY2603618.

5. A method of treating a metabolic disorder, comprising administering to a subject a compound having a structure of Formula I or a pharmaceutically acceptable salt thereof:

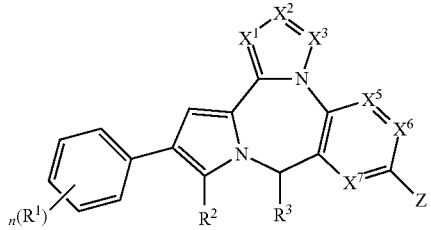

Formula I wherein $X^1$, $X^2$, and $X^3$ are, independently for each occurrence, $CR^5$ or N;

$X^5$, $X^6$, and $X^7$ are, independently for each occurrence, $CR^7$ or N;

$R^1$ is, independently for each occurrence, H, halo, —OH, —CN, or optionally substituted alkyl, alkoxy, —O—$R^{31}$, —O—C(O)—$NR^{31}R^{32}$, or —C(O)—$R^{31}$;

$R^2$ is H, halo, —CN, alkyl, or —C(O)—$OR^{41}$;

$R^3$ is H, alkyl, or cycloalkyl;

$R^5$ is H, halo, —CN or optionally substituted alkyl, alkoxy, aryl, heteroaryl, O—C(O)—$NR^{61}R^{62}$, or —C(O)—$OR^{61}$;

$R^7$ is H, halo, —OH, —CN, or optionally substituted alkyl, alkoxy, —O—C(O)—$NR^{71}{}_2$, or —C(O)—$OR^{71}$;

$R^{31}$ and $R^{32}$ are, independently for each occurrence, optionally substituted alkyl, alkenyl, alkynyl, cycloalkyl, (cycloalkyl)alkyl, aryl, or aralkyl;

$R^{41}$ is optionally substituted alkyl, alkenyl, alkynyl, cycloalkyl, (cycloalkyl)alkyl, aryl, or aralkyl;

$R^{61}$ and $R^{62}$ are, independently for each occurrence, optionally substituted alkyl, alkenyl, alkynyl, cycloalkyl, (cycloalkyl)alkyl, aryl, or aralkyl;

$R^{71}$ is optionally substituted alkyl, alkenyl, alkynyl, cycloalkyl, (cycloalkyl)alkyl, aryl, or aralkyl;

Z is halo or optionally substituted amino, alkylamino, heteroalkylamino, cycloalkylamino, or heterocycloalkylamino; and n is an integer from 0-5; and wherein the metabolic disorder is diabetes, insulin resistance, obesity, or metabolic syndrome.

6. The method of claim 5, wherein the diabetes is Type I, Type II, or gestational diabetes.

7. The method of claim 5, wherein the treating affects glycogenolysis or gluconeogenesis in the subject.

8. The method of claim 5, wherein the treating reduces hepatic glucose production, hyperglycemia, fatty liver, insulin resistance, insulin-resistance-associated inflammation, insulin resistance-associated dyslipidemia, or any combination thereof, in the subject.

9. The method of claim 5, further comprising conjointly administering one or more additional antidiabetic agents selected from metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, dutogliptin, repaglinide, nateglinide, mitiglindine, exenatide, liraglutide, albiglutide and insulin.

10. The method of claim 1, wherein $X^1$ is N; and $X^2$ and $X^3$ are CH.

11. The method of claim 1, wherein $X^1$ and $X^2$ are N; and $X^3$ is CH.

12. The method of claim 1, wherein $X^1$ and $X^3$ are N; and $X^2$ is CH.

13. The method of claim 1, wherein $X^1$, $X^2$, and $X^3$ are N.

14. The method of claim 1, wherein Z is

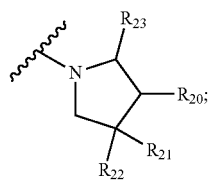

and

R²⁰, R²¹, R²², and R²³ are each independently H, halo, hydroxyl, amino, or optionally substituted alkyl, alkoxy, aminoalkyl, alkylaminoalkyl, alkylamino, cycloalkyl, or heterocycloalkyl; or R²³ and R²⁰ combine to form an optionally substituted 3-, 4-, 5-, or 6-membered ring;

R²¹ and R²⁰ combine to form an optionally substituted 3-, 4-, 5-, or 6-membered ring; or R²¹ and R²² combine to form an optionally substituted 4-, 5-, or 6-membered ring.

15. The method of claim 14, wherein the optionally substituted 4-, 5-, or 6-membered ring comprises a heteroatom.

16. The method of claim 15, wherein the heteroatom is N.

17. The method of claim 1, wherein Z is

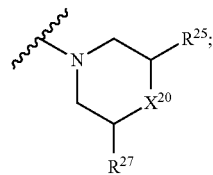

X²⁰ is CR²⁴R²⁶, NH, or O; and

R²⁴, R²⁵, R²⁶, and R²⁷ are each independently H, amino, or optionally substituted alkyl, aminoalkyl, alkylaminoalkyl, alkylamino, cycloalkyl, or heterocycloalkyl; or R²⁴ and R²⁶ combine to form an optionally substituted 4-, 5-, or 6-membered ring.

18. The method of claim 17, wherein the optionally substituted 4-, 5-, or 6-membered ring comprises a heteroatom.

19. The method of claim 18, wherein the heteroatom is N.

20. The method of claim 1, wherein Z is

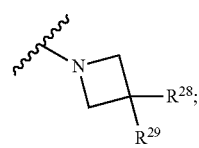

and

R²⁸ and R²⁹ are each independently H, amino, or optionally substituted alkyl, alkoxy, aminoalkyl, alkylaminoalkyl, alkylamino, cycloalkyl, or heterocycloalkyl; or R²⁸ and R²⁹ combine to form an optionally substituted 4-, 5-, or 6-membered ring.

21. The method of claim 20, wherein the optionally substituted 4-, 5-, or 6-membered ring comprises a heteroatom.

22. The method of claim 21, wherein the heteroatom is N.

23. The method of claim 1, wherein Z is

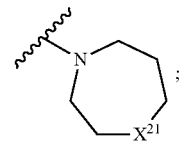

X²¹ is NH or O.

24. The method of claim 1, wherein Z is optionally substituted alkylamino, cycloalkylamino, or heterocycloalkylamino.

25. The method of claim 1, wherein

R¹ is, independently for each occurrence, fluoro, chloro, —CN, —O—R³¹, OCF₃, —O—C(O)—NR³¹R³², or —C(O)—OR³¹; and R³¹ and R³² are, independently for each occurrence, optionally substituted alkyl, alkenyl, alkynyl, cycloalkyl, (cycloalkyl)alkyl, aryl, or aralkyl.

26. The method of claim 25, wherein R¹ is fluoro or —CN.

27. The method of claim 1, wherein R² is —C(O)—OR⁴¹; and

R⁴¹ is optionally substituted alkyl, alkenyl, cycloalkyl, (cycloalkyl)alkyl, aryl, or aralkyl.

28. The method of claim 1, wherein R² is H or chloro.

29. The method of claim 1, wherein R³ is optionally substituted C₁₋₆alkyl or C₃₋₆cycloalkyl.

30. The method of claim 1, wherein R³ is H.

31. The method of claim 1, wherein

R⁵ is optionally substituted alkyl, —O—C(O)—NR⁶¹R⁶² or C(O)—OR⁶¹; and

R⁶¹ and R⁶² are, independently for each occurrence, optionally substituted alkyl, alkenyl, cycloalkyl, (cycloalkyl)alkyl, aryl, or aralkyl.

32. The method of claim 1, wherein R⁷ is —O—C(O)—NR⁷¹₂ or —C(O)—OR⁷¹; and R⁷¹ is optionally substituted alkyl, alkenyl, cycloalkyl, (cycloalkyl)alkyl, aryl, or aralkyl.

33. The method of claim 1, wherein n is 0, 1 or 2.

34. The method of claim 1, wherein the compound of Formula I is selected from

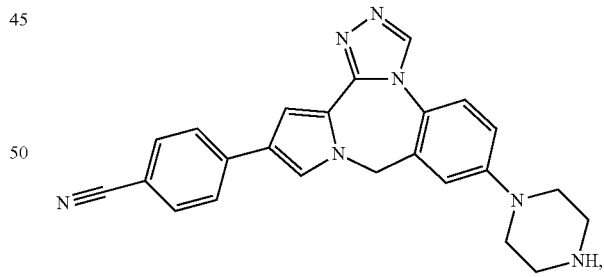

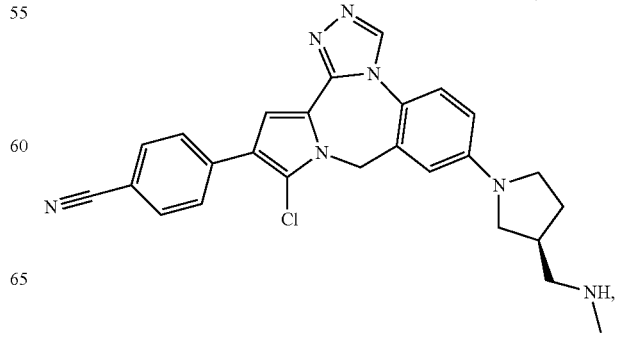

347
-continued
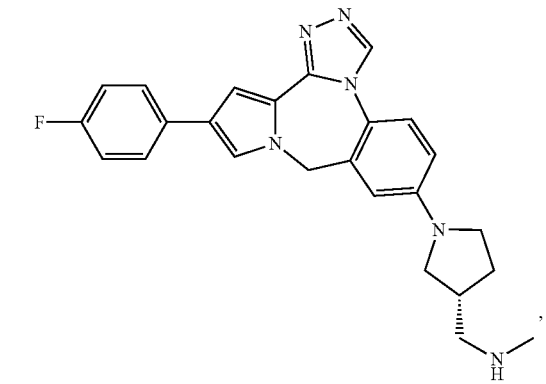
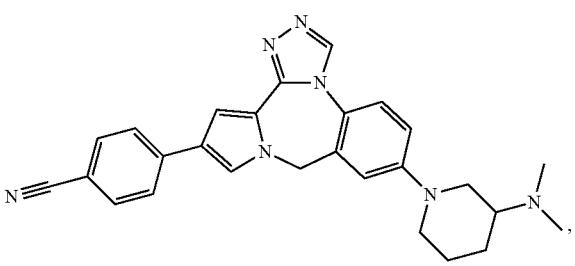
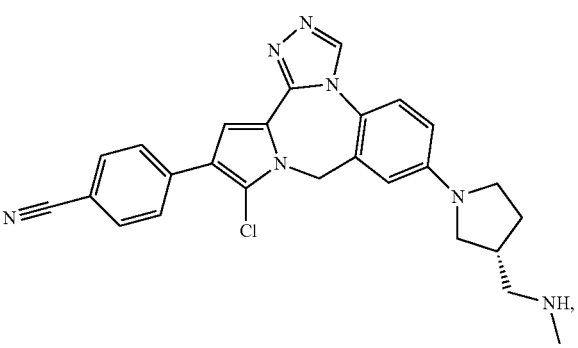
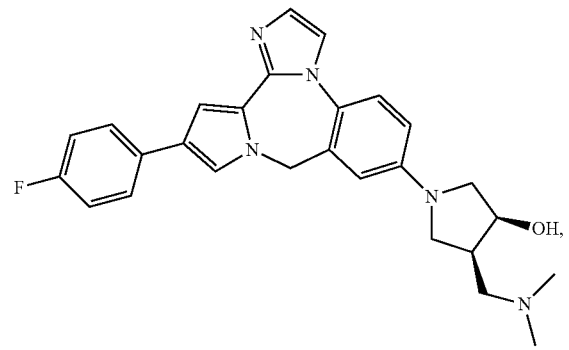
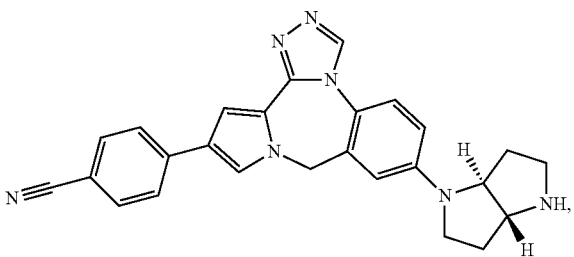
348
-continued
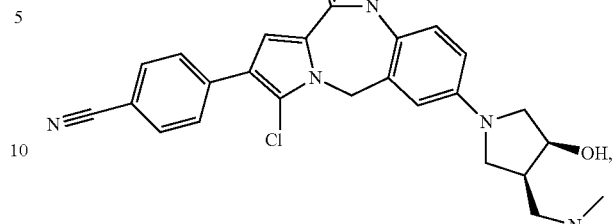
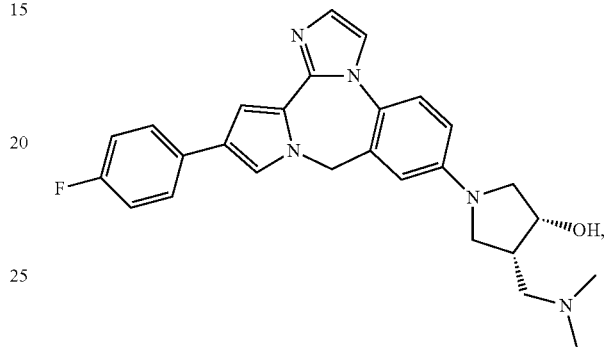
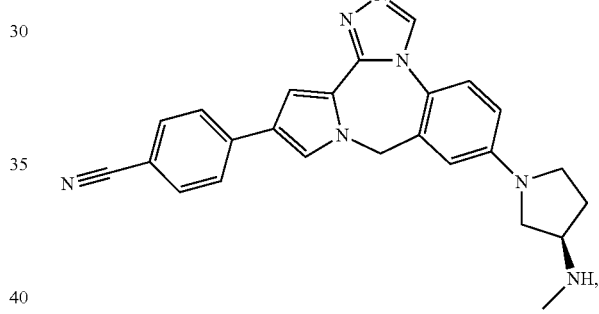
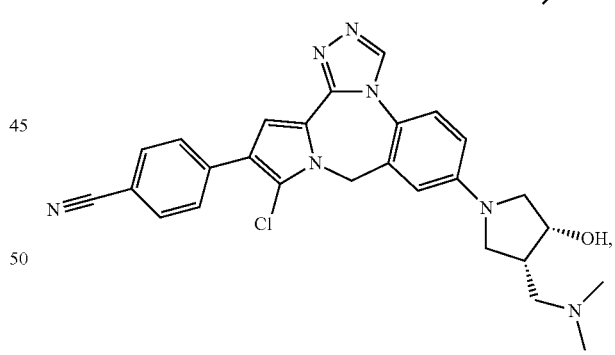
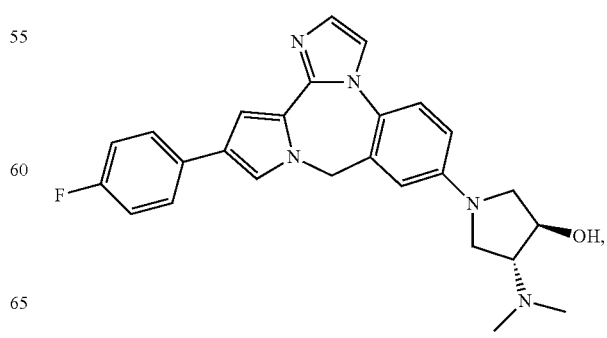

349
-continued
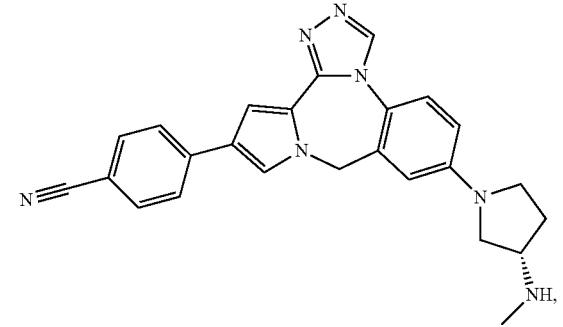
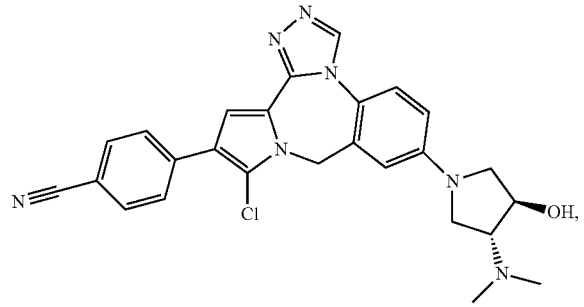
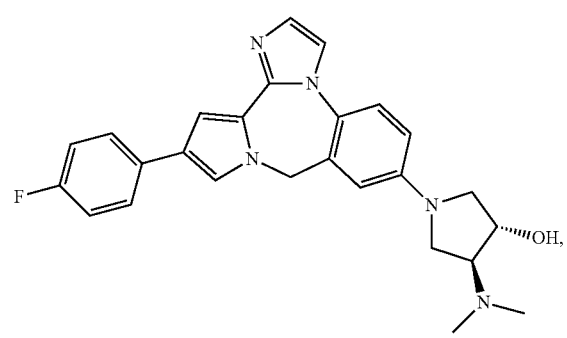
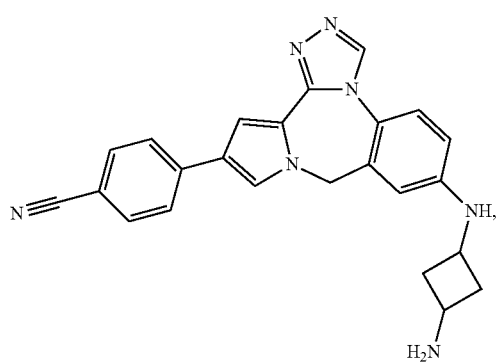
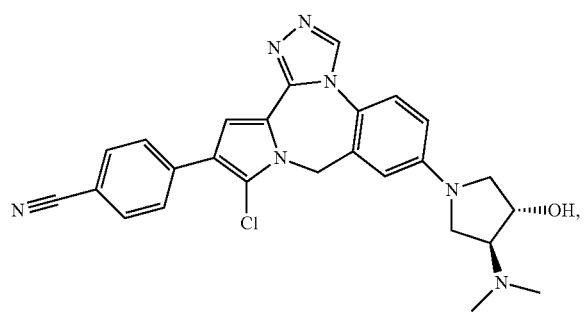
350
-continued
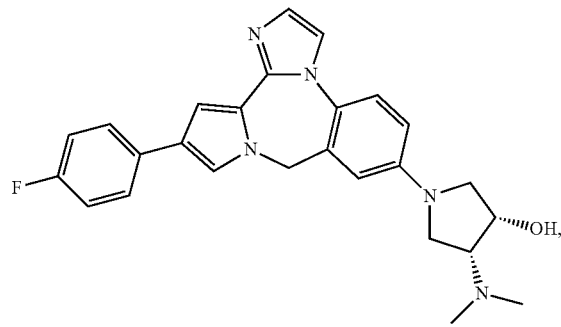
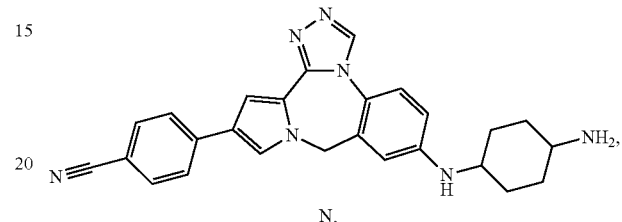
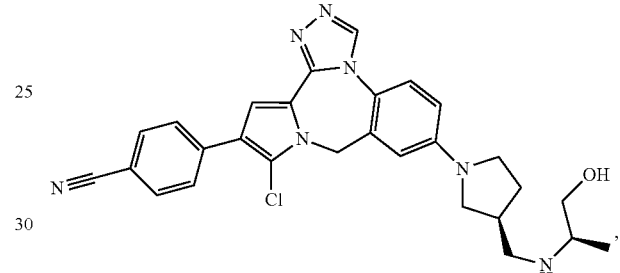
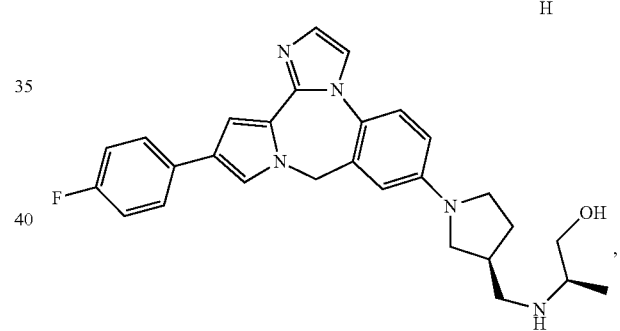
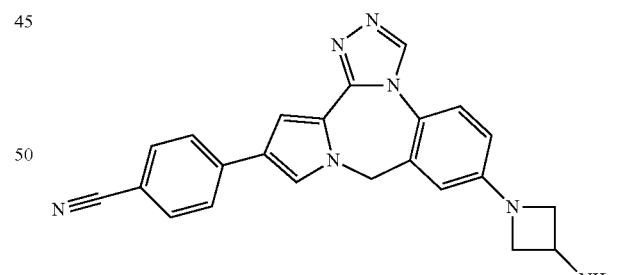
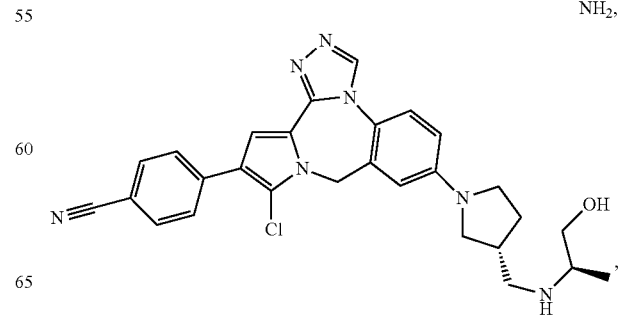

351
-continued
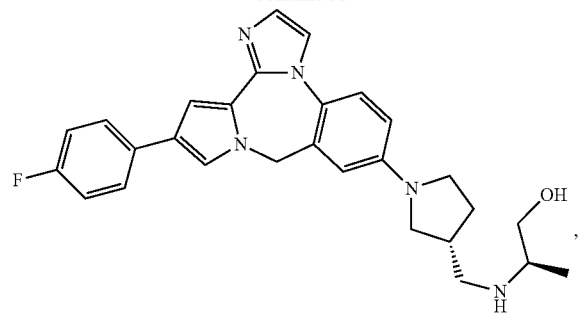
352
-continued
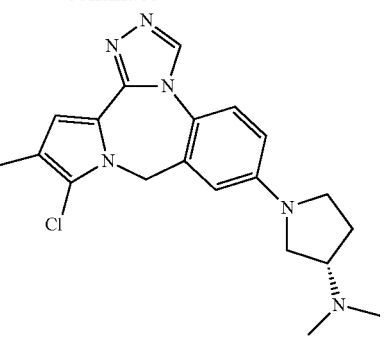
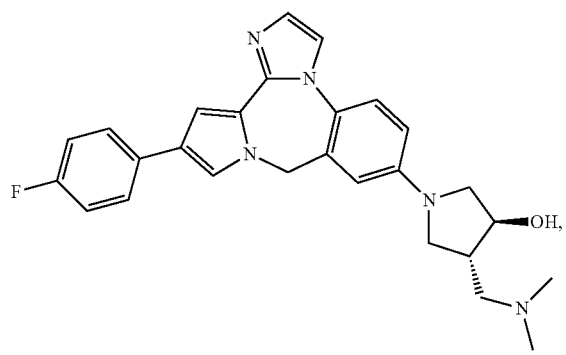
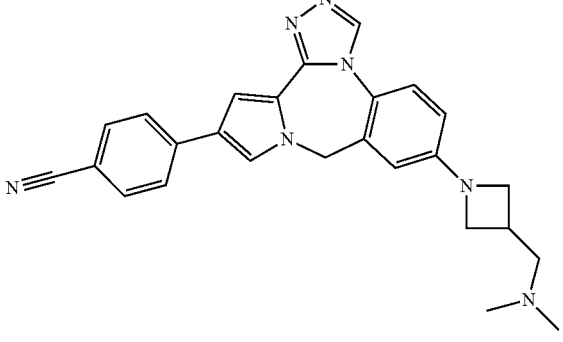
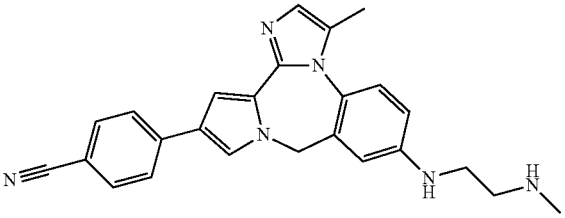
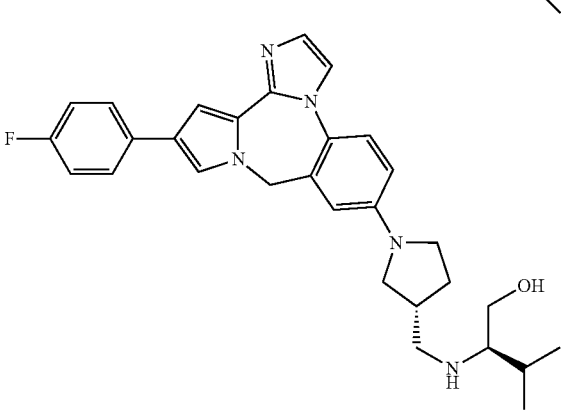

353
-continued
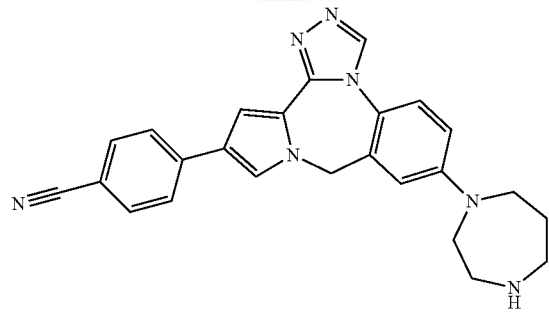
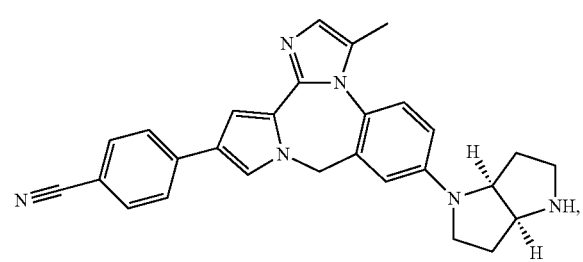
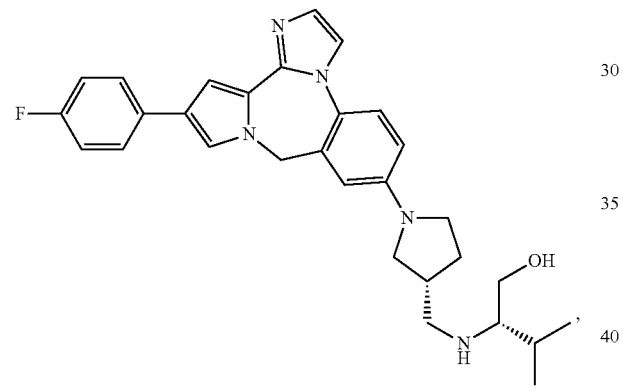
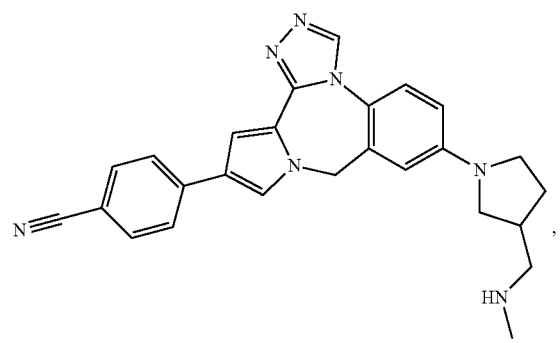
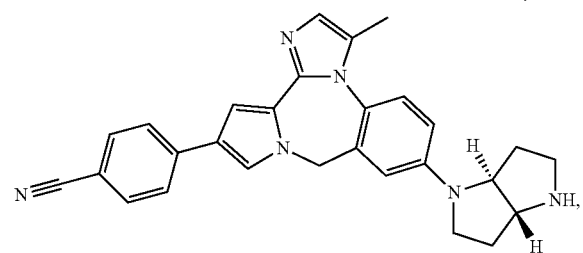
354
-continued
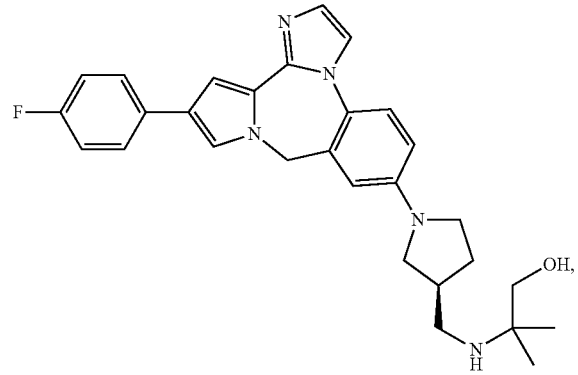
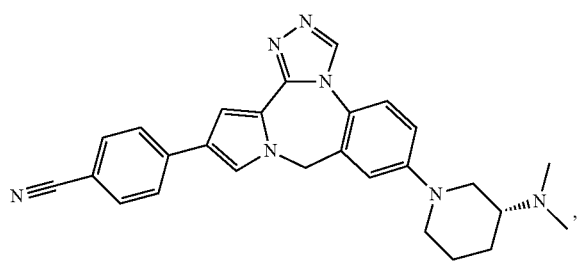
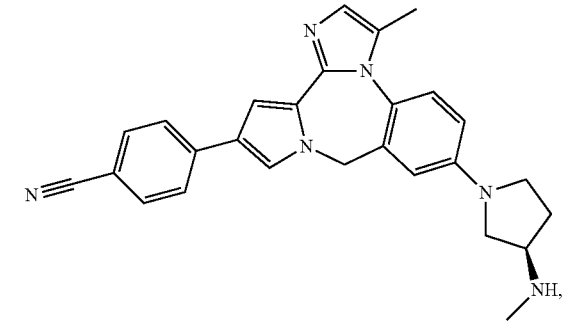
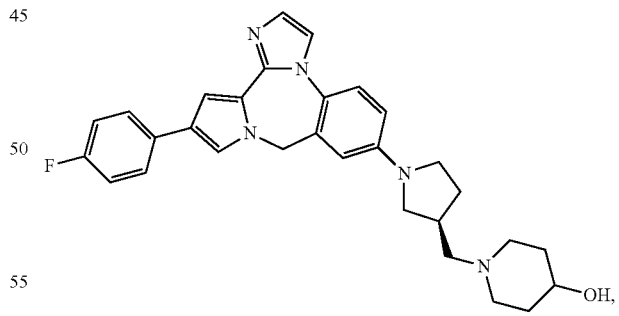
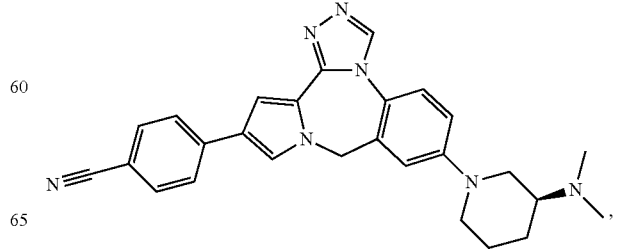

| 355 -continued | 356 -continued |
|---|---|
| 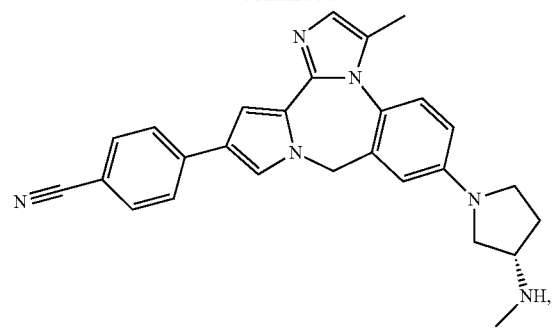 | 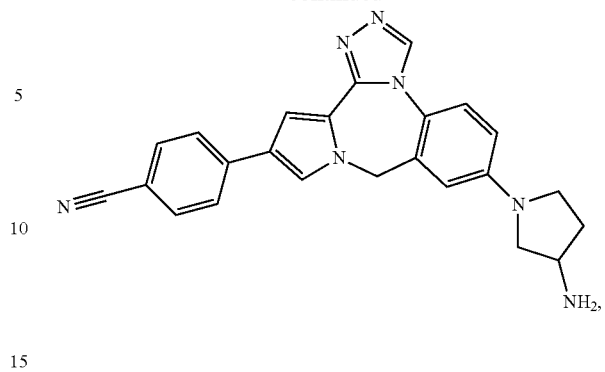 |
| 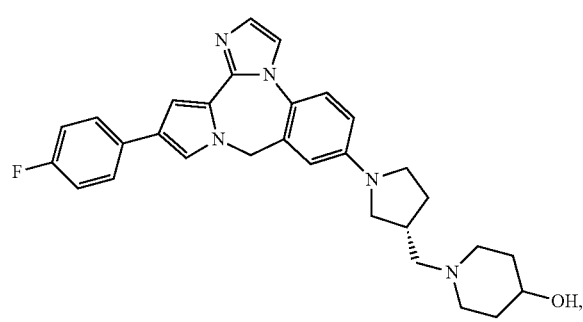 | 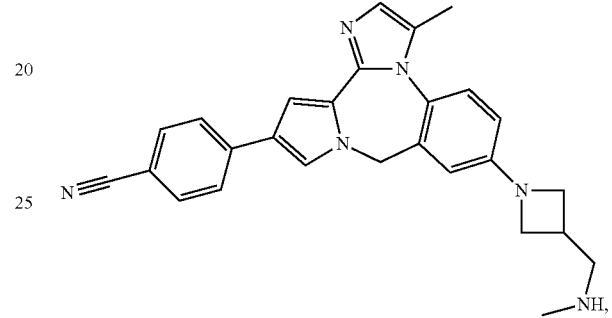 |
| 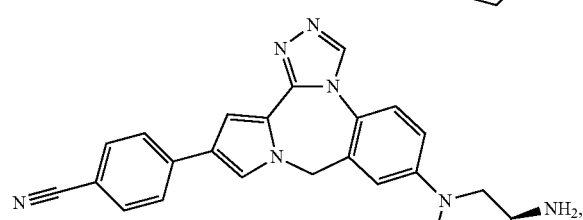 | 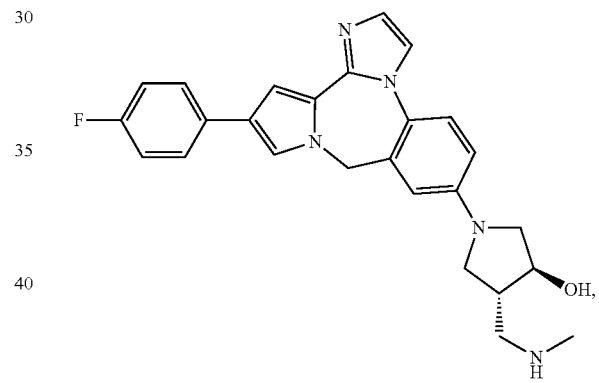 |
| 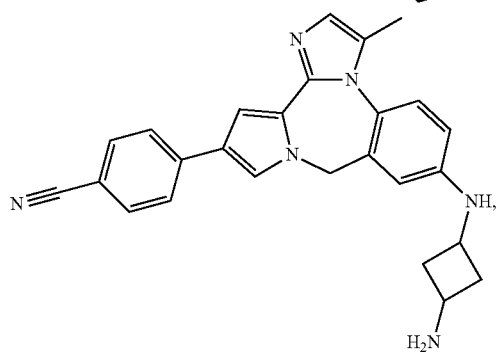 | 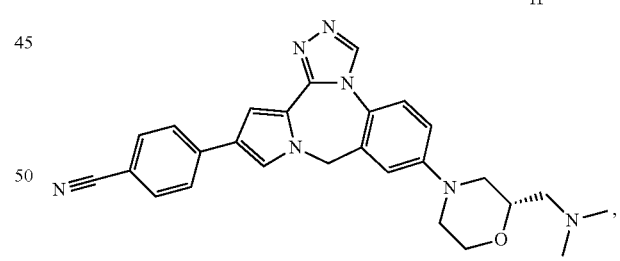 |
| 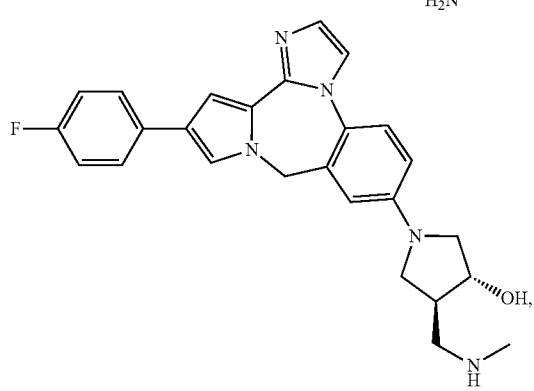 | 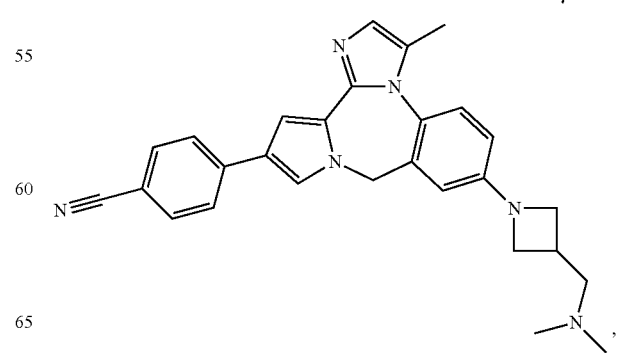 |

357
-continued
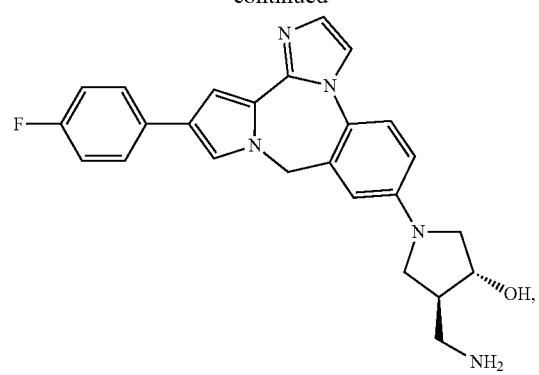
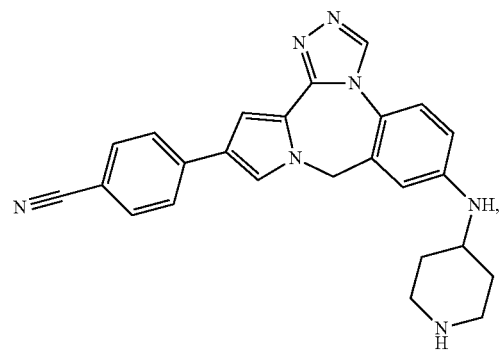
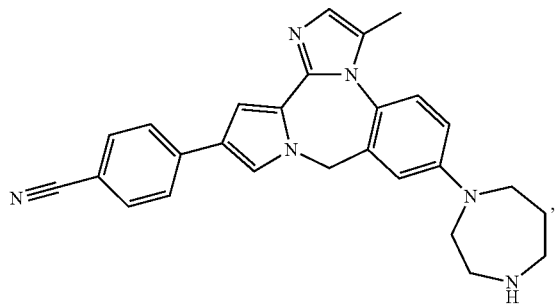
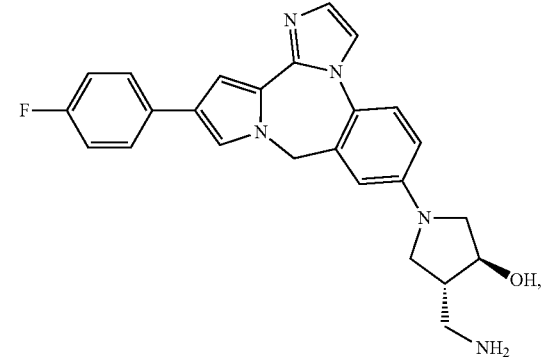
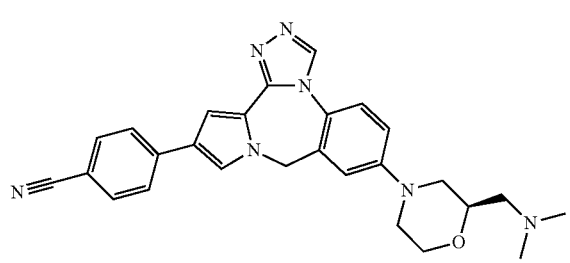
358
-continued
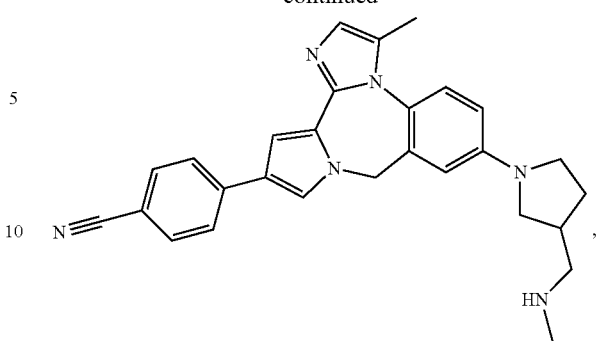
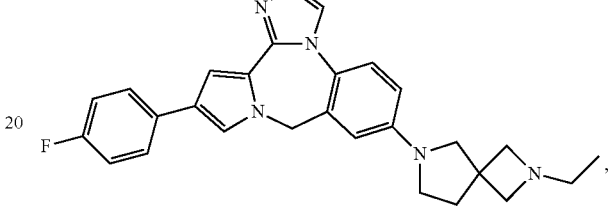
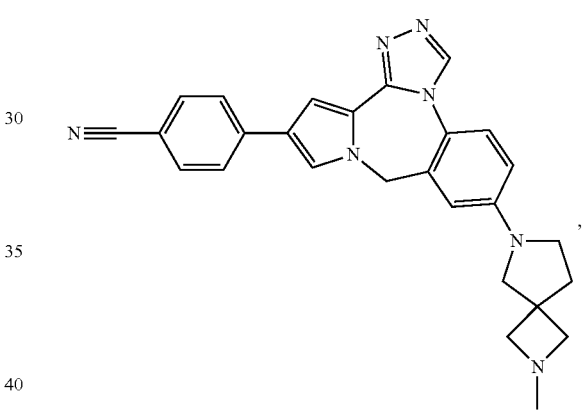
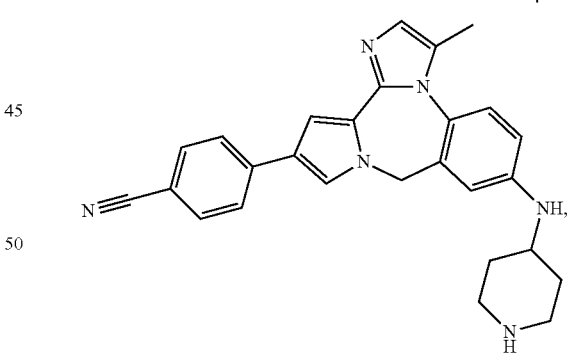
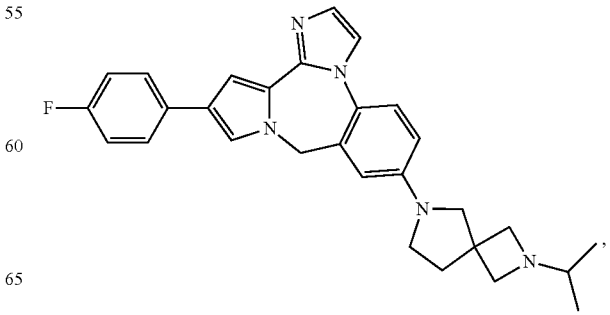

359
-continued
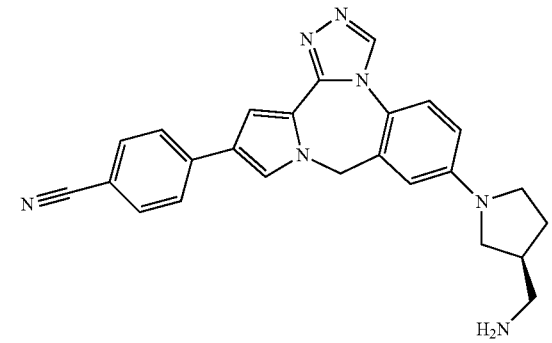
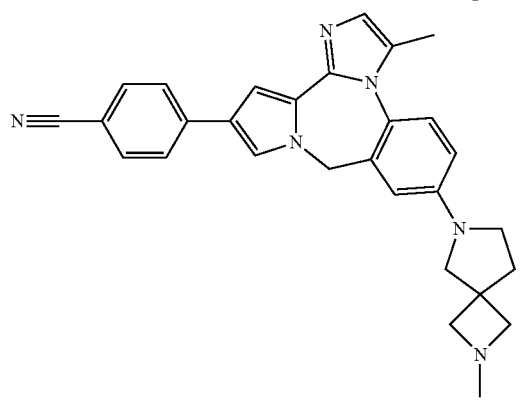
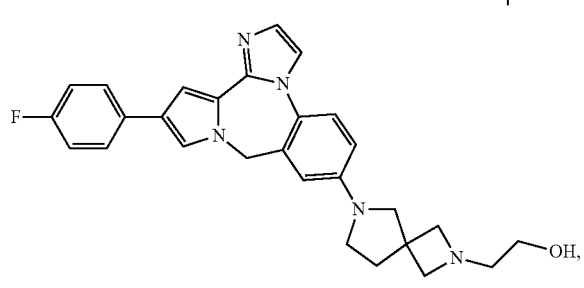
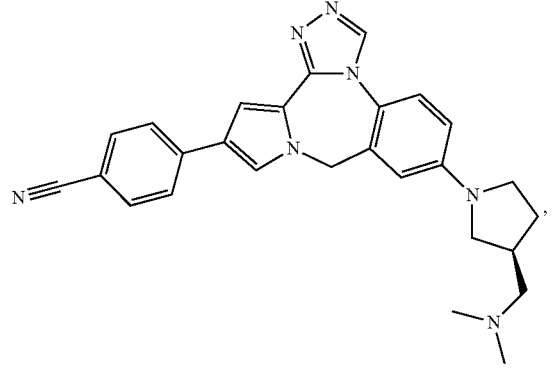
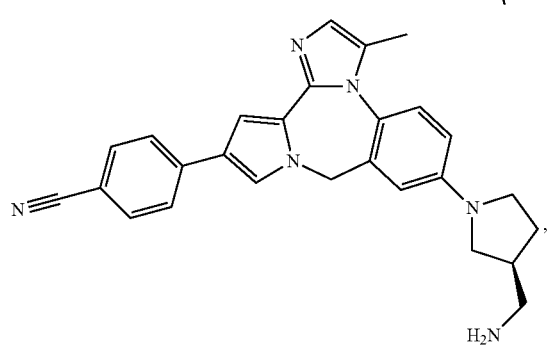
360
-continued
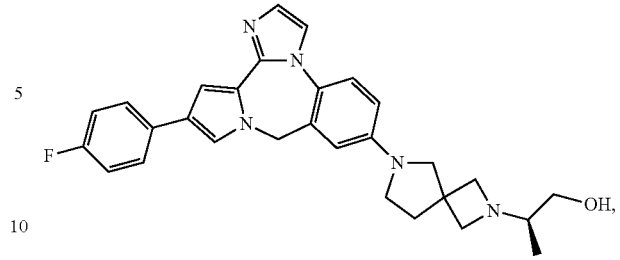
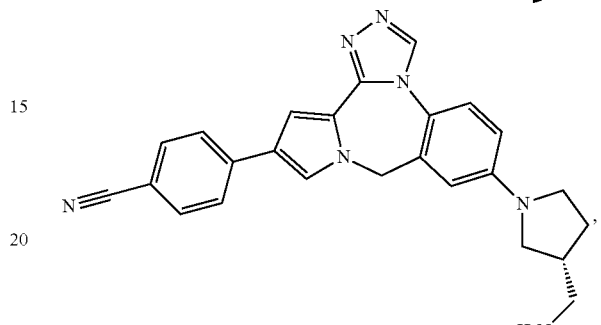
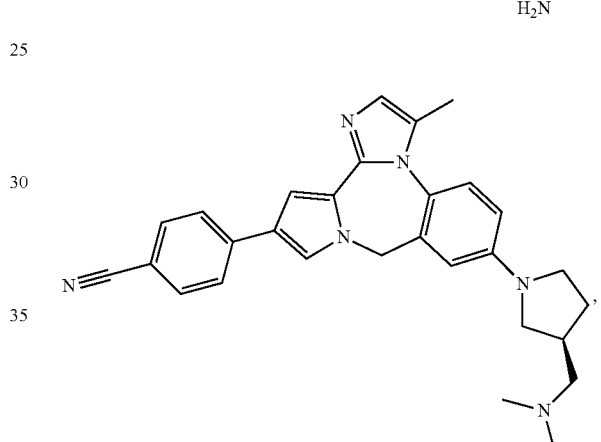
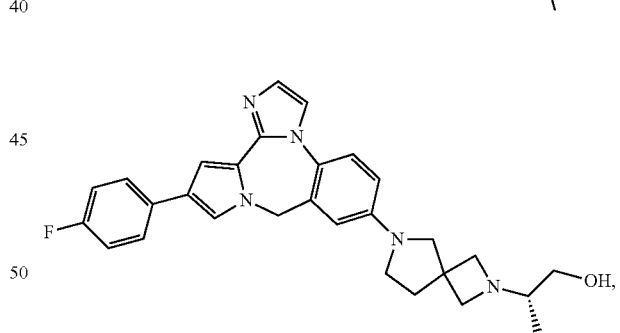
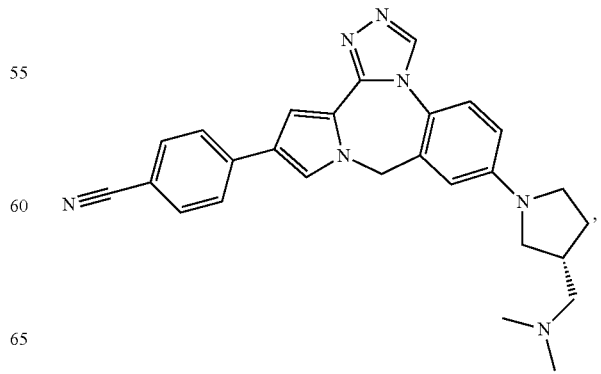

361
-continued
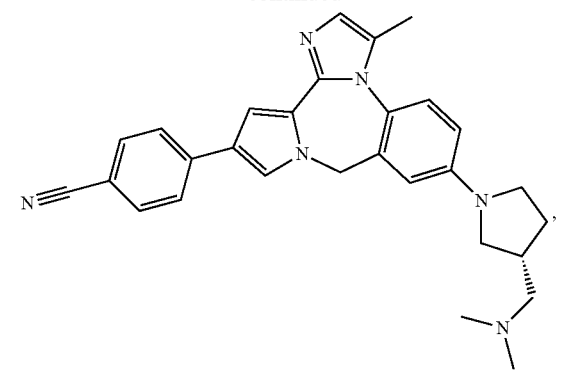
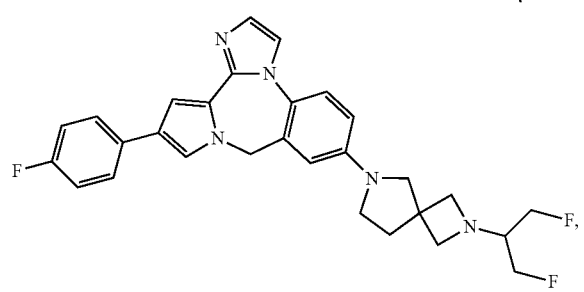
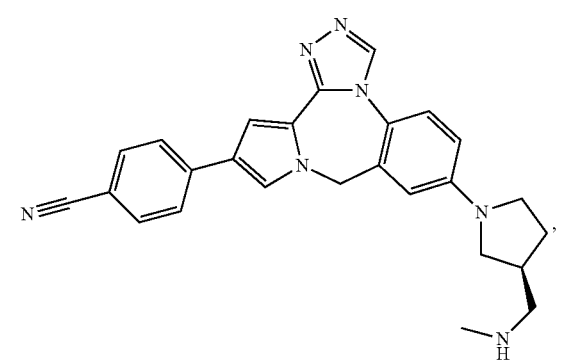
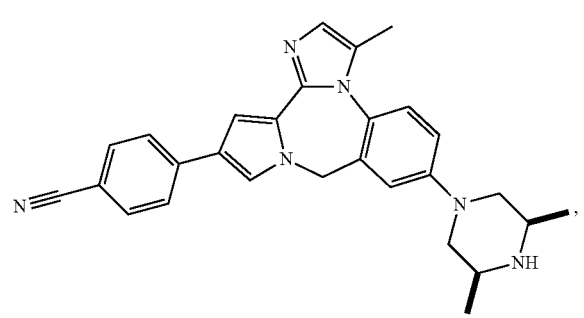
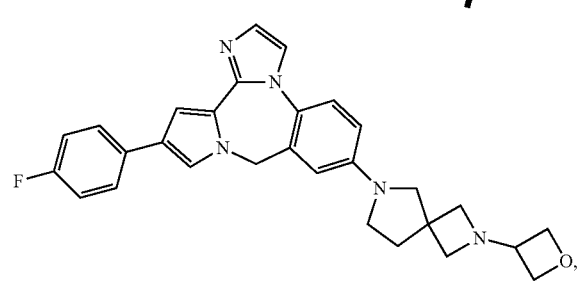
362
-continued
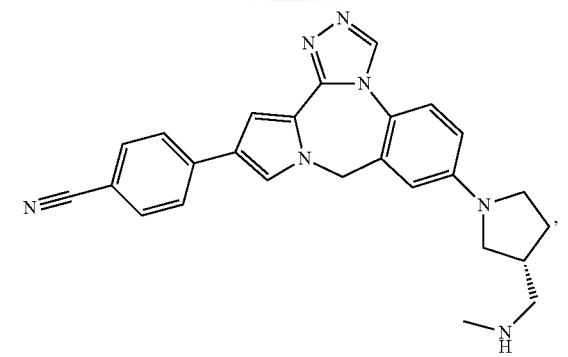
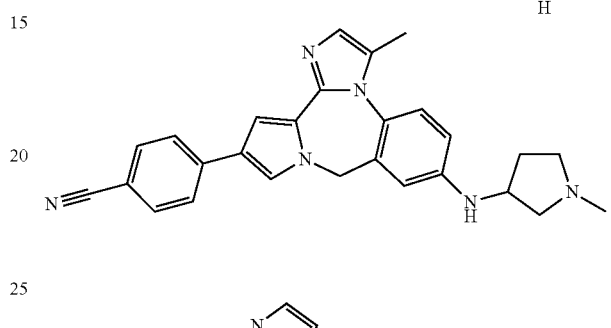
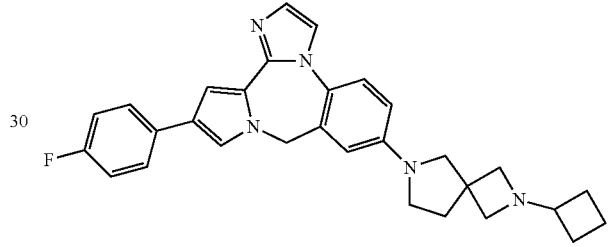
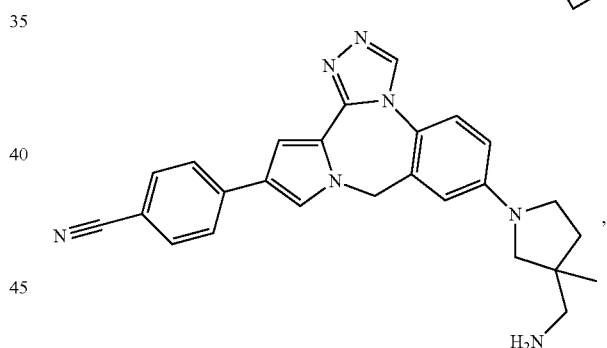
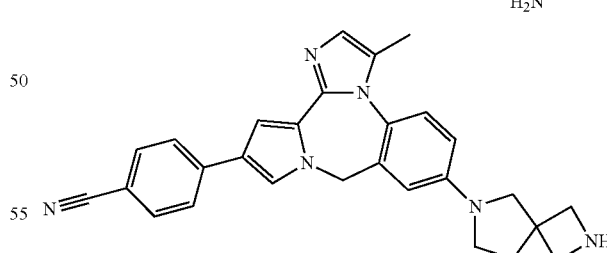
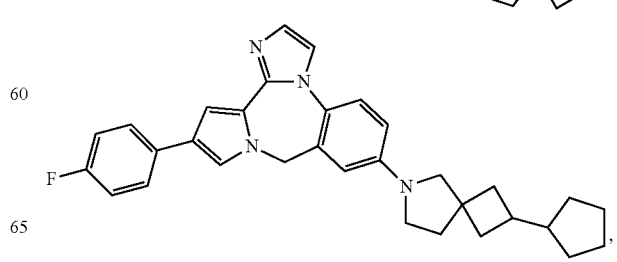

363
-continued
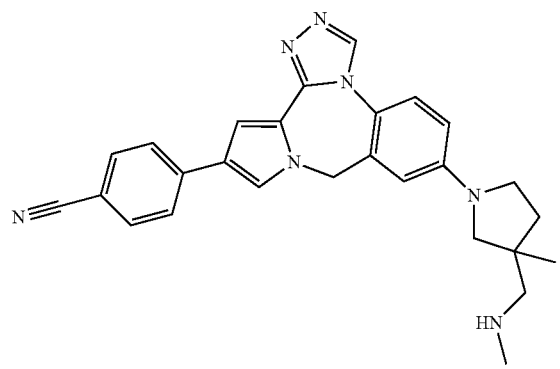
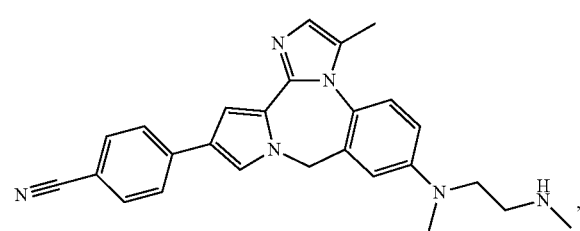
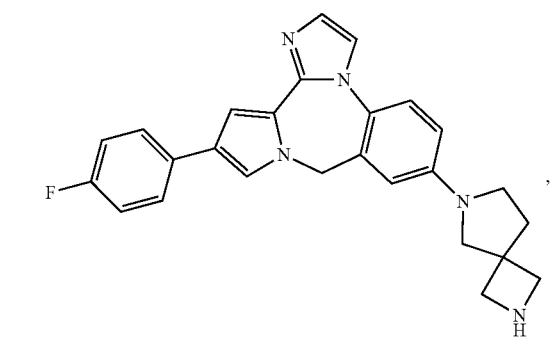
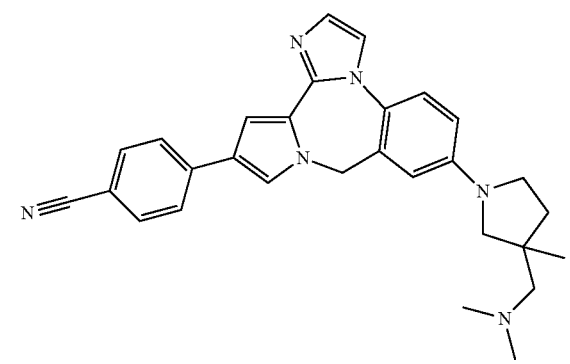
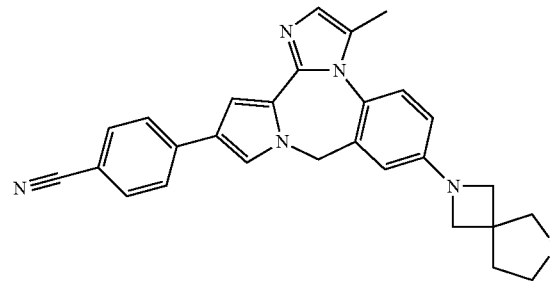
364
-continued
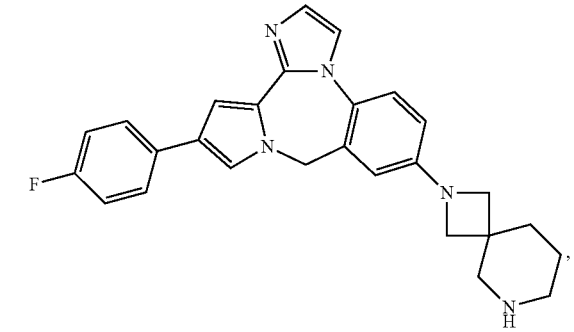
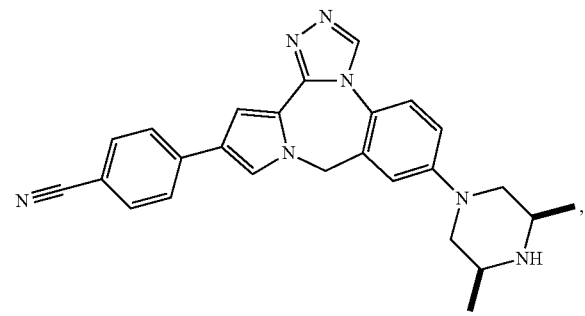
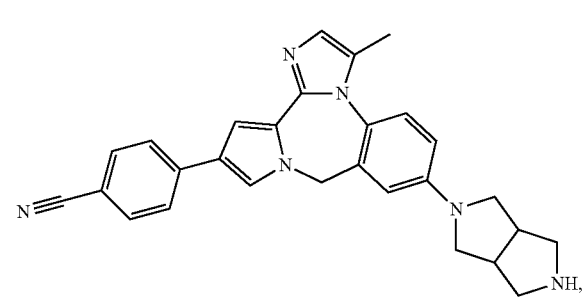
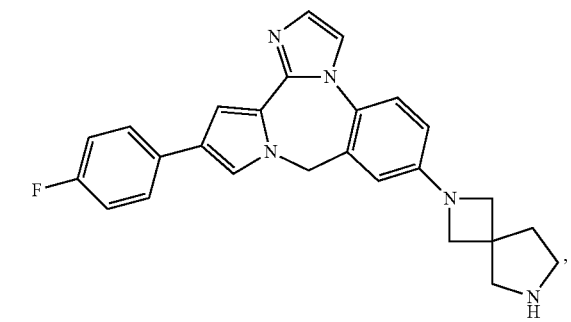
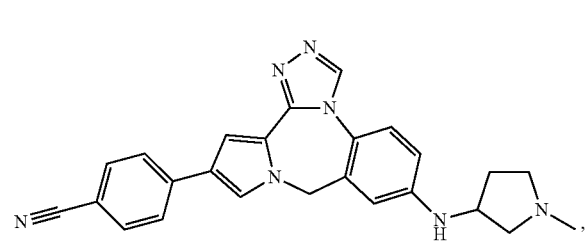

365
-continued
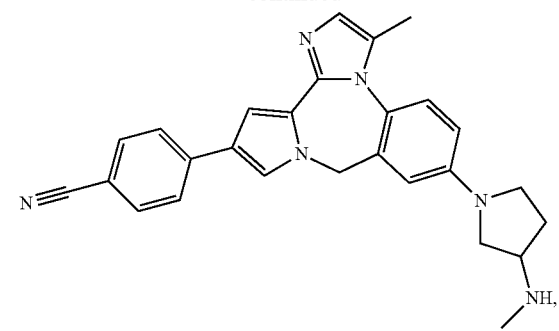
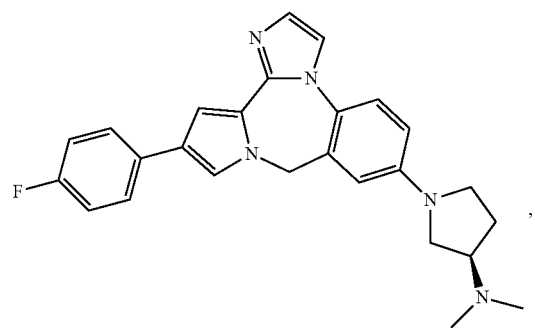
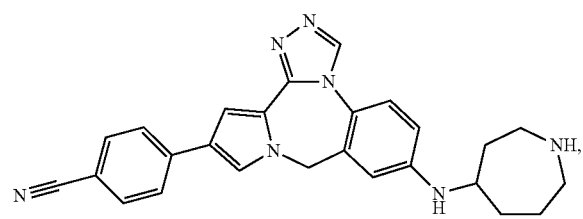
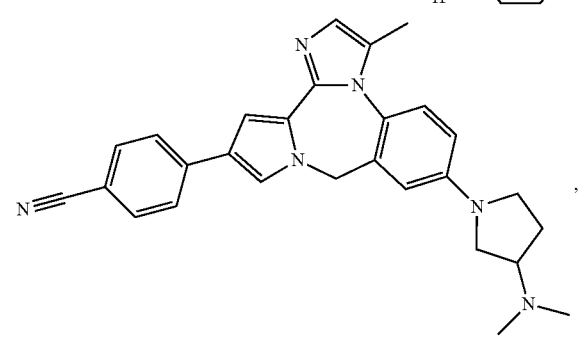
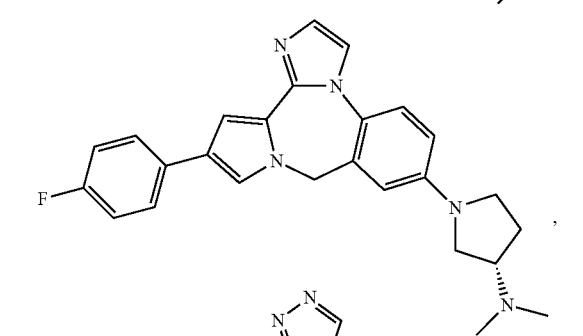
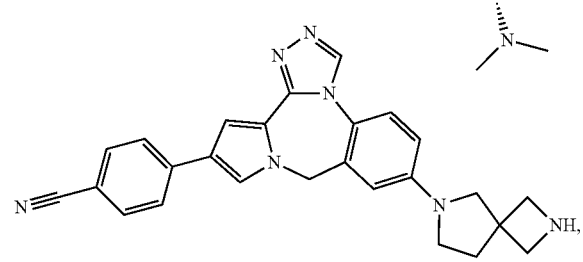
366
-continued
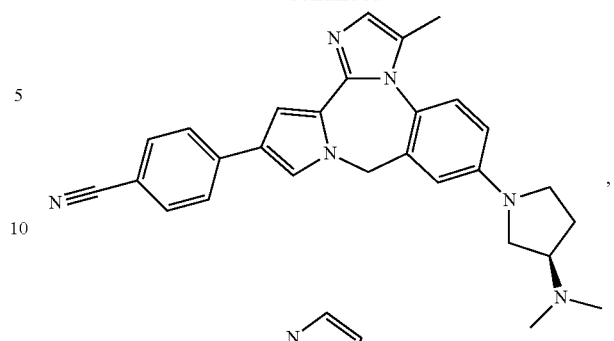
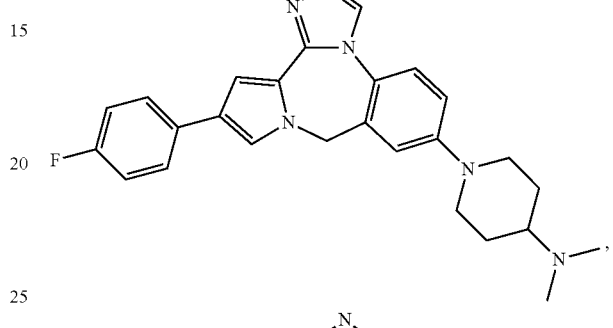
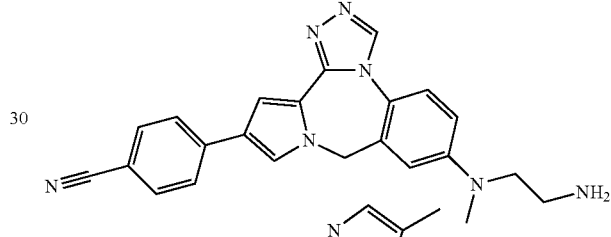
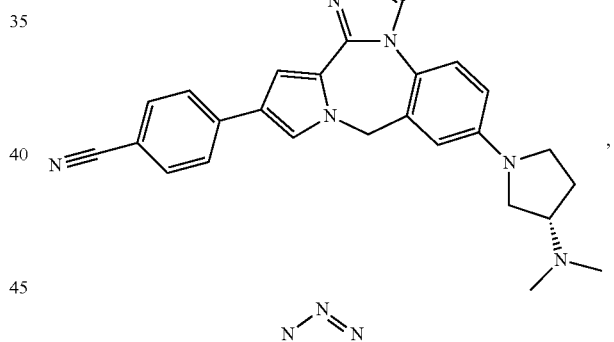
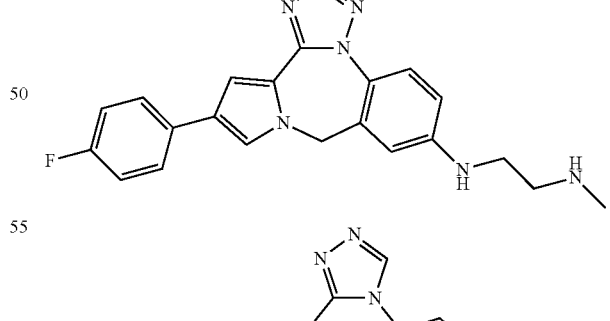
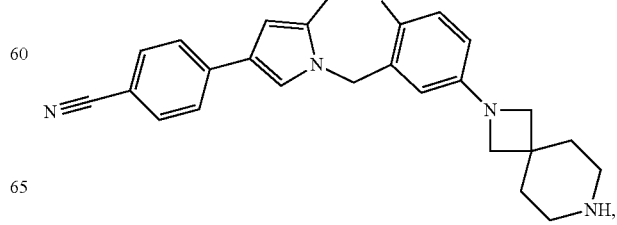

367
-continued
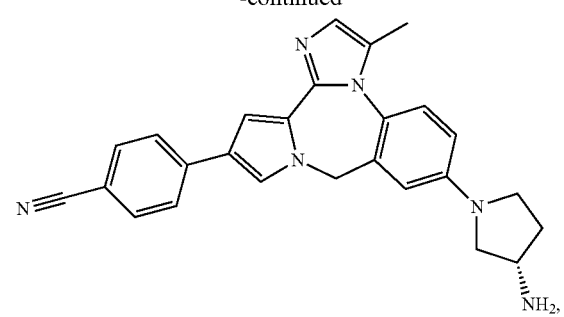
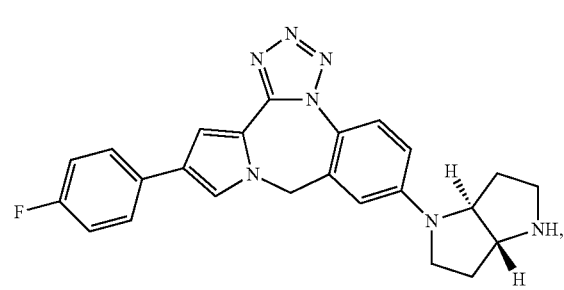
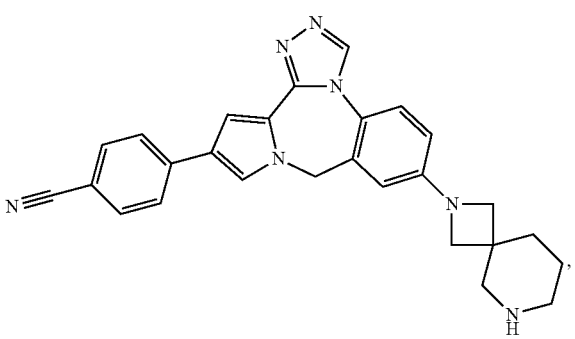
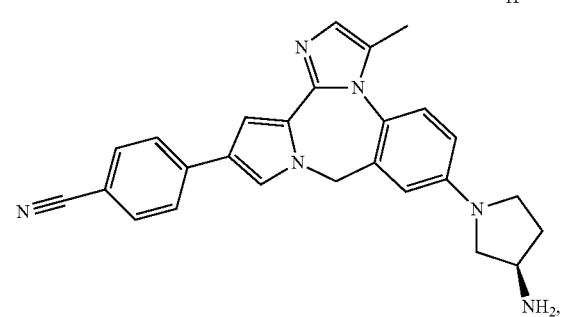
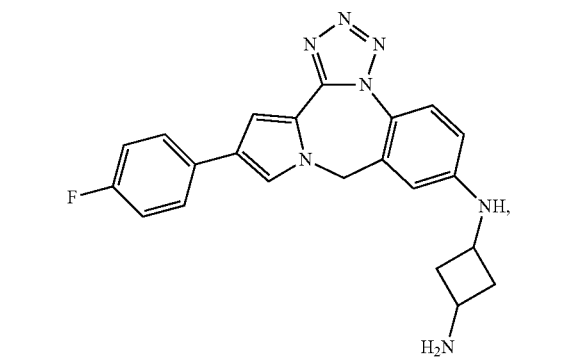
368
-continued
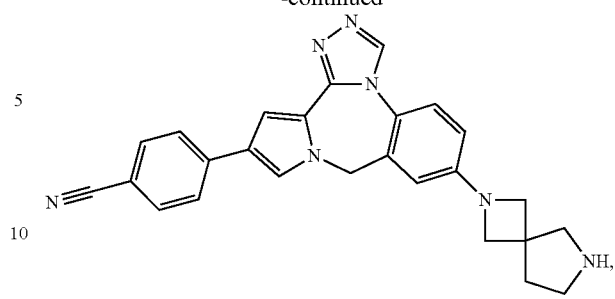
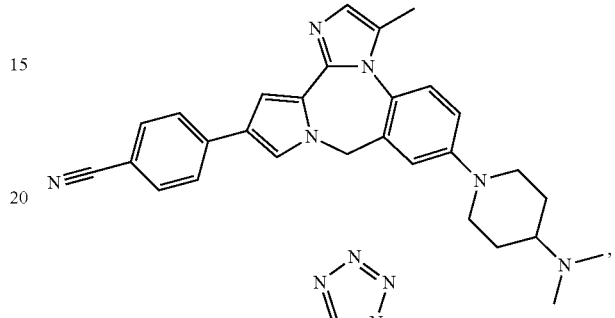
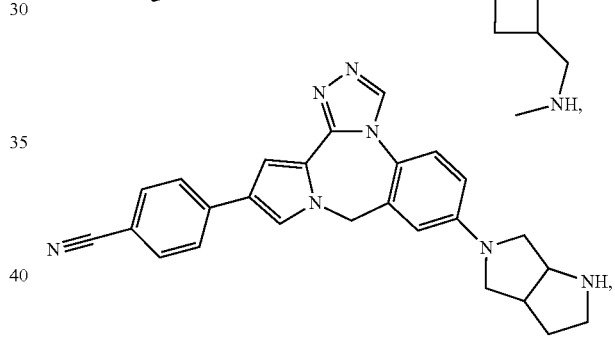
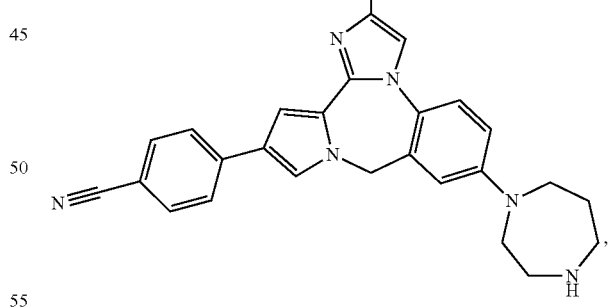
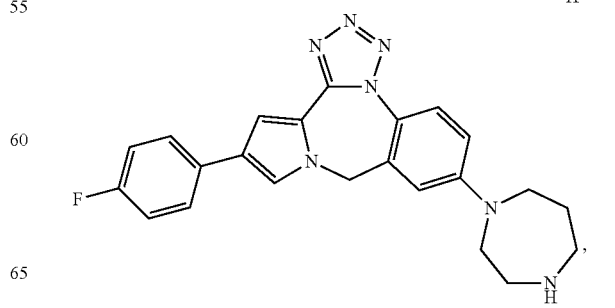

369
-continued
370
-continued
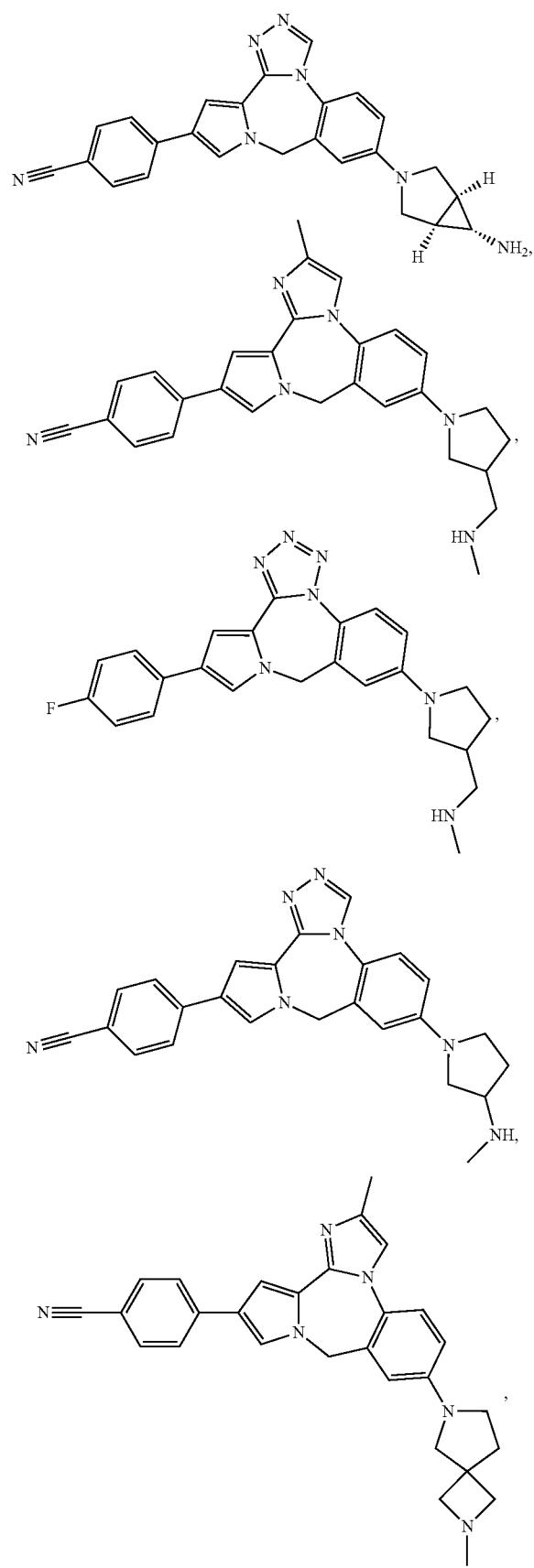
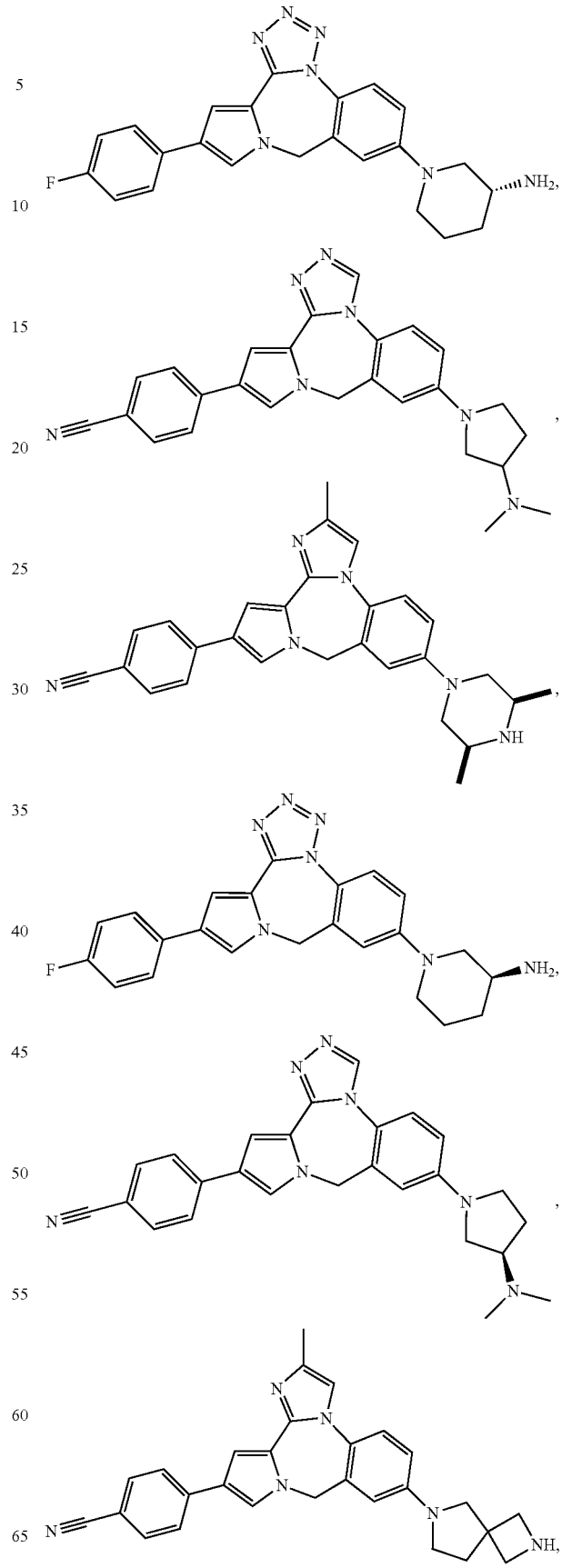

371
-continued
372
-continued
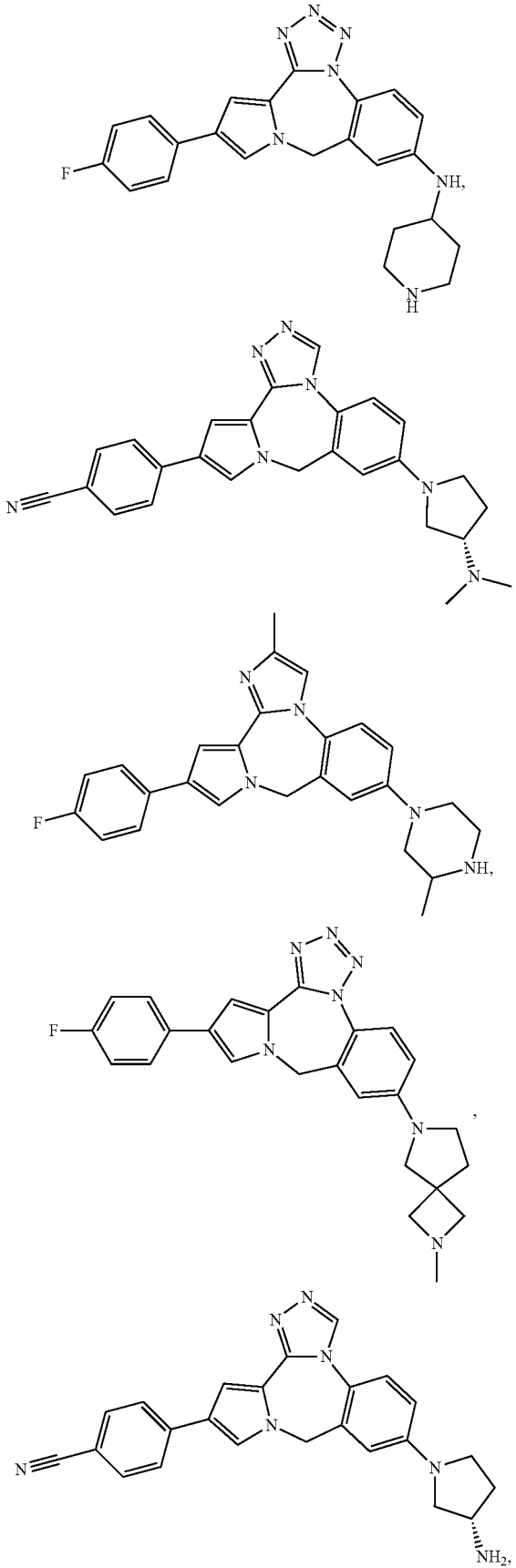
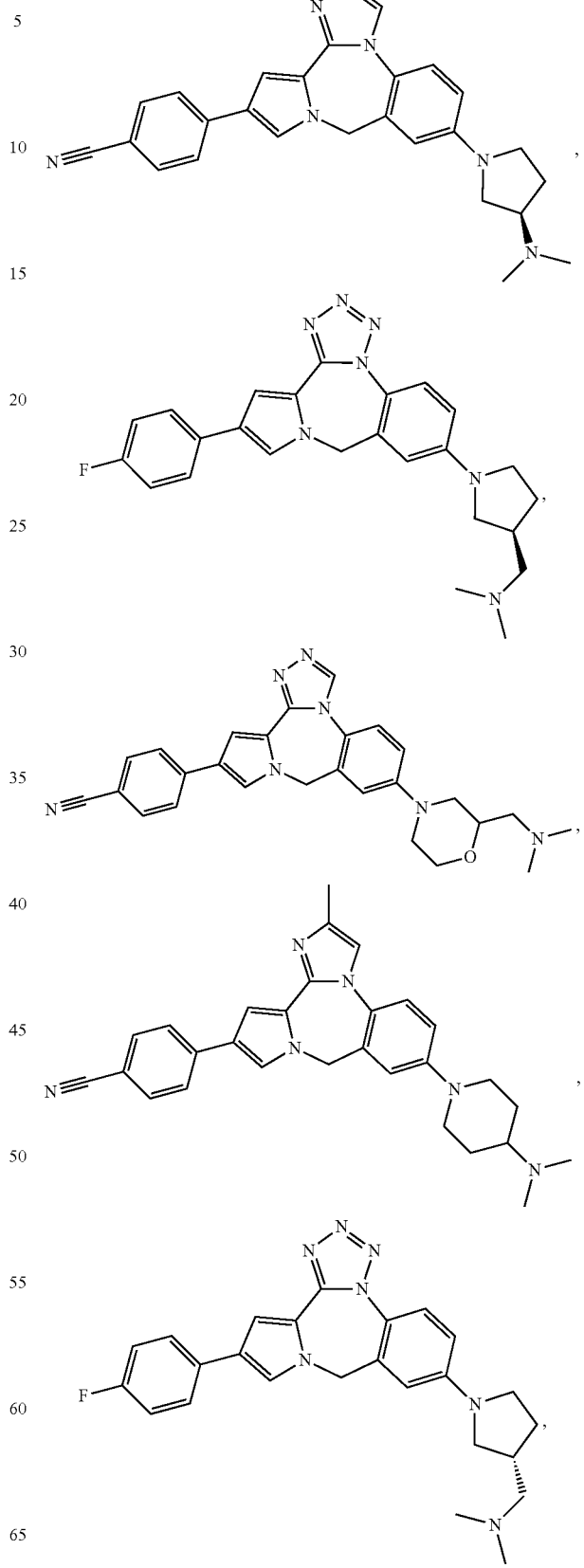

373
-continued
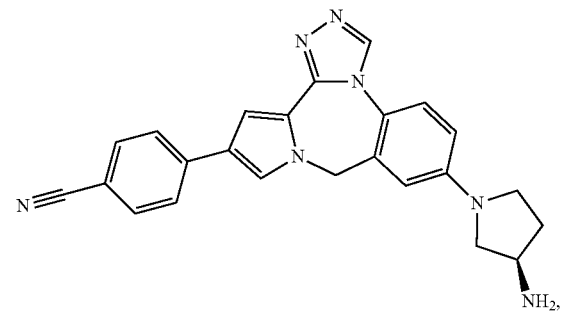
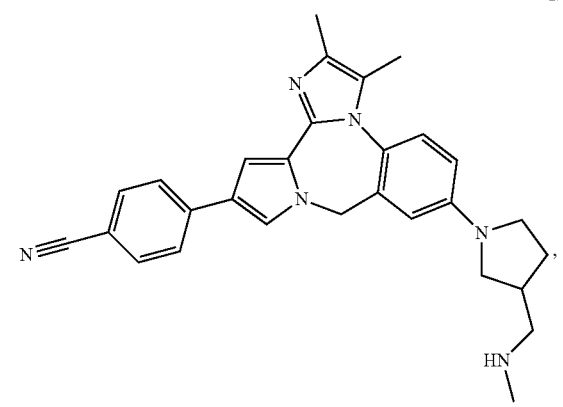
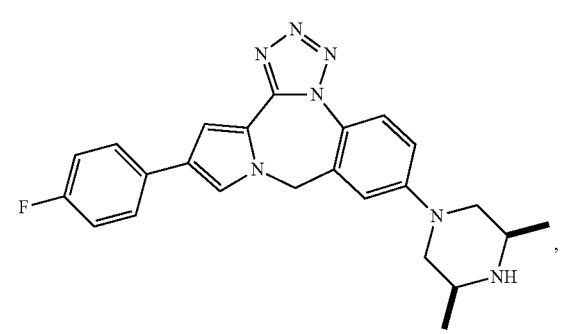
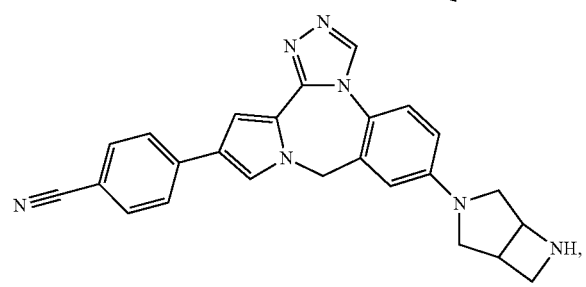
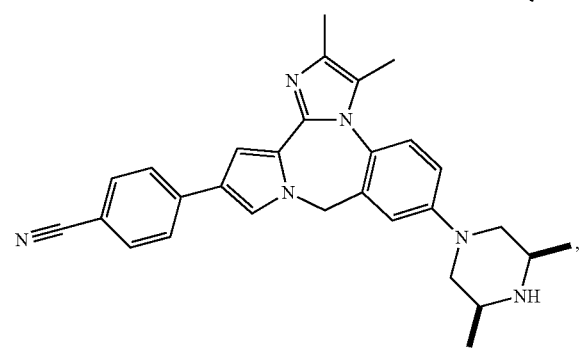
374
-continued
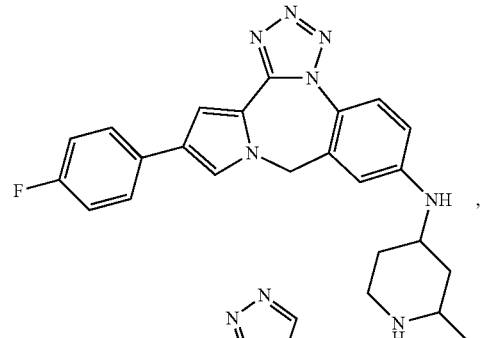
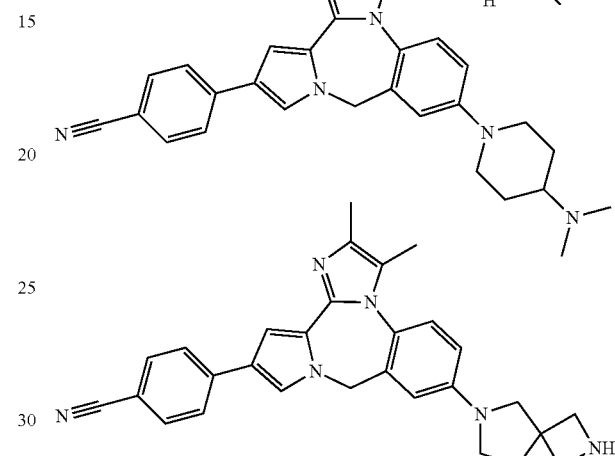
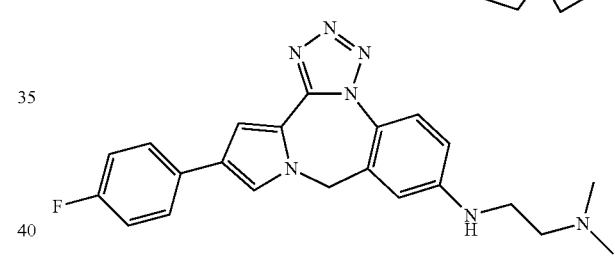
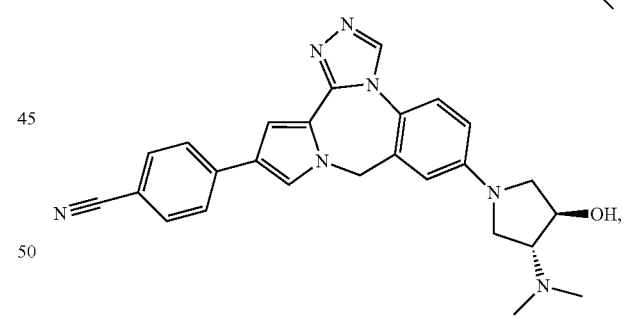
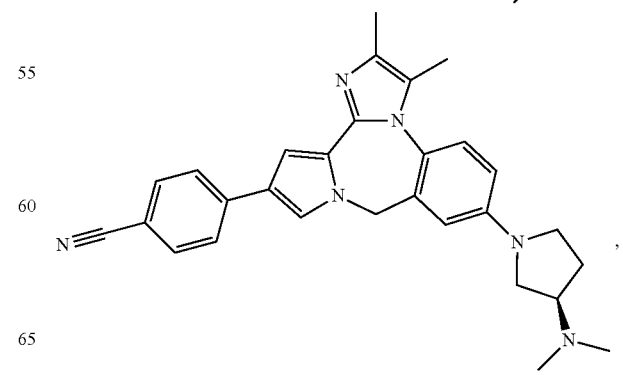

US 10,562,909 B2
375
-continued
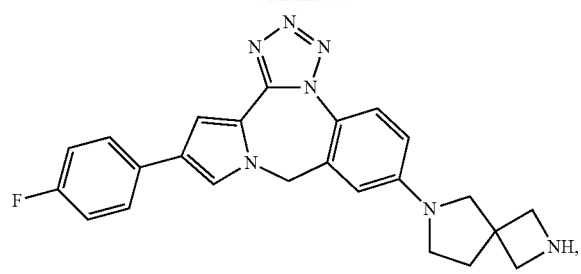
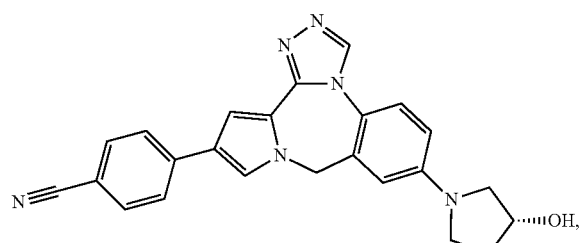
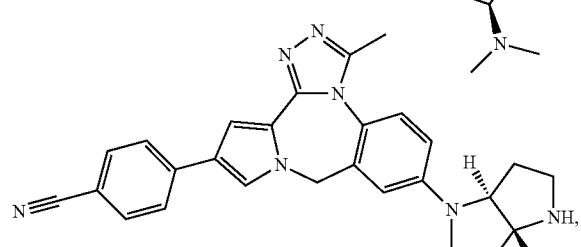
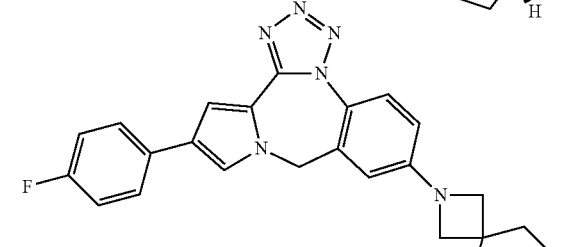
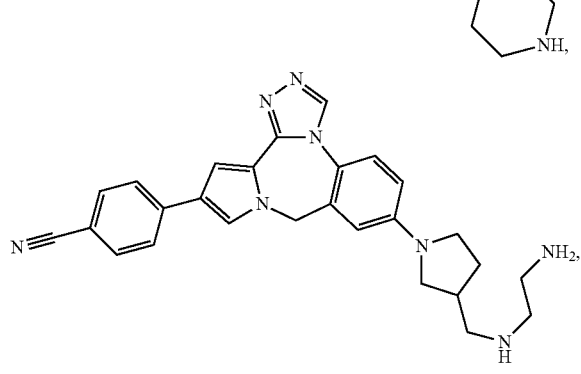
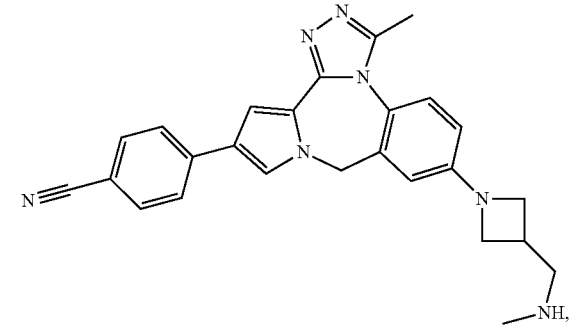
376
-continued
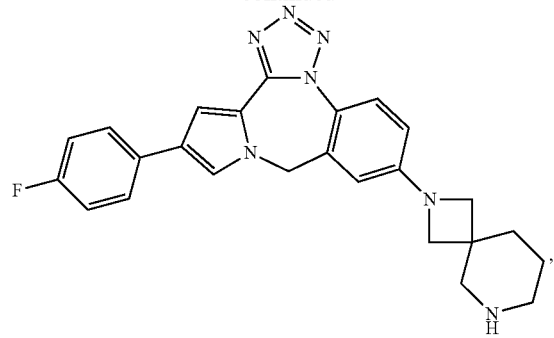
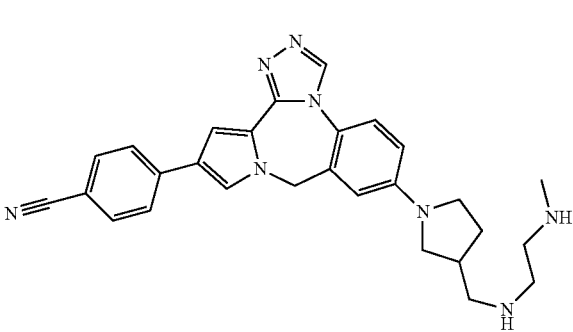
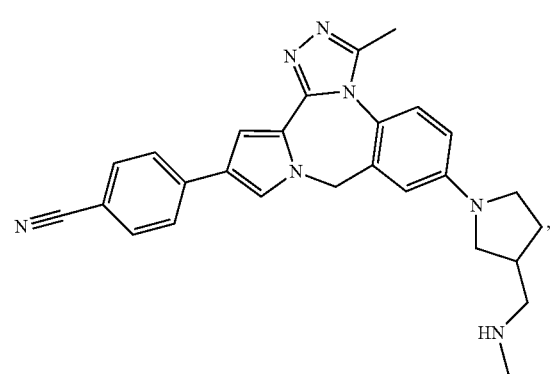
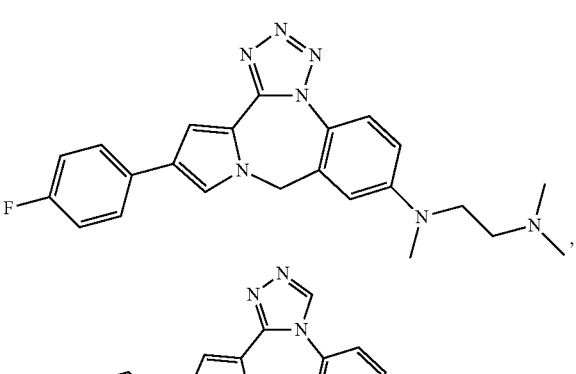
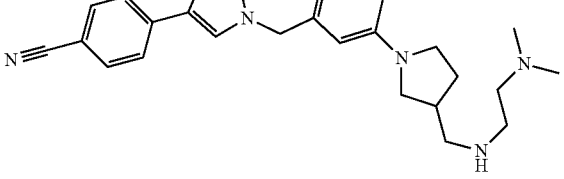

377
-continued
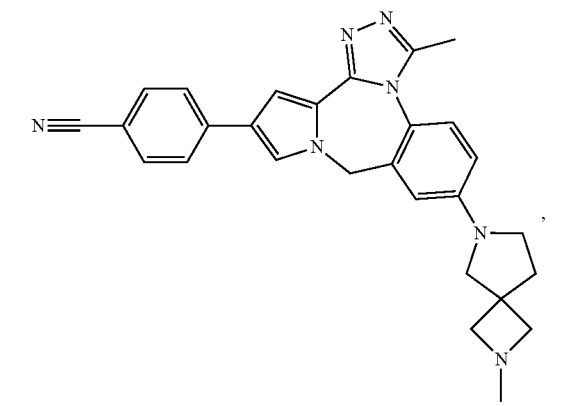
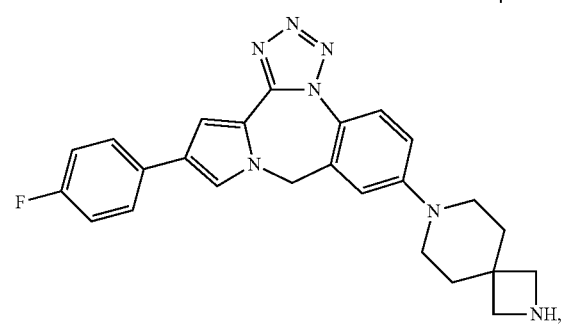
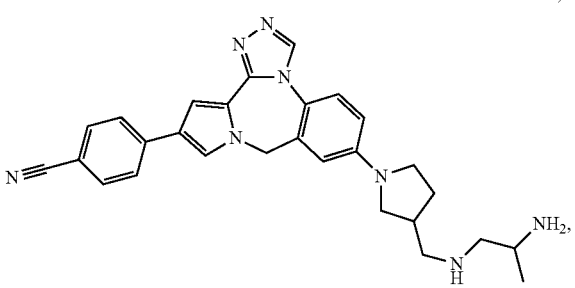
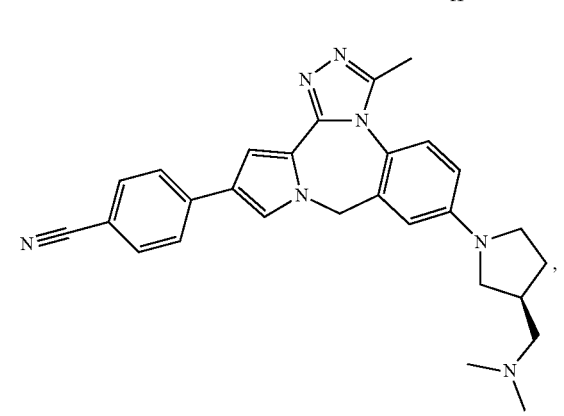
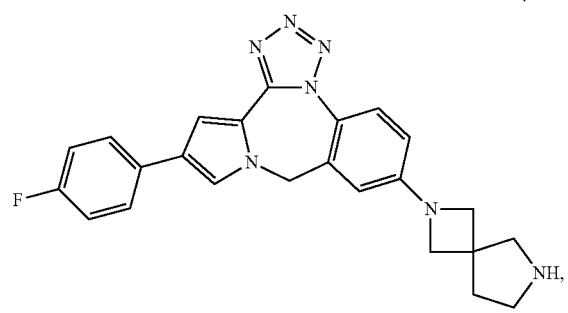
378
-continued
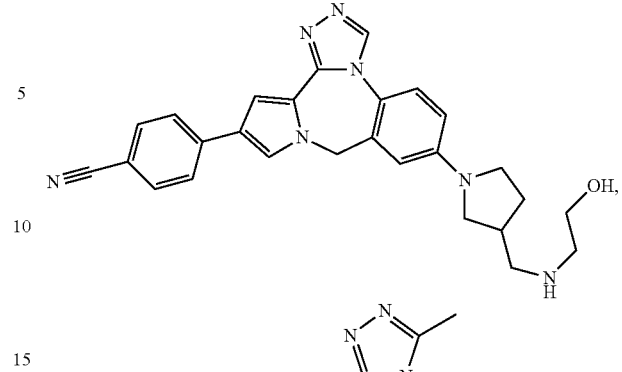
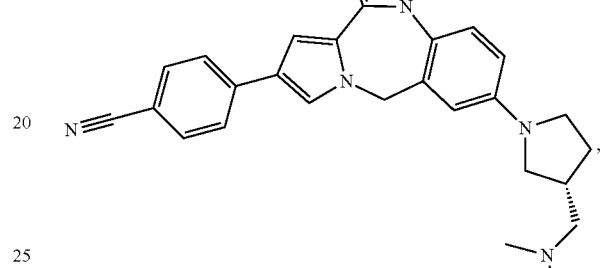
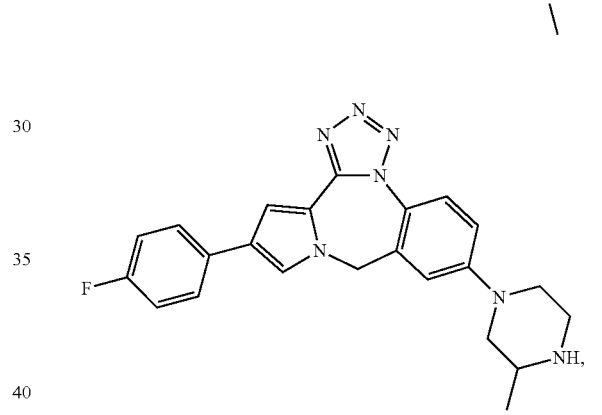
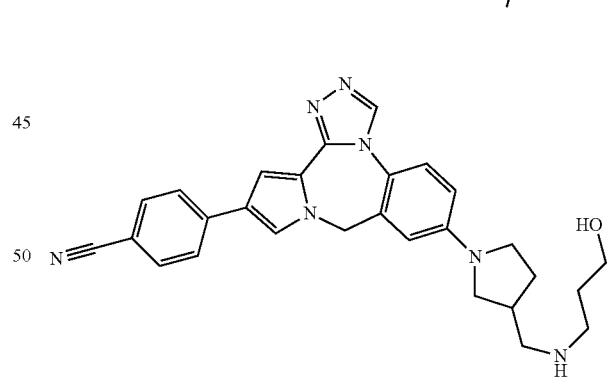
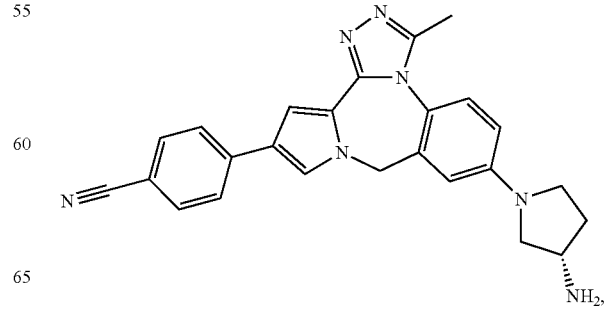

379
-continued
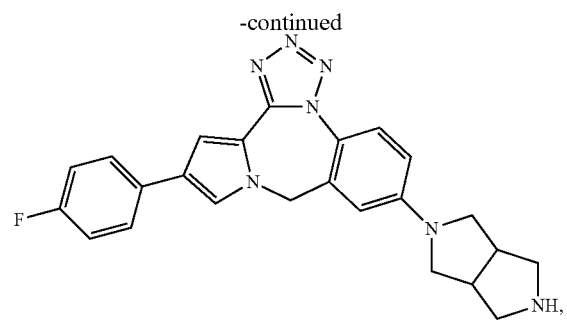
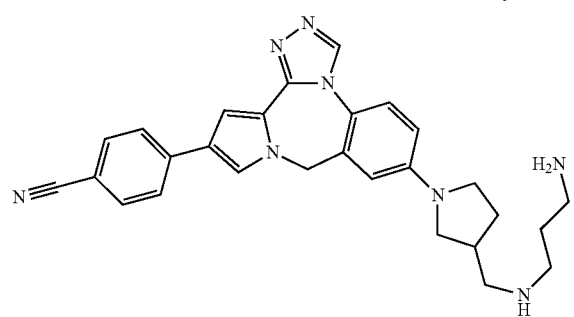
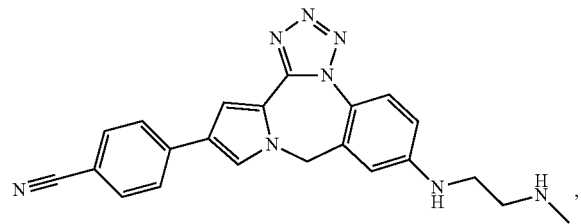
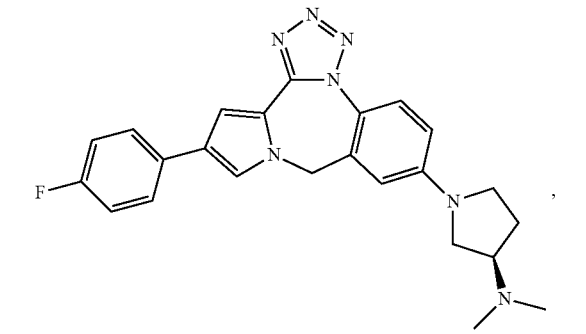
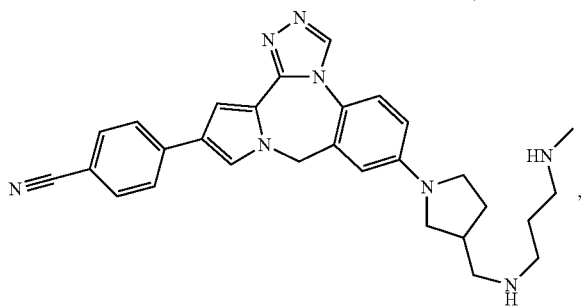
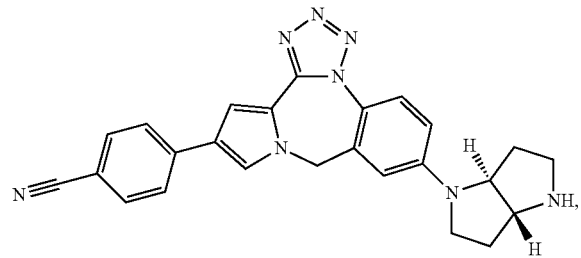
380
-continued
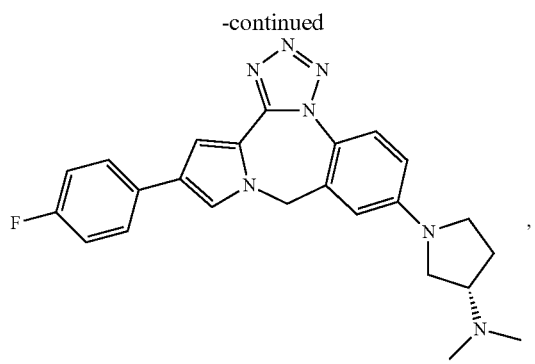
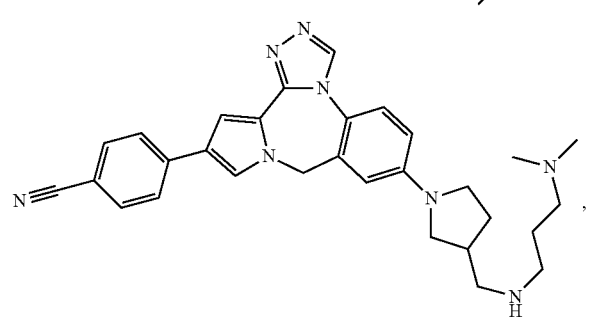
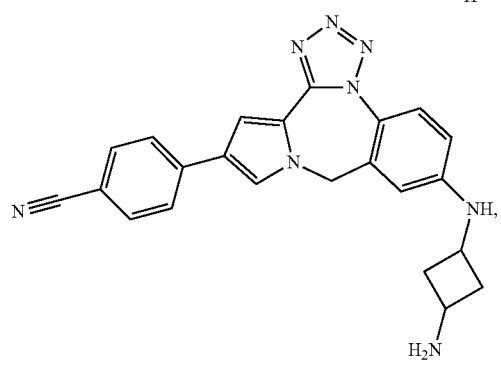
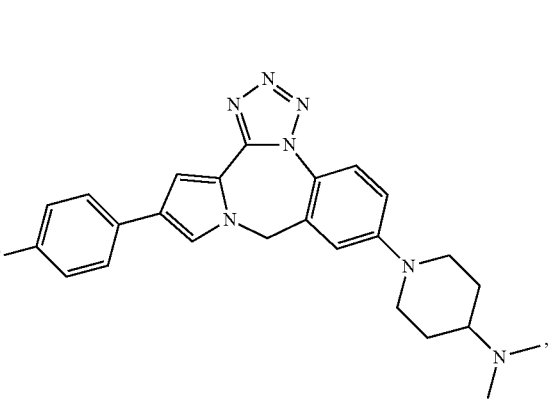
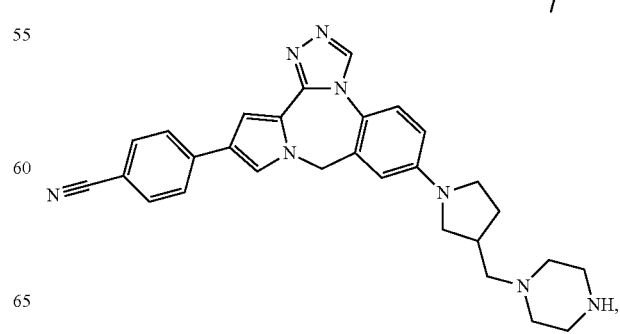

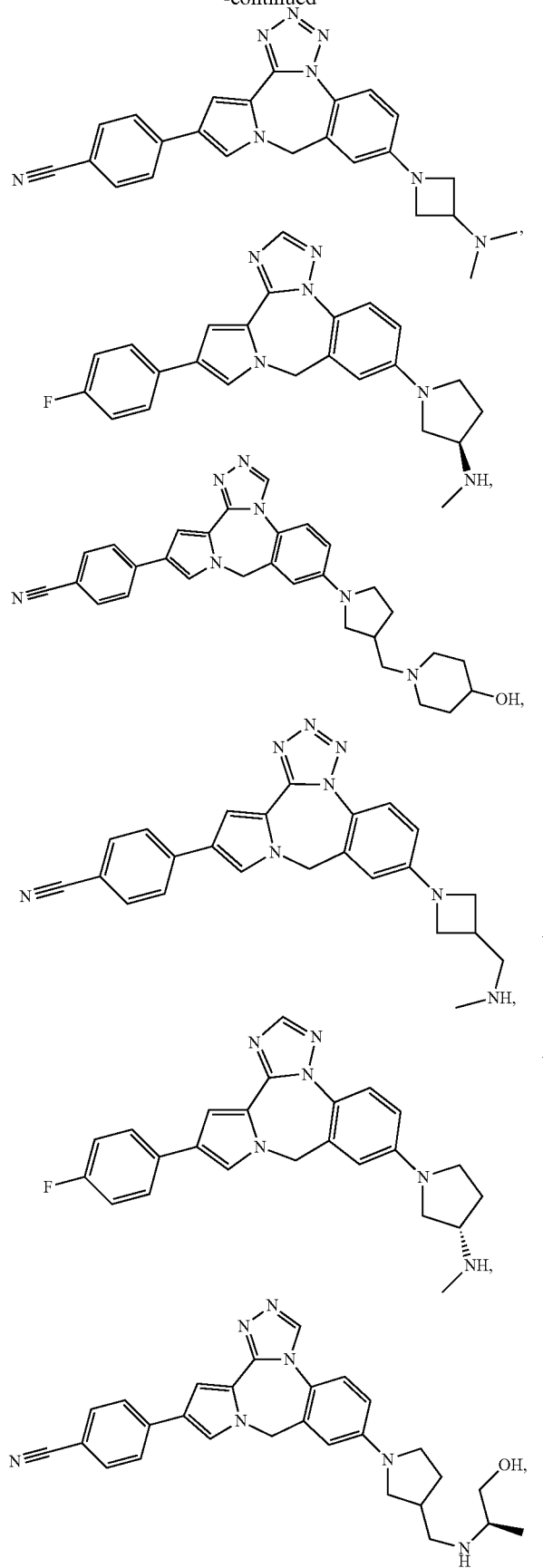
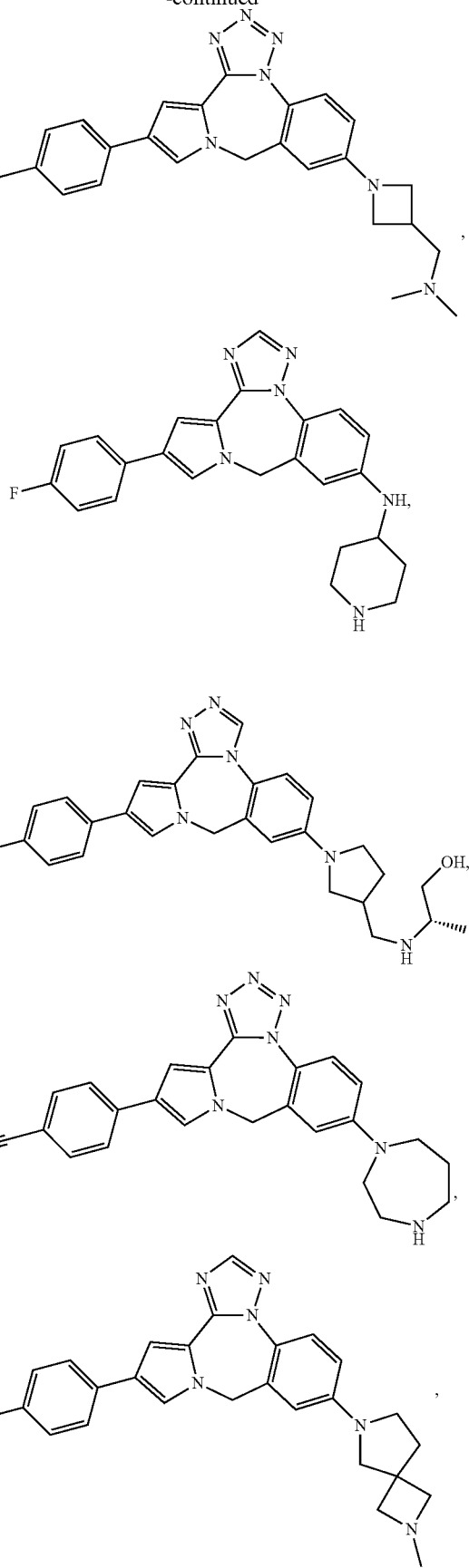

383
-continued
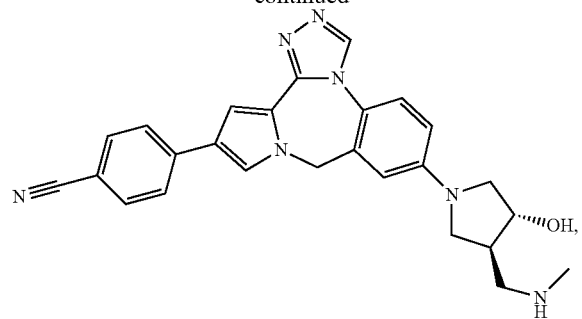
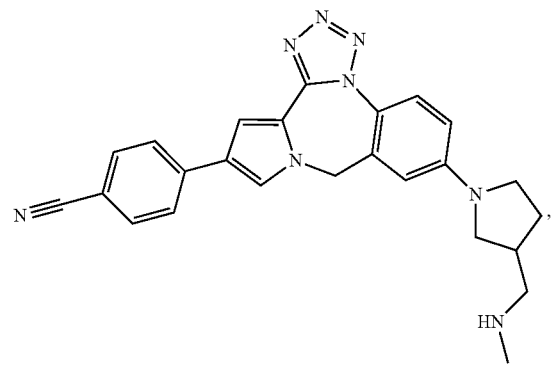
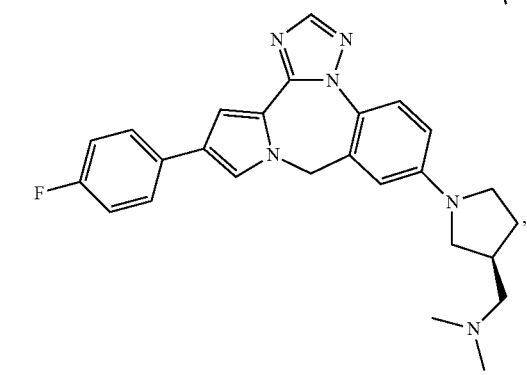
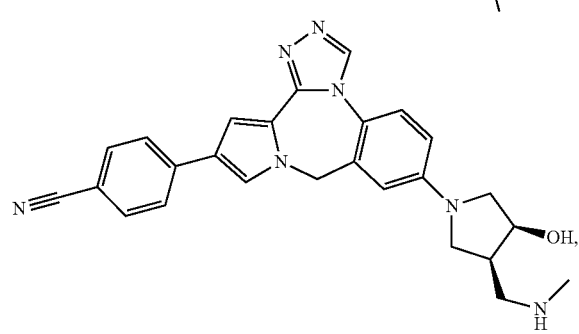
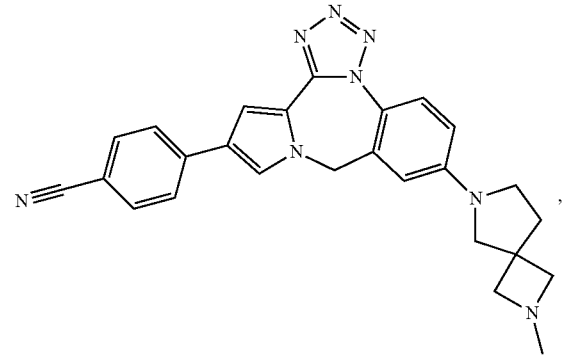
384
-continued
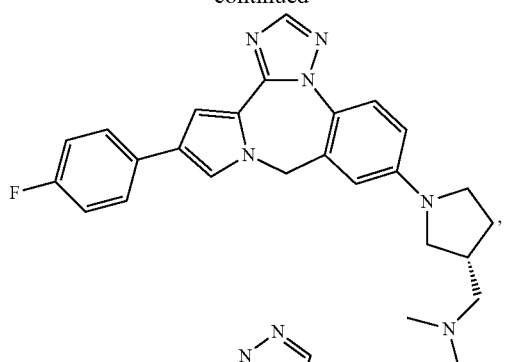
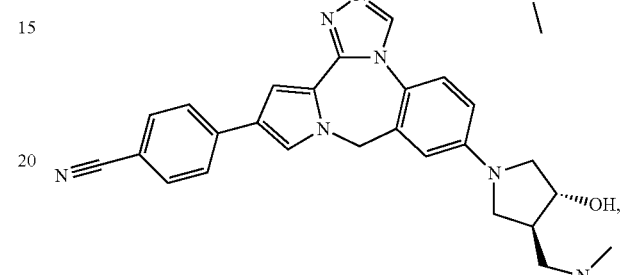
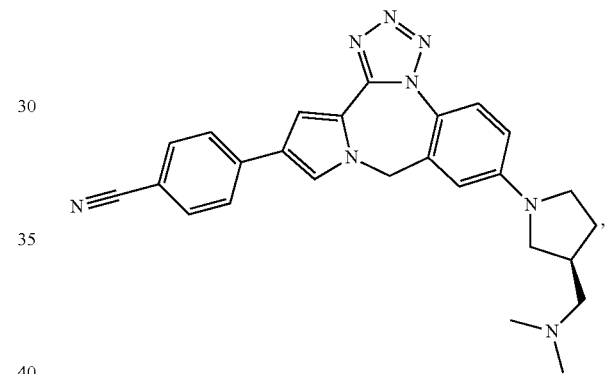
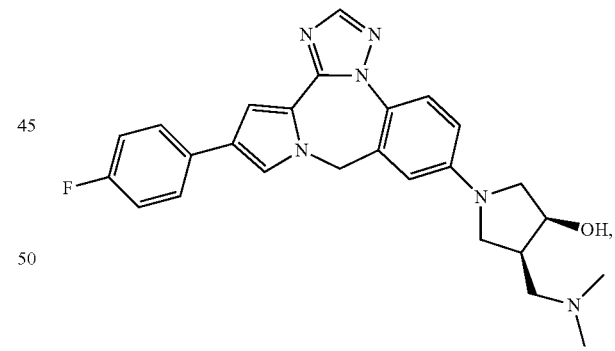
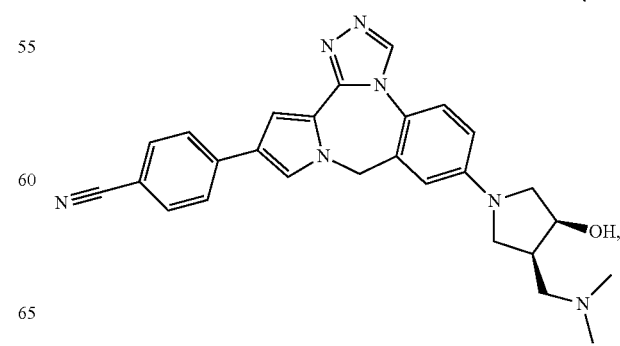

385
-continued
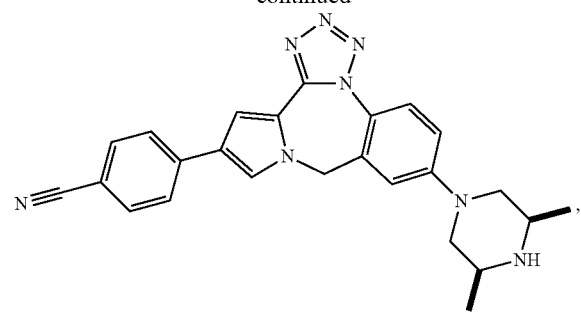
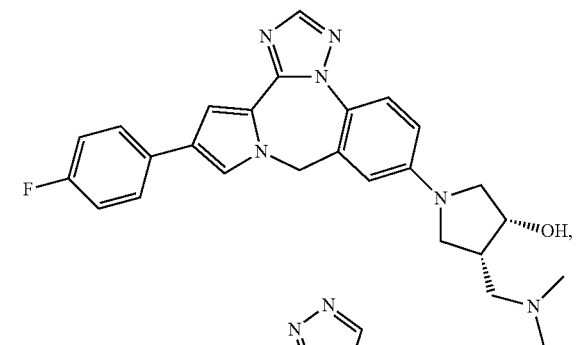
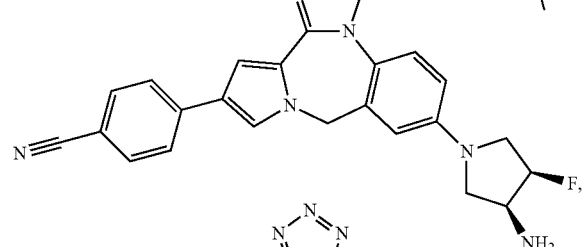
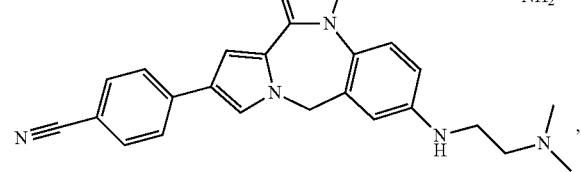
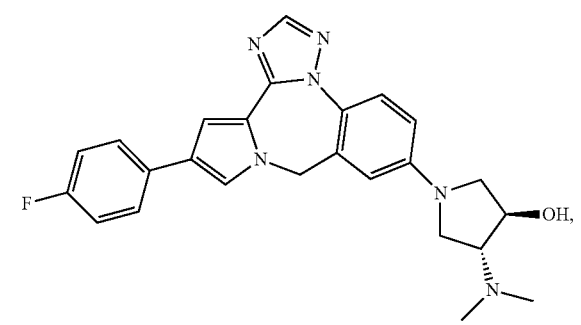
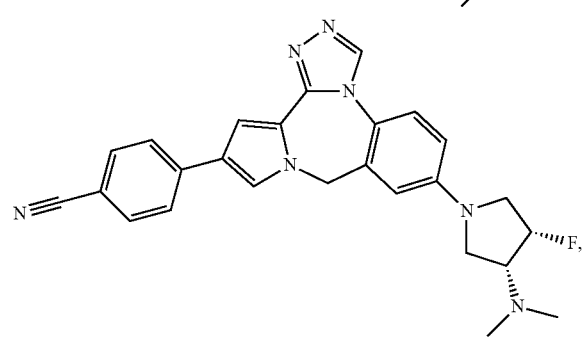
386
-continued
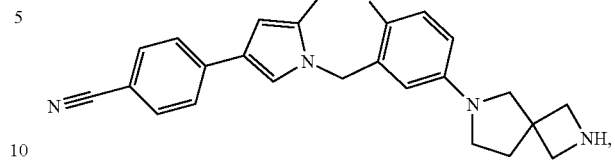
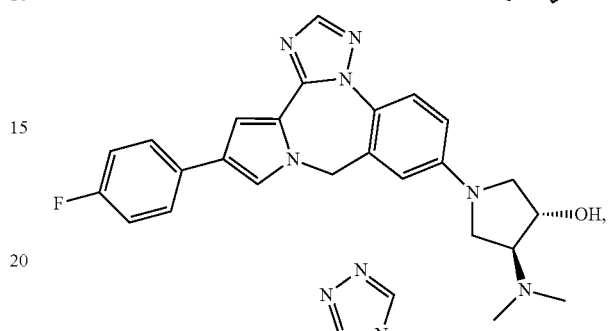
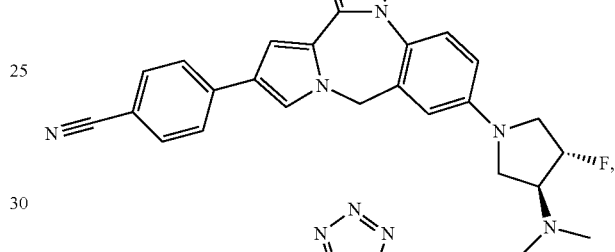
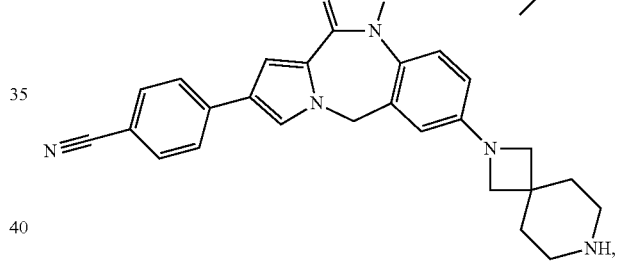
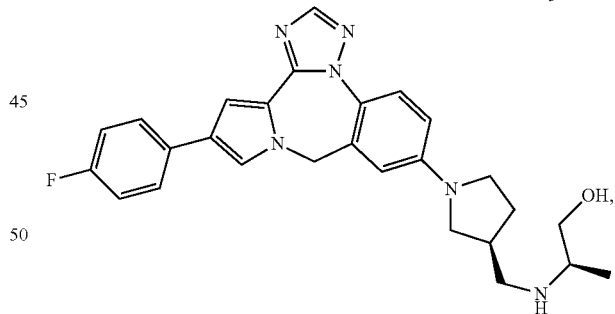
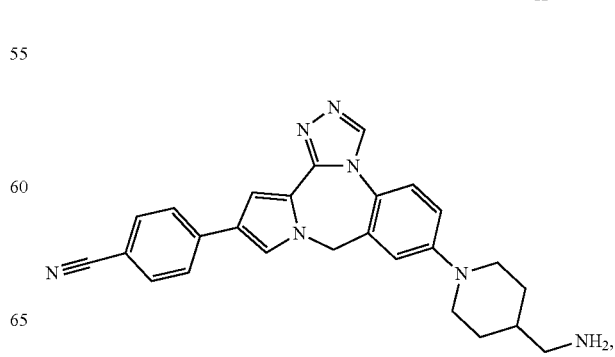

387 -continued
388 -continued
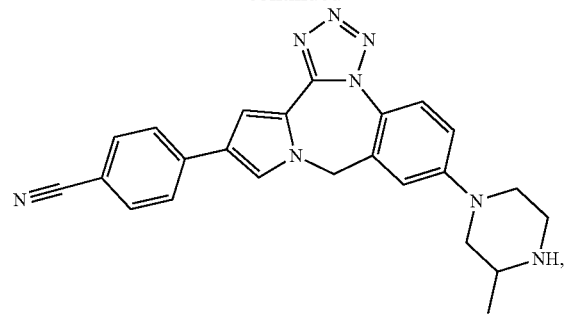
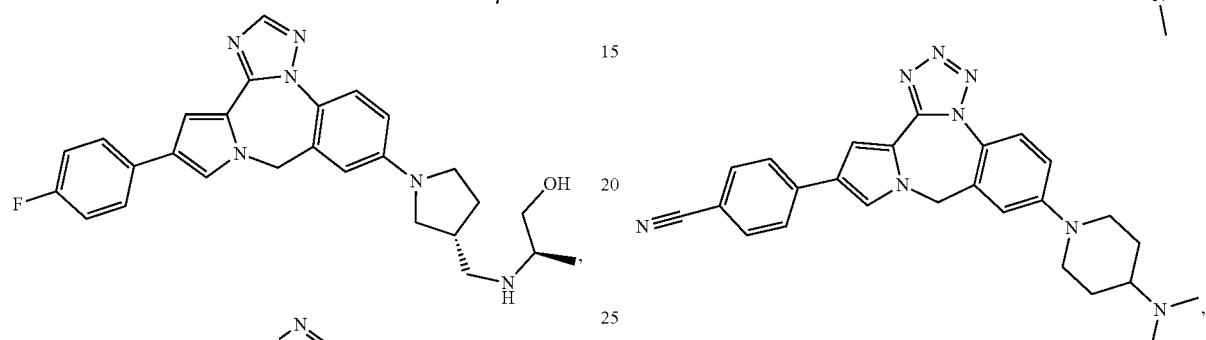
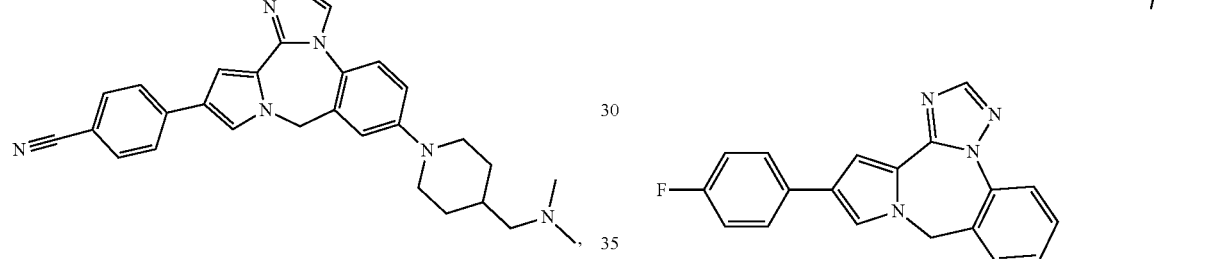
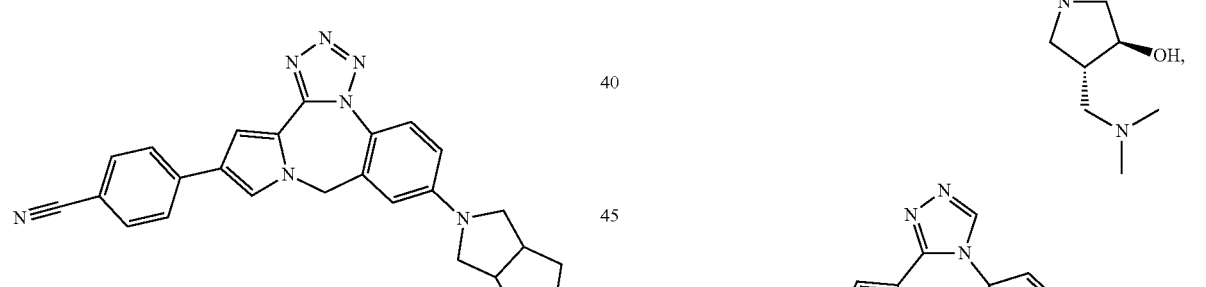
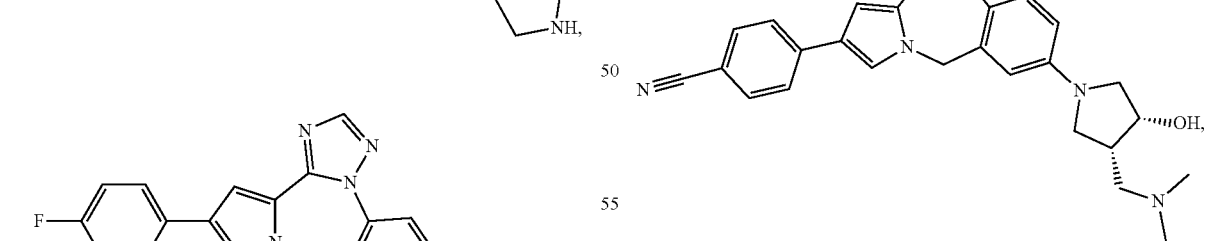
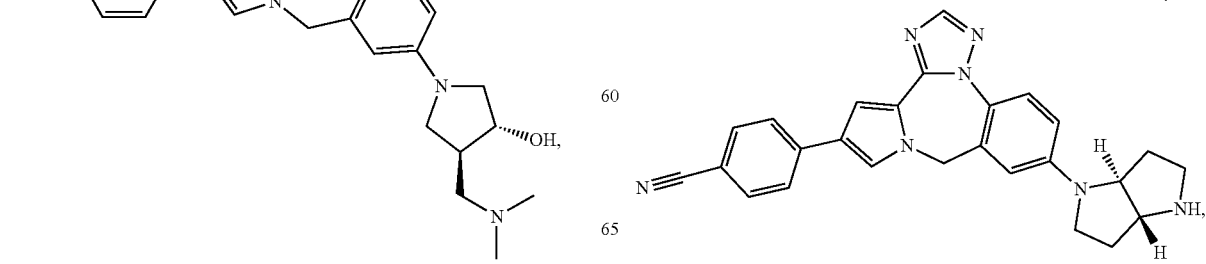

389
-continued
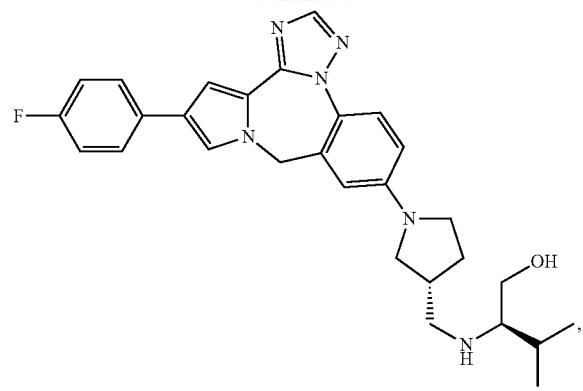
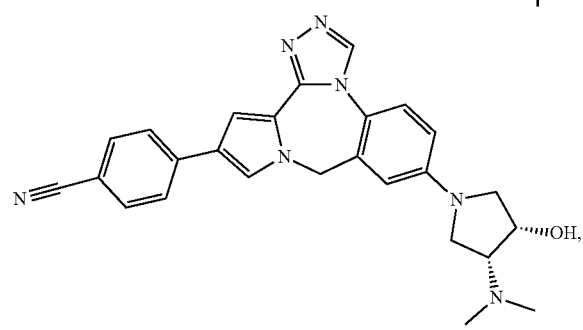
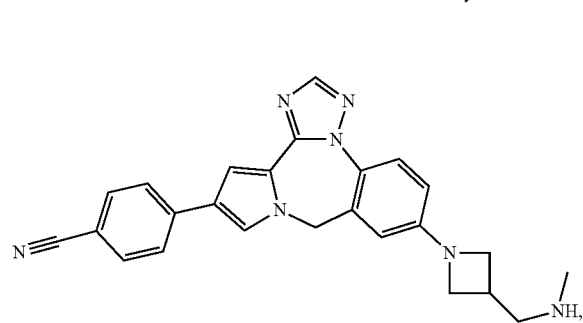
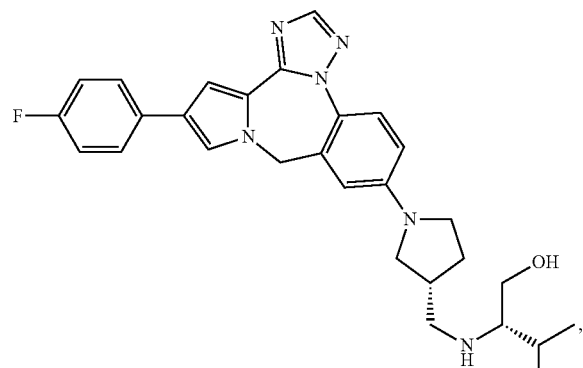
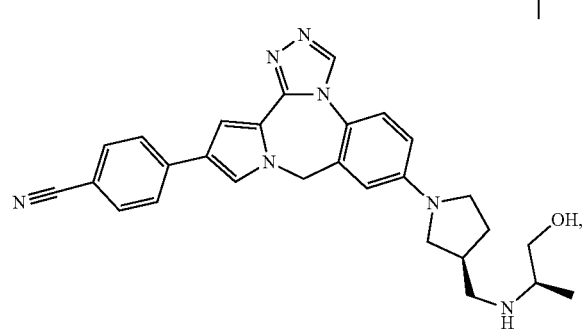
390
-continued
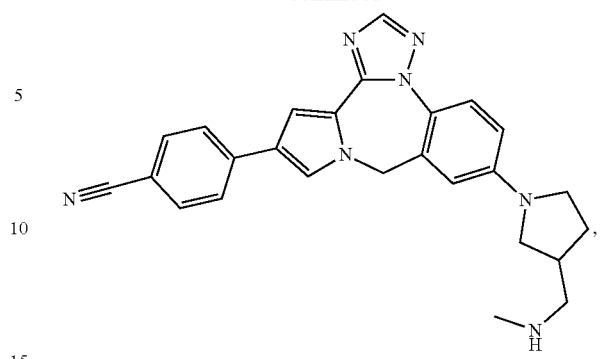
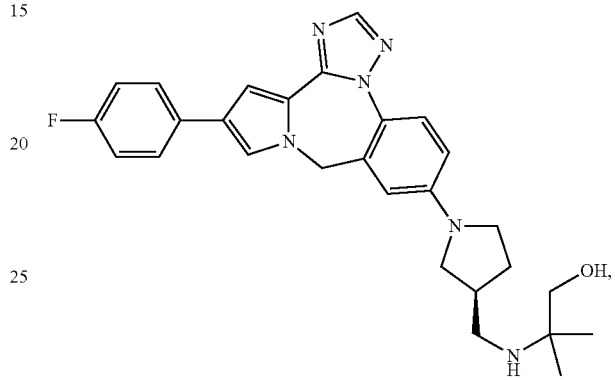
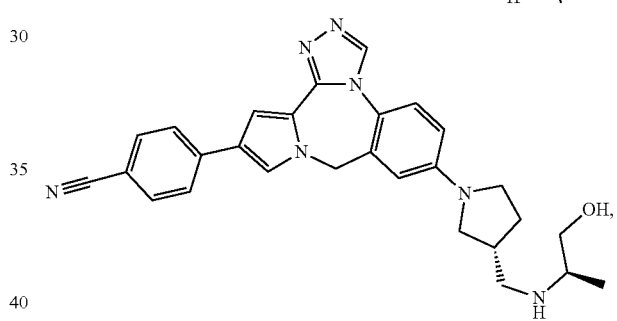
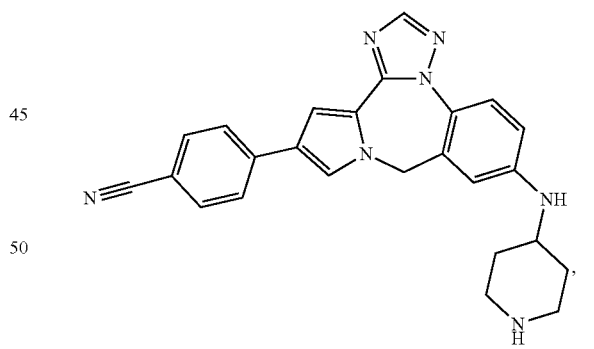
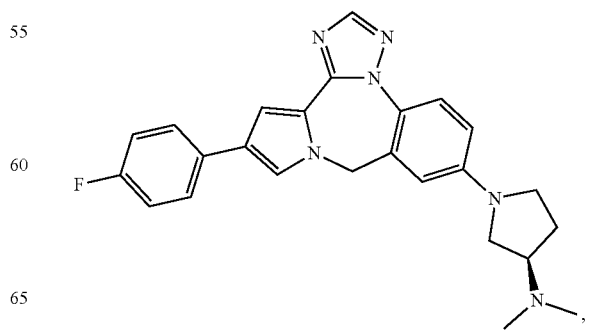

391
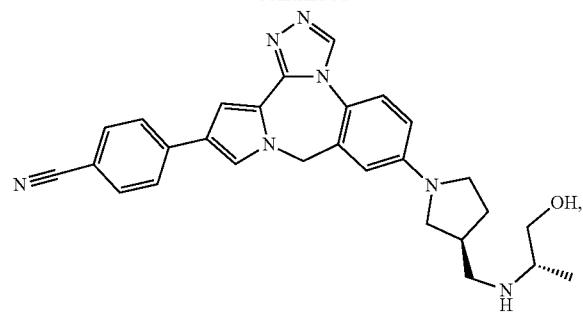
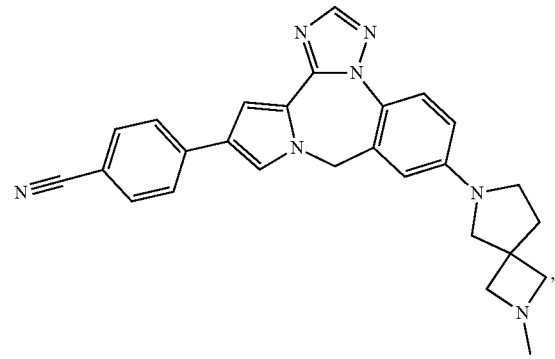
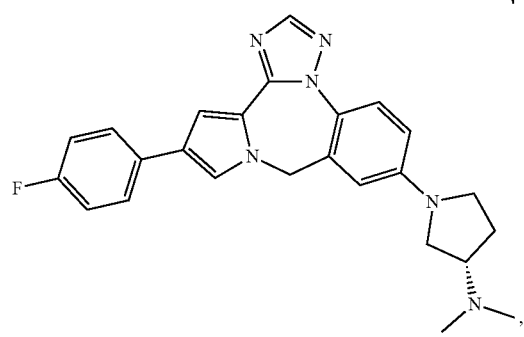
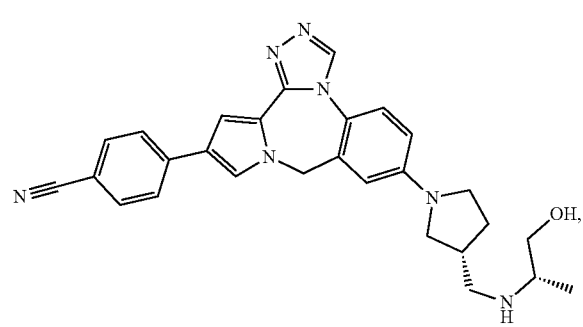
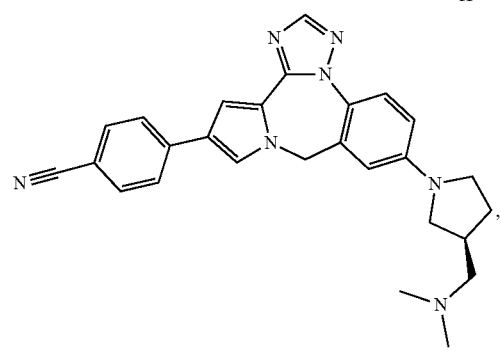
392
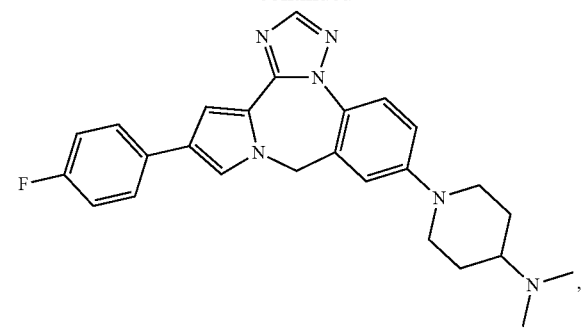
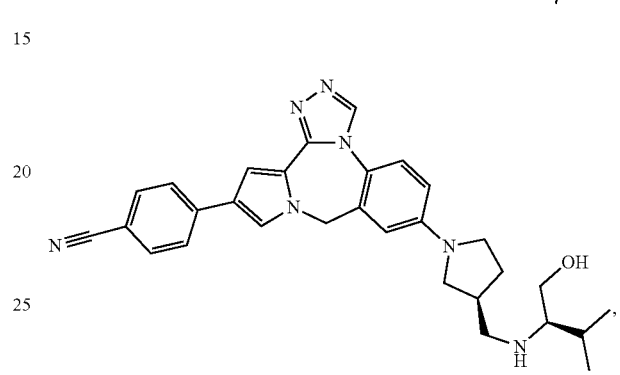
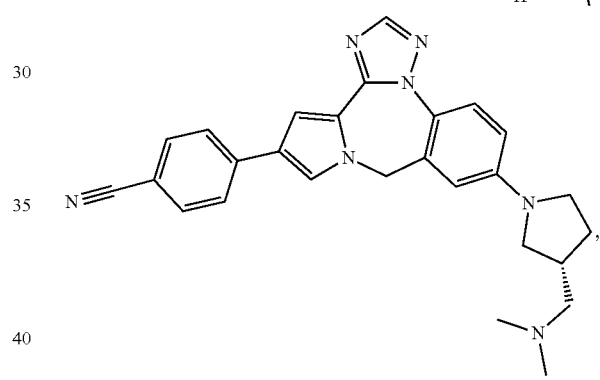
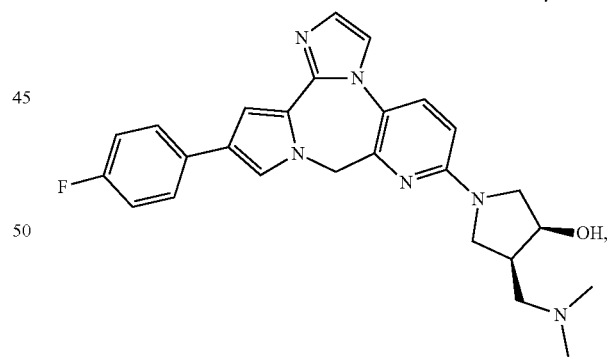
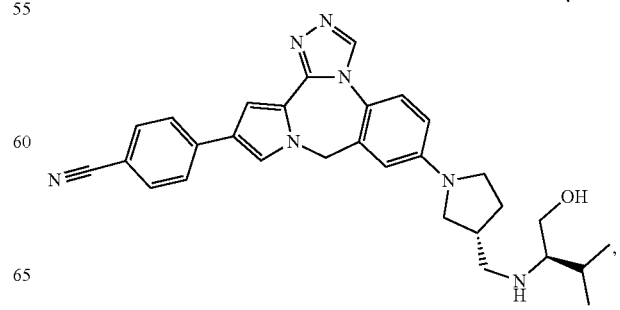

393
-continued
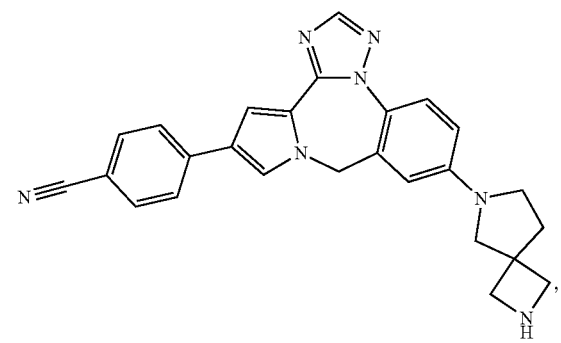
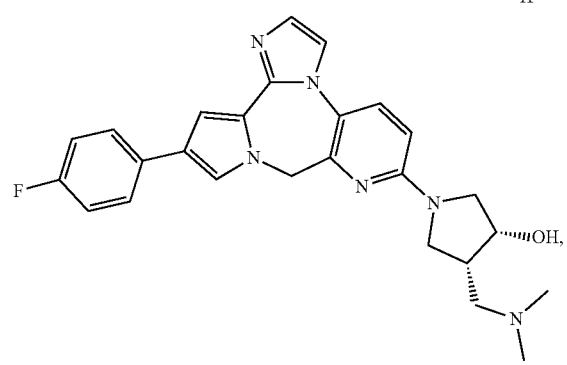
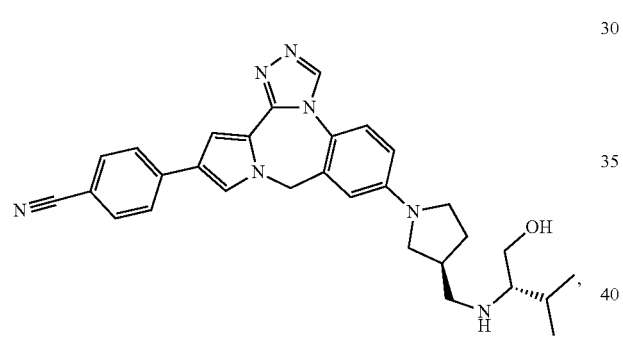
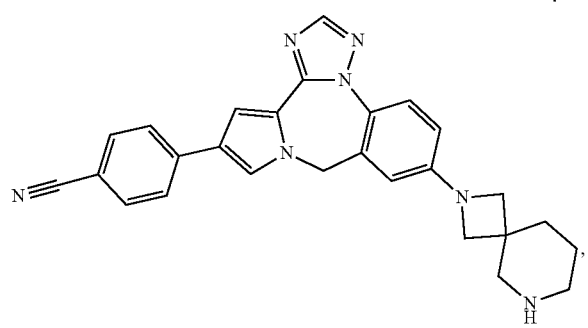
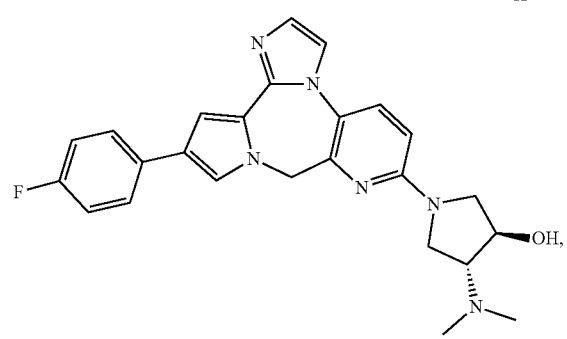
394
-continued
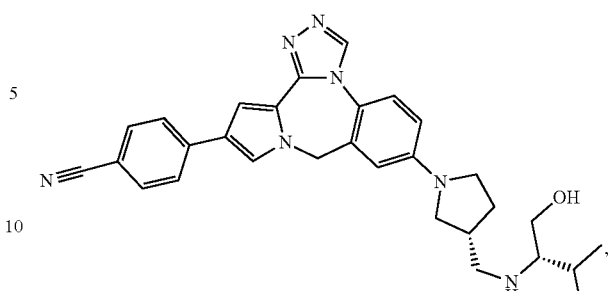
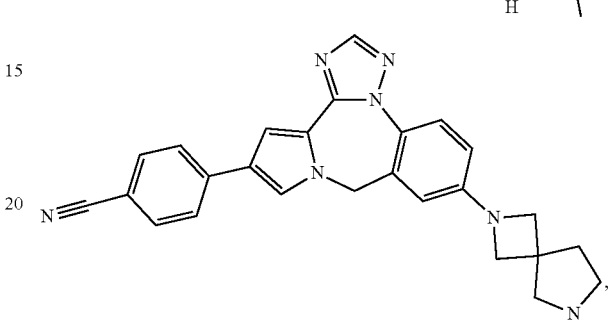
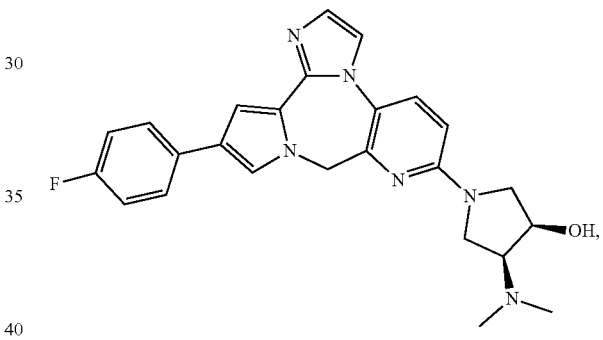
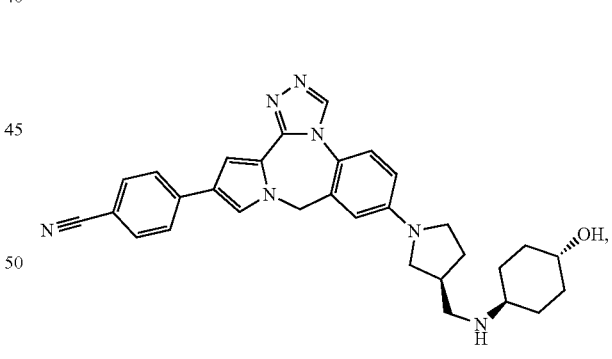
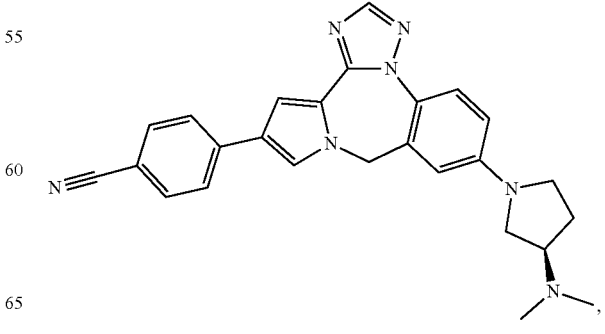

395
-continued
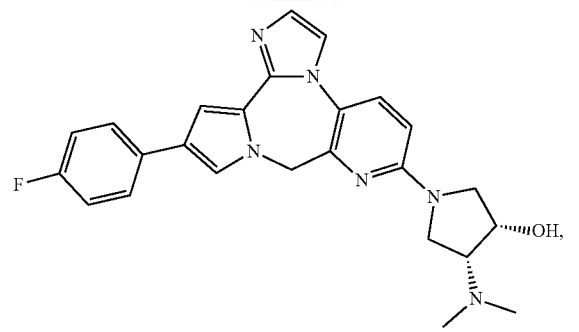
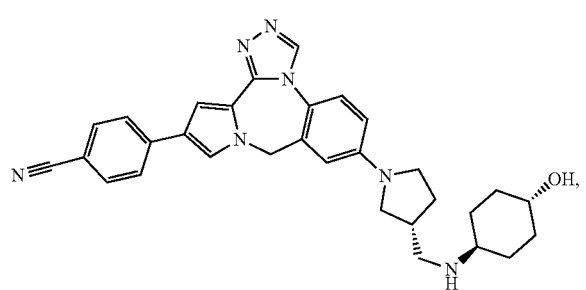
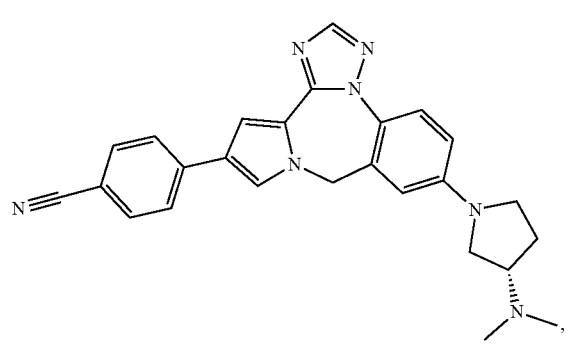
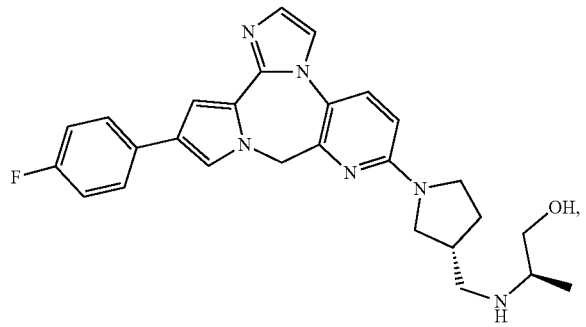
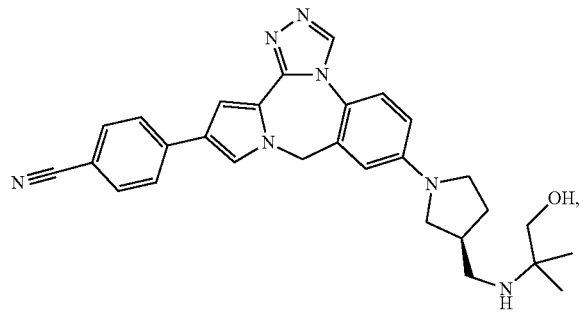
396
-continued
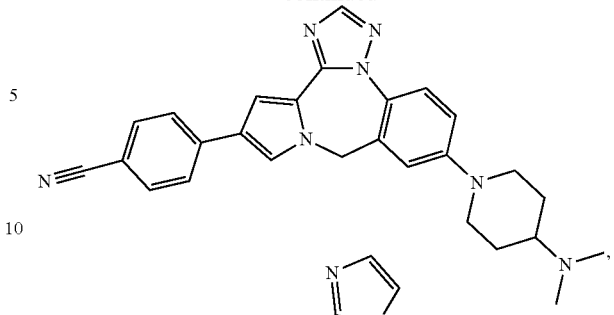
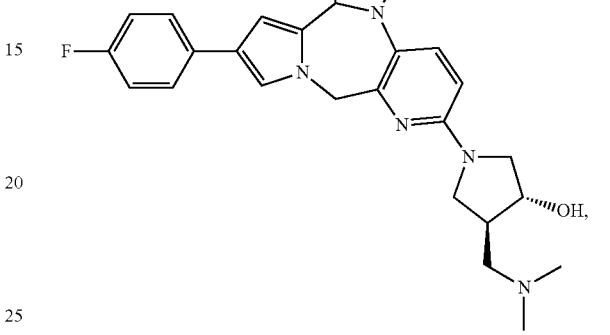
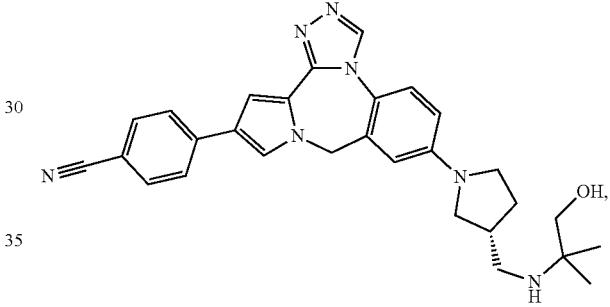
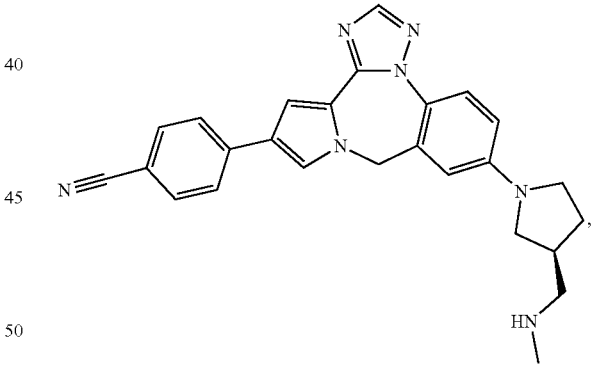
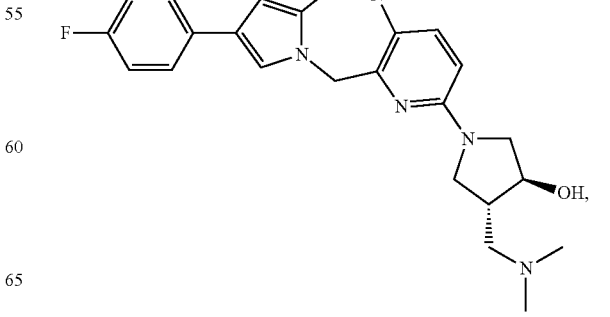

397
-continued
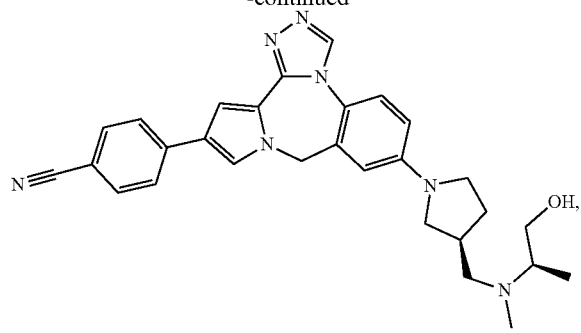
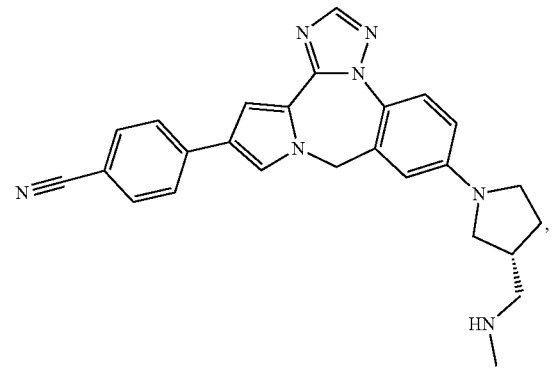
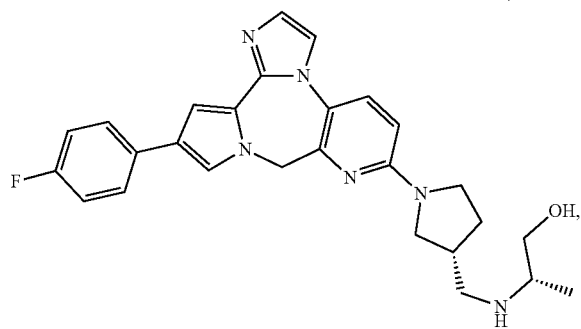
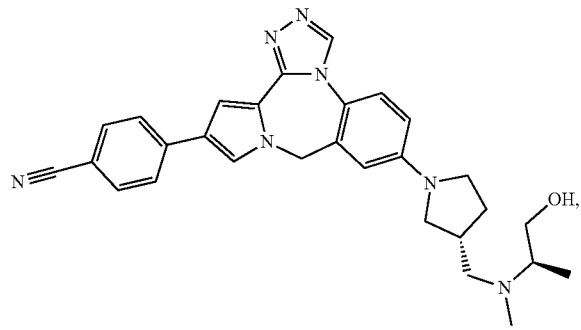
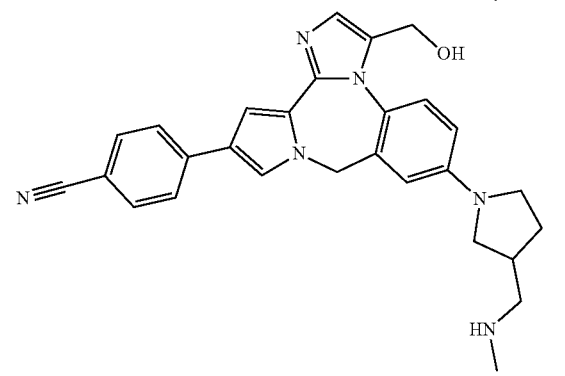
398
-continued
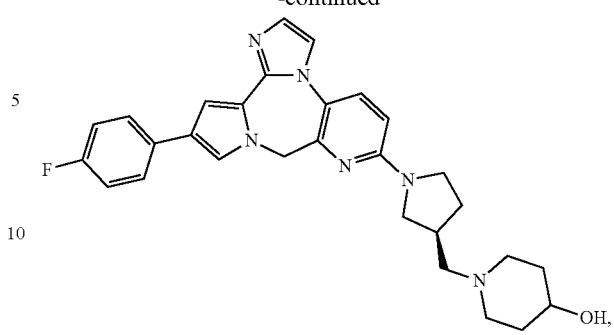
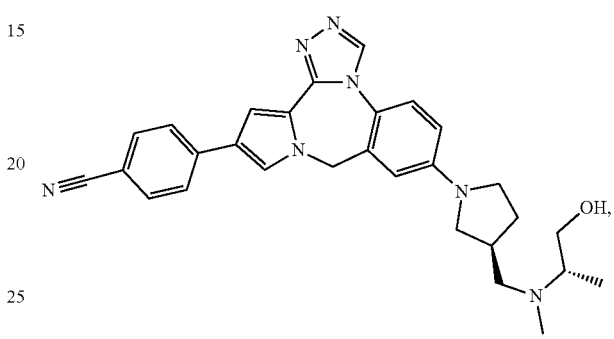
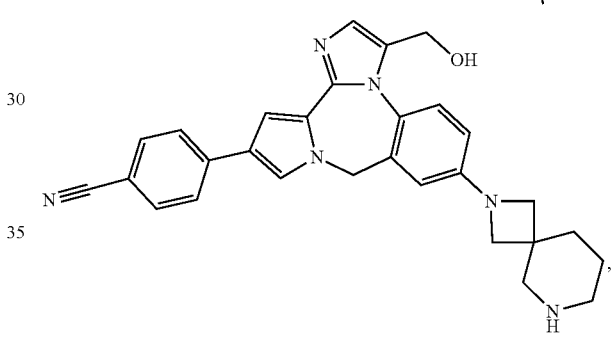
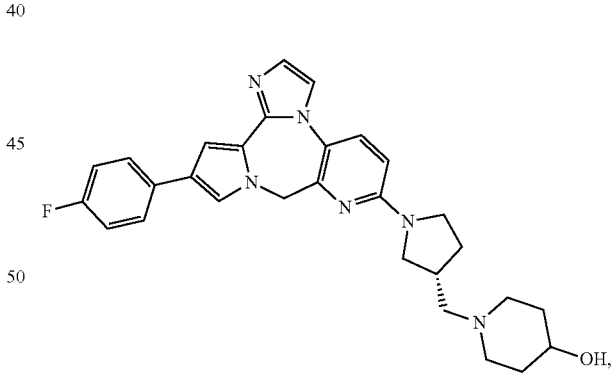
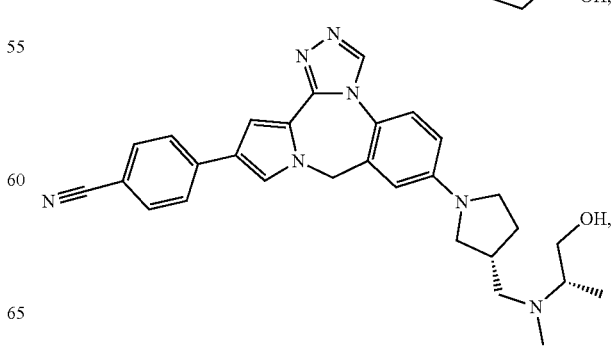

-continued
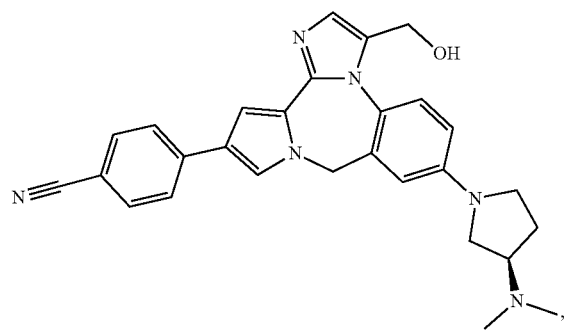
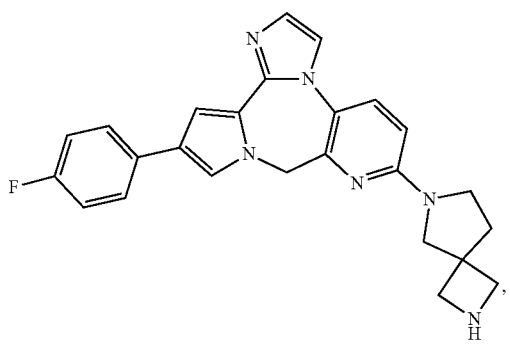
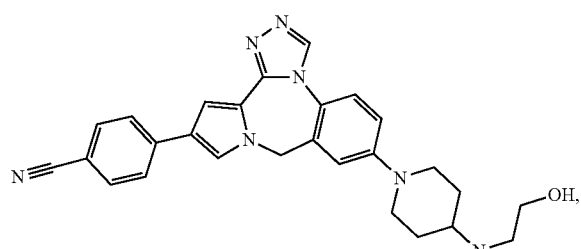
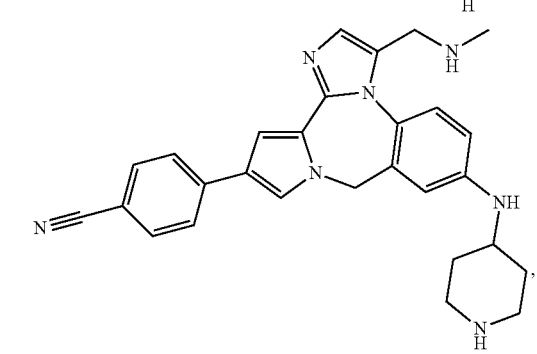
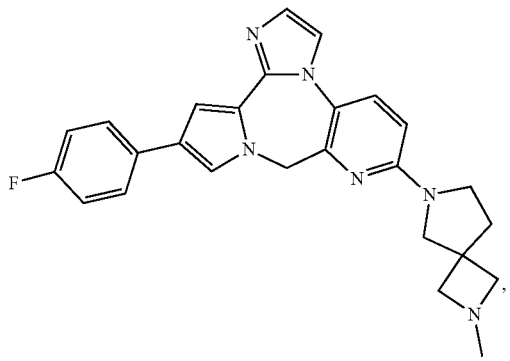
-continued
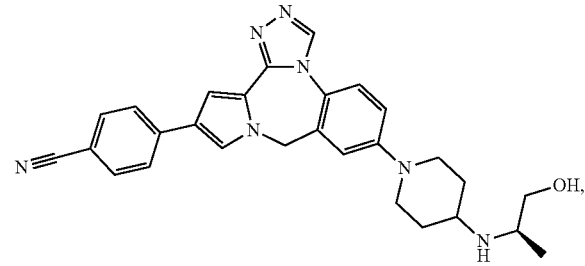
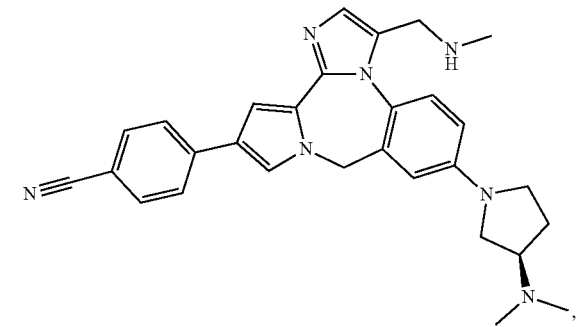
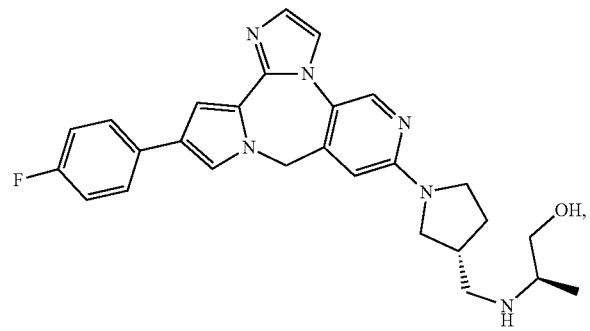
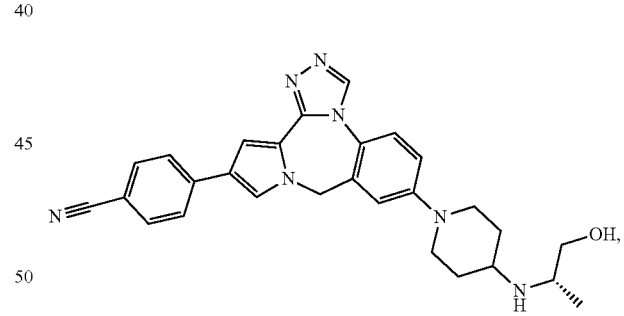
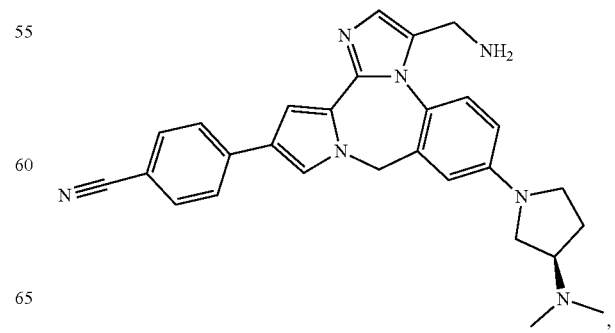

401
-continued
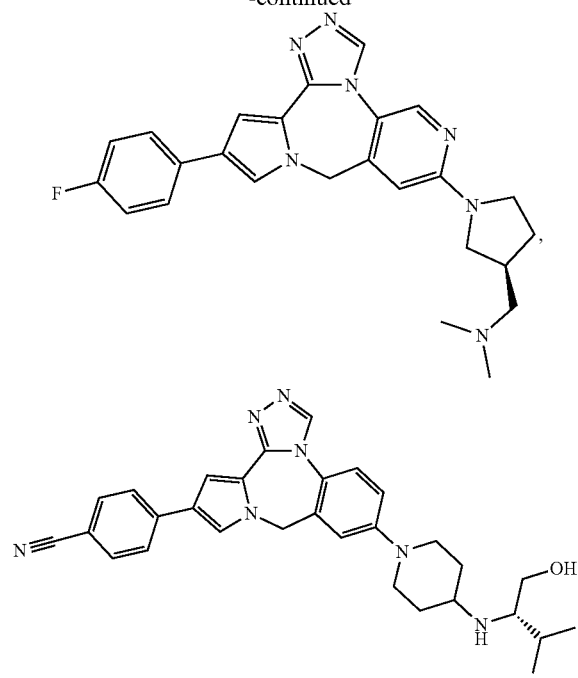
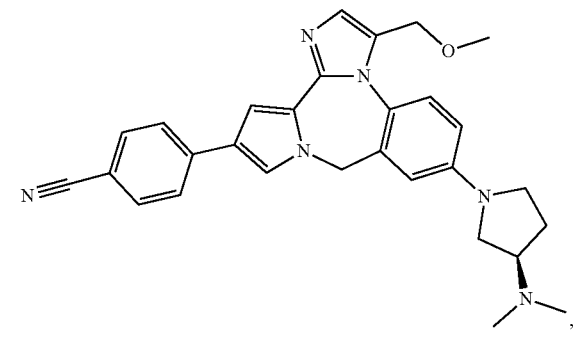
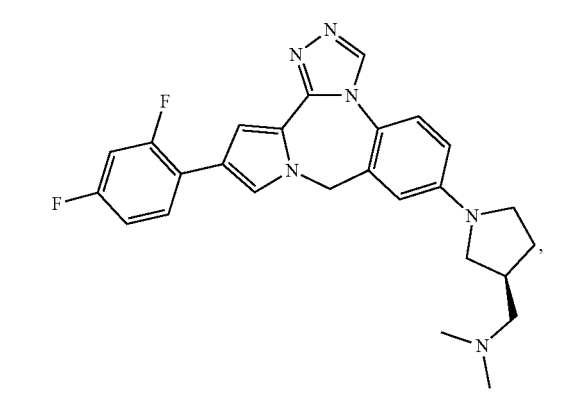
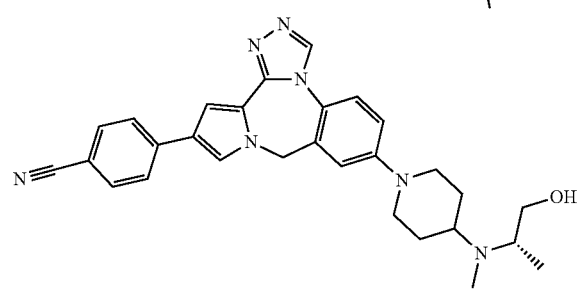
402
-continued
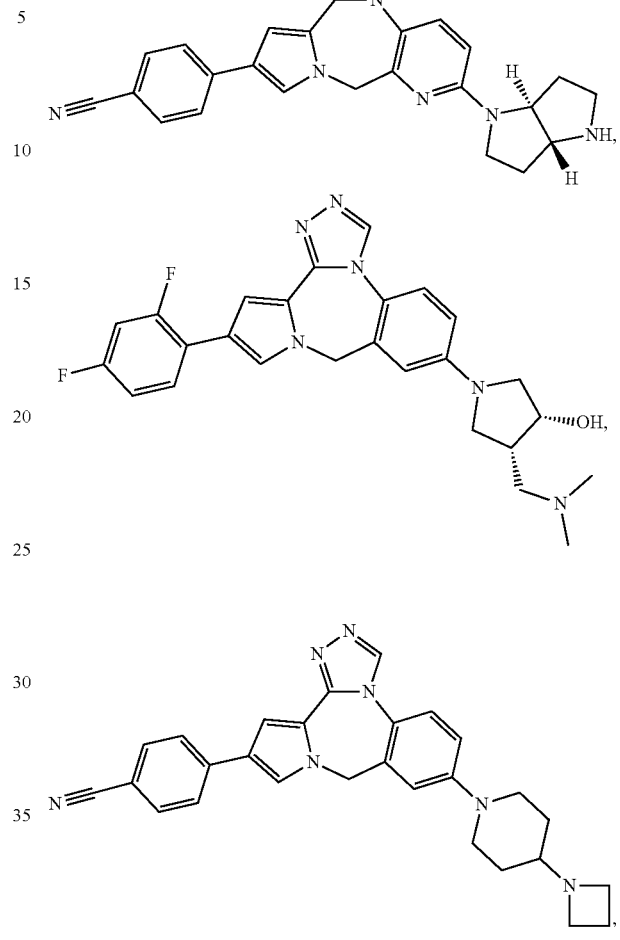
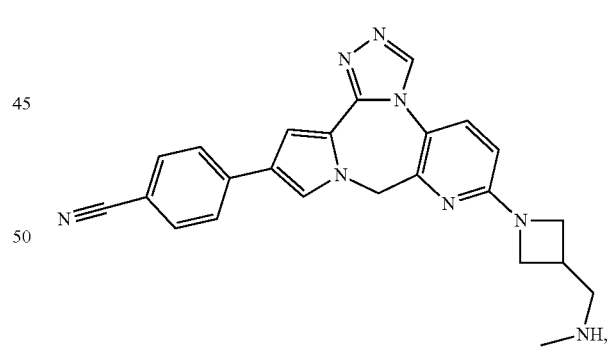
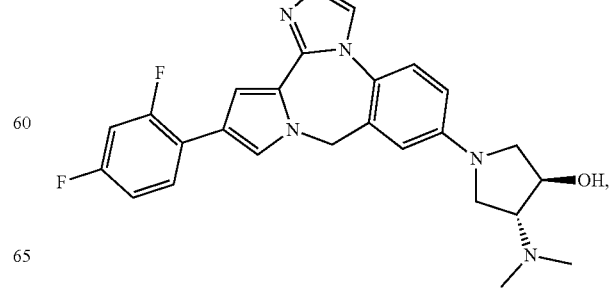

403
-continued
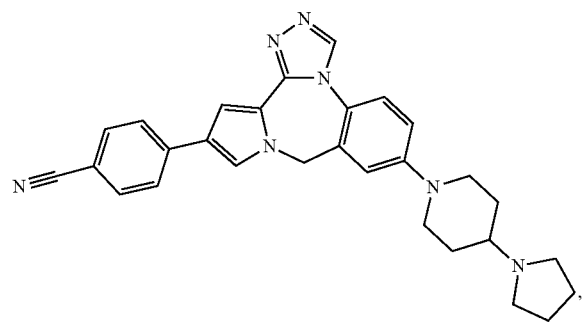
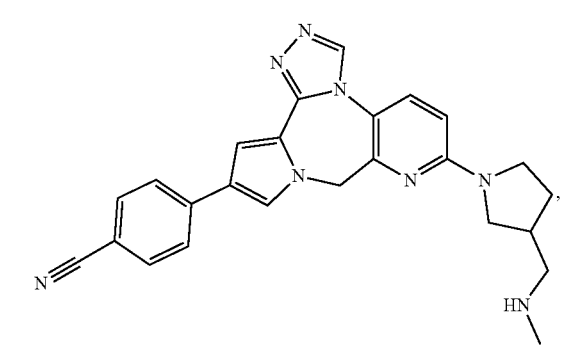
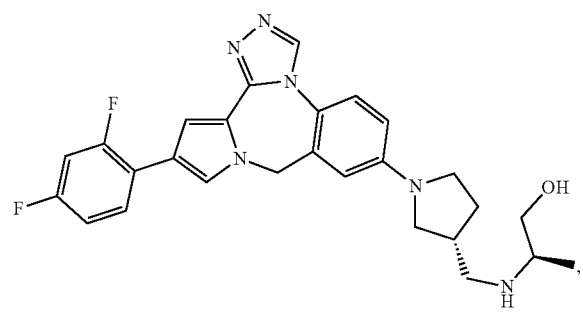
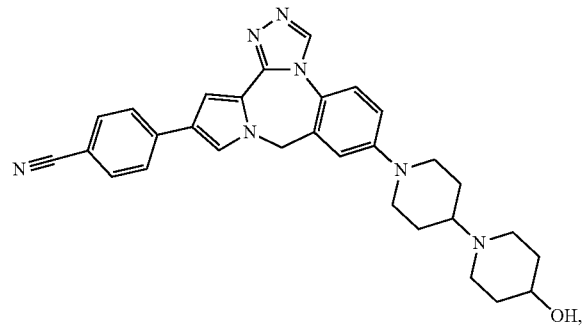
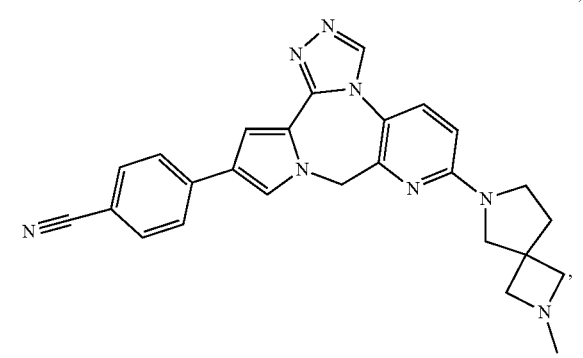
404
-continued
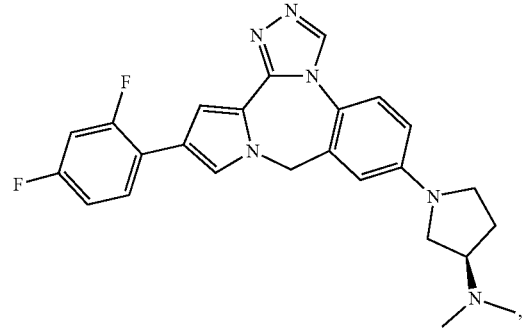
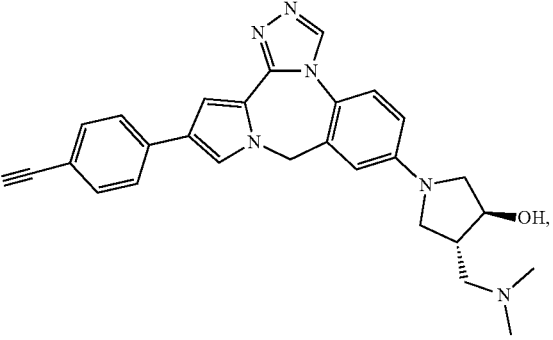
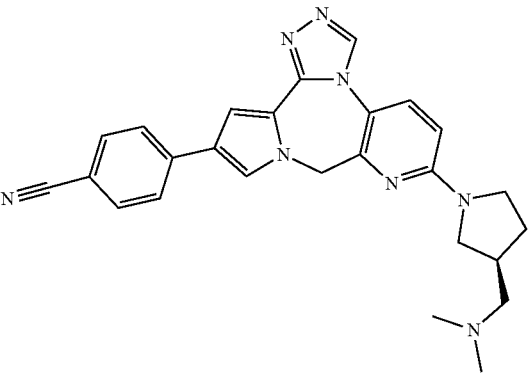
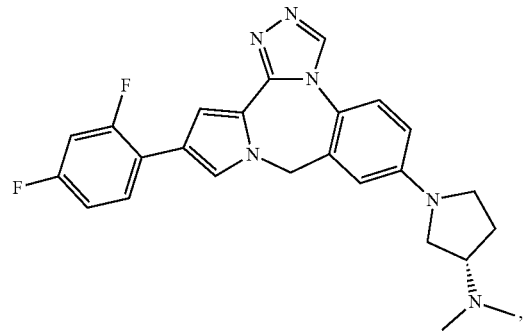
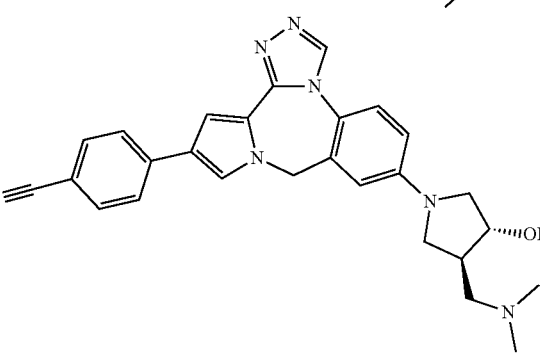

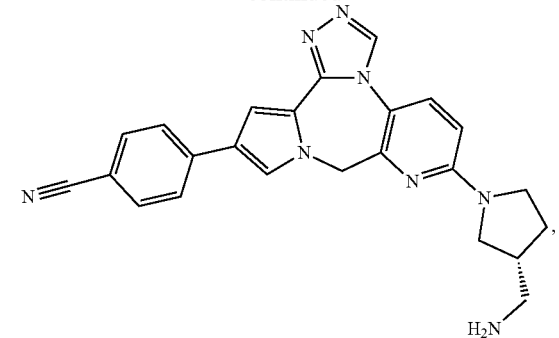
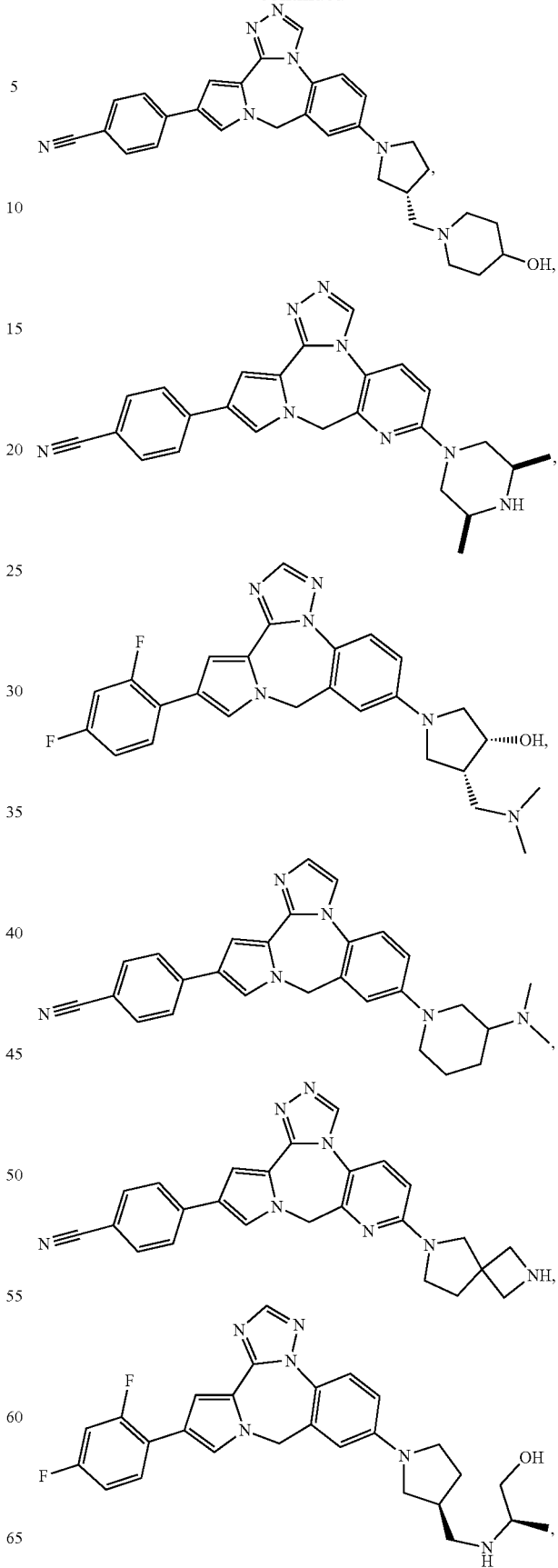

407
-continued
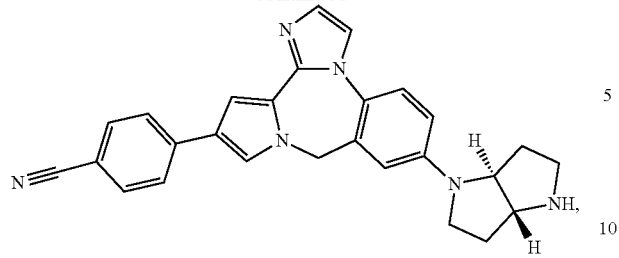
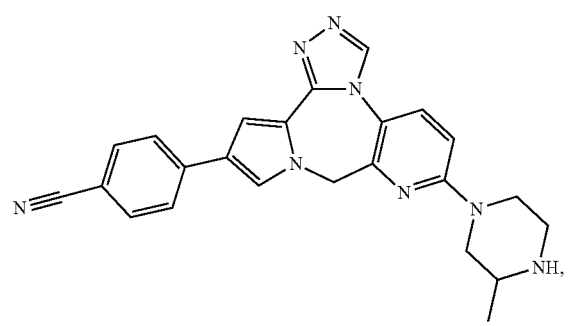
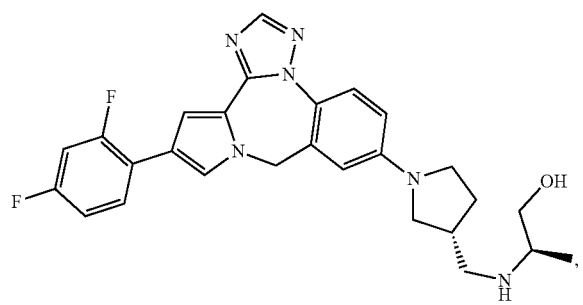
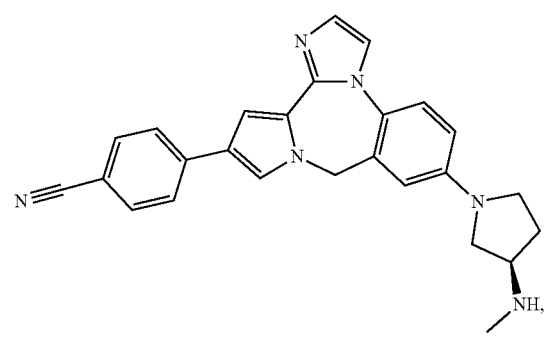
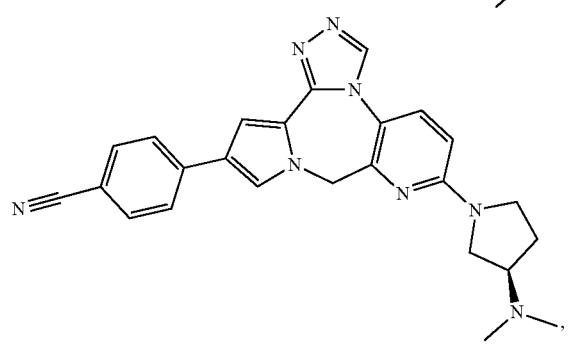
408
-continued
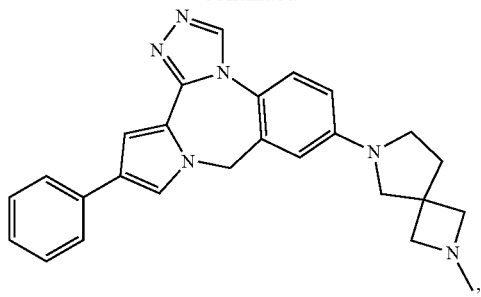
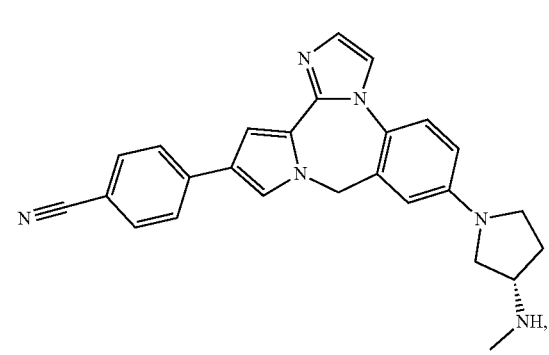
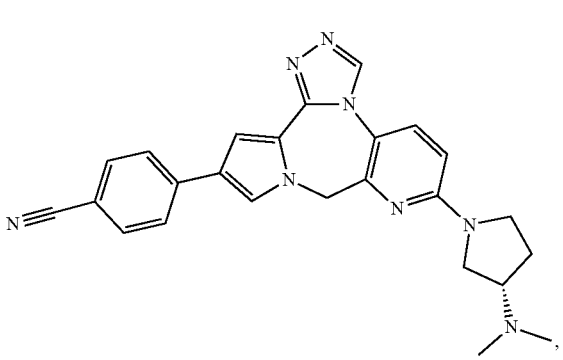
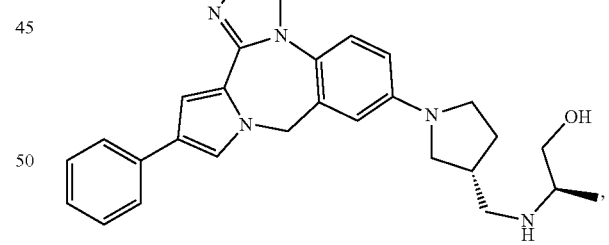
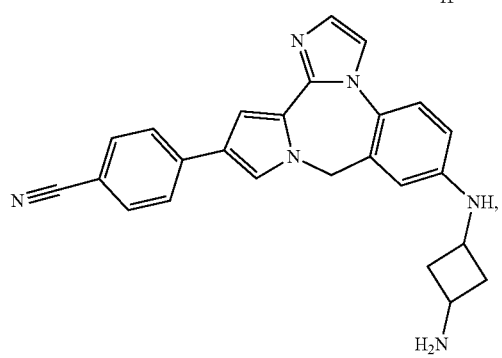

409
-continued
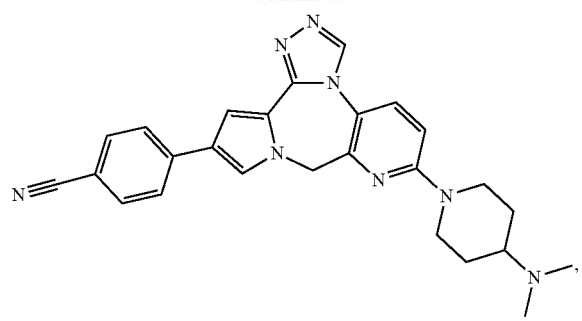
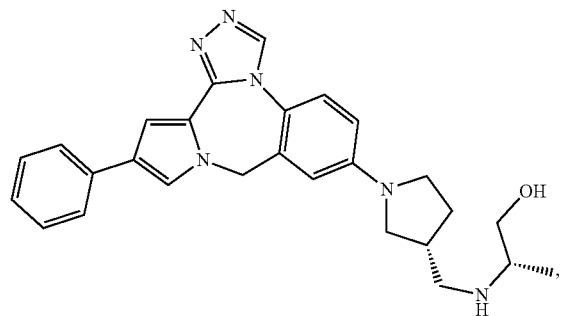
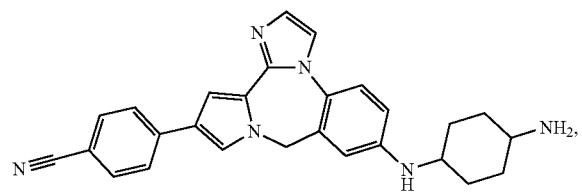
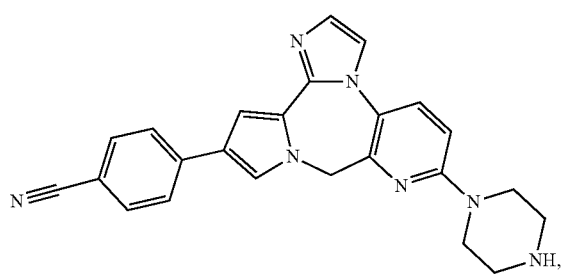
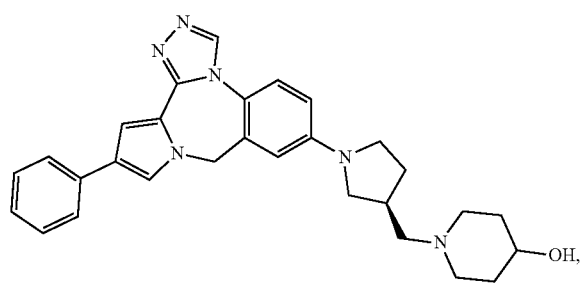
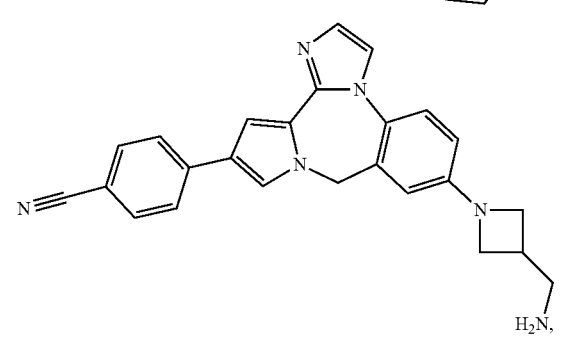
410
-continued
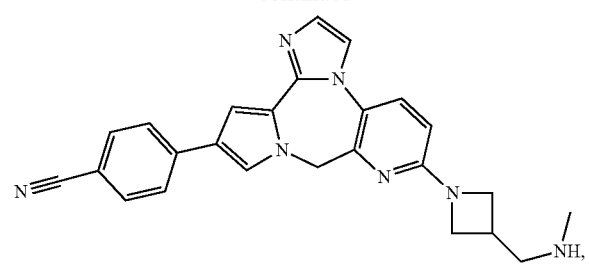
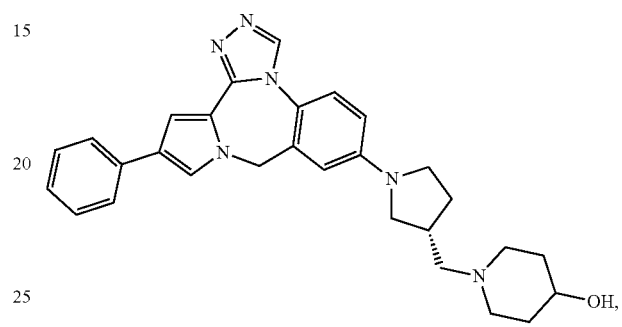
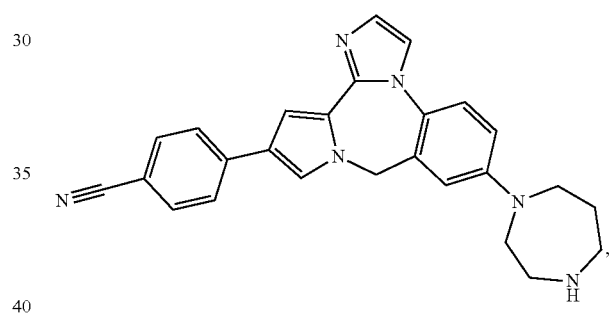
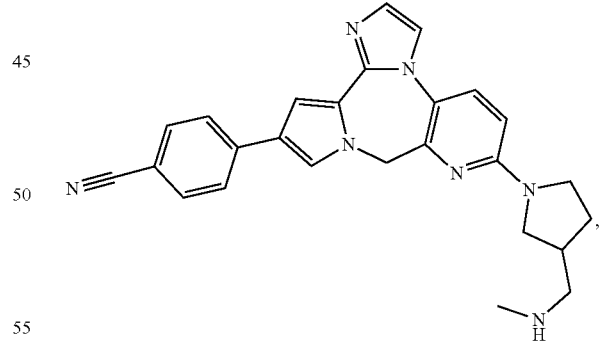
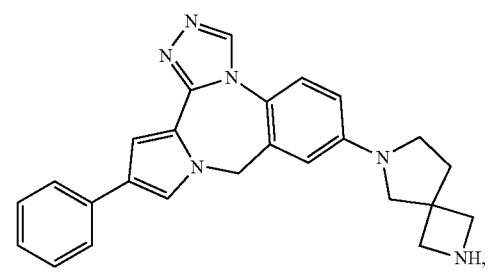

411
-continued
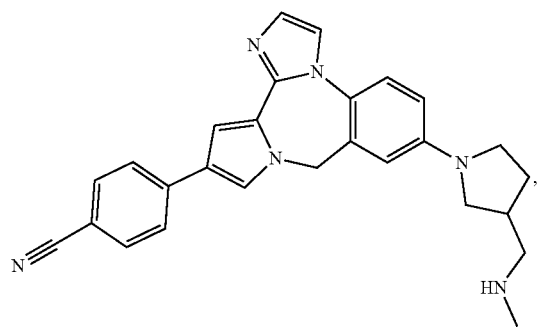
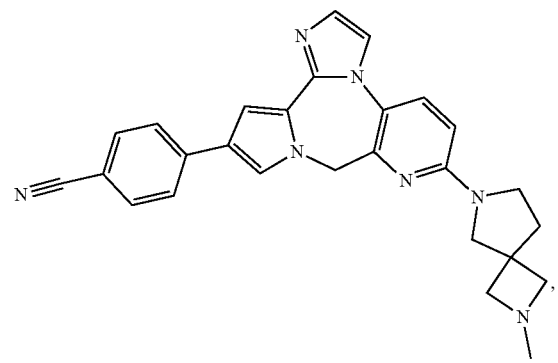
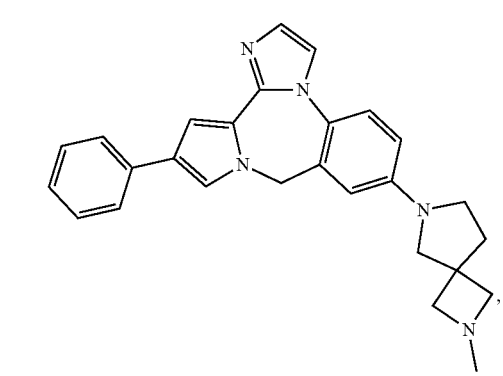
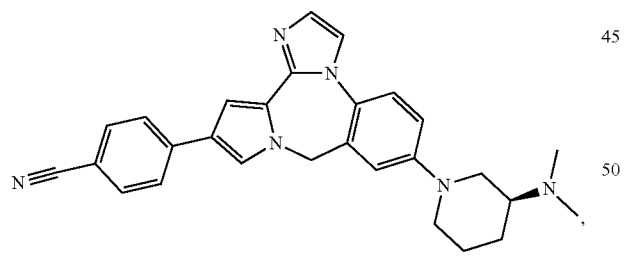
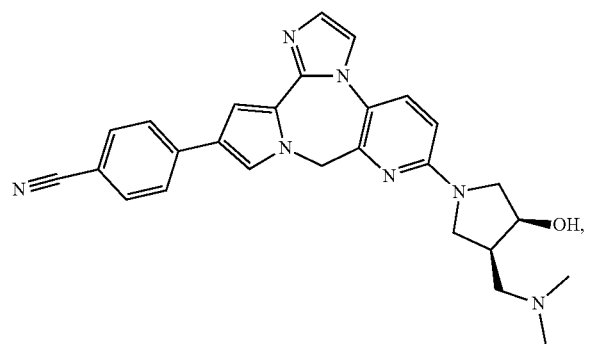
412
-continued
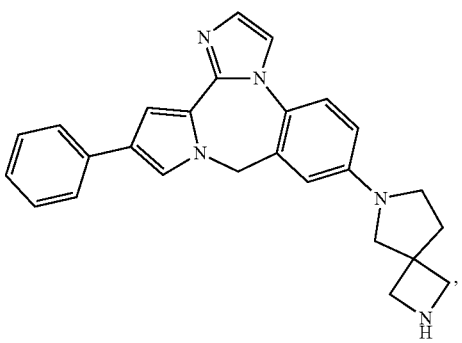
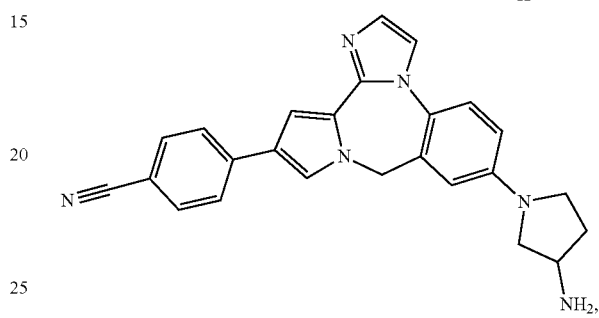
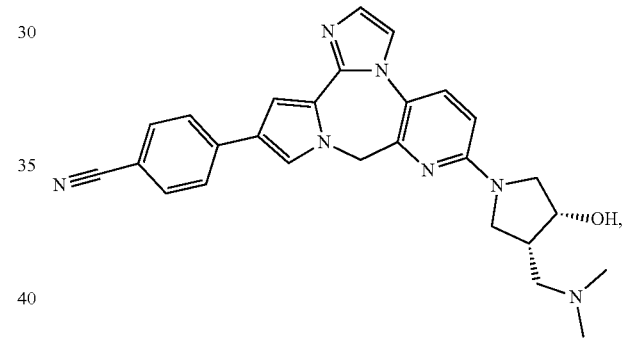
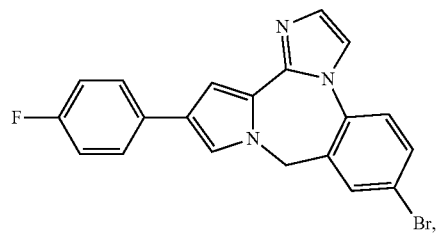
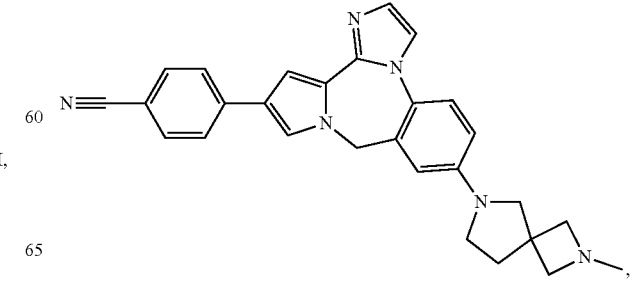

413
-continued
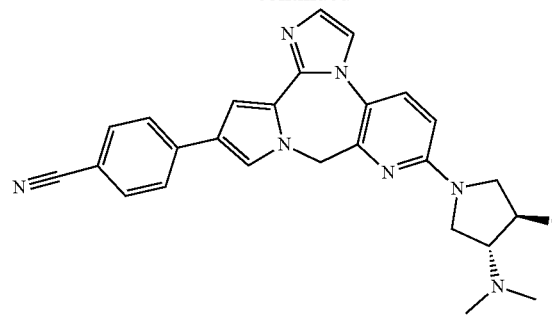
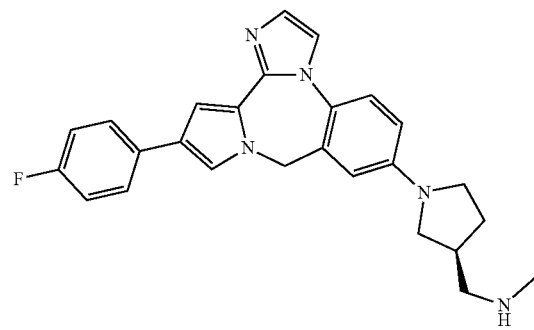
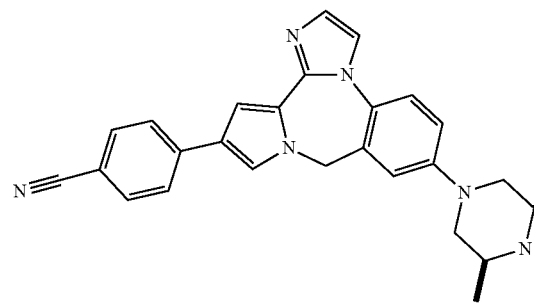
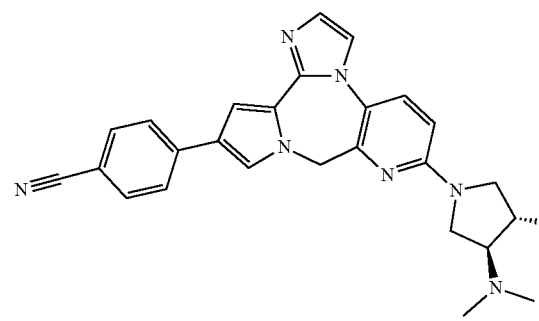
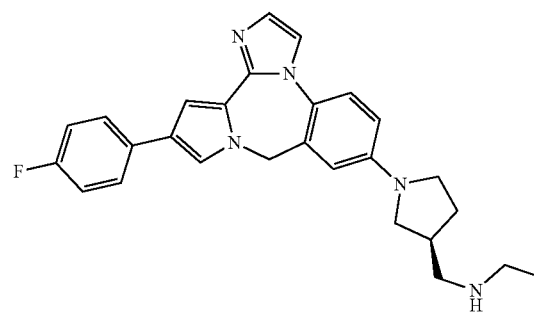
414
-continued
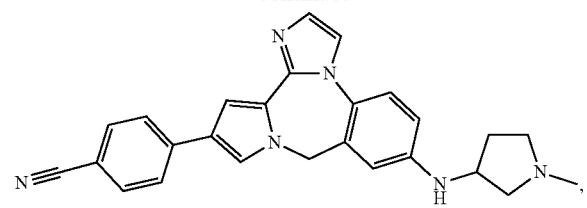
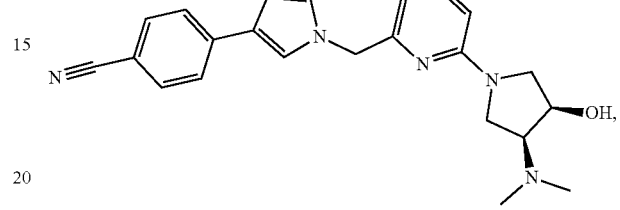
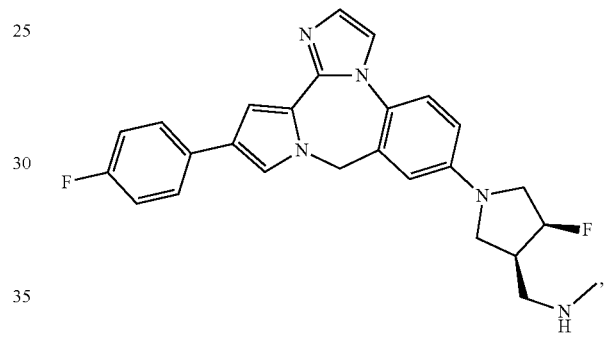
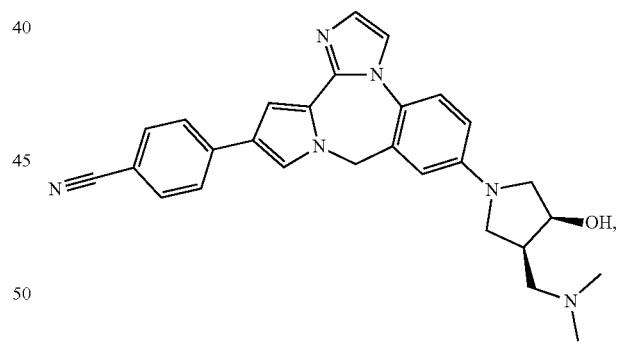
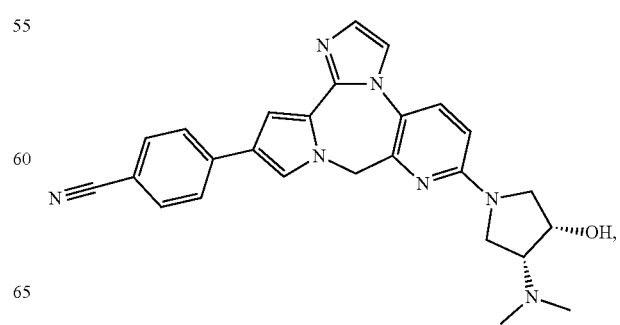

415
-continued
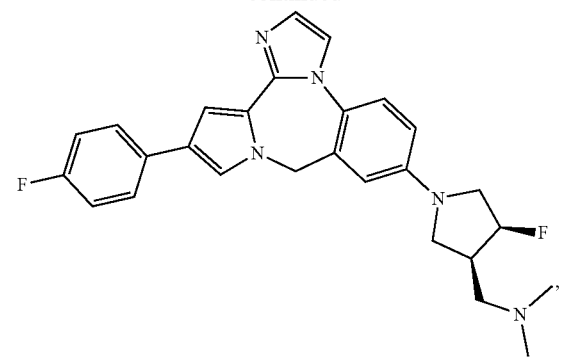
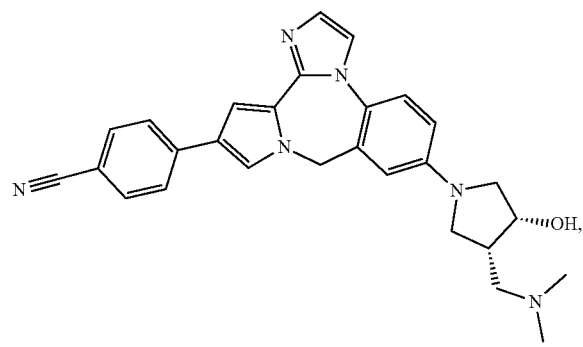
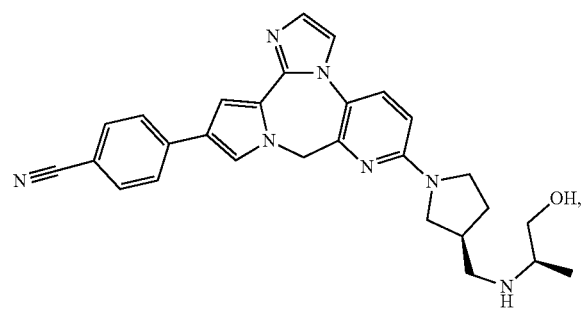
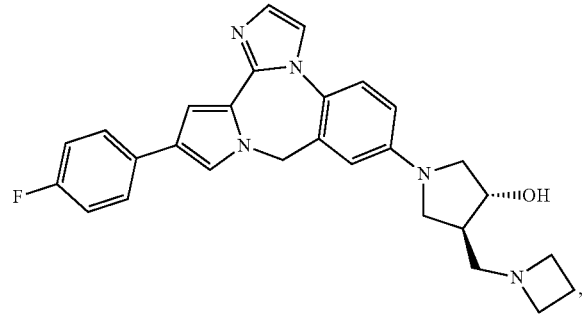
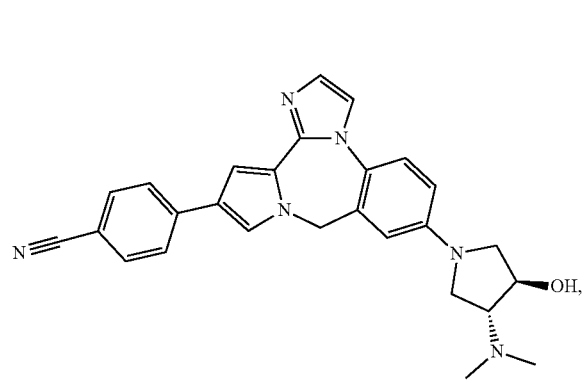
416
-continued
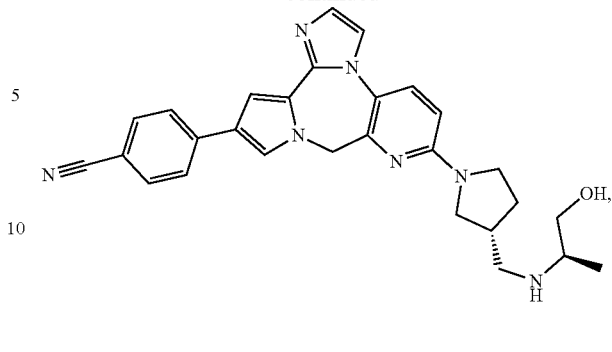
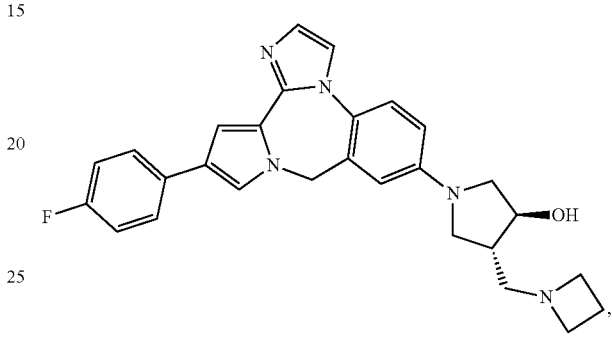
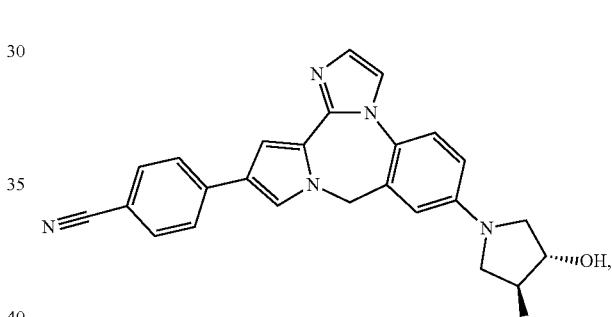
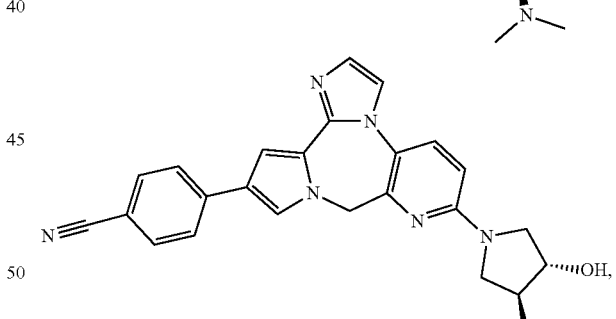
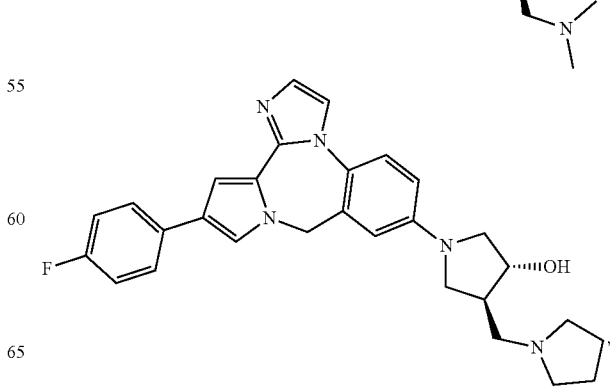

417
-continued
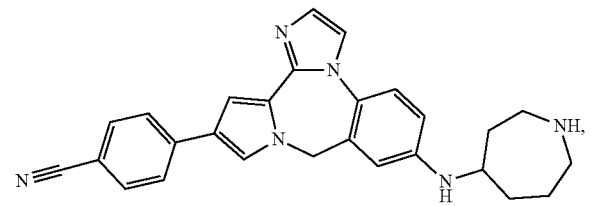
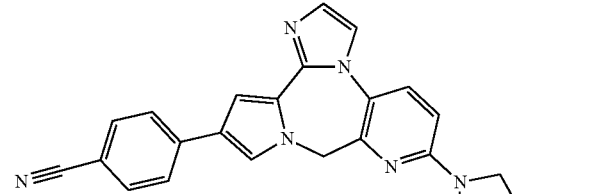
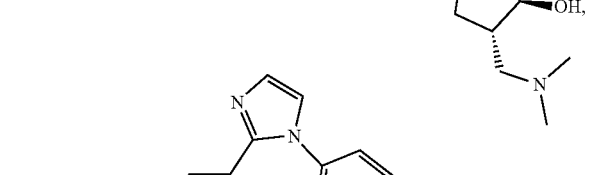
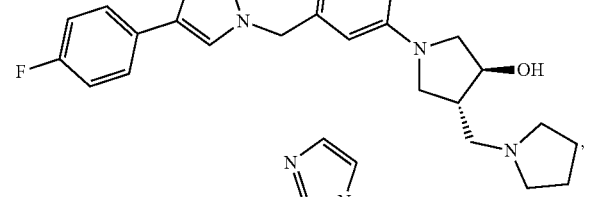
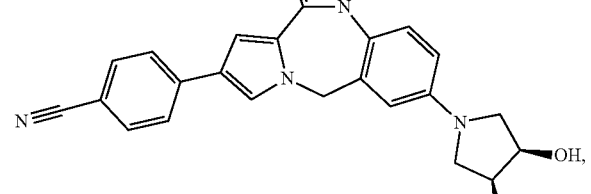
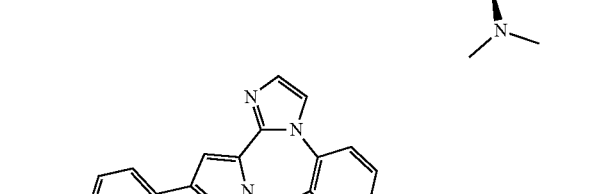
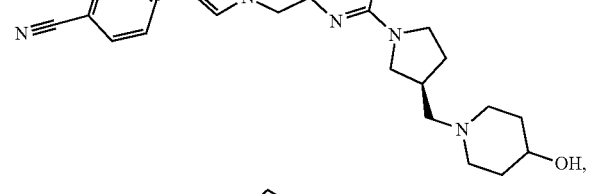
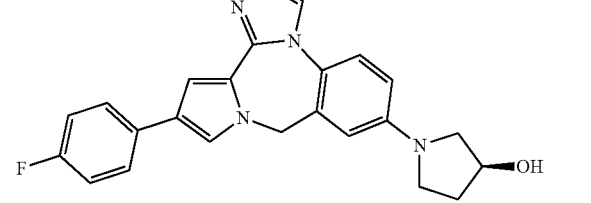
racemic
418
-continued
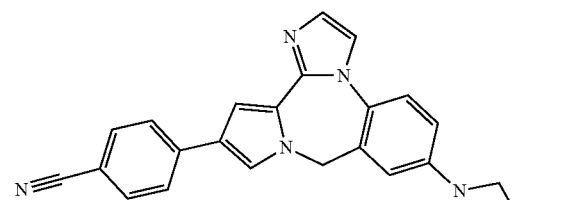
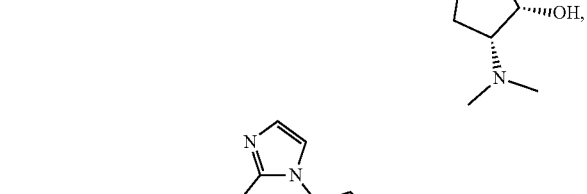
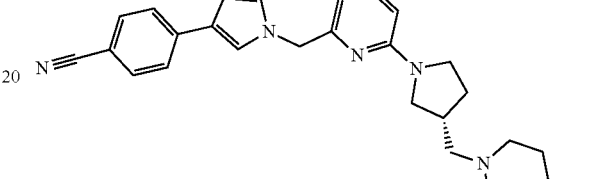
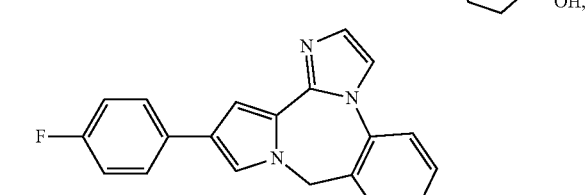
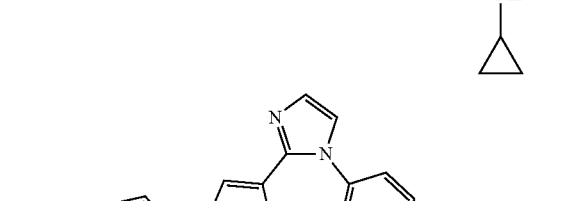
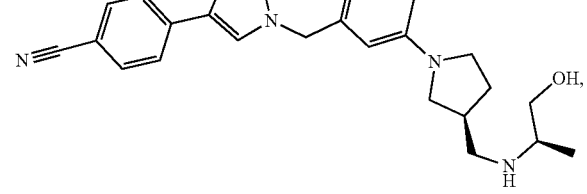
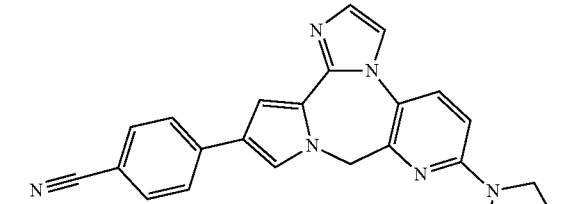

419
-continued
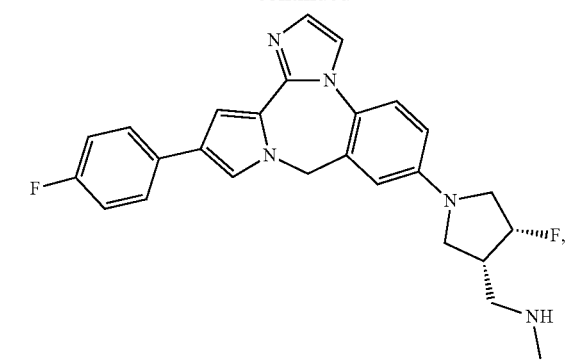
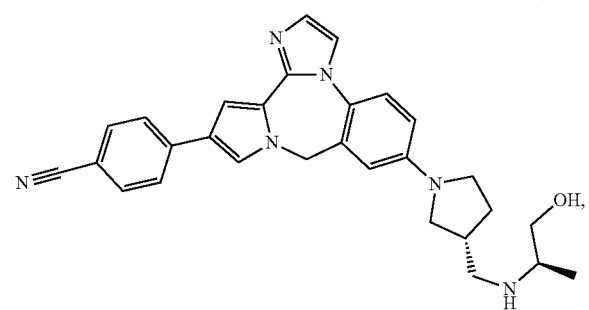
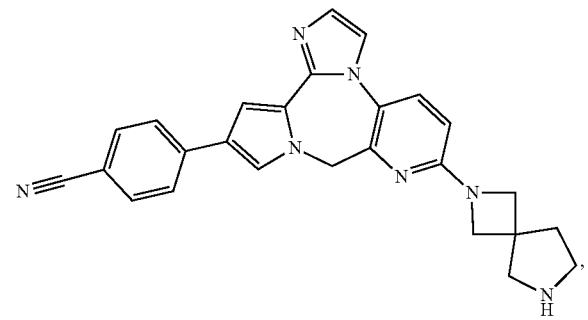
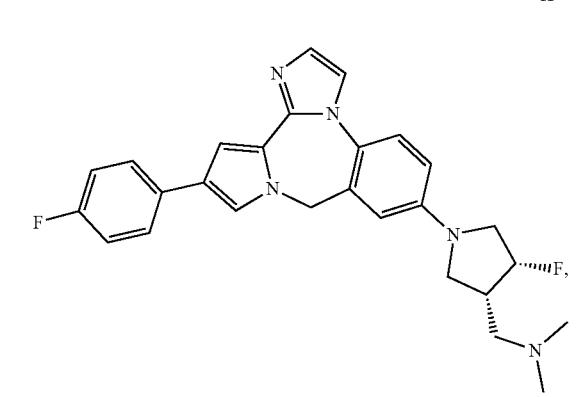
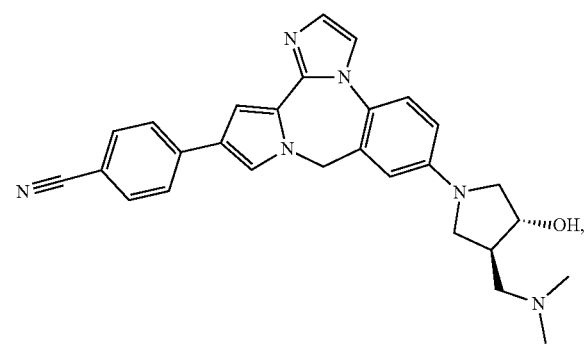
420
-continued
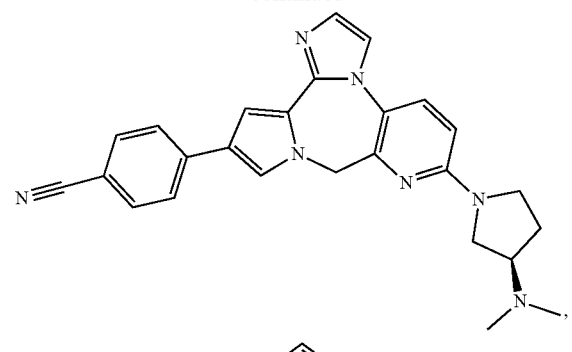
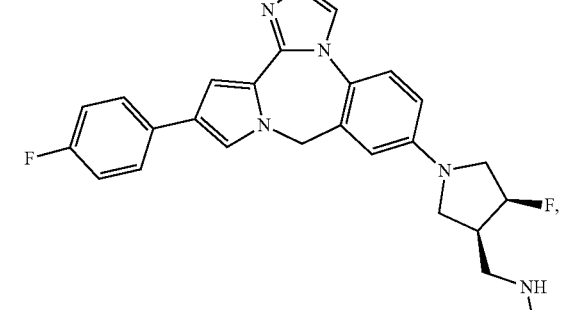
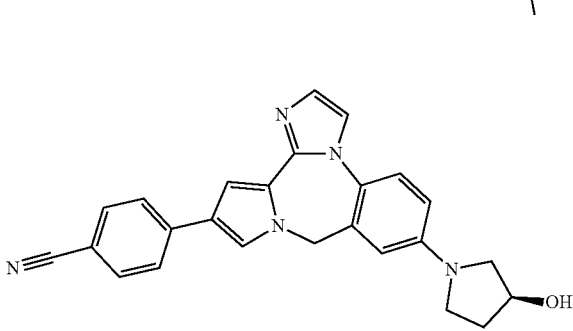
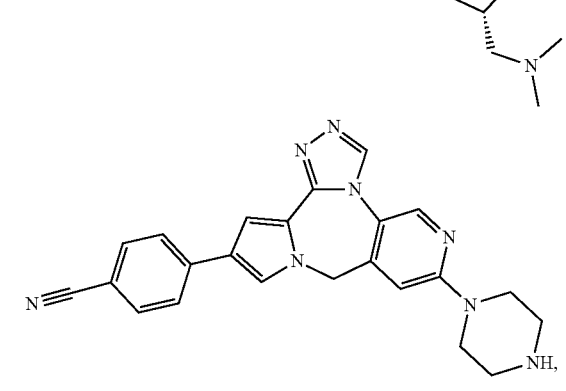
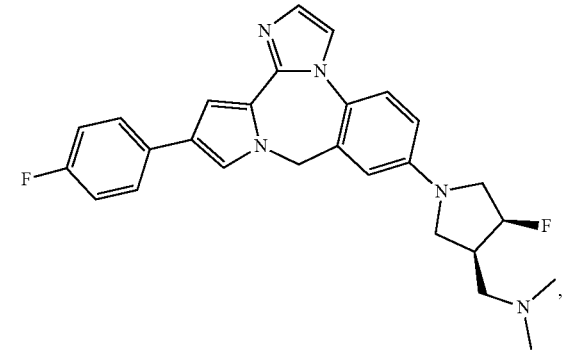

| 421 | 422 |
|---|---|
| -continued | -continued |
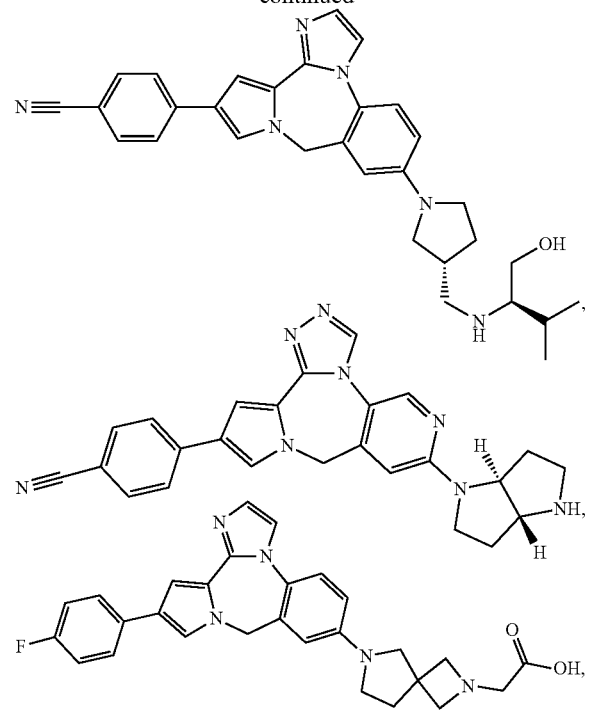
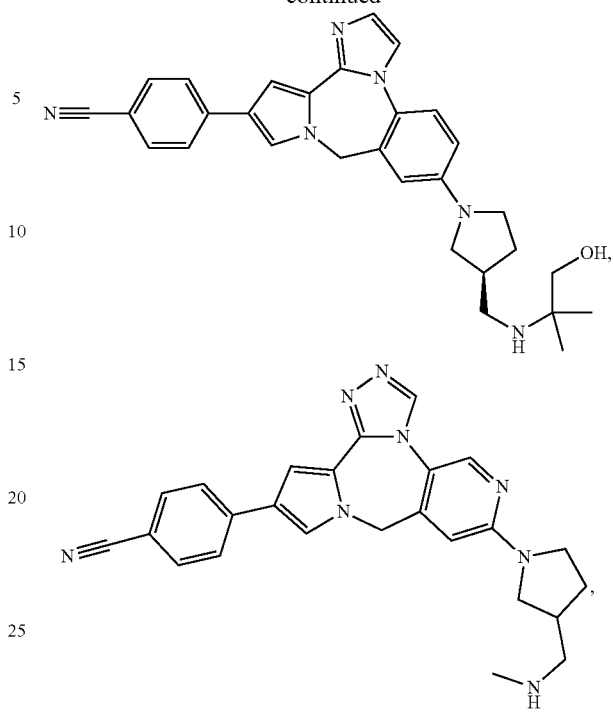
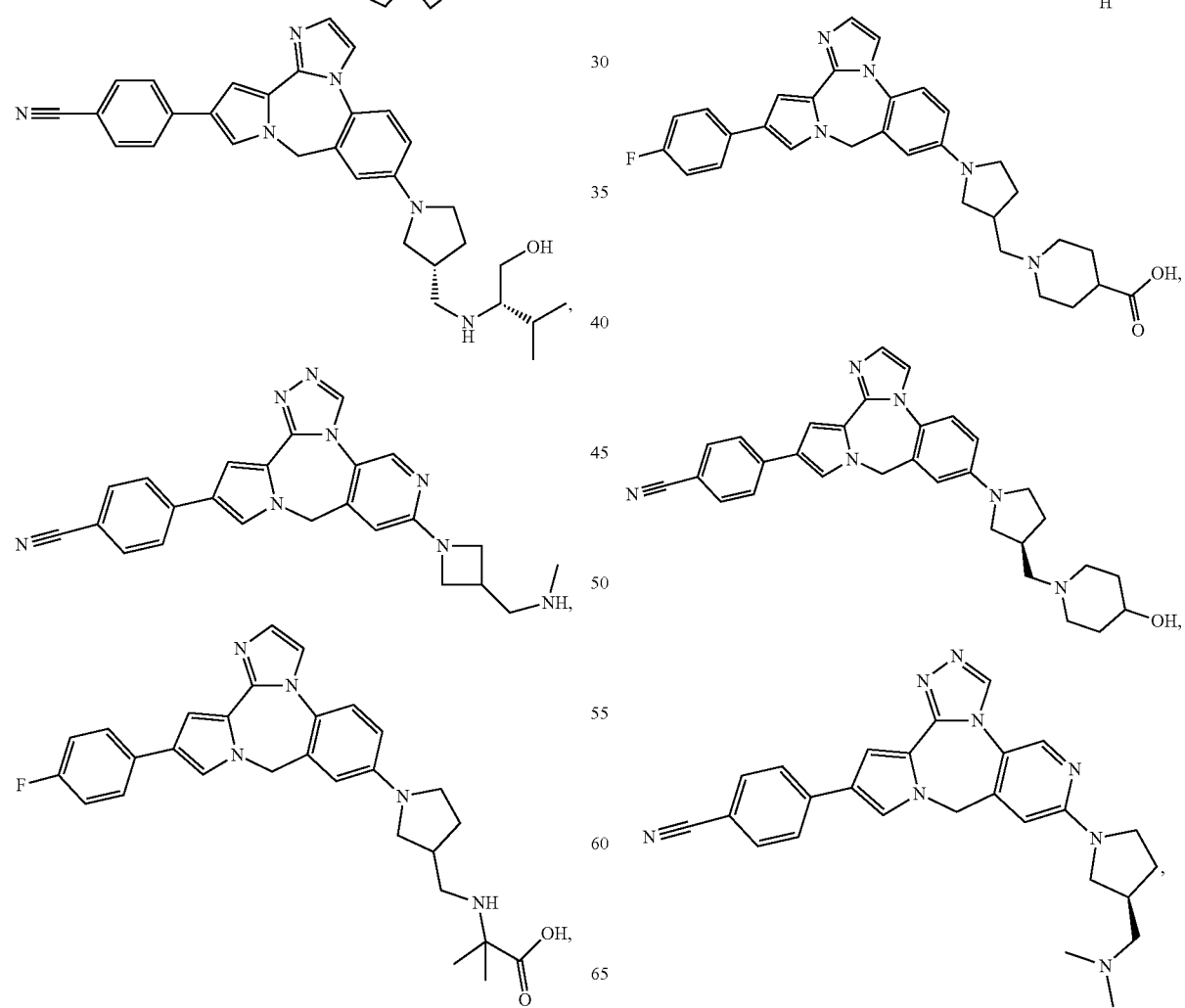

423
-continued
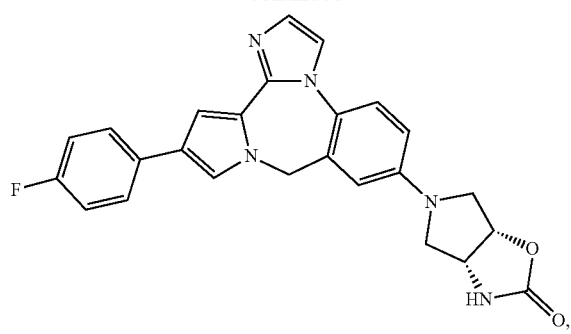
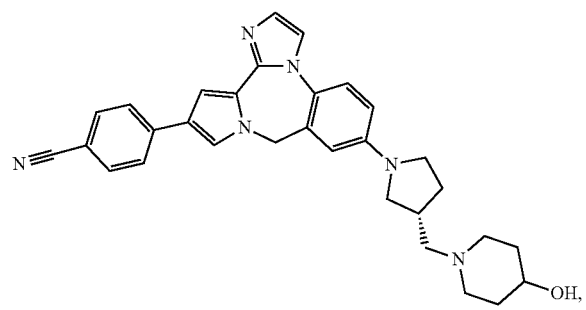
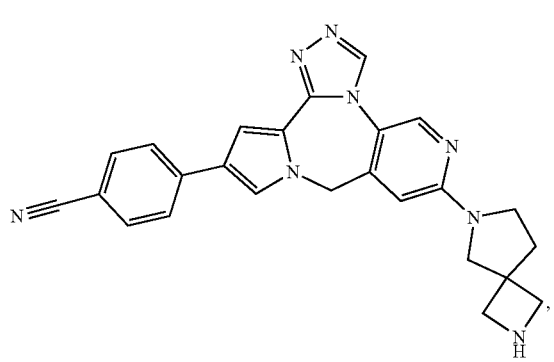
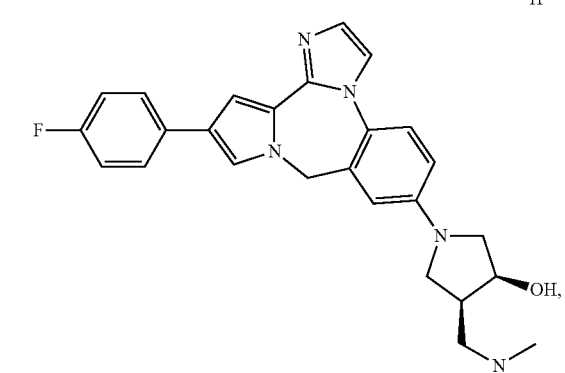
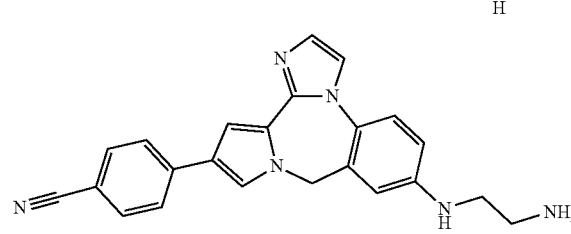
424
-continued
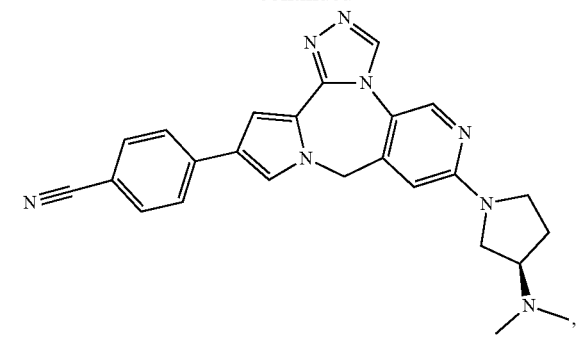
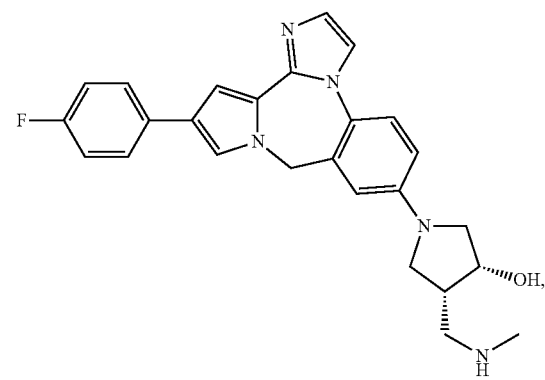
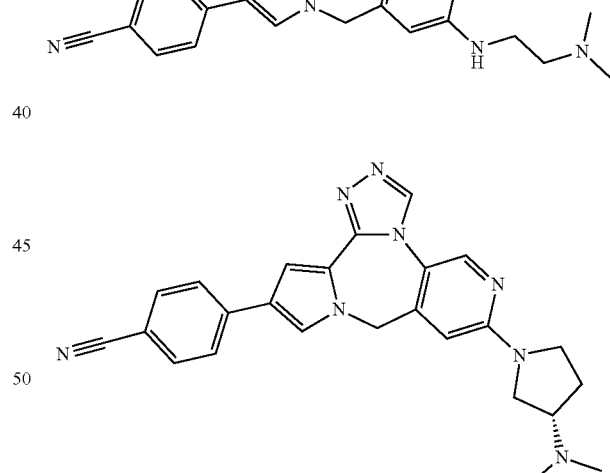
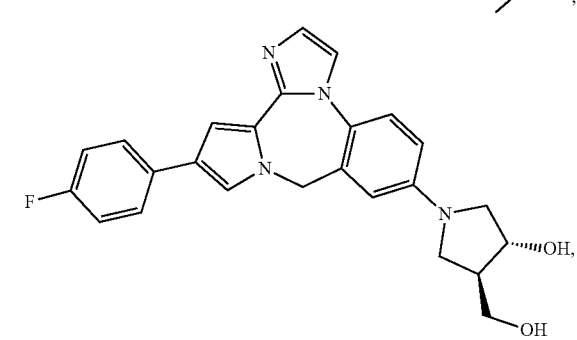

-continued
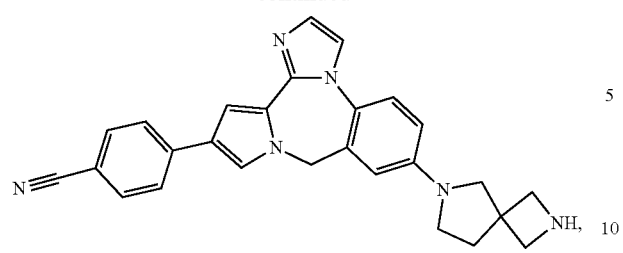
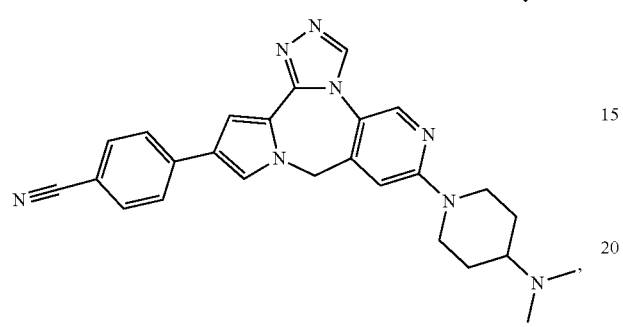
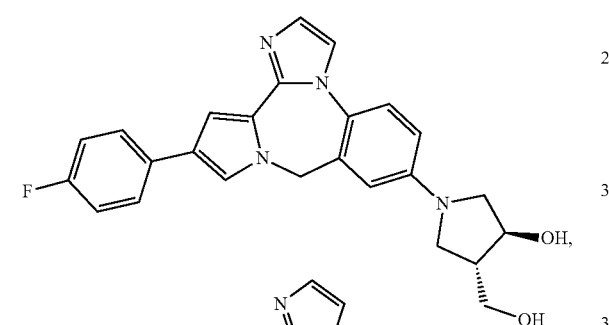
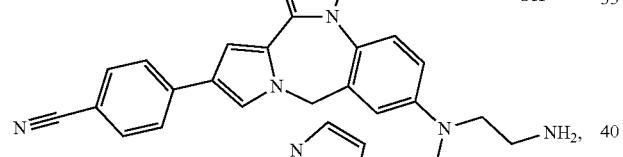
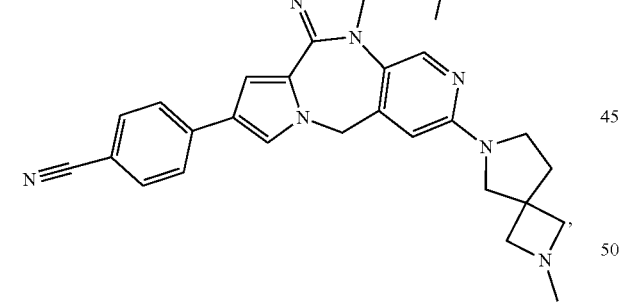
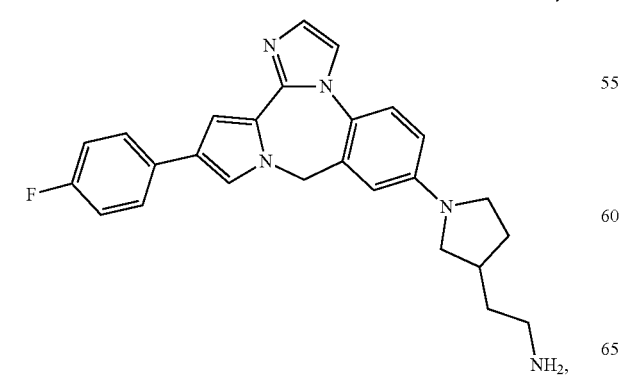
-continued
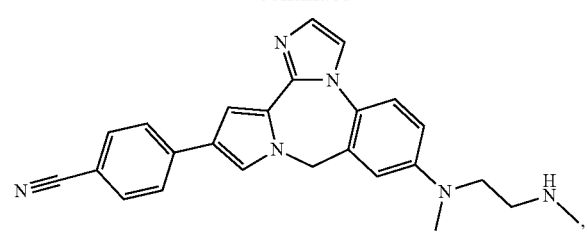
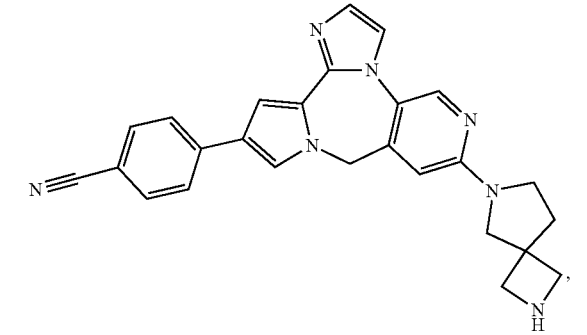
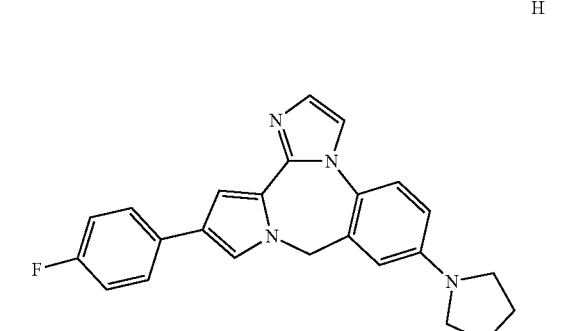
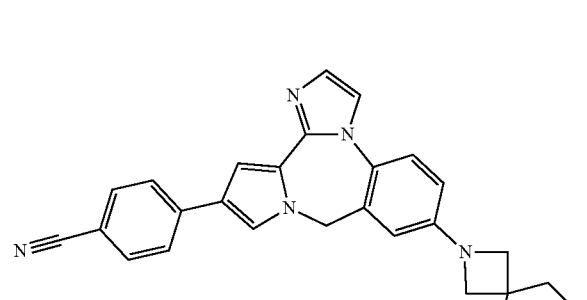
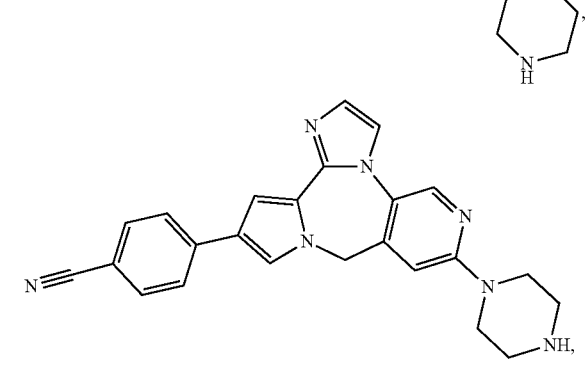

427 -continued
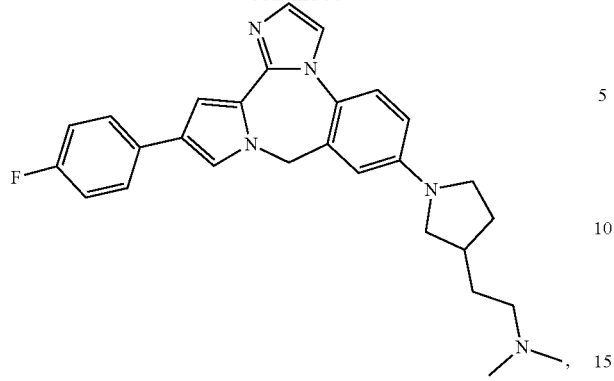
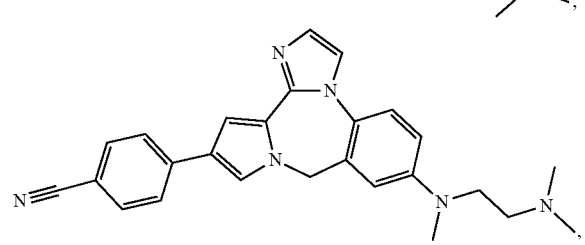
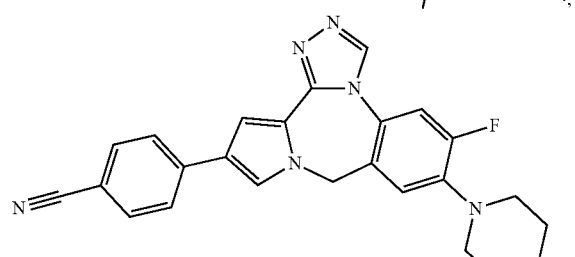
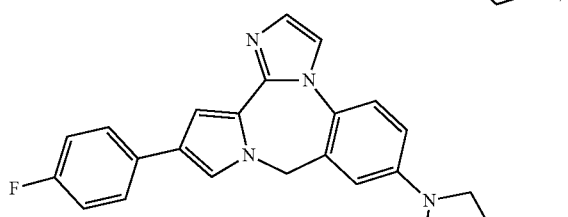
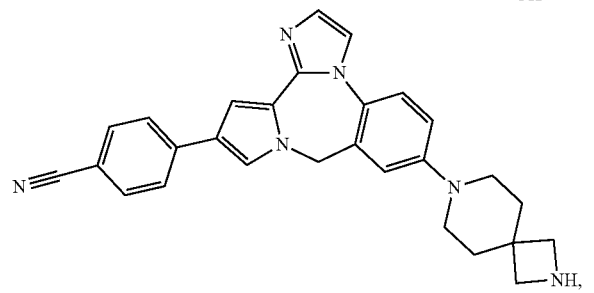
428 -continued
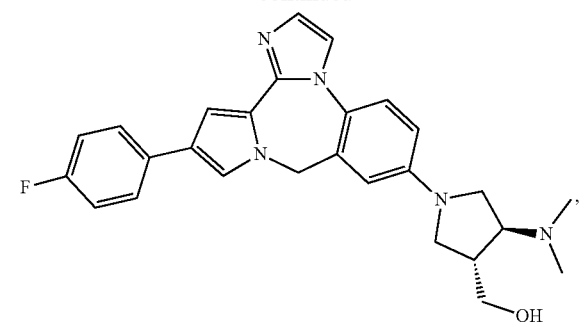
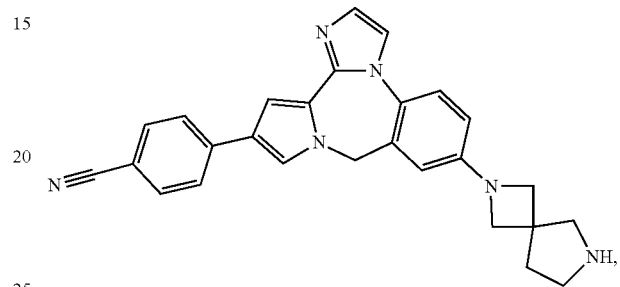
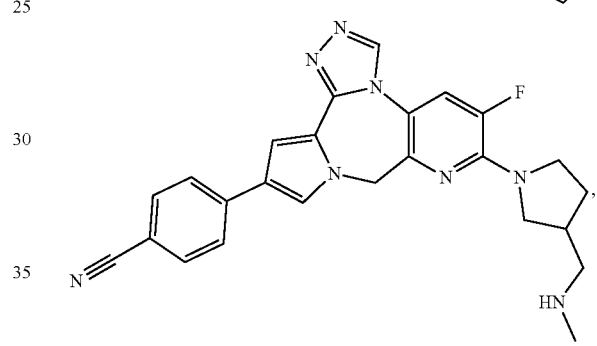
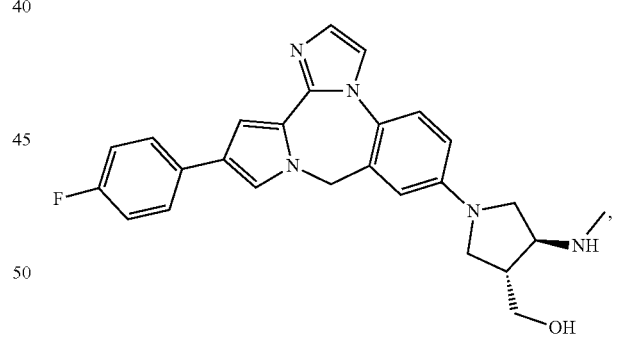
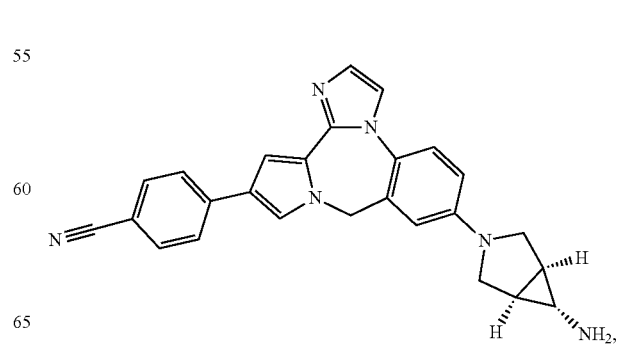

429
-continued
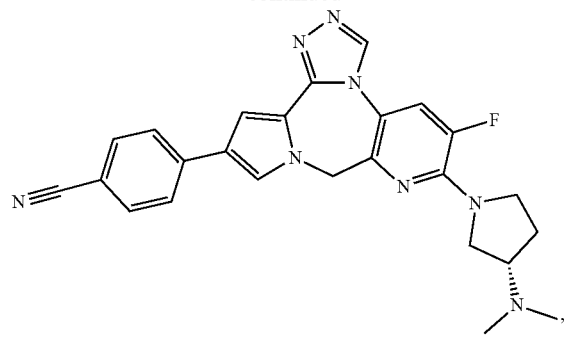
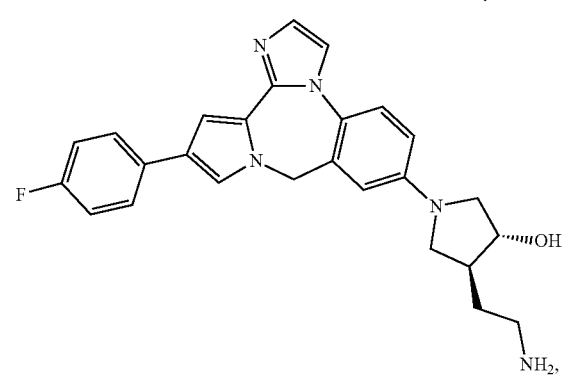
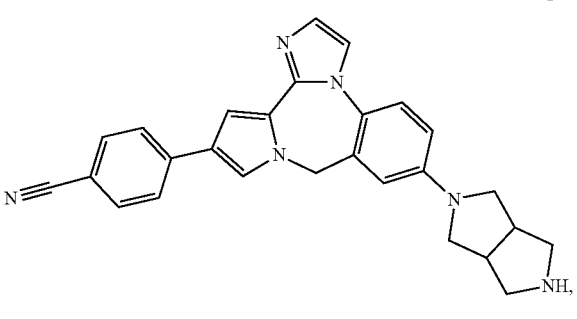
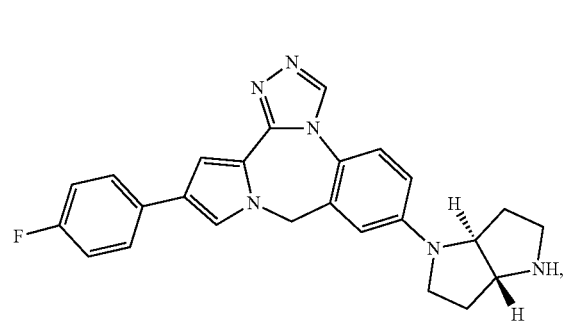
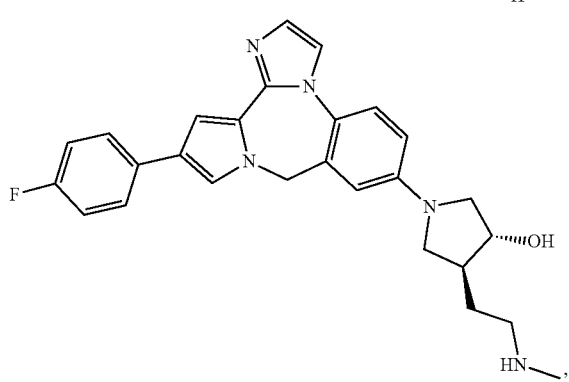
430
-continued
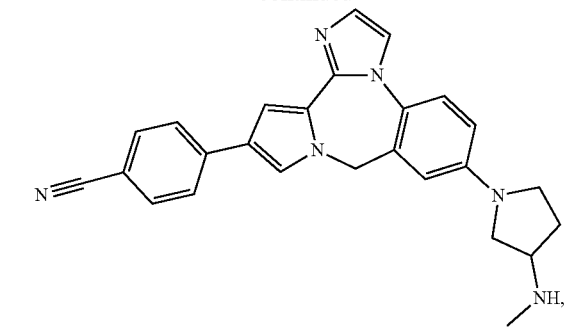
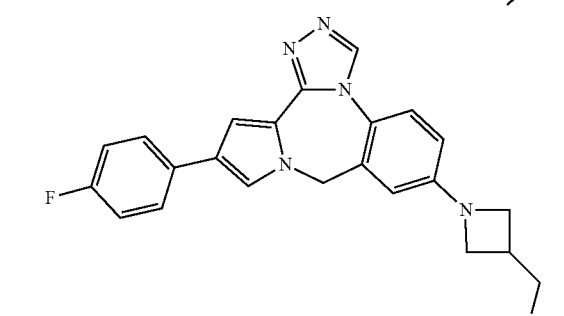
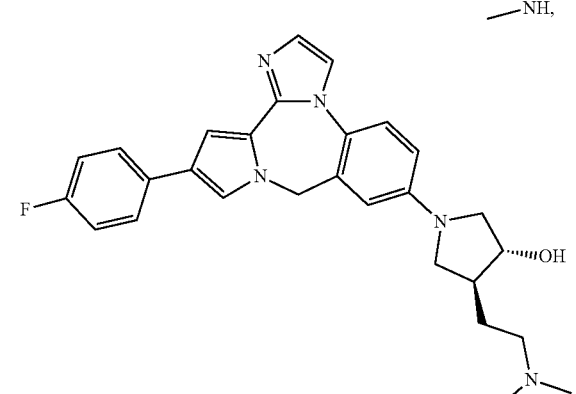
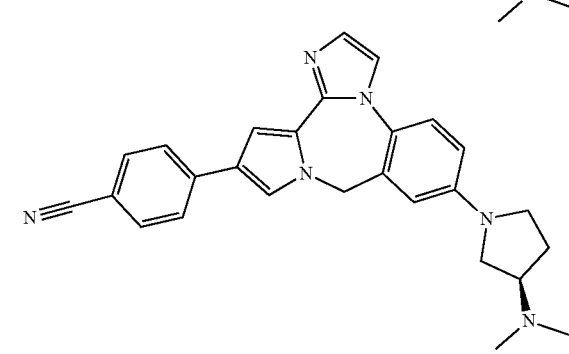
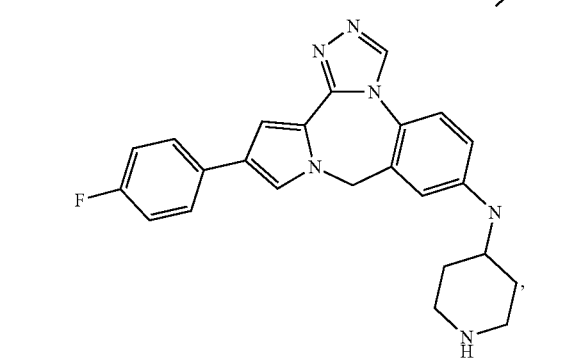

431
-continued
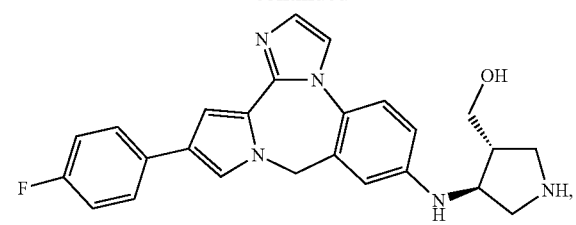
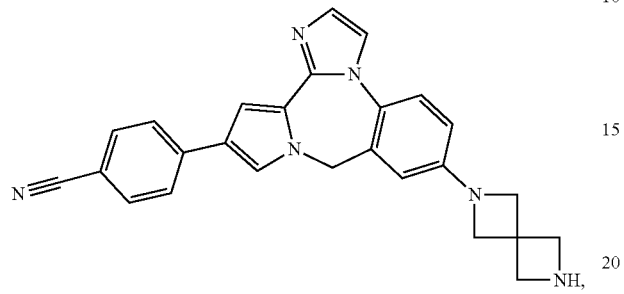
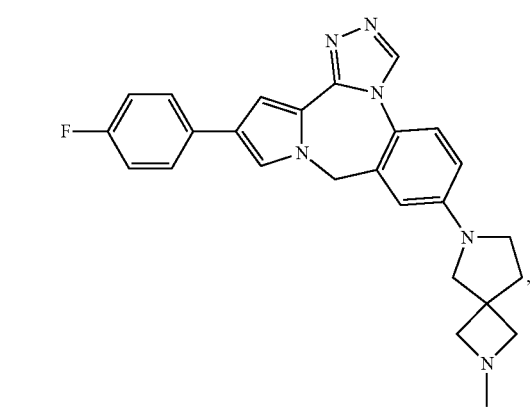
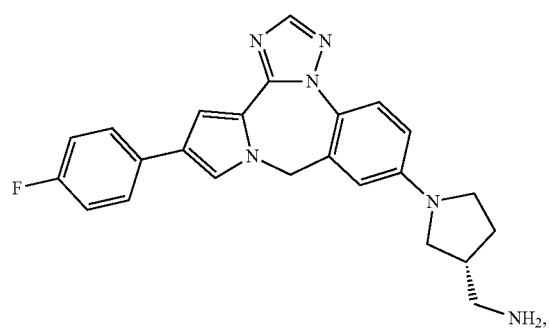
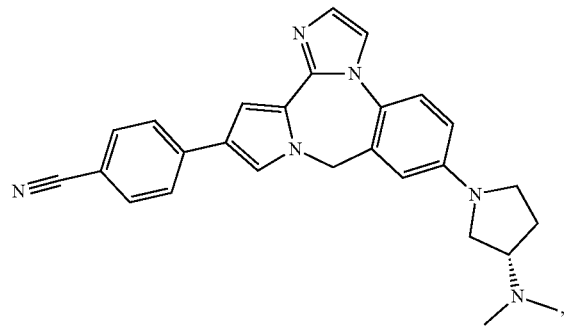
432
-continued
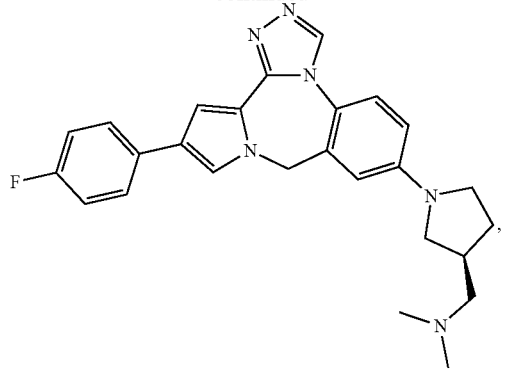
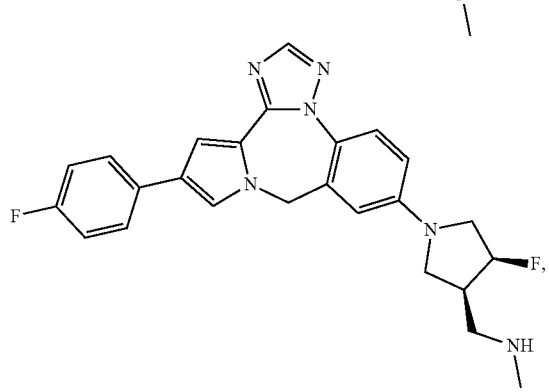
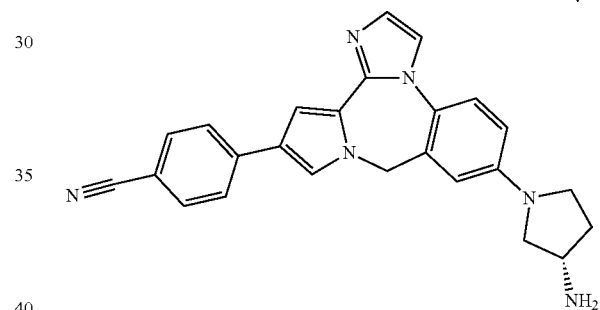
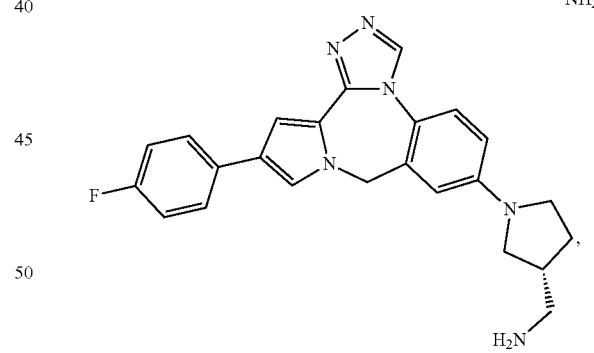
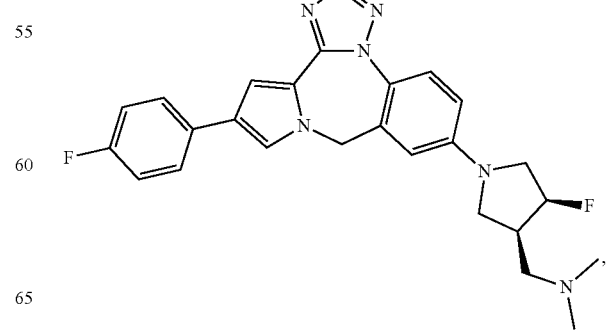

433
-continued
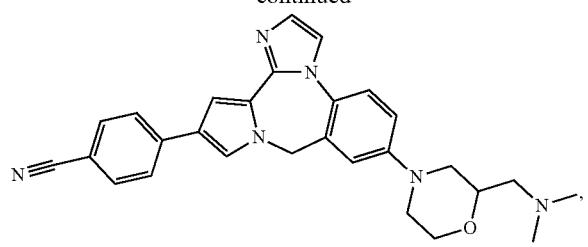
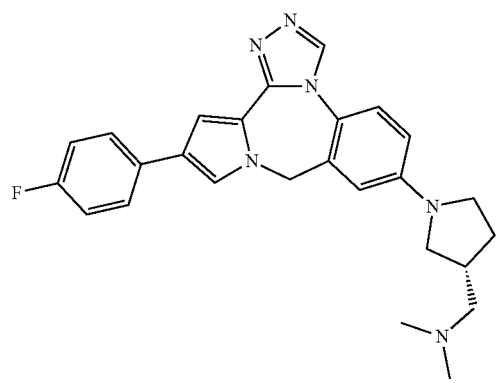
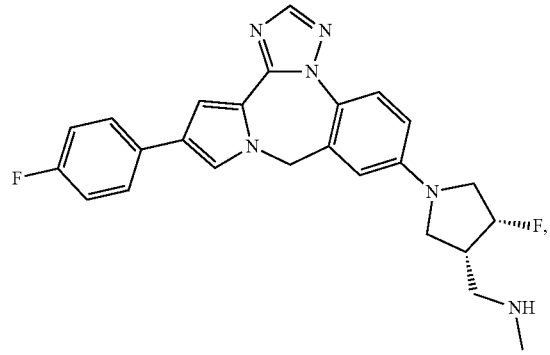
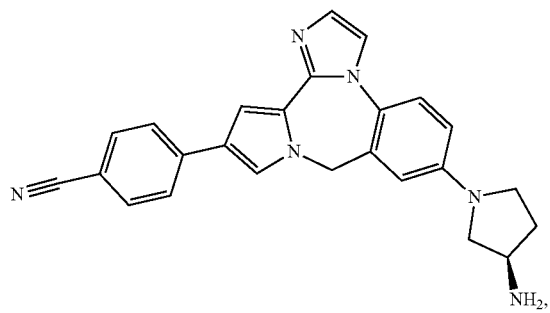
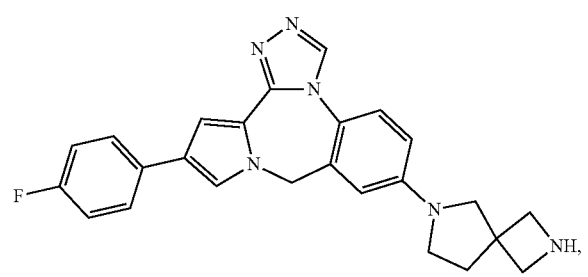
434
-continued
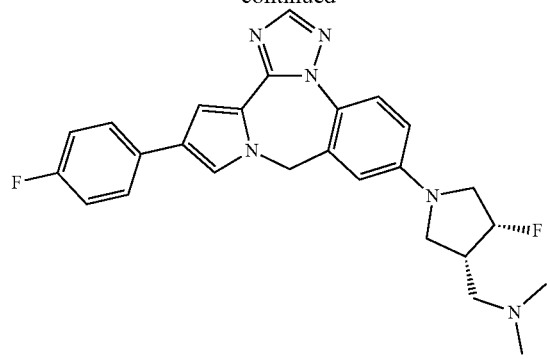
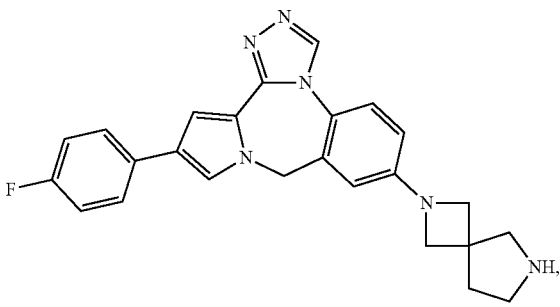
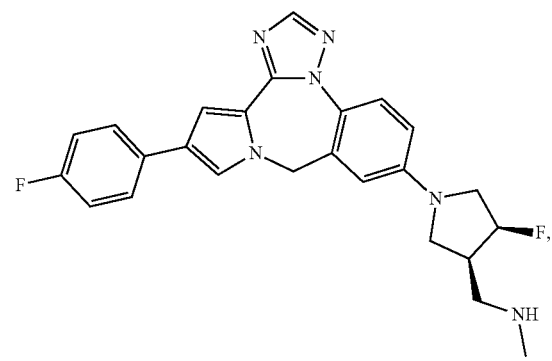
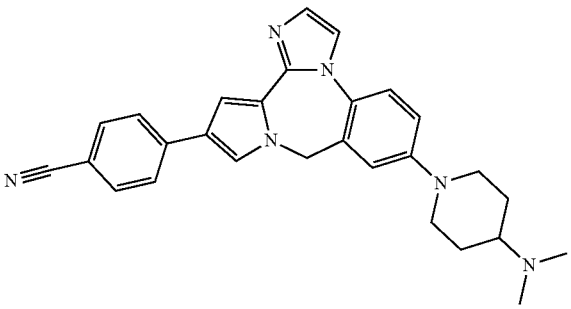

-continued
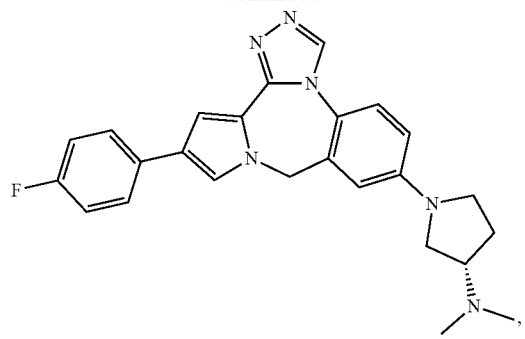
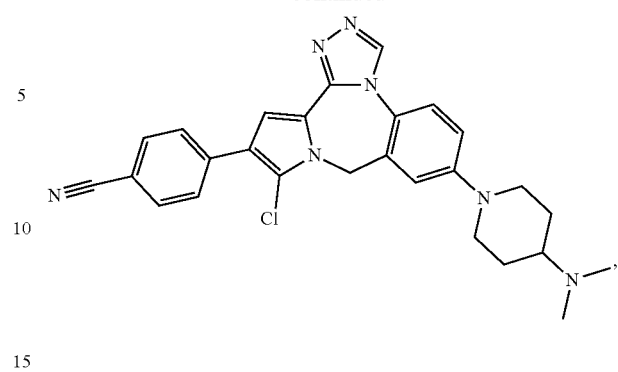
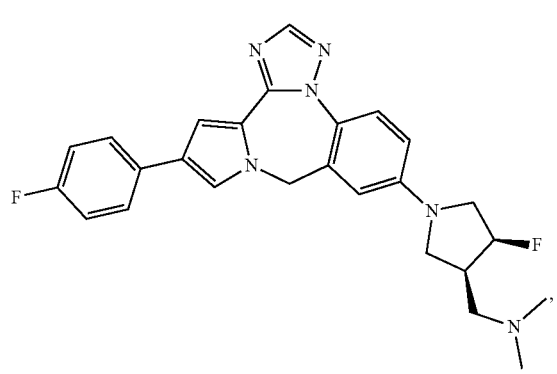
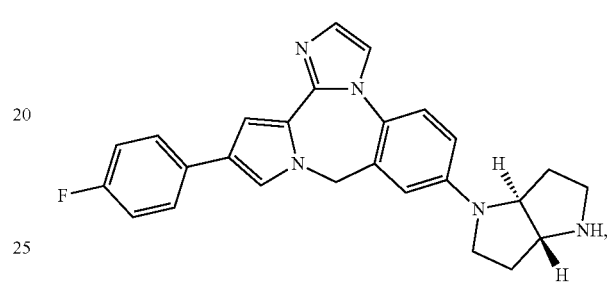
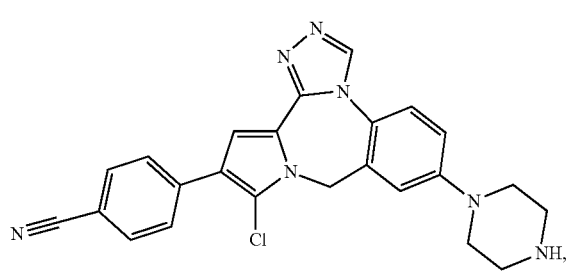
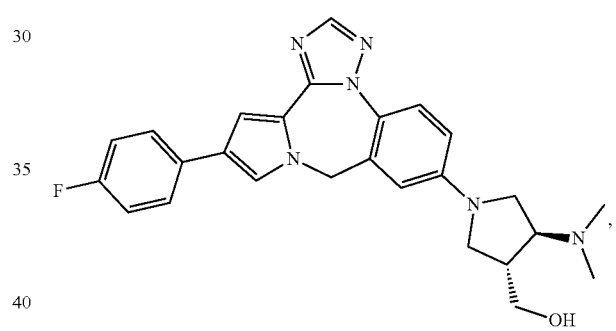
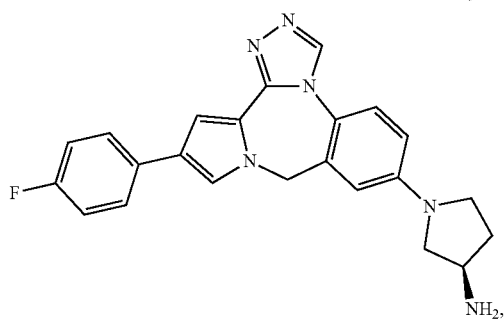
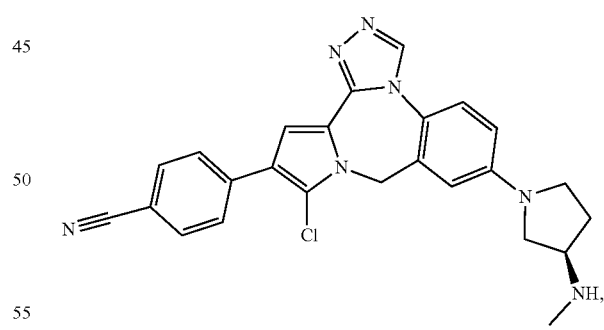
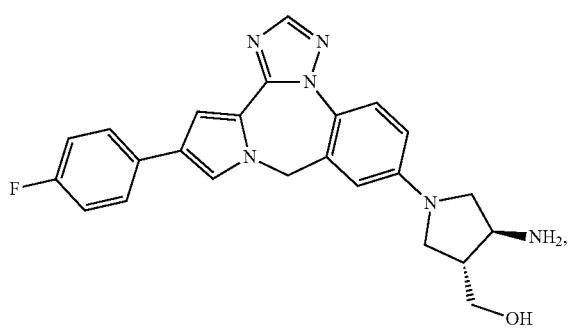
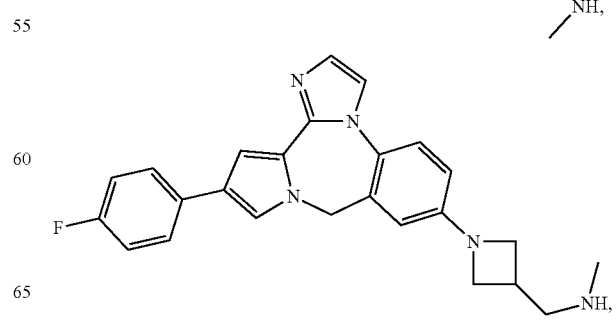

437
-continued
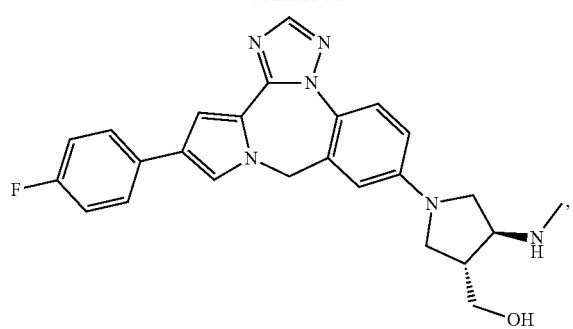
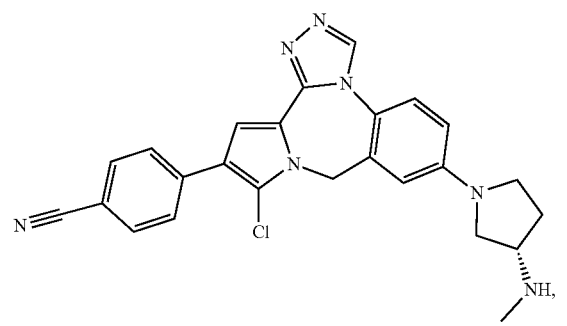
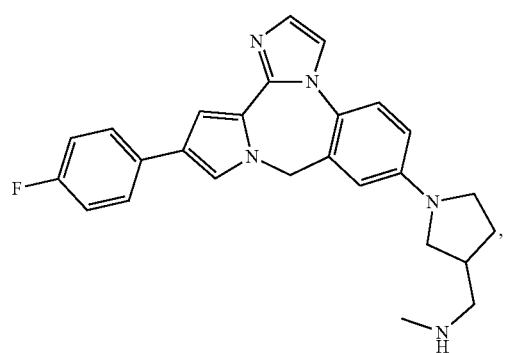
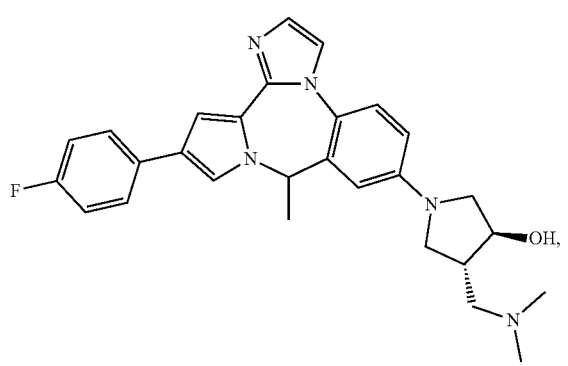
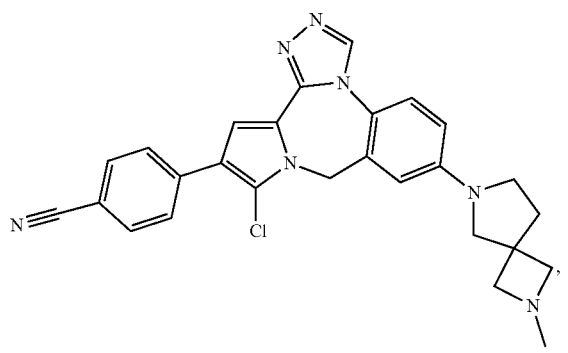
438
-continued
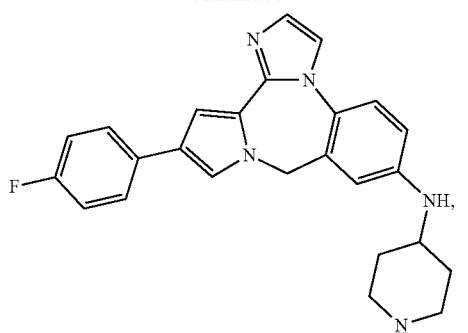
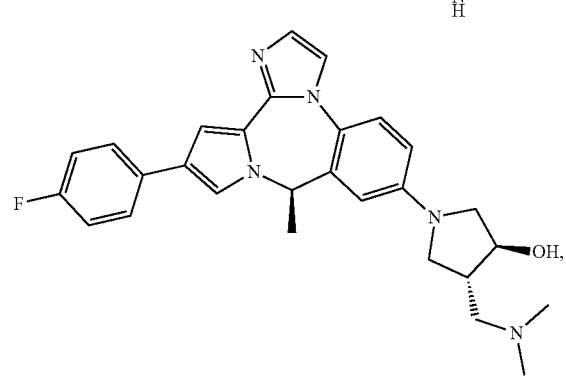
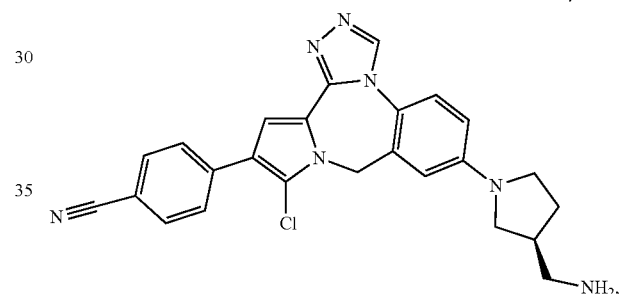
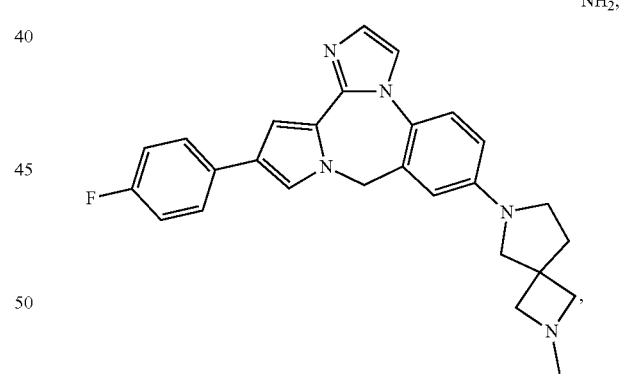
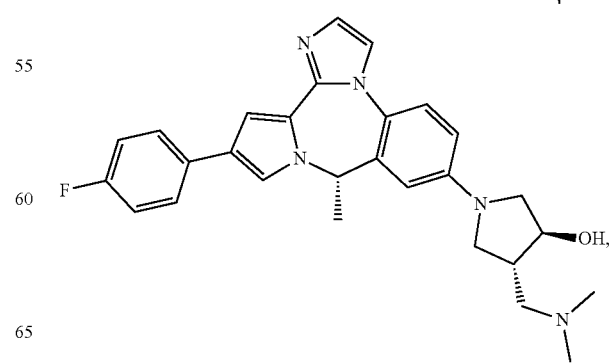

439
-continued
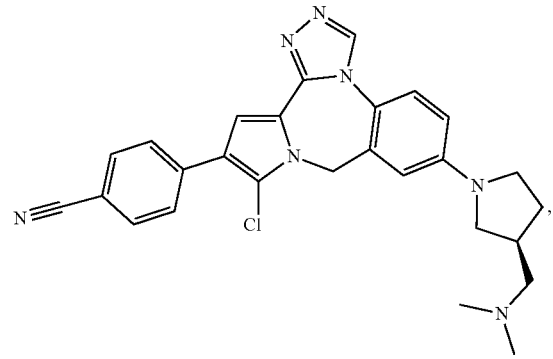
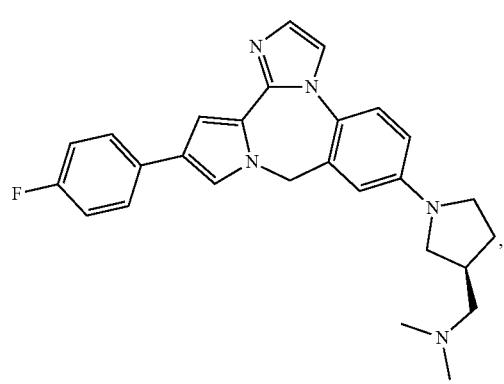
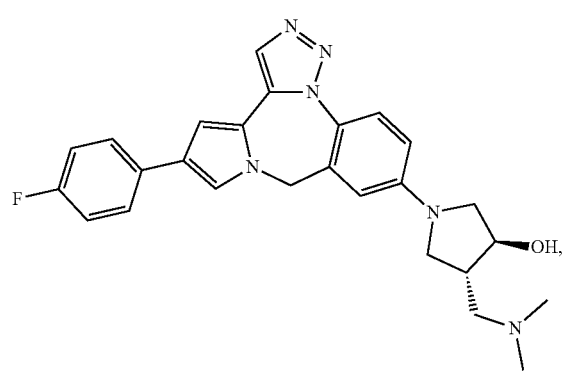
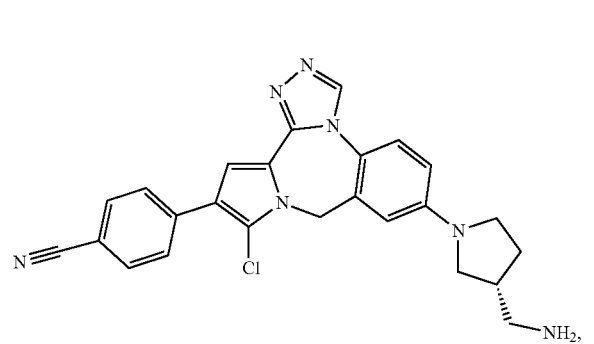
440
-continued
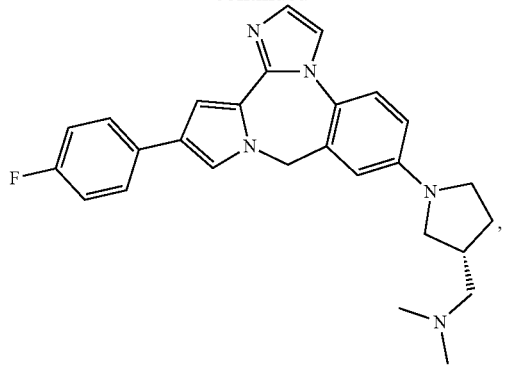
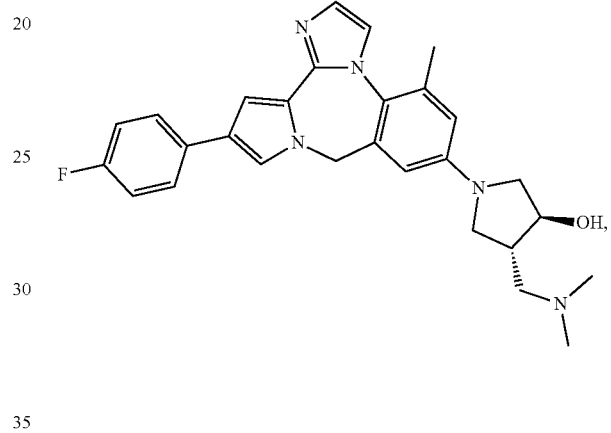
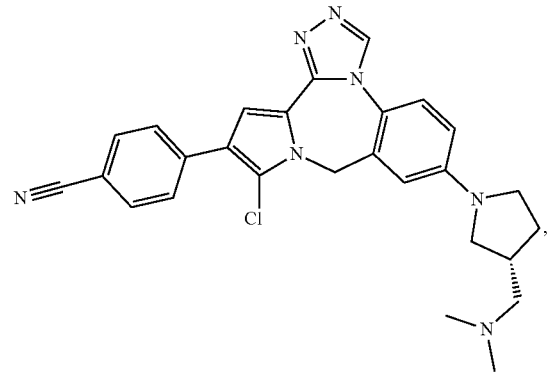
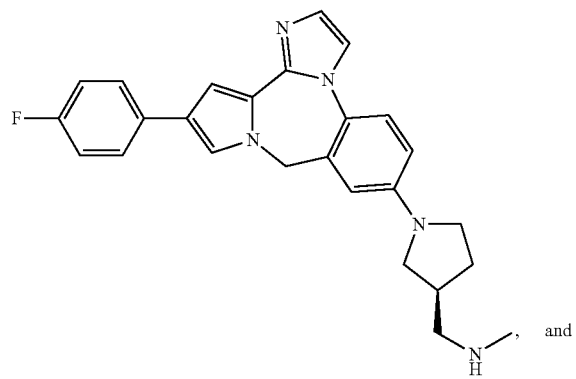
and

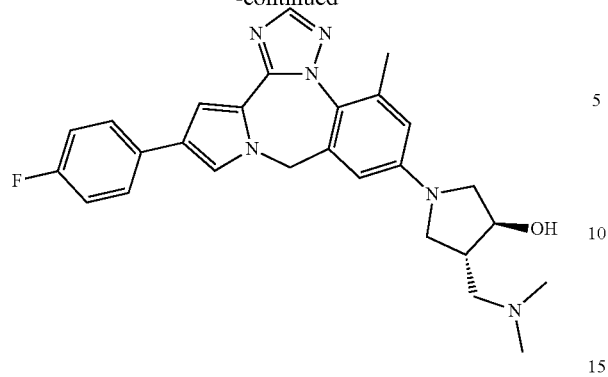
or a pharmaceutically acceptable salt thereof.
* * * * *